United States Patent
Liu et al.

(10) Patent No.: US 8,362,065 B2
(45) Date of Patent: *Jan. 29, 2013

(54) CARBAZOLE CARBOXAMIDE COMPOUNDS USEFUL AS KINASE INHIBITORS

(75) Inventors: Qingjie Liu, Newtown, PA (US); Douglas G. Batt, Wilmington, DE (US); George V. DeLucca, Pennington, NJ (US); Qing Shi, Princeton, NJ (US); Andrew J. Tebben, New Hope, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/292,153

(22) Filed: Nov. 9, 2011

(65) Prior Publication Data

US 2012/0058996 A1 Mar. 8, 2012

Related U.S. Application Data

(63) Continuation of application No. 12/640,119, filed on Dec. 17, 2009, now Pat. No. 8,084,620.

(60) Provisional application No. 61/139,047, filed on Dec. 19, 2008.

(51) Int. Cl.
| | |
|---|---|
| *A61K 31/517* | (2006.01) |
| *A61K 31/404* | (2006.01) |
| *A61K 31/4412* | (2006.01) |
| *A61K 31/45* | (2006.01) |
| *A61K 31/60* | (2006.01) |

(52) U.S. Cl. .............. 514/411; 514/266.23; 514/300; 514/323; 514/249

(58) Field of Classification Search .............. None
See application file for complete search history.

(56) References Cited

U.S. PATENT DOCUMENTS

| 7,491,245 B2 | 2/2009 | Glenn, Jr. et al. | |
|---|---|---|---|
| 8,084,620 B2 * | 12/2011 | Liu et al. | 548/441 |
| 2006/0084650 A1 | 4/2006 | Dong et al. | |
| 2006/0183746 A1 | 8/2006 | Currie et al. | |
| 2008/0045536 A1 | 2/2008 | Vaccaro et al. | |
| 2009/0163545 A1 | 6/2009 | Goldfarb | |

FOREIGN PATENT DOCUMENTS

| WO | WO 01/07409 | 2/2001 |
|---|---|---|
| WO | WO 03/030901 | 4/2003 |
| WO | WO 2004/089940 | 10/2004 |
| WO | WO 2005/005429 | 1/2005 |
| WO | WO 2005/014599 | 2/2005 |
| WO | WO 2005/047290 | 5/2005 |
| WO | WO 2006/034317 | 3/2006 |
| WO | WO 2006/034337 | 3/2006 |
| WO | WO 2006/053121 | 5/2006 |
| WO | WO 2006/099075 | 9/2006 |
| WO | WO 2007/038314 | 4/2007 |
| WO | WO 2007/061764 | 5/2007 |
| WO | WO 2008/021745 | 2/2008 |
| WO | WO 2008/032171 | 3/2008 |
| WO | WO 2008/033858 | 3/2008 |
| WO | WO 2008/064317 | 5/2008 |
| WO | WO 2008/064318 | 5/2008 |
| WO | WO 20081057254 | 5/2008 |
| WO | WO 2008/079965 | 7/2008 |
| WO | WO 2009/075830 | 6/2009 |
| WO | WO 2009/096202 | 8/2009 |
| WO | WO 2009/106597 | 9/2009 |
| WO | PCT/US09/068394 | 12/2009 |

* cited by examiner

*Primary Examiner* — Kamal Saeed
*Assistant Examiner* — Nyeemah A Grazier
(74) *Attorney, Agent, or Firm* — Mary K. VanAtten; Laurelee A. Duncan; Gary D. Greenblatt

(57) ABSTRACT

Compounds having the formula (I), and enantiomers, and diastereomers, pharmaceutically-acceptable salts, thereof,

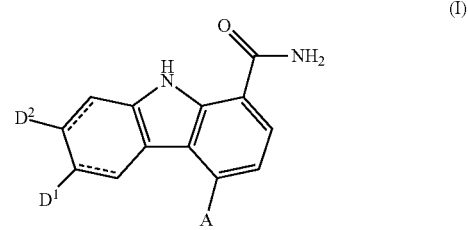

are useful as kinase modulators, including Btk modulation.

20 Claims, No Drawings

CARBAZOLE CARBOXAMIDE COMPOUNDS USEFUL AS KINASE INHIBITORS

This application is a continuation of U.S. Ser. No. 12/640,119, filed Dec. 17, 2009, which claims the benefit of U.S. Provisional Application Ser. No. 61/139,047 filed Dec. 19, 2008 and is incorporated herein by reference.

FIELD OF THE INVENTION

This invention relates to fused carbazole carboxamide compounds useful as kinase inhibitors, including the modulation of Bruton's tyrosine kinase (Btk) and other Tec family kinases such as Itk. Provided herein are fused heterocyclic compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

BACKGROUND OF THE INVENTION

Protein kinases, the largest family of human enzymes, encompass well over 500 proteins. Btk is a member of the Tec family of tyrosine kinases, and is a regulator of early B-cell development, as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

Inhibitors of protein kinases are widely sought and a number of publications report compounds effective in modulating protein kinases. For example, patent publications WO 2005/047290, WO 2005/014599, WO 2005/005429, WO 2006/099075, WO 2006/053121, and US 2006/0183746 disclose certain imidazopyrazine compounds that are said to inhibit protein kinase activity, including Btk activity. Patent publication WO 2008/033858 discloses methods of inhibiting Btk activity with various Btk binding chemical compounds. Patent publication US 2006/0084650 discloses that fused heterocyclic compounds exemplified by imidazopyrimidines and pyrrolotriazines may be used as protein kinase inhibitors. In addition, certain imidazopyridazine and imidazotriazine compounds are disclosed in WO 2007/038314 (published Apr. 5, 2007) and WO 2008/0045536 (published Feb. 21, 2008), both of which are assigned to the present assignee.

The present invention relates to a new class of substituted fused heterocyclic compounds found to be effective inhibitors of protein kinases including Btk and other Tec family kinases such as Itk.

SUMMARY OF THE INVENTION

Modulators of kinase activity which may generally be described as substituted carbazoles, tetrahydrocarbazoles, and related compounds are provided herein.

The invention is directed to compounds of Formula I that which are useful as inhibitors of Btk, and are useful for the treatment of proliferative diseases, allergic diseases, autoimmune diseases and inflammatory diseases, or stereoisomers, tautomers, pharmaceutically acceptable slats, solvates or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Btk comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE EMBODIMENTS OF THE INVENTION

Provided herein is at least one chemical entity chosen from compounds of formula (I):

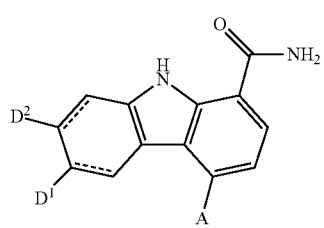

(I)

or an enantiomer, a diastereomer, a prodrug, a salt, or a pharmaceutically-acceptable salt thereof, wherein
the dashed lines are either single or double bonds;

A is halo, $C_{3-10}$ carbocycle substituted with 0-3 B, $C_{6-10}$ mono- or bicyclic aryl substituted with 0-3 B, a 5-14 membered heterocyclyl containing 1-4 heteroatoms selected from N, O, and S, substituted with 0-3 B, a 5-10 membered heteroaryl containing 1-4 heteroatoms selected from N, O, and S, substituted with 0-3 B;

B is $R^1$, halogen, cyano, nitro, $-O-R^1$, $-C(=O)-R^1$, $-C(=O)O-R^1$, $-C(=O)NR^{11}-R^1$, $-S(=O)_2-R^1$, $-NR^{11}C(=O)-R^1$, $-NR^{11}C(=O)NR^{11}-R^1$, $-NR^{11}C(=O)O-R^1$, $-N(C(=O)O-R^1)_2$, $-NR^{11}S(=O)_2-R^1$, $-N(S(=O)_2-R^1)_2$, or $-NR^{11}-R^1$;

$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$;

$R^{1a}$ is hydrogen, C=O, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^d$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-1 $R^a$;

one of $D^1$ and $D^2$ is D and the other is H or halo;

D is $-R^2$, halogen, $-(C(R^{11})_2)_r-R^2$, $-O-R^2$, $-C(=O)-R^2$, $-C(=O)O-R^2$, $-C(=O)NR^{11}-R^2$, $-S(=O)_2-R^2$, $-S(=O)-R^2$, $-NR^{11}C(=O)-R^2$, $-NR^{11}C(=O)NR^{11}-R^2$, $-NR^{11}C(=O)O-R^2$, $-NR^{11}S(=O)_2-R^2$, $-NR^{11}-R^2$, $-C(=O)NR^{11}-O-R^2$, $-OC(=O)O-R^2$, $-O^1C(=O)-R^2$, or CH=N-OH;

with the proviso that A is not halo when D is $-C(=O)O-R^2$, $R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;

$R^{2a}$ is hydrogen, C=O, F, Cl, Br, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-2 $R^a$;

$R^{11}$ is independently hydrogen or $C_{1-4}$ alkyl substituted with 0-1 $R^f$, $CH_2$-phenyl, or $-(CH_2)_r$-5-7 membered heterocycle comprising carbon atoms and 1-4 heteroatoms selected from N, O, and $S(O)_p$;

alternatively, $R^{11}$ and along with another $R^{11}$, $R^1$, or $R^2$ on the same nitrogen atom may join to form an azetidinyl, pyrrolidinyl, piperidinyl, morpholinyl, or 4-($C_{1-6}$ alkyl)piperazinyl;

$R^a$ is hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-1 $R^f$, $C_{1-6}$ haloalkyl, $-(CH_2)_r$-3-14 membered carbocycle, or $-(CH_2)_r$-5-7 membered heterocycle comprising carbon atoms and 1-4 heteroatoms selected from N, O, and $S(O)_p$, alternatively two $R^a$ on adjacent or the same carbon atom form a cyclic acetal of the formula $-O-(CH_2)_n-O-$, or $-O-CF_2-O-$, wherein n is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl substituted with 0-1 $R^f$, $C_{3-6}$ cycloalkyl, or $(CH_2)_r$-phenyl substituted with 0-1 $R^f$;

$R^d$ is hydrogen, F, Cl, Br, $OCF_3$, $CF_3$, CN, $NO_2$, $-OR^e$, $-(CH2)_rC(O)R^c$, $-NR^eR^e$, $-NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

$R^f$ is hydrogen, halo, $NH_2$, OH, or $OCH_3$;

r is 0, 1, 2, 3, or 4; and p is 0, 1, or 2.

In another embodiment, there is provided a compound of formula I, wherein
the dashed lines are either single or double bonds;
A is halo, $C_{3-10}$ cycloalkyl substituted with 0-3 B, $C_{6-10}$ mono- or bicyclic aryl substituted with 0-3 B, a 5-10 membered heterocyclyl containing 1-4 heteroatoms selected from N, O, and S, substituted with 0-3 B, a 5-10 membered heteroaryl containing 1-4 heteroatoms selected from N, O, and S, substituted with 0-3 B;
B is $R^1$, halogen, cyano, nitro, —O—$R^1$, —C(=O)—$R^1$, —C(=O)O—$R^1$, —C(=O)N$R^{11}$—$R^1$, —S(=O)$_2$—$R^1$, —N$R^{11}$C(=O)—$R^1$, —N$R^{11}$C(=O)N$R^{11}$—$R^1$, —N$R^{11}$C(=O)O—$R^1$, —N$R^{11}$S(=O)$_2$—$R^1$, —N(S(=O)$_2$—$R^1$)$_2$, or —N$R^{11}$—$R^1$;
$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$;
$R^{1a}$ is hydrogen, C=O, F, Cl, Br, OCF$_3$, CF$_3$, CHF$_2$, CN, NO$_2$, —(CH$_2$)$_r$O$R^b$, —(CH$_2$)$_r$S$R^b$, —(CH$_2$)$_r$C(O)$R^b$, —(CH$_2$)$_r$C(O)O$R^b$, —(CH$_2$)$_r$OC(O)$R^b$, —(CH$_2$)$_r$N$R^{11}R^{11}$, —(CH$_2$)$_r$C(O)N$R^{11}R^{11}$, —(CH$_2$)$_r$N$R^b$C(O)$R^c$, —(CH$_2$)$_r$N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl substituted with 0-2 $R^d$, $C_{1-6}$ haloalkyl, —(CH$_2$)$_r$-3-14 membered carbocycle substituted with 0-1 $R^a$, or —(CH$_2$)$_r$-5-7 membered heterocycle comprising carbon atoms and 1-4 heteroatoms selected from N, O, and S(O)$_p$ substituted with 0-1 $R^a$;
one of $D^1$ and $D^2$ is D and the other is H;
D is —$R^2$, halogen, —(C($R^{11}$)$_2$)$_r$—$R^2$, —O—$R^2$, —C(=O)—$R^2$, —C(=O)O—$R^2$, —C(=O)N$R^{11}$—$R^2$, —S(=O)$_2$—$R^2$, —N$R^{11}$C(=O)—$R^2$, —N$R^{11}$C(=O)N$R^{11}$—$R^2$, —N$R^{11}$C(=O)O—$R^2$, —N$R^{11}$S(=O)$_2$—$R^2$, or —N$R^{11}$—$R^2$;
$R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;
$R^{2a}$ is hydrogen, C=O, F, Cl, Br, OCF$_3$, CN, NO$_2$, —(CH$_2$)$_r$O$R^b$, —(CH$_2$)$_r$S$R^b$, —(CH$_2$)$_r$C(O)$R^b$, —(CH$_2$)$_r$C(O)O$R^b$, —(CH$_2$)$_r$OC(O)$R^b$, —(CH$_2$)$_r$N$R^{11}R^{11}$, —(CH$_2$)$_r$C(O)N$R^{11}R^{11}$, —(CH$_2$)$_r$N$R^b$C(O)$R^c$, —(CH$_2$)$_r$N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl substituted with 0-2 $R^a$, $C_{1-6}$ haloalkyl, —(CH$_2$)$_r$-3-14 membered carbocycle substituted with 0-1 $R^a$, or —(CH$_2$)$_r$-5-7 membered heterocycle comprising carbon atoms and 1-4 heteroatoms selected from N, O, and S(O)$_p$ substituted with 0-1 $R^a$;
$R^{11}$ is independently hydrogen or $C_{1-4}$ alkyl;
alternatively, $R^{11}$ and along with another $R^{11}$, $R^1$, or $R^2$ on the same nitrogen atom may join to form an azetidinyl, pyrrolidinyl, piperidinyl, morpholinyl, or 4-($C_{1-6}$ alkyl)piperazinyl;
$R^a$ is hydrogen, F, Cl, Br, OCF$_3$, CF$_3$, CHF$_2$, CN, NO$_2$, —(CH$_2$)$_r$O$R^b$, —(CH$_2$)$_r$S$R^b$, —(CH$_2$)$_r$C(O)$R^b$, —(CH$_2$)$_r$C(O)O$R^b$, —(CH$_2$)$_r$OC(O)$R^b$, —(CH$_2$)$_r$N$R^{11}R^{11}$, —(CH$_2$)$_r$C(O)N$R^{11}R^{11}$, —(CH$_2$)$_r$N$R^b$C(O)$R^c$, —(CH$_2$)$_r$N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl, $C_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$, alternatively two $R^a$ on adjacent or the same carbon atom form a cyclic acetal of the formula —O—(CH$_2$)$_n$—O—, or —O—CF$_2$—O—, wherein n is selected from 1 or 2;
$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or (CH$_2$)$_r$-phenyl substituted with 0-2 $R^d$;
$R^c$ is $C_{1-6}$ alkyl, $C_{3-6}$ cycloalkyl, or (CH$_2$)$_r$-phenyl;
$R^d$ is hydrogen, F, Cl, Br, OCF$_3$, CF$_3$, CN, NO$_2$, —O$R^e$, —(CH2)$_r$C(O)$R^b$, —N$R^eR^e$, —N$R^e$C(O)O$R^c$, $C_{1-6}$ alkyl, or (CH$_2$)$_r$-phenyl;
$R^e$ is hydrogen, $C_{1-6}$ alkyl, $C_{3-6}$ cycloalkyl, or (CH$_2$)$_r$-phenyl;
r is 0, 1, 2, 3, or 4; and
p is 0, 1, or 2.
In another embodiment, there is provided a compound of formula I, wherein
D is a —$R^2$, —(CH$_2$)$_r$—$R^2$, —O—$R^2$, —C(=O)—$R^2$, —C(=O)O—$R^2$, —C(=O)N$R^{11}$—$R^2$, —S(=O)$_2$—$R^2$, —S(=O)—$R^2$, —N$R^{11}$C(=O)—$R^2$, —N$R^{11}$C(=O)N$R^{11}$—$R^2$, —N$R^{11}$C(=O)O—$R^2$, —N$R^{11}$S(=O)$_2$—$R^2$, or —N$R^{11}$—$R^2$;
$R^2$ is hydrogen, $C_{1-6}$ alkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;
$R^{2a}$ is hydrogen, C=O, F, Cl, Br, OCF$_3$, CF$_3$, CHF$_2$, CN, NO$_2$, O$R^b$, S$R^b$, —C(O)$R^b$, —C(O)O$R^b$, —OC(O)$R^b$, —N$R^{11}R^{11}$, —C(O)N$R^{11}R^{11}$, —N$R^b$C(O)$R^c$, —N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl substituted with 0-2 $R^a$, —(CH$_2$)$_r$-3-14 membered carbocycle substituted with 0-1 $R^a$, wherein the carbocycle is cyclopropyl, cyclobutyl, cyclopentyl or cyclohexyl; or —(CH$_2$)$_r$-5-7 membered heterocycle comprising carbon atoms and 1-4 heteroatoms selected from N, O, and S(O)$_p$ substituted with 0-1 $R^a$;
r is 0, 1, or 2.
In another embodiment, there is provided a compound of formula I, wherein
A is halo, $C_{6-10}$ mono- or bicyclic aryl substituted with 0-3-B, a 5-10 membered heterocyclyl containing 1-4 heteroatoms selected from N, O, and S, substituted with 0-3 -B, a 5-10 membered heteroaryl containing 1-4 heteroatoms selected from N, O, and S, substituted with 0-3-B;
B is $R^1$, halogen, cyano, nitro, —O—$R^1$, —C(=O)—$R^1$, —C(=O)O—$R^1$, —C(=O)N$R^{11}$—$R^1$, —S(=O)$_2$—$R^1$, —N$R^{11}$C(=O)—$R^1$, —N$R^{11}$C(=O)N$R^{11}$—$R^1$, —N$R^{11}$S(=O)$_2$—$R^1$, —N(S(=O)$_2$—$R^1$)$_2$, or —N$R^{11}$—$R^1$;
$R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$.
In another embodiment, there is provided a compound of formula I, wherein
$R^2$ is hydrogen, $C_{2-6}$ alkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, wherein the heterocyclyl is pyrrolidinyl, piperidinyl, morpholinyl or piperazinyl; a 5-10 membered heteroaryl containing 1-4 heteroatoms selected from N, O, and S, substituted with 0-3 $R^{2a}$, wherein the heteroaryl is pyridinyl, quinolinyl, isoquinolinyl, or thiazolyl.

In another embodiment, there is provided a compound of formula I, wherein

A is $C_{6-10}$ mono- or bicyclic aryl substituted with 0-3-B, a 5-10 membered heterocyclyl containing 1-4 heteroatoms selected from N, O, and S, substituted with 0-3-B, wherein the heterocyclyl is pyrrolidinyl, piperidinyl, morpholinyl or piperazinyl; a 5-10 membered heteroaryl containing 1-4 heteroatoms selected from N, O, and S, substituted with 0-3-B, wherein the heteroaryl is pyridinyl, quinolinyl, isoquinolinyl, indolyl, indazolyl, benzimidazolyl, imidazolyl, pyrazolyl, or thiazolyl;

$R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is pyrrolidinyl, piperidinyl, morpholinyl or piperazinyl; a 5-10 membered heteroaryl containing 1-4 heteroatoms selected from N, O, and S, substituted with 0-3 $R^{1a}$ wherein the heteroaryl is pyridinyl or thiazolyl.

In another embodiment, there is provided a compound of formula I, wherein the compound of formula I is a compound of formula (Ia) or (Ib) or a pharmaceutically acceptable salt thereof

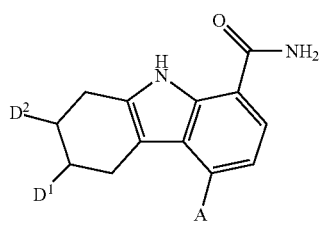

(Ia)

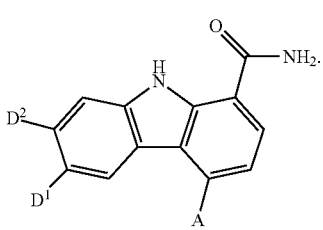

(Ib)

In another embodiment, there is provided a compound of formula I, wherein $R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-6 membered carbocycle, or —$(CH_2)_r$-5-7 membered heterocycle comprising carbon atoms and 1-4 heteroatoms selected from N, O, and $S(O)_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, $OCF_3$, $CF_3$, CN, NO2, —$OR^e$, —$C(O)R^b$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

In another embodiment, there is provided a compound of formula I, wherein a compound of formula (I) is (Ia) or (Ib)

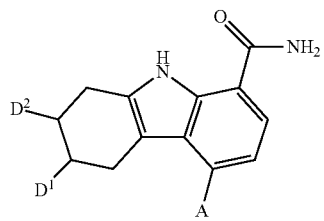

(Ia)

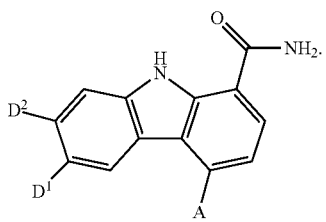

(Ib)

A is $C_{6-10}$ mono- or bicyclic aryl substituted with 0-3-B, wherein the aryl group is phenyl or naphthyl; a 5-10 membered heterocyclyl containing 1-4 heteroatoms selected from N, O, and S, substituted with 0-3-B, wherein the heterocyclyl group is pyrrolidinyl or piperidinyl; or a 5-10 membered heteroaryl containing 1-4 heteroatoms selected from N, O, and S, substituted with 0-3-B, wherein the heteroaryl group is pyridinyl, quinolinyl, isoquinolinyl, indolyl, indazolyl, benzimidazolyl, imidazolyl, pyrazolyl or thiazolyl;

B is $R^1$, halogen, —$C(=O)O$—$R^1$, —$S(=O)_2$—$R^1$, —$NR^{11}C(=O)$—$R^1$, —$NR^{11}C(=O)NR^{11}$—$R^1$, —$NR^{11}S(=O)_2$—$R^1$, $N(S(=O)_2$—$R^1)_2$, or —$NR^{11}$—$R^1$;

$R^1$ is hydrogen, trifluoromethyl, $C_{1-4}$ alkyl substituted with 0-1 $R^{1a}$, phenyl substituted with 0-3 $R^{1a}$, a 5-10 membered heteroaryl containing 1-4 heteroatoms selected from N, O, and S, substituted with 0-3 $R^{1a}$, wherein the heteroaryl is pyridyl or thiazolyl;

One of $D^1$ and $D^2$ is D and the other is hydrogen;

D is $R^2$, —$C(=O)$—$R^2$, —$C(=O)NR^{11}R^2$, $NR^{11}C(=O)R^2$, $NR^{11}C(=O)NR^{11}$—$R^2$, $NR^{11}S(=O)_2$—$R^2$, or —$NR^{11}$—$R^2$;

$R^2$ is hydrogen, $C_{2-6}$ alkyl substituted with 0-3 $R^{2a}$, a 5-10 membered heterocyclyl containing 1-4 heteroatoms selected from N, O, and S, substituted with 0-3 $R^{2a}$ where the heterocyclyl is pyrrolidinyl, piperidinyl, piperazinyl or morpholinyl;

$R^{2a}$ is $C_{1-4}$ alkyl, wherein the alkyl is methyl, ethyl, propyl, i-propyl, butyl, and t-butyl, substituted with 0-1 $R^a$.

In another embodiment, there is provided a compound of formula I, wherein

D is a —$R^2$, —$(CH_2)_r$—$R^2$, —O—$R^2$, —$C(=O)$—$R^2$, —$C(=O)O$—$R^2$, —$C(=O)NR^{11}$—$R^2$, —$S(=O)_2$—$R^2$, —$NR^{11}C(=O)$—$R^2$, —$NR^{11}C(=O)NR^{11}$—$R^2$, —$NR^{11}C(=O)O$—$R^2$, —$NR^{11}S(=O)_2$—$R^2$, or —$NR^{11}$—$R^2$;

$R^2$ is hydrogen, $C_{1-6}$ alkyl substituted with 0-3 $R^{2a}$, $C_{2-6}$ alkenyl substituted with 0-3 $R^{2a}$, $C_{3-10}$ cycloalkyl substituted with 0-3 $R^{2a}$, —$C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;

$R^{2a}$ is hydrogen, C=O, F, Cl, Br, $OCF_3$, $CF_3$, $CHF_2$, CN, $NO_2$, $OR^b$, $SR^b$, —C(O)$R^b$, —C(O)O$R^b$, —OC(O)$R^b$, —$NR^{11}R^{11}$, —C(O)$NR^{11}R^{11}$, —$NR^bC(O)R^c$, —$NR^bC(O)OR^c$, —$NR^bC(O)NR^{11}R^{11}$, —S(O)$_p$$NR^{11}R^{11}$, —$NR^bS(O)_pR^c$, —S(O)$R^c$, —S(O)$_2R^c$, $C_{1-6}$ alkyl substituted with 0-2 $R^a$, —(CH$_2$)$_r$-3-14 membered carbocycle substituted with 0-1 $R^a$, wherein the carbocycle is cyclopropyl, cyclobutyl, cyclopentyl or cyclohexyl; or —(CH$_2$)$_r$-5-7 membered heterocycle comprising carbon atoms and 1-4 heteroatoms selected from N, O, and S(O)$_p$ substituted with 0-2 $R^a$;

r is 0, 1, or 2.

In another embodiment, there is provided a compound of formula I, wherein

A is halo, $C_{3-10}$ carbocycle substituted with 0-3 B $C_{6-10}$ mono- or bicyclic aryl substituted with 0-3-B, a 5-14 membered heterocyclyl containing 1-4 heteroatoms selected from N, O, and S, substituted with 0-3-B, a 5-10 membered heteroaryl containing 1-4 heteroatoms selected from N, O, and S, substituted with 0-3-B;

B is $R^1$, halogen, cyano, nitro, —O—$R^1$, —C(=O)—$R^1$, —C(=O)O—$R^1$, —C(=O)$NR^{11}$—$R^1$, —S(=O)$_2$—$R^1$, —$NR^{11}$C(=O)—$R^1$, —$NR^{11}$C(=O)$NR^{11}$—$R^1$, —$NR^{11}$S(=O)$_2$—$R^1$, —N(S(=O)$_2$—$R^1$)$_2$, or —$NR^{11}$—$R^1$;

$R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$.

In another embodiment, there is provided a compound of formula I, wherein $R^2$ is hydrogen, $C_{1-6}$ alkyl substituted with 0-3 $R^{2a}$, ethenyl, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, wherein the heterocyclyl is pyrrolidinyl, piperidinyl, morpholinyl or piperazinyl, tetrahydropyranyl, oxazolidinyl (oxazolidin-one), imidazolidinyl (imidazolidin-one), dioxalanyl, or

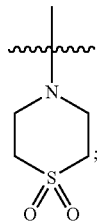

a 5-10 membered heteroaryl containing 1-4 heteroatoms selected from N, O, and S, substituted with 0-3 $R^{2a}$, wherein the heteroaryl is pyrimidinyl, imidazolyl, pyrazinyl, thiadiazolyl, pyridinyl, quinolinyl, isoquinolinyl, or thiazolyl.

In another embodiment, there is provided compound of formula I, wherein

A is $C_6$ carbocycle substituted with 0-3 B, $C_{6-10}$ mono- or bicyclic aryl substituted with 0-3-B, a 5-14 membered heterocyclyl containing 1-4 heteroatoms selected from N, O, and S, substituted with 0-3-B, wherein the heterocyclyl is chromanyl, 3,4-dihydro-2H-benzo[e][1,3]oxazin-2-one, pyrrolidinyl, piperidinyl, morpholinyl or piperazinyl; a 5-10 membered heteroaryl containing 1-4 heteroatoms selected from N, O, and S, substituted with 0-3-B, wherein the heteroaryl is pyridinyl, quinolinyl, isoquinolinyl, indolyl, indazolyl, benzimidazolyl, furanyl, benzofuranyl, dibenzofuranyl, imidazolyl, pyrazolyl, or thiazolyl;

$R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is 4,5,6,7-tetrahydrobenzo[d]thiazolyl, isindolinyl, imidazo[1,2-a]pyrazin-8(7H)-one, 1H-pyrrolo[3,4-c]pyridin-3(2H)-one, 1,3-dihydrofuro[3,4-c]pyridine, phthalazine, isoquinolin-1(2H)-one, isoindolinyl, isoindoline-1,3-dione, quinazolin-4(3H)-one,

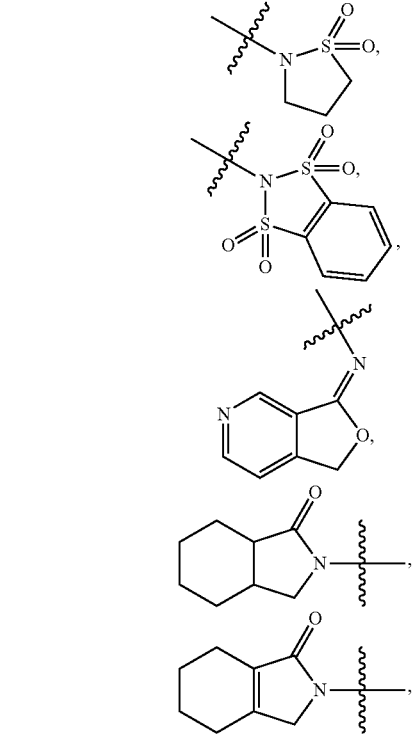

pyrrolidinyl, piperidinyl, morpholinyl or piperazinyl; a 5-10 membered heteroaryl containing 1-4 heteroatoms selected from N, O, and S, substituted with 0-3 $R^{1a}$ wherein the heteroaryl is indazolyl, imidazolyl, pyrimidinyl, benzimidazolyl, benzothiazolyl, quinolinyl, quinazolinyl, quinazolin-4(3H)-one pyridinyl or thiazolyl.

In another embodiment, there is provided a compound of formula I, wherein the compound of formula I is a compound of formula (I) is (Ia) or (Ib)

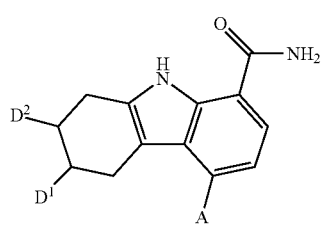

(Ia)

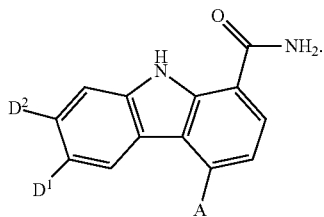

(Ib)

In another embodiment, there is provided a compound of formula I, wherein the compound of formula I is a compound of formula (I) is (Ic) or (Ib)

In another embodiment, there is provided a compound of formula I, wherein the compound of formula I is a compound of formula (I) is (Ic)

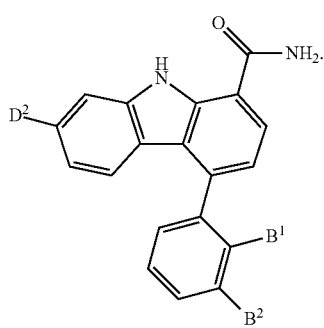

(Ic)

In another embodiment, there is provided a compound of formula I, wherein the compound of formula I is a compound of formula (I) is (Id)

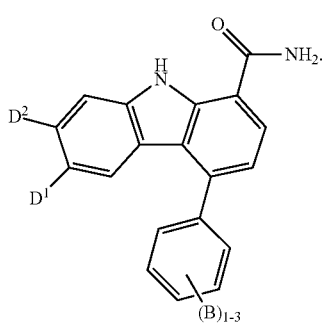

(Id)

In another embodiment, there is provided a compound of formula I, wherein $R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-1 $R^f$, $C_{1-6}$ haloalkyl, —$(CH_2)_r$-3-6 membered carbocycle, or —$(CH_2)_r$-5-7 membered heterocycle comprising carbon atoms and 1-4 heteroatoms selected from N, O, and $S(O)_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl substituted with 0-1 $R^f$, $C_{3-6}$ cycloalkyl, or $(CH_2)_r$-phenyl substituted with 0-1 $R^f$;

$R^d$ is hydrogen, F, Cl, Br, $OCF_3$, $CF_3$, CN, NO2, —$OR^e$, —$C(O)R^e$, —$NR^eR^e$, —$NR^eC(O)OR^e$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

$R^f$ is hydrogen, halo, or $NH_2$;

r is 0 or 1.

In another embodiment, there is provided a compound of formula I, wherein $R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-6 membered carbocycle phenyl, or —$(CH_2)_r$-5-7 membered heterocycle comprising carbon atoms and 1-4 heteroatoms selected from N, O, and $S(O)_p$, wherein the heterocycle is thiazolyl, pyridinyl, piperidinyl, morpholinyl, piperazinyl, pyrrolidinyl, pyrrolidin-one, $R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, $OCF_3$, $CF_3$, CN, NO2, —$OR^e$, —$C(O)R^e$, —$NR^eR^e$, —$NR^eC(O)OR^e$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl.

In another embodiment, there is provided a compound of formula I, wherein the compound of formula (I) is (Ia) or (Ib)

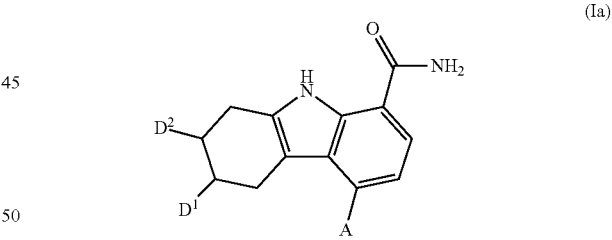

A is $C_{3-10}$ carbocycle substituted with 0-3 B, wherein the carbocycle is cyclohexyl or cyclohexenyl, $C_{6-10}$ mono- or bicyclic aryl substituted with 0-3-B, wherein the aryl group is phenyl or naphthyl; a 5-10 membered heterocyclyl containing 1-4 heteroatoms selected from N, O, and S, substituted with 0-3-B, wherein the heterocyclyl group is chromanyl, 3,4-dihydro-2H-benzo[e][1,3]oxazin-2-one, pyrrolidinyl or piperidinyl; or a 5-10 membered heteroaryl containing 1-4 heteroatoms selected from N, O, and S, substituted with 0-3-B, wherein the heteroaryl group is pyridinyl, quinolinyl, isoquinolinyl, indolyl, indazolyl, benzimidazolyl, furanyl, benzofuranyl, dibenzofuranyl, imidazolyl, pyrazolyl or thiazolyl;

B is $R^1$, halogen, —C(=O)O—$R^1$, —S(=O)$_2$—$R^1$, —NR$^{11}$C(=O)—$R^1$, —NR$^{11}$C(=O)NR$^{11}$—$R^1$, —NR$^{11}$S(=O)$_2$—$R^1$, N(S(=O)$_2$—$R^1$)$_2$, or —NR$^{11}$—$R^1$;

$R^1$ is hydrogen, trifluoromethyl, $C_{1-4}$ alkyl substituted with 0-1 $R^{1a}$, phenyl substituted with 0-3 $R^{1a}$, a 5-10 membered heteroaryl containing 1-4 heteroatoms selected from N, O, and S, substituted with 0-3 $R^{1a}$, wherein the heteroaryl is pyridyl or thiazolyl;

One of $D^1$ and $D^2$ is D and the other is hydrogen;

D is $R^2$, —C(=O)—$R^2$, —OR$^2$, —C(=O)NR$^{11}R^2$, NR$^{11}$C(=O)R$^2$, NR$^{11}$C(=O)NR$^{11}$—$R^2$, NR$^{11}$S(=O)$_2$—$R^2$, or —NR$^{11}$—$R^2$;

$R^2$ is hydrogen, $C_{2-6}$ alkyl substituted with 0-3 $R^{2a}$, a 5-10 membered heterocyclyl containing 1-4 heteroatoms selected from N, O, and S, substituted with 0-3 $R^{2a}$ where the heterocyclyl is tetrazolyl, pyrrolidinyl, piperidinyl, piperazinyl or morpholinyl;

$R^{2a}$ is $C_{1-4}$ alkyl, wherein the alkyl is methyl, ethyl, propyl, i-propyl, butyl, and t-butyl, substituted with 0-1 $R^a$.

In another embodiment, there is provided a compound of formula I, wherein the compound of formula (I) is a compound of formula (Ic):

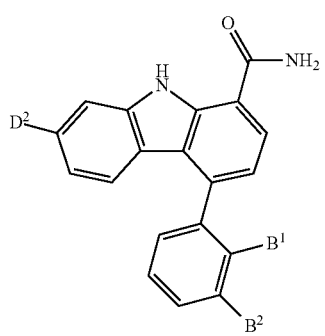

(Ic)

or a salt thereof, wherein $B^1$ is methyl or fluorine;
$B^2$ is $R^{1b}$, —NR$^{11}$C(=O)—$R^{1c}$, —NR$^{11}$C(=O)NR$^{11}$—$R^{1d}$, or —NR$^{11}$—$R^{1e}$;
$R^{1b}$ is

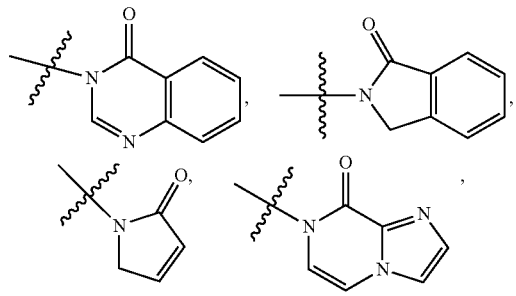

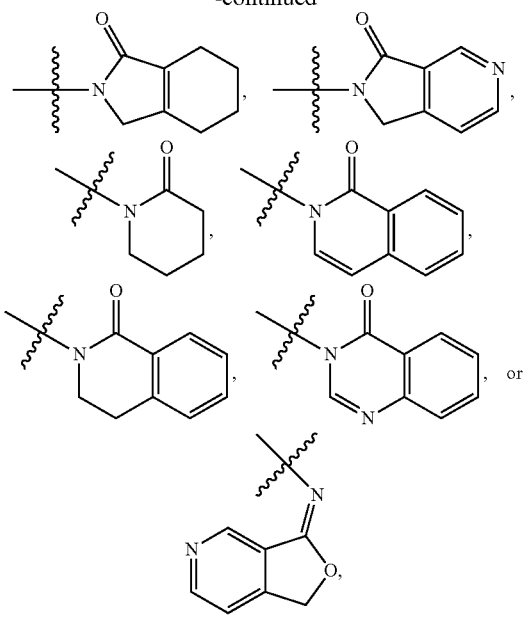

any of which are substituted with 0-3 $R^{1a}$;

$R^{1c}$ is $C_{1-6}$ alkyl, phenyl substituted with 0-2 $R^a$, cyclopropyl, CH$_2$-tetrazolyl, or pyridyl, thiazolyl, imidazolyl, benzimidazolyl, pyrimidinyl, any of which are substituted with 0-2 $R^a$;

$R^{1d}$ is thiazolyl substituted with 0-1 $R^{1a}$;

$R^{1e}$ is quinazolinyl substituted with 0-1 $R^{1a}$;

$R^{1a}$ is selected from hydrogen, halo, CN, methyl, ethyl, CF$_3$, OH, O-methyl, CO$_2$CH$_3$, N(CH$_3$)$_2$, NC(O)CH$_3$, $D^2$ is —$R^2$, —(C(R$^{11}$)$_2$)$_r$—$R^2$, —OR$^2$, —C(=O)—$R^2$, —C(=O)NR$^{11}$—$R^2$, —NR$^{11}$C(=O)—$R^2$, —NR$^{11}$C(=O)NR$^{11}$—$R^2$, —NR$^{11}$—$R^2$,— or —OC(=O)—$R^2$;

provided that $D^2$ is not hydrogen;

$R^2$ is hydrogen, $C_{1-6}$ alkyl substituted with 0-3 $R^{2a}$, $C_{3-10}$ cyclopropyl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from piperazinyl, pyrrolidinyl, tetrahydrofuranyl, morpholinyl, dioxolanyl, piperidinyl, oxazolidinyl (oxazolidin-one), imidazolidinyl (imidazolidin-one),

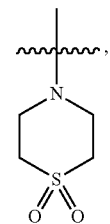

a 5-10 membered heteroaryl containing 1-4 heteroatoms selected from N, O, and S, substituted with 0-3 $R^{2a}$, wherein the heteroaryl is selected from pyridinyl, imidazolyl, pyrazinyl, pyrimidinyl, tetrazolyl, thiadiazolyl;

$R^{2a}$ is hydrogen, —(CH$_2$)$_r$OR$^b$, —(CH$_2$)$_r$OC(O)R$^b$, —(CH$_2$)$_r$NR$^{11}R^{11}$, —NR$^b$C(O)NR$^{11}R^{11}$, —NR$^b$S(O)$_p$R$^c$, $C_{1-6}$ alkyl substituted with 0-2 $R^a$, or —(CH$_2$)$_r$-5-7 membered heterocycle comprising carbon atoms and 1-4 heteroatoms selected from N, O, and S(O)$_p$ substituted with 0-2 $R^a$, wherein the heterocycle is selected from pyridinyl, pyrrolidinyl, pyrrolidinonyl, morpholinyl, imidazolyl, piperidinyl;

$R^{11}$ is hydrogen or $C_{1-4}$ alkyl substituted with 0-1 $R^f$;

$R^a$ is hydrogen, $—OR^b$, $—NR^{11}R^{11}$, or $—(CH_2)_r$-5-7 membered heterocycle comprising carbon atoms and 1-4 heteroatoms selected from N, O, and $S(O)_p$, wherein the heterocycle is imidazolyl or morpholinyl;

$R^b$ is hydrogen, or $C_{1-6}$ alkyl substituted with 0-2 $R^d$;

$R^c$ is $C_{1-6}$ alkyl;

$R^d$ is hydrogen, $—OR^e$, or $—NR^eR^e$;

$R^e$ is hydrogen, or $C_{1-6}$ alkyl;

$R^f$ is hydrogen, $NH_2$, OH, or $OCH_3$.

In another embodiment, there is provided a compound of formula I, wherein $D^1$ is hydrogen and $D^2$ is D.

In another embodiment, there is provided a compound of formula I, wherein $D^2$ is hydrogen and $D^1$ is D.

In another embodiment, there is provided a compound of formula I, wherein the compound of formula I is a compound of formula (Ia). In another embodiment, the compound of formula (I) is a compound of formula (Ib). In another embodiment, the compound of formula (I) is a compound of formula (Ic).

In another embodiment, A is halo, $C_{3-10}$ carbocycle substituted with 0-3 B $C_{6-10}$ mono- or bicyclic aryl substituted with 0-3-B, a 5-14 membered heterocyclyl containing 1-4 heteroatoms selected from N, O, and S, substituted with 0-3-B, a 5-10 membered heteroaryl containing 1-4 heteroatoms selected from N, O, and S, substituted with 0-3-B.

In another embodiment, there is provided a compound of formula I, wherein A is $C_6$ carbocycle substituted with 0-3 B, $C_{6-10}$ mono- or bicyclic aryl substituted with 0-3-B, a 5-14 membered heterocyclyl containing 1-4 heteroatoms selected from N, O, and S, substituted with 0-3-B, wherein the heterocyclyl is, chromanyl, 3,4-dihydro-2H-benzo[e][1,3]oxazin-2-one, pyrrolidinyl, piperidinyl, morpholinyl or piperazinyl; a 5-10 membered heteroaryl containing 1-4 heteroatoms selected from N, O, and S, substituted with 0-3-B, wherein the heteroaryl is pyridinyl, quinolinyl, isoquinolinyl, indolyl, indazolyl, benzimidazolyl, furanyl, benzofuranyl, dibenzofuranyl, imidazolyl, pyrazolyl, or thiazolyl.

In another embodiment, there is provided a compound of formula I, wherein A is $C_{3-10}$ carbocycle substituted with 0-3 B, wherein the carbocycle is cyclohexyl or cyclohexenyl, $C_{6-10}$ mono- or bicyclic aryl substituted with 0-3-B, wherein the aryl group is phenyl or naphthyl; a 5-10 membered heterocyclyl containing 1-4 heteroatoms selected from N, O, and S, substituted with 0-3-B, wherein the heterocyclyl group is chromanyl, 3,4-dihydro-2H-benzo[e][1,3]oxazin-2-one, pyrrolidinyl or piperidinyl; or a 5-10 membered heteroaryl containing 1-4 heteroatoms selected from N, O, and S, substituted with 0-3-B, wherein the heteroaryl group is pyridinyl, quinolinyl, isoquinolinyl, indolyl, indazolyl, benzimidazolyl, furanyl, benzofuranyl, dibenzofuranyl, imidazolyl, pyrazolyl or thiazolyl.

In another embodiment, there is provided a compound of formula I, wherein B is $R^1$, halogen, cyano, nitro, $—O—R^1$, $—C(=O)—R^1$, $—C(=O)O—R^1$, $—C(=O)NR^{11}—R^1$, $—S(=O)_2—R^1$, $—NR^{11}C(=O)—R^1$, $—NR^{11}C(=O)NR^{11}—R^1$, $—NR^{11}S(=O)_2—R^1$, $—N(S(=O)_2—R^1)_2$, or $—NR^{11}—R^1$.

In another embodiment, there is provided a compound of formula I, wherein B is $R^1$, halogen, $—C(=O)O—R^1$, $—S(=O)_2—R^1$, $—NR^{11}C(=O)—R^1$, $—NR^{11}C(=O)NR^{11}—R^1$, $—NR^{11}S(=O)_2—R^1$, $N(S(=O)_2—R^1)_2$, or $—NR^{11}—R^1$;

In another embodiment, there is provided a compound of formula (Ic), wherein $B^1$ is methyl or fluorine;

$B^2$ is $R^{1b}$, $—NR^{11}C(=O)—R^{1c}$, $—NR^{11}C(=O)NR^{11}—R^{1d}$, or $—NR^{11}—R^{1e}$;

$R^{1b}$ is

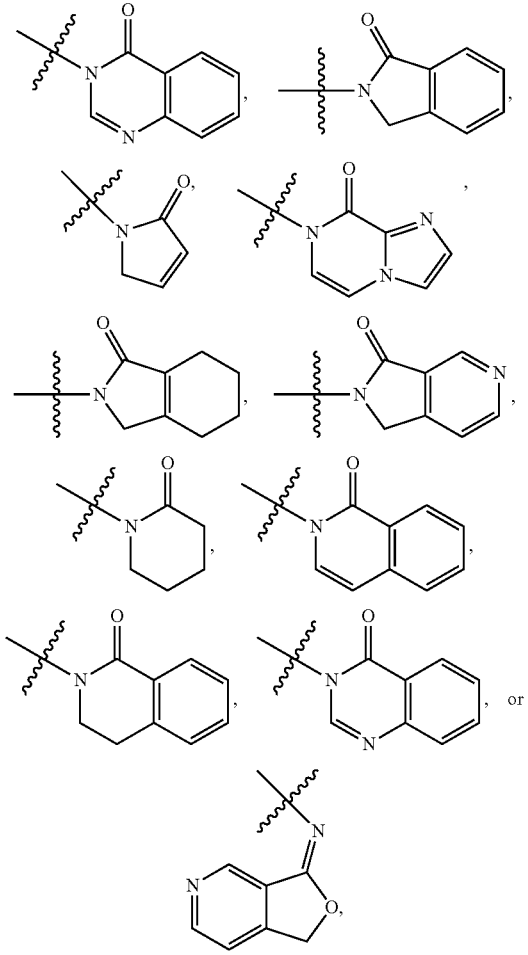

any of which are substituted with 0-3 $R^{1a}$.

In another embodiment, there is provided a compound of formula I, wherein $R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is 4,5,6,7-tetrahydrobenzo[d]thiazolyl, isindolinyl, imidazo[1,2-a]pyrazin-8(7H)-one, 1H-pyrrolo[3,4-c]pyridin-3(2H)-one, 1,3-dihydrofuro[3,4-c]pyridine, phthalazine, isoquinolin-1(2H)-one, isoindolinyl, isoindoline-1,3-dione, quinazolin-4(3H)-one,

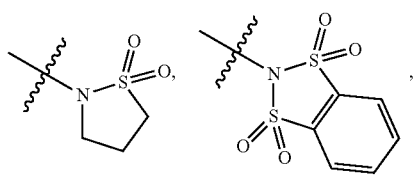

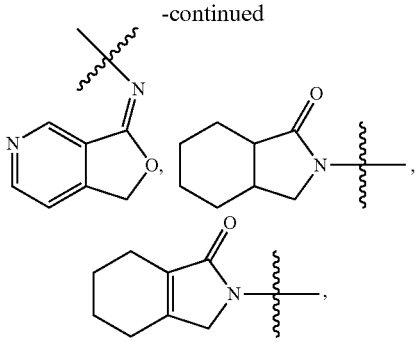

pyrrolidinyl, piperidinyl, morpholinyl or piperazinyl; a 5-10 membered heteroaryl containing 1-4 heteroatoms selected from N, O, and S, substituted with 0-3 $R^{1a}$ wherein the heteroaryl is indazolyl, imidazolyl, pyrimidinyl, benzimidazolyl, benzothiazolyl, quinolinyl, quinazolinyl, quinazolin-4 (3H)-one pyridinyl or thiazolyl.

In another embodiment, there is provided a compound of formula I, wherein $R^1$ is hydrogen, trifluoromethyl, $C_{1-4}$ alkyl substituted with 0-1 $R^{1a}$, phenyl substituted with 0-3 $R^{1a}$, a 5-10 membered heteroaryl containing 1-4 heteroatoms selected from N, O, and S, substituted with 0-3 $R^{1a}$, wherein the heteroaryl is pyridyl or thiazolyl.

In another embodiment, there is provided a compound of formula I, wherein $R^2$ is hydrogen, $C_{1-6}$ alkyl substituted with 0-3 $R^{2a}$, ethenyl, $C_{3-10}$ cycloalkyl substituted with 0-3 $R^{2a}$— $C_{6-10}$ aryl substituted with 0-3 $R^{2a}$, a 5-10 membered heterocyclyl containing 1-4 heteroatoms selected from N, O, and S, substituted with 0-3 $R^{2a}$, wherein the heterocyclyl is pyrrolidinyl, piperidinyl, morpholinyl or piperazinyl, tetrahydropyranyl, oxazolidinyl (oxazolidin-one), imidazolidinyl (imidazolidin-one), dioxalanyl, or

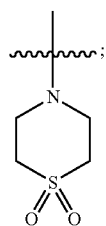 [SMILES: *N1CCS(=O)(=O)CC1]

a 5-10 membered heteroaryl containing 1-4 heteroatoms selected from N, O, and S, substituted with 0-3 $R^{2a}$, wherein the heteroaryl is pyrimidinyl, imidazolyl, pyrazinyl, thiadiazaolyl, pyridinyl, quinolinyl, isoquinolinyl, or thiazolyl.

In another embodiment, there is provided a compound of formula I, wherein $R^2$ is hydrogen, $C_{2-6}$ alkyl substituted with 0-3 $R^{2a}$, a 5-10 membered heterocyclyl containing 1-4 heteroatoms selected from N, O, and S, substituted with 0-3 $R^{2a}$ where the heterocyclyl is tetrazolyl, pyrrolidinyl, piperidinyl, piperazinyl or morpholinyl.

In another embodiment, there is provided a compound of formula I, wherein $R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from piperazinyl, pyrrolidinyl, tetrahydrofuranyl, morpholinyl, dioxolanyl, piperidinyl, oxazolidinyl (oxazolidin-one), imidazolidinyl (imidazolidin-one)

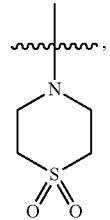

a 5-10 membered heteroaryl containing 1-4 heteroatoms selected from N, O, and S, substituted with 0-3 $R^{2a}$, wherein the heteroaryl is selected from pyridinyl, imidazolyl, pyrazinyl, thiadiazolyl.

In another embodiment, there is provided a compound of formula (I) wherein $R^2$ is hydrogen, $C_{1-6}$ alkyl substituted with 0-3 $R^{2a}$, $C_{3-10}$ cyclopropyl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from piperazinyl, pyrrolidinyl, tetrahydrofuranyl, morpholinyl, dioxolanyl, piperidinyl, oxazolidinyl (oxazolidin-one), imidazolidinyl (imidazolidin-one),

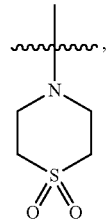

a 5-10 membered heteroaryl containing 1-4 heteroatoms selected from N, O, and S, substituted with 0-3 $R^{2a}$, wherein the heteroaryl is selected from pyridinyl, imidazolyl, pyrazinyl, pyrimidinyl, tetrazolyl, thiadiazolyl.

In another embodiment, $R^{2a}$ is hydrogen, —$(CH_2)_rOR^b$, —$(CH_2)_rOC(O)R^b$, —$(CH_2)_rNR^{11}R^{11}$, —$NR^bC(O)NR^{11}R^{11}$, —$NR^bS(O)_pR^c$, C alkyl substituted with 0-2 $R^a$, or —$(CH_2)_r$-5-7 membered heterocycle comprising carbon atoms and 1-4 heteroatoms selected from N, O, and $S(O)_p$ substituted with 0-2 $R^a$, wherein the heterocycle is selected from pyridinyl, pyrrolidinyl, pyrrolidinonyl, morpholinyl, imidazolyl, piperidinyl.

In another embodiment, one of $D^1$ and $D^2$ is D and the other is H; provided that D is not hydrogen.

In another embodiment, D is a —$R^2$, —$(CH_2)_r$—$R^2$, —O—$R^2$, —C(=O)—$R^2$, —C(=O)O—$R^2$, —C(=O)$NR^{11}$—$R^2$, —S(=O)$_2$—$R^2$, —$NR^{11}$C(=O)—$R^2$, —$NR^{11}$C(=O)$NR^{11}$—$R^2$, —$NR^{11}$C(=O)O—$R^2$, —$NR^{11}$S(=O)$_2$—$R^2$, or —$NR^{11}$—$R^2$.

In another embodiment, D is a —$R^2$, —$(CH_2)_r$—$R^2$, —O—$R^2$, —C(=O)—$R^2$, —C(=O)O—$R^2$, —C(=O)$NR^{11}$—$R^2$, —S(=O)$_2$—$R^2$, —S(=O)—$R^2$, —$NR^{11}$C(=O)—$R^2$, —$NR^{11}$C(=O)$NR^{11}$—$R^2$, —$NR^{11}$C(=O)O—$R^2$, —$NR^{11}$S(=O)$_2$—$R^2$, or —$NR^{11}$—$R^2$.

In another embodiment, D is $R^2$, —C(=O)—$R^2$, —$OR^2$, —C(=O)$NR^{11}R^2$, $NR^{11}$C(=O)$R^2$, $NR^{11}$C(=O)$NR^{11}$—$R^2$, $NR^{11}$S(=O)$_2$—$R^2$, or —$NR^{11}$—$R^2$.

In another embodiment, $D^2$ is —$R^2$, —$(C(R^{11})_2)_r$—$R^2$, —$OR^2$, —$C(=O)$—$R^2$, —$C(=O)NR^{11}$—$R^2$, —$NR^{11}C(=O)$—$R^2$, —$NR^{11}C(=O)NR^{11}$—$R^2$, —$NR^{11}$—$R^2$,— or —$OC(=O)$—$R^2$.

In another embodiment, $D^2$ is —$R^2$, —$(C(R^{11})_2)_r$—$R^2$, —$C(=O)$—$R^2$, —$C(=O)NR^{11}$—$R^2$, —$NR^{11}C(=O)$—$R^2$, —$NR^{11}C(=O)NR^{11}$—$R^2$, —$NR^{11}$—$R^2$,— or —$OC(=O)$—$R^2$.

In another embodiment, $D^2$ is —$R^2$, —$(C(R^{11})_2)_r$—$R^2$, —$C(=O)$—$R^2$, —$C(=O)NR^{11}$—$R^2$, —$NR^{11}C(=O)$—$R^2$, —$NR^{11}C(=O)NR^{11}$—$R^2$, —$NR^{11}$—$R^2$, —$S(=O)$—$R^2$,— or —$OC(=O)$—$R^2$.

In another embodiment, there is provided a pharmaceutical composition comprising one or more compounds of formula I and a pharmaceutically acceptable carrier or diluent.

The present invention is also directed to pharmaceutical compositions useful in treating diseases associated with kinase modulation, including modulation (especially inhibition) of Btk and other Tec family kinases such as Itk, comprising compounds of formula (I), or pharmaceutically-acceptable salts thereof, and pharmaceutically-acceptable carriers or diluents.

The invention further relates to methods of treating diseases associated with the kinase modulation, including the modulation of Btk and other Tec family kinases such as Itk, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula I, wherein the disease is systemic lupus erythematosus (SLE), rheumatoid arthritis, multiple sclerosis (MS), or transplant rejection.

The present invention also provides a method of treating a condition associated with a proliferative disease, an allergic disease, an autoimmune disease or an inflammatory disease, comprising administering to a patient in need of such treatment a therapeutically-effective amount of a compound of formula I.

The present invention also provides a method of treating a condition comprising administering to a patient in need of such treatment a therapeutically-effective amount of a compound of formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies, pemphigus vulgaris and asthma.

The present invention also provides a method for treating a rheumatoid arthritis, comprising administering to a patient in need of such treatment a therapeutically-effective amount of a compound of formula I.

The present invention also provides a method of treating a B-cell mediated disease, comprising administering to a patient in need of such treatment a therapeutically-effective amount of a compound of formula I The present invention also provides a method of treating a B-cell mediated disease, comprising administering to a patient in need of such treatment a therapeutically-effective amount of a compound of formula I, wherein the B-cell mediated disease is a disease modulated by a kinase selected from Btk, Bmx, Itk, Txk and Tec.

The present invention also provides a method of treating diseases, comprising administering to a patient in need of such treatment a therapeutically-effective amount of a compound of formula I, or pharmaceutically acceptable salt thereof, in combination with other therapeutic agents.

The present invention also provides the compounds of the present invention or stereoisomers, tautomers, pharmaceutically acceptable salts, solvates, or prodrugs thereof, for use in therapy.

In another embodiment, compounds of formula I are selected from exemplified examples or combinations of exemplified examples or other embodiments herein.

In another embodiment are compounds having an $IC_{50}$<10 μM in the Btk assay described below.

In another embodiment are compounds having an $IC_{50}$<=5 nM in the Btk assay described below.

The present invention also provides the use of the compounds of the present invention or stereoisomers, tautomers, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

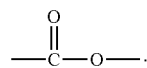

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., ═O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C═C, C═N, or N═N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

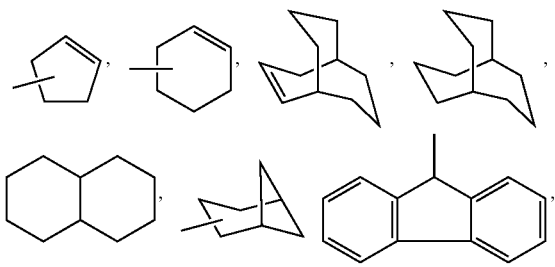

-continued

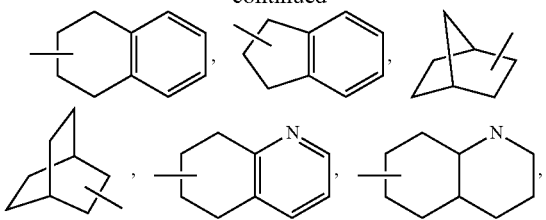

and the like, which optionally may be substituted at any available atoms of the ring(s). Preferred cycloalkyl groups include cyclopropyl, cyclopentyl, cyclohexyl, and

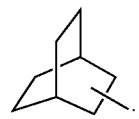

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

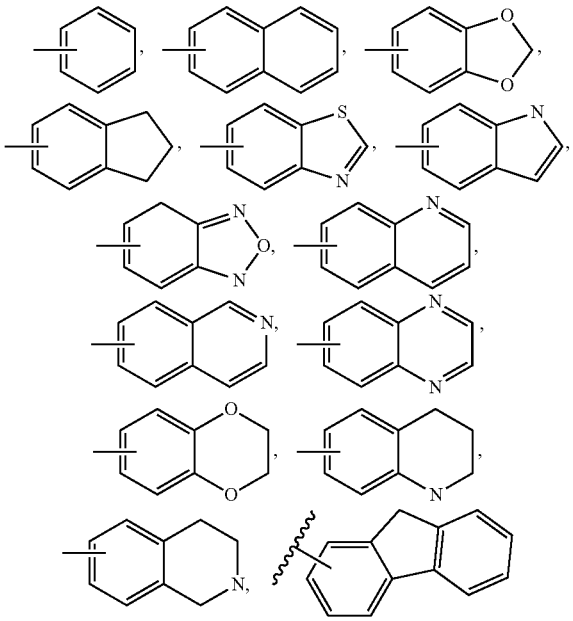

(fluorenyl) and the like, which optionally may be substituted at any available carbon or nitrogen atom. A preferred aryl group is optionally-substituted phenyl.

The terms "heterocycloalkyl", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

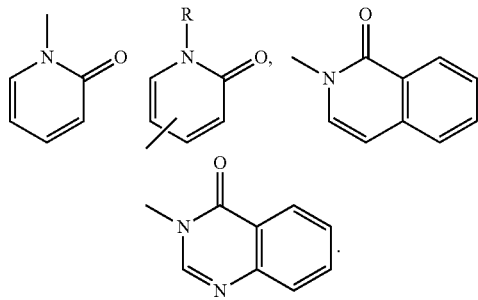

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula (I), preferred heteroaryl groups include

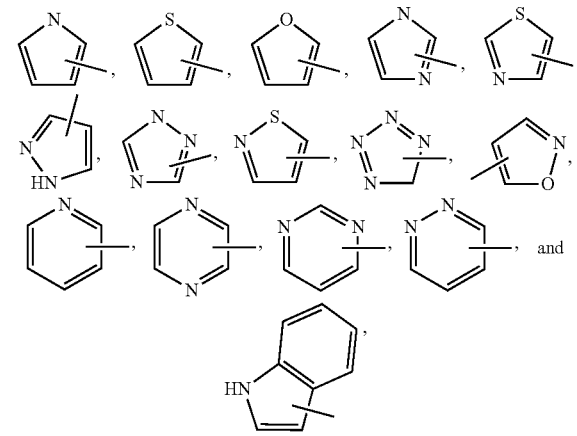

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers, It should further be understood that solvates (e.g., hydrates) of the compounds of Formula (I) are also with the scope of the present invention. Methods of solvation are generally known in the art.

Utility

The compounds of the invention modulate kinase activity, including the modulation of Btk. Other types of kinase activity that may be modulated by the compounds of the instant invention include, but are not limited to, the Tec family of compounds, such as Bmx, Btk, Itk, Txk and Tec, and mutants thereof.

Accordingly, compounds of formula (I) have utility in treating conditions associated with the modulation of kinase activity, and particularly the selective inhibition of Btk activity or the inhibition of Btk and other Tec family kinases such as Itk. Such conditions include B-cell mediated diseases in which cytokine levels are modulated as a consequence of intracellular signaling. Moreover, the compounds of formula (I) have advantageous selectivity for Btk activity and other Tec family kinases such as Itk over Mk2 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of Btk or Btk and other Tec family kinase such as Itk, compounds of Formula (I) are useful in treating cytokine-associated conditions including, but not limited to, inflammatory diseases such as Crohn's and ulcerative colitis, asthma, graft versus host disease, chronic obstructive pumonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the kinse inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit Btk and other Tec family kinases and/or treat diseases.

The methods of treating Btk kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit Btk and/or treat diseases associated with Btk.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses)(AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Biological Assays

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM MgCl$_2$, 0.015% Brij35 and 4 mM DTT in 1.6% DMSO), with a final volume of 30 µL. After incubating at room temperature for 60 min, the reaction was terminated by adding 45 µl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required inhibiting 50% of kinase activity (IC$_{50}$). Compounds were dissolved at 10 mM in dimethylsulfoxide (DMSO) and evaluated at eleven concentrations.

Using this assay, the IC$_{50}$ values of the following compounds were determined. See Table 1.

TABLE 1

| Example | IC$_{50}$ for Inhibition of Btk, µM |
| --- | --- |
| 1-3 | 0.49 |
| 2-2 | 1.3 |
| 2-12 | 0.016 |
| 2-13 | 0.015 |
| 2-16 | 0.016 |
| 2-18 | 0.016 |
| 2-24 | 0.80 |
| 2-25 | 3.1 |
| 2-35 | 0.016 |
| 2-43 | 0.52 |
| 3-9 | 0.017 |
| 3-18 | 2.7 |
| 3-19 | 1.8 |
| 3-39 | 0.016 |
| 3-45 | 0.016 |
| 3-48 | 0.39 |
| 3-49 | 0.69 |
| 3-69 | 0.015 |
| 3-75 | 0.92 |
| 3-83 | 0.94 |
| 3-101 | 0.018 |
| 3-114 | 0.54 |
| 3-116 | 1.6 |
| 3-122 | 0.018 |
| 3-124 | 1.8 |
| 3-130 | 0.002 |
| 4-3 | 0.39 |
| 5-2 | 0.016 |
| 5-7 | 0.018 |
| 5-9 | 0.0019 |
| 5-16 | 0.018 |
| 5-19 | 0.017 |
| 5-42 | 0.015 |
| 5-44 | 0.016 |
| 5-58 | 0.0022 |
| 5-62 | 0.017 |
| 5-69 | 0.002 |
| 5-73 | 0.018 |
| 5-86 | 0.91 |
| 8-3 | 0.016 |
| 10-2 | 4.5 |
| 10-3 | 4.9 |
| 10-4 | 0.017 |
| 11-1 | 0.015 |
| 12-1 | 0.018 |
| 17-1 | 1.1 |
| 19-1 | 0.017 |
| 20-1 | 0.51 |
| 24-1 | 0.017 |
| 24-17 | 0.015 |
| 24-33 | 0.47 |
| 24-34 | 0.41 |
| 31-2 | 0.70 |

TABLE 1-continued

| Example | IC$_{50}$ for Inhibition of Btk, μM |
|---|---|
| 31-3 | 1.5 |
| 33-1 | 0.0019 |
| 34-2 | 0.0020 |
| 38-2 | 0.0021 |
| 38-3 | 0.0014 |
| 39-4 | 0.0017 |
| 41-1 | 0.016 |
| 47-2 | 4.2 |
| 48-2 | 1.7 |
| 50-3 | 1.3 |
| 51-1 | 0.40 |
| 51-4 | 1.6 |
| 52-1 | 0.52 |
| 52-2 | 0.52 |
| 54-7 | 0.83 |
| 57-3 | 0.0021 |
| 57-13 | 0.015 |
| 57-16 | 0.0021 |
| 57-18 | 0.0022 |
| 57-20 | 0.015 |
| 57-37 | 0.0018 |
| 60-1 | 0.018 |
| 61-2 | 0.0022 |
| 66-2 | 0.016 |
| 66-16 | 0.0020 |
| 66-34 | 0.016 |
| 66-37 | 0.015 |
| 67-1 | 0.0022 |
| 70-2 | 0.0022 |
| 70-3 | 0.0023 |
| 70-5 | 0.0016 |
| 70-6 | 0.00080 |
| 70-9 | 0.0015 |
| 70-10 | 0.0010 |
| 70-11 | 0.0014 |
| 70-12 | 0.0013 |
| 70-13 | 0.00070 |
| 70-14 | 0.00090 |
| 73-1 | 0.54 |
| 75-3 | 0.0011 |
| 76-2 | 0.0013 |
| 76-10 | 0.018 |
| 76-15 | 0.0024 |
| 76-18 | 0.0018 |
| 76-25 | 0.0029 |
| 76-32 | 0.0032 |
| 76-41 | 0.018 |
| 76-44 | 0.018 |
| 76-51 | 0.0014 |
| 77-2 | 0.0019 |
| 78-2 | 0.0016 |
| 79-2 | 0.0169 |
| 79-3 | 0.015 |
| 79-4 | 0.016 |
| 80-1 | 0.0019 |
| 81-3 | 0.0019 |
| 81-15 | 0.0039 |
| 81-20 | 0.0022 |
| 82-1 | 0.0019 |
| 83-3 | 0.0014 |
| 83-4 | 0.0011 |

Mouse Splenic B Cell Proliferation Assay

Spleens from Balb/c mice (<12 weeks old) were mashed through screens and red blood cells were removed from splenocytes with RBC lysing buffer (Sigma-Aldrich Chemical Co, St. Louis, Mo.). T cells were depleted by incubation on nylon wool columns (Wako, Richmond, Va.). Resulting splenic B cells prepared this way were routinely >90% CD19$^+$ as measured by FACS analysis. B cells (1×10$^5$ cells per well) were added to serial dilutions of compounds in triplicate in 96-well flat-bottom plates in RPMI 1640 (Invitrogen, Grand Island, N.Y.), supplemented with 10% heat-inactivated fetal calf serum (FCS, Summit Biotechnology, Fort Collins, Colo.), containing 1% L-glutamine (Invitrogen), 50 μg/ml gentamicin (Invitrogen) and 5×10$^{-5}$M β-mercaptoethanol (Sigma-Aldrich). Cells were stimulated with 10 μg/ml of Affinipure F(ab')$_2$ fragment goat anti-mouse IgG IgM (Jackson Immunoresearch, West Grove, Pa.). Cultures were incubated for 72 hours, and pulsed for the last 6 hours with one μCi/well of $^3$-[H]-thymidine (PerkinElmer, Boston, Mass.) prior to harvest on a Packard cell harvester (PerkinElmer), and counted by liquid scintillation on a Packard TopCount NXT (PerkinElmer). The most potent analogs were found to be active below 1 μM.

Human Tonsillar B Cell Proliferation Assay

Tonsils were excised from patients undergoing routine tonsillectomy. Tonsil tissue was minced, mashed through screens and mononuclear cells were isolated on ficoll density gradients (Lymphocyte Separation Media; Mediatech Inc., Herndon, Va.). T cells were depleted from mononuclear cells by rosetting with sheep red blood cells (SRBC, Colorado Serum Company; Denver, Colo.). Tonsillar B cells prepared by this method were routinely >95% CD19$^+$ as measured by FACS analysis. B cells (1×10$^5$ cells per well) were added to serial dilutions of compounds in triplicate in 96-well flat-bottom plates in RPMI 1640, (Invitrogen, Grand Island, N.Y.), supplemented with 10% heat-inactivated fetal calf serum (FCS, Summit Biotechnology, Fort Collins, Colo.), and containing antibiotic/antimycotic (Invitrogen, 1:100 dilution) and gentamicin (Invitrogen, 5 μg/ml). Cells were stimulated with 40 μg/ml AffinPure F(ab')2 Fragment Goat anti Human IgG+IgM (Jackson Immunoresearch, West Grove, Pa.) in a total volume of 0.2 ml. Cultures were incubated for 72 hours, and pulsed for the last 6 hours with one μCi/well of $^3$-[H]-thymidine (PerkinElmer, Boston, Mass.) prior to harvest on a Packard cell harvester (PerkinElmer), and counted by liquid scintillation on a Packard TopCount NXT (PerkinElmer).

Btk Phosphorylation Assay

Ramos cells (~6×10$^6$ cells/ml) were incubated in the presence of Btk inhibitors for 1 hr at 37° C. before being stimulated with anti-human IgM+IgG (F(ab')2 fragment, Jackson ImmunoResearch, catalog #109-006-127) at 50 μg/mL for exactly 2 min at 37° C. Cells were immediately fixed by adding an equal volume of pre-warmed BD PhosFlow Fix buffer I (BD Biosciences, catalog number 557870) to the cell suspension. After incubating at 37° C. for 10 minutes, the cells were washed once with 3 mL FACS washing buffer (1% FBS/PBS) and permeabilized by adding 0.5 mL of cold BD™ Phosflow Perm Buffer III (BD Biosciences, catalog number 558050) and incubating for 30 minutes on ice. The cells were washed an additional two times with 3 mL BD FACS washing buffer, re-suspended in 100 μL FACS washing buffer, stained with 20 μL Alexa647 anti-Btk (pY551) (BD Biosciences, catalog number 558134), incubated at room temperature for 30 minutes in the dark, and washed once with 3 ml of FACS washing buffer. The cells were re-suspended in 100 μL FACS wash buffer and analyzed using FACSCalibur (BD Biosciences). Median fluorescent intensity (MFI) on Alexa 647 (FL-4) data were collected and used for calculations of inhibition.

Ramos FLIPR Assay

Ramos RA1 B cells (ATCC CRL-1596) at a density of 2×10$^6$ cells/ml in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, RT, 5 minutes) and resuspended in RT RPMI minus phenol red with 50 mM HEPES and 10% FBS to a density of 1×10$^6$ cells/ml. 150 μl aliquots (150,000/well) were plated into 96 well poly-D-lysine coated assay plates (BD 35 4640) and briefly centrifuged (Beckmann GS-CKR 800 rpm, 5 minutes, without brake). 50 μl compound dilutions in 0.4% DMSO/RPMI minus phenol red+50 mM HEPES+

10% FBS were added to the wells and the plate was incubated at RT in the dark for 1 hour. Assay plate was briefly centrifuged as above prior to measuring calcium levels.

Using the FLIPR1 (Molecular devices), cells were stimulated by adding goat anti-human IgM (Invitrogen AHI0601) to 2.5 µg/mL. Changes in intracellular calcium concentrations were measured for 180 seconds and percent inhibition was determined relative to peak calcium levels seen in the presence of stimulation only. Biological activity of certain compounds as assessed using this assay is shown in Table 2.

TABLE 2

| Example | $IC_{50}$ for Inhibition of Ramos FLIPR assay, µM |
|---|---|
| 3-61 | 3.0 |
| 3-62 | 2.9 |
| 3-65 | 1.2 |
| 3-66 | 1.4 |
| 3-92 | 1.4 |
| 3-98 | 1.9 |
| 3-120 | 1.3 |
| 3-121 | 1.5 |
| 5-48 | 1.4 |
| 8-1 | 5.4 |
| 11-6 | 0.28 |
| 38-3 | 0.023 |
| 62-1 | 0.25 |
| 66-5 | 0.26 |
| 66-10 | 0.27 |
| 66-14 | 0.26 |
| 66-39 | 0.26 |
| 66-40 | 0.27 |
| 70-13 | 0.011 |
| 70-14 | 0.014 |
| 75-3 | 0.016 |
| 76-7 | 0.24 |
| 76-15 | 0.048 |
| 76-25 | 0.014 |
| 76-26 | 0.018 |
| 76-32 | 0.038 |
| 76-43 | 0.26 |
| 76-49 | 0.014 |
| 76-51 | 0.017 |
| 80-2 | 0.016 |
| 81-1 | 0.015 |
| 81-7 | 0.26 |
| 81-14 | 0.021 |
| 81-15 | 0.042 |
| 82-1 | 0.017 |

NFAT-bla RA1 Reporter Assay

Ramos B cells containing a stable integration of a beta-lactamase reporter gene under the control of an NFAT response element (NFAT-bla RA1, Invitrogen, K1434) at a density of 100×103 cells/well were incubated with test compounds at 37° C. for 30 min prior to stimulation with F(ab')2 anti-human IgM (Jackson ImmunoResearch, 109-006-129) at 2.5 µg/ml for 4.5 hrs at 37° C. After stimulation, Live-BLAzer™-FRET B/G ubstrate (CCF2/AM, or CCF4/AM, Invitrogen) was added to each well and incubated for 90 min at room temperature in the dark. Assay plates were read on an LJL Analyst, with raw emission values subtracted from a media-only blank containing substrate in assay media (no cells). The ratios of 460 nm/530 nm emission (405 nm excitation) were used to calculate the amount of stimulation.

KLH Antigen Challenge and Antibody Measurement

Female BALB/c mice (6-8 weeks old) were immunized intraperitoneally (IP) with 250 µg keyhole limit hemocyanin (KLH) (Pierce, Rockford, Ill.) in phosphate-buffered saline (PBS). Mice in appropriate groups were dosed as indicated. Blood was collected 14 days post-immunization, serum was separated and analyzed for anti-KLH IgG titers by ELISA. Briefly, 96 well plates were coated with KLH in PBS, blocked, and serial dilutions of test serum samples were added. Captured anti-KLH antibodies were detected using horseradish peroxidase-conjugated antibody specific for mouse IgG (Southern Biotechnology Associates, Birmingham, Ala.) and the TMB peroxidase substrate system (Kirkegaard and Perry Laboratories, Gaithersburg, Md.). Optical densities of developed plates were quantitated in a SpectraMax Plus ELISA plate reader (Molecular Devices, Sunnyvale, Calif.). When administered twice daily, the compound of Example 76-15 inhibited the anti-KLH IgG response by 29% and 56% at 10 mg/kg and 30 mg/kg, respectively.

Methods Of Preparation

Compounds of Formula (I) can be prepared by the route outlined in Scheme 1. A 2-hydrazinobenzoic acid 1-1 (where X is either the substituent A of Formula (I) or a suitable precursor to such a substituent, such as bromo) can react with a suitable cyclohexanone 1-2 (where Y represents either the substituent(s) $D^1$ and/or $D^2$ of Formula (I) or a precursor to such substituent(s)) in an appropriate solvent with an appropriate catalyst, for example ethanol with hydrochloric acid, or acetic acid (in which case the solvent also can serve as the catalyst), at a suitable temperature (for example, the reflux temperature of the solvent) to provide the corresponding tetrahydrocarbazole derivative 1-3 (where the dotted lines represent single bonds). This reaction is commonly known as the Fischer indole synthesis, and is well known in the chemical literature (for example, see J. Kamata et al., *Chem. Pharm. Bull.* 2004, 52, 1071). Alternatively, the Fischer indole synthesis can be carried out in two consecutive steps: 1-1 can react with 1-2 under suitable conditions (such as in an appropriate solvent such as ethanol or water, optionally with a suitable catalyst such as p-toluenesulfonic acid) to form the hydrazone 1-4, which can then be reacted further under suitable conditions (for example, ethanol with hydrochloric acid, acetic acid with zinc chloride, or trifluoroacetic acid) to form 1-3 (for example, see J. Lancelot et al, *Chem. Pharm. Bull.* 1983, 31, 2652; X. Li and R. Vince, *Bioorg. Med. Chem.* 2006, 14, 2942; or G. Romeo et al., *Bioorg. Med. Chem.* 2006, 14, 5211).

Figure 1.

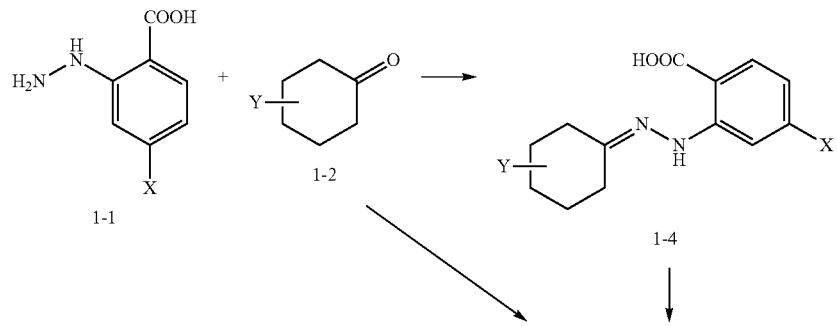

-continued

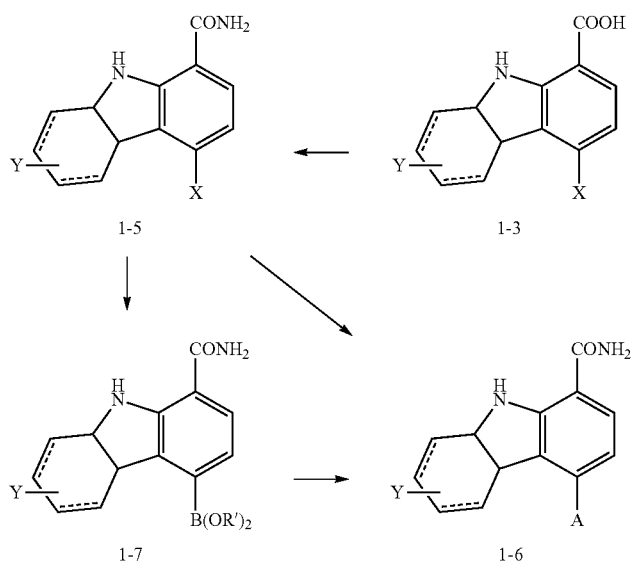

The starting materials shown in Figure 1 can be prepared using methods known in the chemical literature. For example, compound 1-1 can be prepared from the corresponding anthranilic acid (see, for example, L. Street et al., *J. Med. Chem.* 1993, 36, 1529). As another example, compound 1-2 where Y is ethoxycarbonyl attached at the 3-position can be prepared from ethyl 3-hydroxybenzoate (see, for example, J. Hirsch et al., *J. Org. Chem.* 1986, 51, 2218.)

If desired, the tetrahydrocarbazole 1-3 (where the dotted lines represent single bonds) can be converted to the carbazole 1-3 (where the dotted lines represent double bonds) by treatment under suitable oxidizing conditions, for example by treatment with 2,3-dichloro-5,6-dicyanobenzoquinone in a suitable solvent such as toluene, at a suitable temperature (for example, see J. Kamata et al., *Chem. Pharm. Bull.* 2004, 52, 1071). This conversion of a tetrahydrocarbazole to a carbazole may also be performed in a different sequence with the other synthetic transformations outlined in Figure 1, for example at the stage of structure 1-5 or 1-6.

The carboxylic acid 1-3 can be converted to the carboxamide 1-5 using methods well known in the chemical literature, for example by conversion of 1-3 to the acid chloride by treatment with oxalyl chloride or sulfonyl chloride, followed by treatment with ammonia; or by treatment with ammonia in the presence of a coupling reagent such as carbodiimide or N-(3-dimethylaminopropyl)-N'-ethylcarbodiimide hydrochloride, and 1-hydroxybenzotriazole or 1-hydroxy-7-azabenzotriazole.

In the case where X is a suitable precursor to A, such as bromo, 1-5 can be converted to 1-6 using methods known in the literature. For example, 1-5 (X=Br) can be heated with piperidine to provide 1-6 (A=1-piperidyl). Also, 1-5 (X=Br) can be converted to 1-6 (A=for example, an aromatic group such as optionally substituted phenyl, naphthyl, pyridyl, quinolyl, isoquinolyl, or the like) by treatment with a suitable arylboronic acid or arylboronic acid ester in the presence of a suitable catalyst such as (1,1'-bis(diphenylphosphino)ferrocene)dichloropalladium or tetrakis(triphenylphosphine) palladium, with a suitable base such as potassium carbonate or tripotassium phosphate, in a suitable solvent or mixture or solvents, such as toluene, 1,4-dioxane, or toluene-ethanol-water. This reaction, commonly known as the Suzuki coupling, is well known in the chemical literature. Alternatively, compound 1-5 (X=Br) can be converted to a boronate ester 1-7 (where B(OR')$_2$ is, for example, 4,4,5,5-tetramethyl-1,3,2-dioxaborolan-2-yl), for example by treatment with 4,4,4',4',5,5,5',5'-octamethyl-2,2'-bi(1,3,2-dioxaborolane) in the presence of a suitable combination of catalyst and ligand, such as tris(dibenzylideneacetone)dipalladium and tricyclohexylphosphine, with a suitable base such as potassium acetate, in a suitable solvent such as 1,4-dioxane (see, for example, L. Wang et al., *J. Med. Chem.* 2007, 50, 4162). The boronate ester 1-7, or the derived boronic acid 1-7 (R'=H) prepared by hydrolysis of the boronate ester using methods known in the literature, can then be converted to compound 1-6 using the Suzuki coupling reaction or a similar reaction as described above for the direct conversion of 1-5 to 1-6

Many boronic acids and boronate esters suitable for use in conversion of 1-5 to 1-6 (where A is an aryl or heteroaryl group) are commercially available, or may be prepared from corresponding aryl or heteroaryl derivatives such as bromides, chlorides or trifluoromethanesulfonates, using methods known in the literature, for example as described above for the conversion of 1-5 to 1-7. Such aryl bromides, chlorides or trifluoromethanesulfonates are either available commercially, or are known in the chemical literature, or can be prepared using well-known synthetic transformations.

In some cases it may be desirable to convert the primary amide of structure 1-5 to a different functional group, for example to prevent unwanted reactions or to enhance solubility for subsequent synthetic transformations. An example is shown in Figure 2. Compound 2-1 (equivalent to compound 1-5 in Figure 1) can be converted to the corresponding nitrile 2-2, for example by treatment under suitable conditions with phosphorus oxychloride. Compound 2-2 (X=Br) may then be converted to compound 2-4, either directly or through conversion to an intermediate boronate ester or boronic acid 2-3, as described above, followed by hydrolysis of the nitrile 2-4 to the carboxamide 2-5 using methods known in the chemical literature.

Figure 2.

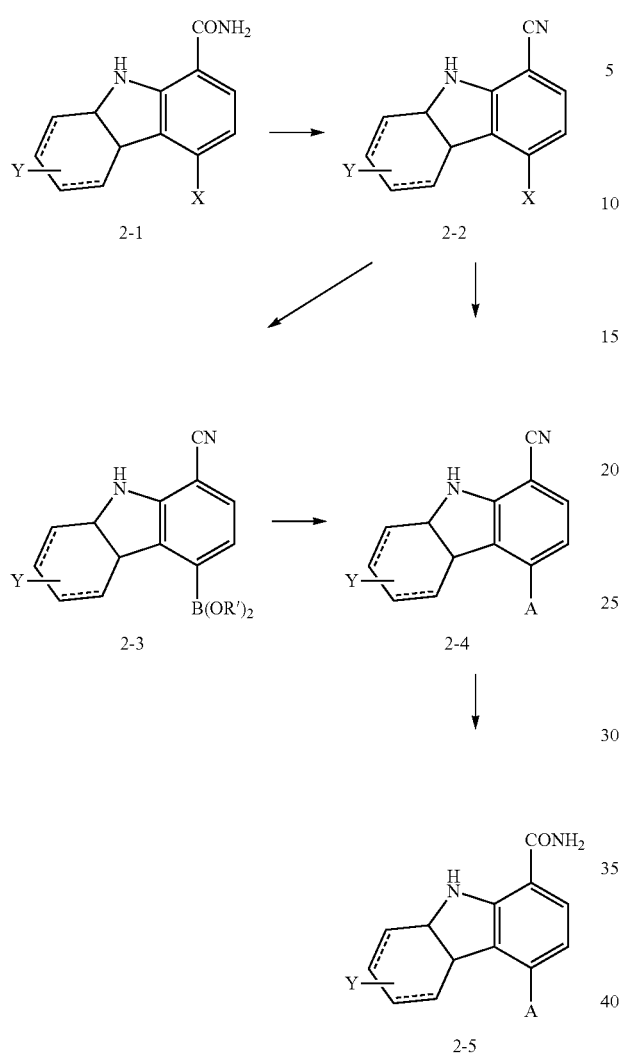

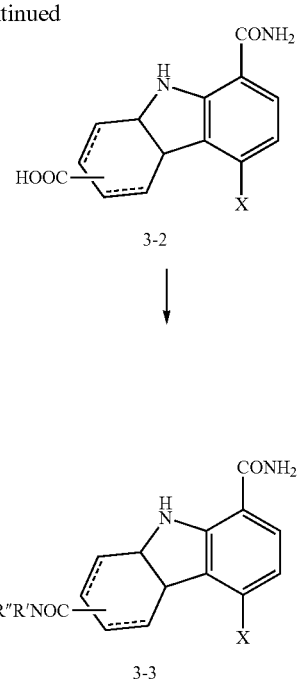

Manipulation of substituents in the compounds of Formula (I) can be performed using a variety of methods which are well known in the chemical literature. For example, as shown in Figure 3, if the substituent Y in compound 1-5 (where X is either A of Formula (I) or a precursor to A) is an ester such as an ethyl ester (compound 3-1), this ester may be converted into another substituent, for example by hydrolysis to the corresponding acid 3-2, for example using a base such as lithium hydroxide or sodium hydroxide in water, followed by conversion to the amide 3-3 using any of a wide variety of methods well known in the chemical literature.

Other examples of manipulation of a substituent are shown in Figure 4. An ester such as the ethyl ester (compound 4-1) may be converted into an alcohol, aldehyde or ketone using standard synthetic methods well known in the literature. For example, treatment of the ester with a reducing agent such as lithium aluminum hydride can provide the primarily carbinol 4-2. Alternatively, the ester can be converted to a tertiary carbinol 4-3 (where R and R' are the same) by treatment with an appropriate organometallic reagent such as an alkylmagnesium halide or an alkyllithium. Alternatively, the ester can be converted to a ketone 4-4, for example by hydrolysis to the carboxylic acid, conversion to an N,O-dialkylhydroxamide and treatment of this intermediate with an appropriate organometallic reagent. A ketone 4-4 can be converted to a tertiary alcohol 4-3 (where R and R' are the same or different) by treatment with an appropriate organometallic reagent, or to a secondary alcohol 4-5 by treatment with a reducing agent such as sodium borohydride or lithium aluminum hydride. Alternatively, a primary alcohol 4-2 can be converted to an aldehyde 4-6, which can be converted to a secondary alcohol 4-5 by treatment with an appropriate organometallic reagent.

Figure 3.

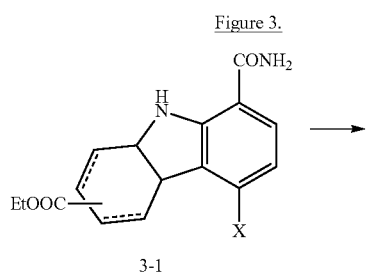

Figure 4.

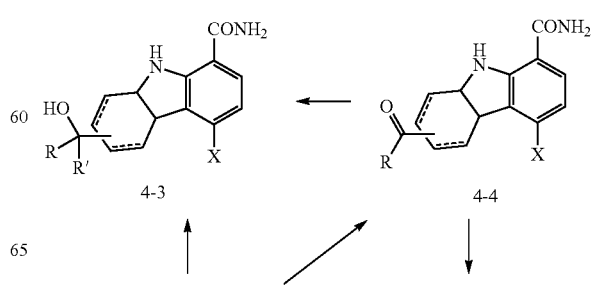

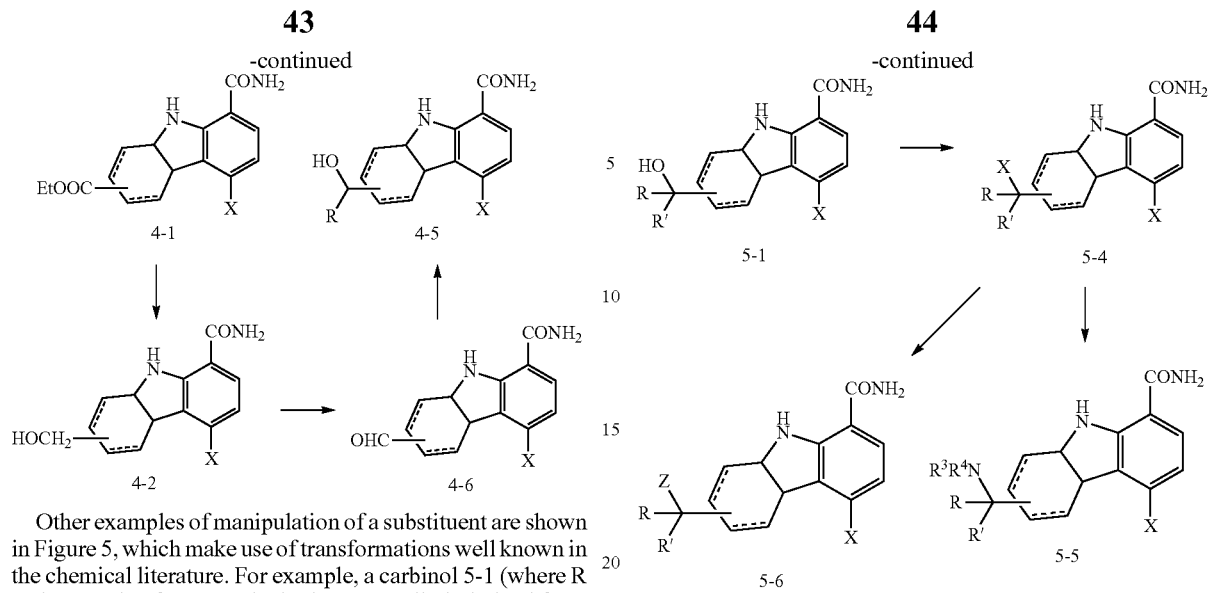

Other examples of manipulation of a substituent are shown in Figure 5, which make use of transformations well known in the chemical literature. For example, a carbinol 5-1 (where R and R' can be, for example, hydrogen or alkyl; derived from an ester using transformations exemplified in Figure 4) can be converted to an ether 5-2 ($R^1$=for example alkyl) by treatment with an alkylating agent such as an alkyl halide or alkyl trifluoromethanesulfonate in the presence of a base such as sodium hydride, or by treatment with a carbinol $R^1OH$ in the presence of a catalyst such as trifluoroacetic acid. Alternatively, a carbinol 5-1 can be converted into an ester 5-3 ($R^2$=for example alkyl or aryl) or carbamate 5-3 ($R^2$=for example alkylamino or dialkylamino) by treatment with an acylating agent such as an acid anhydride, acid chloride or carbamyl chloride in the presence of a base such as a trialkylamine or pyridine, or by treatment with an acid in the presence of a coupling agent such as carbodiimide or N-(3-dimethylaminopropyl)-N'-ethylcarbodiimide hydrochloride, and 1-hydroxybenzotriazole or 1-hydroxy-7-azabenzotriazole. Alternatively, a carbinol 5-1 can be converted into a derivative 5-4, where X is a leaving group such as bromide, methanesulfonate, toluenesulfonate or trifluoromethanesulfonate. The compound 5-4 can then be converted into an amine 5-5 (where $R^3$ and $R^4$ are for example hydrogen, alkyl or aryl, or $R^3$ and $R^4$ form a heterocyclic ring) by treatment with an appropriate amine $HNR^3R^4$. Alternatively, the compound 5-4 can be converted to a primary amine 5-5 (where $R^3$ and $R^4$ are both hydrogen) by treatment with sodium azide to provide 5-4 (where X is $N_3$) followed by treatment with a reducing agent such as triphenylphosphine in the presence of water (commonly known as the Staudinger reduction). The compound 5-4 can also be converted into a heterocyclic derivative 5-6, for example by treatment with a heterocycle ZH under appropriate conditions. Examples of Z in structure 5-6 are 2-oxopyrrolidin-1-yl, 2-oxopiperidin-1-yl, pyrazol-1-yl, and imidazol-1-yl.

Other examples of manipulation of a substituent are shown in Figure 6, which make use of transformations well known in the chemical literature. For example, a carbinol 6-1 having at least one hydrogen beta to the hydroxyl group (where R, R' and R" can be, for example, hydrogen or alkyl; prepared for example using transformations exemplified in Figure 4) can be converted to an alkene 6-2, for example by dehydration in the presence of an acid catalyst, or by conversion of the hydroxyl to a leaving group such as methanesulfonate, toluenesulfonate or trifluoromethanesulfonate followed by treatment with a suitable base. An alkene 6-2 can be converted to 6-3 by reduction of the double bond, for example by treatment with hydrogen in the presence of a suitable catalyst such as palladium on charcoal. Alternatively, a carbinol 6-1 can be directly reduced to 6-3, for example by treatment with a trialkylsilane in the presence of an acid such as trifluoroacetic acid. Alternatively, an alkene such as 6-2 can be converted to a diol 6-4, for example by treatment with 4-methylmorpholine N-oxide in the presence of osmium tetroxide. A diol 6-4 can be converted into a monoester or a diester 6-5 (where one or both of $R^1$ and $R^2$ is an acyl group), or to a monoether or a diether 6-5 (where one or both or $R^1$ and $R^2$ is, for example, an alkyl group), or to a monocarbamate or a dicarbamate 6-5 (where one or both of $R^1$ and $R^2$ is a carbamyl group), or to a compound wherein $R^1$ and $R^2$ are independently alkyl, acyl or carbamyl, or to a compound wherein $R^1$ and $R^2$ form a heterocyclic ring such as a 1,3-dioxolane, a 1,3-dioxane, or a 1,3-dioxolan-2-one, using standard methods well known in the chemical literature.

Figure 5.

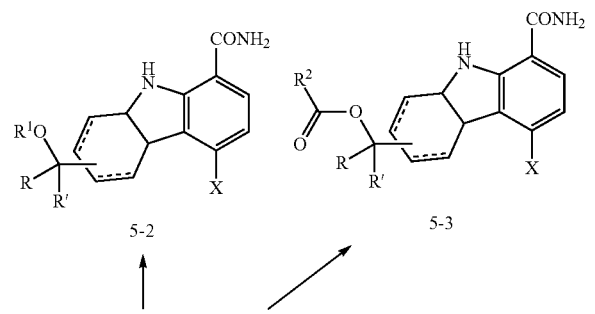

Figure 6.

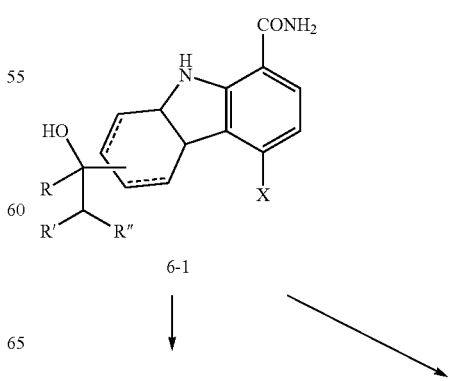

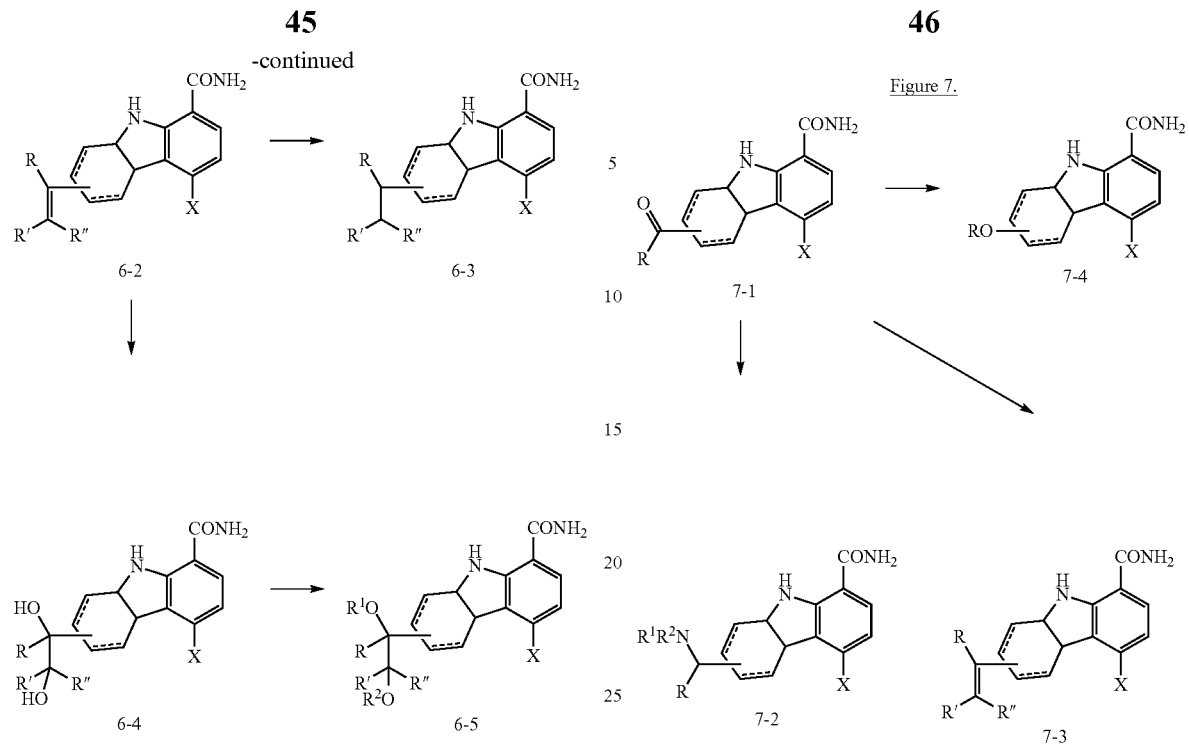

Figure 7.

Other examples of manipulation of a substituent are shown in Figure 7, which make use of transformations well known in the chemical literature. For example, an aldehyde or ketone 7-1 (R=hydrogen or, for example, alkyl, respectively, prepared for example using the transformations shown in Figure 4) can be converted to an amine 7-2 (where, for example, $R^1$ and $R^2$ are independently hydrogen or alkyl, or $R^1$ and $R^2$ together for a heterocyclic ring such as piperidine, pyrrolidine or morpholine) by treatment of 7-1 with an amine $HNR^1R^2$ in the presence of a reducing agent such as sodium triacetoxyborohydride or sodium cyanoborohydride, or by treatment of 7-1 with an amine $HNR^1R^2$ with removal of water to form an intermediate imine followed by reduction of the imine with a suitable reducing agent. Alternatively, 7-1 can be converted to an olefin 7-3 by treatment with a suitable reagent such as an alkyltriarylphosphonium halide or a dialkyl phosphonate in the presence of a suitable base, a transformation well-known in the literature as the Wittig reaction. The resulting olefin 7-3 can then be converted to a variety of other compounds, for example by the transformations of 6-2 in Figure 6 as described above. Alternatively, 7-1 can be converted to a phenolic ester or carbinol ester 7-4 (where R=formyl or acyl) by treatment with an oxidizing reagent such as 3-chloroperoxybenzoic acid, peroxyacetic acid, peroxytrifluoroacetic acid or a mixture of hydrogen peroxide and a strong acid such as sulfuric acid, in a reaction well known in the chemical literature as the Baeyer-Villiger rearrangement. A compound 7-4 (R=formyl or acyl) can be converted into a phenol or carbinol 7-4 (R=H) by hydrolysis under well-known methods. The phenol or carbinol 7-4 can then be converted to, for example, an ester 7-4 (R=acyl), ether 7-4 (R=for example alkyl) or carbamate 7-4 (R=carbamyl) using well-known methods.

Other examples of manipulation of a substituent are shown in Figure 8, which make use of transformations well known in the chemical literature. A carboxylic acid 8-1 (prepared, for example, as shown in Figure 3) can be converted to an acyl azide 8-2, for example by treatment with diphenyl phosphorazidate (diphenyl phosphoryl azide). The acyl azide can be converted without isolation to an isocyanate 8-3, for example by heating. The isocyanate can be converted to a urea 8-4 (where R and R' are independently, for example, hydrogen or alkyl, or taken together can form a ring such as piperidine, pyrrolidine or morpholine). Alternatively, the acyl azide 8-2 can be heated in the presence of an alcohol to provide a carbamate 8-5 (where R is, for example, alkyl or benzyl). The carbamate 8-5 can be converted to a primary amine 8-6 by hydrolysis, or (in the case where R is benzyl) by treatment with, for example, hydrogen or ammonium formate in the presence of a catalyst such as palladium on charcoal, or with hydrogen bromide in acetic acid. In these transformations, an intermediate acyl azide 8-2 and/or isocyanate 8-3 can be isolated, or the entire sequence of steps converting an acid 8-1 to a urea 8-4 or a carbamate 8-5 can be performed without isolating the intermediates.

Figure 8.

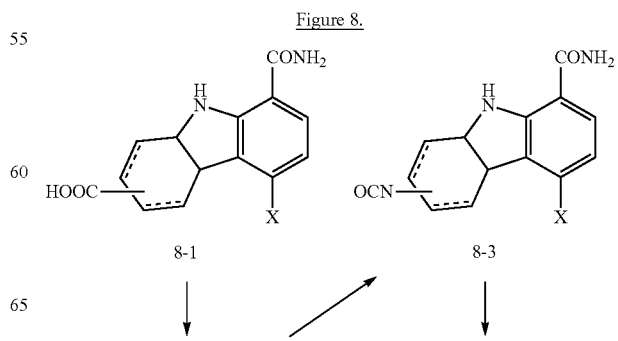

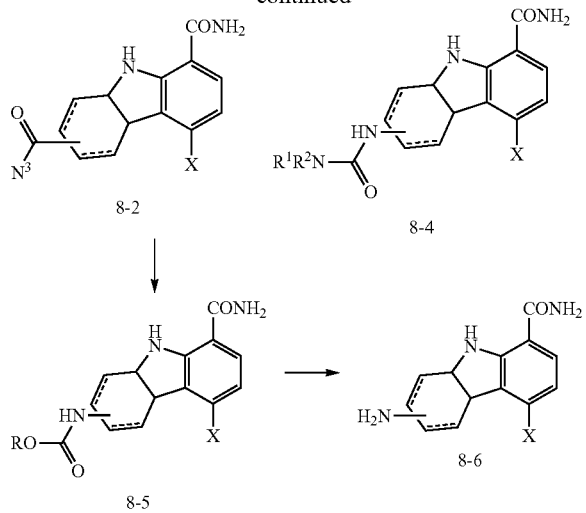

8-2

8-4

8-5

8-6

Another example of manipulation of a substituent is shown in Figure 9. The nitro substituent of compound 9-1 (where Y can represent $D^1$ and/or $D^2$ of Formula (I) or a precursor to $D^1$ and/or $D^2$), prepared for example by Suzuki coupling of compound 1-5 in Figure 1 with a nitro-substituted benzeneboronic acid, can be reduced using well known methods to provide a corresponding aniline 9-2, for example by treatment with hydrogen in the presence of a catalyst such as palladium on charcoal, or by treatment with a reducing agent such as zinc or tin (II) chloride in an acid such as hydrochloric acid, or iron in acetic acid.

Figure 9

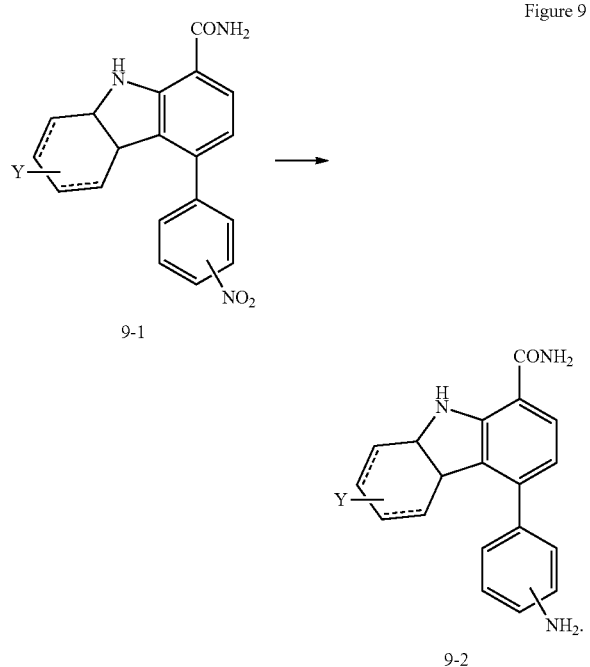

9-1

9-2

Any amine substituent (for example, 5-5 in Figure 5, 7-2 in Figure 7, 8-6 in Figure 8, or 9-2 in Figure 9) wherein the amine is primary or secondary may be converted to other substituents using methods well known in the chemical literature. Examples are reaction with a carboxylic acid, a carboxylic acid halide or a carboxylic acid anhydride to provide an amide; reaction with an isocyanate, aryl carbamate or carbamyl chloride to provide a urea; reaction with a chloroformate ester to provide a carbamate; reaction with a sulfonyl halide or sulfonic anhydride to provide a sulfonamide or sulfonimide; reaction with a sulfamyl halide to provide a sulfamide; and reaction with an aldehyde or ketone in the presence of a suitable reducing agent to provide an alkylated amine.

Another example of transformations of such an amine substituent is reaction with an aryl or heteroaryl halide (such as for example a 2-chloropyridine, 2-chloroquinoline, 2-chloroisoquinoline or 4-chloroquinazoline), either in the presence or absence of a suitable catalyst such as a palladium catalyst, to provide an arylated amine. (The case where a palladium catalyst is used is commonly known in the chemical literature as the Buchwald amination). Another example is reaction with a bifunctional reagent such as, for example, a hydroxyacid or lactone or haloacyl chloride or haloalkanoic acid (to form a lactam) or a divinylsulfone (to form a thiomorpholine dioxide) under suitable conditions. In the case of reaction with such a bifunctional reagent, both reaction steps may be achieved in one synthetic operation, or alternatively reaction with one functionality may be followed by isolation of an intermediate followed by reaction with the other functionality.

Another example of further manipulation of a substituent is the conversion of a suitable substituent on an aryl group (such as bromo, chloro or trifluoromethanesulfonate) to an aryl or heteroaryl group, for example via Suzuki coupling as described previously. Another example of further manipulation of a suitable substituent on an aryl group (such as bromo, chloro or trifluoromethanesulfonate) is the conversion of this substituent to an amine or aniline substituent (by treatment with a primary or secondary amine or aniline under suitable conditions, widely reported in the chemical literature and, when performed in the presence of a suitable catalyst such as a palladium catalyst, commonly know as the Buchwald amination). Another example of further manipulation of a suitable substituent on an aryl group (such as bromo, chloro or trifluoromethanesulfonate) is the conversion of this substituent into an amide by reaction with a primary or secondary amide or a lactam under suitable conditions widely reported in the chemical literature (for example, in the presence of a copper (I) salt and a diamine ligand).

The sequence of synthetic transformations (for example, the order of manipulations of the X and Y substituents and the carboxylic acid group in compound 1-3) can be varied depending on the nature of the compound to be prepared, and can be determined by one skilled in the art through consideration of the stabilities of the various substituents to reaction conditions to be performed.

In some cases, it may be desirable for one or more functional groups in starting materials or intermediates to be present in a protected form. In such cases, removal of the protecting group can be performed at a suitable stage of the synthetic sequence, followed by further manipulation of the functional group if desired. Such protecting groups and their use and removal are well known to those skilled in the art.

In all the transformations described above, and in related transformations, reactions can be performed in suitable solvents, chosen for solubility of or compatibility with the reactants and reagents or for other properties such as boiling point or ability to facilitate the reaction to be performed. Reactions are usually performed at a temperature chosen to provide a convenient rate of reaction, usually from below ambient room temperature to the boiling point of the solvent, or above the boiling point if the reaction is performed in a sealed vessel. The transformations described are generally well known in the chemical literature, and one skilled in the art of organic synthesis will be familiar with appropriate solvents, catalysts, reagents, and conditions suitable for performing the transformations desired, as well as suitable variations of the sequences of transformations used to provide a desired product.

In the case where the dashed lines of Formula (I) represent single bonds and substituents $D^1$ and/or $D^2$ are present, or if substituents $D^1$ and/or $D^2$ bear a chiral center, or if the substituent A bears a chiral center, enantiomers are possible. If the dashed lines represent single bonds and additionally one or more of the substituents A, $D^1$ and/or $D^2$ bears a chiral center, or if the dashed lines represent double bonds and two or more of the substituents A, $D^1$ and/or $D^2$ bear chiral centers, diastereomers are possible. Additionally, in some cases, restricted rotation about certain bonds, particularly the bond attaching substituent A in Formula (I), can give rise to optical isomers, known as atropisomers, even when no chiral atom is present. An enantiomerically or diastereomerically enriched compound can be prepared by using an enantiomerically or diastereomerically enriched starting material (for example, 1-2 for the synthesis outlined in Figure 1, or coupling of 1-5 or 1-7 with an enantiomerically enriched reactant, or acylation of an amine or hydroxyl substituent with an enantiomerically enriched acylating agent). Alternatively, racemic starting materials or reagents can be used, followed by separation of enantiomers or diastereomers, for example by using chiral HPLC or using chemical methods well known in the chemical literature. Such separation can be performed at any suitable stage in the synthetic sequence, or the final compound of Formula (I) can be separated into enantiomers or diastereomers.

EXAMPLES

Preparation of Compounds of Formula (I), and Intermediates Used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, Phenomenex Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

NaHCO3 (aq)—saturated aqueous sodium bicarbonate
brine—saturated aqueous sodium chloride
DCM—dichloromethane
DIEA—N,N-diisopropylethylamine
DMAP—4-(N,N-dimethylamino)pyridine
DMF—N,N-dimethylformamide
DMSO—dimethyl sulfoxide
EDC—N-(3-dimethylaminopropyl)-N'-ethylcarbodiimide hydrochloride
EtOAc—ethyl acetate
HOAT—1-hydroxy-7-azabenzotriazole
HOBT—1-hydroxybenzotriazole hydrate
rt—ambient room temperature (generally about 20-25° C.)
TEA—triethylamine
TFA—trifluoroacetic acid
THF—tetrahydrofuran Intermediate 1-1

Preparation of 2-(3-bromo-2-methylphenyl)isoindolin-1-one

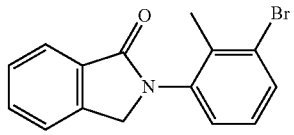 [SMILES: Cc1c(Br)cccc1N1Cc2ccccc2C1=O]

A solution of 3-bromo-2-methylaniline (10 g, 53.7 mmol) in DCM (200 mL) at 0° C. was treated with TEA (14.98 mL, 107 mmol), followed by dropwise addition of 2-(chloromethyl)benzoyl chloride (10.16 g, 53.7 mmol) in DCM (50 mL) over 1 h. The mixture was diluted with DCM (ca. 1 L), washed with NaHCO3 (aq) and water, and concentrated to remove most of the solvent. The precipitate was collected by filtration and washed with DCM (2×10 mL) to provide N-(3-bromo-2-methylphenyl)-2-(chloromethyl)benzamide as a white solid (8.0 g). The filtrate was concentrated further, resulting in additional precipitate which was collected by filtration and washed with DCM (2×10 mL) to provide additional N-(3-bromo-2-methylphenyl)-2-(chloromethyl)benzamide as a white solid (3.06 g), for a combined yield of 61%. Mass spectrum 338, 340, 342 The filtrate was concentrated and purified by column chromatography (hexane-EtOAc) to provide 2-(3-bromo-2-methylphenyl)isoindolin-1-one as a yellow solid (2.0 g, 12%). A solution of the N-(3-bromo-2-methylphenyl)-2-(chloromethyl)benzamide (11.06 g, 32.7 mmol) in DMF (50 mL) was cooled to 0° C. and treated with a mixture of sodium hydride (60% oil dispersion, pre-washed with hexane, 1.70 g, 42.5 mmol) and DMF (10 mL). The mixture was stirred at 0° C. for 1.5 h, then was treated with water. The precipitate was collected by filtration, dried and combined with the material purified by column chromatography (see above) to provide 2-(3-bromo-2-methylphenyl) isoindolin-1-one as a yellow solid (9.41 g, 95%). $^1$H NMR (400 MHz, chloroform-d) δ 7.96 (1 H, d, J=7.5 Hz), 7.58-7.67

(2 H, m), 7.49-7.57 (2 H, m), 7.20-7.25 (1 H, m), 7.15 (1 H, t, J=7.9 Hz), 4.72 (2 H, s), 2.31 (3 H, s). Mass spectrum m/z 302, 304 (M+H)⁺.

Intermediate 1-2

Preparation of 2-(3-bromo-2-methylphenyl)-6-fluoroisoindolin-1-one

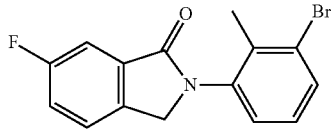 [SMILES: Cc1c(Br)cccc1N1Cc2ccc(F)cc2C1=O]

Step 1 A suspension of 5-fluoro-2-methylbenzoic acid (500 mg, 3.24 mmol), N-bromosuccinimide (606 mg, 3.41 mmol) and benzoyl peroxide (47 mg, 0.195 mmol) in tetrachloromethane (10 mL) was heated at 78° C. for 4 h. The hot mixture was filtered and the filtrate was concentrated to provide crude 2-(bromomethyl)-5-fluorobenzoic acid as a white solid (730 mg), used without further purification. $^1$H NMR (400 MHz, chloroform-d) δ 7.81 (1 H, dd, J=9.2, 2.9 Hz), 7.50 (1 H, dd, J=8.5, 5.4 Hz), 7.23-7.30 (1 H, m), 4.98 (2 H, s).

Step 2 A solution of crude 2-(bromomethyl)-5-fluorobenzoic acid (3.05 g, 13.1 mmol) in DCM (50 mL) was treated with oxalyl chloride (1.66 g, 13.1 mmol) and 6 drops of DMF. The mixture was stirred at rt for 1 h, then was concentrated. The residue was redissolved in DCM (50 mL) and treated with 3-bromo-2-methylaniline (1.705 g, 9.16 mmol). The mixture was stirred at rt for 1 h, then TEA (2.19 mL, 15.7 mmol) was added in portions. The mixture was stirred at rt for 2 h, then was diluted with DCM (100 mL), washed with NaHCO3 (aq) and water, dried and concentrated. The residue was triturated with DCM to provide N-(3-bromo-2-methylphenyl)-2-(bromomethyl)-5-fluorobenzamide as a white solid (0.9 g). The mother liquor was concentrated and the residue was again triturated with DCM to provide additional N-(3-bromo-2-methylphenyl)-2-(bromomethyl)-5-fluorobenzamide as a white solid (0.46 g). The mother liquor was concentrated and the residue was purified by column chromatography (eluting with a gradient from hexane to 70:30 EtOAc-hexane) to provide additional N-(3-bromo-2-methylphenyl)-2-(bromomethyl)-5-fluorobenzamide as a pink solid (1.18 g) for a total of 2.54 g (48%). Mass spectrum m/z 400, 402, 404 (M+H)⁺.

Step 3 A mixture of N-(3-bromo-2-methylphenyl)-2-(bromomethyl)-5-fluorobenzamide (2.54 g, 6.33 mmol) and sodium tert-butoxide (0.913 g, 9.50 mmol) in THF (80 mL) was stirred at rt for 30 min. The mixture was diluted with water and extracted with twice with DCM. The combined organic phases were washed with water, dried and concentrated. The residue was purified by column chromatography (eluting with hexane-EtOAc) to provide 2-(3-bromo-2-methylphenyl)-6-fluoroisoindolin-1-one as a white solid (1.18 g, 58%). $^1$H NMR (400 MHz, chloroform-d) δ 7.59-7.65 (2 H, m), 7.45-7.50 (1 H, m), 7.33 (1 H, td, J=8.6, 2.5 Hz), 7.19-7.24 (1 H, m), 7.15 (1 H, t, J=7.9 Hz), 4.68 (2 H, s), 2.31 (3 H, s). Mass spectrum m/z 320, 322 (M+H)⁺.

Intermediate 1-3

Preparation of 2-(3-bromo-2-methylphenyl)-6-methoxyisoindolin-1-one

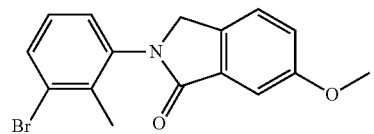 [SMILES: COc1ccc2c(c1)C(=O)N(c1cccc(Br)c1C)C2]

Step 1 A suspension of methyl 5-methoxy-2-methylbenzoate (1.00 g, 5.55 mmol), N-bromosuccinimide (1.037 g, 5.83 mmol) and benzoyl peroxide (81 mg, 0.333 mmol) in tetrachloromethane (10 mL) was heated at 77° C. for 3 h. The mixture was diluted with DCM, washed with NaHCO3 (aq), dried and concentrated to provide crude methyl 2-(bromomethyl)-5-methoxybenzoate as a light yellow solid (1.435 g), used without further purification. $^1$H NMR (400 MHz, chloroform-d) δ 7.48 (1 H, d, J=2.64 Hz), 7.37 (1 H, d, J=8.36 Hz), 7.02 (1 H, dd, J=8.58, 2.86 Hz), 4.93 (2 H, s), 3.95 (3 H, s), 3.85 (3 H, s).

Step 2 A mixture of methyl 2-(bromomethyl)-5-methoxybenzoate (1.435 g, 5.54 mmol), 3-bromo-2-methylaniline (1.03 g, 5.54 mmol) and TEA (1.158 mL, 8.31 mmol) in methanol (5 mL) was heated at 85° C. for 2 h. The mixture was diluted with DCM, washed with NaHCO3 (aq), and dried and concentrated. The residue was purified by column chromatography (eluting with EtOAc-hexane) to provide methyl 2-((3-bromo-2-methylphenylamino)methyl)-5-methoxybenzoate as a yellow oil (361 mg, 18%). Mass spectrum m/z 364, 366 (M+H)⁺.

Step 3 A solution of methyl 2-((3-bromo-2-methylphenylamino)methyl)-5-methoxybenzoate (360 mg, 0.988 mmol) in THF (10 mL) was treated with sodium tert-butoxide (142 mg, 1.483 mmol) and stirred at rt overnight. The mixture was treated with water and extracted twice with DCM. The combined organic phases were washed with water, dried and concentrated. The residue was purified by column chromatography (eluting with EtOAc-hexane) to provide 2-(3-bromo-2-methylphenyl)-6-methoxyisoindolin-1-one as a white solid (246 mg, 75%). $^1$H NMR (400 MHz, chloroform-d) δ 7.62 (1 H, dd, J=7.9, 1.1 Hz), 7.46 (1 H, d, J=2.4 Hz), 7.42 (1 H, d, J=8.4 Hz), 7.15-7.26 (3 H, m), 4.67 (2 H, s), 3.92 (3 H, s), 2.34 (3 H, s). Mass spectrum m/z 332, 334 (M+H)⁺.

The following Intermediates were also prepared using procedures used to prepare Intermediates 1-1 through 1-3.

| Intermediate | Compound name | Mass spectrum |
|---|---|---|
| 1-4 | 2-(3-bromo-2-methylphenyl)-5-methoxyisoindolin-1-one | 332, 334 (M + H)⁺ |
| 1-5 | 2-(3-bromo-2-methylphenyl)-6-(trifluoromethyl)isoindolin-1-one | 370, 372 (M + H)⁺ |
| 1-6 | 2-(3-bromo-2-methylphenyl)-6-methylisoindolin-1-one | 316, 318 (M + H)⁺ |

Intermediate 2-1

Preparation of 2-(3-bromo-2-methylphenyl)-3-oxoisoindoline-5-carbonitrile

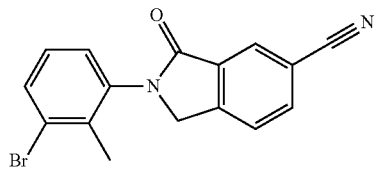 [SMILES: Cc1c(Br)cccc1N1Cc2ccc(C#N)cc2C1=O]

Step 1 A solution of 3-bromo-2-methylaniline (0.67 g, 3.60 mmol) in DCM (18 mL) was treated dropwise with trimethylaluminum (2 M in toluene, 1.801 mL, 3.60 mmol) and the resulting solution was stirred at rt for 30 min. A solution of 3-oxo-1,3-dihydroisobenzofuran-5-carbonitrile (0.573 g, 3.60 mmol) in DCM (18.00 mL) was added and the resulting mixture was stirred at rt overnight. The mixture was diluted with DCM, washed with an aqueous solution of sodium potassium tartrate (Fehling's Reagent II) and water, then was dried and concentrated. The residue was purified by column chromatography (eluting with a gradient from 80:20 hexane-EtOAc to EtOAc) to provide N-(3-bromo-2-methylphenyl)-5-cyano-2-(hydroxymethyl)benzamide as a white solid (170 mg, 14%) which was used without further purification. Mass spectrum m/z 345, 347 (M+H)$^+$.

Step 2 A solution of N-(3-bromo-2-methylphenyl)-5-cyano-2-(hydroxymethyl)benzamide (170 mg, 0.492 mmol) in THF (20 mL) was treated with di-tert-butyl azodicarboxylate (113 mg, 0.492 mmol) and tributylphosphine (0.119 mL, 0.492 mmol) and stirred at rt. After 2 h the mixture was concentrated and the residue was column chromatography (eluting with a gradient from 90:10 to 50:50 hexane-EtOAc) to provide 2-(3-bromo-2-methylphenyl)-3-oxoisoindoline-5-carbonitrile (100 mg, 62%) as a white solid. $^1$H NMR (400 MHz, chloroform-d) δ 8.07 (1 H, d, J=8.1 Hz), 7.82-7.89 (2 H, m), 7.64 (1 H, dd, J=7.8, 1.4 Hz), 7.13-7.25 (2 H, m), 4.78 (2 H, s), 2.30 (3 H, s). Mass spectrum m/z 327, 329 (M+H)$^+$.

Intermediate 3-1

Preparation of 2-(3-bromo-2-methylphenyl)-5-fluoroisoindoline-1,3-dione

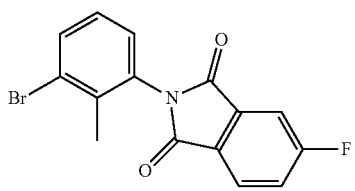 [SMILES: Cc1c(Br)cccc1N1C(=O)c2ccc(F)cc2C1=O]

A mixture of 3-bromo-2-methylaniline (200 mg, 1.075 mmol) and 5-fluoroisobenzofuran-1,3-dione (179 mg, 1.075 mmol) in acetic acid (2 mL) was heated at 100° C. for 4.5 h. The mixture was concentrated and the residue was purified by column chromatography (eluting with a gradient from hexane to 60:40 hexane-EtOAc) to give 2-(3-bromo-2-methylphenyl)-5-fluoroisoindoline-1,3-dione as a white solid (235 mg, 59%). Mass spectrum m/z 334, 336 (M+H)$^+$.

The following Intermediates were also prepared using procedures used to prepare Intermediate 3-1.

| Intermediate | Compound name | Mass spectrum |
|---|---|---|
| 3-2 | 2-(3-bromo-2-methylphenyl)-5-tert-butylisoindoline-1,3-dione | 372, 374 (M + H)$^+$ |
| 3-3 | 2-(3-bromo-2-methylphenyl)-5-chloroisoindoline-1,3-dione | 350, 352 (M + H)$^+$ |
| 3-4 | 2-(3-bromo-2-methylphenyl)-5-methylisoindoline-1,3-dione | 330, 332 (M + H)$^+$ |
| 3-5 | 2-(3-bromo-2-methylphenyl)-4-fluoroisoindoline-1,3-dione | 334, 336 (M + H)$^+$ |
| 3-6 | 2-(3-bromo-2-methylphenyl)hexahydro-1H-isoindole-1,3(2H)-dione | 322, 324 (M + H)$^+$ |
| 3-7 | 2-(3-bromo-2-methylphenyl)-1H-pyrrolo[3,4-c]pyridine-1,3(2H)-dione | 317, 319 (M + H)$^+$ |

Intermediates 4-1 and 4-2

Preparation of 2-(3-bromo-2-methylphenyl)octahydro-1H-isoindol-1-one and 2-(3-bromo-2-methylphenyl)-2,3,4,5,6,7-hexahydro-1H-isoindol-1-one

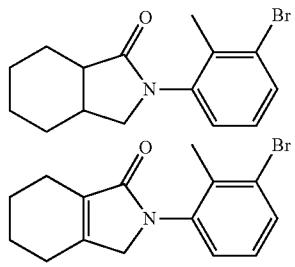

A suspension of 2-(3-bromo-2-methylphenyl)hexahydro-1H-isoindole-1,3(2H)-dione (Intermediate 3-6, 4.5 g, 13.97 mmol) in methanol (150 mL) was treated with sodium borohydride (2.64 g, 69.8 mmol) and stirred at rt for 4 h. The mixture was concentrated, and the residue was dissolved in DCM, washed with NaHCO3 (aq) and water, and dried and concentrated to provide 2-(3-bromo-2-methylphenyl)-3-hydroxyoctahydro-1H-isoindol-1-one as a yellow solid (3.94 g, 87%). Mass spectrum m/z 324, 326 (M+H)$^+$. Without purification, a portion of this material (1.8 g, 5.55 mmol) was dissolved in DCM (50 mL) and treated with triethylsilane (6.46 g, 55.5 mmol). The solution was treated dropwise at rt with TFA (2.14 mL, 27.8 mmol) and stirred at rt for 30 min. The mixture was concentrated and the residue was dissolved in DCM, washed with NaHCO3 (aq) and water. The organic phase was dried and concentrated. The residue was purified by column chromatography (eluting with hexane-EtOAc) to provide 2-(3-bromo-2-methylphenyl)octahydro-1H-isoindol-1-one (Intermediate 4-1, 1.35 g, 79%). $^1$H NMR (400 MHz, chloroform-d) δ 7.48-7.53 (1 H, m), 7.06-7.09 (2 H, m), 3.78 (1 H, dd, J=9.5, 5.7 Hz), 3.19 (1 H, dd, J=9.5, 2.4 Hz), 2.64-2.70 (1 H, m), 2.45-2.54 (1 H, m), 2.30 (3 H, s), 2.10-2.17 (1 H, m), 1.80-1.88 (1 H, m), 1.62-1.71 (2 H, m), 1.56-1.62 (1 H, m), 1.40-1.51 (1 H, m), 1.31 (2 H, s). Mass spectrum m/z 308, 310 (M+H)$^+$. Also isolated was 2-(3-bromo-2-methylphenyl)-2,3,4,5,6,7-hexahydro-1H-isoindol-1-one (Intermediate 4-2, 224 mg, 13%). $^1$H NMR (400 MHz, chloroform-d) δ 7.51-7.55 (1 H, m), 7.05-7.14 (2 H, m), 4.09 (2 H, t, J=1.9 Hz), 2.28-2.37 (4 H, m), 2.28 (3 H, s), 1.73-1.85 (4 H, m). Mass spectrum m/z 306, 308 (M+H)$^+$.

Intermediates 4-3 and 4-4

Preparation of 2-(3-bromo-2-methylphenyl)-6-tert-butylisoindolin-1-one and 2-(3-bromo-2-methylphenyl)-5-tert-butylisoindolin-1-one

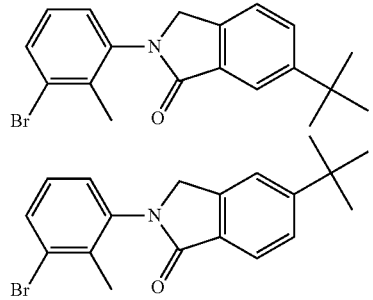

A suspension of 2-(3-bromo-2-methylphenyl)-5-tert-butylisoindoline-1,3-dione (Intermediate 3-2, 1.0 g, 2.69 mmol) in methanol (20 mL) was treated with sodium borohydride (203 mg, 5.37 mmol) and stirred at rt. After a few minutes, additional sodium borohydride (203 mg, 5.37 mmol) was added. After 40 min, the mixture was concentrated, and the residue was dissolved in DCM, washed with water and brine, and dried and concentrated to provide a white solid. This material was dissolved in DCM (10 mL) and treated with TFA (10 mL) and stirred for a few minutes at rt, then was treated with triethylsilane (6.40 mL, 40.1 mmol) and stirred at rt for 2.5 h. The mixture was concentrated and the residue was dissolved in DCM, washed with NaHCO3 (aq) and water. The organic phase was dried and concentrated. The residue was purified by column chromatography (eluting with hexane-EtOAc) to provide 2-(3-bromo-2-methylphenyl)-6-tert-butylisoindolin-1-one (Intermediate 4-3, 134 mg, 28%). $^1$H NMR (400 MHz, chloroform-d) δ 7.99 (1 H, d, J=1.32 Hz), 7.68 (1 H, dd, J=7.91, 1.76 Hz), 7.60 (1 H, dd, J=7.69, 1.10 Hz), 7.45 (1 H, d, J=7.91 Hz), 7.19-7.23 (1 H, m), 7.15 (1 H, t, J=7.69 Hz), 4.68 (2 H, s), 2.31 (3 H, s), 1.39 (9 H, s). Mass spectrum m/z 358, 360 (M+H)$^+$. Also isolated was 2-(3-bromo-2-methylphenyl)-5-tert-butylisoindolin-1-one (Intermediate 4-4, 250 mg, 52%). $^1$H NMR (400 MHz, chloroform-d) δ 7.88 (1 H, d, J=7.91 Hz), 7.59 (2 H, dd, J=8.13, 2.86 Hz), 7.53 (1 H, s), 7.20-7.23 (1 H, m), 7.12-7.17 (1 H, m), 4.69 (2 H, s), 2.31 (3 H, s), 1.40 (9 H, s). Mass spectrum m/z 358, 260 (M+H)$^+$.

The following Intermediates were also prepared using procedures used to prepare Intermediate 4-1 through 4-4.

| Intermediate | Compound name | Mass spectrum |
|---|---|---|
| 4-5 | 2-(3-bromo-2-methylphenyl)-7-fluoroisoindolin-1-one | 320, 322 (M + H)$^+$ |
| 4-6 | 2-(3-bromo-2-methylphenyl)-4-fluoroisoindolin-1-one | 320, 322 (M + H)$^+$ |
| 4-7 | 2-(3-bromo-2-methylphenyl)-5-methylisoindolin-1-one | 316, 318 (M + H)$^+$ |
| 4-8 | 2-(3-bromo-2-methylphenyl)-5-fluoroisoindolin-1-one | 320, 322 (M + H)$^+$ |

Intermediate 5-1

Preparation of 2-(5-bromo-4-methylpyridin-3-yl)-5-methylisoindolin-1-one

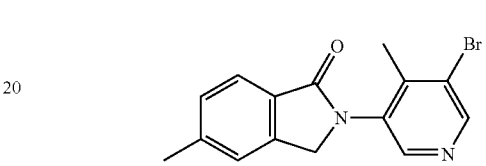

Step 1 A mixture of 5-methylisoindoline-1,3-dione (5.00 g, 31.0 mmol) and tin shavings (8.84 g, 74.5 mmol) in acetic acid (30 mL) and concentrated hydrochloric acid (15 mL) was heated at reflux for 3 h. The hot solution was filtered and the residual tin shavings were washed with acetic acid. The filtrate was concentrated and the residue was diluted with DCM (200 mL), and washed with water (20 mL) and brine (20 mL), dried and concentrated. The precipitate which formed during the concentration was collected by filtration and washed with DCM (5 mL) and dried under vacuum to give 5-methylisoindolin-1-one (2.3 g, 50%). $^1$H NMR (400 MHz, chloroform-d) δ 7.70 (1 H, d, J=7.77 Hz), 7.43 (1 H, s), 7.35 (1 H, d, J=7.77 Hz), 4.46 (2 H, s), 2.48 (3 H, s). Mass spectrum m/z 148.0 (M+H)$^+$.

Step 2 A mixture of 3,5-dibromo-4-methylpyridine (2.00 g, 7.97 mmol), 6-methylisoindolin-1-one (1.173 g, 7.97 mmol), copper (I) iodide (0.076 g, 0.399 mmol), potassium carbonate (2.203 g, 15.94 mmol) and N$^1$,N$^2$-dimethylethane-1,2-diamine (0.070 g, 0.797 mmol) in 1,4-dioxane (20 mL) was heated at 100° C. for 15 h. The mixture was cooled to rt, filtered through Celite and washed with DCM. The filtrate was diluted with DCM (100 mL) and washed with water (10 mL) and brine (10 mL), then was dried and concentrated. The residue was purified by column chromatography (eluting with a gradient from 80:20 hexane-EtOAc to EtOAc) to give 2-(5-bromo-4-methylpyridin-3-yl)-5-methylisoindolin-1-one (760 mg, 30%). $^1$H NMR (400 MHz, chloroform-d) δ 8.68 (1 H, s), 8.42 (1 H, s), 7.84 (1 H, d, J=7.77 Hz), 7.37 (1 H, d, J=7.77 Hz), 7.34 (1 H, s), 4.73 (2 H, s), 2.50 (3 H, s), 2.35 (3 H, s). Mass spectrum m/z 317, 319 (M+H)$^+$.

The following Intermediate was also prepared using procedures used to prepare Intermediate 5-1.

| Intermediate | Compound name | Mass spectrum |
|---|---|---|
| 5-2 | 2-(5-bromo-4-methylpyridin-3-yl)isoindolin-1-one | 351.2 (M + H)$^+$ |

Intermediate 6-1

Preparation of 2-(3-fluoro-4-iodopyridin-2-yl)isoindolin-1-one

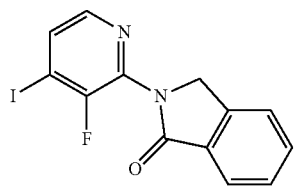 [SMILES: O=C1c2ccccc2CN1c1nccc(I)c1F]

A mixture of 3-fluoro-2,4-diiodopyridine (300 mg, 0.860 mmol), isoindolin-1-one (114 mg, 0.860 mmol), copper (I) iodide (8.19 mg, 0.043 mmol), potassium carbonate (238 mg, 1.720 mmol) and $N^1,N^2$-dimethylethane-1,2-diamine (7.58 mg, 0.086 mmol) in 1,4-dioxane (5 mL) was heated at 110° C. in a sealed tube for 15 h. The mixture was cooled to rt, filtered through Celite and washed with DCM. The filtrate was concentrated and the residue was purified by column chromatography (eluting with a gradient from 80:20 hexane-EtOAc to EtOAc) to give 2-(3-fluoro-4-iodopyridin-2-yl)isoindolin-1-one (125 mg, 41%). $^1$H NMR (400 MHz, chloroform-d) δ 7.86-8.06 (2 H, m), 7.41-7.71 (4 H, m), 5.04 (2 H, s). Mass spectrum m/z 354.9 (M+H)$^+$.

Intermediate 7-1

Preparation of 3-(3-bromo-2-methylphenyl)-2-methylquinazolin-4(3H)-one

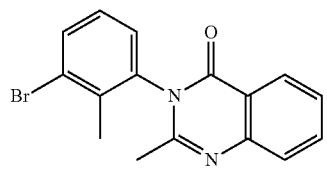 [SMILES: Cc1c(Br)cccc1-n1c(C)nc2ccccc2c1=O]

A solution of 2-methyl-4H-benzo[d][1,3]oxazin-4-one (300 mg, 1.862 mmol), 3-bromo-2-methylaniline (346 mg, 1.862 mmol), and triethoxymethane (276 mg, 1.862 mmol) in THF (2 mL) was heated overnight in a sealed tube at 100° C. The mixture was cooled to rt and diluted with DCM. The solution was washed with water and NaHCO3 (aq), and dried and concentrated. The residue was purified by column chromatography (eluting with a gradient from 90:10 to 50:50 hexane-EtOAc) and the crude product was triturated in hexane to give 3-(3-bromo-2-methylphenyl)-2-methylquinazolin-4(3H)-one as an off-white solid (120 mg, 20%). $^1$H NMR (400 MHz, chloroform-d) δ 8.28 (1 H, dd, J=7.92, 1.10 Hz), 7.77-7.82 (1 H, m), 7.68-7.73 (2 H, m), 7.47-7.52 (1 H, m), 7.22-7.25 (1 H, m), 7.13-7.17 (1 H, m), 2.20 (6H, s). Mass spectrum m/z 329, 331 (M+H)$^+$.

Intermediate 8-1

Preparation of 3-(3-bromo-2-methylphenyl)quinazolin-4 (3H)-one

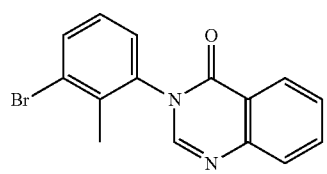 [SMILES: Cc1c(Br)cccc1-n1cnc2ccccc2c1=O]

A mixture of 1H-benzo[d][1,3]oxazine-2,4-dione (200 mg, 1.226 mmol), 3-bromo-2-methylaniline (228 mg, 1.226 mmol), and trimethoxymethane (390 mg, 3.68 mmol) in THF (2 mL) was heated overnight in a sealed tube at 100° C. The mixture was cooled to rt and concentrated, and the residue was purified by column chromatography (eluting with 90:10 to 50:50 hexane-EtOAc) to give 3-(3-bromo-2-methylphenyl)quinazolin-4(3H)-one (140 mg, 36%). $^1$H NMR (400 MHz, chloroform-d) δ 8.37 (1 H, dd, J=8.3, 1.2 Hz), 7.97 (1 H, s), 7.76-7.86 (2 H, m), 7.72 (1 H, t, J=4.6 Hz), 7.57 (1 H, ddd, J=8.0, 6.7, 1.5 Hz), 7.21-7.28 (2 H, m), 2.26 (3 H, s). Mass spectrum m/z 315, 317 (M+H)$^+$.

The following Intermediates were also prepared using procedures used to prepare Intermediate 8-1.

| Intermediate | Compound name | Mass spectrum |
|---|---|---|
| 8-2 | 3-(3-bromo-2-methylphenyl)-5-fluoroquinazolin-4(3H)-one | 333, 335 (M + H)$^+$ |
| 8-3 | 3-(3-bromo-2-methylphenyl)-6-chloroquinazolin-4(3H)-one | 349, 351, 353 (M + H)$^+$ |

Intermediate 9-1

Preparation of 3-(3-bromo-2-methylphenyl)-6-fluoroquinazolin-4(3H)-one

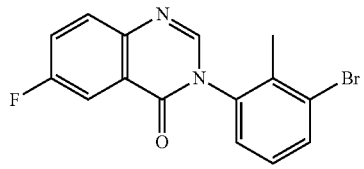 [SMILES: Cc1c(Br)cccc1-n1cnc2ccc(F)cc2c1=O]

A mixture of 2-amino-5-fluorobenzoic acid (1.00 g, 6.45 mmol), 3-bromo-2-methylaniline (1.199 g, 6.45 mmol) and triethoxymethane (0.955 g, 6.45 mmol) in THF (2 mL) was heated at 110° C. overnight in a sealed tube. The mixture was cooled to rt and diluted with EtOAc. The solution was washed with NaHCO3 (aq) and water, then was dried and concentrated. The residue was purified by column chromatography (eluting with a gradient from 80:20 to 70:30 hexane-EtOAc) to give 3-(3-bromo-2-methylphenyl)-6-fluoroquinazolin-4

(3H)-one as a white solid (1.2 g, 56%). ¹H NMR (400 MHz, chloroform-d) δ 8.00 (1 H, dd, J=8.4, 3.1 Hz), 7.93 (1 H, s), 7.81 (1 H, dd, J=9.0, 4.8 Hz), 7.74 (1 H, dd, J=6.9, 2.3 Hz), 7.50-7.58 (1 H, m), 7.21-7.26 (2 H, m), 2.25 (3 H, s). Mass spectrum m/z 333, 335 (M+H)⁺.

The following Intermediates were also prepared using procedures used to prepare Intermediate 9-1.

| Intermediate | Compound name | Mass spectrum |
|---|---|---|
| 9-2 | 3-(3-bromo-2-methylphenyl)-6-methylquinazolin-4(3H)-one | 329, 331 (M + H)⁺ |
| 9-3 | 3-(3-bromo-2-methylphenyl)-8-fluoroquinazolin-4(3H)-one | 333, 335 (M + H)⁺ |
| 9-4 | 3-(3-bromo-2-methylphenyl)-8-methoxyquinazolin-4(3H)-one | 345, 347 (M + H)⁺ |
| 9-5 | 3-(3-bromo-2-methylphenyl)-5-methoxyquinazolin-4(3H)-one | 345, 347 (M + H)⁺ |
| 9-6 | 3-(3-bromo-2-methylphenyl)-7-methoxyquinazolin-4(3H)-one | 345, 347 (M + H)⁺ |
| 9-7 | 3-(3-bromo-2-methylphenyl)-6-(trifluoromethoxy)quinazolin-4(3H)-one | 399, 401 (M + H)⁺ |
| 9-8 | 3-(3-bromo-2-methylphenyl)-8-methylquinazolin-4(3H)-one | 329, 331 (M + H)⁺ |
| 9-9 | 3-(3-bromo-2-methylphenyl)-6-methoxyquinazolin-4(3H)-one | 345, 347 (M + H)⁺ |
| 9-10 | 3-(3-bromo-2-methylphenyl)-7-fluoroquinazolin-4(3H)-one | 333, 335 (M + H)⁺ |

Intermediate 10-1

Preparation of 2-(3-bromo-2-methylphenyl)isoquinolin-1(2H)-one

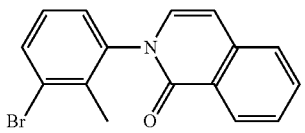

Step 1 A mixture of 3-bromo-2-methylaniline (1 g, 5.37 mmol) and isochroman-1,3-dione (0.872 g, 5.37 mmol) in acetic acid (15 mL) was heated overnight at 100° C. in a sealed tube. The mixture was cooled to rt and concentrated, and the residue was purified by column chromatography (eluting with a gradient from 80:20 hexane-EtOAc to EtOAc) to give 2-(3-bromo-2-methylphenyl)isoquinoline-1,3(2H, 4H)-dione as a tan solid (630 mg, 36%). Mass spectrum m/z 330, 332 (M+H)⁺.

Step 2 A suspension of 2-(3-bromo-2-methylphenyl)isoquinoline-1,3(2H, 4H)-dione (630 mg, 1.908 mmol) in methanol (100 mL) was treated with sodium borohydride (217 mg, 5.72 mmol) at rt. After 1.5 h, additional sodium borohydride (120 mg) was added. After 7 h, the mixture was concentrated and the mmol). The suspension was heated at 100° C. overnight. The mixture was cooled to rt, diluted with water and extracted with EtOAc. The organic phase was washed with brine, dried and concentrated. The residue was purified by column chromatography (eluting with a gradient from 85:15 to 20:80 hexane-EtOAc) to provide N-(3-bromo-2-methylphenyl)-1-(2,2-diethoxyethyl)-1H-imidazole-2-carboxamide as a white solid (0.81 g, 82%). ¹H NMR (400 MHz, DMSO-d₆) δ 10.17 (1 H, s), 7.51 (1 H, d, J=2.6 Hz), 7.49 (1 H, d, J=2.6 Hz), 7.44 (1 H, d, J=1.1 Hz), 7.18 (1 H, t, J=8.0 Hz), 7.10 (1H, d, J=1.1 Hz), 4.75 (1 H, t, J=5.4 Hz), 4.52 (2 H, d, J=5.3 Hz), 3.63 (2 H, dq, J=9.7, 7.0 Hz), 3.35-3.44 (2 H, m), 2.31 (3 H, s), 1.05 (6 H, t, J=7.0 Hz). Mass spectrum m/z 396, 398 (M+H)⁺.

Step 3 A suspension of N-(3-bromo-2-methylphenyl)-1-(2,2-diethoxyethyl)-1H-imidazole-2-carboxamide (0.81 g, 2.044 mmol) in water (10.2 mL) was treated with 1 M hydrochloric acid (8.2 mL, 8.2 mmol) and the mixture was heated at reflux overnight. The mixture was cooled to rt, treated with NaHCO3 (aq), and extracted with EtOAc. A precipitate was collected by filtration to provide a white solid (0.33 g), which was a mixture (ca. 1:1) of 7-(3-bromo-2-methylphenyl)imidazo[1,2-a]pyrazin-8(7H)-one and 7-(3-bromo-2-methylphenyl)-6-hydroxy-6,7-dihydroimidazo[1,2-a]pyrazin-8(5H)-one (Mass spectrum m/z 322, 324 (M+H)⁺). The filtrate was dried and concentrated to afford 7-(3-bromo-2-methylphenyl)imidazo[1,2-a]pyrazin-8(7H)-one as a white solid (0.34 g, 66%) contaminated with a small amount of 7-(3-bromo-2-methylphenyl)-6-hydroxy-6,7-dihydroimidazo[1,2-a]pyrazin-8(5H)-one. Mass spectrum m/z 304, 306 (M+H)⁺. The mixtures could be converted to 7-(3-bromo-2-methylphenyl)imidazo[1,2-a]pyrazin-8(7H)-one, TFA salt, by heating with TFA at reflux for 2 h.

Intermediate 12-1

Preparation of (4-bromo-1H-indol-2-yl)(pyrrolidin-1-yl)methanone

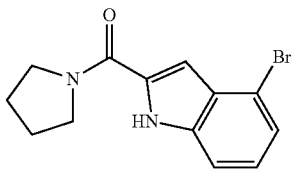 [SMILES: O=C(c1cc2c(Br)cccc2[nH]1)N1CCCC1]

A mixture of 4-bromo-1H-indole-2-carboxylic acid (250 mg, 1.04 mmol), pyrrolidine (0.129 mL, 1.56 mmol), and HOAT (213 mg, 1.56 mmol) in acetonitrile (5 mL) was treated with DIEA (0.364 mL, 2.08 mmol) and EDC (399 mg, 2.08 mmol) residue was partitioned between water and DCM. The organic phase was dried and concentrated to give 2-(3-bromo-2-methylphenyl)-3-hydroxy-3,4-dihydroisoquinolin-1(2H)-one as a light yellow foam (600 mg, 95%), used without further purification. Mass spectrum m/z 332, 334 (M+H)⁺.

Step 3 A solution of crude 2-(3-bromo-2-methylphenyl)-3-hydroxy-3,4-dihydroisoquinolin-1(2H)-one (600 mg, 1.806 mmol) in DCM (30 mL) was treated with triethylsilane (15 mL, 94 mmol) and the resulting mixture was treated slowly with TFA (1.392 mL, 18.06 mmol). The mixture was stirred at rt for 2 h, then was concentrated and the residue was dissolved in DCM. The solution was washed with NaHCO3 (aq) and water, then was dried and concentrated. The residue was purified by column chromatography (eluting with a gradient from 80:20 to 60:40 hexane-EtOAc) to give 2-(3- bromo-2-methylphenyl)isoquinolin-1(2H)-one as a white solid (380 mg, 67%). Mass spectrum m/z 314, 316 (M+H)+.

Intermediate 11-1

Preparation of (3-bromo-2-methylphenyl)imidazo[1,2-a]pyrazin-8(7H)-one

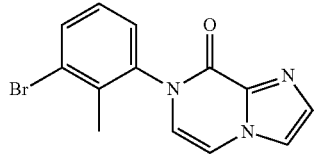 [SMILES: Cc1c(Br)cccc1-n1ccn2ccnc2c1=O]

Step 1 A solution of 3-bromo-2-methylaniline (0.63 g, 3.39 mmol), 1H-imidazole-2-carboxylic acid (0.455 g, 4.06 mmol), HOAT (0.830 g, 6.10 mmol), and EDC (1.298 g, 6.77 mmol) in 2:1 DCM-THF (100 mL) was treated with DIEA (1.774 mL, 10.16 mmol) and stirred at rt overnight. Additional 1H-imidazole-2-carboxylic acid (0.6 eq, 0.228 g), EDC (0.64 g), HOAT (0.41 g), and DIEA (0.8 mL) were added and the mixture was stirred at rt for 6 days. The mixture was partitioned between NaHCO3 (aq) and DCM, and the organic phase was washed with brine, dried and concentrated. The residue was purified by column chromatography (eluting with a gradient from DCM to 94:6 DCM-methanol) to provide N-(3-bromo-2-methylphenyl)-1H-imidazole-2-carboxamide as a solid (80% purity, 0.76 g, 64%). Mass spectrum m/z 280, 282 (M+H)+.

Step 2 A solution of N-(3-bromo-2-methylphenyl)-1H-imidazole-2-carboxamide (0.70 g, 2.499 mmol) in DMF (12.5 mL) was treated with potassium carbonate (0.794 g, 5.75 mmol) and 2-bromo-1,1-diethoxyethane (0.395 mL, 2.62 and the mixture was stirred at rt. After 18.25 h, the mixture was diluted with EtOAc, filtered to remove some tan solid, and washed sequentially with 1 M hydrochloric acid and NaHCO3 (aq), and dried and concentrated to provide (4-bromo-1H-indol-2-yl)(pyrrolidin-1-yl)methanone as a tan solid (205 mg, 67%). 1H NMR (400 MHz, DMSO-d6) δ 11.96 (s, 1 H) 7.46 (d, J=7.9 Hz, 1 H) 7.27 (d, J=7.5 Hz, 1 H) 7.06-7.17 (m, 1 H) 6.82 (s, 1 H) 3.85 (t, J=6.8 Hz, 2 H) 3.55 (t, J=6.8 Hz, 2 H) 1.93-2.04 (m, 2 H) 1.81-1.92 (m, 2 H). Mass spectrum m/z 293, 295 (M+H)+.

The following Intermediates were also prepared using procedures used to prepare Intermediate 12-1.

| Inter-mediate | Compound name | Mass spectrum |
|---|---|---|
| 12-2 | 4-bromo-N-ethyl-1H-indole-2-carboxamide | 267, 269 (M + H)+ |
| 12-3 | 4-bromo-N-(4-fluorophenyl)-1H-indole-2-carboxamide | 333, 335 (M + H)+ |

Intermediate 13-1

Preparation of 2-(3-bromo-2-methylphenyl)isoindoline

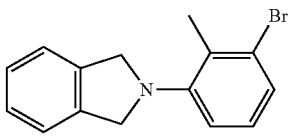 [SMILES: Cc1c(Br)cccc1N1Cc2ccccc2C1]

A mixture of 3-bromo-2-methylaniline (372 mg, 2.00 mmol), 1,2-bis(chloromethyl)benzene (385 mg, 2.20 mmol), and potassium carbonate (304 mg, 2.20 mmol) in water (2 mL) was heated via microwave irradiation in a sealed tube at 120° C. for 25 min. The mixture was extracted with EtOAc and the organic phase was washed with water, dried and concentrated. The residue was purified by column chromatography (eluting with a gradient from hexane to 30:70 EtOAc-hexane) to provide 2-(3-bromo-2-methylphenyl)isoindoline as a light yellow oil (360 mg, 63%). Mass spectrum m/z 288, 290 (M+H)+.

Intermediate 14-1

Preparation of 8-methyl-2-phenylchroman-7-yl trifluoromethanesulfonate

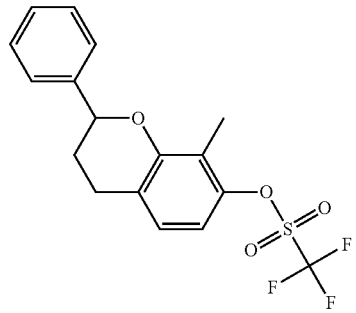 [SMILES: Cc1c(OS(=O)(=O)C(F)(F)F)ccc2c1OC(c1ccccc1)CC2]

Step 1 A suspension of (E)-3-phenylprop-2-en-1-ol (2.22 g, 16.51 mmol) and 2-methylbenzene-1,3-diol (2.05 g, 16.51 mmol) in 1,2-dichloroethane (100 mL) was treated with p-toluenesulfonic acid monohydrate (0.157 g, 0.826 mmol) and the mixture was heated at reflux for 1 h. The mixture was cooled to rt and concentrated, and the residue was subjected to column chromatography (eluting with a gradient from 90:10 to 75:25 hexane-EtOAc) provided a mixture of 4-cinnamyl-2-methylbenzene-1,3-diol and 4,6-dicinnamyl-2-methylbenzene-1,3-diol (2:1, 1.97 g). This material (1.89 g) was dissolved in toluene (60 mL) and treated with p-toluenesulfonic acid monohydrate (299 mg, 1.57 mmol) and heated at reflux for 6 h. The mixture was cooled to rt, diluted with EtOAc (100 mL), washed with NaHCO3 (aq) (2×30 mL), water (30 mL) and brine (30 mL), dried and concentrated. Column chromatography (eluting with a gradient from 95:5 to 70:30 hexane-EtOAc) provided 8-methyl-2-phenylchroman-7-ol as a brown liquid (ca. 85% purity, 672 mg, 17%) used without further purification. 1H NMR (400 MHz, chloroform-d) δ 7.35-7.50 (4 H, m), 7.27-7.35 (1 H, m), 6.79 (1 H, d, J=8.36 Hz), 6.38 (1 H, d, J=8.14 Hz), 5.07 (1 H, dd, J=10.12, 2.42 Hz), 4.64 (1 H, s), 2.83-3.02 (1 H, m), 2.71 (1 H, ddd, J=16.01, 4.90, 3.74 Hz), 2.16-2.27 (1 H, m), 2.14 (3 H, s), 1.86-2.04 (1 H, m). Mass spectrum m/z 241.0 (M+H)⁺.

Step 2 Trifluoromethanesulfonic anhydride (0.613 mL, 3.63 mmol) was added dropwise to a solution of 8-methyl-2-phenylchroman-7-ol (671 mg, 2.79 mmol) in DCM (10 mL) and pyridine (10 mL) at 0° C. After 30 min, the mixture was diluted with EtOAc (70 mL), washed with water (2×30 mL) and brine (30 mL), dried and concentrated. The residue was purified by column chromatography (eluting with a gradient from 95:5 to 85:15 hexane-EtOAc) to give 8-methyl-2-phenylchroman-7-yl trifluoromethanesulfonate as colorless liquid (925 mg, 89%). ¹H NMR (400 MHz, chloroform-d) δ 7.28-7.61 (5 H, m), 6.97 (1 H, d, J=8.58 Hz), 6.79 (1 H, d, J=8.58 Hz), 5.11 (1 H, dd, J=10.23, 2.31 Hz), 2.99 (1 H, ddd, J=16.73, 11.11, 5.83 Hz), 2.68-2.88 (1 H, m), 2.17-2.32 (4 H, m), 1.88-2.12 (1 H, m). Mass spectrum m/z 390.0 (M+H)⁺.

Intermediate 15-1

Preparation of 6-bromo-3-phenyl-3,4-dihydro-2H-benzo[e][1,3]oxazin-2-one

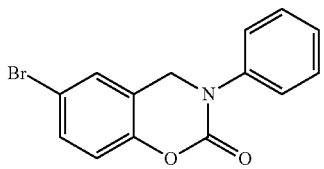 [SMILES: O=C1Oc2ccc(Br)cc2CN1c1ccccc1]

Step 1 Aniline (1.50 mL, 16.42 mmol) was added to a solution of 5-bromo-2-hydroxybenzaldehyde (3.00 g, 14.92 mmol) in 1,2-dichloroethane (100 mL). After 10 min at rt, sodium triacetoxyborohydride (4.74 g, 22.39 mmol) was added. The mixture was stirred at rt. After four days, additional aniline (1.50 mL, 16.42 mmol) and sodium triacetoxyborohydride (4.74 g, 22.39 mmol) were added. After two more days, saturated aqueous ammonium chloride (200 mL) was added. The mixture was stirred at rt for 3 h. The phases were separated and the aqueous phase was extracted with DCM (2×50 mL). The combined organic phases were dried and concentrated. The residue was treated with toluene (25 mL) and hexanes (25 mL) and the mixture was stirred for 30 min. The precipitate was washed with 1:1 mixture of toluene-hexanes (3 mL) and dried under vacuum to give 4-bromo-2-((phenylamino)methyl)phenol as a white solid (2.64 g, 64%). ¹H NMR (400 MHz, DMSO-d₆) δ 8.70 (1 H, br. s.), 7.18-7.46 (4 H, m), 6.95 (1 H, t, J=7.48 Hz), 6.80-6.90 (2 H, m), 6.77 (1 H, d, J=8.58 Hz), 4.39 (2 H, s), 3.98 (1 H, br. s.). Mass spectrum m/z 278, 280 (M+H)⁺.

Step 2 Carbonyldiimidazole (0.874 g, 5.39 mmol) and DMAP (0.088 g, 0.719 mmol) were added to a solution of 4-bromo-2-((phenylamino)methyl)phenol (1.00 g, 3.60 mmol) in DCM (100 mL) and the resulting mixture was stirred at rt for 60 h. The mixture was diluted with hexanes (100 mL), washed with NaHCO3 (aq) (2×25 mL), 1 M hydrochloric acid (25 mL) and brine (25 mL), dried and filtered through a pad of silica gel. The solids were rinsed with 1:1 EtOAc-hexane and the filtrate was concentrated to give 6-bromo-3-phenyl-3,4-dihydro-2H-benzo[e][1,3]oxazin-2-one as a white solid (1.09 g, 100%). ¹H NMR (400 MHz, DMSO-d₆) δ 7.41-7.56 (3 H, m), 7.30-7.41 (3 H, m), 7.21-7.29 (1 H, m), 7.01 (1 H, d, J=8.80 Hz), 4.80 (2 H, s). Mass spectrum m/z 304, 306 (M+H)⁺.

Intermediate 16-1

Preparation of 3-bromo-6-hydroxy-2-methyl-N-phenylbenzamide

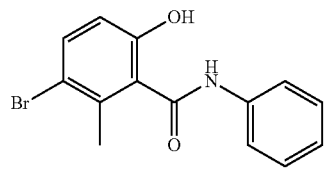 [SMILES: Cc1c(Br)ccc(O)c1C(=O)Nc1ccccc1]

Step 1 A solution of ethyl 2-hydroxy-6-methylbenzoate (2.04 g, 11.32 mmol) in methanol (25 mL) was treated at rt with 1 M aqueous sodium hydroxide (45.3 mL, 45.3 mmol) and the mixture was heated at reflux for 6 h. The mixture was cooled to rt and the methanol was removed under vacuum. The aqueous residue was treated with 1 M hydrochloric acid to pH ca. 1. The precipitate was collected by filtration, washed with water and dried under vacuum to give 2-hydroxy-6-methylbenzoic acid as a white solid (1.62 g, 94%). ¹H NMR (400 MHz, methanol-d₄) δ 7.26 (1 H, t, J=7.92 Hz), 6.75 (2 H, t, J=7.92 Hz), 2.55 (3 H, s). Mass spectrum m/z 153.1 (M+H)⁺.

Step 2 A suspension of 2-hydroxy-6-methylbenzoic acid (1.32 g, 8.68 mmol) in acetonitrile (20 mL) at −20° C. was treated with tetrafluoroboric acid dimethyl ether complex (1.109 mL, 9.11 mmol), followed by portionwise addition of N-bromosuccinimide (1.699 g, 9.54 mmol) over 30 min. The mixture was warmed to 0° C. and stirred for 1 h, then was treated with 40% aqueous sodium bisulfate (10 mL). The acetonitrile was removed under vacuum and the aqueous residue was extracted with EtOAc (3×40 mL). The combined organic layers were washed with water and brine, dried and concentrated to give 3-bromo-6-hydroxy-2-methylbenzoic acid as a white solid (1.60 g, 80%). ¹H NMR (400 MHz, methanol-d₄) δ 7.47 (1 H, d, J=8.80 Hz), 6.67 (1 H, d, J=8.80 Hz), 2.50 (3 H, s). Mass spectrum m/z 231, 233 (M−H)⁻.

Step 3 Thionyl chloride (0.111 mL, 1.524 mmol) was added to a solution of benzotriazole (594 mg, 4.99 mmol) in DCM (8 mL) at rt and the mixture was stirred for 30 min. A solution of 3-bromo-6-hydroxy-2-methylbenzoic acid (320 mg, 1.385 mmol) in THF (8.00 mL) was added and the mixture was stirred at rt for 2 hrs. The mixture was filtered and the solid was washed with DCM (3 mL). The filtrate was concentrated, and the residue was dissolved in aniline (2 g, 21.48 mmol) and heated in a sealed tube by microwave irradiation at 150° C. for 10 min. The mixture was diluted with EtOAc (100 mL) and washed with 2 M hydrochloric acid (20 mL), water (10 mL) and brine (10 mL), dried and concentrated. The residue was triturated with DCM (4 mL) to give the 3-bromo- 6-hydroxy-2-methyl-N-phenylbenzamide as light-colored solid (290 mg, 68%). Mass spectrum m/z 306, 308 (M+H)+.

Intermediate 17-1

Preparation of 6-bromo-5-methyl-3-phenyl-3,4-dihydro-2H-benzo[e][1,3]oxazin-2-one

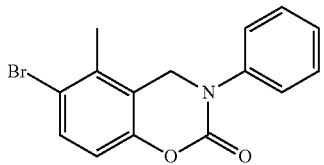 [SMILES: Cc1c(Br)ccc2c1CN(c1ccccc1)C(=O)O2]

A solution of 3-bromo-6-hydroxy-2-methyl-N-phenylbenzamide (Intermediate 16-1, 50 mg, 0.163 mmol) in THF (2 mL) was treated at rt with lithium aluminum hydride (50 mg, 1.317 mmol) and the mixture was heated at reflux for 2 h. It was then cooled to rt and carefully treated with saturated aqueous ammonium chloride (2 mL). The mixture was diluted with DCM (60 mL) and washed with water (5 mL) and brine (5 mL), dried and concentrated to give the 4-bromo-3-methyl-2-((phenylamino)methyl)phenol (45 mg). Without purification, this material was dissolved in DCM (3 1M) and treated with carbonyldiimidazole (30.5 mg, 0.188 mmol) and DMAP (2.091 mg, 0.017 mmol) at rt and the mixture was stirred for 1 h. The mixture was diluted with DCM (60 mL) and washed with NaHCO3 (aq) (5 mL) and brine (5 mL), dried and concentrated. The residue was purified by column chromatography (eluting with a gradient from 95:5 to 50:50 hexane-EtOAc) to give 6-bromo-5-methyl-3-phenyl-3,4-dihydro-2H-benzo[e][1,3]oxazin-2-one (25 mg). $^1$H NMR (400 MHz, chloroform-d) δ 7.33-7.57 (6 H, m), 6.88 (1 H, d, J=8.88 Hz), 4.82 (2 H, s), 2.30 (3 H, s). Mass spectrum m/z 318, 320 (M+H)+.

Intermediate 18-1

Preparation of 6-bromo-5-methyl-3-phenyl-2H-benzo[e][1,3]oxazin-4(3H)-one

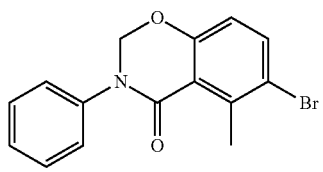 [SMILES: Cc1c(Br)ccc2c1C(=O)N(c1ccccc1)CO2]

A mixture of 3-bromo-6-hydroxy-2-methyl-N-phenylbenzamide (Intermediate 16-1, 40 mg, 0.131 mmol) and paraformaldehyde (11.77 mg, 0.392 mmol) in TFA (1 mL) was heated at 100° C. for 4 h. The TFA was removed under vacuum, and the residue was diluted with EtOAc (80 mL), washed with NaHCO3 (aq) (10 mL), water (10 mL) and brine (10 mL), and dried and concentrated. The residue was purified by column chromatogaphy (eluting with a gradient from 95:5 to 70:30 hexane-EtOAc) to give 6-bromo-5-methyl-3-phenyl-2H-benzo[e][1,3]oxazin-4(3H)-one (25 mg, 45%). $^1$H NMR (400 MHz, chloroform-d) δ 7.63 (1 H, d, J=8.80 Hz), 7.37-7.50 (3 H, m), 7.29-7.35 (2 H, m), 6.81 (1 H, d, J=8.80 Hz), 5.48 (2 H, s), 2.80 (3 H, s). Mass spectrum m/z 318, 320 (M+H)+.

Intermediate 19-1

Preparation of 6-bromo-5-methyl-3-phenyl-2H-benzo[e][1,3]oxazine-2,4(3H)-dione

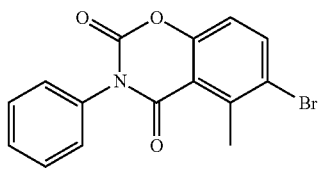 [SMILES: Cc1c(Br)ccc2oc(=O)n(-c3ccccc3)c(=O)c12]

Step 1 A solution of 3-bromo-6-hydroxy-2-methyl-N-phenylbenzamide (Intermediate 16-1, 40 mg, 0.131 mmol) in pyridine (1 mL) was treated with ethyl chloroformate (0.015 mL, 0.157 mmol) at rt and the mixture was heated to 100° C. for 2 h. Additional ethyl chloroformate (0.015 mL, 0.157 mmol) was added and the mixture was stirred at 100° C. for 15 h. The mixture was cooled and diluted with EtOAc (80 mL), and the solution was washed with NaHCO3 (aq) (10 mL), water (2×10 mL) and brine (10 mL), and dried and concentrated. The residue was purified by column chromatogaphy (eluting with a gradient from 95:5 to 70:30 hexane-EtOAc) to give 6-bromo-5-methyl-3-phenyl-2H-benzo[e][1,3]oxazine-2,4(3H)-dione (19 mg, 44%). $^1$H NMR (400 MHz, chloroform-d) δ 7.90 (1 H, d, J=9.02 Hz), 7.43-7.68 (3 H, m), 7.27-7.40 (2 H, m), 7.12 (1 H, d, J=8.80 Hz), 2.90 (3H, s). Mass spectrum m/z 332, 334 (M+H)+.

Intermediate 20-1

Preparation of N-(3-bromo-2-methylphenyl)-1H-indazol-3-amine

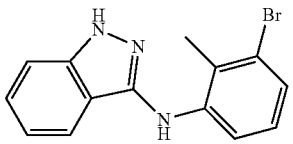 [SMILES: Cc1c(Br)cccc1Nc1n[nH]c2ccccc12]

Step 1 A mixture of 3-bromo-2-methylaniline (1.66 mL, 13.4 mmol), 2-fluorobenzoic acid (1.883 g, 13.4 mmol), and HOAT (2.74 g, 20.2 mmol) in EtOAc (60 mL) was treated with DIEA (4.7 mL, 26.9 mmol) and EDC (5.15 g, 26.9 mmol) and the mixture was stirred at rt. After 19 h, the mixture was diluted with EtOAc and washed with water, 1 M hydrochloric acid (twice), NaHCO3 (aq) (twice) and brine, dried and concentrated to provide N-(3-bromo-2-methylphenyl)-2-fluorobenzamide as tan fluffy needles (4.11 g, 99%). $^1$H NMR (400 MHz, chloroform-d) δ 8.34-8.50 (1 H, m), 8.20 (1 H, td, J=7.9, 1.8 Hz), 7.96 (1 H, d, J=8.1 Hz), 7.50-7.59 (1 H, m), 7.44 (1 H, dd, J=8.0, 0.8 Hz), 7.30-7.37 (1 H, m), 7.21 (1 H, dd, J=12.8, 7.9 Hz), 7.12 (1 H, t, J=8.0 Hz), 2.45 (3 H, s). Mass spectrum m/z 308, 310 (M+H)+.

Step 2 A mixture of N-(3-bromo-2-methylphenyl)-2-fluorobenzamide (2.00 g, 6.49 mmol) and 2,4-bis-(4-methoxyphenyl)-1,3-dithia-2,4-diphosphetane 2,4-disulfide (Lawesson reagent, 1.575 g, 3.89 mmol) in toluene (25 mL)

was heated at reflux. After 3.5 h, the solution was cooled to rt and concentrated to provide a dark yellow solid. This was purified by column chromatography (eluting with a gradient from 95:5 to 90:10 hexane-EtOAc) to provide N-(3-bromo-2-methylphenyl)-2-fluorobenzothioamide as a yellow solid (1.892 g, 90%). $^1$H NMR (400 MHz, chloroform-d) δ 9.18 (1 H, d, J=7.7 Hz), 8.23 (1 H, td, J=8.0, 1.8 Hz), 7.60 (1 H, d, J=7.9 Hz), 7.45-7.52 (1 H, m), 7.43 (1 H, d, J=7.7 Hz), 7.23-7.30 (1 H, m), 7.11-7.21 (2 H, m), 2.41 (3 H, s). Mass spectrum m/z 324, 326 (M+H)$^+$.

Step 3 A yellow solution of N-(3-bromo-2-methylphenyl)-2-fluorobenzothioamide (500 mg, 1.542 mmol) in DMSO (5 mL) was treated with anhydrous hydrazine (0.484 mL, 15.42 mmol) and heated at 150° C. After 2 h 20 min the solution was cooled to rt, diluted with NaHCO3 (aq) and extracted twice with EtOAc. The combined organic phases were washed twice with water and once with brine, dried and concentrated. The residue was purified by column chromatography (eluting with a gradient from 85:15 to 50:50 hexane-EtOAc) to provide N-(3-bromo-2-methylphenyl)-1H-indazol-3-amine as a tan waxy solid (162 mg, 35%). $^1$H NMR (400 MHz, chloroform-d) δ 9.38 (1 H, br. s.), 7.49 (1 H, d, J=8.1 Hz), 7.45 (1 H, d, J=7.9 Hz), 7.40 (2 H, d, J=3.5 Hz), 7.19 (1 H, dd, J=7.9, 0.9 Hz), 7.10 (1 H, dt, J=8.1, 4.0 Hz), 6.98 (1 H, t, J=8.1 Hz), 6.10 (1 H, s), 2.49 (3 H, s). Mass spectrum m/z 302, 304 (M+H)$^+$.

Intermediate 21-1

Preparation of tert-butyl 3-bromo-6-(4-fluorophenyl)-1H-indole-1-carboxylate

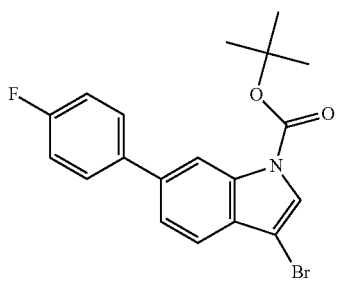 [SMILES: CC(C)(C)OC(=O)n1cc(Br)c2ccc(-c3ccc(F)cc3)cc21]

Step 1 A mixture of 6-bromo-1H-indole (0.25 g, 1.275 mmol), 4-fluorophenylboronic acid (0.178 g, 1.275 mmol), and 2 M aqueous sodium carbonate (2.0 mL, 4.00 mmol) in toluene (10 mL) and ethanol (2.500 mL) was purged with argon and treated with tetrakis(triphenylphosphine)palladium (0.074 g, 0.064 mmol). The mixture was heated at 90° C. After 17 h, the mixture was cooled to rt and partitioned between water and EtOAc. The organic phase was dried and concentrated. The residue was purified by column chromatography (eluting with a gradient from 95:5 to 60:40 hexane-EtOAc) to provide 6-(4-fluorophenyl)-1H-indole as a white solid (175.5 mg, 65%). $^1$H NMR (400 MHz, DMSO-d$_6$) δ 11.17 (1 H, br. s.), 7.65-7.71 (2 H, m), 7.56-7.62 (2 H, m), 7.37 (1 H, t, J=2.9 Hz), 7.22-7.31 (3 H, m), 6.44 (1 H, t, J=2.0 Hz). Mass spectrum m/z 212.2 (M+H)$^+$.

Step 2 A solution of 6-(4-fluorophenyl)-1H-indole (172 mg, 0.814 mmol) in THF (5 mL) was treated with di-tert-butyldicarbonate (213 mg, 0.977 mmol) and DMAP (24.87 mg, 0.204 mmol) and stirred at rt. After 21 h, the mixture was concentrated and the residue was dissolved in EtOAc and washed with 0.2 M hydrochloric acid. The organic phase was dried and concentrated. The residue was purified by column chromatography (eluting with a gradient from 95:5 to 50:50 hexane-EtOAc) to provide tert-butyl 6-(4-fluorophenyl)-1H-indole-1-carboxylate as a colorless gum (199.7 mg, 79%). $^1$H NMR (400 MHz, chloroform-d) δ 8.39 (1 H, br. s.), 7.54-7.67 (4 H, m), 7.43 (1 H, dd, J=8.1, 1.5 Hz), 7.13 (2 H, t, J=8.6 Hz), 6.58 (1H, d, J=3.5 Hz), 1.68 (9 H, s). Mass spectrum m/z 312.2 (M+H)$^+$.

Step 3 A solution of tert-butyl 6-(4-fluorophenyl)-1H-indole-1-carboxylate (187.8 mg, 0.603 mmol) in THF (4 mL) was treated with N-bromosuccinimide (118 mg, 0.663 mmol) and stirred at rt. After 18 h, the solution was diluted with ether, washed with 2×10 mL aqueous sodium bisulfite (ca. 1.5 M), then with NaHCO3 (aq), dried and concentrated. The residue was purified by column chromatography (eluting with a gradient from hexane to 90:10 hexane-EtOAc) provide tert-butyl 3-bromo-6-(4-fluorophenyl)-1H-indole-1-carboxylate as a white glassy foam (134 mg, 57%). $^1$H NMR (400 MHz, chloroform-d) δ 8.39 (1 H, br. s.), 7.59-7.68 (3 H, m), 7.54-7.59 (1 H, m), 7.48-7.53 (1 H, m), 7.14 (2 H, t, J=8.7 Hz), 1.67 (9 H, s).

Intermediate 22-1

Preparation of 3-(3-bromo-2-methylbenzylidene)indolin-2-one

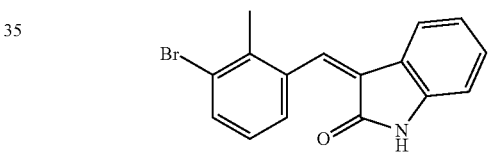

Step 1 A mixture of (3-bromo-2-methylphenyl)methanol (prepared according to the procedures reported in US Pat. Appl. 2006/0173183, 500 mg, 2.49 mmol) in THF (20 mL) was stirred at rt and treated with 1,1,1-tris(acetyloxy)-1,1-dihydro-1,2-benziodoxol-3-(1H)-one (Dess-Martin periodinane, 1.58 g, 3.73 mmol). After 2 h, the mixture was diluted with ether (ca. 100 mL) and washed with 5% aqueous sodium bisulfite, NaHCO3 (aq) and brine, dried and concentrated. The residue was purified by column chromatography (eluting with a gradient from hexane to 55:45 hexane-EtOAc) to provide 3-bromo-2-methylbenzaldehyde as a colorless oil (343 mg, 70%). $^1$H NMR (400 MHz, chloroform-d) δ 10.26 (1 H, s), 7.78 (2 H, ddd, J=9.7, 8.0, 1.2 Hz), 7.20-7.27 (1 H, m), 2.75 (3 H, s).

Step 2 A solution of 3-bromo-2-methylbenzaldehyde (200 mg, 1.01 mmol) and indolin-2-one (134 mg, 1.01 mmol) in ethanol (10 mL) was treated with piperidine (0.099 mL, 1.01 mmol) and heated at 80-85° C. After 15.25 h, the solution was cooled to rt and concentrated. The residue was purified by column chromatography (eluting with a gradient from 80:20 to 30:70 hexane-ethyl acetate) to provide 3-(3-bromo-2-methylbenzylidene)indolin-2-one as a bright yellow solid (94.9 mg, 30%). $^1$H NMR (400 MHz, chloroform-d) δ 7.89 (1 H, br. s.), 7.85 (1 H, s), 7.64 (1 H, d, J=7.9 Hz), 7.47 (1 H, d, J=7.7 Hz), 7.20 (1 H, td, J=7.7, 1.1 Hz), 7.07-7.16 (2 H, m), 6.87 (1

H, d, J=7.9 Hz), 6.81 (1 H, td, J=7.6, 1.0 Hz), 2.43 (3 H, s). Mass spectrum m/z 314, 316 (M+H)⁺.

Intermediate 23-1

Preparation of 7-bromo-3,4-dihydroisoquinolin-1(2H)-one

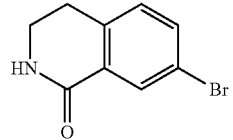

Sodium azide (0.431 g, 6.63 mmol) was added slowly to a mixture of 6-bromo-2,3-dihydro-1H-inden-1-one (1 g, 4.74 mmol) and methanesulfonic acid (15 mL, 231 mmol) in DCM (30 mL) at 0° C. The mixture was stirred at rt for 15 hrs, then was carefully quenched with 1 M aqueous sodium hydroxide (50 mL). The aqueous layer was extracted with DCM (3×50 mL), and the combined organic layers were washed with water (20 mL) and brine (20 mL), dried and concentrated. The residue was purified by column chromatography (eluting with a gradient from 90:10 hexane-EtOAc to EtOAc) to give 7-bromo-3,4-dihydroisoquinolin-1(2H)-one as white solid (650 mg, 61%). ¹H NMR (400 MHz, chloroform-d) δ 8.35 (1 H, br. s.), 7.08-7.17 (1 H, m), 6.98-7.06 (1 H, m), 6.95 (1 H, d, J=1.98 Hz), 2.93 (2 H, t, J=7.59 Hz), 2.49-2.68 (2 H, m). Mass spectrum m/z 226, 228 (M+H)⁺.

Intermediate 24-1

Preparation of 7-bromo-2-(4-fluorophenyl)-3,4-dihydroisoquinolin-1(2H)-one

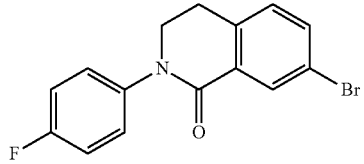 [SMILES: O=C1c2cc(Br)ccc2CCN1c1ccc(F)cc1]

A mixture of 7-bromo-3,4-dihydroisoquinolin-1(2H)-one (Intermediate 23-1, 60 mg, 0.265 mmol), 1-fluoro-4-iodobenzene (118 mg, 0.531 mmol), potassium carbonate (36.7 mg, 0.265 mmol) and copper (I) iodide (10.11 mg, 0.053 mmol) in DMF (1.000 mL) was heated at 130° C. for 5 h. The mixture was cooled to rt and filtered through a Celite pad, and the solids were washed with EtOAc. The filtrate was washed with water and brine, dried and concentrated. The residue was purified by column chromatography (eluting with a gradient from 90:10 to 60:40 hexane-EtOAc) to give 7-bromo-2-(4-fluorophenyl)-3,4-dihydroisoquinolin-1(2H)-one (40 mg, 47%). ¹H NMR (400 MHz, chloroform-d) δ 7.15-7.27 (4 H, m), 7.04-7.13 (2 H, m), 6.48 (1 H, d, J=1.94 Hz), 2.96-3.08 (2 H, m), 2.73-2.84 (2 H, m). Mass spectrum m/z 320, 322 (M+H)⁺.

Intermediate 25-1

Preparation of 4-bromo-1-(4-fluorobenzyl)-1H-indole

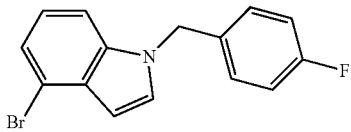

A suspension of sodium hydride (60% oil dispersion, 112 mg, 2.81 mmol) in THF (12 mL) was stirred at rt and treated with a solution of 4-bromo-1H-indole (500 mg, 2.55 mmol) in THF (3 mL). After 1-2 min, the mixture was treated with 4-fluorobenzyl bromide (0.318 mL, 2.55 mmol) and the slightly cloudy solution was stirred at rt. After 20 h, the mixture was concentrated. The residue was partitioned between EtOAc and 0.1 M hydrochloric acid, and the aqueous phase was again extracted with EtOAc. The combined organic layers were washed with brine, dried and concentrated. The residue was purified by column chromatography (eluting with a gradient from 90:10 to 50:50 hexane-EtOAc) to provide 4-bromo-1-(4-fluorobenzyl)-1H-indole as a colorless oil (461.4 mg, 85% purity, 51%) contaminated by ca. 15% by weight of 4-bromo-1,3-bis(4-fluorobenzyl)-1H-indole. ¹H NMR (400 MHz, chloroform-d) δ 7.28 (1 H, dd, J=7.6, 0.8 Hz), 7.19 (1 H, d, J=8.4 Hz), 7.16 (1 H, d, J=3.3 Hz), 6.94-7.09 (5 H, m), 6.60 (1 H, dd, J=3.1, 0.9 Hz), 5.28 (2 H, s). Mass spectrum m/z 304, 306 (M+H)⁺.

Intermediate 26-1

Preparation of (5-bromonaphthalen-1-yl)(4-fluorophenyl)methanone

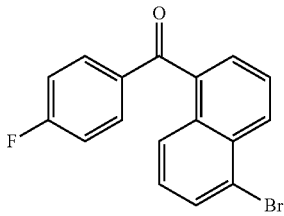 [SMILES: O=C(c1ccc(F)cc1)c1cccc2c(Br)cccc12]

Step 1 A solution of 5-bromo-1-naphthoic acid (prepared according to the procedure of Hausamann, Chem. Ber., 1876, 9, 1519; 2.00 g, 7.97 mmol) in THF (50 mL) was treated with TEA (2.22 mL, 15.93 mmol), then with isobutyl chloroformate (1.088 g, 7.97 mmol) and the resulting suspension was stirred at rt. After 25 min, the mixture was treated with additional TEA (2.22 mL, 15.93 mmol), then with a solution of N,O-dimethylhydroxylamine hydrochloric acid salt (0.777 g, 7.97 mmol) in water (5 mL), and the mixture was stirred at rt. After 2.5 h, the mixture was concentrated and the residue was taken up in EtOAc and water. The mixture was filtered, the layers were separated, and the organic phase was washed with NaHCO3 (aq), dried and concentrated to provide 5-bromo- N-methoxy-N-methyl-1-naphthamide as a pasty solid (1.03 g, 30%) contaminated with ca. 30% isobutyl 5-bromo-1-naphthoate. Mass spectrum m/z 294, 296 (M+H)+. Without further purification, a solution of this material (1.01 g, 2.404 mmol) in THF (15 mL) was stirred on ice and treated with (4-fluorophenyl)magnesium bromide, 2M in ether (7.21 mL, 14.42 mmol). The solution was stirred on ice and allowed to slowly warm to rt. After 16 h, the mixture was treated with 1 M hydrochloric acid and extracted twice with EtOAc. The combined organic layers were dried and concentrated. The residue was purified by column chromatography (eluting with a gradient from hexane to 85:15 hexane-EtOAc) to provide (5-bromonaphthalen-1-yl)(4-fluorophenyl)methanone as a pale yellow viscous oil (658 mg, 83%). 1H NMR (400 MHz, methanol-d4) δ 8.49 (1 H, d, J=8.6 Hz), 7.95 (1 H, d, J=8.6 Hz), 7.86-7.93 (3 H, m), 7.74 (1 H, dd, J=8.5, 7.2 Hz), 7.64-7.68 (1 H, m), 7.40 (1 H, dd, J=8.5, 7.6 Hz), 7.25 (2 H, t, J=8.8 Hz). Mass spectrum m/z 329, 331 (M+H)+.

Intermediate 27-1

Preparation of 1-(3-bromo-2-methylphenyl)piperidin-2-one

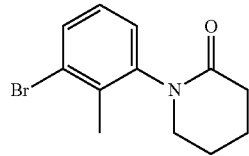

A solution of 3-bromo-2-methylaniline (1 g, 5.37 mmol) in DCM (15 mL) was treated with TEA (0.749 mL, 5.37 mmol) and then dropwise with a solution of 5-bromopentanoyl chloride (1.072 g, 5.37 mmol) in DCM (4 mL). The mixture was stirred at rt for 30 min, then was diluted with DCM, washed with water and brine, and dried and concentrated. The residue was dissolved in THF (100 mL) and added to a suspension of sodium hydride (60% oil dispersion, pre-washed with hexane, 0.430 g, 10.75 mmol) in THF (50 mL). The resulting mixture was stirred overnight at rt. The mixture was concentrated and the residue was acidified with 1 M hydrochloric acid. The mixture was extracted with DCM and the organic phase was washed with water, dried and concentrated to give 1-(3-bromo-2-methylphenyl)piperidin-2-one as a tan oil (1.4 g, 97%). 1H NMR (400 MHz, chloroform-d) δ 7.49-7.54 (1 H, m), 7.07-7.13 (2 H, m), 3.38-3.60 (2 H, m), 2.54-2.59 (2 H, m), 2.26 (3 H, s), 1.91-2.02 (4H, m). Mass spectrum m/z 268, 270 (M+H)+.

Intermediate 28-1

Preparation of N-(3-bromo-2-methylphenyl)cyclopropanecarboxamide

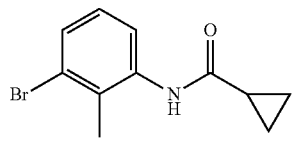

A solution of 3-bromo-2-methylaniline (2.00 g, 10.75 mmol) in DCM (20 mL) was treated with TEA (3.00 mL, 21.50 mmol) and then with a solution of 4-bromobutanoyl chloride (2.392 g, 12.90 mmol) in DCM (10 mL), and the resulting mixture was stirred at rt. After 2.5 h, the mixture was diluted with DCM, washed with NaHCO3 (aq) and water, and dried and concentrated. The residue was dissolved in THF (20 mL) and treated with hexane-washed sodium hydride (60% oil dispersion, 0.860 g, 21.50 mmol). The mixture was stirred at rt for 1.5 h, then was concentrated. The residue was dissolved in DCM, washed with water, 1 M hydrochloric acid and brine, and dried and concentrated. The residue was purified by column chromatography (eluting with a gradient from 80:20 hexane-EtOAc to EtOAc) to provide N-(3-bromo-2-methylphenyl)cyclopropanecarboxamide (900 mg, 33%) as a white solid. Mass spectrum m/z 254, 256 (M+H)+.

Intermediate 29-1 and 29-2

Preparation of 7-(3-bromo-2-methylphenyl)-2-methylimidazo[1,2-a]pyrazin-8(7H)-one and 7-(3-bromo-2-methylphenyl)-3-methylimidazo[1,2-a]pyrazin-8(7H)-one

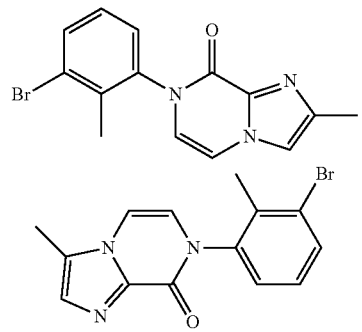

Following the procedures used to prepare Intermediate 11-1 but substituting 4-methyl-1H-imidazole-2-carboxylic acid for 1H-imidazole-2-carboxylic acid, a mixture of 7-(3-bromo-2-methylphenyl)-2-methylimidazo[1,2-a]pyrazin-8(7H)-one and 7-(3-bromo-2-methylphenyl)-3-methylimidazo[1,2-a]pyrazin-8(7H)-one was prepared in 5% overall yield. Mass spectrum m/z 318, 320 (M+H)+.

Intermediate 30-1

Preparation of 1-(3-bromo-2-methylphenyl)-3-m-tolylimidazolidin-2-one

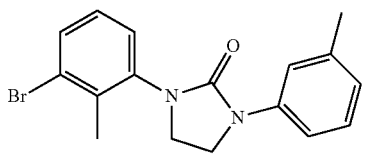 [SMILES: Cc1cccc(N2CCN(c3cccc(Br)c3C)C2=O)c1]

A suspension of 1,3-dibromo-2-methylbenzene (185 mg, 0.740 mmol), 1-m-tolylimidazolidin-2-one (50 mg, 0.284 mmol), copper (I) iodide (5.40 mg, 0.028 mmol), tripotassium phophosphate (120 mg, 0.567 mmol) and (+/−)-trans-1,2-diaminocyclohexane (3.4 µL, 0.028 mmol) in 1,4-dioxane (1 mL) was purged with nitrogen and heated at 120° C. in a sealed tube. After 21.5 h, the mixture was concentrated and the residue was purified by column chromatography (eluting with a gradient from hexane to 50:50 hexane-EtOAc) to provide 1-(3-bromo-2-methylphenyl)-3-m-tolylimidazolidin-2-one as a white solid (70 mg, 70%). ¹H NMR (400 MHz, chloroform-d) δ 7.51-7.54 (1 H, m), 7.49 (1 H, s), 7.34 (1 H, dd, J=8.05, 1.94 Hz), 7.24 (2 H, d, J=8.05 Hz), 7.11 (1 H, t, J=7.91 Hz), 6.90 (1 H, d, J=7.49 Hz), 3.98-4.04 (2 H, m), 3.81-3.87 (2 H, m), 2.38 (3 H, s), 2.36 (3 H, s). Mass spectrum m/z 345, 347 (M+H)⁺.

Intermediate 30-2

Preparation of 1-benzyl-3-(3-bromo-2-methylphenyl)imidazolidin-2-one

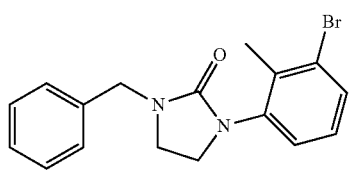 [SMILES: Cc1c(Br)cccc1N1CCN(Cc2ccccc2)C1=O]

Step 1 A solution of imidazolidin-2-one (500 mg, 5.81 mmol) in DMF (30 mL) was stirred on ice and treated with sodium hydride, 60% oil dispersion (264 mg, 6.60 mmol). The mixture was stirred at rt for 50 min, then was treated with (bromomethyl)benzene (0.691 mL, 5.81 mmol). After 2 h, the mixture was poured into water and extracted three times with EtOAc. The combined organic layers were dried and concentrated, and the residue was purified by column chromatography (eluting with EtOAc) to provide 1-benzylimidazolidin-2-one as a white solid (160 mg, 16%). ¹H NMR (400 MHz, chloroform-d) δ 7.22-7.39 (5 H, m), 4.53 (1 H, br. s.), 4.37 (2 H, s), 3.25-3.46 (4 H, m).

Step 2 A mixture of 1,3-dibromo-2-methylbenzene (0.147 mL, 1.064 mmol), 1-benzylimidazolidin-2-one (75 mg, 0.426 mmol), copper (I) iodide (8.11 mg, 0.043 mmol), (+/−)-trans-1,2-diaminocyclohexane (5.1 mL, 0.043 mmol) and tripotassium phosphate (181 mg, 0.851 mmol) in dioxane (2 mL) was sonicated while bubbling with argon for 1 min. The mixture was heated in a sealed tube at 120° C. After 18.25 h, the mixture was cooled to rt, diluted with EtOAc and filtered through Celite. The filtrate was concentrated and the residue was purified by column chromatography (eluting with a gradient from 20:80 EtOAc-hexane to EtOAc) to provide 1-benzyl-3-(3-bromo-2-methylphenyl)imidazolidin-2-one as a waxy white solid (36 mg, 25%). ¹H NMR (400 MHz, chloroform-d) δ 7.49 (1 H, dd, J=7.9, 0.9 Hz), 7.28-7.40 (5 H, m), 7.19 (1 H, dd, J=7.8, 1.0 Hz), 7.08 (1 H, t, J=7.9 Hz), 4.46 (2 H, s), 3.64 (2 H, dd, J=8.8, 6.8 Hz), 3.37 (2 H, dd, J=8.8, 7.0 Hz), 2.36 (3 H, s). Mass spectrum m/z 346.8 (M+H)⁺.

The following Intermediates were also prepared using procedures used to prepare Intermediates 30-1 and 30-2.

| Intermediate | Compound name | Mass spectrum |
|---|---|---|
| 30-3 | 1-(3-bromo-2-methylphenyl)-3-phenylimidazolidin-2-one | 331, 333 (M + H)⁺ |
| 30-4 | 1-(3-bromo-2-methylphenyl)-3-tert-butylimidazolidin-2-one | 311, 313 (M + H)⁺ |

Intermediates 31-1 and 31-2

Preparation of 1-(3-bromo-2-methylbenzyl)-1H-indazole and 2-(3-bromo-2-methylbenzyl)-2H-indazole

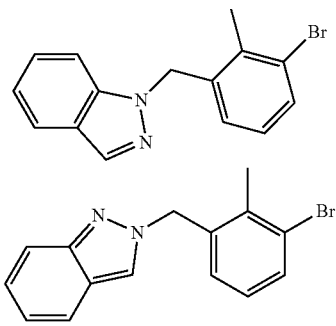

A mixture of 1-bromo-3-(bromomethyl)-2-methylbenzene (prepared according to the procedures reported in US Pat. Appl. 2006/0173183, 250 mg, 0.947 mmol), 1H-indazole (112 mg, 0.947 mmol) and potassium carbonate (131 mg, 0.947 mmol) in acetonitrile (5 mL) was heated with stirring at 80° C. After 18.25 h, the mixture was cooled to rt, diluted with water and extracted three times with EtOAc. The combined organic layers were dried and concentrated. The residue was purified by column chromatography (eluting with a gradient from 95:5 to 65:35 hexane-EtOAc) to provide 1-(3-bromo-2-methylbenzyl)-1H-indazole as an oil which crystallized on standing (Intermediate 31-1, 74 mg, 26%). ¹H NMR (400 MHz, chloroform-d) δ 8.06 (1 H, d, J=0.9 Hz), 7.76 (1 H, dt, J=8.1, 1.0 Hz), 7.48 (1 H, d, J=7.9 Hz), 7.30-7.37 (1 H, m), 7.26-7.30 (1 H, m), 7.16 (1 H, ddd, J=8.0, 6.8, 1.0 Hz), 6.93 (1 H, t, J=7.8 Hz), 6.70 (1 H, d, J=7.7 Hz), 5.61 (2 H, s), 2.45 (3 H, s). Mass spectrum m/z 301, 303 (M+H)⁺. Also obtained was 2-(3-bromo-2-methylbenzyl)-2H-indazole as a pale yellow gum (Intermediate 31-2, 164 mg, 58%). ¹H NMR (400 MHz, chloroform-d) δ 7.68-7.76 (2 H, m), 7.54-7.63 (2 H, m), 7.28 (1 H, ddd, J=8.2, 7.2, 1.1 Hz), 6.97-7.10 (3 H, m), 5.63 (2 H, s), 2.37 (3 H, s). Mass spectrum m/z 301, 303 (M+H)⁺.

Intermediate 31-3

Preparation of 1-(3-bromo-2-methylbenzyl)-1H-benzo[d]imidazole

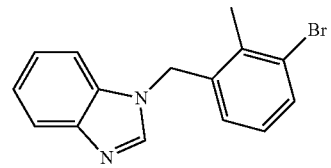 [SMILES: Cc1c(Br)cccc1Cn1cnc2ccccc21]

A mixture of 1-bromo-3-(bromomethyl)-2-methylbenzene (250 mg, 0.947 mmol), 1H-benzo[d]imidazole (336 mg, 2.84 mmol) and potassium carbonate (131 mg, 0.947 mmol) in acetonitrile (5 mL) was stirred at rt for 5 h, The mixture was diluted with EtOAc and filtered, and the solid was washed with EtOAc. The filtrate was washed with water, dried and concentrated. The residue was purified by column chromatography (eluting with a gradient from 60:40 hexane-EtOAc to EtOAc). to provide 1-(3-bromo-2-methylbenzyl)-1H-benzo[d]imidazole as a white solid (233 mg, 82%). ¹H NMR (400 MHz, chloroform-d) δ 8.14 (1 H, s), 7.68-7.78 (1 H, m), 7.56 (1 H, d, J=7.9 Hz), 7.36-7.44 (1 H, m), 7.25-7.34 (2 H, m), 7.03 (1 H, t, J=7.8 Hz), 6.82 (1 H, d, J=7.7 Hz), 5.58 (2 H, s), 2.45 (3 H, s). Mass spectrum m/z 301, 303 (M+H)⁺.

Intermediate 32-1

Preparation of N-(3-bromo-2-methylphenyl)-7-methoxyquinazolin-4-amine

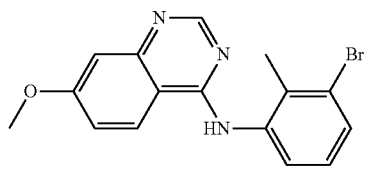 [SMILES: COc1ccc2c(Nc3cccc(Br)c3C)ncnc2c1]

Step 1 A mixture of 2-amino-4-methoxybenzoic acid (0.5 g, 2.99 mmol) and formamidine acetate (0.623 g, 5.98 mmol) in 2-methoxyethanol (4 mL) was heated at 130° C. After 15.25 h, the mixture was cooled to rt. The resulting precipitate was collected by filtration, washed with methanol and dried to provide 7-methoxyquinazolin-4-ol as a tan solid (473 mg, 90%). ¹H NMR (400 MHz, DMSO-d₆) δ 12.08 (1 H, br. s.), 8.06 (1 H, s), 8.03 (1 H, d, J=9.5 Hz), 7.03-7.14 (2 H, m), 3.90 (3 H, s).

Step 2 A suspension of 7-methoxyquinazolin-4-ol (400 mg, 2.271 mmol) in phosphorus oxychloride (7 mL, 75 mmol) was heated at reflux for 3 h. The solution was concentrated and the residue was suspended in EtOAc and stirred on an ice bath with NaHCO3 (aq) until all the solid was dissolved and gas evolution ceased. The layers were separated and the organic phase was dried and concentrated to provide 4-chloro-7-methoxyquinazoline as a light yellow-tan solid (438 mg, 99%). ¹H NMR (400 MHz, chloroform-d) δ 8.94 (1 H, s), 8.15 (1 H, d, J=9.7 Hz), 7.29-7.37 (2 H, m), 4.00 (3 H, s).

Step 3 A mixture of 4-chloro-7-methoxyquinazoline (200 mg, 1.028 mmol) and 3-bromo-2-methylaniline (0.253 mL, 2.055 mmol) in isopropanol (11 mL) was treated with hydrogen chloride (4 M in 1,4-dioxane, 0.385 mL, 1.541 mmol) and heated in a sealed tube by microwave irradiation at 140° C. for 45 min. On cooling a precipitate formed which was collected by filtration and dried under vacuum to provide the hydrochloric acid salt of N-(3-bromo-2-methylphenyl)-7-methoxyquinazolin-4-amine as a tan solid (281 mg, 68%). ¹H NMR (400 MHz, methanol-d₄) δ 8.65 (1 H, s), 8.48 (1 H, d, J=9.2 Hz), 7.69 (1 H, dd, J=8.0, 1.0 Hz), 7.51 (1 H, dd, J=9.4, 2.5 Hz), 7.37 (1 H, dd, J=7.9, 0.9 Hz), 7.26-7.30 (1 H, m), 7.24 (1 H, d, J=2.4 Hz), 4.08 (3 H, s), 2.36 (3 H, s). Mass spectrum m/z 344, 346 (M+H)⁺. The filtrate was concentrated and the residue was partitioned between NaHCO3 (aq) and EtOAc. The organic phase was dried and concentrated, and the residue was purified by column chromatography (eluting with a gradient from 75:25 to 25:75 hexane-EtOAc) to provide N-(3-bromo-2-methylphenyl)-7-methoxyquinazolin-4-amine as an off-white solid (61 mg, 17%). ¹H NMR (400 MHz, chloroform-d) δ 8.64 (1H, s), 7.76 (1H, d, J=9.0 Hz), 7.62 (1H, dd, J=8.0, 0.8 Hz), 7.51 (1H, dd, J=8.1, 0.9 Hz), 7.08-7.20 (3H, m), 5.30 (1H, s), 3.96 (3H, s), 2.41 (3H, s). Mass spectrum m/z 344, 346 (M+H)⁺.

The following Intermediates were also prepared using procedures used to prepare Intermediate 32-1.

| Intermediate | Compound name | Mass spectrum |
|---|---|---|
| 32-2 | N-(3-bromo-2-methylphenyl)-6-methylquinazolin-4-amine | 328, 330 (M + H)⁺ |
| 32-3 | N-(3-bromo-2-methylphenyl)-7-fluoroquinazolin-4-amine | 332, 334 (M + H)⁺ |
| 32-4 | N-(3-bromo-2-methylphenyl)-6-fluoroquinazolin-4-amine | 332, 334 (M + H)⁺ |
| 32-5 | N-(3-bromo-2-methylphenyl)-7-methylquinazolin-4-amine | 328, 330 (M + H)⁺ |
| 32-6 | N-(3-bromo-2-methylphenyl)-5-fluoroquinazolin-4-amine | 332, 334 (M + H)⁺ |
| 32-7 | N-(3-bromo-2-methylphenyl)-8-fluoroquinazolin-4-amine | 332, 334 (M + H)⁺ |
| 32-8 | N-(3-bromo-2-methylphenyl)-6-methoxyquinazolin-4-amine | 344, 346 (M + H)⁺ |
| 32-9 | N-(3-bromo-2-methylphenyl)quinazolin-4-amine | 314, 316 (M + H)⁺ |

Intermediate 33-1

Preparation of N-(3-bromo-2-methylphenyl)-4-methylpyridin-2-amine

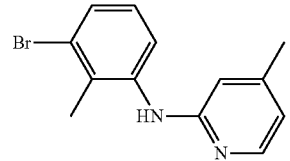 [SMILES: Cc1ccnc(Nc2cccc(Br)c2C)c1]

A mixture of 3-bromo-2-methylaniline (200 mg, 1.075 mmol), 2-fluoro-4-methylpyridine (155 mg, 1.397 mmol) and potassium tert-butoxide (193 mg, 1.72 mmol) in DMSO (4 mL) was heated in a sealed tube via microwave irradiation at 190° C. for 40 min. The mixture was partitioned between EtOAc and water, and the organic phase was washed with brine, dried and concentrated. The residue was purified by column chromatography (eluting with a gradient from hexane to 85:15 hexane-EtOAc) to provide N-(3-bromo-2-methylphenyl)-4-methylpyridin-2-amine as a yellow solid (100 mg, 34%). ¹H NMR (400 MHz, chloroform-d) δ 8.05 (1H, d, J=5.3 Hz), 7.38 (2H, d, J=8.1 Hz), 7.06 (1H, t, J=8.0 Hz), 6.58 (1H, d, J=5.3 Hz), 6.40 (1H, s), 6.23 (1H, br. s.), 2.37 (3H, s), 2.23 (3H, s). Mass spectrum m/z 277, 279 (M+H)⁺.

The following Intermediates were also prepared using procedures used to prepare Intermediate 33-1.

| Intermediate | Compound name | Mass spectrum |
|---|---|---|
| 33-2 | N-(3-bromo-2-methylphenyl)-5-methylpyridin-2-amine | 277, 279 (M + H)⁺ |
| 33-3 | N-(3-bromo-2-methylphenyl)pyridin-2-amine | 263, 265 (M + H)⁺ |
| 33-4 | N-(3-bromo-2-methylphenyl)-3-methylpyridin-2-amine | 277, 279 (M + H)⁺ |

Intermediate 34-1

Preparation of 3-bromo-2-fluoroaniline

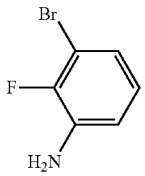

A solution of 1-bromo-2-fluoro-3-nitrobenzene (1.10 g, 5.00 mmol) in ethanol-acetic acid-water (2:2:1) (25 mL) was treated with iron powder (1.396 g, 25.0 mmol) and the mixture was heated at reflux for 1 h. The mixture was cooled to rt and filtered through a Celite pad. The filtrate was concentrated and the residue was partitioned between EtOAc and NaHCO3 (aq). The organic phase was washed with brine, dried and concentrated to provide 3-bromo-2-fluoroaniline as a brown oil (880 mg, 93%). $^1$H NMR (400 MHz, chloroform-d) δ 6.85-6.92 (1H, m), 6.80 (1H, td, J=8.0, 1.2 Hz), 6.66-6.73 (1H, m), 3.81 (2H, br. s.).

Intermediate 35-1

Preparation of N-(3-bromo-2-fluorophenyl)-4-fluoro-N-methylbenzamide

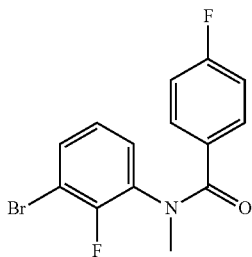 [SMILES: CN(C(=O)c1ccc(F)cc1)c1cccc(Br)c1F]

Step 1 A solution of Intermediate 34-1 (205 mg, 1.079 mmol) in formic acid (0.611 mL, 16.18 mmol) was heated at 90° C. for 5.5 h. The mixture was concentrated and partitioned between EtOAc and NaHCO3 (aq). The organic phase was washed with brine, dried and concentrated, and the residue was purified column chromatography (eluting with a gradient from 85:15 to 70:30 hexane-EtOAc) to provide N-(3-bromo-2-fluorophenyl)formamide as an off-white solid (216 mg, 92%). $^1$H NMR (400 MHz, chloroform-d) δ 8.49 (1H, s), 8.27-8.37 (1H, m), 7.44 (1H, br. s.), 7.30 (1H, ddd, J=8.1, 6.6, 1.5 Hz), 7.04 (1H, td, J=8.2, 1.5 Hz), 1.58 (3H, s). Mass spectrum m/z 218, 220 (M+H)$^+$.

Step 2 A suspension of N-(3-bromo-2-fluorophenyl)formamide (216 mg, 0.991 mmol) in THF (8 mL) was treated with borane dimethyl sulfide complex (2.0 M in THF, 1.486 mL, 2.97 mmol) and the resulting mixture was heated at reflux for 2 h. 1 M hydrochloric acid was added and the mixture was again heated at reflux for 1 h. The mixture was cooled to rt and concentrated and the residue was partitioned between NaHCO3 (aq) and EtOAc. The organic phase was washed with brine, dried and concentrated to provide 3-bromo-2-fluoro-N-methylaniline as a light yellow oil (60 mg, 30%). Mass spectrum m/z 204, 206 (M+H)$^+$.

Step 3 A solution of 3-bromo-2-fluoro-N-methylaniline (32 mg, 0.157 mmol) and diisopropylamine (0.055 mL, 0.314 mmol) in DCM (2 mL) was treated with 4-fluorobenzoyl chloride (0.028 mL, 0.235 mmol) and the mixture was stirred at rt for 2 h. The mixture was partitioned between DCM and NaHCO3 (aq). The organic phase was washed with brine, dried and concentrated. The residue was purified by column chromatography (eluting with a gradient from 90:10 to 80:20 hexane-EtOAc) to provide N-(3-bromo-2-fluorophenyl)-4-fluoro-N-methylbenzamide as a white solid (35 mg, 68%). Mass spectrum m/z 326, 328 (M+H)$^+$.

Intermediate 35-2

Preparation of N-(2-chloropyridin-4-yl)-4-fluorobenzamide

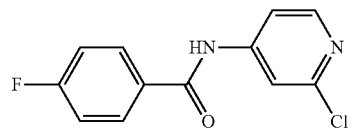

A solution of 2-bromopyridin-4-amine (500 mg, 2.89 mmol) in pyridine (8 mL) was stirred on ice and treated with 4-fluorobenzoyl chloride (0.376 mL, 3.18 mmol). The resulting solution was stirred at rt for 20.25 h, then was concentrated and the residue was partitioned between EtOAc and water. The organic phase was washed with NaHCO3 (aq) and water, dried and concentrated. The residue was purified by column chromatography (eluting with a gradient from 80:20 to 20:80 hexane-EtOAc) to provide N-(2-chloropyridin-4-yl)-4-fluorobenzamide as a white glassy solid (532 mg, 73%). $^1$H NMR (400 MHz, chloroform-d) δ 8.29 (d, J=5.5 Hz, 1H) 8.14 (br. s., 1 H) 7.89 (dd, J=8.8, 5.1 Hz, 2H) 7.77 (d, J=2.0 Hz, 1H) 7.48 (dd, J=5.7, 2.0 Hz, 1H) 7.18 (t, J=8.6 Hz, 2H). Mass spectrum m/z 251, 253 (M+H)$^+$.

Intermediate 35-3

Preparation of N-(3-bromo-4-fluorobenzyl)acetamide

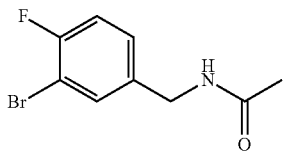

A solution of (3-bromo-4-fluorophenyl)methanamine hydrochloric acid salt (500 mg, 2.079 mmol) in pyridine (6 mL) was stirred on ice and treated with acetic anhydride (0.235 mL, 2.495 mmol). The resulting solution was stirred at rt for 17 h, then was concentrated. The residue was stirred in 1 M hydrochloric acid, forming a precipitate which was collected by filtration, rinsed with water and dried to provide N-(3-bromo-4-fluorobenzyl)acetamide as a white solid (435 mg, 85%). $^1$H NMR (400 MHz, chloroform-d) δ 7.47 (dd, J=6.6, 2.2 Hz, 1H) 7.20 (ddd, J=8.6, 4.6, 2.2 Hz, 1H) 7.07 (t, J=8.3 Hz, 1H) 5.84 (br. s., 1H) 4.38 (d, J=5.9 Hz, 2H) 2.04 (s, 3 H). Mass spectrum m/z 246, 248 (M+H)⁺.

Intermediate 35-4

Preparation of N-(3-bromo-2-methylphenyl)-4-(dimethylamino)benzamide

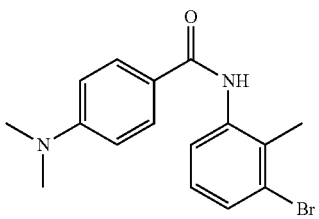 [SMILES: Cc1c(Br)cccc1NC(=O)c1ccc(N(C)C)cc1]

A suspension of 4-(dimethylamino)benzoic acid (100 mg, 0.605 mmol) in DCM (3 mL) was treated with 1-chloro-N,N,2-trimethylprop-1-en-1-amine (0.120 mL, 0.908 mmol) and the resulting solution was stirred at rt for 1.5 h. 3-Bromo-2-methylaniline (0.053 mL, 0.432 mmol) was added, followed by DIEA (0.264 mL, 1.513 mmol). The mixture was stirred at rt for 1 h, then was diluted with DCM and NaHCO3 (aq). The layers were separated and the organic phase was washed with brine, dried and concentrated. The residue was purified by column chromatography (eluting with a gradient from 85:15 to 65:35 hexane-EtOAc) to provide N-(3-bromo-2-methylphenyl)-4-(dimethylamino)benzamide as a light yellow solid (77 mg, 53%). ¹H NMR (400 MHz, DMSO-d₆) δ 9.75 (s, 1H) 7.85 (d, J=9.0 Hz, 2H) 7.49 (dd, J=8.0, 1.0 Hz, 1H) 7.30 (dd, J=7.9, 0.9 Hz, 1H) 7.15 (t, J=7.9 Hz, 1H) 6.75 (d, J=9.0 Hz, 2H) 2.99 (s, 6H) 2.25 (s, 3H). Mass spectrum m/z 331, 333 (M−H)⁻.

The following Intermediates were also prepared using procedures used to prepare Intermediates 35-1 through 35-4.

| Intermediate | Compound name | Mass spectrum |
|---|---|---|
| 35-5 | N-(3-bromo-4-fluorophenyl)acetamide | 232, 234 (M + H)⁺ |
| 35-6 | N-(3-bromophenyl)-4-fluorobenzamide | 294, 296 (M + H)⁺ |
| 35-7 | N-(3-bromo-2-fluorophenyl)-4-fluorobenzamide | 312, 314 (M + H)⁺ |
| 35-8 | N-(3-bromo-2-fluorophenyl)-4-(dimethylamino)benzamide | 337, 339 (M + H)⁺ |
| 35-9 | N-(3-bromophenyl)-4-fluoro-N-methylbenzamide | 308, 310 (M + H)⁺ |
| 35-10 | N-(5-bromo-2-fluorophenyl)-4-fluorobenzamide | 312, 314 (M + H)⁺ |
| 35-11 | N-(3-bromo-4-fluorophenyl)-4-fluorobenzamide | 312, 314 (M + H)⁺ |
| 35-12 | N-(3-bromo-4-fluorobenzyl)-4-fluorobenzamide | 326, 328 (M + H)⁺ |
| 35-13 | N-(3-bromo-2-fluorophenyl)acetamide | 232, 234 (M + H)⁺ |

Intermediate 36-1

Preparation of 3-bromo-4-fluoro-N-(4-fluorophenyl)benzamide

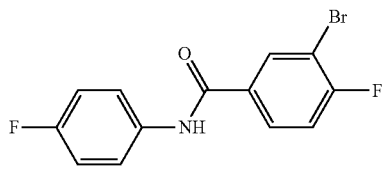 [SMILES: O=C(Nc1ccc(F)cc1)c1ccc(F)c(Br)c1]

A solution of 3-bromo-4-fluorobenzoic acid (976 mg, 4.46 mmol) in DCM (25 mL) was stirred at rt and treated with oxalyl chloride (1.950 mL, 22.28 mmol), followed by a drop of DMF, causing gas evolution to commence. After 2.5 h, the solution was heated to boiling for 1-2 min and allowed to cool to rt. After 3 h total, the solution was concentrated to provide 3-bromo-4-fluorobenzoyl chloride as a white solid (1.00 g, 94%). A portion of this material (200 mg, 0.842 mmol) was added to an ice-cold solution of 4-fluoroaniline (0.081 mL, 0.842 mmol) in pyridine (4 mL), and the solution was stirred at rt for 65 h The solution was concentrated and the residue was stirred in 1 M hydrochloric acid, forming a precipitate which was collected by filtration, washed with water and dried to provide 3-bromo-4-fluoro-N-(4-fluorophenyl)benzamide as an off-white solid (227.5 mg, 80%). ¹H NMR (400 MHz, DMSO-d₆) δ 10.38 (s, 1H) 8.29 (dd, J=6.7, 2.1 Hz, 1H) 8.01 (ddd, J=8.6, 4.8, 2.2 Hz, 1H) 7.75 (dd, J=9.0, 5.1 Hz, 2H) 7.55 (t, J=8.6 Hz, 1H) 7.20 (t, J=8.9 Hz, 2H). Mass spectrum m/z 312, 314 (M+H)⁺.

Intermediate 36-2

Preparation of 3-bromo-2-fluoro-N,N-dimethylbenzamide

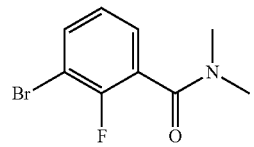

A suspension of 3-bromo-2-fluorobenzoic acid (1.009 g, 4.61 mmol) in DCM (25 mL) was stirred at rt and treated with oxalyl chloride (2.016 mL, 23.04 mmol), followed by a drop of DMF, causing gas evolution to commence. After 2.5 h, the solution was heated to boiling for 1-2 min and allowed to cool to rt. After 3 h total, the solution was concentrated to provide 3-bromo-2-fluorobenzoyl chloride as a dark yellow liquid (1.078 g, 99%). A portion of this (200 mg, 0.842 mmol) was dissolved in THF (1.5 mL) and added to a solution of dimethylamine (2 M in methanol, 2.0 mL, 4.00 mmol) in THF (2 mL). The mixture was stirred at rt for 18 h, then was concentrated. The residue was dissolved in EtOAc, washed sequentially with 1 M hydrochloric acid, NaHCO3 (aq) and brine, and dried and concentrated to provide 3-bromo-2-fluoro-N,N-dimethylbenzamide as a light yellow oil (192 mg, 93%). ¹H NMR (400 MHz, chloroform-d) δ 7.60 (ddd, J=8.1, 6.5, 1.6 Hz, 1H) 7.32 (ddd, J=7.6, 5.9, 1.6 Hz, 1H) 7.09 (td, J=7.8, 0.7 Hz, 1H) 3.14 (s, 3H) 2.93 (d, J=1.5 Hz, 3H). Mass spectrum m/z 246, 248 (M+H)⁺.

The following Intermediates were also prepared using procedures used to prepare Intermediates 36-1 and 36-2.

| Intermediate | Compound name | Mass spectrum |
|---|---|---|
| 36-3 | 3-bromo-2-fluoro-N-(4-fluorophenyl)benzamide | 312, 314 (M + H)+ |
| 36-4 | 3-bromo-4-fluorobenzamide | 218, 220 (M + H)+ |
| 36-5 | 3-bromo-2-fluorobenzamide | 218, 220 (M + H)+ |
| 36-6 | 3-bromo-2-fluoro-N-methylbenzamide | 232, 234 (M + H)+ |
| 36-7 | 3-bromo-4-fluoro-N,N-dimethylbenzamide | 246, 248 (M + H)+ |

Intermediate 37-1

Preparation of N-(3-bromo-2-fluorophenyl)-N-(methylsulfonyl)methanesulfonamide

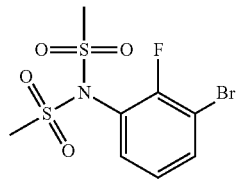 [SMILES: CS(=O)(=O)N(c1cccc(Br)c1F)S(C)(=O)=O]

A solution of 3-bromo-2-fluoroaniline (Intermediate 34-1, 160 mg, 0.842 mmol) and DIEA (0.368 mL, 2.105 mmol) in DCM (3 mL) was stirred at ca. −5° C. and treated with methanesulfonyl chloride (0.098 mL, 1.263 mmol) and stirred at that temperature for 2 h. The mixture was partitioned between DCM and NaHCO3 (aq). The organic phase was washed with brine, dried and concentrated to provide N-(3-bromo-2-fluorophenyl)-N-(methylsulfonyl)methanesulfonamide as a yellow solid (308 mg, quantitative), used without further purification. $^1$H NMR (400 MHz, chloroform-d) δ 7.70 (1H, ddd, J=8.1, 6.4, 1.5 Hz), 7.33 (1H, ddd, J=8.1, 6.5, 1.6 Hz), 7.15 (1H, td, J=8.1, 1.4 Hz), 3.46 (6H, s). Mass spectrum m/z 363, 365 (M+NH$_4$)+.

Intermediate 38-1

Preparation of 1-(3-bromo-4-fluorophenyl)-3-(4-methylthiazol-2-yl)urea

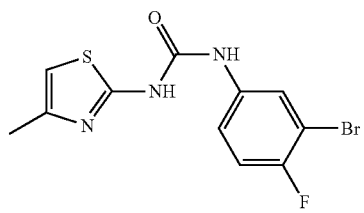 [SMILES: Cc1csc(NC(=O)Nc2ccc(F)c(Br)c2)n1]

Step 1 A solution of 2-amino-4-methylthiazole (11.42 g, 0.10 mol) in DCM was cooled to 0° C. and treated with TEA (12.1 g, 0.12 mol), then phenyl chloroformate (15.6 g, 0.10 mol) was added dropwise with stirring. The mixture was stirred for 10 minutes, then was washed with NaHCO3 (aq), water and brine, and dried and concentrated. The residue was purified by column chromatography (eluting with 60:40 hexane-EtOAc) to give phenyl 4-methylthiazol-2-ylcarbamate as a white solid (12 g, 51%). $^1$H NMR (300 MHz, chloroform-d) δ 12.38 (bs, 1H) 7.47-7.40 (m, 2H) 7.30-7.19 (m, 3H) 6.52 (d, J=1.1 Hz, 1H) 2.41 (d, J=0.8 Hz, 3H).

Step 2 A solution of 3-bromo-4-fluoroaniline (250 mg, 1.316 mmol) in THF (6 mL) was stirred on ice and treated with TEA (0.367 mL, 2.63 mmol), then with phenyl 4-methylthiazol-2-ylcarbamate (308 mg, 1.316 mmol) and the resulting solution was stirred at rt for 70 h. The mixture was concentrated and the residue was stirred in 1 M hydrochloric acid, forming a precipitate which was collected by filtration, rinsed with water and dried under vacuum to provide 1-(3-bromo-4-fluorophenyl)-3-(4-methylthiazol-2-yl)urea as an off white solid (400 mg, 92%). $^1$H NMR (400 MHz, DMSO-d$_6$) δ 9.62 (s, 1H) 7.94 (dd, J=6.3, 2.5 Hz, 1H) 7.37-7.45 (m, 1H) 7.32 (t, J=8.7 Hz, 1H) 6.67 (d, J=1.1 Hz, 1H) 2.23 (d, J=1.1 Hz, 3H). Mass spectrum m/z 330, 332 (M+H)+.

The following Intermediate was also prepared using procedures used to prepare Intermediate 38-1.

| Intermediate | Compound name | Mass spectrum |
|---|---|---|
| 38-2 | 1-(3-bromo-4-fluorobenzyl)-3-(4-methylthiazol-2-yl)urea | 344, 346 (M + H)+ |

Intermediate 39-1

Preparation of 6-bromo-2-(4-fluorophenyl)-7-methyl-1H-benzo[d]imidazole

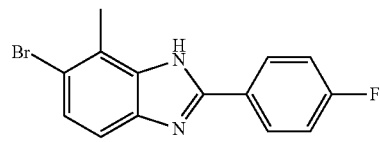 [SMILES: Cc1c(Br)ccc2nc(-c3ccc(F)cc3)[nH]c12]

A solution of 4-bromo-3-methylbenzene-1,2-diamine (prepared according to the procedure of PCT Pat. Appl. WO 2008/021851, 400 mg, 1.989 mmol) in DCM (10 mL) was treated with TEA (0.693 mL, 4.97 mmol), then was treated dropwise with 4-fluorobenzoyl chloride (0.282 mL, 2.387 mmol). The mixture was stirred at rt for 70 min, then was concentrated. The residue was suspended in ethanol (25 mL), treated with concentrated hydrochloric acid (3 mL, 36.5 mmol) and heated at 90-95° C. After 42.5 h, the mixture was cooled to rt and the ethanol was removed under vacuum. The residual paste was suspended in water and the pH was adjusted to ca. 8 with NaHCO3 (aq). The precipitate was collected by filtration, washed with water and dried under vacuum to provide 6-bromo-2-(4-fluorophenyl)-7-methyl-1H-benzo[d]imidazole as a pale pink solid (636 mg, 95%). $^1$H NMR (400 MHz, DMSO-$d_6$) δ 8.24 (2H, dd, J=8.9, 5.4 Hz), 7.33-7.45 (4H, m), 2.57 (3H, s). Mass spectrum m/z 305, 307 (M+H)$^+$.

Intermediate 40-1

Preparation of N,N-bis(tert-butyloxycarbonyl)-5-bromo-4-methylthiazol-2-ylamine

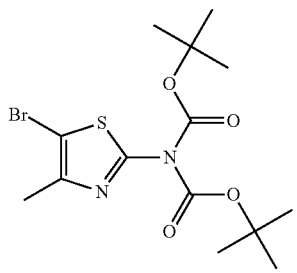 [SMILES: Cc1nc(N(C(=O)OC(C)(C)C)C(=O)OC(C)(C)C)sc1Br]

Step 1 A solution of 5-bromo-4-methylthiazol-2-amine (2.00 g, 10.36 mmol) in pyridine (10 mL) was treated portionwise at rt with di-tert-butyl dicarbonate (2.487 g, 11.40 mmol). After stirring at rt overnight significant starting material remained. The mixture was cooled to 0° C. and treated with lithium hexamethyldisilazide (1 M in THF, 25.9 mL, 25.9 mmol) followed by di-tert-butyl dicarbonate (2.487 g, 11.40 mmol). The mixture was warmed to rt for 1 h, then was diluted with EtOAc, washed twice with 0.5 M hydrochloric acid, then with 1 M aqueous sodium hydroxide, dried and concentrated. Purification of the residue by column chromatography (elution with hexane-EtOAc) provided tert-butyl 5-bromo-4-methylthiazol-2-ylcarbamate (814 mg, 27%). $^1$H NMR (400 MHz, chloroform-d) δ 2.27 (3H, s), 1.53 (9H, s). Mass spectrum m/z 293, 295 (M+H)$^+$.

Step 2 A mixture of di-tert-butyl dicarbonate (667 mg, 3.05 mmol), tert-butyl 5-bromo-4-methylthiazol-2-ylcarbamate (814 mg, 2.78 mmol) and DMAP (339 mg, 2.78 mmol) in DCM (10 mL) was stirred at rt overnight. The mixture was concentrated and the residue was purified by column chromatography (eluting with hexane-EtOAc) to provide N,N-bis(tert-butyloxycarbonyl)-5-bromo-4-methylthiazol-2-ylamine. Mass spectrum m/z 393, 395 (M+H)$^+$.

Intermediate 41-1

Preparation of 2-(3-bromo-2-methylphenyl)-3,4-dihydroisoquinolin-1(2H)-one

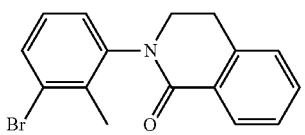

Step 1 A solution of 2,3-dihydro-1H-inden-1-one (1 g, 7.57 mmol) in DCM (10 mL) was treated with methanesulfonic acid (10 mL) and cooled to 0° C. Sodium azide (0.984 g, 15.13 mmol) was added and the mixture was stirred at 0° C. for 2 h, then at rt overnight. The mixture was made basic with 20% aqueous sodium hydroxide and extracted with DCM. The organic phase was washed with water, dried and concentrated. The residue was purified by column chromatography (eluting with hexane-EtOAc) to provide 3,4-dihydroquinolin-2(1H)-one as a white solid (655 mg, 60%). $^1$H NMR (400 MHz, methanol-$d_4$) δ 7.08-7.19 (2H, m), 6.92-6.99 (1H, m), 6.85 (1H, d, J=7.9 Hz), 5.47 (1H, s), 2.92 (2H, t, J=7.6 Hz), 2.49-2.58 (2H, m). Mass spectrum m/z 148.1 (M+H)$^+$. Also obtained was 3,4-dihydroisoquinolin-1(2H)-one as a colorless oil (162 mg, 15%). $^1$H NMR (400 MHz, methanol-$d_4$) δ 7.93 (1H, dd, J=7.8, 1.0 Hz), 7.44-7.52 (1H, m), 7.35 (1H, td, J=7.6, 1.2 Hz), 7.29 (1H, d, J=7.7 Hz), 3.50 (2H, t, J=6.6 Hz), 2.98 (2H, t, J=6.7 Hz). Mass spectrum m/z 148.1 (M+H)$^+$.

Step 2 A mixture of 1,3-dibromo-2-methylbenzene (340 mg, 1.359 mmol), 3,4-dihydroisoquinolin-1(2H)-one (100 mg, 0.679 mmol) and potassium carbonate (94 mg, 0.679 mmol) in DMSO (2 mL) was purged with nitrogen, treated with copper (I) iodide (25.9 mg, 0.136 mmol) and heated at 150° C. for 3.5 h. The mixture was combined with that from a second reaction using 1,3-dibromo-2-methylbenzene (2.59 g, 10.36 mmol) and 3,4-dihydroisoquinolin-1(2H)-one (508 mg, 3.45 mmol), diluted with DCM and filtered through Celite. The filtrate was washed with 5% aqueous ammonium hydroxide, dried and concentrated. The residue was purified by column chromatography (eluting with hexane-EtOAc) to provide 2-(3-bromo-2-methylphenyl)-3,4-dihydroisoquinolin-1(2H)-one as a yellow solid (142 mg, 11%). $^1$H NMR (400 MHz, chloroform-d) δ 8.15 (1H, dd, J=7.70, 1.10 Hz), 7.55 (1H, dd, J=7.92, 1.10 Hz), 7.46-7.51 (1H, m), 7.37-7.42 (1H, m), 7.24-7.28 (1H, m), 7.17-7.21 (1H, m), 7.09-7.16 (1H, m), 3.95 (1H, ddd, J=12.21, 10.12, 4.73 Hz), 3.73 (1 H, ddd, J=11.94, 6.33, 5.28 Hz), 3.26 (1H, ddd, J=15.74, 10.23, 5.28 Hz), 3.06-3.14 (1H, m), 2.36 (3H, s). Mass spectrum m/z 316, 318 (M+H)$^+$.

The following Intermediates were also prepared using procedures used to prepare Intermediate 41-1.

| Intermediate | Compound name | Mass spectrum |
|---|---|---|
| 41-2 | 2-(3-bromo-2-methylphenyl)-6-methoxy-3,4-dihydroisoquinolin-1(2H)-one | 346, 348 (M + H)$^+$ |
| 41-3 | 2-(3-bromo-2-methylphenyl)-5-hydroxy-3,4-dihydroisoquinolin-1(2H)-one | 332, 334 (M + H)$^+$ |
| 41-4[a] | 5-(3-bromo-2-methylphenoxy)-3,4-dihydroisoquinolin-1(2H)-one | 332, 334 (M + H)$^+$ |
| 41-5 | 2-(3-bromo-2-methylphenyl)-7-chloro-3,4-dihydroisoquinolin-1(2H)-one | 350, 352 (M + H)$^+$ |
| 41-6 | 2-(3-bromo-2-methylphenyl)-6-fluoro-3,4-dihydroisoquinolin-1(2H)-one | 334, 336 (M + H)$^+$ |

[a]Obtained from the same reaction used to prepare Intermediate 41-3

The following Intermediates were also prepared using procedures of Step 2 used to prepare Intermediate 41-1.

| Intermediate | Compound name | Mass spectrum |
|---|---|---|
| 41-7 | 1-(3-bromo-2-methylphenyl)-3,4-dimethyl-1H-pyrrol-2(5H)-one | 280, 282 (M + H)$^+$ |
| 41-8 | 1-(3-bromo-2-methylphenyl)-3-methylpyridin-2(1H)-one | 278, 280 (M + H)$^+$ |
| 41-9 | 1-(3-bromo-2-methylphenyl)-4,4-dimethylpyrrolidin-2-one | 282, 284 (M + H)$^+$ |
| 41-10 | 1-(3-bromo-2-methylphenyl)-5-oxopyrrolidine-3-carboxylic acid | 298, 300 (M + H)$^+$ |

Intermediate 42-1

Preparation of 1-(3-bromo-2-methylbenzylidene)-1,3-dihydroisobenzofuran

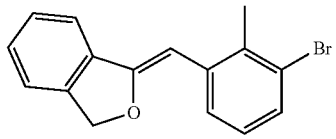 [SMILES: Cc1c(Br)cccc1/C=C1\OCc2ccccc21]

Step 1 A mixture of (2-ethynylphenyl)methanol (100 mg, 0.757 mmol), 1,3-dibromo-2-methylbenzene (189 mg, 0.757 mmol) and TEA (0.211 mL, 1.513 mmol) in THF (2 mL) was purged with nitrogen and treated with copper (I) iodide (2.88 mg, 0.015 mmol) and bis(triphenylphosphine)palladium(II) chloride (26.6 mg, 0.038 mmol). The mixture was heated in a sealed tube at 60° C. for 1.5 h. The mixture was filtered, the filtrate was washed with NaHCO3 (aq) and water, and dried and concentrated. The residue was purified by column chromatography (eluting with hexane-EtOAc) to provide (2-((3-bromo-2-methylphenyl)ethynyl)phenyl)methanol as a white solid (130 mg, 57%). $^1$H NMR (400 MHz, chloroform-d) δ 7.44-7.58 (4H, m), 7.39 (1H, td, J=7.54, 1.43 Hz), 7.27-7.34 (1H, m), 7.00-7.09 (1H, m), 4.93 (2H, d, J=6.38 Hz), 2.64 (3H, s). Mass spectrum m/z 323, 325 (M+Na)$^+$.

Step 2 A solution of (2-((3-bromo-2-methylphenyl)ethynyl)phenyl)-methanol (50 mg, 0.166 mmol) and tetrabutylammonium fluoride, 1.0 M in THF (0.332 mL, 0.332 mmol) in THF (0.5 mL) was heated at 67° C. for 2 h. The mixture was diluted with EtOAc, washed twice with water and once with brine, dried and concentrated. The residue was purified by column chromatography (eluting with a gradient from hexane to 80:20 EtOAc-hexane) to provide 1-(3-bromo-2-methylbenzylidene)-1,3-dihydroisobenzofuran as a light yellow solid (36 mg, 72%). $^1$H NMR (400 MHz, chloroform-d) δ 8.00-8.06 (1H, m), 7.58-7.64 (1H, m), 7.32-7.41 (4H, m), 7.04 (1H, t, J=7.92 Hz), 6.07 (1H, s), 5.49 (2H, s), 2.51 (3H, s). Mass spectrum m/z 301, 303 (M+H)$^+$.

Intermediate 43-1

Preparation of tert-butyl 5-bromothiazol-2-yl(isopropyl)carbamate

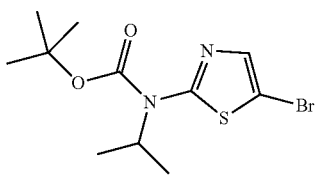 [SMILES: CC(C)N(C(=O)OC(C)(C)C)c1ncc(Br)s1]

Step 1 Di-tert-butyl dicarbonate (28.90 g, 132.4 mmol) was added portionwise to a suspension of 2-amino-5-bromothiazole hydrobromide (28.64 g, 110.3 mmol) in pyridine (100 mL) over 20 min at rt. The mixture was stirred at rt overnight, then was concentrated. The residue was partitioned between 0.5 M hydrochloric acid (200 mL) and EtOAc (200 mL). The organic layer was dried and concentrated, and the residue was filtered through a pad of silica gel using 90:10 hexane-EtOAc. The filtrate was concentrated to give tert-butyl-5-bromothiazol-2-ylcarbamate as a white solid (19.5 g, 63%). $^1$H NMR (400 MHz, chloroform-d) δ 7.27 (s, 1H) 1.60 (s, 9H). Mass spectrum m/z 223, 225 (M+H)$^+$.

Step 2 A solution of tert-butyl 5-bromothiazol-2-ylcarbamate (3 g, 10.7 mmol), isopropanol (6.40 g, 107.4 mmol) and triphenylphosphine (5.63 g, 21.5 mmol) in THF (30 mL) was treated with diethyl azodicarboxylate (3.74 g, 21.5 mmol) dropwise at 0° C. and was stirred overnight while warming slowly to rt. The mixture was concentrated and the residue was dissolved in DCM (20 mL), filtered to remove undissolved solid and concentrated. The residue was purified by column chromatography (eluting with hexane) to give tert-butyl 5-bromothiazol-2-yl(isopropyl)carbamate as a light yellow oil (3.10 g, 90%). $^1$H NMR (400 MHz, chloroform-d) δ 7.34 (s, 1H) 5.29 (m, 1H) 1.59 (s, 9H) 1.45 (d, 6.8 Hz, 6H). Mass spectrum m/z 265, 267 (M+H—C$_4$H$_9$)$^+$.

Intermediates 44-1 and 44-2

Preparation of 2-(3-bromo-2-methylphenyl)-2,3-dihydro-1H-pyrrolo[3,4-c]pyridin-1-one and (Z)-3-bromo-N-(furo[3,4-c]pyridin-1(3H)-ylidene)-2-methylaniline

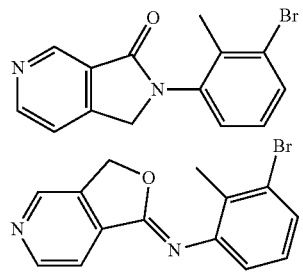

A suspension of 2-(3-bromo-2-methylphenyl)-1H-pyrrolo[3,4-c]pyridine-1,3(2H)-dione (4.7 g, 14.82 mmol) in methanol (200 mL) was treated with sodium borohydride (2 g, 52.9 mmol) and stirred at rt for 1 h. The mixture was concentrated and the residue was treated with NaHCO3 (aq). The mixture was extracted several times with a mixture of DCM and methanol. The combined organic phases were washed with water, dried and concentrated to give a mixture of N-(3-bromo-2-methylphenyl)-4-(hydroxymethyl)-nicotinamide and N-(3-bromo-2-methylphenyl)-3-(hydroxymethyl)isonicotinamide as an off-white solid. Mass spectrum m/z 321, 323 (M+H)$^+$. Without purification, this material was suspended in THF (250 mL) and treated with triphenylphosphine (polymer supported, 3 mmol P/g resin, 18.44 g, 54.8 mmol) and diethyl azodicarboxylate (6.45 g, 37.1 mmol) and the mixture was stirred at rt for 4 h. The mixture was filtered and concentrated, and the residue was dissolved in DCM, washed with water, NaHCO3 (aq) and brine, and dried and concentrated. The residue was subjected to column chromatography (eluting with EtOAc) to provide 2-(3-bromo-2-methylphenyl)-2,3-dihydro-1H-pyrrolo[3,4-c]pyridin-1-one as a white solid (Intermediate 44-1, 2.7 g, 60%). $^1$H NMR (400 MHz, chloroform-d) δ 9.21 (1H, d, J=0.88 Hz), 8.84 (1H, d, J=5.06 Hz), 7.63 (1H, dd, J=7.70, 1.32 Hz), 7.51 (1H, dd, J=5.06, 0.88 Hz), 7.22 (1H, dt, J=7.70, 1.32 Hz), 7.17 (1H, d, J=7.92 Hz), 4.76 (2H, s), 2.31 (3H, s). Mass spectrum m/z 303, 305 (M+H)$^+$. Also obtained was (Z)-3-bromo-N-(furo[3,4-c]pyridin-1(3H)-ylidene)-2-methylaniline as a white solid (Intermediate 44-2, 760 mg, 17%), which also contained the isomeric (Z)-3-bromo-N-(furo[3,4-c]pyridin-3(1H)-ylidene)-2-methylaniline. ¹H NMR (400 MHz, chloroform-d) δ 9.26 (1H, s), 8.80 (1H, d, J=5.06 Hz), 7.42 (1H, dd, J=5.06, 0.88 Hz), 7.31-7.35 (1H, m), 7.02-7.08 (2H, m), 5.39 (2H, s), 2.35 (3H, s). Mass spectrum m/z 303, 305 (M+H)⁺.

Intermediate 45-1

Preparation of 1-(3-bromo-2-methylphenyl)-5-oxopyrrolidine-3-carboxamide

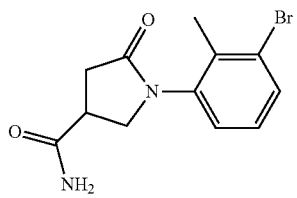 [SMILES: Cc1c(Br)cccc1N1CC(C(N)=O)CC1=O]

A mixture of 1-(3-bromo-2-methylphenyl)-5-oxopyrrolidine-3-carboxylic acid (Intermediate 41-10, 100 mg, 0.335 mmol), EDC (129 mg, 0.671 mmol), HOBT (103 mg, 0.671 mmol) and 28% aqueous ammonia in THF (2 mL) was stirred at rt for 5 h. The mixture was diluted with ethyl acetate, washed with NaHCO3 (aq) and water, and dried and concentrated. The residue was purified by column chromatography (eluting with 90:10 DCM-methanol) to provide 1-(3-bromo-2-methylphenyl)-5-oxopyrrolidine-3-carboxamide as a white solid (26 mg, 26%). Mass spectrum m/z 297, 299 (M+H)⁺.

Intermediate 46-1

Preparation of 5-bromo-2-(ethoxycarbonyl)-2,3,4,9-tetrahydro-1H-carbazole-8-carboxylic acid

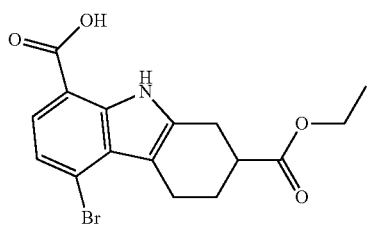 [SMILES: CCOC(=O)C1CCc2c([nH]c3c(C(=O)O)ccc(Br)c23)C1]

Step 1 A solution of sodium nitrite (2.448 g, 35.5 mmol) in water (12 mL) was added dropwise to a suspension of 2-amino-4-bromobenzoic acid (7.30 g, 33.8 mmol) in concentrated hydrochloric acid (34 mL) at −5° C., at such rate that the temperature did not exceed 0° C. The resulting suspension was stirred at −5° C. for 10 min and was then added dropwise to a rapidly stirred solution of tin (II) chloride (13.46 g, 71.0 mmol) in concentrated hydrochloric acid (10 mL) at −5° C., at such a rate that the temperature did not exceed 0° C. The resulting suspension was warmed to rt and stirred for 1 h. The precipitate was collected by filtration, washed with water, and dried to provide 4-bromo-2-hydrazinylbenzoic acid hydrochloric acid salt as a pale tan solid (7.79 g, 86%). ¹H NMR (400 MHz, DMSO-d₆) δ 9.14 (br. s., 1H) 7.79 (d, J=8.35 Hz, 1H) 7.34 (d, J=1.76 Hz, 1H) 7.13 (dd, J=8.35, 1.76 Hz, 1H). Mass spectrum m/z 231, 233 (M+H)⁺.

Step 2 A stirred suspension of 4-bromo-2-hydrazinylbenzoic acid hydrochloric acid salt (16.35 g, 58.1 mmol) in acetic acid (171 mL) was treated with ethyl 3-oxocyclohexanecarboxylate (9.88 g, 58.1 mmol) at rt. The mixture was stirred at reflux for 2.5 h, then was cooled to rt and concentrated to afford a brown solid. This was suspended in EtOAc (20 mL) and the precipitate was collected by filtration, washed with EtOAc and air dried to provide 5-bromo-2-(ethoxycarbonyl)-2,3,4,9-tetrahydro-1H-carbazole-8-carboxylic acid (11.46 g). The filtrate was concentrated and the residue was resuspended in EtOAc, the precipitate collected by filtration and dried to provide additional product (0.82 g) for a total of 12.28 g (58%). ¹H NMR (400 MHz, DMSO-d₆) δ 13.10 (br. s., 1H) 11.06 (s, 1H) 7.50 (d, J=8.13 Hz, 1H) 7.19 (d, J=8.13 Hz, 1H) 4.07-4.15 (m, 2H) 3.08-3.19 (m, 1H) 2.99-3.08 (m, 1H) 2.89-2.99 (m, 2H) 2.79-2.89 (m, 1H) 2.09-2.22 (m, 1H) 1.75-1.89 (m, 1H) 1.20 (t, J=7.14 Hz, 3H). Mass spectrum m/z 366.0, 368.0 (M+H)⁺.

The following Intermediates were also prepared using the procedures used to prepare Intermediate 46-1 but using the appropriate ketone in place of ethyl 3-oxocyclohexanecarboxylate.

| Intermediate | Compound name | Mass spectrum |
|---|---|---|
| 46-2 | 5-bromo-3-(ethoxycarbonyl)-2,3,4,9-tetrahydro-1H-carbazole-8-carboxylic acid | 366, 368 (M + H)⁺ |
| 46-3 | 5-bromo-2,3,4,9-tetrahydro-1H-carbazole-8-carboxylicacid | 294, 296 (M + H)⁺ |

Intermediate 47-1

Preparation of ethyl 5-bromo-8-carbamoyl-2,3,4,9-tetrahydro-1H-carbazole-2-carboxylate

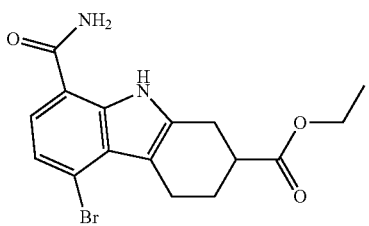 [SMILES: CCOC(=O)C1CCc2c([nH]c3c(C(N)=O)ccc(Br)c23)C1]

A suspension of 5-bromo-2-(ethoxycarbonyl)-2,3,4,9-tetrahydro-1H-carbazole-8-carboxylic acid (Intermediate 46-1, 12.28 g, 33.5 mmol), EDC (7.71 g, 40.2 mmol), and HOBT (6.16 g, 40.2 mmol) in THF-DCM (4:1, 335 mL) was treated with 28% aqueous ammonium hydroxide (7.83 mL, 201 mmol), and the resulting suspension was stirred at rt overnight. The mixture was concentrated and the residue was suspended in water. The precipitate was collected by filtration, washed with water and EtOAc and dried to give ethyl 5-bromo-8-carbamoyl-2,3,4,9-tetrahydro-1H-carbazole-2-carboxylate (8.92 g). The filtrate was concentrated and the residue was suspended in methanol. A solid was collected by filtration, washed with methanol and air dried to afford additional product (0.39 g) for a total of 9.31 g (76%). ¹H NMR (400 MHz, DMSO-d₆) δ 11.08 (s, 1H) 8.02 (br. s., 1H) 7.43 (d, J=8.13 Hz, 1H) 7.39 (br. s., 1H) 7.14 (d, J=8.13 Hz, 1H) 4.02-4.17 (m, 2H) 3.07-3.18 (m, 1H) 2.97-3.06 (m, 1H) 2.86-

2.98 (m, 2H) 2.77-2.86 (m, 1H) 2.09-2.19 (m, 1H) 1.72-1.86 (m, 1H) 1.20 (t, J=7.14 Hz, 3H). Mass spectrum m/z 365, 367 (M+H)⁺.

The following Intermediate was also prepared using the procedure used to prepare Intermediate 47-1 but using Intermediate 46-2 in place of Intermediate 46-1.

| Intermediate | Compound name | Mass spectrum |
|---|---|---|
| 47-2 | ethyl 5-bromo-8-carbamoyl-2,3,4,9-tetrahydro-1H-carbazole-3-carboxylate | 365, 367 (M + H)⁺ |

Intermediate 47-3

Preparation of 5-bromo-2,3,4,9-tetrahydro-1H-carbazole-8-carboxamide

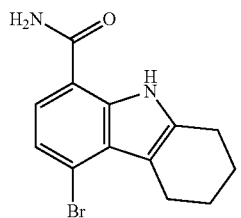 [SMILES: NC(=O)c1ccc(Br)c2c3c([nH]c12)CCCC3]

A mixture of 5-bromo-2,3,4,9-tetrahydro-1H-carbazole-8-carboxylic acid (Intermediate 46-3, 70% purity, mixed with Intermediate 47-3 from an incomplete reaction done according to the procedure used to prepare Intermediate 47-1; 3 g, 7.14 mmol) in THF (80 mL) and DCM (20 mL) was treated with HOAT (1.166 g, 8.57 mmol) and EDC (1.642 g, 8.57 mmol). The mixture was stirred at rt for 2.5 h, then was treated with anhydrous ammonia gas for ca. 2 min, forming a very thick slurry. The mixture was stirred for 30 min, then was treated again with ammonia gas for ca. 1 min. After stirring for another hour, the mixture was diluted with water and EtOAc (dissolving the solid). The layers were separated and the aqueous phase was extracted again with EtOAc. The combined organic layers were washed twice with 0.1 M aqueous sodium hydroxide, then with 1 M hydrochloric acid and brine, dried and concentrated to provide 5-bromo-2,3,4,9-tetrahydro-1H-carbazole-8-carboxamide as a pale orange-tan solid (2.47 g, 84%, including the product from the incomplete reaction yielding the starting material). ¹H NMR (400 MHz, DMSO-d₆) δ 10.95 (1H, s), 8.02 (1H, br. s.), 7.44 (1H, d, J=7.9 Hz), 7.38 (1H, br. s.), 7.14 (1H, d, J=8.1 Hz), 2.99 (2H, br. s.), 2.75 (2H, br. s.), 1.78 (4H, br. s.). Mass spectrum m/z 293, 295 (M+H)⁺.

Intermediate 48-1

Preparation of ethyl 5-bromo-8-carbamoyl-9H-carbazole-2-carboxylate

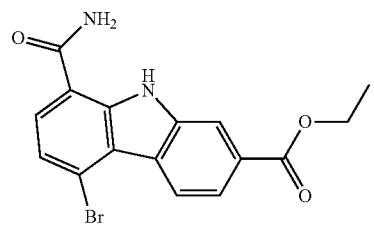 [SMILES: CCOC(=O)c1ccc2c(c1)[nH]c1c(C(N)=O)ccc(Br)c12]

A stirred suspension of ethyl 5-bromo-8-carbamoyl-2,3,4,9-tetrahydro-1H-carbazole-2-carboxylate (Intermediate 47-1, 9.31 g, 25.5 mmol) and 2,3-dichloro-5,6-dicyano-1,4-benzoquinone (12.73 g, 56.1 mmol) in toluene (127 mL) was heated at reflux for 3 h. The mixture was cooled to rt and the precipitate was collected by filtration, washed with toluene and water, and air dried. The solid was suspended in methanol and the precipitate was collected by filtration, washed with methanol and air dried to provide ethyl 5-bromo-8-carbamoyl-9H-carbazole-2-carboxylate (7.68 g). The filtrate was concentrated and the residue was suspended in methanol. The precipitate was collected by filtration, washed with methanol and air dried to provide additional product (0.60 g) for a total of 8.28 g (90%). ¹H NMR (400 MHz, DMSO-d₆) δ 12.03 (s, 1H) 8.69 (d, J=8.57 Hz, 1H) 8.51 (d, J=1.10 Hz, 1H) 8.26 (br. s., 1H) 7.93 (d, J=8.13 Hz, 1H) 7.87 (dd, J=8.57, 1.54 Hz, 1H) 7.63 (br. s., 1H) 7.50 (d, J=8.13 Hz, 1H) 4.37 (q, J=7.03 Hz, 2H) 1.37 (t, J=7.14 Hz, 3H). Mass spectrum m/z 361, 363 (M+H)⁺.

The following Intermediates were also prepared using the procedure used to prepare Intermediate 48-1 but using the appropriate material in place of Intermediate 47-1.

| Intermediate | Compound name | Mass spectrum |
|---|---|---|
| 48-2 | ethyl 5-bromo-8-carbamoyl-9H-carbazole-3-carboxylate | 361, 363 (M + H)⁺ |
| 48-3 | 4-bromo-9H-carbazole-1-carboxamide | 289, 291 (M + H)⁺ |

Intermediate 49-1

Preparation of 5-bromo-8-carbamoyl-9H-carbazole-2-carboxylic acid

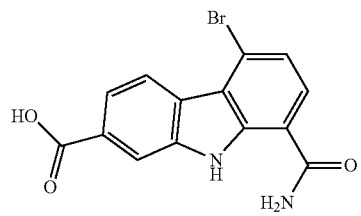 [SMILES: NC(=O)c1ccc(Br)c2c1[nH]c1cc(C(=O)O)ccc12]

A suspension of ethyl 5-bromo-8-carbamoyl-9H-carbazole-2-carboxylate (Intermediate 48-1, 1.81 g, 5.01 mmol) and lithium hydroxide monohydrate (0.601 g, 15.03 mmol) in THF-ethanol-water (3:1:1, 50 mL) was heated at reflux for 2 h. The mixture was cooled to rt and concentrated. The residue was stirred in water and treated with 1 M hydrochloric acid to pH 1-2. The precipitate was collected by filtration, washed with water, and dried to afford 5-bromo-8-carbamoyl-9H-carbazole-2-carboxylic acid as a light brown solid (1.84 g, ca. 90% purity, 99%). $^1$H NMR (400 MHz, DMSO-$d_6$) δ 12.95 (br. s., 1H) 12.02 (s, 1H) 8.69 (d, J=8.53 Hz, 1H) 8.47 (s, 1H) 8.28 (br. s., 1H) 7.94 (d, J=8.28 Hz, 2H) 7.87 (d, J=8.28 Hz, 1H) 7.65 (br. s., 1H) 7.51 (d, J=8.03 Hz, 1H). Mass spectrum m/z 331, 333 (M−H)$^−$.

The following Intermediates were also prepared using the procedure used to prepare Intermediate 49-1 but using the appropriate material in place of Intermediate 48-1.

| Intermediate | Compound name | Mass spectrum |
|---|---|---|
| 49-2 | 5-bromo-8-carbamoyl-9H-carbazole-3-carboxylic acid | 331, 333 (M − H)$^−$ |
| 49-3 | 5-bromo-8-carbamoyl-2,3,4,9-tetrahydro-1H-carbazole-2-carboxylic acid | 335, 337 (M − H)$^−$ |

Intermediate 50-1

Preparation of 2-methyl-3-(4,4,5,5-tetramethyl-1,3,2-dioxaborolan-2-yl)aniline

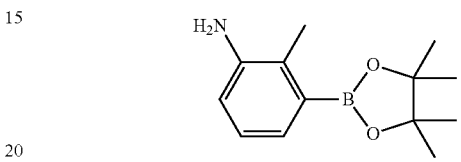

A mixture of 3-bromo-2-methylaniline (4.00 g, 21.5 mmol), 4,4,4',4',5,5,5',5'-octamethyl-2,2'-bi(1,3,2-dioxaborolane) (6.55 g, 25.8 mmol) and potassium acetate (4.22 g, 43.0 mmol) in 1,4-dioxane (44.8 mL) and DMSO (9.0 mL) was purged with nitrogen for 10 min. [1,1'-Bis(diphenylphosphino)ferrocene]-dichloropalladium DCM adduct (0.527 g, 0.645 mmol) was added, the mixture was purged for another 5 min then was heated at reflux for 2 h. The mixture was cooled and filtered through Celite. The solids were washed with EtOAc, and the combined filtrates were washed with water and brine, and dried and concentrated. The residue was purified by column chromatography (eluting with hexane-EtOAc using a gradient from 95:5 to 85:15) to provide 2-methyl-3-(4,4,5,5-tetramethyl-1,3,2-dioxaborolan-2-yl)aniline as a light yellow waxy solid (4.4 g, 88%), used without further purification. $^1$H NMR (400 MHz, chloroform-d) δ 7.21 (1H, dd, J=7.3, 1.0 Hz), 7.02 (1H, t, J=7.7 Hz), 6.75 (1H, dd, J=7.8, 1.0 Hz), 3.54 (2H, br. s.), 2.37 (3H, s), 1.34 (12H, s). Mass spectrum m/z 233.3, 234.3, 235.3 (M+H)$^+$.

The following Intermediates were also prepared using the procedure used to prepare Intermediate 50-1 or closely related procedures.

| Intermediate | Starting Material[a] | Compound name | Mass spectrum |
|---|---|---|---|
| 50-2 | | 2-methyl-3-(4,4,5,5-tetramethyl-1,3,2-dioxaborolan-2-yl)benzonitrile | [b] |
| 50-3 | | 3,5-difluoro-4-(4,4,5,5-tetramethyl-1,3,2-dioxaborolan-2-yl)aniline | 256.3 (M + H)$^+$ |
| 50-4 | Intermediate 1-1 | 2-(2-methyl-3-(4,4,5,5-tetramethyl-1,3,2-dioxaborolan-2-yl)phenyl)isoindolin-1-one | 350.3 (M + H)$^+$ |
| 50-5 | Intermediate 1-2 | 6-fluoro-2-(2-methyl-3-(4,4,5,5-tetramethyl-1,3,2-dioxaborolan-2-yl)phenyl)isoindolin-1-one | 368.1 (M + H)$^+$ |
| 50-6 | Intermediate 1-4 | 5-methoxy-2-(2-methyl-3-(4,4,5,5-tetramethyl-1,3,2-dioxaborolan-2-yl)phenyl)isoindolin-1-one | 380.1 (M + H)$^+$ |
| 50-7 | Intermediate 1-5 | 2-(2-methyl-3-(4,4,5,5-tetramethyl-1,3,2-dioxaborolan-2-yl)phenyl)-6-(trifluoromethyl)isoindolin-1-one | 418.1 (M + H)$^+$ |
| 50-8 | Intermediate 1-6 | 6-methyl-2-(2-methyl-3-(4,4,5,5-tetramethyl-1,3,2-dioxaborolan-2-yl)phenyl)isoindolin-1-one | 364.0 (M + H)$^+$ |
| 50-9 | Intermediate 2-1 | 2-(2-methyl-3-(4,4,5,5-tetramethyl-1,3,2-dioxaborolan-2-yl)phenyl)-3-oxoisoindoline-5-carbonitrile | 375.3 (M + H)$^+$ |

-continued

| Intermediate | Starting Material[a] | Compound name | Mass spectrum |
|---|---|---|---|
| 50-10 | Intermediate 3-1 | 5-fluoro-2-(2-methyl-3-(4,4,5,5-tetramethyl-1,3,2-dioxaborolan-2-yl)phenyl)isoindoline-1,3-dione | 382.1 (M + H)+ |
| 50-11 | Intermediate 3-2 | 5-tert-butyl-2-(2-methyl-3-(4,4,5,5-tetramethyl-1,3,2-dioxaborolan-2-yl)phenyl)isoindoline-1,3-dione | 420.2 (M + H)+ |
| 50-12 | Intermediate 4-1 | 2-(2-methyl-3-(4,4,5,5-tetramethyl-1,3,2-dioxaborolan-2-yl)phenyl)octahydro-1H-isoindol-1-one | 356.1 (M + H)+ |
| 50-13 | Intermediate 4-2 | 2-(2-methyl-3-(4,4,5,5-tetramethyl-1,3,2-dioxaborolan-2-yl)phenyl)-2,3,4,5,6,7-hexahydro-1H-isoindol-1-one | 354.2 (M + H)+ |
| 50-14 | Intermediate 4-3 | 6-tert-butyl-2-(2-methyl-3-(4,4,5,5-tetramethyl-1,3,2-dioxaborolan-2-yl)phenyl)isoindolin-1-one | 406.2 (M + H)+ |
| 50-15 | Intermediate 4-4 | 5-tert-butyl-2-(2-methyl-3-(4,4,5,5-tetramethyl-1,3,2-dioxaborolan-2-yl)phenyl)isoindolin-1-one | 406.2 (M + H)+ |
| 50-16 | Intermediate 4-5 | 7-fluoro-2-(2-methyl-3-(4,4,5,5-tetramethyl-1,3,2-dioxaborolan-2-yl)phenyl)isoindolin-1-one | 368.3 (M + H)+ |
| 50-17 | Intermediate 4-6 | 4-fluoro-2-(2-methyl-3-(4,4,5,5-tetramethyl-1,3,2-dioxaborolan-2-yl)phenyl)isoindolin-1-one | 368.3 (M + H)+ |
| 50-18 | Intermediate 4-7 | 5-methyl-2-(2-methyl-3-(4,4,5,5-tetramethyl-1,3,2-dioxaborolan-2-yl)phenyl)isoindolin-1-one | 364.2 (M + H)+ |
| 50-19 | Intermediate 4-8 | 5-fluoro-2-(2-methyl-3-(4,4,5,5-tetramethyl-1,3,2-dioxaborolan-2-yl)phenyl)isoindolin-1-one | 368.2 (M + H)+ |
| 50-20 | Intermediate 5-1 | 5-methyl-2-(4-methyl-5-(4,4,5,5-tetramethyl-1,3,2-dioxaborolan-2-yl)pyridin-3-yl)isoindolin-1-one | 365.2 (M + H)+ |
| 50-21 | Intermediate 5-2 | 2-(4-methyl-5-(4,4,5,5-tetramethyl-1,3,2-dioxaborolan-2-yl)pyridin-3-yl)isoindolin-1-on | 351.2 (M + H)+ |
| 50-22 | Intermediate 6-1 | 2-(3-fluoro-4-(4,4,5,5-tetramethyl-1,3,2-dioxaborolan-2-yl)pyridin-2-yl)isoindolin-1-one | 355 (M + H)+ |
| 50-23 | Intermediate 7-1 | 2-methyl-3-(2-methyl-3-(4,4,5,5-tetramethyl-1,3,2-dioxaborolan-2-yl)phenyl)quinazolin-4(3H)-one | 377.3 (M + H)+ |
| 50-24 | Intermediate 8-1 | 3-(2-methyl-3-(4,4,5,5-tetramethyl-1,3,2-dioxaborolan-2-yl)phenyl)quinazolin-4(3H)-one | 363.3 (M + H)+ |
| 50-25 | Intermediate 8-2 | 5-fluoro-3-(2-methyl-3-(4,4,5,5-tetramethyl-1,3,2-dioxaborolan-2-yl)phenyl)quinazolin-4(3H)-one | 381.3 (M + H)+ |
| 50-26 | Intermediate 8-3 | 6-chloro-3-(2-methyl-3-(4,4,5,5-tetramethyl-1,3,2-dioxaborolan-2-yl)phenyl)quinazolin-4(3H)-one | 397, 399 (M + H)+ |
| 50-27 | Intermediate 9-1 | 6-fluoro-3-(2-methyl-3-(4,4,5,5-tetramethyl-1,3,2-dioxaborolan-2-yl)phenyl)quinazolin-4(3H)-one | 381.3 (M + H)+ |
| 50-28 | Intermediate 9-2 | 6-methyl-3-(2-methyl-3-(4,4,5,5-tetramethyl-1,3,2-dioxaborolan-2-yl)phenyl)quinazolin-4(3H)-one | 377.3 (M + H)+ |
| 50-29 | Intermediate 10-1 | 2-(2-methyl-3-(4,4,5,5-tetramethyl-1,3,2-dioxaborolan-2-yl)phenyl)isoquinolin-1(2H)-on | 362.3 (M + H)+ |
| 50-30 | Intermediate 11-1 | 7-(2-methyl-3-(4,4,5,5-tetramethyl-1,3,2-dioxaborolan-2-yl)phenyl)imidazo[1,2-a]pyrazin-8(7H)-one | 352.1 (M + H)+ |
| 50-31 | Intermediate 12-1 | pyrrolidin-1-yl(4-(4,4,5,5-tetramethyl-1,3,2-dioxaborolan-2-yl)-1H-indol-2-yl)methanone | 341.1 (M + H)+ |
| 50-32 | Intermediate 13-1 | 2-(2-methyl-3-(4,4,5,5-tetramethyl-1,3,2-dioxaborolan-2-yl)phenyl)isoindoline | 336.2 (M + H)+ |
| 50-33 | Intermediate 17-1 | 5-methyl-3-phenyl-6-(4,4,5,5-tetramethyl-1,3,2-dioxaborolan-2-yl)-3,4-dihydro-2H-benzo[e][1,3]oxazin-2-one | 366.1 (M + H)+ |
| 50-34 | Intermediate 18-1 | 5-methyl-3-phenyl-6-(4,4,5,5-tetramethyl-1,3,2-dioxaborolan-2-yl)-2H-benzo[e][1,3]oxazin-4(3H)-one | 366.1 (M + H)+ |
| 50-35 | Intermediate 19-1 | 5-methyl-3-phenyl-6-(4,4,5,5-tetramethyl-1,3,2-dioxaborolan-2-yl)-2H-benzo[e][1,3]oxazine-2,4(3H)-dione | 380.1 (M + H)+ |

-continued

| Intermediate | Starting Material[a] | Compound name | Mass spectrum |
|---|---|---|---|
| 50-36 | Intermediate 20-1 | N-(2-methyl-3-(4,4,5,5-tetramethyl-1,3,2-dioxaborolan-2-yl)phenyl)-1H-indazol-3-amine | 350.3 (M + H)+ |
| 50-37 | Intermediate 21-1 | tert-butyl 6-(4-fluorophenyl)-3-(4,4,5,5-tetramethyl-1,3,2-dioxaborolan-2-yl)-1H-indole-1-carboxylate | 438.2 (M + H)+ |
| 50-38 | Intermediate 9-7 | 3-(2-methyl-3-(4,4,5,5-tetramethyl-1,3,2-dioxaborolan-2-yl)phenyl)-6-(trifluoromethoxy)quinazolin-4(3H)-one | 447.1 (M + H)+ |
| 50-39 | Intermediate 23-1 | 7-(4,4,5,5-tetramethyl-1,3,2-dioxaborolan-2-yl)-3,4-dihydroisoquinolin-1(2H)-one | 274.1 (M + H)+ |
| 50-40 | Intermediate 24-1 | 2-(4-fluorophenyl)-7-(4,4,5,5-tetramethyl-1,3,2-dioxaborolan-2-yl)-3,4-dihydroisoquinolin-1(2H)-one | 368.1 (M + H)+ |
| 50-41 | Intermediate 25-1 | 1-(4-fluorobenzyl)-4-(4,4,5,5-tetramethyl-1,3,2-dioxaborolan-2-yl)-1H-indole | 352.2 (M + H)+ |
| 50-42 | Intermediate 26-1 | (4-fluorophenyl)(5-(4,4,5,5-tetramethyl-1,3,2-dioxaborolan-2-yl)naphthalen-1-yl)methanone | 377.24 (M + H)+ |
| 50-43 | Intermediate 27-1 | 1-(2-methyl-3-(4,4,5,5-tetramethyl-1,3,2-dioxaborolan-2-yl)phenyl)piperidin-2-one | 316.3 (M + H)+ |
| 50-44 | Intermediate 28-1 | N-(2-methyl-3-(4,4,5,5-tetramethyl-1,3,2-dioxaborolan-2-yl)phenyl)cyclopropanecarboxamide | 302.2 (M + H)+ |
| 50-45 | Intermediate 34-1 | 2-fluoro-3-(4,4,5,5-tetramethyl-1,3,2-dioxaborolan-2-yl)aniline | 238.1 (M + H)+ |
| 50-46 | Intermediate 39-1 | 2-(4-fluorophenyl)-7-methyl-6-(4,4,5,5-tetramethyl-1,3,2-dioxaborolan-2-yl)-1H-benzo[d]imidazole | 353.2 (M + H)+ |
| 50-47 | Intermediate 40-1 | N,N-bis(tert-butyloxycarbonyl)-5-(4,4,5,5-tetramethyl-1,3,2-dioxaborolan-2-yl)-4-methylthiazol-2-ylamine | 441.2 (M + H)+ |
| 50-48 | Intermediate 9-3 | 8-fluoro-3-(2-methyl-3-(4,4,5,5-tetramethyl-1,3,2-dioxaborolan-2-yl)phenyl)quinazolin-4(3H)-one | 381.2 (M + H)+ |
| 50-49 | Intermediate 44-1 | 2-(2-methyl-3-(4,4,5,5-tetramethyl-1,3,2-dioxaborolan-2-yl)phenyl)-1H-pyrrolo[3,4-c]pyridin-3(2H)-one | 351.5 (M + H)+ |
| 50-50 | Intermediate 44-2 | (Z)—N-(furo[3,4-c]pyridin-1(3H)-ylidene)-2-methyl-3-(4,4,5,5-tetramethyl-1,3,2-dioxaborolan-2-yl)aniline | 351.3 (M + H)+ |
| 50-51 | Intermediate 9-4 | 8-methoxy-3-(2-methyl-3-(4,4,5,5-tetramethyl-1,3,2-dioxaborolan-2-yl)phenyl)quinazolin-4(3H)-one | 393.1 (M + H)+ |
| 50-52 | Intermediate 9-5 | 5-methoxy-3-(2-methyl-3-(4,4,5,5-tetramethyl-1,3,2-dioxaborolan-2-yl)phenyl)quinazolin-4(3H)-one | 393.1 (M + H)+ |
| 50-53 | Intermediate 9-6 | 7-methoxy-3-(2-methyl-3-(4,4,5,5-tetramethyl-1,3,2-dioxaborolan-2-yl)phenyl)quinazolin-4(3H)-one | 393.1 (M + H)+ |
| 50-54 | Intermediate 32-9 | N-(2-methyl-3-(4,4,5,5-tetramethyl-1,3,2-dioxaborolan-2-yl)phenyl)quinazolin-4-amine | 362.0 (M + H)+ |
| 50-55 | Intermediate 32-6 | 5-fluoro-N-(2-methyl-3-(4,4,5,5-tetramethyl-1,3,2-dioxaborolan-2-yl)phenyl)quinazolin-4-amine | 379.9 (M + H)+ |
| 50-56 | Intermediate 32-3 | 7-fluoro-N-(2-methyl-3-(4,4,5,5-tetramethyl-1,3,2-dioxaborolan-2-yl)phenyl)quinazolin-4-amine | 380.0 (M + H)+ |
| 50-57 | Intermediate 32-7 | 8-fluoro-N-(2-methyl-3-(4,4,5,5-tetramethyl-1,3,2-dioxaborolan-2-yl)phenyl)quinazolin-4-amine | 380.0 (M + H)+ |
| 50-58 | Intermediate 9-8 | 8-methyl-3-(2-methyl-3-(4,4,5,5-tetramethyl-1,3,2-dioxaborolan-2-yl)phenyl)quinazolin-4(3H)-one | 377.1 (M + H)+ |
| 50-59 | Intermediate 9-9 | 6-methoxy-3-(2-methyl-3-(4,4,5,5-tetramethyl-1,3,2-dioxaborolan-2-yl)phenyl)quinazolin-4(3H)-one | 393.1 (M + H)+ |
| 50-60 | Intermediate 9-10 | 7-fluoro-3-(2-methyl-3-(4,4,5,5-tetramethyl-1,3,2-dioxaborolan-2-yl)phenyl)quinazolin-4(3H)-one | 381.1 (M + H)+ |

[a]Starting materials are not indicated if commercially available.
[b] 1H NMR (400 MHz, methanol-d4) δ 7.96 (1 H, dd, J = 7.59, 1.21 Hz), 7.72 (1 H, dd, J = 7.70, 1.32 Hz), 7.33 (1 H, t, J = 7.37 Hz), 2.72 (3 H, s), 1.37 (12 H, s).

Intermediates 51-1 and 51-2

Preparation of 6-chloro-2-(2-methyl-3-(4,4,5,5-tetramethyl-1,3,2-dioxaborolan-2-yl)phenyl)isoindolin-1-one and 5-chloro-2-(2-methyl-3-(4,4,5,5-tetramethyl-1,3,2-dioxaborolan-2-yl)phenyl)isoindolin-1-one

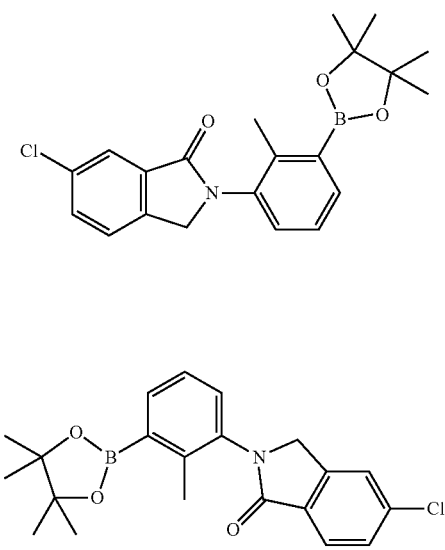

A suspension of crude 2-(3-bromo-2-methylphenyl)-5-chloroisoindoline-1,3-dione (Intermediate 3-3, 3.77 g, 10.75 mmol) in methanol (100 mL) was treated with sodium borohydride (1.017 g, 26.9 mmol) and stirred at rt for 2 h. The mixture was concentrated to give a solid which was suspended in DCM (20 mL) and treated with triethylsilane (18.12 mL, 113 mmol) and stirred at rt. After a few minutes, the mixture was treated slowly with TFA (4.37 mL, 56.7 mmol) and stirred for 10 min. Additional TFA (4.37 mL, 56.7 mmol) was added and the solution was stirred at rt for 1.5 h. The mixture was concentrated and the residue was dissolved in DCM. The solution was washed with NaHCO3 (aq) and water, and dried and concentrated. The residue was purified column chromatography (eluting with 25:75 EtOAc-hexane) to give a solid, containing both 2-(3-bromo-2-methylphenyl)-6-chloroisoindolin-1-one and 2-(3-bromo-2-methylphenyl)-5-chloroisoindolin-1-one. Using the procedure used to prepare Intermediate 50-1, this material (0.85 g, 2.53 mmol) was converted to a mixture of 6-chloro-2-(2-methyl-3-(4,4,5,5-tetramethyl-1,3,2-dioxaborolan-2-yl)phenyl)isoindolin-1-one and 5-chloro-2-(2-methyl-3-(4,4,5,5-tetramethyl-1,3,2-dioxaborolan-2-yl)phenyl)isoindolin-1-one which was separated by column chromatography (eluting with a gradient from 95:5 to 75:25 hexane-EtOAc). 6-chloro-2-(2-methyl-3-(4,4,5,5-tetramethyl-1,3,2-dioxaborolan-2-yl)phenyl)isoindolin-1-one (Intermediate 51-1, 126 mg, 13%): $^1$H NMR (400 MHz, chloroform-d) δ 7.94 (1H, d, J=1.9 Hz), 7.83 (1H, dd, J=7.1, 1.8 Hz), 7.57 (1H, dd, J=8.0, 1.9 Hz), 7.44 (1H, d, J=8.0 Hz), 7.27-7.33 (2H, m), 4.66 (2H, s), 2.41 (3H, s), 1.35 (12H, s). Mass spectrum m/z 384, 386 (M+H)$^+$. 5-chloro-2-(2-methyl-3-(4,4,5,5-tetramethyl-1,3,2-dioxaborolan-2-yl)phenyl)isoindolin-1-one (Intermediate 51-2, 315 mg, 33%): $^1$H NMR (400 MHz, chloroform-d) δ 7.88 (1H, d, J=8.6 Hz), 7.82 (1H, dd, J=7.1, 1.8 Hz), 7.48-7.54 (2H, m), 7.27-7.32 (2H, m), 4.66 (2H, s), 2.41 (3H, s), 1.35 (12H, s). Mass spectrum m/z 384, 386 (M+H)$^+$.

Intermediate 52-1

Preparation of 4,4,5,5-tetramethyl-2-(8-methyl-2-phenylchroman-7-yl)-1,3,2-dioxaborolane

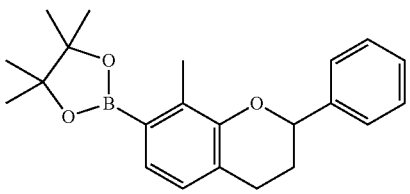 [SMILES: Cc1c(B2OC(C)(C)C(C)(C)O2)ccc2c1OC(c1ccccc1)CC2]

A mixture of 8-methyl-2-phenylchroman-7-yl trifluoromethanesulfonate (Intermediate 14-1, 0.300 g, 0.806 mmol), 4,4,4',4',5,5,5',5'-octamethyl-2,2'-bi(1,3,2-dioxaborolane) (0.246 g, 0.967 mmol), [1,1'-bis(diphenylphosphino)ferrocene]-dichloropalladium DCM adduct (0.066 g, 0.081 mmol), diphenylphosphorylferrocene (0.045 g, 0.081 mmol) and tripotassium phosphate (0.342 g, 1.611 mmol) in DMF was heated in a sealed tube under nitrogen at 80° C. for 15 h. The mixture was cooled and diluted with EtOAc (30 mL), washed with saturated aqueous ammonium chloride (10 mL), water (10 mL) and brine (10 mL), dried and concentrated. The residue was purified by column chromatography (eluting with a gradient from 97.5:2.5 to 95:5 hexane-EtOAc) to give 4,4,5,5-tetramethyl-2-(8-methyl-2-phenylchroman-7-yl)-1,3,2-dioxaborolane as colorless liquid (ca. 85% purity). $^1$H NMR (400 MHz, chloroform-d) δ 7.35-7.46 (4H, m), 7.26-7.35 (2H, m), 6.92 (1H, d, J=7.48 Hz), 5.11 (1H, dd, J=9.79, 2.31 Hz), 2.98 (1H, ddd, J=16.84, 11.11, 6.16 Hz), 2.70-2.83 (1H, m), 2.40-2.54 (3H, m), 2.15-2.30 (1H, m), 1.92-2.04 (1H, m), 1.34 (12H, s). Mass spectrum m/z 351.1 (M+H)$^+$.

The following Intermediates were also prepared using the procedure used to prepare Intermediate 52-1.

| Intermediate | Starting material | Compound name | Mass spectrum |
|---|---|---|---|
| 52-2 | Intermediate 15-1 | 3-phenyl-6-(4,4,5,5-tetramethyl-1,3,2-dioxaborolan-2-yl)-3,4-dihydro-2H-benzo[e][1,3]oxazin-2-one | 352.3 (M + H)$^+$ |

Intermediate 53-1

Preparation of 4-fluoro-N-(2-methyl-3-(4,4,5,5-tetramethyl-1,3,2-dioxaborolan-2-yl)phenyl)benzamide

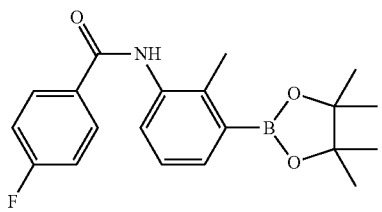 [SMILES: Cc1c(NC(=O)c2ccc(F)cc2)cccc1B1OC(C)(C)C(C)(C)O1]

A solution of 2-methyl-3-(4,4,5,5-tetramethyl-1,3,2-dioxaborolan-2-yl)aniline (Intermediate 50-1, 1.10 g, 4.72 mmol) in EtOAc (25 mL) was treated with TEA (0.789 mL, 5.66 mmol), then with 4-fluorobenzoyl chloride (0.577 mL, 4.81 mmol) and the mixture was stirred at rt. After 22 h, the mixture was diluted with EtOAc, washed twice with water, then with brine, and dried and concentrated to provide 4-fluoro-N-(2-methyl-3-(4,4,5,5-tetramethyl-1,3,2-dioxaborolan-2-yl)phenyl)benzamide as a glassy foam (1.705 g, ca. 90% purity, 92%). $^1$H NMR (400 MHz, chloroform-d) δ 7.96 (d, J=7.5 Hz, 1H) 7.90 (dd, J=8.6, 5.3 Hz, 2H) 7.66 (dd, J=7.4, 1.2 Hz, 1H) 7.63 (br. s., 1H) 7.22-7.29 (m, 1H) 7.18 (t, J=8.6 Hz, 2H) 2.53 (s, 3H) 1.36 (s, 12H). Mass spectrum m/z 356.1 (M+H)$^+$.

Intermediate 54-1

Preparation of tert-butyl-isopropyl(5-(4,4,5,5-tetramethyl-1,3,2-dioxaborolan-2-yl)thiazol-2-yl)carbamate

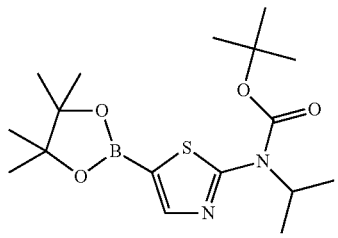 [SMILES: CC(C)N(C(=O)OC(C)(C)C)c1ncc(B2OC(C)(C)C(C)(C)O2)s1]

A solution of tert-butyl 5-bromothiazol-2-yl(isopropyl)carbamate (Intermediate 43-1, 7.5 g, 23.3 mmol) in THF (50 mL) was treated with n-butyllithium (1.6 M in hexane, 21.8 mL, 34.88 mmol) dropwise at −78° C. The resulting solution was stirred at −78° C. for 10 min, then was treated dropwise with 2-isopropoxy-4,4,5,5-tetramethyl-1,3,2-dioxaborolane (6.49 g, 34.9 mmol). The mixture was stirred at −78° C. for 2 h, then was warmed to rt and treated with 50% aqueous ammonium chloride (50 mL). The mixture was extracted with EtOAc (100 mL) and the organic layer was washed with water and brine, and dried and concentrated. The residue was slurried in hexane (30 mL) and the precipitate was collected by filtration, washed with hexane (20 mL) and dried to give tert-butyl-isopropyl(5-(4,4,5,5-tetramethyl-1,3,2-dioxaborolan-2-yl)thiazol-2-yl)carbamate as a yellow solid (4.17 g, 48%). $^1$H NMR (400 MHz, chloroform-d) δ 7.95 (s, 1H) 5.37 (m, 1H) 1.60 (s, 9H) 1.44 (d, 6.7 Hz, 6H) 1.34 (s, 12H).

Intermediate 55-1

Preparation of 2-(3-bromo-2-methylphenyl)-5-hydroxyisoindolin-1-one

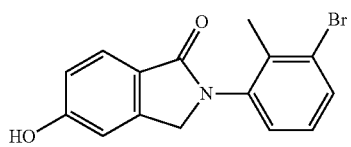

A mixture of 2-(3-bromo-2-methylphenyl)-5-methoxyisoindolin-1-one (Intermediate 1-4, 100 mg, 0.30 mmol) and 1.0 M boron tribromide in DCM (900 μL, 0.90 mmol) was stirred at rt for 4 h. The reaction mixture was diluted with DCM, washed with NaHCO3 (aq) and dried and concentrated. The residue was purified by column chromatography (eluting with EtOAc-hexane) to provide 2-(3-bromo-2-methylphenyl)-5-hydroxyisoindolin-1-one as an off-white solid (62 mg, 65%). $^1$H NMR (400 MHz, chloroform-d) δ 10.27 (1H, br. s.), 7.64 (1H, dd, J=7.9, 0.9 Hz), 7.59 (1H, d, J=8.4 Hz), 7.44 (1H, d, J=7.3 Hz), 7.25 (1H, t, J=7.9 Hz), 6.98 (1H, d, J=1.5 Hz), 6.93 (1H, dd, J=8.3, 2.1 Hz), 4.77 (2H, s), 2.20 (3H, s). Mass spectrum m/z 318, 320 (M+H)$^+$.

Intermediate 56-1

Preparation of 1-(3-bromo-2-methylphenyl)-4-phenyl-1H-imidazol-2(3H)-one

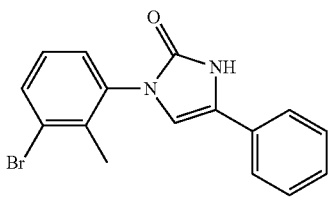 [SMILES: Cc1c(Br)cccc1-n1cc(-c2ccccc2)[nH]c1=O]

Step 1 A mixture of 3-bromo-2-methylaniline (0.620 mL, 5.03 mmol) and sodium bicarbonate (565 mg, 6.73 mmol) in acetonitrile (4.5 mL) was treated with 2-bromo-1-phenylethanone (500 mg, 2.51 mmol) and the mixture was stirred at rt. After 24 h, the suspension was filtered and the precipitate was suspended and sonicated in water, collected again by filtration, washed with water and dried to provide 2-(3-bromo-2-methylphenylamino)-1-phenylethanone as an off-white solid (508 mg, 67%). $^1$H NMR (400 MHz, chloroform-d) δ 8.00-8.06 (2H, m), 7.61-7.68 (1H, m), 7.53 (2H, t, J=7.6 Hz), 6.94-7.01 (2H, m), 6.51-6.58 (1H, m), 5.06 (1H, t, J=4.1 Hz), 4.62 (2H, d, J=4.4 Hz), 2.40 (3H, s). Mass spectrum m/z 304, 306 (M+H)$^+$.

Step 2 Following the procedure of Congiu et al. (Bioorg. Med. Chem. Lett., 2008, 989), 2-(3-bromo-2-methylphenylamino)-1-phenylethanone (250 mg, 0.822 mmol) was converted, following purification by column chromatography (eluting with a gradient from 25:75 EtOAc-hexane to EtOAc) to 1-(3-bromo-2-methylphenyl)-4-phenyl-1H-imidazol-2(3H)-one as a white solid (59 mg, 22%). $^1$H NMR (400 MHz, DMSO-d$_6$) δ 11.00 (1H, s), 7.70 (1H, dd, J=8.0, 1.0 Hz), 7.59

(2H, d, J=7.3 Hz), 7.34-7.43 (3H, m), 7.21-7.32 (3H, m), 2.27 (3H, s). Mass spectrum m/z 329, 331 (M+H)$^+$.

Intermediate 57-1

Preparation of racemic benzyl 1-(3-bromo-2-methylphenyl)-2-oxopyrrolidin-3-ylcarbamate

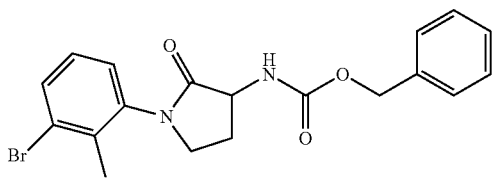 [SMILES: Cc1c(Br)cccc1N1CCC(NC(=O)OCc2ccccc2)C1=O]

Step 1 A solution of 3-bromo-2-methylaniline (0.662 mL, 5.37 mmol) and racemic 2-(benzyloxycarbonylamino)-4-(methylthio)butanoic acid (1.523 g, 5.37 mmol) in acetonitrile (25 mL) was treated with 1-hydroxy-7-azabenzotriazole (0.878 g, 6.45 mmol), diisopropylethylamine (1.877 mL, 10.75 mmol) and EDC (1.236 g, 6.45 mmol) and stirred at rt. After 20.5 h, the mixture was diluted with water and ethyl acetate. The organic phase was separated, washed with 1 M aqueous HCl and NaHCO3 (aq) and filtered to remove a flocculent white solid. The filtrate was dried and concentrated, and the residue was recrystallized from ethanol to give racemic benzyl 1-(3-bromo-2-methylphenylamino)-4-(methylthio)-1-oxobutan-2-ylcarbamate as a tan solid (1.33 g, 69%). $^1$H NMR (400 MHz, chloroform-d) δ 8.08 (1H, br. s.), 7.68 (1H, d, J=7.9 Hz), 7.39 (1H, d, J=7.9 Hz), 7.34 (5H, s), 7.04 (1H, t, J=8.0 Hz), 5.58 (1H, d, J=7.9 Hz), 5.14 (2H, s), 4.53 (1H, q, J=7.0 Hz), 2.55-2.72 (2H, m), 2.28 (3H, br. s.), 2.17-2.27 (1H, m), 2.12 (3H, s), 2.01-2.10 (1H, m). Mass spectrum m/z 451, 453 (M+H)$^+$.

Step 2 A mixture of racemic benzyl 1-(3-bromo-2-methylphenylamino)-4-(methylthio)-1-oxobutan-2-ylcarbamate (1.31 g, 2.90 mmol) and DCM (4 mL) was diluted with iodomethane (7.5 mL, 120 mmol) and the mixture was stirred at rt. After 24.5 h, the mixture (a solution with an insoluble reddish oil) was concentrated under vacuum. The residue was treated three times with DCM and concentrated under vacuum to provide racemic (3-(benzyloxycarbonylamino)-4-(3-bromo-2-methylphenylamino)-4-oxobutyl)dimethylsulfonium iodide as an orange-yellow glassy foam (1.75 g, 97%). $^1$H NMR (400 MHz, chloroform-d) δ9.16 (1H, br. s.), 7.28-7.46 (7H, m), 6.99 (1H, t, J=8.0 Hz), 6.71 (1H, d, J=6.8 Hz), 5.11 (2H, s), 4.84 (1H, br. s.), 3.75 (1H, br. s.), 3.54 (1H, br. s.), 3.14 (3H, br. s.), 2.96 (3H, s), 2.75 (1H, br. s.), 2.33-2.41 (1H, m), 2.30 (3H, br. s.). Mass spectrum m/z 465, 467 (M)$^+$.

Step 3 A solution of racemic (3-(benzyloxycarbonylamino)-4-(3-bromo-2-methylphenylamino)-4-oxobutyl) dimethylsulfonium iodide (1.96 g, 3.30 mmol) in anhydrous DMSO (33 mL) was stirred at rt and treated with cesium carbonate (2.69 g, 8.26 mmol) in 3 portions over 25 min. After 4.5 h, the mixture was diluted with EtOAc, washed three times with water and twice with brine, dried and concentrated to provide racemic benzyl 1-(3-bromo-2-methylphenyl)-2-oxopyrrolidin-3-ylcarbamate as a tan solid (1.248 g, 94%). $^1$H NMR (400 MHz, chloroform-d) δ 7.52-7.58 (1H, m), 7.30-7.40 (5H, m), 7.10 (2H, d, J=5.1 Hz), 5.47 (1H, br. s.), 5.15 (2H, s), 4.39 (1H, ddd, J=10.6, 8.3, 5.2 Hz), 3.72 (1H, td, J=9.9, 6.4 Hz), 3.60 (1H, t, J=9.4 Hz), 2.27 (3H, s), 2.11-2.26 (2H, m). Mass spectrum m/z 425, 427 (M+Na)$^+$.

Example 1-1

Preparation of 4-bromo-7-(4-methylpiperazine-1-carbonyl)-9H-carbazole-1-carboxamide

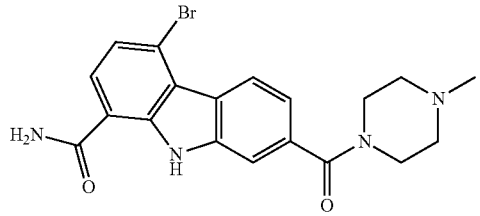 [SMILES: CN1CCN(C(=O)c2ccc3c(c2)[nH]c2c(C(N)=O)ccc(Br)c23)CC1]

A suspension of 5-bromo-8-carbamoyl-9H-carbazole-2-carboxylic acid (Intermediate 49-1, 1.84 g, 4.97 mmol), EDC (1.334 g, 6.96 mmol), and HOBT (1.066 g, 6.96 mmol) in THF-DCM-DMF (4:1:1) (124 mL) was treated with 1-methylpiperazine (1.656 mL, 14.91 mmol) and the mixture was stirred at rt for 3 days. The mixture was concentrated and the residue was partitioned between DCM and NaHCO3 (aq). The organic phase was washed with brine, dried and concentrated to afford an oil. This was purified by column chromatography (DCM-2 M methanolic ammonia, 100:0 to 95:5 to 92.5:7.5). The resulting solid was suspended in EtOAc, collected by filtration and dried to provide 4-bromo-7-(4-methylpiperazine-1-carbonyl)-9H-carbazole-1-carboxamide (1.57 g, 76%). $^1$H NMR (400 MHz, DMSO-d$_6$) δ 11.83 (s, 1H) 8.57 (d, J=8.13 Hz, 1H) 8.20 (br. s., 1H) 7.84 (d, J=8.35 Hz, 1H) 7.79 (s, 1H) 7.56 (br. s., 1H) 7.42 (d, J=8.13 Hz, 1H) 7.22 (d, J=8.13 Hz, 1H) 3.30-3.70 (m, 4H) 2.19-2.39 (m, 4H) 2.16 (s, 3H). Mass spectrum m/z 415, 417 (M+H)$^+$.

The following Examples and Intermediates were also prepared using the procedures used to prepare Example 1-1, or closely related procedures.

| Example/ Intermediate | Starting material | Compound name | Mass spectrum |
|---|---|---|---|
| 1-2 | Intermediate 49-2 | 4-bromo-6-(4-methylpiperazine-1-carbonyl)-9H-carbazole-1-carboxamide | 415, 417 (M + H)$^+$ |
| 1-3 | Intermediate 49-3 | 5-bromo-2-(4-methylpiperazine-1-carbonyl)-2,3,4,9-tetrahydro-1H-carbazole-8-carboxamide | 419, 421 (M + H)$^+$ |
| Intermediate 1-4(a) | Intermediate 49-1 | 4-bromo-7-(morpholine-4-carbonyl)-9H-carbazole-1-carboxamide | 402, 404 (M + H)$^+$ |

-continued

| Example/Intermediate | Starting material | Compound name | Mass spectrum |
|---|---|---|---|
| Intermediate 1-5(a) | Intermediate 49-3 | 5-bromo-$N^2$-(3-(dimethylamino)propyl)-2,3,4,9-tetrahydro-1H-carbazole-2,8-dicarboxamide | 421, 423 (M + H)$^+$ |
| Intermediate 1-6(a) | Intermediate 49-3 | 5-bromo-$N^2$-(4-(dimethylamino)butyl)-2,3,4,9-tetrahydro-1H-carbazole-2,8-dicarboxamide | 435, 437 (M + H)$^+$ |
| Intermediate 1-7(a) | Intermediate 49-3 | 5-bromo-$N^2$-(tetrahydro-2H-pyran-4-yl)-2,3,4,9-tetrahydro-1H-carbazole-2,8-dicarboxamide | 420, 422 (M + H)$^+$ |
| Intermediate 1-8(a) | Intermediate 49-3 | 5-bromo-$N^2$-(1-methylpiperidin-4-yl)-2,3,4,9-tetrahydro-1H-carbazole-2,8-dicarboxamide | 433, 435 (M + H)$^+$ |
| Intermediate 1-9(a) | Intermediate 49-3 | 5-bromo-$N^2$-methyl-$N^2$-(1-methylpiperidin-4-yl)-2,3,4,9-tetrahydro-1H-carbazole-2,8-dicarboxamide | 447, 449 (M + H)$^+$ |
| Intermediate 1-10(a) | Intermediate 49-1 | 4-bromo-$N^7$,$N^7$-dimethyl-9H-carbazole-1,7-dicarboxamide | 360, 362 (M + H)$^+$ |

Example 2-1

Preparation of 4-(5-aminonaphthalen-1-yl)-7-(4-methylpiperazine-1-carbonyl)-9H-carbazole-1-carboxamide

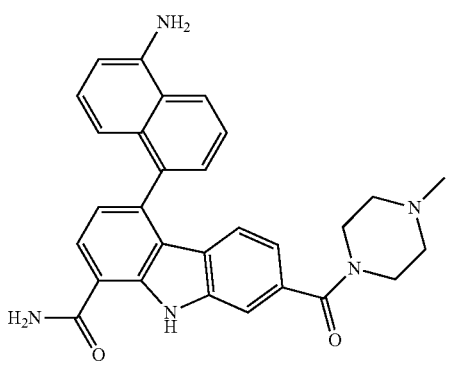 [SMILES: CN1CCN(C(=O)c2ccc3c(c2)[nH]c2c(C(N)=O)ccc(-c4cccc5c(N)cccc45)c23)CC1]

Step 1 A solution of tris(dibenzylideneacetone)dipalladium (27.6 mg, 0.031 mmol) and tricyclohexylphosphine (1.0 M in toluene, 0.144 mL, 0.144 mmol) in 1,4-dioxane (8 mL) was purged with argon for 10 min. 4-Bromo-7-(4-methylpiperazine-1-carbonyl)-9H-carbazole-1-carboxamide (Example 1-1, 500 mg, 1.204 mmol), 4,4,4',4',5,5,5',5'-octamethyl-2,2'-bi(1,3,2-dioxaborolane) (336 mg, 1.324 mmol) and potassium acetate (177 mg, 1.806 mmol) were added, bubbling was continued for another 5 min, and the mixture was heated in a sealed tube with stirring at 85-90° C. for 18 h. The mixture was cooled to rt and diluted with water and EtOAc and the layers were separated. The aqueous phase was extracted twice with EtOAc, and the combined organic phases were dried and concentrated. The residue was taken up in acetonitrile, filtered, and the filtrate was concentrated to give 7-(4-methylpiperazine-1-carbonyl)-4-(4,4,5,5-tetramethyl-1,3,2-dioxaborolan-2-yl)-9H-carbazole-1-carboxamide as a yellow-tan glassy foam (602 mg) which was used without further purification. $^1$H NMR (400 MHz, DMSO-$d_6$) δ 11.65 (s, 1H) 8.86 (d, J=8.3 Hz, 1H) 8.25 (br. s., 1H) 7.95 (d, J=7.7 Hz, 1H) 7.90-7.94 (m, 2H) 7.58 (d, J=7.5 Hz, 1H) 7.16 (d, J=6.8 Hz, 1H) 3.36-3.72 (m, 4H) 2.34 (br. s., 4H) 2.21 (s, 3 H) 1.43 (s, 12H); aliphatic impurities were observed. Mass spectrum m/z 463.34 (M+H)$^+$.

Step 2 A mixture of 7-(4-methylpiperazine-1-carbonyl)-4-(4,4,5,5-tetramethyl-1,3,2-dioxaborolan-2-yl)-9H-carbazole-1-carboxamide (the crude product prepared according to Step 1, 40 mg, 0.065 mmol), 5-bromonaphthalen-1-amine (21.61 mg, 0.097 mmol), and potassium carbonate (13.45 mg, 0.097 mmol) in toluene (1.5 mL) and ethanol (0.75 mL) was treated with [1,1'-bis(diphenylphosphino)-ferrocene]dichloropalladium(II) DCM complex (5.3 mg, 0.007 mmol) and purged with argon for ca. 5 min. The mixture was heated at 90° C. for 19 h, then was cooled to rt and concentrated. The residue was purified by preparative HPLC, then was partitioned between EtOAc and NaHCO3 (aq), the aqueous phase was extracted again with EtOAc, and the combined organic phases were dried and concentrated to provide 4-(5-aminonaphthalen-1-yl)-7-(4-methylpiperazine-1-carbonyl)-9H-carbazole-1-carboxamide as a light yellow solid (13.1 mg, 42%). $^1$H NMR (400 MHz, DMSO-$d_6$) δ 11.71 (s, 1H) 8.22-8.27 (m, 2H) 8.07 (d, J=7.7 Hz, 1H) 7.73 (s, 1H) 7.55 (br. s., 1H) 7.52 (dd, J=8.6, 6.8 Hz, 1H) 7.42 (dd, J=6.9, 1.0 Hz, 1H) 7.09 (d, J=7.7 Hz, 1H) 6.96 (dd, J=8.2, 7.6 Hz, 1H) 6.64-6.70 (m, 2H) 6.49 (d, J=8.3 Hz, 1H) 6.38 (d, J=8.1 Hz, 1H) 5.85 (s, 2H) 3.48-3.59 (m, 4H) 2.17-2.37 (m, 4H) 2.14 (s, 3H). Mass spec m/z 478.10 (M+H)$^+$.

Example 2-2

Preparation of 4-(isoquinolin-1-yl)-7-(4-methylpiperazine-1-carbonyl)-9H-carbazole-1-carboxamide

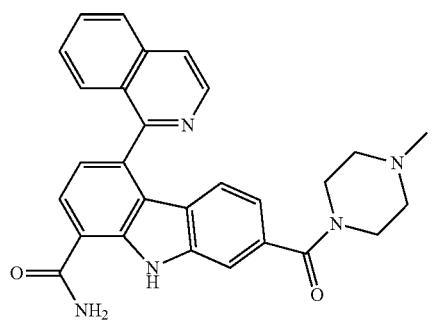 [SMILES: CN1CCN(C(=O)c2ccc3c(c2)[nH]c2c(C(N)=O)ccc(-c4nccc5ccccc45)c23)CC1]

Using the procedure of Step 2 of Example 2-1, 7-(4-methylpiperazine-1-carbonyl)-4-(4,4,5,5-tetramethyl-1,3,2-dioxaborolan-2-yl)-9H-carbazole-1-carboxamide (the crude product prepared according to Step 1 of Example 2-1, 40 mg, 0.065 mmol) and 1-chloroisoquinoline (15.92 mg, 0.097 mmol) were converted to 4-(isoquinolin-1-yl)-7-(4-methylpiperazine-1-carbonyl)-9H-carbazole-1-carboxamide (6 mg, 20%). $^1$H NMR (400 MHz, DMSO-d$_6$) δ 11.82 (s, 1H) 8.71 (d, J=5.5 Hz, 1H) 8.32 (br. s., 1H) 8.15 (d, J=7.7 Hz, 2H) 8.06 (d, J=5.3 Hz, 1H) 7.80 (ddd, J=8.2, 6.5, 1.5 Hz, 1H) 7.77 (s, 1H) 7.63 (br. s., 1H) 7.46-7.55 (m, 2H) 7.25 (d, J=7.9 Hz, 1 H) 6.71 (dd, J=8.2, 1.4 Hz, 1H) 6.24 (d, J=8.1 Hz, 1H) 3.46-3.62 (m, 4H) 2.18-2.34 (m, 4H) 2.16 (s, 3H). Mass spectrum m/z 464.3 (M+H)$^+$.

Example 2-3

Preparation of 4-(7-fluoro-1H-indol-6-yl)-7-(4-methylpiperazine-1-carbonyl)-9H-carbazole-1-carboxamide

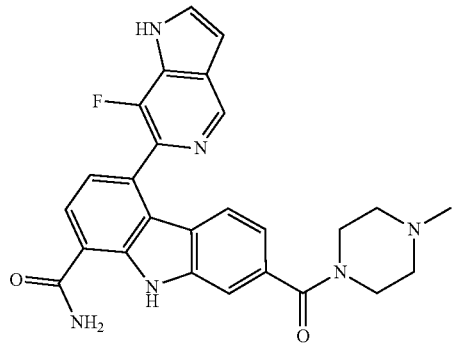 [SMILES: CN1CCN(C(=O)c2ccc3c(c2)[nH]c2c(C(N)=O)ccc(-c4ncc5cc[nH]c5c4F)c23)CC1]

A mixture of 7-(4-methylpiperazine-1-carbonyl)-4-(4,4,5,5-tetramethyl-1,3,2-dioxaborolan-2-yl)-9H-carbazole-1-carboxamide (prepared according to the procedure of Step 1 of Example 2-1, 75 mg, 0.065 mmol), 6-bromo-7-fluoro-1H-indole (prepared according to U.S. pat. appl. 2007/112005, 18.7 mg, 0.087 mmol), and 2 M aqueous sodium carbonate (0.081 mL, 0.162 mmol) in toluene (0.8 mL) and ethanol (0.2 mL) was purged with argon, treated with tetrakis(triphenylphosphine)palladium (7.5 mg, 0.007 mmol) and heated at 90° C. After 16 h, the mixture was cooled to rt. The residue was purified by preparative HPLC. The resulting TFA salt was partitioned between NaHCO3 (aq) and EtOAc, and the organic extracts were dried and concentrated to provide 4-(7-fluoro-1H-indol-6-yl)-7-(4-methylpiperazine-1-carbonyl)-9H-carbazole-1-carboxamide as an off-white solid (9 mg, 30%). $^1$H NMR (400 MHz, methanol-d$_4$) δ 7.99 (d, J=7.5 Hz, 1H) 7.68 (d, J=0.9 Hz, 1H) 7.52 (d, J=7.9 Hz, 1H) 7.39 (d, J=3.5 Hz, 1H) 7.25 (dd, J=8.1, 1.1 Hz, 1H) 7.21 (d, J=7.5 Hz, 1H) 7.08 (dd, J=8.1, 6.4 Hz, 1H) 6.92 (dd, J=8.1, 1.5 Hz, 1H) 6.63 (t, J=3.3 Hz, 1H) 3.77 (br. s., 2H) 3.49 (br. s., 2H) 2.51 (br. s., 2H) 2.39 (br. s., 2H) 2.30 (s, 3H). Mass spectrum m/z 470.1 (M+H)$^+$.

Example 2-4

Preparation of 5-(1-carbamoyl-7-(morpholine-4-carbonyl)-9H-carbazol-4-yl)-1-naphthoic acid

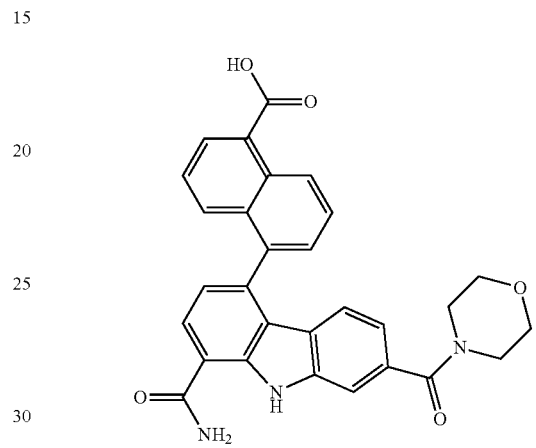

Using the procedures of Example 2-1, 4-bromo-7-(morpholine-4-carbonyl)-9H-carbazole-1-carboxamide (Intermediate 1-4(a)) and 4-bromo-1-naphthoic acid (prepared according to the procedure of Hausamann, *Chem. Ber.*, 1876, 9, 1519) were converted to 5-(1-carbamoyl-7-(morpholine-4-carbonyl)-9H-carbazol-4-yl)-1-naphthoic acid in 42% overall yield. $^1$H NMR (400 MHz, methanol-d$_4$) δ 13.32 (br. s., 1H) 11.80 (s, 1H) 9.03 (d, J=9.0 Hz, 1H) 8.29 (br. s., 1H) 8.08-8.17 (m, 2H) 7.82 (dd, J=8.7, 7.1 Hz, 1H) 7.78 (s, 1H) 7.64 (d, J=6.4 Hz, 1H) 7.61 (br. s., 1H) 7.55 (d, J=8.3 Hz, 1H) 7.37 (dd, J=8.3, 7.3 Hz, 1H) 7.16 (d, J=7.7 Hz, 1H) 6.72 (dd, J=8.3, 1.3 Hz, 1H) 6.28 (d, J=8.3 Hz, 1H) 3.53 (br. s., 8H). Mass spectrum m/z 494.3 (M+H)$^+$.

The Examples in the following table were also prepared using the procedures used to prepare Examples 2-1 through 2-4, or closely related procedures.

| Example | Starting materials | Compound name | Mass Spectrum |
|---|---|---|---|
| 2-5 | Example 1-1 [a] | 3-(1-carbamoyl-7-(4-methylpiperazine-1-carbonyl)-9H-carbazol-4-yl)-2-fluorobenzoic acid (prepared as the TFA salt) | 475.3 (M + H)$^+$ |
| 2-6 | Example 1-1 [a] | 2-(3-(1-carbamoyl-7-(4-methylpiperazine-1-carbonyl)-9H-carbazol-4-yl)-4-fluorophenyl)acetic acid (prepared as the TFA salt) | 489.3 (M + H)$^+$ |
| 2-7 | Example 1-1 [a] | 4-(5-amino-2-fluorophenyl)-7-(4-methylpiperazine-1-carbonyl)-9H-carbazole-1-carboxamide | 446.3 (M + H)$^+$ |
| 2-8 | Example 1-1 [a] | 4-(2-fluoro-5-(trifluoromethyl)phenyl)-7-(4-methylpiperazine-1-carbonyl)-9H-carbazole-1-carboxamide | 499.3 (M + H)$^+$ |
| 2-9 | Example 1-1 [a] | 4-(2-fluoro-5-methylphenyl)-7-(4-methylpiperazine-1-carbonyl)-9H-carbazole-1-carboxamide | 445.3 (M + H)$^+$ |

| Example | Starting materials | Compound name | Mass Spectrum |
|---|---|---|---|
| 2-10 | Example 1-1 [a] | 4-(5-cyano-2-fluorophenyl)-7-(4-methylpiperazine-1-carbonyl)-9H-carbazole-1-carboxamide | 456.3 (M + H)+ |
| 2-11 | Example 1-1 [a] | 4-(5-acetyl-2-fluorophenyl)-7-(4-methylpiperazine-1-carbonyl)-9H-carbazole-1-carboxamide | 473.3 (M + H)+ |
| 2-12 | Example 1-1 [a] | 4-(2,5-difluorophenyl)-7-(4-methylpiperazine-1-carbonyl)-9H-carbazole-1-carboxamide | 449.2 (M + H)+ |
| 2-13 | Example 1-1 [a] | 4-(5-chloro-2-fluorophenyl)-7-(4-methylpiperazine-1-carbonyl)-9H-carbazole-1-carboxamide | 465, 467 (M + H)+ |
| 2-14 | Example 1-1 [a] | 4-(2,6-difluorophenyl)-7-(4-methylpiperazine-1-carbonyl)-9H-carbazole-1-carboxamide | 449.2 (M + H)+ |
| 2-15 | Example 1-1 [a] | 4-(5-acetamidoisoquinolin-8-yl)-7-(4-methylpiperazine-1-carbonyl)-9H-carbazole-1-carboxamide | 521.4 (M + H)+ |
| 2-16 | Intermediate 1-4(a) [a] | 3-(1-carbamoyl-7-(morpholine-4-carbonyl)-9H-carbazol-4-yl)-4-fluorobenzoic acid | 462.2 (M + H)+ |
| 2-17 | Intermediate 1-4(a) [a] | 2-(3-(1-carbamoyl-7-(morpholine-4-carbonyl)-9H-carbazol-4-yl)-4-fluorophenyl)acetic acid | 476.2 (M + H)+ |
| 2-18 | Example 1-2 [a] | 4-(2-fluorophenyl)-6-(4-methylpiperazine-1-carbonyl)-9H-carbazole-1-carboxamide | 431.2 (M + H)+ |
| 2-19 | Example 1-1 [a] | 4-(1H-indazol-6-yl)-7-(4-methylpiperazine-1-carbonyl)-9H-carbazole-1-carboxamide | 453.1 (M + H)+ |
| 2-20 | Example 1-1 [a] | 4-(4-amino-2-fluorophenyl)-7-(4-methylpiperazine-1-carbonyl)-9H-carbazole-1-carboxamide | 446.1 (M + H)+ |
| 2-21 | Example 1-1 [a] | 4-(4-acetamido-2-fluorophenyl)-7-(4-methylpiperazine-1-carbonyl)-9H-carbazole-1-carboxamide | 488.1 (M + H)+ |
| 2-22 | Example 1-1 [a] | 4-(isoquinolin-8-yl)-7-(4-methylpiperazine-1-carbonyl)-9H-carbazole-1-carboxamide | 464.3 (M + H)+ |
| 2-23 | Example 1-1 [a] | 3-(1-carbamoyl-7-(4-methylpiperazine-1-carbonyl)-9H-carbazol-4-yl)-4-fluorobenzoic acid (prepared as the TFA salt) | 475.3 (M + H)+ |
| 2-24 | Example 1-1, Intermediate 12-2 | 4-(2-(ethylcarbamoyl)-1H-indol-4-yl)-7-(4-methylpiperazine-1-carbonyl)-9H-carbazole-1-carboxamide | 523.2 (M + H)+ |
| 2-25 | Example 1-1, Intermediate 12-3 | 4-(2-(4-fluorophenylcarbamoyl)-1H-indol-4-yl)-7-(4-methylpiperazine-1-carbonyl)-9H-carbazole-1-carboxamide | 589.2 (M + H)+ |
| 2-26 | Example 1-1, Intermediate 30-1 | 4-(2-methyl-3-(2-oxo-3-m-tolylimidazolidin-1-yl)phenyl)-7-(4-methylpiperazine-1-carbonyl)-9H-carbazole-1-carboxamide | 601.5 (M + H)+ |
| 2-27 | Example 1-1, Intermediate 6-1 | 4-(3-fluoro-2-(1-oxoisoindolin-2-yl)pyridin-4-yl)-7-(4-methylpiperazine-1-carbonyl)-9H-carbazole-1-carboxamide (prepared as the TFA salt) | 563.3 (M + H)+ |
| 2-28 | Example 1-1 [b] | 5-(1-carbamoyl-7-(4-methylpiperazine-1-carbonyl)-9H-carbazol-4-yl)-1-naphthoic acid (prepared as the TFA salt) | 507.3 (M + H)+ |
| 2-29 | Example 1-1 [a] | 4-(1-carbamoyl-7-(4-methylpiperazine-1-carbonyl)-9H-carbazol-4-yl)-3-fluorobenzoic acid (prepared as the TFA salt) | 475.3 (M + H)+ |
| 2-30 | Example 1-1, Intermediate 33-1 | 4-(2-methyl-3-(4-methylpyridin-2-ylamino)phenyl)-7-(4-methylpiperazine-1-carbonyl)-9H-carbazole-1-carboxamide (prepared as the TFA salt) | 533.3 (M + H)+ |
| 2-31 | Example 1-1, Intermediate 33-2 | 4-(2-methyl-3-(5-methylpyridin-2-ylamino)phenyl)-7-(4-methylpiperazine-1-carbonyl)-9H-carbazole-1-carboxamide (prepared as the TFA salt) | 533.3 (M + H)+ |
| 2-32 | Example 1-1, Intermediate 33-3 | 4-(2-methyl-3-(pyridin-2-ylamino)phenyl)-7-(4-methylpiperazine-1-carbonyl)-9H-carbazole-1-carboxamide | 519.3 (M + H)+ |
| 2-33 | Example 1-1, Intermediate 33-4 | 4-(2-methyl-3-(3-methylpyridin-2-ylamino)phenyl)-7-(4-methylpiperazine-1-carbonyl)-9H-carbazole-1-carboxamide | 519.3 (M + H)+ |
| 2-34 | Example 1-1, Intermediate 35-4 | 4-(3-(4-(dimethylamino)benzamido)-2-methylphenyl)-7-(4-methylpiperazine-1-carbonyl)-9H-carbazole-1-carboxamide | 589.4 (M + H)+ |
| 2-35 | Example 1-1, Intermediate 35-5 | 4-(5-acetamido-2-fluorophenyl)-7-(4-methylpiperazine-1-carbonyl)-9H-carbazole-1-carboxamide | 488.3 (M + H)+ |
| 2-36 | Example 1-1, Intermediate 35-6 | 4-(3-(4-fluorobenzamido)phenyl)-7-(4-methylpiperazine-1-carbonyl)-9H-carbazole-1-carboxamide | 550.3 (M + H)+ |

-continued

| Example | Starting materials | Compound name | Mass Spectrum |
|---|---|---|---|
| 2-37 | Example 1-1, Intermediate 35-3 | 4-(5-(acetamidomethyl)-2-fluorophenyl)-7-(4-methylpiperazine-1-carbonyl)-9H-carbazole-1-carboxamide | 502.3 (M + H)+ |
| 2-38 | Example 1-1, Intermediate 35-7 | 4-(2-fluoro-3-(4-fluorobenzamido)phenyl)-7-(4-methylpiperazine-1-carbonyl)-9H-carbazole-1-carboxamide | 568.2 (M + H)+ |
| 2-39 | Example 1-1, Intermediate 35-8 | 4-(3-(4-(dimethylamino)benzamido)-2-fluorophenyl)-7-(4-methylpiperazine-1-carbonyl)-9H-carbazole-1-carboxamide | 593.3 (M + H)+ |
| 2-40 | Example 1-1, Intermediate 35-1 | 4-(2-fluoro-3-(4-fluoro-N-methylbenzamido)phenyl)-7-(4-methylpiperazine-1-carbonyl)-9H-carbazole-1-carboxamide | 582.3 (M + H)+ |
| 2-41 | Example 1-1, Intermediate 35-9 | 4-(3-(4-fluoro-N-methylbenzamido)phenyl)-7-(4-methylpiperazine-1-carbonyl)-9H-carbazole-1-carboxamide | 564.1 (M + H)+ |
| 2-42 | Example 1-1, Intermediate 35-10 | 4-(4-fluoro-3-(4-fluorobenzamido)phenyl)-7-(4-methylpiperazine-1-carbonyl)-9H-carbazole-1-carboxamide | 568.1 (M + H)+ |
| 2-43 | Example 1-1, Intermediate 35-2 | 4-(4-(4-fluorobenzamido)pyridin-2-yl)-7-(4-methylpiperazine-1-carbonyl)-9H-carbazole-1-carboxamide | 551.3 (M + H)+ |
| 2-44 | Example 1-1, Intermediate 35-11 | 4-(2-fluoro-5-(4-fluorobenzamido)phenyl)-7-(4-methylpiperazine-1-carbonyl)-9H-carbazole-1-carboxamide | 568.1 (M + H)+ |
| 2-45 | Example 1-1, Intermediate 35-12 | 4-(2-fluoro-5-((4-fluorobenzamido)methyl)phenyl)-7-(4-methylpiperazine-1-carbonyl)-9H-carbazole-1-carboxamide | 582.1 (M + H)+ |
| 2-46 | Example 1-1, Intermediate 35-13 | 4-(3-acetamido-2-fluorophenyl)-7-(4-methylpiperazine-1-carbonyl)-9H-carbazole-1-carboxamide | 488.3 (M + H)+ |
| 2-47 | Example 1-1, Intermediate 36-1 | 4-(2-fluoro-5-(4-fluorophenylcarbamoyl)phenyl)-7-(4-methylpiperazine-1-carbonyl)-9H-carbazole-1-carboxamide | 568.2 (M + H)+ |
| 2-48 | Example 1-1, Intermediate 36-3 | 4-(2-fluoro-3-(4-fluorophenylcarbamoyl)phenyl)-7-(4-methylpiperazine-1-carbonyl)-9H-carbazole-1-carboxamide | 568.2 (M + H)+ |
| 2-49 | Example 1-1, Intermediate 36-4 | 4-(5-carbamoyl-2-fluorophenyl)-7-(4-methylpiperazine-1-carbonyl)-9H-carbazole-1-carboxamide (prepared as the TFA salt) | 474.2 (M + H)+ |
| 2-50 | Example 1-1, Intermediate 36-5 | 4-(3-carbamoyl-2-fluorophenyl)-7-(4-methylpiperazine-1-carbonyl)-9H-carbazole-1-carboxamide, (prepared as the TFA salt) | 474.2 (M + H)+ |
| 2-51 | Example 1-1, Intermediate 36-6 | 4-(2-fluoro-3-(methylcarbamoyl)phenyl)-7-(4-methylpiperazine-1-carbonyl)-9H-carbazole-1-carboxamide | 488.2 (M + H)+ |
| 2-52 | Example 1-1, Intermediate 36-7 | 4-(5-(dimethylcarbamoyl)-2-fluorophenyl)-7-(4-methylpiperazine-1-carbonyl)-9H-carbazole-1-carboxamide (prepared as the TFA salt) | 502.2 (M + H)+ |
| 2-53 | Example 1-1, Intermediate 36-2 | 4-(3-(dimethylcarbamoyl)-2-fluorophenyl)-7-(4-methylpiperazine-1-carbonyl)-9H-carbazole-1-carboxamide (prepared as the TFA salt) | 502.2 (M + H)+ |
| 2-54 | Example 1-1, Intermediate 37-1 | 4-(2-fluoro-3-(methylsulfonamido)phenyl)-7-(4-methylpiperazine-1-carbonyl)-9H-carbazole-1-carboxamide | 524.1 (M + H)+ |
| 2-55 | Example 1-1, Intermediate 38-1 | 4-(2-fluoro-5-(3-(4-methylthiazol-2-yl)ureido)phenyl)-7-(4-methylpiperazine-1-carbonyl)-9H-carbazole-1-carboxamide | 586.1 (M + H)+ |
| 2-56 | Example 1-1, Intermediate 38-2 | 4-(2-fluoro-5-((3-(4-methylthiazol-2-yl)ureido)methyl)phenyl)-7-(4-methylpiperazine-1-carbonyl)-9H-carbazole-1-carboxamide | 600.1 (M + H)+ |

[a] Commercially available aryl halide.
[b] 4-bromo-1-naphthoic acid (prepared according to the procedure of Hausamann, *Chem. Ber.*, 1876, 9, 1519).

Example 3-1

Preparation of 4-(2-fluorophenyl)-7-(4-methylpiperazine-1-carbonyl)-9H-carbazole-1-carboxamide

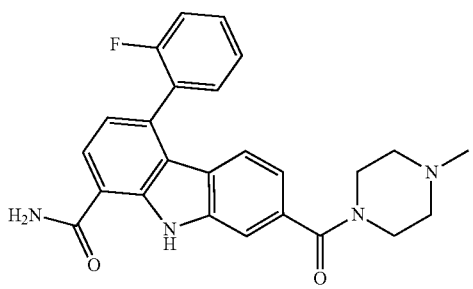 [SMILES: CN1CCN(C(=O)c2ccc3c(c2)[nH]c2c(C(N)=O)ccc(-c4ccccc4F)c23)CC1]

A suspension of 4-bromo-7-(4-methylpiperazine-1-carbonyl)-9H-carbazole-1-carboxamide (Example 1-1, 25 mg, 0.06 mmol), 2-fluorophenyl-boronic acid (0.17 mg, 0.12 mmol), potassium carbonate (21 mg, 0.15 mmol), and [1,1'-bis(diphenylphosphino)ferrocene]dichloropalladium (5 mg, 0.006 mmol) in toluene-ethanol (2:1, 2.4 mL) was purged with nitrogen for 5 min, then was heated at 90° C. overnight. The mixture was concentrated and purified by preparative HPLC to provide 4-(2-fluorophenyl)-7-(4-methylpiperazine-1-carbonyl)-9H-carbazole-1-carboxamide, TFA salt, as a white solid (23 mg, 70%). $^1$H NMR (400 MHz, DMSO-$d_6$) δ 11.79 (s, 1H) 8.26 (br. s., 1H) 8.06 (d, J=7.91 Hz, 1H) 7.86 (s, 1H) 7.57-7.67 (m, 2H) 7.55 (td, J=7.58, 1.76 Hz, 1H) 7.39-7.49 (m, 2H) 7.13 (d, J=7.69 Hz, 1H) 7.07-7.11 (m, 1H) 7.02-7.07 (m, 1H) 3.81 (br. s., 4H) 3.10-3.30 (m, 4H) 2.79 (s, 3H). Mass spectrum m/z 431.2 (M+H)$^+$.

Example 3-2

Preparation of 4-(3-amino-2-methylphenyl)-7-(4-methylpiperazine-1-carbonyl)-9H-carbazole-1-carboxamide

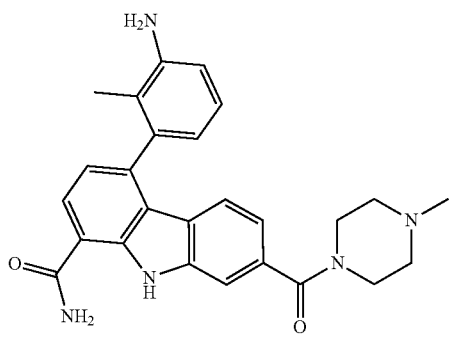 [SMILES: Cc1c(N)cccc1-c1ccc(C(N)=O)c2[nH]c3cc(C(=O)N4CCN(C)CC4)ccc3c12]

A suspension of 4-bromo-7-(4-methylpiperazine-1-carbonyl)-9H-carbazole-1-carboxamide (Example 1-1, 300 mg, 0.722 mmol), tetrakis-(triphenylphosphine)palladium (33.4 mg, 0.029 mmol), 2 M aqueous sodium carbonate (0.9 mL, 1.806 mmol), and 2-methyl-3-(4,4,5,5-tetramethyl-1,3,2-dioxaborolan-2-yl)aniline (Intermediate 50-1, 253 mg, 1.084 mmol) in toluene-ethanol (4:1, 15 mL) was purged with nitrogen for 5 min and then heated at reflux for 7.5 h. The mixture was concentrated and the residue was partitioned between chloroform and water. The aqueous phase was extracted with chloroform and the combined organic phases were washed with brine, dried and concentrated. The residue was purified by column chromatography (eluting with DCM-2 M methanolic ammonia, gradient from 100:0 to 95:5) to provide 4-(3-amino-2-methylphenyl)-7-(4-methylpiperazine-1-carbonyl)-9H-carbazole-1-carboxamide as a white solid (207 mg, 65%). $^1$H NMR (400 MHz, DMSO-$d_6$) δ 11.65 (s, 1H) 8.16 (br. s., 1H) 7.97 (d, J=7.91 Hz, 1H) 7.78 (s, 1H) 7.48 (br. s., 1H) 7.08 (t, J=7.80 Hz, 1H) 6.81-6.97 (m, 4H) 6.49-6.65 (m, 1H) 3.12-3.25 (m, 4H) 2.92-3.10 (m, 4H) 2.76 (s, 3H) 1.70 (s, 3H). Mass spectrum m/z 442.2 (M+H)$^+$.

Example 3-3

Preparation of 4-(4-methylnaphthalen-1-yl)-7-(4-methylpiperazine-1-carbonyl)-9H-carbazole-1-carboxamide

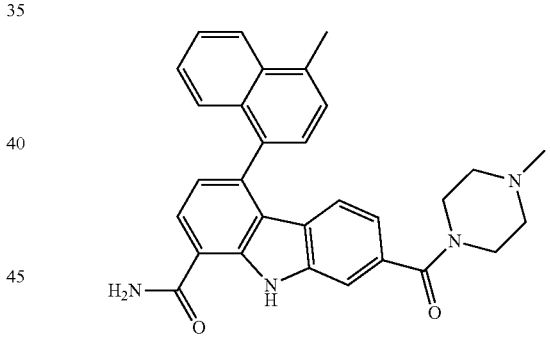

Using the procedure of Example 3-1, 4-bromo-7-(4-methylpiperazine-1-carbonyl)-9H-carbazole-1-carboxamide (Example 1-1, 25 mg, 0.06 mmol) and 4-methylnaphthaleneboronic acid (23 mg, 0.12 mmol) were converted to 4-(4-methylnaphthalen-1-yl)-7-(4-methylpiperazine-1-carbonyl)-9H-carbazole-1-carboxamide, isolated as the TFA salt following HPLC purification. This material was partitioned between EtOAc and NaHCO3 (aq), and the aqueous phase was extracted twice with EtOAc. The combined organic phases were dried and concentrated to provide 4-(4-methylnaphthalen-1-yl)-7-(4-methylpiperazine-1-carbonyl)-9H-carbazole-1-carboxamide (23 mg, 79%). $^1$H NMR (400 MHz, DMSO-$d_6$) δ 11.76 (s, 1 H) 8.26 (br. s., 1H) 8.16 (d, J=8.3 Hz, 1H) 8.10 (d, J=7.7 Hz, 1H) 7.75 (s, 1H) 7.52-7.62 (m, 3H) 7.45 (d, J=7.0 Hz, 1H) 7.28-7.38 (m, 2H) 7.11 (d, J=7.7 Hz, 1H) 6.67 (dd, J=8.2, 1.4 Hz, 1H) 6.37 (d, J=8.1

Hz, 1H) 3.32-3.67 (m, 4H) 2.80 (s, 3H) 2.16-2.35 (m, 4H) 2.14 (s, 3H). Mass spectrum m/z 477.3 (M+H)+.

Examples 3-4 and 3-5

Preparation of 7-(4-methylpiperazine-1-carbonyl)-4-(4-(2,2,2-trifluoroacetamido)naphthalen-1-yl)-9H-carbazole-1-carboxamide and 4-(4-aminonaphthalen-1-yl)-7-(4-methylpiperazine-1-carbonyl)-9H-carbazole-1-carboxamide

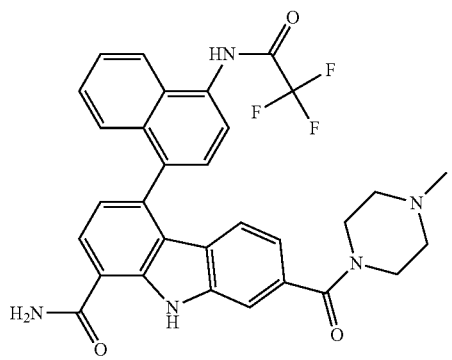

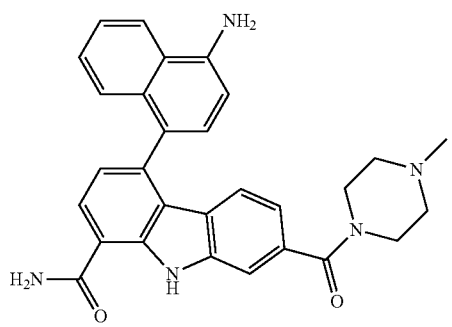

Using the procedure of Example 3-3, 4-bromo-7-(4-methylpiperazine-1-carbonyl)-9H-carbazole-1-carboxamide (Example 1-1, 25 mg, 0.06 mmol) and 4-(2,2,2-trifluoroacetamido)naphthalen-1-ylboronic acid (34 mg, 0.12 mmol) were converted to 7-(4-methylpiperazine-1-carbonyl)-4-(4-(2,2,2-trifluoroacetamido)naphthalen-1-yl)-9H-carbazole-1-carboxamide (9.7 mg, 28%). $^1$H NMR (400 MHz, DMSO-$d_6$) δ 11.76 (s, 1H) 11.63 (br. s., 1H) 8.25 (br. s., 1H) 8.09 (d, J=7.7 Hz, 1H) 8.04 (d, J=8.3 Hz, 1H) 7.75 (d, J=7.5 Hz, 1H) 7.73 (d, J=0.7 Hz, 1 H) 7.54-7.61 (m, 3H) 7.31-7.38 (m, 2H) 7.14 (d, J=7.7 Hz, 1H) 6.63 (dd, J=8.1, 1.5 Hz, 1H) 6.33 (d, J=8.1 Hz, 1H) 3.44-3.56 (m, 4H) 2.14-2.31 (m, 4H) 2.11 (s, 3H). Mass spectrum m/z 574.3 (M+H)+. Also obtained was 4-(4-aminonaphthalen-1-yl)-7-(4-methylpiperazine-1-carbonyl)-9H-carbazole-1-carboxamide (14 mg, 50%). $^1$H NMR (400 MHz, DMSO-$d_6$) δ 11.63 (s, 1H) 8.15 (d, J=8.3 Hz, 2H) 8.01 (d, J=7.5 Hz, 1H) 7.68 (s, 1H) 7.48 (br. s., 1H) 7.32 (t, J=7.3 Hz, 1H) 7.11-7.23 (m, 3 H) 7.03 (d, J=7.7 Hz, 1H) 6.79 (d, J=7.7 Hz, 1H) 6.64 (d, J=8.3 Hz, 1H) 6.49 (d, J=7.9 Hz, 1H) 5.93 (s, 2H) 3.34-3.60 (m, 4H) 2.13-2.31 (m, 4H) 2.10 (s, 3H). Mass spectrum m/z 478.3 (M+H)+.

Examples 3-6 and 3-7

Preparation of 4-(6-chloropyridin-3-yl)-7-(4-methylpiperazine-1-carbonyl)-9H-carbazole-1-carboxamide and 4-(6-chloro-2,3'-bipyridin-5-yl)-7-(4-methylpiperazine-1-carbonyl)-9H-carbazole-1-carboxamide

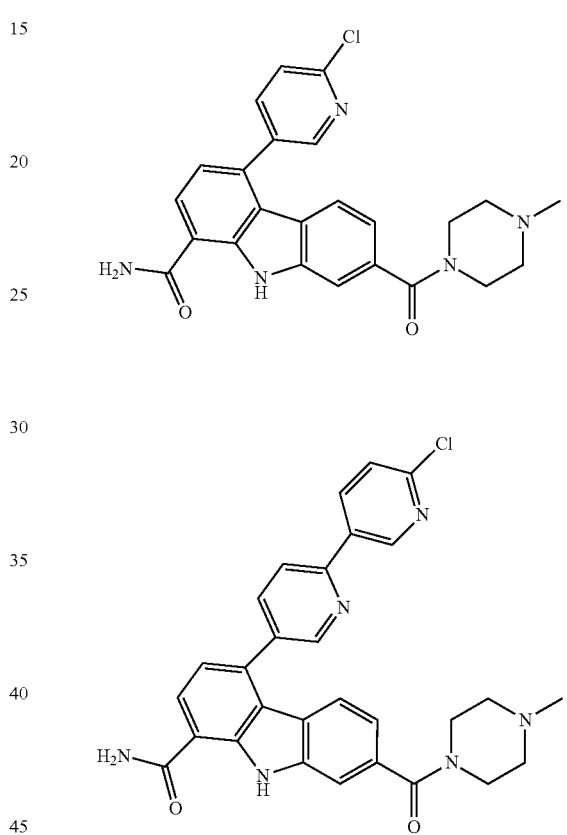

Using the procedure of Example 3-2, 4-bromo-7-(4-methylpiperazine-1-carbonyl)-9H-carbazole-1-carboxamide (Example 1-1, 25 mg, 0.060 mmol) and 6-chloropyridin-3-ylboronic acid (19 mg, 0.120 mmol) was converted to 4-(6-chloropyridin-3-yl)-7-(4-methylpiperazine-1-carbonyl)-9H-carbazole-1-carboxamide, TFA salt, as a light yellow solid (11 mg, 26%). $^1$H NMR (400 MHz, DMSO-$d_6$) δ 11.87 (s, 1H) 9.85 (br. s., 1H) 8.65 (d, J=2.0 Hz, 1H) 8.29 (br. s., 1H) 8.13 (dd, J=8.2, 2.5 Hz, 1H) 8.09 (d, J=7.9 Hz, 1H) 7.90 (s, 1H) 7.77 (d, J=8.3 Hz, 1H) 7.62 (br. s., 1H) 7.30 (d, J=8.3 Hz, 1H) 7.16 (d, J=7.9 Hz, 1H) 7.10 (dd, J=8.2, 1.4 Hz, 1H) 3.03-3.27 (m, 8H) 2.82 (s, 3H). Mass spectrum m/z 448.1 (M+H)+. Also isolated was 4-(6'-chloro-2,3'-bipyridin-5-yl)-7-(4-methylpiperazine-1-carbonyl)-9H-carbazole-1-carboxamide, TFA salt, as a yellow solid (6 mg, 11%). $^1$H NMR (400 MHz, DMSO-$d_6$) δ 11.89 (s, 1H) 9.99 (br. s., 1H) 9.26 (d, J=2.4 Hz, 1H) 8.96 (d, J=2.2 Hz, 1H) 8.66 (dd, J=8.3, 2.4 Hz, 1H) 8.35 (d, J=8.1 Hz, 1H) 8.30 (br. s., 1H) 8.22 (dd, J=8.1, 2.2 Hz, 1H) 8.12 (d, J=7.9 Hz, 1H) 7.92 (s, 1H) 7.72 (d, J=8.6 Hz, 1H) 7.62 (br. s., 1H) 7.41 (d, J=8.3 Hz, 1H) 7.22 (d, J=7.7 Hz, 1H) 7.09 (dd, J=8.2, 1.4 Hz, 1H) 3.02-3.53 (m, 8H) 2.82 (s, 3H). Mass spectrum m/z 525.2 (M+H)⁺.

Example 3-8

Preparation of 4-(4-methoxyphenyl)-6-(4-methylpiperazine-1-carbonyl)-9H-carbazole-1-carboxamide

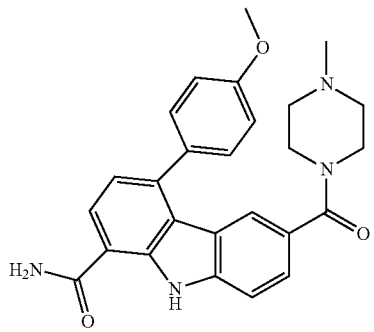 [SMILES: COc1ccc(-c2ccc(C(N)=O)c3[nH]c4ccc(C(=O)N5CCN(C)CC5)cc4c23)cc1]

Using the procedure of Example 3-1,4-bromo-6-(4-methylpiperazine-1-carbonyl)-9H-carbazole-1-carboxamide (Example 1-2, 25 mg, 0.06 mmol) and 4-methoxyphenylboronic acid (14 mg, 0.09 mmol) were converted into 4-(4-methoxyphenyl)-6-(4-methylpiperazine-1-carbonyl)-9H-carbazole-1-carboxamide, TFA salt, (8 mg, 22%). $^1$H NMR (400 MHz, DMSO-$d_6$) δ 11.84 (s, 1H) 8.22 (br. s., 1 H) 8.03 (d, J=7.69 Hz, 1H) 7.83 (d, J=8.35 Hz, 1H) 7.53-7.62 (m, 4H) 7.51 (dd, J=8.57, 1.54 Hz, 1H) 7.14 (d, J=8.79 Hz, 2H) 7.06 (d, J=7.69 Hz, 1H) 4.11-4.38 (m, 2H) 3.88 (s, 3H) 3.10-3.28 (m, 4H) 2.87-3.04 (m, 2H) 2.81 (s, 3H). Mass spectrum m/z 443.3 (M+H)⁺.

Example 3-9

Preparation of 4-(2-fluorophenyl)-7-(morpholine-4-carbonyl)-9H-carbazole-1-carboxamide

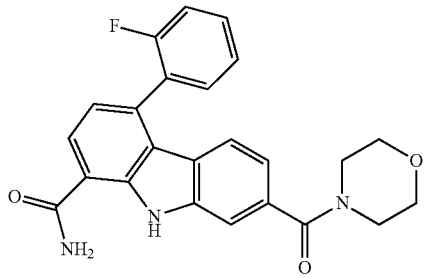 [SMILES: NC(=O)c1ccc(-c2ccccc2F)c2c1[nH]c1cc(C(=O)N3CCOCC3)ccc12]

Using the procedure of Example 3-1,4-bromo-7-(morpholine-4-carbonyl)-9H-carbazole-1-carboxamide (Intermediate 1-4(a), 25 mg, 0.06 mmol) and 2-fluorophenylboronic acid (17.4 mg, 0.124 mmol) were converted into 4-(2-fluorophenyl)-7-(morpholine-4-carbonyl)-9H-carbazole-1-carboxamide (15.9 mg, 61%). $^1$H NMR (400 MHz, DMSO-$d_6$) δ 11.76 (s, 1H) 8.25 (br. s., 1H) 8.06 (d, J=7.9 Hz, 1H) 7.82 (s, 1H) 7.53-7.66 (m, 3H) 7.40-7.48 (m, 2H) 7.12 (d, J=7.7 Hz, 1H) 7.09 (dd, J=8.2, 0.8 Hz, 1H) 6.99 (dd, J=8.2, 1.0 Hz, 1H) 3.59 (br. s., 8H). Mass spectrum m/z 418.2 (M+H)⁺.

Example 3-10

Preparation of 5-(2-fluorophenyl)-2-(4-methylpiperazine-1-carbonyl)-2,3,4,9-tetrahydro-1H-carbazole-8-carboxamide

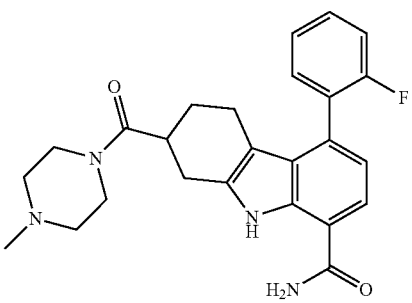 [SMILES: CN1CCN(C(=O)C2CCc3c([nH]c4c(C(N)=O)ccc(-c5ccccc5F)c34)C2)CC1]

Following the procedure of Example 3-1,5-bromo-2-(4-methylpiperazine-1-carbonyl)-2,3,4,9-tetrahydro-1H-carbazole-8-carboxamide (Example 1-3, 30 mg, 0.072 mmol) and 2-fluorophenylboronic acid (20 mg, 0.143 mmol) were converted into 5-(2-fluorophenyl)-2-(4-methylpiperazine-1-carbonyl)-2,3,4,9-tetrahydro-1H-carbazole-8-carboxamide, TFA salt, as white solid (25 mg, 62%). $^1$H NMR (400 MHz, DMSO-$d_6$) δ 10.92 (d, 1H) 8.04 (br. s., 1H) 7.62 (d, J=7.47 Hz, 1H) 7.42-7.50 (m, 1H) 7.17-7.41 (m, 4H) 6.76-6.89 (m, 1H) 4.37-4.57 (m, 1H) 4.09-4.29 (m, 2H) 3.46-3.62 (m, 2H) 2.83-3.15 (m, 6H) 2.80 (s, 3H) 2.10-2.42 (m, 1 H) 1.86-2.07 (m, 1H) 1.68-1.84 (m, 1H) 1.27-1.60 (m, 1H). Mass spectrum m/z 435.3 (M+H)⁺.

Example 3-11

Preparation of ethyl 8-carbamoyl-5-(2,6-difluorophenyl)-2,3,4,9-tetrahydro-1H-carbazole-2-carboxylate

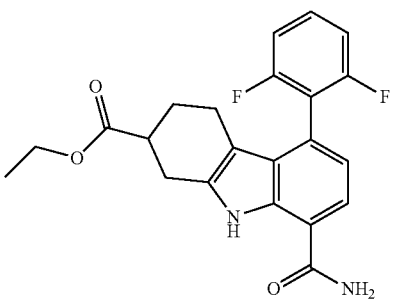 [SMILES: CCOC(=O)C1CCc2c([nH]c3c(C(N)=O)ccc(-c4c(F)cccc4F)c23)C1]

A mixture of ethyl 5-bromo-8-carbamoyl-2,3,4,9-tetrahydro-1H-carbazole-2-carboxylate (Intermediate 47-1, 20 mg, 0.055 mmol), 2,6-difluorophenylboronic acid (17.3 mg, 0.110 mmol), dicyclohexyl(2',6'-dimethoxybiphenyl-2-yl) phosphine (4.5 mg, 11.0 mmol), potassium carbonate (15.1 mg, 0.110 mmol) and tris(dibenzylideneacetone)dipalladium (5.0 mg, 0.005 mmol) in THF (2 mL) was purged with nitrogen for 2 min, then was heated in a sealed tube overnight. The mixture was filtered and concentrated, and the residue was purified by preparative HPLC. The appropriate effluent fractions were made basic with 1 M aqueous sodium hydroxide and extracted twice with DCM. The combined organic phases were washed with water, dried and concentrated to provide ethyl 8-carbamoyl-5-(2,6-difluorophenyl)-2,3,4,9-tetrahydro-1H-carbazole-2-carboxylate as a light yellow solid (10 mg, 44%). $^1$H NMR (400 MHz, chloroform-d) δ 10.10 (1H, br. s.), 7.31-7.44 (2H, m), 6.95-7.06 (3H, m), 4.10-4.22 (2H, m), 2.96-3.12 (2H, m), 2.80 (1H, dddd, J=17.52, 5.99, 3.08, 2.86 Hz), 2.27-2.41 (1H, m), 2.15-2.27 (1H, m), 2.04-2.14 (1H, m), 1.69-1.85 (1H, m), 1.26 (3H, t, J=7.25 Hz). Mass spectrum m/z 399.1 (M+H)$^+$.

Example 3-12

Preparation of ethyl 8-carbamoyl-5-(2-fluorophenyl)-9H-carbazole-2-carboxylate

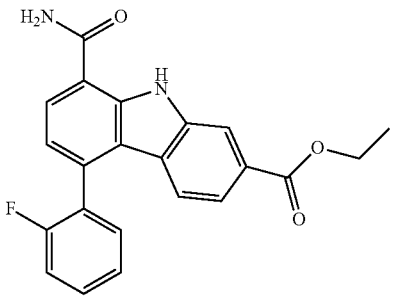 [SMILES: CCOC(=O)c1ccc2c(c1)[nH]c1c(C(N)=O)ccc(-c3ccccc3F)c12]

Following the procedure of Example 3-1, ethyl 5-bromo-8-carbamoyl-9H-carbazole-2-carboxylate (Intermediate 48-1, 1.00 g, 2.35 mmol) and 2-fluorophenylboronic acid (395 mg, 2.82 mmol) were converted into ethyl 8-carbamoyl-5-(2-fluorophenyl)-9H-carbazole-2-carboxylate as white solid (72%). $^1$H NMR (400 MHz, DMSO-d$_6$) δ 11.91 (1H, s), 8.46 (1H, s), 8.26 (1H, br. s.), 8.09 (1H, d, J=7.7 Hz), 7.52-7.68 (4H, m), 7.39-7.49 (2H, m), 7.15 (2H, d, J=7.9 Hz), 4.32 (2H, q, J=7.0 Hz), 1.33 (3H, t, J=7.1 Hz). Mass spectrum m/z 377.1 (M+H)$^+$.

Example 3-13

Preparation of 4-(3-amino-2-methylphenyl)-9H-carbazole-1-carboxamide

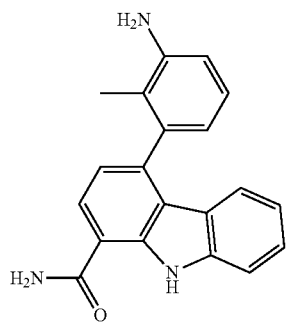 [SMILES: Cc1c(N)cccc1-c1ccc(C(N)=O)c2[nH]c3ccccc3c12]

Using the procedure of Example 3-2,4-bromo-9H-carbazole-1-carboxamide (Intermediate 48-3, 100 mg, 0.35 mmol) was converted into 4-(3-amino-2-methylphenyl)-9H-carbazole-1-carboxamide as an off-white solid (109 mg, 64%). $^1$H NMR (400 MHz, DMSO-d$_6$) δ 7.93 (1H, d, J=7.7 Hz), 7.57 (1H, d, J=8.1 Hz), 7.33 (1H, ddd, J=8.2, 7.1, 1.2 Hz), 7.16 (1H, t, J=7.8 Hz), 6.98-7.02 (2H, m), 6.95 (1H, dd, J=7.9, 0.9 Hz), 6.87-6.93 (1H, m), 6.72 (1H, dd, J=7.5, 0.9 Hz), 1.85 (3H, s). Mass spectrum m/z 316.2 (M+H)$^+$.

Example 3-14

Preparation of 5-(3-(4-fluorobenzamido)-2-methylphenyl)-2,3,4,9-tetrahydro-1H-carbazole-8-carboxamide

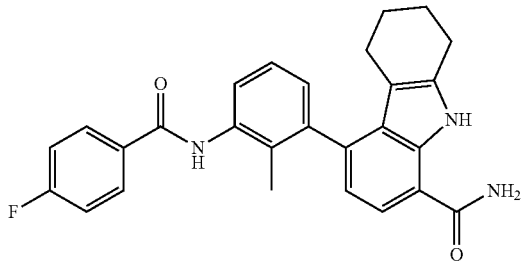 [SMILES: Cc1c(NC(=O)c2ccc(F)cc2)cccc1-c1ccc(C(N)=O)c2[nH]c3c(c12)CCCC3]

Using the procedure of Example 3-2,5-bromo-2,3,4,9-tetrahydro-1H-carbazole-8-carboxamide (Intermediate 47-3, 30 mg, 0.102 mmol) and 4-fluoro-N-(2-methyl-3-(4,4,5,5-tetramethyl-1,3,2-dioxaborolan-2-yl)phenyl)benzamide (Intermediate 53-1, 36.3 mg, 0.102 mmol) were converted into 5-(3-(4-fluorobenzamido)-2-methylphenyl)-2,3,4,9-tetrahydro-1H-carbazole-8-carboxamide as an off-white solid (5.7 mg, 12%). $^1$H NMR (400 MHz, DMSO-d$_6$) δ 8.04-8.15 (2H, m), 7.62 (1H, d, J=7.5 Hz), 7.32-7.43 (3H, m), 7.27 (1H, t, J=7.6 Hz), 7.09 (1H, d, J=7.3 Hz), 6.73 (1H, d, J=7.7 Hz), 4.06 (2H, s), 2.74 (2H, br. s.), 1.89 (3H, s), 1.65-1.75 (2H, m), 1.48-1.60 (2H, m). Mass spectrum m/z 442.3 (M+H)$^+$.

The following compounds were also prepared using procedures demonstrated in Examples 3-1 through 3-14 and similar procedures.

| Example/ Intermediates | Starting materials | Compound name | Mass spectrum |
|---|---|---|---|
| 3-15 | Example 1-1 [a] | 4-(2,3-difluorophenyl)-7-(4-methylpiperazine-1-carbonyl)-9H-carbazole-1-carboxamide (prepared as the TFA salt) | 449.2 (M + H)+ |
| 3-16 | Example 1-1 [a] | 4-(2,3-dichlorophenyl)-7-(4-methylpiperazine-1-carbonyl)-9H-carbazole-1-carboxamide (prepared as the TFA salt) | 481.1 (M + H)+ |
| 3-17 | Example 1-1 [a] | 4-(2,4-dichlorophenyl)-7-(4-methylpiperazine-1-carbonyl)-9H-carbazole-1-carboxamide (prepared as the TFA salt) | 481.1 (M + H)+ |
| 3-18 | Example 1-1 [a] | 4-(2-ethoxynaphthalen-1-yl)-7-(4-methylpiperazine-1-carbonyl)-9H-carbazole-1-carboxamide | 507.4 (M + H)+ |
| 3-19 | Example 1-1 [a] | 7-(4-methylpiperazine-1-carbonyl)-4-(quinolin-8-yl)-9H-carbazole-1-carboxamide | 464.3 (M + H)+ |
| 3-20 | Example 1-1 [a] | 4-(isoquinolin-5-yl)-7-(4-methylpiperazine-1-carbonyl)-9H-carbazole-1-carboxamide | 464.3 (M + H)+ |
| 3-21 | Example 1-1 [a] | 7-(4-methylpiperazine-1-carbonyl)-4-(quinolin-5-yl)-9H-carbazole-1-carboxamide | 464.3 (M + H)+ |
| 3-22 | Example 1-1 [a] | 4-(isoquinolin-4-yl)-7-(4-methylpiperazine-1-carbonyl)-9H-carbazole-1-carboxamide | 464.3 (M + H)+ |
| 3-23 | Example 1-1 [a] | 7-(4-methylpiperazine-1-carbonyl)-4-(quinolin-4-yl)-9H-carbazole-1-carboxamide | 464.3 (M + H)+ |
| 3-24 | Example 1-1 [a] | 4-(4-aminophenyl)-7-(4-methylpiperazine-1-carbonyl)-9H-carbazole-1-carboxamide (prepared as the TFA salt) | 428.2 (M + H)+ |
| 3-25 | Example 1-1 [a] | 7-(4-methylpiperazine-1-carbonyl)-4-(pyridin-3-yl)-9H-carbazole-1-carboxamide, TFA salt | 414.2 (M + H)+ |
| 3-26 | Example 1-1 [a] | 4-(4-hydroxyphenyl)-7-(4-methylpiperazine-1-carbonyl)-9H-carbazole-1-carboxamide (prepared as the TFA salt) | 429.2 (M + H)+ |
| 3-27 | Example 1-2 [a] | 4-(3-methoxyphenyl)-6-(4-methylpiperazine-1-carbonyl)-9H-carbazole-1-carboxamide (prepared as the TFA salt) | 443.3 (M + H)+ |
| 3-28 | Example 1-2 [a] | 4-(4-acetamidophenyl)-6-(4-methylpiperazine-1-carbonyl)-9H-carbazole-1-carboxamide (prepared as the TFA salt) | 470.3 (M + H)+ |
| 3-29 | Example 1-2 [a] | 4-(3-acetamidophenyl)-6-(4-methylpiperazine-1-carbonyl)-9H-carbazole-1-carboxamide (prepared as the TFA salt) | 470.3 (M + H)+ |
| 3-30 | Example 1-2 [a] | 6-(4-methylpiperazine-1-carbonyl)-4-(naphthalen-1-yl)-9H-carbazole-1-carboxamide (prepared as the TFA salt) | 463.3 (M + H)+ |
| 3-31 | Example 1-1 [a] | 4-(1H-indol-6-yl)-6-(4-methylpiperazine-1-carbonyl)-9H-carbazole-1-carboxamide | 452.2 (M + H)+ |
| 3-32 | Example 1-1 [a] | 4-(1H-indol-4-yl)-6-(4-methylpiperazine-1-carbonyl)-9H-carbazole-1-carboxamide | 452.2 (M + H)+ |
| 3-33 | Example 1-1 [a] | 4-(3-fluoropyridin-4-yl)-7-(4-methylpiperazine-1-carbonyl)-9H-carbazole-1-carboxamide | 432.1 (M + H)+ |
| 3-34 | Example 1-1 [a] | 7-(4-methylpiperazine-1-carbonyl)-4-(3-methylpyridin-4-yl)-9H-carbazole-1-carboxamide | 428.1 (M + H)+ |
| 3-35 | Example 1-1 [a] | 4-(3-chlorophenyl)-7-(4-methylpiperazine-1-carbonyl)-9H-carbazole-1-carboxamide (prepared as the TFA salt) | 447.2 (M + H)+ |
| 3-36 | Example 1-1 [a] | 4-(4-chlorophenyl)-7-(4-methylpiperazine-1-carbonyl)-9H-carbazole-1-carboxamide(prepared as the TFA salt) | 447.2 (M + H)+ |
| 3-37 | Example 1-1, Intermediate 50-45 | 4-(3-amino-2-fluorophenyl))-7-(4-methylpiperazine-1-carbonyl)-9H-carbazole-1-carboxamide | 446.1 (M + H)+ |
| 3-38 | Example 1-1 [a] | 4-(2-fluoro-5-methoxyphenyl)-7-(4-methylpiperazine-1-carbonyl)-9H-carbazole-1-carboxamide | 461.2 (M + H)+ |
| 3-39 | Example 1-1 [a] | 4-(5-ethoxy-2-fluorophenyl)-7-(4-methylpiperazine-1-carbonyl)-9H-carbazole-1-carboxamide | 475.1 (M + H)+ |
| 3-40 | Example 1-1 [a] | 4-(2-fluoro-5-(hydroxymethyl)phenyl)-7-(4-methylpiperazine-1-carbonyl)-9H-carbazole-1-carboxamide | 461.1 (M + H)+ |
| 3-41 | Example 1-1 [a] | 4-(4-methyl-2-(4-(trifluoromethyl)phenyl)thiazol-5-yl)-7-(4-methylpiperazine-1-carbonyl)-9H-carbazole-1-carboxamide (prepared as the TFA salt) | 578.2 (M + H)+ |
| 3-42 | Example 1-1 [a] | 4-(2-ethylphenyl)-7-(4-methylpiperazine-1-carbonyl)-9H-carbazole-1-carboxamide | 441.2 (M + H)+ |

-continued

| Example/Intermediates | Starting materials | Compound name | Mass spectrum |
|---|---|---|---|
| 3-43 | Example 1-1 [a] | 7-(4-methylpiperazine-1-carbonyl)-4-(2-(trifluoromethyl)phenyl)-9H-carbazole-1-carboxamide | 481.2 (M + H)+ |
| 3-44 | Example 1-1 [a] | 4-(2,6-dimethylphenyl)-7-(4-methylpiperazine-1-carbonyl)-9H-carbazole-1-carboxamide | 441.2 (M + H)+ |
| 3-45 | Example 1-1 [a] | 7-(4-methylpiperazine-1-carbonyl)-4-phenyl-9H-carbazole-1-carboxamide (prepared as the TFA salt) | 413.1 (M + H)+ |
| 3-46 | Example 1-1 [a] | 4-(5-amino-2-methylphenyl)-7-(4-methylpiperazine-1-carbonyl)-9H-carbazole-1-carboxamide | 442.2 (M + H)+ |
| 3-47 | Example 1-1 [a] | 4-(1H-indol-4-yl)-7-(4-methylpiperazine-1-carbonyl)-9H-carbazole-1-carboxamide | 452.2 (M + H)+ |
| 3-48 | Example 1-1 [a] | 4-(biphenyl-3-yl)-7-(4-methylpiperazine-1-carbonyl)-9H-carbazole-1-carboxamide | 489.4 (M + H)+ |
| 3-49 | Example 1-1 [a] | 4-(dibenzo[b,d]furan-4-yl)-7-(4-methylpiperazine-1-carbonyl)-9H-carbazole-1-carboxamide | 503.4 (M + H)+ |
| 3-50 | Example 1-1, Intermediate 50-2 | 4-(3-cyano-2-methylphenyl)-7-(4-methylpiperazine-1-carbonyl)-9H-carbazole-1-carboxamide (prepared as the TFA salt) | 452.3 (M + H)+ |
| 3-51 | Example 1-1, Intermediate 50-3 | 4-(4-amino-2,6-difluorophenyl)-7-(4-methylpiperazine-1-carbonyl)-9H-carbazole-1-carboxamide | 464.3 (M + H)+ |
| 3-52 | Example 1-1 [a] | 4-(4-methoxyphenyl)-7-(4-methylpiperazine-1-carbonyl)-9H-carbazole-1-carboxamide (prepared as the TFA salt) | 443.3 (M + H)+ |
| 3-53 | Example 1-1 [a] | 4-(3-methoxyphenyl)-7-(4-methylpiperazine-1-carbonyl)-9H-carbazole-1-carboxamide (prepared as the TFA salt) | 443.3 (M + H)+ |
| 3-54 | Example 1-1 [a] | 4-(2,4-difluorophenyl)-7-(4-methylpiperazine-1-carbonyl)-9H-carbazole-1-carboxamide(prepared as the TFA salt) | 449.3 (M + H)+ |
| 3-55 | Example 1-1 [a] | 7-(4-methylpiperazine-1-carbonyl)-4-(4-phenoxyphenyl)-9H-carbazole-1-carboxamide (prepared as the TFA salt) | 505.3 (M + H)+ |
| 3-56 | Example 1-1 [a] | 4-(3,4-dichlorophenyl)-7-(4-methylpiperazine-1-carbonyl)-9H-carbazole-1-carboxamide (prepared as the TFA salt) | 481.2 (M + H)+ |
| 3-57 | Example 1-1 [a] | 4-(1-carbamoyl-7-(4-methylpiperazine-1-carbonyl)-9H-carbazol-4-yl)benzoic acid (prepared as the TFA salt) | 457.3 (M + H)+ |
| 3-58 | Example 1-1 [a] | 3-(1-carbamoyl-7-(4-methylpiperazine-1-carbonyl)-9H-carbazol-4-yl)benzoic acid (prepared as the TFA salt) | 457.3 (M + H)+ |
| 3-59 | Example 1-1 [a] | 4-(4-acetamidophenyl)-7-(4-methylpiperazine-1-carbonyl)-9H-carbazole-1-carboxamide (prepared as the TFA salt) | 470.3 (M + H)+ |
| 3-60 | Example 1-1 [a] | 4-(3-acetamidophenyl)-7-(4-methylpiperazine-1-carbonyl)-9H-carbazole-1-carboxamide (prepared as the TFA salt) | 470.4 (M + H)+ |
| 3-61 | Example 1-1 [a] | 4-(4-(methylcarbamoyl)phenyl)-7-(4-methylpiperazine-1-carbonyl)-9H-carbazole-1-carboxamide (prepared as the TFA salt) | 470.3 (M + H)+ |
| 3-62 | Example 1-1 [a] | 4-(3-(methylcarbamoyl)phenyl)-7-(4-methylpiperazine-1-carbonyl)-9H-carbazole-1-carboxamide (prepared as the TFA salt) | 470.4 (M + H)+ |
| 3-63 | Example 1-1 [a] | 7-(4-methylpiperazine-1-carbonyl)-4-(naphthalen-2-yl)-9H-carbazole-1-carboxamide (prepared as the TFA salt) | 463.3 (M + H)+ |
| 3-64 | Example 1-1 [a] | 7-(4-methylpiperazine-1-carbonyl)-4-(naphthalen-1-yl)-9H-carbazole-1-carboxamide (prepared as the TFA salt) | 463.3 (M + H)+ |
| 3-65 | Example 1-1 [a] | 4-(4-tert-butylphenyl)-7-(4-methylpiperazine-1-carbonyl)-9H-carbazole-1-carboxamide | 469.4 (M + H)+ |
| 3-66 | Example 1-1 [a] | 7-(4-methylpiperazine-1-carbonyl)-4-(3-(methylsulfonamido)phenyl)-9H-carbazole-1-carboxamide (prepared as the TFA salt) | 506.3 (M + H)+ |
| 3-67 | Example 1-1 [a] | 7-(4-methylpiperazine-1-carbonyl)-4-o-tolyl-9H-carbazole-1-carboxamide (prepared as the TFA salt) | 427.4 (M + H)+ |
| 3-68 | Example 1-1 [a] | 4-(3-chloro-2-methylphenyl)-7-(4-methylpiperazine-1-carbonyl)-9H-carbazole-1-carboxamide (prepared as the TFA salt) | 461.2 (M + H)+ |

-continued

| Example/Intermediates | Starting materials | Compound name | Mass spectrum |
|---|---|---|---|
| 3-69 | Example 1-1 [a] | 4-(2-chlorophenyl)-7-(4-methylpiperazine-1-carbonyl)-9H-carbazole-1-carboxamide (prepared as the TFA salt) | 447.2 (M + H)+ |
| 3-70 | Example 1-1 [a] | 4-(2-methoxyphenyl)-7-(4-methylpiperazine-1-carbonyl)-9H-carbazole-1-carboxamide (prepared as the TFA salt) | 443.2 (M + H)+ |
| 3-71 | Example 1-3 [a] | 5-(2,4-difluorophenyl)-2-(4-methylpiperazine-1-carbonyl)-2,3,4,9-tetrahydro-1H-carbazole-8-carboxamide (prepared as the TFA salt) | 453.2 (M + H)+ |
| 3-72 | Example 1-3 [a] | 5-(2,3-difluorophenyl)-2-(4-methylpiperazine-1-carbonyl)-2,3,4,9-tetrahydro-1H-carbazole-8-carboxamide (prepared as the TFA salt) | 453.2 (M + H)+ |
| 3-73 | Example 1-3 [a] | 5-(4-acetamidophenyl)-2-(4-methylpiperazine-1-carbonyl)-2,3,4,9-tetrahydro-1H-carbazole-8-carboxamide (prepared as the TFA salt) | 474.3 (M + H)+ |
| 3-74 | Example 1-3 [a] | 2-(4-methylpiperazine-1-carbonyl)-5-(naphthalen-1-yl)-2,3,4,9-tetrahydro-1H-carbazole-8-carboxamide (prepared as the TFA salt) | 467.3 (M + H)+ |
| 3-75 | Example 1-1, Intermediate 50-31 | 7-(4-methylpiperazine-1-carbonyl)-4-(2-(pyrrolidine-1-carbonyl)-1H-indol-4-yl)-9H-carbazole-1-carboxamide | 549.2 (M + H)+ |
| 3-76 | Example 1-1, Intermediate 50-4 | 4-(2-methyl-3-(1-oxoisoindolin-2-yl)phenyl)-7-(4-methylpiperazine-1-carbonyl)-9H-carbazole-1-carboxamide | 558.2 (M + H)+ |
| 3-77 | Example 1-1, Intermediate 50-32 | 4-(3-(isoindolin-2-yl)-2-methylphenyl)-7-(4-methylpiperazine-1-carbonyl)-9H-carbazole-1-carboxamide | 544.3 (M + H)+ |
| 3-78 | Example 1-1, Intermediate 50-5 | 4-(3-(6-fluoro-1-oxoisoindolin-2-yl)-2-methylphenyl)-7-(4-methylpiperazine-1-carbonyl)-9H-carbazole-1-carboxamide | 576.3 (M + H)+ |
| 3-79 | Example 1-1, Intermediate 50-15 | 4-(3-(5-tert-butyl-1-oxoisoindolin-2-yl)-2-methylphenyl)-7-(4-methylpiperazine-1-carbonyl)-9H-carbazole-1-carboxamide | 614.4 (M + H)+ |
| 3-80 | Intermediate 48-3, Intermediate 50-4 | 4-(2-methyl-3-(1-oxoisoindolin-2-yl)phenyl)-9H-carbazole-1-carboxamide | 432.2 (M + H)+ |
| 3-81 | Example 1-1, Intermediate 52-1 | 4-(8-methyl-2-phenylchroman-7-yl)-7-(4-methylpiperazine-1-carbonyl)-9H-carbazole-1-carboxamide | 559.2 (M + H)+ |
| 3-82 | Example 1-1, Intermediate 50-33 | 7-(4-methylpiperazine-1-carbonyl)-4-(2-oxo-3-phenyl-3,4-dihydro-2H-benzo[e][1,3]oxazin-6-yl)-9H-carbazole-1-carboxamide | 560.4 (M + H)+ |
| 3-83 | Example 1-1, Intermediate 50-37 | 4-(6-(4-fluorophenyl)-1H-indol-3-yl)-7-(4-methylpiperazine-1-carbonyl)-9H-carbazole-1-carboxamide | 546.3 (M + H)+ |
| 3-84 | Intermediate 48-1, Intermediate 50-4 | ethyl 8-carbamoyl-5-(2-methyl-3-(1-oxoisoindolin-2-yl)phenyl)-9H-carbazole-2-carboxylate | 526.1 (M + Na)+ |
| 3-85 | Example 1-1, Intermediate 50-46 | 4-(2-(4-fluorophenyl)-7-methyl-1H-benzo[d]imidazol-6-yl)-7-(4-methylpiperazine-1-carbonyl)-9H-carbazole-1-carboxamide | 561.2 (M + H)+ |
| 3-86 | Example 1-1, Intermediate 50-39 | 7-(4-methylpiperazine-1-carbonyl)-4-(1-oxo-1,2,3,4-tetrahydroisoquinolin-7-yl)-9H-carbazole-1-carboxamide (prepared as the TFA salt) | 482.2 (M + H)+ |
| 3-87 | Example 1-1, Intermediate 50-40 | 4-(2-(4-fluorophenyl)-1-oxo-1,2,3,4-tetrahydroisoquinolin-7-yl)-7-(4-methylpiperazine-1-carbonyl)-9H-carbazole-1-carboxamide | 576.3 (M + H)+ |
| 3-88 | Example 1-1, Intermediate 50-41 | 4-(1-(4-fluorobenzyl)-1H-indol-4-yl)-7-(4-methylpiperazine-1-carbonyl)-9H-carbazole-1-carboxamide | 560.3 (M + H)+ |
| 3-89 | Example 1-1, Intermediate 50-33 | 4-(5-methyl-2-oxo-3-phenyl-3,4-dihydro-2H-benzo[e][1,3]oxazin-6-yl)-7-(4-methylpiperazine-1-carbonyl)-9H-carbazole-1-carboxamide (prepared as the TFA salt) | 574.3 (M + H)+ |
| 3-90 | Example 1-1, Intermediate | 4-(5-methyl-4-oxo-3-phenyl-3,4-dihydro-2H-benzo[e][1,3]oxazin-6-yl)-7-(4- | 574.3 (M + H)+ |

-continued

| Example/ Intermediates | Starting materials | Compound name | Mass spectrum |
|---|---|---|---|
| | 50-34 | methylpiperazine-1-carbonyl)-9H-carbazole-1-carboxamide (prepared as the TFA salt) | |
| 3-91 | Example 1-1, Intermediate 50-35 | 4-(4-hydroxy-2-methyl-3-(phenylcarbamoyl)phenyl)-7-(4-methylpiperazine-1-carbonyl)-9H-carbazole-1-carboxamide (prepared as the TFA salt) | 562.3 (M + H)+ |
| 3-92 | Example 1-1, Intermediate 50-21 | 4-(4-methyl-5-(1-oxoisoindolin-2-yl)pyridin-3-yl)-7-(4-methylpiperazine-1-carbonyl)-9H-carbazole-1-carboxamide (prepared as the TFA salt) | 559.4 (M + H)+ |
| 3-93 | Intermediate 1-4(a), Intermediate 50-21 | 4-(4-methyl-5-(1-oxoisoindolin-2-yl)pyridin-3-yl)-7-(morpholine-4-carbonyl)-9H-carbazole-1-carboxamide (prepared as the TFA salt) | 546.4 (M + H)+ |
| 3-94 | Example 1-1, Intermediate 50-20 | 4-(4-methyl-5-(5-methyl-1-oxoisoindolin-2-yl)pyridin-3-yl)-7-(4-methylpiperazine-1-carbonyl)-9H-carbazole-1-carboxamide (prepared as the TFA salt) | 573.4 (M + H)+ |
| 3-95 | Intermediate 1-4(a), Intermediate 50-20 | 4-(4-methyl-5-(5-methyl-1-oxoisoindolin-2-yl)pyridin-3-yl)-7-(morpholine-4-carbonyl)-9H-carbazole-1-carboxamide (prepared as the TFA salt) | 560.3 (M + H)+ |
| 3-96 | Example 1-1, Intermediate 50-42 | 4-(5-(4-fluorobenzoyl)naphthalen-1-yl)-7-(4-methylpiperazine-1-carbonyl)-9H-carbazole-1-carboxamide | 585.4 (M + H)+ |
| 3-97 | Intermediate 48-3, Intermediate 53-1 | 4-(3-(4-fluorobenzamido)-2-methylphenyl)-9H-carbazole-1-carboxamide | 438.2 (M + H)+ |
| 3-98 | Example 1-1, Intermediate 50-36 | 4-(3-(1H-indazol-3-ylamino)-2-methylphenyl)-7-(4-methylpiperazine-1-carbonyl)-9H-carbazole-1-carboxamide | 558.5 (M + H)+ |
| 3-99 | Intermediate 47-3, Intermediate 50-4 | 5-(2-methyl-3-(1-oxoisoindolin-2-yl)phenyl)-2,3,4,9-tetrahydro-1H-carbazole-8-carboxamide | 436.3 (M + H)+ |
| Intermediate 3-100 | Intermediate 48-1, Intermediate 53-1 | ethyl 8-carbamoyl-5-(3-(4-fluorobenzamido)-2-methylphenyl)-9H-carbazole-2-carboxylate | 510.13 (M + H)+ |
| 3-101 | Intermediate 1-5(a), Intermediate 50-4 | $N^2$-(3-(dimethylamino)propyl)-5-(2-methyl-3-(1-oxoisoindolin-2-yl)phenyl)-2,3,4,9-tetrahydro-1H-carbazole-2,8-dicarboxamide | 564.2 (M + H)+ |
| 3-102 | Intermediate 1-6(a), Intermediate 50-4 | $N^2$-(4-(dimethylamino)butyl)-5-(2-methyl-3-(1-oxoisoindolin-2-yl)phenyl)-2,3,4,9-tetrahydro-1H-carbazole-2,8-dicarboxamide | 578.2 (M + H)+ |
| 3-103 | Intermediate 1-5(a) [a] | $N^2$-(3-(dimethylamino)propyl)-5-(2-fluoro-5-methoxyphenyl)-2,3,4,9-tetrahydro-1H-carbazole-2,8-dicarboxamide | 467.2 (M + H)+ |
| 3-104 | Intermediate 1-5(a) [a] | $N^2$-(3-(dimethylamino)propyl)-5-(5-ethoxy-2-fluorophenyl)-2,3,4,9-tetrahydro-1H-carbazole-2,8-dicarboxamide | 481.2 (M + H)+ |
| 3-105 | Intermediate 1-5(a) [a] | $N^2$-(3-(dimethylamino)propyl)-5-(2-fluoro-5-(hydroxymethyl)phenyl)-2,3,4,9-tetrahydro-1H-carbazole-2,8-dicarboxamide | 467.2 (M + H)+ |
| 3-106 | Intermediate 1-7(a), Intermediate 50-4 | 5-(2-methyl-3-(1-oxoisoindolin-2-yl)phenyl)-$N^2$-(tetrahydro-2H-pyran-4-yl)-2,3,4,9-tetrahydro-1H-carbazole-2,8-dicarboxamide | 563.2 (M + H)+ |
| 3-107 | Intermediate 1-7(a), Intermediate 50-32 | 5-(3-(isoindolin-2-yl)-2-methylphenyl)-$N^2$-(tetrahydro-2H-pyran-4-yl)-2,3,4,9-tetrahydro-1H-carbazole-2,8-dicarboxamide | 549.3 (M + H)+ |
| 3-108 | Intermediate 1-8(a), Intermediate 53-1 | 5-(3-(4-fluorobenzamido)-2-methylphenyl)-$N^2$-(1-methylpiperidin-4-yl)-2,3,4,9-tetrahydro-1H-carbazole-2,8-dicarboxamide | 582.3 (M + H)+ |
| 3-109 | Intermediate 1-8(a), [a] | 5-(2,4-dimethylthiazol-5-yl)-$N^2$-(1-methylpiperidin-4-yl)-2,3,4,9-tetrahydro-1H-carbazole-2,8-dicarboxamide | 466.2 (M + H)+ |
| 3-110 | Intermediate 1-8(a), Intermediate 50-4 | 5-(2-methyl-3-(1-oxoisoindolin-2-yl)phenyl)-$N^2$-(1-methylpiperidin-4-yl)-2,3,4,9-tetrahydro-1H-carbazole-2,8-dicarboxamide | 576.3 (M + H)+ |

| Example/ Intermediates | Starting materials | Compound name | Mass spectrum |
|---|---|---|---|
| 3-111 | Intermediate 1-8(a), Intermediate 54-1 | tert-butyl 5-(8-carbamoyl-2-(1-methylpiperidin-4-ylcarbamoyl)-2,3,4,9-tetrahydro-1H-carbazol-5-yl)thiazol-2-yl(isopropyl)carbamate | 595.3 (M + H)+ |
| 3-112 | Intermediate 1-8(a), [a] | 5-(furan-3-yl)-N2-(1-methylpiperidin-4-yl)-2,3,4,9-tetrahydro-1H-carbazole-2,8-dicarboxamide | 421.1 (M + H)+ |
| 3-113 | Intermediate 1-8(a), [a] | 5-(benzofuran-2-yl)-N2-(1-methylpiperidin-4-yl)-2,3,4,9-tetrahydro-1H-carbazole-2,8-dicarboxamide | 471.2 (M + H)+ |
| 3-114 | Intermediate 1-7(a), [a] | 5-(3-formylfuran-2-yl)-N2-(tetrahydro-2H-pyran-4-yl)-2,3,4,9-tetrahydro-1H-carbazole-2,8-dicarboxamide | 436.1 (M + H)+ |
| 3-115 | Intermediate 1-7(a), [a] | 5-(1-methyl-1H-pyrazol-5-yl)-N2-(tetrahydro-2H-pyran-4-yl)-2,3,4,9-tetrahydro-1H-carbazole-2,8-dicarboxamide | 422.2 (M + H)+ |
| 3-116 | Intermediate 1-7(a), [a] | tert-butyl 4-(8-carbamoyl-2-(tetrahydro-2H-pyran-4-ylcarbamoyl)-2,3,4,9-tetrahydro-1H-carbazol-5-yl)-1H-pyrazole-1-carboxylate | 408.2 (M + H − Boc)+ |
| 3-117 | Intermediate 1-7(a), [a] | 5-cyclohexenyl-N2-(tetrahydro-2H-pyran-4-yl)-2,3,4,9-tetrahydro-1H-carbazole-2,8-dicarboxamide | 422.3 (M + H)+ |
| 3-118 | Example 1-3, Intermediate 50-19 | 5-(3-(5-fluoro-1-oxoisoindolin-2-yl)-2-methylphenyl)-2-(4-methylpiperazine-1-carbonyl)-2,3,4,9-tetrahydro-1H-carbazole-8-carboxamide | 580.4 (M + H)+ |
| 3-119 | Example 1-3, Intermediate 50-5 | 5-(3-(6-fluoro-1-oxoisoindolin-2-yl)-2-methylphenyl)-2-(4-methylpiperazine-1-carbonyl)-2,3,4,9-tetrahydro-1H-carbazole-8-carboxamide | 580.4 (M + H)+ |
| 3-120 | Example 1-3, Intermediate 50-18 | 5-(2-methyl-3-(5-methyl-1-oxoisoindolin-2-yl)phenyl)-2-(4-methylpiperazine-1-carbonyl)-2,3,4,9-tetrahydro-1H-carbazole-8-carboxamide | 576.4 (M + H)+ |
| 3-121 | Example 1-3, Intermediate 50-8 | 5-(2-methyl-3-(6-methyl-1-oxoisoindolin-2-yl)phenyl)-2-(4-methylpiperazine-1-carbonyl)-2,3,4,9-tetrahydro-1H-carbazole-8-carboxamide | 576.4 (M + H)+ |
| 3-122 | Example 1-3, Intermediate 50-4 | 5-(2-methyl-3-(1-oxoisoindolin-2-yl)phenyl)-2-(4-methylpiperazine-1-carbonyl)-2,3,4,9-tetrahydro-1H-carbazole-8-carboxamide | 562.4 (M + H)+ |
| 3-123 | Example 1-3, Intermediate 50-43 | 5-(2-methyl-3-(2-oxopiperidin-1-yl)phenyl)-2-(4-methylpiperazine-1-carbonyl)-2,3,4,9-tetrahydro-1H-carbazole-8-carboxamide | 528.4 (M + H)+ |
| 3-124 | Intermediate 1-7(a), Intermediate 50-47 | 5-(2-(N,N-bis(tert-butoxycarbonyl)amino)-4-methylthiazol-5-yl)-2-(4-methylpiperazine-1-carbonyl)-2,3,4,9-tetrahydro-1H-carbazole-8-carboxamide | 654.4 (M + H)+ |
| 3-125 | Intermediate 1-9(a), Intermediate 50-4 | N2-methyl-5-(2-methyl-3-(1-oxoisoindolin-2-yl)phenyl)-N2-(1-methylpiperidin-4-yl)-2,3,4,9-tetrahydro-1H-carbazole-2,8-dicarboxamide | 590.4 (M + H)+ |
| 3-126 | Intermediate 1-9(a), Intermediate 50-19 | 5-(3-(5-fluoro-1-oxoisoindolin-2-yl)-2-methylphenyl)-N2-methyl-N2-(1-methylpiperidin-4-yl)-2,3,4,9-tetrahydro-1H-carbazole-2,8-dicarboxamide | 608.4 (M + H)+ |
| 3-127 | Intermediate 1-9(a), Intermediate 50-18 | N2-methyl-5-(2-methyl-3-(5-methyl-1-oxoisoindolin-2-yl)phenyl)-N2-(1-methylpiperidin-4-yl)-2,3,4,9-tetrahydro-1H-carbazole-2,8-dicarboxamide | 604.5 (M + H)+ |
| 3-128 | Intermediate 1-9(a), Intermediate 50-29 | N2-methyl-5-(2-methyl-3-(1-oxoisoquinolin-2(1H)-yl)phenyl)-N2-(1-methylpiperidin-4-yl)-2,3,4,9-tetrahydro-1H-carbazole-2,8-dicarboxamide | 602.5 (M + H)+ |
| 3-129 | Intermediate 1-9(a), Intermediate 50-9 | 5-(3-(6-cyano-1-oxoisoindolin-2-yl)-2-methylphenyl)-N2-methyl-N2-(1-methylpiperidin-4-yl)-2,3,4,9-tetrahydro-1H-carbazole-2,8-dicarboxamide | 615.5 (M + H)+ |
| 3-130 | Intermediate 1-9(a), Intermediate 50-7 | N2-methyl-5-(2-methyl-3-(1-oxo-6-(trifluoromethyl)isoindolin-2-yl)phenyl)-N2-(1-methylpiperidin-4-yl)-2,3,4,9-tetrahydro-1H-carbazole-2,8-dicarboxamide | 658.3 (M + H)+ |
| 3-131 | Example 1-3, Intermediate 50-20 | 5-(4-methyl-5-(5-methyl-1-oxoisoindolin-2-yl)pyridin-3-yl)-2-(4-methylpiperazine-1-carbonyl)-2,3,4,9-tetrahydro-1H-carbazole-8-carboxamide (prepared as the TFA salt) | 577.3 (M + H)+ |

-continued

| Example/Intermediates | Starting materials | Compound name | Mass spectrum |
|---|---|---|---|
| 3-132 | Intermediate 48-1, Intermediate 50-24 | ethyl 8-carbamoyl-5-(2-methyl-3-(4-oxoquinazolin-3(4H)-yl)phenyl)-9H-carbazole-2-carboxylate | 517.0 (M + H)+ |
| 3-133 | Intermediate 48-1, Intermediate 50-48 | ethyl 8-carbamoyl-5-(3-(8-fluoro-4-oxoquinazolin-3(4H)-yl)-2-methylphenyl)-9H-carbazole-2-carboxylate | 535.1 (M + H)+ |
| 3-134 | Intermediate 48-1, Intermediate 50-27 | ethyl 8-carbamoyl-5-(3-(6-fluoro-4-oxoquinazolin-3(4H)-yl)-2-methylphenyl)-9H-carbazole-2-carboxylate | 535.3 (M + H)+ |
| 3-135 | Intermediate 48-1, Intermediate 50-29 | ethyl 8-carbamoyl-5-(2-methyl-3-(6-methyl-4-oxoquinazolin-3(4H)-yl)phenyl)-9H-carbazole-2-carboxylate | 531.3 (M + H)+ |
| 3-136 | Intermediate 1-7(a), Intermediate 50-10 | 4-(3-(5-fluoro-1,3-dioxoisoindolin-2-yl)-2-methylphenyl)-$N^7$-(tetrahydro-2H-pyran-4-yl)-9H-carbazole-1,7-dicarboxamide[b] | 591.3 (M + H)+ |
| 3-137 | Example 1-1 [a] | 4-(2-fluoro-3-methoxyphenyl)-7-(4-methylpiperazine-1-carbonyl)-9H-carbazole-1-carboxamide | 461.2 (M + H)+ |
| 3-138 | Intermediate 48-1, Intermediate 50-8 | ethyl 8-carbamoyl-5-(2-methyl-3-(6-methyl-1-oxoisoindolin-2-yl)phenyl)-9H-carbazole-2-carboxylate | 518.1 (M + H)+ |
| 3-139 | Intermediate 48-1, Intermediate 50-5 | ethyl 8-carbamoyl-5-(3-(6-fluoro-1-oxoisoindolin-2-yl)-2-methylphenyl)-9H-carbazole-2-carboxylate | 544.1 (M + Na)+ |
| 3-140 | Intermediate 48-1, Intermediate 50-17 | ethyl 8-carbamoyl-5-(3-(4-fluoro-1-oxoisoindolin-2-yl)-2-methylphenyl)-9H-carbazole-2-carboxylate | 544.1 (M + Na)+ |
| 3-141 | Intermediate 48-3, Intermediate 50-27 | 4-(3-(6-fluoro-4-oxoquinazolin-3(4H)-yl)-2-methylphenyl)-9H-carbazole-1-carboxamide | 463.1 (M + H)+ |
| 3-142 | Intermediate 48-3, Intermediate 50-24 | 4-(2-methyl-3-(4-oxoquinazolin-3(4H)-yl)phenyl)-9H-carbazole-1-carboxamide | 445.1 (M + H)+ |
| 3-143 | Intermediate 1-10(a), Intermediate 50-5 | 4-(3-(6-fluoro-1-oxoisoindolin-2-yl)-2-methylphenyl)-$N^7$,$N^7$-dimethyl-9H-carbazole-1,7-dicarboxamide | 521.0 (M + H)+ |
| 3-144 | Intermediate 1-10(a), Intermediate 50-24 | $N^7$,$N^7$-dimethyl-4-(2-methyl-3-(4-oxoquinazolin-3(4H)-yl)phenyl)-9H-carbazole-1,7-dicarboxamide | 516.0 (M + H)+ |
| 3-145 | Intermediate 1-10(a), Intermediate 50-8 | $N^7$,$N^7$-dimethyl-4-(2-methyl-3-(6-methyl-1-oxoisoindolin-2-yl)phenyl)-9H-carbazole-1,7-dicarboxamide | 517.1 (M + H)+ |
| 3-146 | Intermediate 48-3, Intermediate 50-48 | 4-(3-(8-fluoro-4-oxoquinazolin-3(4H)-yl)-2-methylphenyl)-9H-carbazole-1-carboxamide | 463.1 (M + H)+ |

[a] Commercially available boronic acid or boronate ester.
[b] Obtained as a byproduct from reaction of 5-fluoro-2-(2-methyl-3-(4,4,5,5-tetramethyl-1,3,2-dioxaborolan-2-yl)phenyl)isoindoline-1,3-dione (Intermediate 50-10) with 5-bromo-$N^2$-(tetrahydro-2H-pyran-4-yl)-2,3,4,9-tetrahydro-1H-carbazole-2,8-dicarboxamide (Intermediate 1-7(a)).

Examples 4-1 and 4-2

Preparation of 5-(2-(isopropylamino)thiazol-5-yl)-$N^2$-(1-methylpiperidin-4-yl)-2,3,4,9-tetrahydro-1H-carbazole-2,8-dicarboxamide and 4-(2-(isopropylamino)thiazol-5-yl)-$N^7$-(1-methylpiperidin-4-yl)-9H-carbazole-1,7-dicarboxamide

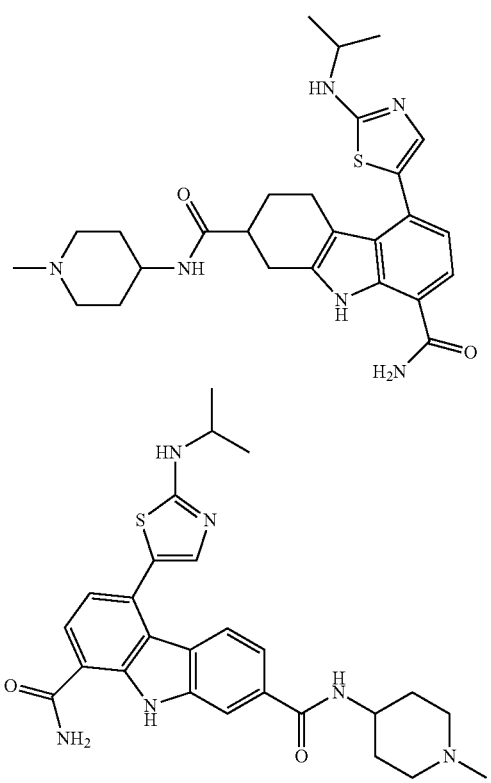

A solution of tert-butyl 5-(8-carbamoyl-2-(1-methylpiperidin-4-ylcarbamoyl)-2,3,4,9-tetrahydro-1H-carbazol-5-yl)thiazol-2-yl(isopropyl)carbamate (Example 3-111, 35 mg, 0.059 mmol) in DCM (1 mL) and TFA (1 mL) was stirred at rt for 2 h. The solution was concentrated and the residue was partitioned between DCM and 1 M aqueous sodium bicarbonate. The organic phase was concentrated and the residue was purified by preparative HPLC. The appropriate effluent fractions were made basic with 1 M aqueous sodium hydroxide, extracted twice with DCM, and the combined organic phases were washed with water, dried and concentrated to provide 5-(2-(isopropylamino)thiazol-5-yl)-$N^2$-(1-methylpiperidin-4-yl)-2,3,4,9-tetrahydro-1H-carbazole-2,8-dicarboxamide (Example 4-1, 18 mg, 61%) as a white solid. $^1$H NMR (400 MHz, methanol-$d_4$) δ 7.51 (1H, d, J=7.91 Hz), 6.95 (1H, d, J=7.91 Hz), 6.89 (1H, s), 3.81-3.89 (1H, m), 3.64-3.73 (1H, m), 2.79-3.07 (4H, m), 2.59-2.75 (3H, m), 2.27 (3H, s), 2.09-2.18 (2H, m), 1.97-2.06 (1H, m), 1.84-1.92 (2H, m), 1.70-1.83 (1H, m), 1.48-1.61 (2H, m), 1.27 (6H, d, J=6.15 Hz). Mass spectrum m/z 495.2 (M+H)$^+$. Also obtained was 4-(2-(isopropylamino)thiazol-5-yl)-$N^7$-(1-methylpiperidin-4-yl)-9H-carbazole-1,7-dicarboxamide as a white solid (Example 4-2, 5.2 mg, 18%). $^1$H NMR (400 MHz, methanol-$d_4$) δ 8.04-8.10 (2H, m), 7.88-7.93 (1H, m), 7.52-7.58 (1H, m), 7.25 (1H, s), 7.14-7.20 (1H, m), 3.87-3.98 (2H, m), 2.88-2.97 (2H, m), 2.31 (3H, s), 2.15-2.24 (2H, m), 1.95-2.03 (2H, m), 1.64-1.79 (2H, m), 1.32 (6H, d, J=6.59 Hz). Mass spectrum m/z 491.2 (M+H)$^+$.

The following compound was also prepared from Example 3-124 using procedures used to prepare Example 4-1:

| Example | Compound name | Mass spectrum |
|---|---|---|
| 4-3 | 5-(2-amino-4-methylthiazol-5-yl)-$N^2$-(tetrahydro-2H-pyran-4-yl)-2,3,4,9-tetrahydro-1H-carbazole-2,8-dicarboxamide | 454.2 (M + H)$^+$ |

Example 5-1

Preparation of 4-(3-(4-tert-butylbenzamido)-2-methylphenyl)-7-(4-methylpiperazine-1-carbonyl)-9H-carbazole-1-carboxamide

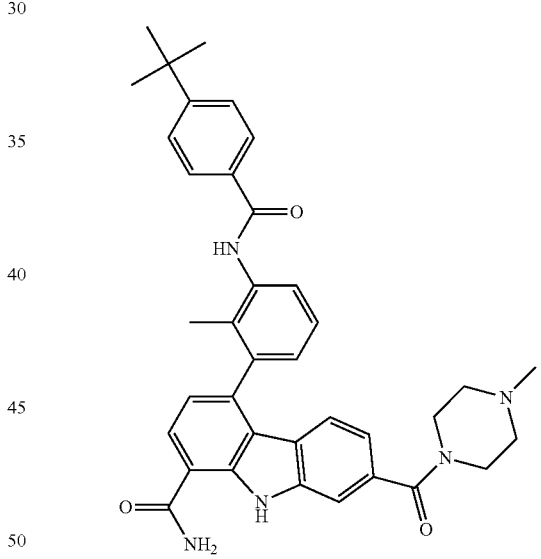

A solution of 4-(3-amino-2-methylphenyl)-7-(4-methylpiperazine-1-carbonyl)-9H-carbazole-1-carboxamide (Example 3-2, 40 mg, 0.045 mmol) and TEA (0.013 mL, 0.091 mmol) in THF (2 mL) was treated with 4-tert-butylbenzoyl chloride (0.016 mL, 0.091 mmol). The mixture was stirred at rt for 1 h, then was concentrated and purified by preparative HPLC to provide 4-(3-(4-tert-butylbenzamido)-2-methylphenyl)-7-(4-methylpiperazine-1-carbonyl)-9H-carbazole-1-carboxamide, TFA salt, as a white solid (22 mg, 65%). $^1$H NMR (400 MHz, DMSO-$d_6$) δ 11.76 (s, 1H) 10.03 (s, 1H) 8.25 (br. s., 1H) 8.08 (d, J=7.69 Hz, 1H) 7.94 (d, J=8.57 Hz, 2H) 7.85 (s, 1H) 7.47-7.61 (m, 4H) 7.41 (t, J=7.69 Hz, 1H)

7.20 (d, J=7.03 Hz, 1H) 6.98-7.07 (m, 3H) 2.93-3.50 (m, 8H) 2.81 (s, 3H) 1.90 (s, 3H) 1.30 (s, 9H). Mass spectrum m/z 602.4 (M+H)$^+$.

Example 5-2

Preparation of 4-(3-acetamido-2-methylphenyl)-7-(4-methylpiperazine-1-carbonyl)-9H-carbazole-1-carboxamide

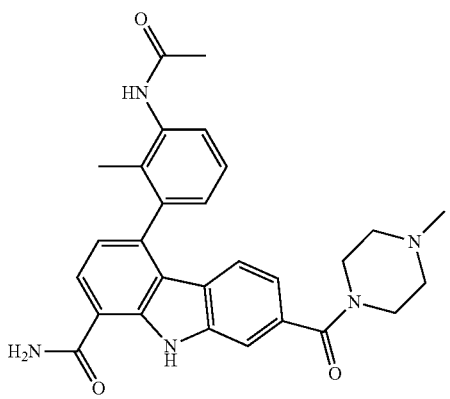 [SMILES: CC(=O)Nc1cccc(-c2ccc(C(N)=O)c3[nH]c4cc(C(=O)N5CCN(C)CC5)ccc4c23)c1C]

A solution of 4-(3-amino-2-methylphenyl)-7-(4-methylpiperazine-1-carbonyl)-9H-carbazole-1-carboxamide (Example 3-2, 20 mg, 0.045 mmol) and DIEA (0.024 mL, 0.136 mmol) in DCM (2 mL) was treated with acetyl chloride (4 µL, 0.054 mmol). The mixture was stirred at rt for 2 h, then was concentrated and purified by preparative HPLC to provide 4-(3-acetamido-2-methylphenyl)-7-(4-methylpiperazine-1-carbonyl)-9H-carbazole-1-carboxamide, TFA salt, as a white solid (18 mg, 66%). $^1$H NMR (400 MHz, DMSO-d$_6$) δ 11.69 (1H, s), 9.44 (1H, s), 8.18 (1H, br. s.), 8.00 (1H, d, J=7.7 Hz), 7.78 (1H, s), 7.50 (2H, d, J=7.3 Hz), 7.28 (1H, t, J=7.7 Hz), 7.05 (1H, d, J=7.3 Hz), 6.88-6.98 (2H, m), 6.83 (1H, d, J=8.1 Hz), 2.86-3.11 (4H, m), 2.75 (3H, s), 2.02 (3H, s), 1.80 (3H, s). Mass spectrum m/z 484.3 (M+H)$^+$.

Example 5-3

Preparation of 4-(3-(5-fluoropicolinamido)-2-methylphenyl)-7-(4-methylpiperazine-1-carbonyl)-9H-carbazole-1-carboxamide

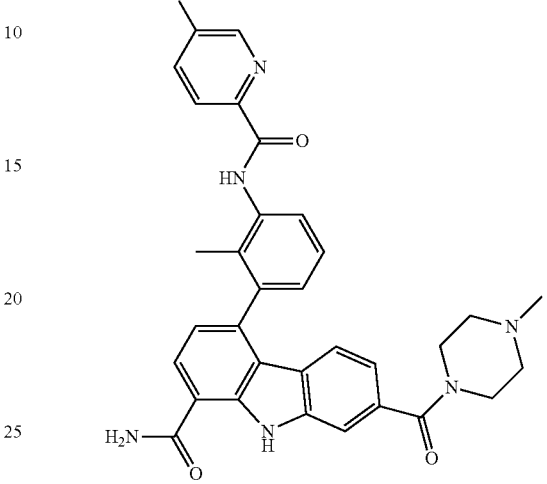

A mixture of 4-(3-amino-2-methylphenyl)-7-(4-methylpiperazine-1-carbonyl)-9H-carbazole-1-carboxamide (Example 3-2, 100 mg, 0.204 mmol), 5-fluoropicolinic acid (43.1 mg, 0.306 mmol), and HOAT (41.6 mg, 0.306 mmol) in acetonitrile (2 mL) was treated with DIEA (0.053 mL, 0.306 mmol) and EDC (78 mg, 0.408 mmol) and the mixture was stirred at rt. After 18 h, the mixture was diluted with methanol and purified by preparative HPLC. The aqueous residue from concentration of the appropriate effluent fractions was made basic with NaHCO3 (aq) and extracted three times with EtOAc. The combined organic phases were dried and concentrated to provide 4-(3-(5-fluoropicolinamido)-2-methylphenyl)-7-(4-methylpiperazine-1-carbonyl)-9H-carbazole-1-carboxamide as a light gray powder (111.5 mg, 92%). $^1$H NMR (400 MHz, methanol-d$_4$) δ 8.58 (d, J=3.1 Hz, 1H) 8.31 (dd, J=8.8, 4.8 Hz, 1H) 7.96-8.03 (m, 2H) 7.82 (td, J=8.6, 2.6 Hz, 1H) 7.68 (d, J=0.9 Hz, 1H) 7.45 (t, J=7.9 Hz, 1H) 7.23 (dd, J=7.5, 0.9 Hz, 1H) 7.09 (d, J=7.9 Hz, 1H) 7.03-7.08 (m, 1H) 6.95-7.00 (m, 1H) 3.78 (br. s., 2H) 3.49 (br. s., 2H) 2.52 (br. s., 2H) 2.40 (br. s., 2H) 2.31 (s, 3H) 2.04 (s, 3H). Mass spectrum m/z 565.2 (M+H)$^+$.

The following compounds were also prepared using procedures demonstrated in Examples 5-1 through 5-3 and similar procedures. In this table, "starting material" refers to the amine reacted with the appropriate commercially available carboxylic acid or acid chloride.

| Example | Starting material | Compound name | Mass spectrum |
|---|---|---|---|
| 5-4 | Example 3-2 | 4-(3-(4-fluorobenzamido)-2-methylphenyl)-7-(4-methylpiperazine-1-carbonyl)-9H-carbazole-1-carboxamide (prepared as the TFA salt) | 564.3 (M + H)$^+$ |
| 5-5 | Example 3-2 | 4-(2-methyl-3-(picolinamido)phenyl)-6-(4-methylpiperazine-1-carbonyl)-9H-carbazole-1-carboxamide | 547.2 (M + H)$^+$ |
| 5-6 | Example 3-2 | N-(3-(1-carbamoyl-6-(4-methylpiperazine-1-carbonyl)-9H-carbazol-4-yl)-2-methylphenyl)thiazole-2-carboxamide | 553.2 (M + H)$^+$ |

-continued

| Example | Starting material | Compound name | Mass spectrum |
|---|---|---|---|
| 5-7 | Example 3-2 | 4-(2-methyl-3-(nicotinamido)phenyl)-7-(4-methylpiperazine-1-carbonyl)-9H-carbazole-1-carboxamide | 547.2 (M + H)+ |
| 5-8 | Example 3-2 | 4-(3-(isonicotinamido)-2-methylphenyl)-7-(4-methylpiperazine-1-carbonyl)-9H-carbazole-1-carboxamide | 547.2 (M + H)+ |
| 5-9 | Example 3-2 | 4-(3-(1H-imidazole-2-carboxamido)-2-methylphenyl)-7-(4-methylpiperazine-1-carbonyl)-9H-carbazole-1-carboxamide (prepared as the TFA salt) | 536.3 (M + H)+ |
| 5-10 | Example 3-2 | 4-(2-methyl-3-(pyrimidine-4-carboxamido)phenyl)-7-(4-methylpiperazine-1-carbonyl)-9H-carbazole-1-carboxamide | 548.2 (M + H)+ |
| 5-11 | Example 3-2 | 4-(3-(1H-benzo[d]imidazole-2-carboxamido)-2-methylphenyl)-7-(4-methylpiperazine-1-carbonyl)-9H-carbazole-1-carboxamide | 586.2 (M + H)+ |
| 5-12 | Example 3-2 | 4-(2-fluoro-4-(4-fluorobenzamido)phenyl)-7-(4-methylpiperazine-1-carbonyl)-9H-carbazole-1-carboxamide | 568.1 (M + H)+ |
| 5-13 | Example 3-2 | 4-(3-(5-ethylpicolinamido)-2-methylphenyl)-7-(4-methylpiperazine-1-carbonyl)-9H-carbazole-1-carboxamide | 575.2 (M + H)+ |
| 5-14 | Example 3-2 | 4-(3-(5-butylpicolinamido)-2-methylphenyl)-7-(4-methylpiperazine-1-carbonyl)-9H-carbazole-1-carboxamide | 603.3 (M + H)+ |
| 5-15 | Example 3-2 | 4-(2-methyl-3-(1-methyl-1H-imidazole-2-carboxamido)phenyl)-7-(4-methylpiperazine-1-carbonyl)-9H-carbazole-1-carboxamide | 550.2 (M + H)+ |
| 5-16 | Example 3-2 | N-(3-(1-carbamoyl-7-(4-methylpiperazine-1-carbonyl)-9H-carbazol-4-yl)-2-methylphenyl)-4-isopropylthiazole-2-carboxamide | 595.2 (M + H)+ |
| 5-17 | Example 3-2 | N-(3-(1-carbamoyl-7-(4-methylpiperazine-1-carbonyl)-9H-carbazol-4-yl)-2-methylphenyl)-4,5,6,7-tetrahydrobenzo[d]thiazole-2-carboxamide | 607.2 (M + H)+ |
| 5-18 | Example 3-2 | N-(3-(1-carbamoyl-7-(4-methylpiperazine-1-carbonyl)-9H-carbazol-4-yl)-2-methylphenyl)-5-methylthiazole-2-carboxamide | 567.2 (M + H)+ |
| 5-19 | Example 3-2 | 4-(3-(3-hydroxypicolinamido)-2-methylphenyl)-7-(4-methylpiperazine-1-carbonyl)-9H-carbazole-1-carboxamide (prepared as the TFA salt) | 563.2 (M + H)+ |
| 5-20 | Example 3-2 | 4-(2-methyl-3-(pyrimidine-2-carboxamido)phenyl)-7-(4-methylpiperazine-1-carbonyl)-9H-carbazole-1-carboxamide | 548.2 (M + H)+ |
| 5-21 | Example 3-2 | N-(3-(1-carbamoyl-7-(4-methylpiperazine-1-carbonyl)-9H-carbazol-4-yl)-2-methylphenyl)benzo[d]thiazole-2-carboxamide | 603.2 (M + H)+ |
| 5-22 | Example 3-2 | 4-(2-methyl-3-(1-methyl-1H-benzo[d]imidazole-2-carboxamido)phenyl)-7-(4-methylpiperazine-1-carbonyl)-9H-carbazole-1-carboxamide | 600.2 (M + H)+ |
| 5-23 | Example 3-2 | 4-(3-(5-chloropicolinamido)-2-methylphenyl)-7-(4-methylpiperazine-1-carbonyl)-9H-carbazole-1-carboxamide | 581.2 (M + H)+ |
| 5-24 | Example 3-2 | 4-(3-(5-bromopicolinamido)-2-methylphenyl)-7-(4-methylpiperazine-1-carbonyl)-9H-carbazole-1-carboxamide | 625, 627 (M + H)+ |
| 5-25 | Example 3-2 | 4-(2-methyl-3-(5-(trifluoromethyl)picolinamido)phenyl)-7-(4-methylpiperazine-1-carbonyl)-9H-carbazole-1-carboxamide | 615.2 (M + H)+ |
| 5-26 | Example 3-2 | 4-(3-(6-hydroxypicolinamido)-2-methylphenyl)-7-(4-methylpiperazine-1-carbonyl)-9H-carbazole-1-carboxamide (prepared as the TFA salt) | 563.2 (M + H)+ |
| 5-27 | Example 3-2 | 4-(3-(5-hydroxypicolinamido)-2-methylphenyl)-7-(4-methylpiperazine-1-carbonyl)-9H-carbazole-1-carboxamide (prepared as the TFA salt) | 563.2 (M + H)+ |
| 5-28 | Example 3-2 | 4-(2-methyl-3-(5-methylpicolinamido)phenyl)-7-(4-methylpiperazine-1-carbonyl)-9H-carbazole-1-carboxamide | 561.3 (M + H)+ |
| 5-29 | Example 3-2 | 4-(3-(5-bromopyrimidine-2-carboxamido)-2-methylphenyl)-7-(4-methylpiperazine-1-carbonyl)-9H-carbazole-1-carboxamide | 626, 628 (M + H)+ |

-continued

| Example | Starting material | Compound name | Mass spectrum |
|---|---|---|---|
| 5-30 | Example 3-2 | N-(3-(1-carbamoyl-7-(4-methylpiperazine-1-carbonyl)-9H-carbazol-4-yl)-2-methylphenyl)-2-chlorothiazole-5-carboxamide | 587.1 (M + H)+ |
| 5-31 | Example 3-2 | 4-(3-(5-cyanopicolinamido)-2-methylphenyl)-7-(4-methylpiperazine-1-carbonyl)-9H-carbazole-1-carboxamide | 572.2 (M + H)+ |
| 5-32 | Example 3-2 | 4-(2-methyl-3-(5-(pyrrolidin-1-yl)picolinamido)phenyl)-7-(4-methylpiperazine-1-carbonyl)-9H-carbazole-1-carboxamide | 616.3 (M + H)+ |
| 5-33 | Example 3-37 | 4-(2-fluoro-3-(picolinamido)phenyl)-7-(4-methylpiperazine-1-carbonyl)-9H-carbazole-1-carboxamide | 551.2 (M + H)+ |
| 5-34 | Example 3-37 | 4-(2-fluoro-3-(5-fluoropicolinamido)phenyl)-7-(4-methylpiperazine-1-carbonyl)-9H-carbazole-1-carboxamide | 569.2 (M + H)+ |
| 5-35 | Example 3-37 | 4-(3-(5-cyanopicolinamido)-2-fluorophenyl)-7-(4-methylpiperazine-1-carbonyl)-9H-carbazole-1-carboxamide | 576.2 (M + H)+ |
| 5-36 | Example 3-37 | 4-(2-fluoro-3-(5-(pyrrolidin-1-yl)picolinamido)phenyl)-7-(4-methylpiperazine-1-carbonyl)-9H-carbazole-1-carboxamide | 620.3 (M + H)+ |
| 5-37 | Example 3-37 | 4-(2-fluoro-3-(pyrimidine-4-carboxamido)phenyl)-7-(4-methylpiperazine-1-carbonyl)-9H-carbazole-1-carboxamide | 552.2 (M + H)+ |
| 5-38 | Example 3-37 | N-(3-(1-carbamoyl-7-(4-methylpiperazine-1-carbonyl)-9H-carbazol-4-yl)-2-fluorophenyl)thiazole-2-carboxamide | 557.1 (M + H)+ |
| 5-39 | Example 3-37 | 4-(2-fluoro-3-(1-methyl-1H-imidazole-2-carboxamido)phenyl)-7-(4-methylpiperazine-1-carbonyl)-9H-carbazole-1-carboxamide | 554.2 (M + H)+ |
| 5-40 | Example 3-2 | 4-(2-methyl-3-(2-(pyridin-2-yl)acetamido)phenyl)-7-(4-methylpiperazine-1-carbonyl)-9H-carbazole-1-carboxamide | 561.2 (M + H)+ |
| 5-41 | Example 3-2 | 4-(2-methyl-3-(1-(pyridin-2-yl)cyclopropanecarboxamido)phenyl)-7-(4-methylpiperazine-1-carbonyl)-9H-carbazole-1-carboxamide | 587.3 (M + H)+ |
| 5-42 | Example 3-2 | 4-(3-(1-(4-fluorophenyl)cyclopropanecarboxamido)-2-methylphenyl)-7-(4-methylpiperazine-1-carbonyl)-9H-carbazole-1-carboxamide | 604.2 (M + H)+ |
| 5-43 | Example 3-2 | 4-(3-(1-(4-fluorophenyl)cyclobutanecarboxamido)-2-methylphenyl)-7-(4-methylpiperazine-1-carbonyl)-9H-carbazole-1-carboxamide | 618.2 (M + H)+ |
| 5-44 | Example 3-2 | 4-(3-(2-(4-chlorophenyl)-2-methylpropanamido)-2-methylphenyl)-7-(4-methylpiperazine-1-carbonyl)-9H-carbazole-1-carboxamide | 622.2 (M + H)+ |
| 5-45 | Example 3-2 | 4-(3-benzamido-2-methylphenyl)-7-(4-methylpiperazine-1-carbonyl)-9H-carbazole-1-carboxamide | 546.3 (M + H)+ |
| 5-46 | Example 3-13 | 4-(2-methyl-3-(1-methyl-1H-benzo[d]imidazole-2-carboxamido)phenyl)-9H-carbazole-1-carboxamide | 474.4 (M + H)+ |
| 5-47 | Example 3-13 | 4-(2-methyl-3-(1-methyl-1H-imidazole-2-carboxamido)phenyl)-9H-carbazole-1-carboxamide | 424.3 (M + H)+ |
| 5-48 | Example 3-51 | 4-(2,6-difluoro-4-(4-fluorobenzamido)phenyl)-7-(4-methylpiperazine-1-carbonyl)-9H-carbazole-1-carboxamide | 586.4 (M + H)+ |
| 5-49 | Example 3-2 | 4-(3-(cyclopropanecarboxamido)-2-methylphenyl)-7-(4-methylpiperazine-1-carbonyl)-9H-carbazole-1-carboxamide (prepared as the TFA salt) | 509.9 (M + H)+ |
| 5-50 | Example 3-2 | 4-(3-(cyclohexanecarboxamido)-2-methylphenyl)-7-(4-methylpiperazine-1-carbonyl)-9H-carbazole-1-carboxamide (prepared as the TFA salt) | 551.9 (M + H)+ |
| 5-51 | Example 3-2 | 4-(3-(2-chlorobenzamido)-2-methylphenyl)-7-(4-methylpiperazine-1-carbonyl)-9H-carbazole-1-carboxamide (prepared as the TFA salt) | 579.8 (M + H)+ |
| 5-52 | Example 3-2 | 4-(3-(3-chlorobenzamido)-2-methylphenyl)-7-(4-methylpiperazine-1-carbonyl)-9H- | 579.8 (M + H)+ |

| Example | Starting material | Compound name | Mass spectrum |
|---|---|---|---|
| | | carbazole-1-carboxamide (prepared as the TFA salt) | |
| 5-53 | Example 3-2 | 4-(3-(dimethylamino)benzamido)-2-methylphenyl)-7-(4-methylpiperazine-1-carbonyl)-9H-carbazole-1-carboxamide (prepared as the TFA salt) | 588.9 (M + H)+ |
| 5-54 | Example 3-2 | 4-(3-(4-cyanobenzamido)-2-methylphenyl)-7-(4-methylpiperazine-1-carbonyl)-9H-carbazole-1-carboxamide (prepared as the TFA salt) | 570.8 (M + H)+ |
| 5-55 | Example 3-2 | 4-(3-(4-chlorobenzamido)-2-methylphenyl)-7-(4-methylpiperazine-1-carbonyl)-9H-carbazole-1-carboxamide (prepared as the TFA salt) | 579.8 (M + H)+ |
| 5-56 | Example 3-2 | 4-(3-(4-acetamidobenzamido)-2-methylphenyl)-7-(4-methylpiperazine-1-carbonyl)-9H-carbazole-1-carboxamide (prepared as the TFA salt) | 602.8 (M + H)+ |
| 5-57 | Example 3-2 | 4-(3-(4-methoxybenzamido)-2-methylphenyl)-7-(4-methylpiperazine-1-carbonyl)-9H-carbazole-1-carboxamide (prepared as the TFA salt) | 575.8 (M + H)+ |
| 5-58 | Example 3-2 | 4-(2-methyl-3-(4-methylbenzamido)phenyl)-7-(4-methylpiperazine-1-carbonyl)-9H-carbazole-1-carboxamide (prepared as the TFA salt) | 559.8 (M + H)+ |
| 5-59 | Example 3-2 | 4-(3-isobutyramido-2-methylphenyl)-7-(4-methylpiperazine-1-carbonyl)-9H-carbazole-1-carboxamide (prepared as the TFA salt) | 511.9 (M + H)+ |
| 5-60 | Example 3-2 | 4-(3-(2-cyanoacetamido)-2-methylphenyl)-7-(4-methylpiperazine-1-carbonyl)-9H-carbazole-1-carboxamide (prepared as the TFA salt) | 508.8 (M + H)+ |
| 5-61 | Example 3-2 | 4-(3-(3,3-dimethylbutanamido)-2-methylphenyl)-7-(4-methylpiperazine-1-carbonyl)-9H-carbazole-1-carboxamide (prepared as the TFA salt) | 539.9 (M + H)+ |
| 5-62 | Example 3-2 | 4-(2-methyl-3-(3-methylbutanamido)phenyl)-7-(4-methylpiperazine-1-carbonyl)-9H-carbazole-1-carboxamide (prepared as the TFA salt) | 525.8 (M + H)+ |
| 5-63 | Example 3-2 | 4-(2-methyl-3-(4-methylpentanamido)phenyl)-7-(4-methylpiperazine-1-carbonyl)-9H-carbazole-1-carboxamide (prepared as the TFA salt) | 539.9 (M + H)+ |
| 5-64 | Example 3-2 | 4-(2-methyl-3-pivalamidophenyl)-7-(4-methylpiperazine-1-carbonyl)-9H-carbazole-1-carboxamide (prepared as the TFA salt) | 525.9 (M + H)+ |
| 5-65 | Example 3-2 | 4-(3-(2-(dimethylamino)acetamido)-2-methylphenyl)-7-(4-methylpiperazine-1-carbonyl)-9H-carbazole-1-carboxamide (prepared as the TFA salt) | 526.9 (M + H)+ |
| 5-66 | Example 3-2 | 4-(2-methyl-3-(2-phenylacetamido)phenyl)-7-(4-methylpiperazine-1-carbonyl)-9H-carbazole-1-carboxamide (prepared as the TFA salt) | 559.8 (M + H)+ |
| 5-67 | Example 3-2 | 4-(2-methyl-3-pent-4-ynamidophenyl)-7-(4-methylpiperazine-1-carbonyl)-9H-carbazole-1-carboxamide (prepared as the TFA salt) | 521.9 (M + H)+ |
| 5-68 | Example 3-2 | 4-(2-methyl-3-pentanamidophenyl)-7-(4-methylpiperazine-1-carbonyl)-9H-carbazole-1-carboxamide (prepared as the TFA salt) | 525.9 (M + H)+ |
| 5-69 | Example 3-2 | 4-(2-methyl-3-(4-sulfamoylbenzamido)phenyl)-7-(4-methylpiperazine-1-carbonyl)-9H-carbazole-1-carboxamide (prepared as the TFA salt) | 624.8 (M + H)+ |
| 5-70 | Example 3-2 | 4-(2-methyl-3-(2-methyl-2-phenylpropanamido)phenyl)-7-(4-methylpiperazine-1-carbonyl)-9H-carbazole-1-carboxamide (prepared as the TFA salt) | 587.9 (M + H)+ |
| 5-71 | Example 3-2 | 4-(3-(2-(dimethylamino)benzamido)-2-methylphenyl)-7-(4-methylpiperazine-1- | 588.8 (M + H)+ |

-continued

| Example | Starting material | Compound name | Mass spectrum |
|---|---|---|---|
| 5-72 | Example 3-2 | carbonyl)-9H-carbazole-1-carboxamide (prepared as the TFA salt) N-(3-(1-carbamoyl-7-(4-methylpiperazine-1-carbonyl)-9H-carbazol-4-yl)-2-methylphenyl)-2-phenylthiazole-4-carboxamide (prepared as the TFA salt) | 628.8 $(M + H)^+$ |
| 5-73 | Example 3-2 | 4-(3-(1-cyanocyclopropanecarboxamido)-2-methylphenyl)-7-(4-methylpiperazine-1-carbonyl)-9H-carbazole-1-carboxamide (prepared as the TFA salt) | 534.8 $(M + H)^+$ |
| 5-74 | Example 3-2 | N-(3-(1-carbamoyl-7-(4-methylpiperazine-1-carbonyl)-9H-carbazol-4-yl)-2-methylphenyl)thiazole-4-carboxamide (prepared as the TFA salt) | 552.8 $(M + H)^+$ |
| 5-75 | Example 3-2 | 4-(2-methyl-3-(3-morpholinopropanamido)phenyl)-7-(4-methylpiperazine-1-carbonyl)-9H-carbazole-1-carboxamide (prepared as the TFA salt) | 582.9 $(M + H)^+$ |
| 5-76 | Example 3-2 | 4-(3-(3-(1H-imidazol-1-yl)propanamido)-2-methylphenyl)-7-(4-methylpiperazine-1-carbonyl)-9H-carbazole-1-carboxamide (prepared as the TFA salt) | 563.8 $(M + H)^+$ |
| 5-77 | Example 3-2 | 4-(3-(2-(1H-tetrazol-5-yl)acetamido)-2-methylphenyl)-7-(4-methylpiperazine-1-carbonyl)-9H-carbazole-1-carboxamide (prepared as the TFA salt) | 551.8 $(M + H)^+$ |
| 5-78 | Example 3-2 | 4-(2-methyl-3-(3-(2-oxopyrrolidin-1-yl)propanamido)phenyl)-7-(4-methylpiperazine-1-carbonyl)-9H-carbazole-1-carboxamide (prepared as the TFA salt) | 580.8 $(M + H)^+$ |
| 5-79 | Example 3-2 | 4-(2-methyl-3-(2-(pyrazin-2-yl)acetamido)phenyl)-7-(4-methylpiperazine-1-carbonyl)-9H-carbazole-1-carboxamide (prepared as the TFA salt) | 561.8 $(M + H)^+$ |
| 5-80 | Example 3-2 | 4-(3-biphenyl-4-ylcarboxamido-2-methylphenyl)-7-(4-methylpiperazine-1-carbonyl)-9H-carbazole-1-carboxamide (prepared as the TFA salt) | 622.0 $(M + H)^+$ |
| 5-81 | Example 3-2 | methyl 4-(3-(1-carbamoyl-7-(4-methylpiperazine-1-carbonyl)-9H-carbazol-4-yl)-2-methylphenylcarbamoyl)benzoate (prepared as the TFA salt) | 603.9 $(M + H)^+$ |
| 5-82 | Example 3-2 | 4-(2-methyl-3-(3-phenylpropanamido)phenyl)-7-(4-methylpiperazine-1-carbonyl)-9H-carbazole-1-carboxamide (prepared as the TFA salt) | 573.9 $(M + H)^+$ |
| 5-83 | Example 3-46 | 4-(2-methyl-5-(1-methyl-1H-imidazole-2-carboxamido)phenyl)-7-(4-methylpiperazine-1-carbonyl)-9H-carbazole-1-carboxamide | 550.2 $(M + H)^+$ |
| 5-84 | Example 3-46 | 4-(5-(4-fluorobenzamido)-2-methylphenyl)-7-(4-methylpiperazine-1-carbonyl)-9H-carbazole-1-carboxamide | 564.2 $(M + H)^+$ |
| 5-85 | Example 4-1 | 5-(2-(N-isopropylacetamido)thiazol-5-yl)-$N^2$-(1-methylpiperidin-4-yl)-2,3,4,9-tetrahydro-1H-carbazole-2,8-dicarboxamide | 495.2 $(M + H)^+$ |
| 5-86 | Example 4-3 | 5-(2-benzamido-4-methylthiazol-5-yl)-$N^2$-(tetrahydro-2H-pyran-4-yl)-2,3,4,9-tetrahydro-1H-carbazole-2,8-dicarboxamide | 558.1 $(M + H)^+$ |

Example 6-1

Preparation of 4-(1-(4-fluorobenzoyl)-1H-indol-4-yl)-7-(4-methylpiperazine-1-carbonyl)-9H-carbazole-1-carboxamide

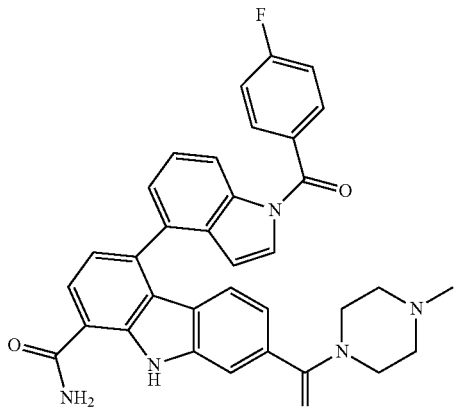

A solution of 4-(1H-indol-4-yl)-7-(4-methylpiperazine-1-carbonyl)-9H-carbazole-1-carboxamide (Example 3-47, 50 mg, 0.100 mmol) in DCM (1 mL) was treated sequentially with DMAP (3.7 mg, 0.030 mmol), TEA (0.028 mL, 0.199 mmol) and 4-fluorobenzoyl chloride (0.013 mL, 0.110 mmol). The mixture was stirred at rt for 17 h, then was treated with additional 4-fluorobenzoyl chloride (0.013 mL, 0.110 mmol) and TEA (0.028 mL, 0.199 mmol) and stirring was continued for 111 h. The mixture was concentrated and the residue was dissolved in methanol and purified by preparative HPLC. The appropriate effluent fractions were partitioned between NaHCO3 (aq) and EtOAc, and the aqueous phase was extracted twice more with EtOAc. The combined organic phases were dried and concentrated to provide 4-(1-(4-fluorobenzoyl)-1H-indol-4-yl)-7-(4-methylpiperazine-1-carbonyl)-9H-carbazole-1-carboxamide as a yellow solid (19.5 mg, 31%). $^1$H NMR (400 MHz, methanol-$d_4$) δ 8.51 (1H, d, J=8.3 Hz), 8.03 (1H, d, J=7.9 Hz), 7.84 (2H, dd, J=8.8, 5.3 Hz), 7.68 (1H, s), 7.57 (1H, t, J=7.7 Hz), 7.46 (1H, d, J=7.5 Hz), 7.26-7.36 (3H, m), 7.20 (1H, d, J=7.9 Hz), 6.96 (1H, d, J=7.9 Hz), 6.86 (1H, dd, J=8.3, 1.3 Hz), 6.19 (1H, d, J=4.0 Hz), 3.77 (2H, br. s.), 3.46 (2H, br. s.), 2.51 (2H, br. s.), 2.38 (2H, br. s.), 2.30 (3H, s). Mass spectrum m/z 574.3 (M+H)$^+$.

Example 7-1

Preparation of 4-(3-(5-fluoropicolinamido)-2-methylphenyl)-7-(4-methylpiperazine-1-carbonyl)-9H-carbazole-1-carboxamide as the hydrochloric acid salt

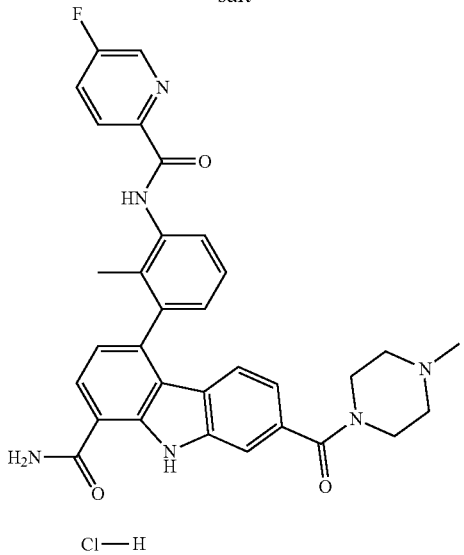

A solution of 4-(3-(5-fluoropicolinamido)-2-methylphenyl)-7-(4-methylpiperazine-1-carbonyl)-9H-carbazole-1-carboxamide (Example 5-3, 32.7 mg, 0.058 mmol) in EtOAc (1 mL) was treated with hydrogen chloride, 4 M in 1,4-dioxane (0.1 mL, 0.400 mmol). The resulting solid was suspended in additional EtOAc with sonication, and the precipitate was collected by filtration, rinsed with EtOAc and dried to provide the hydrochloric acid salt of 4-(3-(5-fluoropicolinamido)-2-methylphenyl)-7-(4-methylpiperazine-1-carbonyl)-9H-carbazole-1-carboxamide as an off-white powder (30.5 mg, 88%). $^1$H NMR (400 MHz, methanol-$d_4$) δ 8.58 (d, J=2.6 Hz, 1H) 8.31 (dd, J=8.8, 4.4 Hz, 1H) 8.03 (d, J=7.5 Hz, 1H) 7.99 (d, J=8.3 Hz, 1H) 7.82 (td, J=8.6, 2.6 Hz, 1H) 7.76 (s, 1H) 7.46 (t, J=7.7 Hz, 1H) 7.23 (d, J=7.5 Hz, 1H) 7.10 (s, 3H) 3.32-3.61 (m, 4H) 3.09-3.24 (m, 2H) 2.94 (s, 3H) 2.03 (s, 3H). Mass spectrum m/z 565.2 (M+H)$^+$.

Example 8-1

Preparation of 4-(3-(3-(3,4-dimethylphenyl)ureido)-2-methylphenyl)-7-(4-methylpiperazine-1-carbonyl)-9H-carbazole-1-carboxamide

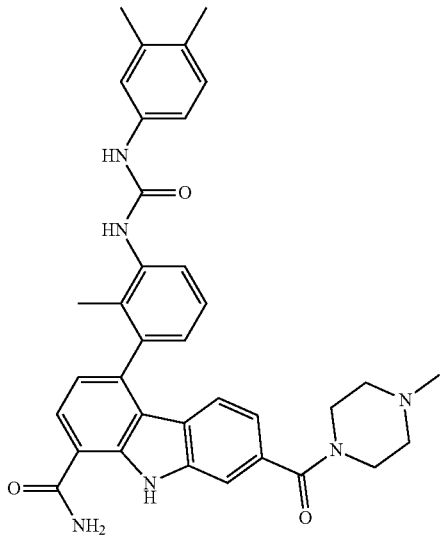 [SMILES: Cc1ccc(NC(=O)Nc2cccc(-c3ccc(C(N)=O)c4[nH]c5cc(C(=O)N6CCN(C)CC6)ccc5c34)c2C)cc1C]

A solution of 4-(3-amino-2-methylphenyl)-7-(4-methylpiperazine-1-carbonyl)-9H-carbazole-1-carboxamide (Example 3-2, 25 mg, 0.028 mmol) and TEA (8 µL, 0.057 mmol) in DCM (2 mL) was treated with 4-isocyanato-1,2-dimethylbenzene (8.33 mg, 0.057 mmol) and the mixture was stirred at rt overnight. The mixture was concentrated and purified by preparative HPLC to provide 4-(3-(3-(3,4-dimethylphenyl)ureido)-2-methylphenyl)-7-(4-methylpiperazine-1-carbonyl)-9H-carbazole-1-carboxamide, TFA salt, as a white solid (11 mg, 53%). $^1$H NMR (400 MHz, DMSO-d6) δ 11.70 (s, 1H) 8.87 (s, 1H) 8.19 (br. s., 1H) 8.00 (t, J=7.40 Hz, 3H) 7.78 (s, 1H) 7.51 (br. s., 1H) 7.27 (t, J=7.78 Hz, 1H) 7.19 (s, 1H) 7.13 (d, J=6.78 Hz, 1H) 6.87-7.00 (m, 4H) 6.81 (d, J=8.03 Hz, 1H) 3.34-3.57 (m, 4H) 2.97-3.17 (m, 4H) 2.69 (br. s., 3H) 2.13 (s, 3H) 2.09 (s, 3H) 1.85 (s, 3H). Mass spectrum m/z 589.4 (M+H)$^+$.

Example 8-2

Preparation of 4-(2-methyl-3-(3-thiazol-2-ylureido)phenyl)-7-(4-methylpiperazine-1-carbonyl)-9H-carbazole-1-carboxamide

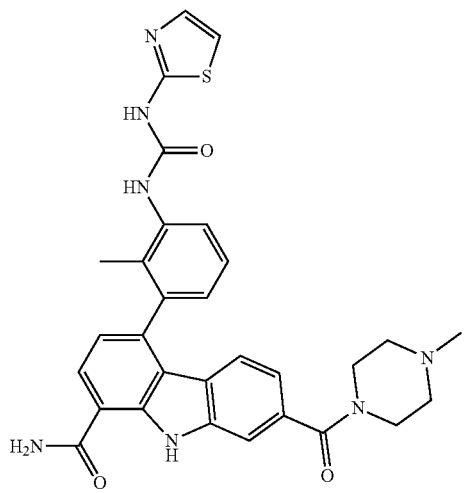 [SMILES: Cc1c(NC(=O)Nc2nccs2)cccc1-c1ccc(C(N)=O)c2[nH]c3cc(C(=O)N4CCN(C)CC4)ccc3c12]

A solution of 4-(3-amino-2-methylphenyl)-7-(4-methylpiperazine-1-carbonyl)-9H-carbazole-1-carboxamide (Example 3-2, 25 mg, 0.028 mmol) and TEA (8 μL, 0.057 mmol) in DCM (2 mL) was treated with phenyl thiazol-2-ylcarbamate (12.47 mg, 0.057 mmol) and stirred at rt overnight. The mixture was concentrated and purified by preparative HPLC to provide 4-(2-methyl-3-(3-thiazol-2-ylureido)phenyl)-7-(4-methylpiperazine-1-carbonyl)-9H-carbazole-1-carboxamide, TFA salt, as a white solid (10 mg, 45%) contaminated with about 15% of 4-(3-amino-2-methylphenyl)-7-(4-methylpiperazine-1-carbonyl)-9H-carbazole-1-carboxamide. $^1$H NMR (400 MHz, DMSO-$d_6$) δ 11.80 (s, 1H) 8.58 (br. s., 1H) 8.28 (br. s., 1H) 8.08 (t, J=7.40 Hz, 2H) 7.87 (s, 1H) 7.60 (br. s., 1H) 7.36-7.44 (m, 2H) 7.15 (d, J=3.51 Hz, 1H) 7.00-7.10 (m, 4H) 6.88 (d, J=8.28 Hz, 1H) 2.98-3.56 (m, 8H) 2.83 (br. s., 3H) 1.94 (s, 3H). Mass spectrum m/z 568.3 (M+H)$^+$.

The following compounds were also prepared using procedures demonstrated in Examples 8-1 through 8-2 and similar procedures. In this table, "starting material" refers to the amine reacted with the appropriate urea-forming reagent.

| Example | Starting material | Compound name | Mass spectrum |
|---|---|---|---|
| 8-3 | Example 3-2 | 4-(2-methyl-3-(3-phenylureido)phenyl)-7-(4-methylpiperazine-1-carbonyl)-9H-carbazole-1-carboxamide (prepared as the TFA salt) | 560.8 (M + H)$^+$ |
| 8-4 | Example 3-2 | 4-(3-(3-(4-chlorophenyl)ureido)-2-methylphenyl)-7-(4-methylpiperazine-1-carbonyl)-9H-carbazole-1-carboxamide (prepared as the TFA salt) | 594.8 (M + H)$^+$ |
| 8-5 | Example 3-2 | 4-(3-(3-(4-methoxyphenyl)ureido)-2-methylphenyl)-7-(4-methylpiperazine-1-carbonyl)-9H-carbazole-1-carboxamide (prepared as the TFA salt) | 590.8 (M + H)$^+$ |

Example 9-1

Preparation of 4-(3-(isopropylamino)-2-methylphenyl)-7-(4-methylpiperazine-1-carbonyl)-9H-carbazole-1-carboxamide

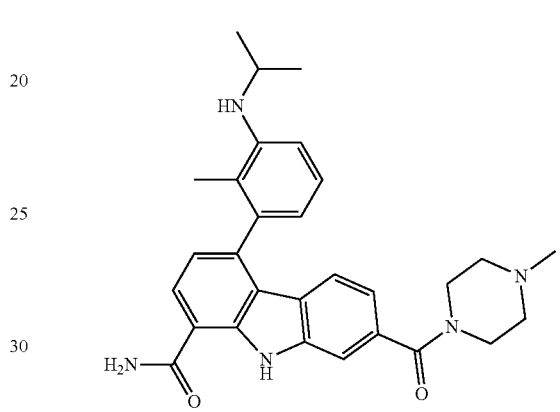

Sodium triacetoxyborohydride (41 mg, 0.193 mmol) was added to a solution of 4-(3-amino-2-methylphenyl)-7-(4-methylpiperazine-1-carbonyl)-9H-carbazole-1-carboxamide (Example 3-2, 30 mg, 0.068 mmol), acetic acid (0.03 mL, 0.524 mmol) and acetone (0.170 mL, 2.315 mmol) in DCM (0.3 mL) and the mixture was stirred at rt for 4 h. The solvent was evaporated and the residue was dissolved in water and purified by preparative HPLC and lyophilization to provide 4-(3-(isopropylamino)-2-methylphenyl)-7-(4-methylpiperazine-1-carbonyl)-9H-carbazole-1-carboxamide, TFA salt, as a white powder (31.7 mg, 56%). $^1$H NMR (400 MHz, methanol-$d_4$) δ 8.07 (1H, d, J=7.70 Hz), 7.79 (1H, s), 7.58-7.66 (2H, m), 7.50-7.54 (1H, m), 7.11 (1H, d, J=7.70 Hz), 7.03 (1H, dd, J=8.14, 1.54 Hz), 6.82 (1H, d, J=7.92 Hz), 3.84 (1H, dt, J=13.04, 6.57 Hz), 3.37-3.69 (4H, m), 3.05-3.27 (4H, m), 2.94 (3H, s), 2.11 (3H, s), 1.50 (3H, d, J=6.38 Hz), 1.45 (3H, d, J=6.60 Hz). Mass spectrum m/z 484.2 (M+H)$^+$.

The following compounds were also prepared using procedures demonstrated in Example 9-1 and similar procedures, substituting the appropriate aldehyde or ketone for acetone.

| Example | Compound name | Mass spectrum |
|---|---|---|
| 9-2 | 4-(3-(4-fluorobenzylamino)-2-methylphenyl)-7-(4-methylpiperazine-1-carbonyl)-9H-carbazole-1-carboxamide | 550.2 (M + H)$^+$ |
| 9-3 | 4-(3-(1-(4-fluorophenyl)ethylamino)-2-methylphenyl)-7-(4-methylpiperazine-1-carbonyl)-9H-carbazole-1-carboxamide | 564.3 (M + H)$^+$ |

Example 10-1

Preparation of 4-(2-methyl-3-(N-(methylsulfonyl)methylsulfonamido)phenyl)-7-(4-methylpiperazine-1-carbonyl)-9H-carbazole-1-carboxamide

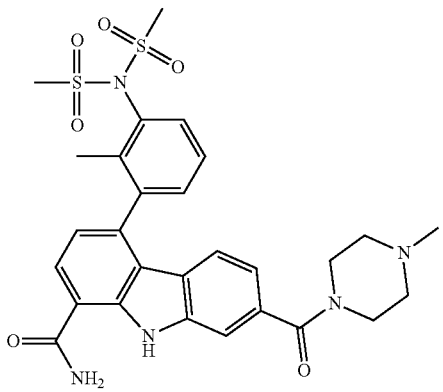 [SMILES: Cc1c(-c2ccc(C(N)=O)c3[nH]c4cc(C(=O)N5CCN(C)CC5)ccc4c23)cccc1N(S(C)(=O)=O)S(C)(=O)=O]

A solution of 4-(3-amino-2-methylphenyl)-7-(4-methylpiperazine-1-carbonyl)-9H-carbazole-1-carboxamide (Example 3-2, 20 mg, 0.045 mmol) and DIEA (0.024 mL, 0.136 mmol) in DCM (2 mL) was treated with methanesulfonyl chloride (4 µL, 0.054 mmol) and stirred at rt for 2 h. Additional methanesulfonyl chloride was added and the mixture was stirred at rt overnight. The mixture was concentrated and purified by preparative HPLC to provide 4-(2-methyl-3-(N-(methylsulfonyl)methylsulfonamido)phenyl)-7-(4-methylpiperazine-1-carbonyl)-9H-carbazole-1-carboxamide, TFA salt, as a white solid (16 mg, 46%). $^1$H NMR (400 MHz, DMSO-$d_6$) δ 11.72 (s, 1H) 8.21 (br. s., 1H) 8.04 (d, J=7.9 Hz, 1H) 7.77 (s, 1 H) 7.63 (dd, J=7.9, 1.1 Hz, 1H) 7.53 (br. s., 1H) 7.45 (t, J=7.8 Hz, 1H) 7.37 (d, J=8.6 Hz, 1H) 7.03 (d, J=7.7 Hz, 1H) 6.83-6.88 (m, 1H) 6.76-6.83 (m, 1H) 3.53 (s, 6H) 2.93-3.20 (m, 8H) 2.75 (s, 3H) 1.97 (s, 3H). Mass spectrum m/z 598.2 (M+H)$^+$.

Examples 10-2 and 10-3

Preparation of two rotational isomers of 4-(3-(N-isopropylmethylsulfonamido)-2-methylphenyl)-7-(4-methylpiperazine-1-carbonyl)-9H-carbazole-1-carboxamide

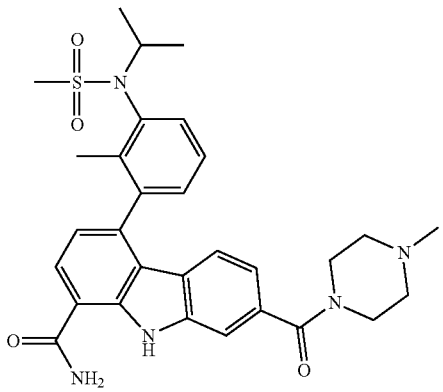 [SMILES: Cc1c(-c2ccc(C(N)=O)c3[nH]c4cc(C(=O)N5CCN(C)CC5)ccc4c23)cccc1N(C(C)C)S(C)(=O)=O]

Methanesulfonyl chloride (1.3 µL, 0.016 mmol) was added to a stirred solution of 4-(3-(isopropylamino)-2-methylphenyl)-7-(4-methylpiperazine-1-carbonyl)-9H-carbazole-1-carboxamide, TFA salt (Example 9-1, 13 mg, 0.016 mmol) in pyridine (0.2 mL) at rt. After 30 min, additional methanesulfonyl chloride (2.4 µL) was added and the mixture was stirred overnight. The mixture was treated with 1 M hydrochloric acid (0.56 mL), dissolved in methanol and purified by preparative HPLC to provide two rotational isomers of 4-(3-(N-isopropylmethylsulfonamido)-2-methylphenyl)-7-(4-methylpiperazine-1-carbonyl)-9H-carbazole-1-carboxamide, isolated separately as TFA salts after lyophilization. Isomer A (3.3 mg, 31%) $^1$H NMR (400 MHz, chloroform-d) δ 9.58 (1H, s), 7.81 (1H, d, J=7.70 Hz), 7.68 (1H, s), 7.41-7.47 (1H, m), 7.32-7.37 (2H, m), 7.11 (1H, d, J=7.70 Hz), 7.05 (1H, d, J=8.14 Hz), 6.86 (1H, d, J=8.14 Hz), 4.60-4.72 (1H, m), 3.66 (3H, br. s.), 3.05 (8H, br. s.), 2.90 (3H, s), 1.91 (3H, s), 1.40 (3H, d, J=6.60 Hz), 1.12 (3H, d, J=6.82 Hz). Mass spectrum m/z 562.1 (M+H)$^+$. Isomer B (2.9 mg, 27%) $^1$H NMR (400 MHz, chloroform-d) δ 9.41 (1H, br. s.), 7.84 (1H, d, J=7.70 Hz), 7.69 (1H, s), 7.46 (1H, t, J=7.81 Hz), 7.36 (2H, t, J=8.25 Hz), 7.13 (1H, d, J=7.70 Hz), 7.05 (1H, dd, J=8.25, 1.21 Hz), 6.92 (1H, d, J=8.36 Hz), 4.71-4.82 (1H, m), 3.67 (3H, br. s.), 2.59-3.07 (11H, m), 1.90 (3H, s), 1.43 (3H, d, J=6.60 Hz), 1.10 (3H, d, J=6.60 Hz). Mass spectrum m/z 562.2 (M+H)$^+$.

Examples 10-4 and 10-5

Preparation of 4-(3-(3-chloropropylsulfonamido)-2-methylphenyl)-7-(4-methylpiperazine-1-carbonyl)-9H-carbazole-1-carboxamide and 4-(3-(3-chloro-N-(3-chloropropylsulfonyl)propylsulfonamido)-2-methylphenyl)-7-(4-methylpiperazine-1-carbonyl)-9H-carbazole-1-carboxamide

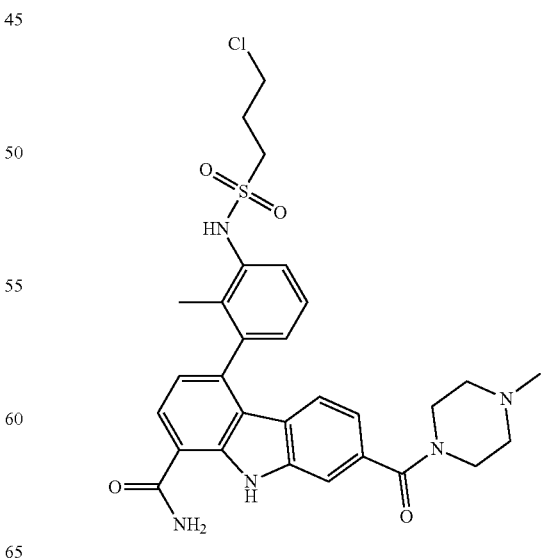

-continued

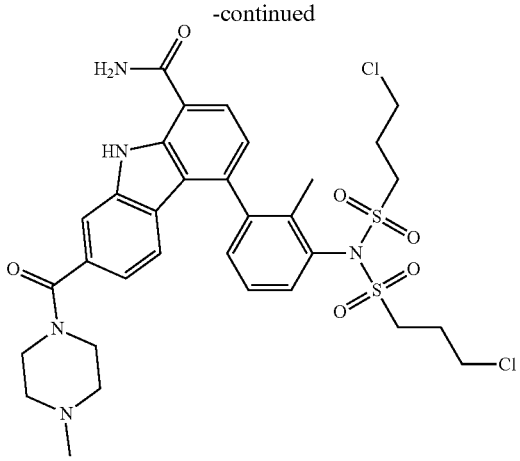

Using the procedure of Examples 10-2 and 10-3,4-(3-amino-2-methylphenyl)-7-(4-methylpiperazine-1-carbonyl)-9H-carbazole-1-carboxamide (Example 3-2, 33.5 mg, 0.076 mmol) was converted into 4-(3-(3-chloropropylsulfonamido)-2-methylphenyl)-7-(4-methylpiperazine-1-carbonyl)-9H-carbazole-1-carboxamide (Example 10-4, 12.6 mg, 24%), isolated as the TFA salt after HPLC purification and lyophilization. $^1$H NMR (400 MHz, DMSO-$d_6$) δ 11.77 (1H, s), 9.79 (1H, br. s.), 9.41 (1H, s), 8.26 (1H, br. s.), 8.07 (1H, d, J=7.92 Hz), 7.85 (1H, s), 7.53-7.62 (1H, m), 7.47-7.51 (1H, m), 7.41 (1H, t, J=7.70 Hz), 7.21 (1H, dd, J=7.48, 1.10 Hz), 7.03 (1H, d, J=7.70 Hz), 6.97 (1H, dd, J=8.14, 1.32 Hz), 6.83 (1H, d, J=8.14 Hz), 3.80 (2H, t, J=6.49 Hz), 3.36-3.64 (8H, m), 3.30-3.36 (2H, m), 2.82 (3H, br. s.), 2.18-2.29 (2H, m), 2.00 (3H, s). Mass spectrum m/z 582.1 (M+H)$^+$. Also isolated as the TFA salt was 4-(3-(3-chloro-N-(3-chloropropylsulfonyl)propylsulfonamido)-2-methylphenyl)-7-(4-methylpiperazine-1-carbonyl)-9H-carbazole-1-carboxamide as a white powder (Example 10-5, 3.7 mg, 6%). $^1$H NMR (400 MHz, DMSO-$d_6$) δ 11.79 (1H, s), 9.85 (1H, br. s.), 8.28 (1H, br. s.), 8.11 (1H, d, J=7.92 Hz), 7.84 (1H, s), 7.70 (1H, dd, J=7.92, 1.10 Hz), 7.58-7.63 (1H, m), 7.55 (1H, t, J=7.81 Hz), 7.45 (1H, dd, J=7.59, 0.99 Hz), 7.09 (1H, d, J=7.70 Hz), 6.92 (1H, dd, J=8.14, 1.54 Hz), 6.83 (1H, d, J=8.14 Hz), 3.76-4.04 (10 H, m), 2.96-3.66 (5H, m), 2.81 (3H, br. s.), 2.23-2.35 (4H, m), 2.06 (3H, s). Mass spectrum m/z 722.0 (M+H)$^+$.

The following compounds were also prepared using procedures demonstrated in Example 10-1 through 10-5, using the appropriate sulfonyl chloride.

| Example | Compound name | Mass spectrum |
|---|---|---|
| 10-6 | 4-(2-methyl-3-(phenylsulfonamido)phenyl)-7-(4-methylpiperazine-1-carbonyl)-9H-carbazole-1-carboxamide (prepared as the TFA salt) | 581.8 (M + H)$^+$ |
| 10-7 | 4-(3-(4-chlorophenylsulfonamido)-2-methylphenyl)-7-(4-methylpiperazine-1-carbonyl)-9H-carbazole-1-carboxamide (prepared as the TFA salt) | 615.7 (M + H)$^+$ |
| 10-8 | 4-(3-(4-methoxyphenylsulfonamido)-2-methylphenyl)-7-(4-methylpiperazine-1-carbonyl)-9H-carbazole-1-carboxamide (prepared as the TFA salt) | 611.8 (M + H)$^+$ |
| 10-9 | 4-(3-(1,1,3,3,-tetraoxobenzo[d][1,3,2]dithiazol-2-yl)-2-methylphenyl)-7-(4-methylpiperazine-1-carbonyl)-9H-carbazole-1-carboxamide (prepared as the TFA salt) | 644.0 (M + H)$^+$ |

Example 11-1

Preparation of 4-(3-(isoquinolin-1-ylamino)-2-methylphenyl)-7-(4-methylpiperazine-1-carbonyl)-9H-carbazole-1-carboxamide

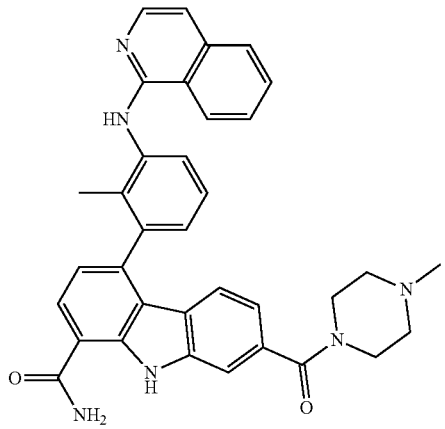 [SMILES: Cc1c(Nc2nccc3ccccc23)cccc1-c1ccc(C(N)=O)c2[nH]c3cc(C(=O)N4CCN(C)CC4)ccc3c12]

A suspension of 4-(3-amino-2-methylphenyl)-7-(4-methylpiperazine-1-carbonyl)-9H-carbazole-1-carboxamide (Example 3-2, 35 mg, 0.079 mmol) and 1-chloroisoquinoline (19.45 mg, 0.119 mmol) in isopropanol (0.5 mL) was treated with 4M hydrogen chloride in 1,4-dioxane (3 drops) and the mixture was heated in a sealed tube by microwave irradiation at 140° C. for 45 min. Additional 4 M hydrogen chloride in 1,4-dioxane (1 drop) was added and the mixture was again heated in a sealed tube by microwave irradiation at 140° C. for 60 min. The mixture was concentrated and the residue was purified by preparative HPLC. The appropriate effluent fractions were concentrated and the residue was partitioned between NaHCO3 (aq) and EtOAc, and the aqueous phase was extracted twice more with EtOAc. The combined organic phases were dried and concentrated to provide 4-(3-(isoquinolin-1-ylamino)-2-methylphenyl)-7-(4-methylpiperazine-1-carbonyl)-9H-carbazole-1-carboxamide as a white solid (16 mg, 32%). $^1$H NMR (400 MHz, methanol-$d_4$) δ 8.28 (1H, d, J=8.3 Hz), 7.91 (1H, d, J=7.8 Hz), 7.72 (1H, d, J=6.1 Hz), 7.66 (1H, d, J=8.3 Hz), 7.56-7.61 (2H, m), 7.48 (1H, ddd, J=8.0, 7.2, 0.8 Hz), 7.44 (1H, d, J=7.5 Hz), 7.34 (1H, t, J=7.8 Hz), 7.22 (1H, d, J=8.0 Hz), 7.14 (1H, d, J=6.7 Hz), 7.06 (1H, d, J=7.8 Hz), 6.97 (1H, d, J=6.1 Hz), 6.94 (1H, dd, J=8.2, 1.5 Hz), 3.71 (2H, br. s.), 3.42 (2H, br. s.), 2.45 (2H, br. s.), 2.32 (2H, br. s.), 2.23 (3H, s), 1.81 (3H, s). Mass spectrum m/z 569.4 (M+H)$^+$.

Example 11-2

Preparation of 4-(2-methyl-3-(phthalazin-1-ylamino)phenyl)-7-(4-methylpiperazine-1-carbonyl)-9H-carbazole-1-carboxamide

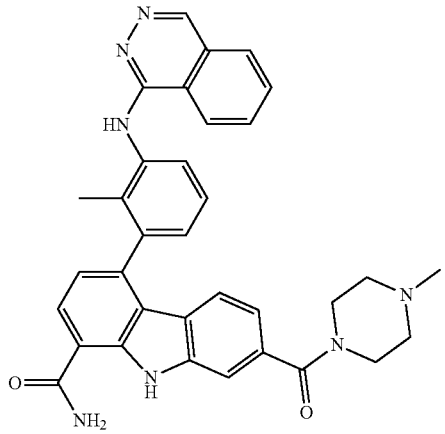 [SMILES: Cc1c(Nc2nncc3ccccc23)cccc1-c1ccc(C(N)=O)c2[nH]c3cc(C(=O)N4CCN(C)CC4)ccc3c12]

Using the procedure of Example 11-1 but only heating at 140° C. for 45 min, 4-(3-amino-2-methylphenyl)-7-(4-methylpiperazine-1-carbonyl)-9H-carbazole-1-carboxamide (Example 3-2, 35 mg, 0.079 mmol) and 1-chlorophthalazine (19.57 mg, 0.119 mmol) were converted to 4-(2-methyl-3-(phthalazin-1-ylamino)phenyl)-7-(4-methylpiperazine-1-carbonyl)-9H-carbazole-1-carboxamide as a light yellow solid (7.3 mg, 15%). $^1$H NMR (400 MHz, methanol-$d_4$) δ 8.88 (1H, br. s.), 8.47 (1H, d, J=7.0 Hz), 8.03 (1H, d, J=7.7 Hz), 7.91-8.01 (3H, m), 7.70 (1H, s), 7.51-7.59 (1H, m), 7.47 (1H, t, J=7.7 Hz), 7.24-7.34 (2H, m), 7.18 (1H, d, J=7.9 Hz), 7.09 (1H, dd, J=8.1, 1.3 Hz), 3.83 (2H, br. s.), 3.54 (2H, br. s.), 2.57 (2H, br. s.), 2.44 (2H, br. s.), 2.35 (3H, s), 1.96 (3H, s). Mass spectrum m/z 570.4 (M+H)$^+$.

Example 11-3

Preparation of 4-(2-methyl-3-(quinazolin-4-ylamino)phenyl)-9H-carbazole-1-carboxamide

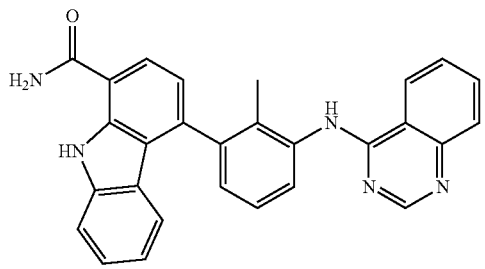 [SMILES: Cc1c(Nc2ncnc3ccccc23)cccc1-c1ccc(C(N)=O)c2[nH]c3ccccc3c12]

Using the procedure of Example 11-1 but heating at 140° C. twice for 30 min and once for 45 min, 4-(3-amino-2-methylphenyl)-9H-carbazole-1-carboxamide (Example 3-13, 26.4 mg, 0.084 mmol) and 4-chloroquinazoline (20.67 mg, 0.126 mmol) were converted to 4-(2-methyl-3-(quinazolin-4-ylamino)phenyl)-9H-carbazole-1-carboxamide as a white solid (8.0 mg, 20%). $^1$H NMR (400 MHz, methanol-$d_4$) δ 8.37 (1H, s), 8.31 (1H, dd, J=8.4, 0.9 Hz), 7.86 (1H, d, J=7.9 Hz), 7.75-7.83 (1H, m), 7.66-7.73 (1H, m), 7.56 (1H, ddd, J=8.3, 7.0, 1.2 Hz), 7.49 (1H, d, J=8.4 Hz), 7.35-7.46 (2H, m), 7.22-7.31 (2H, m), 7.12 (1H, d, J=7.7 Hz), 7.00 (1H, d, J=7.9 Hz), 6.84-6.92 (1H, m), 1.84 (3H, s). Mass spectrum m/z 444.2 (M+H)$^+$.

The following compounds were also prepared using procedures demonstrated in Examples 11-1 through 11-3, starting with Example 3-2 and the appropriate substituted chloroquinazoline (prepared according to the procedures of Steps 1 and 2 of Intermediate 32-1).

| Example | Compound name | Mass spectrum |
|---|---|---|
| 11-4 | 4-(2-methyl-3-(quinazolin-4-ylamino)phenyl)-7-(4-methylpiperazine-1-carbonyl)-9H-carbazole-1-carboxamide | 570.4 (M + H)$^+$ |
| 11-5 | 4-(3-(6-chloroquinazolin-4-ylamino)-2-methylphenyl)-7-(4-methylpiperazine-1-carbonyl)-9H-carbazole-1-carboxamide | 604.4 (M + H)$^+$ |
| 11-6 | 4-(3-(7-chloroquinazolin-4-ylamino)-2-methylphenyl)-7-(4-methylpiperazine-1-carbonyl)-9H-carbazole-1-carboxamide | 604.5 (M + H)$^+$ |
| 11-7 | 4-(3-(7-fluoroquinazolin-4-ylamino)-2-methylphenyl)-7-(4-methylpiperazine-1-carbonyl)-9H-carbazole-1-carboxamide | 588.5 (M + H)$^+$ |
| 11-8 | 4-(3-(6-fluoroquinazolin-4-ylamino)-2-methylphenyl)-7-(4-methylpiperazine-1-carbonyl)-9H-carbazole-1-carboxamide | 588.5 (M + H)$^+$ |
| 11-9 | 4-(2-methyl-3-(7-methylquinazolin-4-ylamino)phenyl)-7-(4-methylpiperazine-1-carbonyl)-9H-carbazole-1-carboxamide | 584.5 (M + H)$^+$ |
| 11-10 | 4-(2-methyl-3-(6-methylquinazolin-4-ylamino)phenyl)-7-(4-methylpiperazine-1-carbonyl)-9H-carbazole-1-carboxamide | 584.5 (M + H)$^+$ |

Example 12-1

Preparation of 4-(3-(1,1-dioxoisothiazolidin-2-yl)-2-methylphenyl)-7-(4-methylpiperazine-1-carbonyl)-9H-carbazole-1-carboxamide

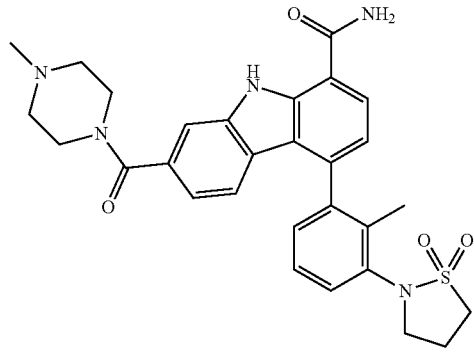 [SMILES: Cc1c(-c2ccc(C(N)=O)c3[nH]c4cc(C(=O)N5CCN(C)CC5)ccc4c23)cccc1N1CCCS1(=O)=O]

A solution of 4-(3-(3-chloropropylsulfonamido)-2-methylphenyl)-7-(4-methylpiperazine-1-carbonyl)-9H-carbazole-1-carboxamide, TFA salt (Example 10-4, 10.7 mg, 0.015 mmol) in THF (0.5 mL) was treated with a solution of lithium hexamethyldisilazide (1 M in THF, 0.092 mL, 0.092 mmol) at rt. After warming to 60° C. and adding DMF (0.2 mL) and stirring for 5 h, the mixture was concentrated and the residue was purified by preparative HPLC to provide 4-(3-(1,1-dioxoisothiazolidin-2-yl)-2-methylphenyl)-7-(4-methylpiperazine-1-carbonyl)-9H-carbazole-1-carboxamide, isolated as the TFA salt (3.5 mg, 34%). $^1$H NMR (400 MHz, DMSO-$d_6$) δ 11.77 (1H, s), 9.85 (1H, br. s.), 8.26 (1H, br. s.), 8.08 (1H, d, J=7.70 Hz), 7.85 (1H, s), 7.61 (1H, dd, J=8.03, 0.99 Hz), 7.48 (1H, t, J=7.70 Hz), 7.30-7.34 (1H, m), 7.06 (1H, d, J=7.70 Hz), 6.97 (1H, dd, J=8.25, 1.43 Hz), 6.86 (1H, d, J=8.14 Hz),

Examples 13-1 and 13-2

Preparation of two diastereomers of 4454(4-fluorophenyl)(hydroxy)methyl)naphthalen-1-yl)-7-(4-methylpiperazine-1-carbonyl)-9H-carbazole-1-carboxamide

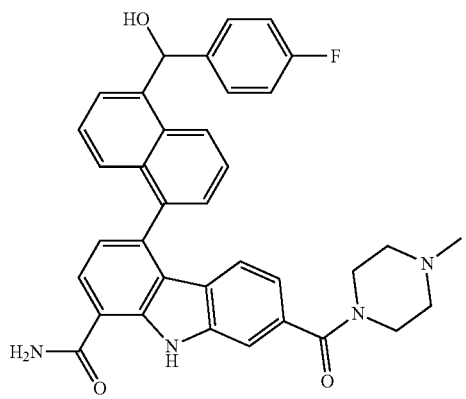 [SMILES: CN1CCN(C(=O)c2ccc3c(c2)[nH]c2c(C(N)=O)ccc(-c4cccc5c(C(O)c6ccc(F)cc6)cccc45)c23)CC1]

A solution of 4-(5-(4-fluorobenzoyl)naphthalen-1-yl)-7-(4-methylpiperazine-1-carbonyl)-9H-carbazole-1-carboxamide (Example 3-96, 30 mg, 0.051 mmol) in ethanol (0.5 mL) was treated with a couple granules of sodium borohydride and stirred at rt. After 90 min, the mixture was treated with 2 drops of 1 M hydrochloric acid and purified by preparative HPLC to provide two diastereomers of 4-(5-((4-fluorophenyl)(hydroxy)methyl)naphthalen-1-yl)-7-(4-methylpiperazine-1-carbonyl)-9H-carbazole-1-carboxamide. Diastereomer 1 (Example 13-1) was isolated as a white powder (10.4 mg, 31%). $^1$H NMR (400 MHz, methanol-$d_4$) δ 8.23 (1H, d, J=8.6 Hz), 7.99 (1H, d, J=7.7 Hz), 7.48-7.61 (3H, m), 7.36-7.46 (3H, m), 7.31 (1H, d, J=8.4 Hz), 7.19 (1H, dd, J=8.4, 7.0 Hz), 7.12 (1H, d, J=7.7 Hz), 7.02 (2H, t, J=8.8 Hz), 6.59 (1H, dd, J=8.1, 1.5 Hz), 6.51 (1H, s), 6.31 (1H, d, J=8.1 Hz), 3.68 (2H, br. s.), 3.35 (2H, br. s.), 2.43 (2H, br. s.), 2.28 (2H, br. s.), 2.23 (3H, s). Mass spectrum m/z 587.4 (M+H)$^+$. Diastereomer 2 (Example 13-2) was isolated as a white powder (8 mg, 23%). $^1$H NMR (400 MHz, methanol-$d_4$) δ 8.19 (1H, d, J=8.6 Hz), 7.99 (1H, d, J=7.9 Hz), 7.61 (1H, d, J=6.8 Hz), 7.59 (1H, s), 7.49-7.56 (1H, m), 7.43 (1H, dd, J=6.8, 0.7 Hz), 7.38 (2H, dd, J=8.5, 5.4 Hz), 7.26-7.32 (1H, m), 7.16-7.24 (1H, m), 7.11 (1H, d, J=7.7 Hz), 7.00 (2H, t, J=8.8 Hz), 6.61 (1H, dd, J=8.1, 1.3 Hz), 6.58 (1H, s), 6.36 (1H, d, J=8.1 Hz), 3.68 (2H, br. s.), 3.35 (2H, br. s.), 2.43 (2H, br. s.), 2.28 (2H, br. s.), 2.22 (3H, s). Mass spectrum m/z 587.4 (M+H)$^+$.

Example 14-1

Preparation of 5-cyclohexyl-$N^2$-(tetrahydro-2H-pyran-4-yl)-2,3,4,9-tetrahydro-1H-carbazole-2,8-dicarboxamide

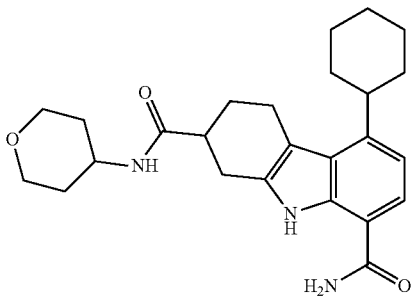 [SMILES: NC(=O)c1ccc(C2CCCCC2)c2c3c([nH]c12)CC(C(=O)NC1CCOCC1)CC3]

A solution of 5-cyclohexenyl-$N^2$-(tetrahydro-2H-pyran-4-yl)-2,3,4,9-tetrahydro-1H-carbazole-2,8-dicarboxamide (Example 3-117, 28 mg, 0.066 mmol) in methanol (10 mL) was combined with 10% palladium on charcoal (80 mg) and shaken under an atmosphere of hydrogen (45 psi) for 1 h. The mixture was filtered, the solid was rinsed with methanol and the filtrates were concentrated to provide 5-cyclohexyl-$N^2$-(tetrahydro-2H-pyran-4-yl)-2,3,4,9-tetrahydro-1H-carbazole-2,8-dicarboxamide as an off-white solid (28 mg, quantitative). $^1$H NMR (400 MHz, methanol-$d_4$) δ 7.46-7.50 (1H, m), 6.91 (1H, d, J=8.05 Hz), 3.89-3.98 (3H, m), 3.46-3.54 (2H, m), 3.13 (1H, dd, J=14.43, 4.16 Hz), 2.95-3.06 (2H, m), 2.87-2.94 (1H, m), 2.65-2.73 (1H, m), 2.15 (1H, dd, J=11.10, 3.05 Hz), 1.77-1.99 (8H, m), 1.47-1.61 (6H, m), 1.26-1.40 (2H, m). Mass spectrum m/z 424.3 (M+H)$^+$.

Example 15-1

Preparation of 7-(4-methylpiperazine-1-carbonyl)-4-(piperidin-1-yl)-9H-carbazole-1-carboxamide

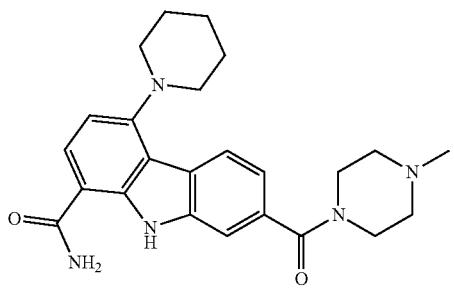 [SMILES: CN1CCN(C(=O)c2ccc3c(c2)[nH]c2c(C(N)=O)ccc(N4CCCCC4)c23)CC1]

A mixture of 4-bromo-7-(4-methylpiperazine-1-carbonyl)-9H-carbazole-1-carboxamide (Example 1-1, 30 mg, 0.072 mmol) and piperidine (1 mL) was heated overnight via microwave irradiation at 170° C. in a sealed tube. The mixture was cooled to rt and purified by preparative HPLC to provide 7-(4-methylpiperazine-1-carbonyl)-4-(piperidin-1-yl)-9H-carbazole-1-carboxamide, TFA salt, as a white solid (22 mg, 56%). $^1$H NMR (400 MHz, DMSO-$d_6$) δ 11.61 (s, 1H) 8.05 (d, J=8.35 Hz, 2 H) 7.95 (d, J=8.13 Hz, 1H) 7.85 (d, J=1.32 Hz, 1H) 7.32 (dd, J=8.13, 1.54 Hz, 2H) 6.82 (d, J=8.35 Hz, 1H) 3.92-4.13 (m, 4H) 3.21-3.57 (m, 6H) 3.14 (d, J=13.40 Hz, 6H) 2.84 (s, 3H) 1.66 (br. s., 2H). Mass spectrum m/z 420.3 (M+H)⁺.

Example 16-1

Preparation of (R)-benzyl 1-(1-carbamoyl-7-(4-methylpiperazine-1-carbonyl)-9H-carbazol-4-yl)piperidin-3-ylcarbamate

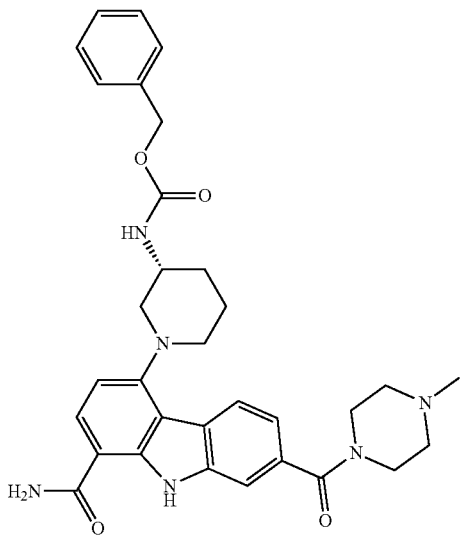 [SMILES: CN1CCN(C(=O)c2ccc3c(c2)[nH]c2c(C(N)=O)ccc(N4CCC[C@@H](NC(=O)OCc5ccccc5)C4)c23)CC1]

Step 1 A suspension of ethyl 5-bromo-8-carbamoyl-9H-carbazole-2-carboxylate (Intermediate 48-1, 2.2 g, 6.09 mmol) in phosphorus oxychloride (45.4 mL, 487 mmol) was heated at 105° C. for 1 h. The suspension was cooled to rt and concentrated to give a brown solid, which was suspended in water. The precipitate was collected by filtration, washed with water and dried to provide ethyl 5-bromo-8-cyano-9H-carbazole-2-carboxylate (2.05 g, 98%) as light brown solid. ¹H NMR (400 MHz, DMSO-d₆) δ 12.78 (s, 1H) 8.71 (d, J=8.57 Hz, 1H) 8.24 (s, 1H) 7.95 (d, J=8.57 Hz, 1H) 7.89 (d, J=8.13 Hz, 1H) 7.61 (d, J=8.13 Hz, 1H) 4.39 (q, J=7.10 Hz, 2H) 1.37 (t, 2H). Mass spectrum m/z 360, 362 (M+NH₄)⁺.

Step 2 A mixture of cesium carbonate (0.960 g, 2.95 mmol), (RS)-2,2'-bis(diphenylphosphino)-1,1'-binaphthalene (0.059 g, 0.095 mmol), tris(dibenzylideneacetone)dipalladium (0.058 g, 0.063 mmol), ethyl 5-bromo-8-cyano-9H-carbazole-2-carboxylate (0.85 g, 2.105 mmol) and (R)-benzyl piperidin-3-ylcarbamate (0.493 g, 2.105 mmol) was suspended in 1,4-dioxane (70 mL). The mixture was purged with nitrogen and heated at 100° C. for 18 h. The mixture was cooled to rt and concentrated. The residue was partitioned between EtOAc and NaHCO3 (aq). The organic phase was washed with brine, dried and concentrated. The residue was purified by column chromatography (eluting with a gradient from 80:20 to 60:40 hexane-EtOAc) to provide (R)-ethyl 5-(3-(benzyloxycarbonylamino)piperidin-1-yl)-8-cyano-9H-carbazole-2-carboxylate as a brown solid (0.68 g, 70% purity, 37% yield), used without further purification. Mass spectrum m/z 497.2 (M+H)⁺.

Step 3 A solution of (R)-ethyl 5-(3-(benzyloxycarbonylamino)piperidin-1-yl)-8-cyano-9H-carbazole-2-carboxylate (0.67 g, 1.349 mmol) and potassium hydroxide (0.379 g, 6.75 mmol) in 10:1 ethanol-water (33 mL) was heated at 85° C. for 2 h. The mixture was cooled to rt and the precipitate was collected by filtration, washed with ethanol and dried to afford (R)-5-(3-(benzyloxycarbonylamino)piperidin-1-yl)-8-cyano-9H-carbazole-2-carboxylic acid as a yellow solid (130 mg, 21%). Mass spectrum m/z 469.1 (M+H)⁺. (R)-5-(3-aminopiperidin-1-yl)-8-cyano-9H-carbazole-2-carboxylic acid was also isolated from filtrates (150 mg, 33%). Mass spectrum m/z 335.2 (M+H)⁺.

Step 4 A solution of (R)-5-(3-(benzyloxycarbonylamino)piperidin-1-yl)-8-cyano-9H-carbazole-2-carboxylic acid (130 mg, 0.277 mmol), EDC (74.5 mg, 0.388 mmol), HOBT (59.5 mg, 0.388 mmol), and 1-methylpiperazine (0.092 mL, 0.832 mmol) in THF-DCM-DMF (4:1:1, 6 mL) was stirred at rt over a weekend. The mixture was concentrated and partitioned between EtOAc and NaHCO3 (aq). The organic phase was washed with brine, dried and concentrated. The residue was purified by column chromatography (eluting with a gradient from 100:0 to 92.5:7.5 DCM-2 M methanolic ammonia) to provide (R)-benzyl 1-(1-cyano-7-(4-methylpiperazine-1-carbonyl)-9H-carbazol-4-yl)piperidin-3-ylcarbamate as a yellow solid (60 mg). ¹H NMR (400 MHz, DMSO-d₆) δ 12.31 (s, 1H) 8.09 (d, J=8.13 Hz, 1H) 7.82 (d, J=8.35 Hz, 1H) 7.64 (s, 1H) 7.49 (d, J=7.69 Hz, 1H) 7.24-7.40 (m, 6 H) 6.93 (d, J=8.35 Hz, 1H) 4.87-5.11 (m, 2H) 3.00-3.96 (m, 12H) 2.83 (s, 3H) 2.55-2.70 (m, 1H) 1.73-2.08 (m, 3H) 1.34-1.57 (m, 1H).). Mass spectrum m/z 551.2 (M+H)⁺.

Step 5 A solution of (R)-benzyl 1-(1-cyano-7-(4-methylpiperazine-1-carbonyl)-9H-carbazol-4-yl)piperidin-3-ylcarbamate (108 mg, 0.196 mmol) in DMSO (2 mL) was treated with 22% aqueous potassium hydroxide (0.208 mL, 0.981 mmol), and then dropwise with a solution of 30% aqueous hydrogen peroxide (0.200 mL, 1.961 mmol). The mixture was stirred at rt for 2.5 h. Water was added, the resulting suspension was stirred at rt for 15 min, and the solid was collected by filtration, washed with water and dried to afford (R)-benzyl 1-(1-carbamoyl-7-(4-methylpiperazine-1-carbonyl)-9H-carbazol-4-yl)piperidin-3-ylcarbamate as an off-white solid (89 mg, 80%). ¹H NMR (400 MHz, methanol-d₄) δ 8.17 (d, J=8.13 Hz, 1H) 7.81 (d, J=8.35 Hz, 1H) 7.66 (s, 1H) 7.30 (d, J=7.91 Hz, 1H) 7.09-7.26 (m, 5 H) 6.82 (d, J=8.35 Hz, 1H) 4.90-5.03 (m, 2H) 3.87-3.99 (m, 1H) 3.57-3.68 (m, 1 H) 3.27-3.54 (m, 5H) 3.06-3.19 (m, 4H) 2.69-2.82 (m, 1H) 2.47-2.65 (m, 1H) 1.98-2.11 (m, 1H) 1.83-1.97 (m, 2H) 1.32-1.53 (m, 1H). Mass spectrum m/z 569.3 (M+H)⁺.

Example 17-1

Preparation of (R)-4-(3-aminopiperidin-1-yl)-7-(4-methylpiperazine-1-carbonyl)-9H-carbazole-1-carboxamide

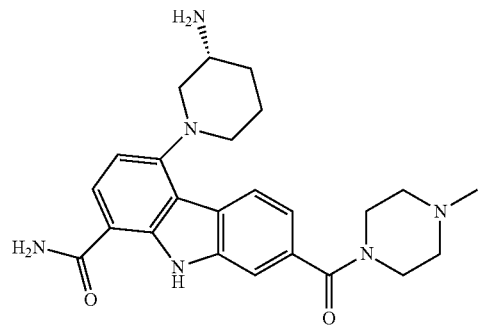 [SMILES: CN1CCN(C(=O)c2ccc3c(c2)[nH]c2c(C(N)=O)ccc(N4CCC[C@@H](N)C4)c23)CC1]

A mixture of (R)-benzyl 1-(1-carbamoyl-7-(4-methylpiperazine-1-carbonyl)-9H-carbazol-4-yl)piperidin-3-ylcarbamate (Example 16-1, 80 mg, 0.141 mmol), 10% palladium on carbon (14.97 mg, 0.014 mmol) and ammonium formate (53.2 mg, 0.844 mmol) in methanol (8 mL) was flushed with nitrogen and heated at 75° C. for 1 h. The mixture was cooled to rt, diluted with methanol and filtered through a Celite pad. The filtrate was concentrated to provide (R)-4-(3-aminopiperidin-1-yl)-7-(4-methylpiperazine-1-carbonyl)-9H-carbazole-1-carboxamide as a white solid (75 mg, 98%). $^1$H NMR (400 MHz, methanol-$d_4$) δ 8.13 (d, J=8.13 Hz, 1H) 7.86 (d, J=8.35 Hz, 1H) 7.68 (s, 1H) 7.29 (d, J=9.67 Hz, 1H) 6.86 (d, J=8.35 Hz, 1H) 3.54-3.72 (m, 2H) 3.24-3.53 (m, 5H) 2.88 (s, 3H) 2.11-2.29 (m, 1H) 1.92-2.11 (m, 2H) 1.44-1.73 (m, 1H). Mass spectrum m/z 435.2 (M+H)$^+$.

Example 18-1

Preparation of (R)-4-(3-acetamidopiperidin-1-yl)-7-(4-methylpiperazine-1-carbonyl)-9H-carbazole-1-carboxamide

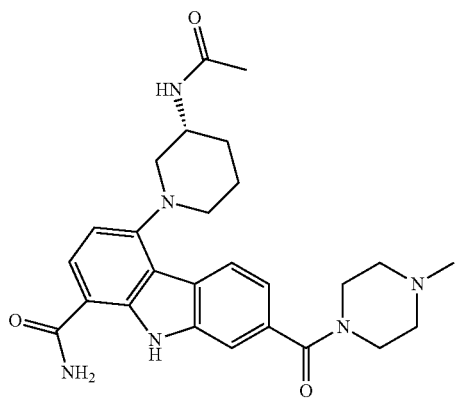 [SMILES: CC(=O)N[C@@H]1CCCN(c2ccc(C(N)=O)c3[nH]c4cc(C(=O)N5CCN(C)CC5)ccc4c23)C1]

A solution of (R)-4-(3-aminopiperidin-1-yl)-7-(4-methylpiperazine-1-carbonyl)-9H-carbazole-1-carboxamide (Example 17-1, 25 mg, 0.058 mmol) and TEA (0.016 mL, 0.115 mmol) in DCM-THF (2:1, 3 mL) was treated with acetyl chloride (4.9 mL, 0.069 mmol). The mixture was stirred at rt for 1.5 h, then was then concentrated and the residue was purified by preparative HPLC. The product, isolated as the TFA salt, was partitioned between DCM and NaHCO3 (aq). The organic phase was washed with brine, dried and concentrated to provide (R)-4-(3-acetamidopiperidin-1-yl)-7-(4-methylpiperazine-1-carbonyl)-9H-carbazole-1-carboxamide as a white solid (12 mg, 39%). $^1$H NMR (500 MHz, ethanol-$d_6$) δ 8.24 (d, J=7.97 Hz, 1H) 7.89 (d, J=8.52 Hz, 1H) 7.69 (s, 1H) 7.32 (d, J=9.35 Hz, 1H) 6.90 (d, J=8.52 Hz, 1H) 4.21-4.32 (m, 1H) 3.73-3.93 (m, 2H) 3.42-3.72 (m, 5H) 2.96-3.11 (m, 1H) 2.39-2.63 (m, 4H) 2.35 (s, 3H) 2.06-2.15 (m, 1H) 1.97-2.06 (m, 2H) 1.95 (s, 3H) 1.48-1.59 (m, 1H). Mass spectrum m/z 477.3 (M+H)$^+$.

The following compound was also prepared using the procedure demonstrated in Example 18-1, substituting benzoyl chloride for acetyl chloride.

| Example | Compound name | Mass spectrum |
|---|---|---|
| 18-2 | (R)-4-(3-benzamidopiperidin-1-yl)-7-(4-methylpiperazine-1-carbonyl)-9H-carbazole-1-carboxamide | 539.3 (M + H)$^+$ |

Example 19-1

Preparation of (R)-7-(4-methylpiperazine-1-carbonyl)-4-(3-(3-thiazol-2-ylureido)piperidin-1-yl)-9H-carbazole-1-carboxamide

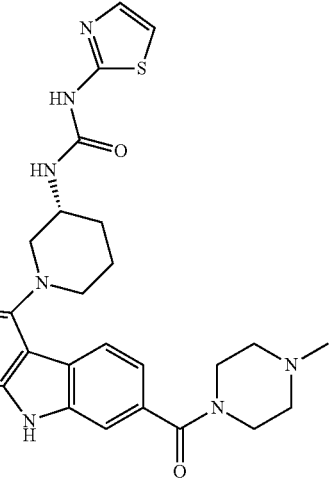

A solution of (R)-4-(3-aminopiperidin-1-yl)-7-(4-methylpiperazine-1-carbonyl)-9H-carbazole-1-carboxamide (Example 17-1, 23 mg, 0.053 mmol) and TEA (0.015 mL, 0.106 mmol) in THF (3 mL) was treated with phenyl thiazol-2-ylcarbamate (17.49 mg, 0.079 mmol). The mixture was stirred at 60° C. for 1.5 h, then at 70° C. for 2 h, then was concentrated and purified by preparative HPLC. The isolated TFA salt was partitioned between DCM and NaHCO3 (aq), and the organic phase was dried and concentrated to provide (R)-7-(4-methylpiperazine-1-carbonyl)-4-(3-(3-thiazol-2-ylureido)piperidin-1-yl)-9H-carbazole-1-carboxamide as a white solid (14 mg, 43%). $^1$H NMR (400 MHz, methanol-$d_4$) δ 8.27 (1H, d, J=7.9 Hz), 7.87 (1H, d, J=8.3 Hz), 7.68 (1H, d, J=1.1 Hz), 7.28 (1H, d, J=7.9 Hz), 7.18 (1H, br. s.), 6.93 (1H, d, J=3.7 Hz), 6.87 (1H, d, J=8.3 Hz), 4.25 (1H, br.), 3.82 (2H, br.), 3.41-3.68 (3H, m), 3.19 (3H, br.), 2.36-2.63 (4H, m), 2.33 (3H, s), 1.84-2.20 (3H, m), 1.71 (1H, br. s.). Mass spectrum m/z 561.3 (M+H)$^+$.

Example 20-1

Preparation of 7-(4-methylpiperazine-1-carbonyl)-4-(2-oxopiperidin-1-yl)-9H-carbazole-1-carboxamide

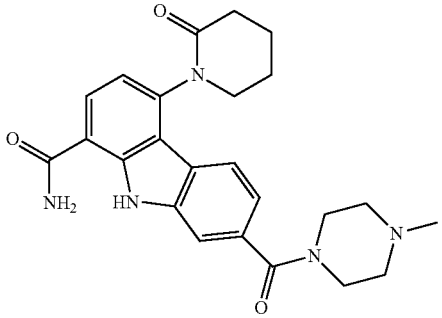 [SMILES: CN1CCN(C(=O)c2ccc3c(c2)[nH]c2c(C(N)=O)ccc(N4CCCCC4=O)c23)CC1]

Step 1 A mixture of 4-bromo-7-(4-methylpiperazine-1-carbonyl)-9H-carbazole-1-carboxamide (Example 1-1, 118.1 mg, 0.284 mmol), sodium azide (37.0 mg, 0.569 mmol), copper (I) iodide (36.4 mg, 0.191 mmol), (RS)-proline (24.6 mg, 0.214 mmol), 1 M aqueous sodium hydroxide (0.191 mL, 0.191 mmol), ethanol (1.5 mL) and water (0.191 mL) was purged with argon and heated at 95° C. in a sealed tube. After 17.5 h, the mixture was cooled to rt, filtered through a pad of silica gel, and the solids were rinsed with methanol. The filtrate was concentrated and treated with 1 M hydrochloric acid, and the resulting precipitate was collected by filtration and dried to provide impure 4-azido-7-(4-methylpiperazine-1-carbonyl)-9H-carbazole-1-carboxamide, hydrochloric acid salt, as a light brown solid (31.8 mg, 27%). The filtrate was purified by preparative HPLC to provide 4-azido-7-(4-methylpiperazine-1-carbonyl)-9H-carbazole-1-carboxamide, TFA salt, as a brown solid (20.7 mg, 15%). $^1$H NMR (400 MHz, methanol-$d_4$) δ 8.37 (1H, d, J=8.14 Hz), 7.97 (1H, d, J=8.14 Hz), 7.73 (1H, s), 7.33 (1H, dd, J=8.14, 1.32 Hz), 7.06 (1H, d, J=8.36 Hz), 3.34-3.72 (6H, m), 3.26 (2H, br. s.), 2.96 (3H, s). Mass spectrum m/z 378.2 (M+H)$^+$.

Step 2 A suspension of impure 4-azido-7-(4-methylpiperazine-1-carbonyl)-9H-carbazole-1-carboxamide, hydrochloric acid salt (31.8 mg, 0.060 mmol), ammonium chloride (25 mg, 0.467 mmol) and powdered zinc (60 mg, 0.918 mmol) in methanol (1 mL) and THF (1 mL) was stirred at rt. After 1 h, the mixture was purified by column chromatography (eluting with a gradient from DCM to 80:20 DCM-methanol) to provide 4-amino-7-(4-methylpiperazine-1-carbonyl)-9H-carbazole-1-carboxamide as a light yellow solid (11.8 mg, 56%). Mass spectrum m/z 352.3 (M+H)$^+$.

Step 3 A solution of 4-amino-7-(4-methylpiperazine-1-carbonyl)-9H-carbazole-1-carboxamide (11.8 mg, 0.034 mmol) and TEA (0.047 mL, 0.336 mmol) in DCM (0.5 mL) and DMF (0.25 mL) was treated with 5-chloropentanoyl chloride (0.017 mL, 0.134 mmol) and stirred at rt. Additional 5-chloropentanoyl chloride (0.017 mL, 0.134 mmol) was added after 3 h and the mixture was stirred at rt overnight. The mixture was concentrated and partitioned between EtOAc and saturated aqueous ammonium chloride. The aqueous phase was purified by preparative HPLC to provide 4-(5-chloropentanamido)-7-(4-methylpiperazine-1-carbonyl)-9H-carbazole-1-carboxamide, TFA salt, as a light yellow solid (6.6 mg, 34%). $^1$H NMR (400 MHz, methanol-$d_4$) δ 8.15 (1H, d, J=8.14 Hz), 7.96 (1H, d, J=8.14 Hz), 7.77 (1H, d, J=0.88 Hz), 7.27-7.38 (2H, m), 3.68 (2H, br. s.), 3.33-3.63 (4H, m), 3.12-3.29 (2H, m), 2.97 (3H, s), 2.68 (2H, br. s.), 1.98 (4H, br. s.). Mass spectrum m/z 470.4 (M+H)$^+$.

Step 4 A solution of 4-(5-chloropentanamido)-7-(4-methylpiperazine-1-carbonyl)-9H-carbazole-1-carboxamide, TFA salt (6.6 mg, 0.011 mmol) in DMF (0.5 mL) was treated with sodium hydride (60% oil dispersion, 12.7 mg, 0.318 mmol) and the mixture was stirred at rt for 35 min. The mixture was concentrated, taken up in saturated aqueous ammonium chloride and purified by preparative HPLC to provide 7-(4-methylpiperazine-1-carbonyl)-4-(2-oxopiperidin-1-yl)-9H-carbazole-1-carboxamide, isolated as the TFA salt, as a white powder after lyophilization (4.3 mg, 69%). $^1$H NMR (400 MHz, methanol-$d_4$) δ 8.03 (1H, d, J=7.92 Hz), 7.96 (1H, d, J=8.14 Hz), 7.79 (1H, d, J=0.88 Hz), 7.36 (1H, dd, J=8.03, 1.43 Hz), 7.17 (1H, d, J=7.92 Hz), 3.84-3.93 (1H, m), 3.73-3.82 (1H, m), 3.34-3.64 (4H, m), 3.13-3.27 (2H, m), 2.97 (3H, s), 2.60-2.82 (2H, m), 2.08-2.25 (4H, m). Mass spectrum m/z 434.4 (M+H)$^+$.

Example 21-1

Preparation of 4-(5-methyl-4-(phenylcarbamoyl)-1H-1,2,3-triazol-1-yl)-7-(4-methylpiperazine-1-carbonyl)-9H-carbazole-1-carboxamide

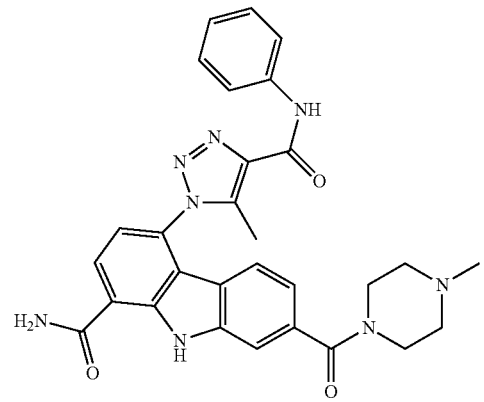 [SMILES: Cc1c(C(=O)Nc2ccccc2)nnn1-c1ccc(C(N)=O)c2[nH]c3cc(C(=O)N4CCN(C)CC4)ccc3c12]

A solution of 4-azido-7-(4-methylpiperazine-1-carbonyl)-9H-carbazole-1-carboxamide (free base, prepared from the material prepared according to Step 1 of Example 20-1, 24.1 mg, 0.036 mmol) and 3-oxo-N-phenylbutanamide (17.5 mg, 0.099 mmol) in ethanol (0.5 mL) and THF (0.5 mL) was added at 0° C. to a solution of sodium ethoxide prepared from sodium (6.7 mg, 0.291 mmol) and ethanol (0.5 mL). After 2 h, the mixture was warmed to rt and stirred overnight. The mixture was concentrated and the residue was purified by preparative HPLC to provide 4-(5-methyl-4-(phenylcarbamoyl)-1H-1,2,3-triazol-1-yl)-7-(4-methylpiperazine-1-carbonyl)-9H-carbazole-1-carboxamide, TFA salt, as a light yellow powder after lyophilization (2.6 mg, 10%). $^1$H NMR (400 MHz, methanol-$d_4$) δ 8.19 (1H, d, J=7.92 Hz), 7.85 (1H, s), 7.77-7.82 (2H, m), 7.41 (3H, t, J=7.70 Hz), 7.17-7.23 (2H, m), 6.75 (1H, d, J=8.14 Hz), 3.34-3.64 (4H, m), 3.09-3.27 (2H, m), 2.95 (3H, s), 2.48 (3H, s). Mass spectrum m/z 537.3 (M+H)$^+$.

Example 22-1

Preparation of 7-(4-methylpiperazine-1-carbonyl)-4-(4-phenyl-1H-1,2,3-triazol-1-yl)-9H-carbazole-1-carboxamide

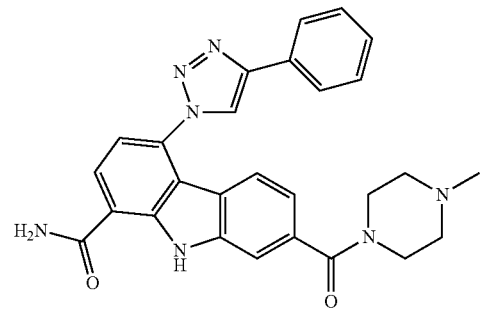 [SMILES: CN1CCN(C(=O)c2ccc3c(c2)[nH]c2c(C(N)=O)ccc(-n4cc(-c5ccccc5)nn4)c23)CC1]

A solution of 4-azido-7-(4-methylpiperazine-1-carbonyl)-9H-carbazole-1-carboxamide (free base, prepared from the material prepared according to Step 1 of Example 20-1, 10 mg, 0.026 mmol), ethynylbenzene (3.2 μL, 0.029 mmol), copper (II) sulfate (0.42 mg, 0.003 mmol) and sodium L-ascorbate (1.1 mg, 0.005 mmol) in THF (0.5 mL) and water (0.1 mL) was stirred at 45° C. overnight. The reaction was not complete, so the mixture was stirred at 45° C. for 4.5 h, then at 95° C. overnight. The mixture was concentrated, and the residue was dissolved in a mixture of methanol and 1 M hydrochloric acid (2:1), filtered and purified by preparative HPLC and lyophilization to provide 7-(4-methylpiperazine-1-carbonyl)-4-(4-phenyl-1H-1,2,3-triazol-1-yl)-9H-carbazole-1-carboxamide, TFA salt, as a white powder (5.2 mg, 33%). $^1$H NMR (400 MHz, methanol-d$_4$) δ 8.90 (1 H, s), 8.16 (1 H, d, J=7.92 Hz), 8.00-8.04 (2 H, m), 7.84 (1 H, s), 7.50-7.55 (2 H, m), 7.48 (1 H, d, J=7.92 Hz), 7.40-7.46 (1 H, m), 7.36 (1 H, d, J=8.80 Hz), 7.20 (1 H, dd, J=8.25, 1.43 Hz), 3.33-3.68 (4 H, m), 3.10-3.28 (2 H, m), 2.95 (3 H, s). Mass spectrum m/z 480.3 (M+H)$^+$.

Example 23-1

Preparation of 8-carbamoyl-5-(3-(4-fluorobenzamido)-2-methylphenyl)-9H-carbazole-2-carboxylic acid

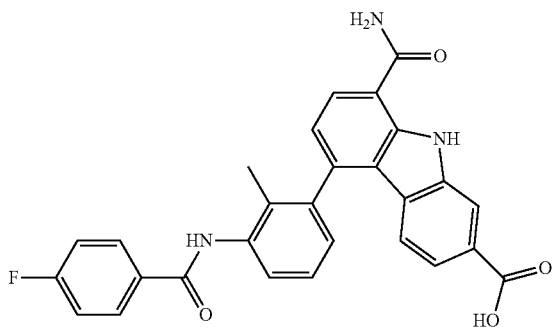 [SMILES: Cc1c(NC(=O)c2ccc(F)cc2)cccc1-c1ccc(C(N)=O)c2[nH]c3cc(C(=O)O)ccc3c12]

A suspension of ethyl 8-carbamoyl-5-(3-(4-fluorobenzamido)-2-methylphenyl)-9H-carbazole-2-carboxylate (Intermediate 3-100, 1.63 g, 3.20 mmol) in ethanol (12 mL) was treated with 1 M aqueous sodium hydroxide (1.5 mL, 1.500 mmol), forming a yellow suspension which was heated at 90-95° C. for 30 min. The mixture was cooled to rt and acidified with 1 M hydrochloric acid. The precipitate was collected by filtration, washed with water and dried to provide 8-carbamoyl-5-(3-(4-fluorobenzamido)-2-methylphenyl)-9H-carbazole-2-carboxylic acid as an off-white solid (1.496 g, 92%). $^1$H NMR (400 MHz, DMSO-d$_6$) δ 12.76 (br. s., 1 H) 11.84 (s, 1 H) 10.15 (s, 1 H) 8.38 (s, 1 H) 8.24 (br. s., 1 H) 8.03-8.13 (m, 3 H) 7.56 (br. s., 1 H) 7.46-7.54 (m, 2 H) 7.42 (t, J=7.7 Hz, 1 H) 7.35 (t, J=9.0 Hz, 2 H) 7.23 (dd, J=7.5, 1.3 Hz, 1 H) 7.04 (d, J=7.5 Hz, 1 H) 7.01 (d, J=8.3 Hz, 1 H) 1.88 (s, 3 H). Mass spectrum m/z 482.1 (M+H)$^+$.

Example 23-2

Preparation of 8-carbamoyl-5-(2-fluorophenyl)-9H-carbazole-2-carboxylic acid

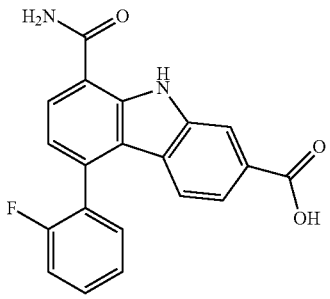 [SMILES: NC(=O)c1ccc(-c2ccccc2F)c2c1[nH]c1cc(C(=O)O)ccc12]

A suspension of ethyl 8-carbamoyl-5-(2-fluorophenyl)-9H-carbazole-2-carboxylate (Example 3-12, 0.8 g, 2.126 mmol) and lithium hydroxide monohydrate (0.255 g, 6.38 mmol) in THF-ethanol-water (3:1:1) (25.0 mL) was heated at reflux for 4 h. The mixture was concentrated and the residue was suspended in water. The pH was adjusted to 1-2 by addition of 1 M hydrochloric acid. The precipitate was collected by filtration, washed with water and dried to provide 8-carbamoyl-5-(2-fluorophenyl)-9H-carbazole-2-carboxylic acid as a yellow solid (520 mg, 71%). $^1$H NMR (400 MHz, DMSO-d$_6$) δ 12.77 (br. s., 1 H) 11.87 (s, 1 H) 8.41 (m, 1 H) 8.26 (br. s., 1 H) 8.08 (d, J=7.69 Hz, 1 H) 7.50-7.67 (m, 4 H) 7.40-7.49 (m, 2 H) 7.09-7.17 (m, 2 H). Mass spectrum m/z 349.1 (M+H)$^+$.

The following compound was also prepared using procedures demonstrated in Example 23-1, using

| Intermediate | Starting material | Compound name | Mass spectrum |
|---|---|---|---|
| Intermediate 23-3 | Example 3-11 | 8-carbamoyl-5-(2,6-difluorophenyl)-2,3,4,9-tetrahydro-1H-carbazole-2-carboxylic acid | 371.1 (M + H)$^+$ |

Example 24-1

Preparation of 4-(3-(4-fluorobenzamido)-2-methylphenyl)-9H-carbazole-1,7-dicarboxamide

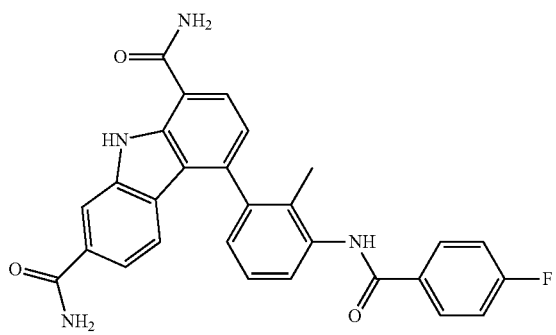 [SMILES: Cc1c(NC(=O)c2ccc(F)cc2)cccc1-c1ccc(C(N)=O)c2[nH]c3cc(C(N)=O)ccc3c12]

A mixture of 8-carbamoyl-5-(3-(4-fluorobenzamido)-2-methylphenyl)-9H-carbazole-2-carboxylic acid (Example 23-1, 30 mg, 0.062 mmol) and HOAT (12.72 mg, 0.093 mmol) in THF (0.4 mL) was treated with 28% aqueous ammonium hydroxide (0.052 mL, 0.374 mmol) and EDC (23.89 mg, 0.125 mmol) and the mixture was stirred at rt. After 22.5 h, the mixture was concentrated and purified by preparative HPLC. The appropriate effluent fractions were concentrated and the residue was treated with NaHCO3 (aq) and extracted three times with EtOAc. The combined organic phases were dried and concentrated to provide 4-(3-(4-fluorobenzamido)-2-methylphenyl)-9H-carbazole-1,7-dicarboxamide as an off-white solid (9.6 mg, 29%). $^1$H NMR (400 MHz, methanol-d$_4$) δ 8.11 (d, J=1.3 Hz, 1 H) 8.03-8.08 (m, 2 H) 8.01 (d, J=7.9 Hz, 1 H) 7.51-7.55 (m, 1 H) 7.41-7.48 (m, 2 H) 7.29 (dd, J=7.5, 1.3 Hz, 1 H) 7.24 (t, J=8.8 Hz, 2 H) 7.08-7.12 (m, 2 H) 1.98 (s, 3 H). Mass spectrum m/z 481.1 (M+H)⁺.

Example 24-2

Preparation of 4-(2-fluorophenyl)-N⁷-(1-methylpiperidin-4-yl)-9H-carbazole-1,7-dicarboxamide

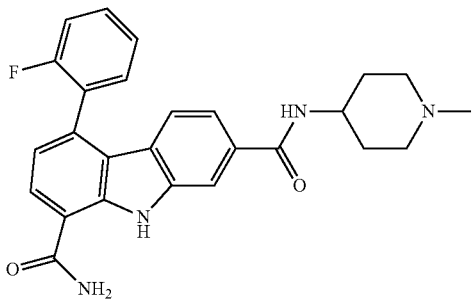 [SMILES: CN1CCC(NC(=O)c2ccc3c(c2)[nH]c2c(C(N)=O)ccc(-c4ccccc4F)c23)CC1]

A mixture of 8-carbamoyl-5-(2-fluorophenyl)-9H-carbazole-2-carboxylic acid (Example 23-2, 30 mg, 0.086 mmol), EDC (23.11 mg, 0.121 mmol), HOBT (18.46 mg, 0.121 mmol), DIEA (30 µL, 0.172 mmol), and 1-methylpiperidin-4-amine (9.83 mg, 0.086 mmol) in THF and DMF (4:1, 2 mL) was stirred at rt overnight. The mixture was concentrated and purified by preparative HPLC. The isolated product was partitioned between DCM and NaHCO3 (aq). The organic phase was dried and concentrated to provide 4-(2-fluorophenyl)-N⁷-(1-methylpiperidin-4-yl)-9H-carbazole-1,7-dicarboxamide as a white solid (25 mg, 62%). ¹H NMR (400 MHz, DMSO-d₆) δ 11.75 (s, 1 H) 8.24 (br. s., 1 H) 8.20 (s, 1 H) 8.13 (d, J=7.69 Hz, 1 H) 8.05 (d, J=7.91 Hz, 1 H) 7.52-7.68 (m, 3 H) 7.33-7.48 (m, 3 H) 7.13 (d, J=7.69 Hz, 1 H) 7.05 (d, J=8.35 Hz, 1 H) 3.64-3.80 (m, 1 H) 2.69-2.79 (m, 2 H) 1.87-2.00 (m, 2 H) 1.70-1.80 (m, 2 H) 1.48-1.65 (m, 2 H). Mass spectrum m/z 445.2 (M+H)⁺.

Example 24-3

Preparation of 5-(2,6-difluorophenyl)-N²-(2-(dimethylamino)ethyl)-2,3,4,9-tetrahydro-1H-carbazole-2,8-dicarboxamide

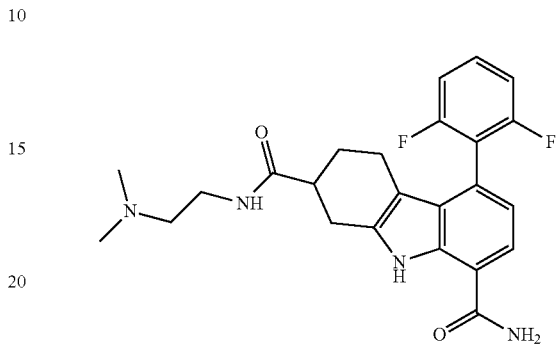

Using the procedure of Example 24-2, 8-carbamoyl-5-(2,6-difluorophenyl)-2,3,4,9-tetrahydro-1H-carbazole-2-carboxylic acid (Intermediate 23-3, 20 mg, 0.054 mmol) and N¹,N¹-dimethylethane-1,2-diamine (7.1 mg, 0.081 mmol) were converted to 5-(2,6-difluorophenyl)-N²-(2-(dimethylamino)ethyl)-2,3,4,9-tetrahydro-1H-carbazole-2,8-dicarboxamide (25 mg, 62%). ¹H NMR (400 MHz, chloroform-d) δ 10.08 (1 H, br. s.), 7.35-7.39 (2 H, m), 6.99 (3 H, d, J=8.35 Hz), 6.20 (2 H, br. s.), 3.28-3.43 (3 H, m), 2.84-3.13 (2 H, m), 2.54-2.62 (1 H, m), 2.27-2.45 (3 H, m), 2.18 (6 H, s), 1.91-2.03 (1 H, m), 1.74-1.86 (1 H, m). Mass spectrum m/z 441.1 (M+H)⁺.

The following compounds were also prepared using procedures demonstrated in Examples 24-1 through 24-3, starting with the appropriate carboxylic acid (prepared according to Examples 23-1 through 23-3) and the appropriate amine.

| Example | Starting material | Compound name | Mass spectrum |
|---|---|---|---|
| 24-4 | Example 23-2 | N⁷-(2-(dimethylamino)ethyl)-4-(2-fluorophenyl)-N⁷-methyl-9H-carbazole-1,7-dicarboxamide | 432.9 (M + H)⁺ |
| 24-5 | Example 23-2 | 4-(2-fluorophenyl)-7-(4-(2-methoxyethyl)piperazine-1-carbonyl)-9H-carbazole-1-carboxamide | 475.2 (M + H)⁺ |
| 24-6 | Example 23-2 | 4-(2-fluorophenyl)-7-(4-(3-methoxypropyl)piperazine-1-carbonyl)-9H-carbazole-1-carboxamide | 489.3 (M + H)⁺ |
| 24-7 | Example 23-2 | 7-(4-(dimethylamino)piperidine-1-carbonyl)-4-(2-fluorophenyl)-9H-carbazole-1-carboxamide | 459.2 (M + H)⁺ |
| 24-8 | Example 23-2 | 4-(2-fluorophenyl)-N⁷-methyl-N⁷-(2-(methylsulfonyl)ethyl)-9H-carbazole-1,7-dicarboxamide | 468.1 (M + H)⁺ |
| 24-9 | Example 23-2 | 7-((S)-3-(dimethylamino)pyrrolidine-1-carbonyl)-4-(2-fluorophenyl)-9H-carbazole-1-carboxamide | 445.5 (M + H)⁺ |
| 24-10 | Example 23-2 | 7-((R)-3-(dimethylamino)pyrrolidine-1-carbonyl)-4-(2-fluorophenyl)-9H-carbazole-1-carboxamide | 445.5 (M + H)⁺ |
| 24-11 | Intermediate 23-3 | 5-(2,6-difluorophenyl)-N²-(4-(dimethylamino)butyl)-2,3,4,9-tetrahydro-1H-carbazole-2,8-dicarboxamide | 469.2 (M + H)⁺ |
| 24-12 | Intermediate 23-3 | 5-(2,6-difluorophenyl)-2-(4-methylpiperazine-1-carbonyl)-2,3,4,9-tetrahydro-1H-carbazole-8-carboxamide | 453.2 (M + H)⁺ |

-continued

| Example | Starting material | Compound name | Mass spectrum |
|---|---|---|---|
| 24-13 | Intermediate 23-3 | 5-(2,6-difluorophenyl)-$N^2$-(3-(dimethylamino)propyl)-2,3,4,9-tetrahydro-1H-carbazole-2,8-dicarboxamide | 455.1 $(M+H)^+$ |
| 24-14 | Intermediate 23-3 | 5-(2,6-difluorophenyl)-$N^2$-(1-methylpiperidin-4-yl)-2,3,4,9-tetrahydro-1H-carbazole-2,8-dicarboxamide | 467.2 $(M+H)^+$ |
| 24-15 | Intermediate 23-3 | 5-(2,6-difluorophenyl)-$N^2$-(tetrahydro-2H-pyran-4-yl)-2,3,4,9-tetrahydro-1H-carbazole-2,8-dicarboxamide | 454.2 $(M+H)^+$ |
| 24-16 | Example 23-1 | 4-(3-(4-fluorobenzamido)-2-methylphenyl)-$N^7$-(2-(1-(RS)-methylpyrrolidin-2-yl)ethyl)-9H-carbazole-1,7-dicarboxamide (prepared as the TFA salt) | 592.0 $(M+H)^+$ |
| 24-17 | Example 23-1 | 4-(3-(4-fluorobenzamido)-2-methylphenyl)-7-(4-(2-hydroxyethyl)piperazine-1-carbonyl)-9H-carbazole-1-carboxamide (prepared as the TFA salt) | 594.0 $(M+H)^+$ |
| 24-18 | Example 23-1 | 4-(3-(4-fluorobenzamido)-2-methylphenyl)-$N^7$-(2-morpholinoethyl)-9H-carbazole-1,7-dicarboxamide (prepared as the TFA salt) | 594.0 $(M+H)^+$ |
| 24-19 | Example 23-1 | 4-(3-(4-fluorobenzamido)-2-methylphenyl)-$N^7$-(pyridin-3-ylmethyl)-9H-carbazole-1,7-dicarboxamide (prepared as the TFA salt) | 572.0 $(M+H)^+$ |
| 24-20 | Example 23-1 | 4-(3-(4-fluorobenzamido)-2-methylphenyl)-$N^7$-(pyridin-4-ylmethyl)-9H-carbazole-1,7-dicarboxamide (prepared as the TFA salt) | 572.0 $(M+H)^+$ |
| 24-21 | Example 23-1 | $N^7$-(3-(1H-imidazol-1-yl)propyl)-4-(3-(4-fluorobenzamido)-2-methylphenyl)-9H-carbazole-1,7-dicarboxamide (prepared as the TFA salt) | 589.0 $(M+H)^+$ |
| 24-22 | Example 23-1 | 7-(4-(dimethylamino)piperidine-1-carbonyl)-4-(3-(4-fluorobenzamido)-2-methylphenyl)-9H-carbazole-1-carboxamide (prepared as the TFA salt) | 592.0 $(M+H)^+$ |
| 24-23 | Example 23-1 | 4-(3-(4-fluorobenzamido)-2-methylphenyl)-$N^7$-methyl-$N^7$-(pyridin-3-ylmethyl)-9H-carbazole-1,7-dicarboxamide (prepared as the TFA salt) | 586.1 $(M+H)^+$ |
| 24-24 | Example 23-1 | 4-(3-(4-fluorobenzamido)-2-methylphenyl)-$N^7$-methyl-$N^7$-(1-(RS)-methylpyrrolidin-3-yl)-9H-carbazole-1,7-dicarboxamide (prepared as the TFA salt) | 578.0 $(M+H)^+$ |
| 24-25 | Example 23-1 | 4-(3-(4-fluorobenzamido)-2-methylphenyl)-$N^7$-(2-phenylpropan-2-yl)-9H-carbazole-1,7-dicarboxamide (prepared as the TFA salt) | 599.0 $(M+H)^+$ |
| 24-26 | Example 23-1 | 4-(3-(4-fluorobenzamido)-2-methylphenyl)-$N^7$-(pyridin-3-yl)-9H-carbazole-1,7-dicarboxamide (prepared as the TFA salt) | 557.9 $(M+H)^+$ |
| 24-27 | Example 23-1 | $N^7$-(3-(dimethylamino)phenyl)-4-(3-(4-fluorobenzamido)-2-methylphenyl)-9H-carbazole-1,7-dicarboxamide (prepared as the TFA salt) | 600.0 $(M+H)^+$ |
| 24-28 | Example 23-1 | $N^7$-(2-amino-2-oxoethyl)-4-(3-(4-fluorobenzamido)-2-methylphenyl)-9H-carbazole-1,7-dicarboxamide (prepared as the TFA salt) | 537.9 $(M+H)^+$ |
| 24-29 | Example 23-1 | 4-(3-(4-fluorobenzamido)-2-methylphenyl)-7-(4-(hydroxymethyl)piperidine-1-carbonyl)-9H-carbazole-1-carboxamide (prepared as the TFA salt) | 580.0 $(M+H)^+$ |
| 24-30 | Example 23-1 | 4-(3-(4-fluorobenzamido)-2-methylphenyl)-$N^7$-(3-hydroxybenzyl)-9H-carbazole-1,7-dicarboxamide (prepared as the TFA salt) | 586.9 $(M+H)^+$ |
| 24-31 | Example 23-1 | 4-(3-(4-fluorobenzamido)-2-methylphenyl)-7-(3-oxopiperazine-1-carbonyl)-9H-carbazole-1-carboxamide (prepared as the TFA salt) | 563.9 $(M+H)^+$ |
| 24-32 | Example 23-1 | 4-(3-(4-fluorobenzamido)-2-methylphenyl)-$N^7$-(thiazol-2-yl)-9H-carbazole-1,7-dicarboxamide (prepared as the TFA salt) | 563.9 $(M+H)^+$ |
| 24-33 | Example 23-1 | 4-(3-(4-fluorobenzamido)-2-methylphenyl)-$N^7$-(3-methoxyphenyl)-9H-carbazole-1,7-dicarboxamide (prepared as the TFA salt) | 586.9 $(M+H)^+$ |
| 24-34 | Example 23-1 | 4-(3-(4-fluorobenzamido)-2-methylphenyl)-$N^7$-(4-fluorophenyl)-9H-carbazole-1,7-dicarboxamide (prepared as the TFA salt) | 575.0 $(M+H)^+$ |

-continued

| Example | Starting material | Compound name | Mass spectrum |
|---|---|---|---|
| 24-35 | Example 23-1 | $N^7$-tert-butyl-4-(3-(4-fluorobenzamido)-2-methylphenyl)-9H-carbazole-1,7-dicarboxamide (prepared as the TFA salt) | 537.0 $(M + H)^+$ |
| 24-36 | Example 23-1 | $N^7$-benzyl-4-(3-(4-fluorobenzamido)-2-methylphenyl)-9H-carbazole-1,7-dicarboxamide (prepared as the TFA salt) | 571.0 $(M + H)^+$ |
| 24-37 | Example 23-1 | 4-(3-(4-fluorobenzamido)-2-methylphenyl)-$N^7$-methyl-$N^7$-phenyl-9H-carbazole-1,7-dicarboxamide (prepared as the TFA salt) | 571.0 $(M + H)^+$ |
| 24-38 | Example 23-1 | $N^7$-cyclopropyl-4-(3-(4-fluorobenzamido)-2-methylphenyl)-9H-carbazole-1,7-dicarboxamide (prepared as the TFA salt) | 520.9 $(M + H)^+$ |
| 24-39 | Example 23-1 | 4-(3-(4-fluorobenzamido)-2-methylphenyl)-$N^7$-(pyridin-2-yl)-9H-carbazole-1,7-dicarboxamide (prepared as the TFA salt) | 558.0 $(M + H)^+$ |
| 24-40 | Example 23-1 | 4-(3-(4-fluorobenzamido)-2-methylphenyl)-$N^7$-(pyridin-2-ylmethyl)-9H-carbazole-1,7-dicarboxamide (prepared as the TFA salt) | 572.1 $(M + H)^+$ |

Example 25-1

Preparation of (2S)-2-(8-carbamoyl-5-(3-(4-fluorobenzamido)-2-methylphenyl)-9H-carbazole-2-carboxamido)-3-methylbutanoic acid

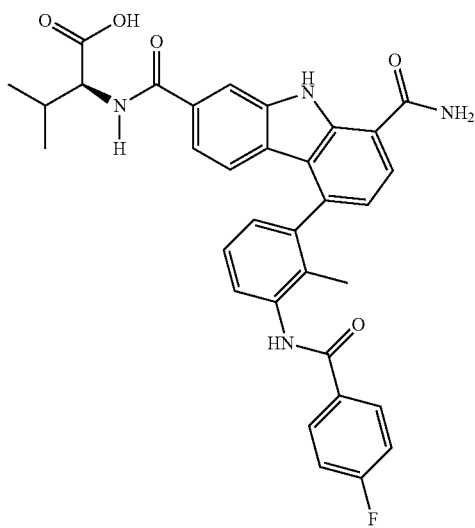 [SMILES: Cc1c(NC(=O)c2ccc(F)cc2)cccc1-c1ccc(C(N)=O)c2[nH]c3cc(C(=O)N[C@H](C(=O)O)C(C)C)ccc3c12]

A mixture of 8-carbamoyl-5-(3-(4-fluorobenzamido)-2-methylphenyl)-9H-carbazole-2-carboxylic acid (Example 23-1, 19.3 mg, 0.04 mmol), EDC (9.6 mg, 0.05 mmol), HOBT (7.7 mg, 0.0.05 mmol), DIEA (25.8 mg, 0.20 mmol), and (S)-tert-butyl 2-amino-3-methylbutanoate hydrochloric acid salt (10.5 mg, 0.05 mmol) in DMF (0.36 mL) was agitated at rt for 21 h. The mixture was concentrated and the residue was agitated in DCM (0.5 mL) and TFA (0.5 mL) for 2 h. The mixture was concentrated and the residue was purified by preparative HPLC to provide (2S)-2-(8-carbamoyl-5-(3-(4-fluorobenzamido)-2-methylphenyl)-9H-carbazole-2-carboxamido)-3-methylbutanoic acid, TFA salt (15.3 mg, 55%). Mass spectrum m/z 581.0 $(M+H)^+$.

The following compounds were also prepared using procedures demonstrated in Example 25-1.

| Example | Compound name | Mass spectrum |
|---|---|---|
| 25-2 | (2S,3S)-2-(8-carbamoyl-5-(3-(4-fluorobenzamido)-2-methylphenyl)-9H-carbazole-2-carboxamido)-3-methylpentanoic acid (prepared as the TFA salt) | 595.0 $(M + H)^+$ |
| 25-3 | 2-(8-carbamoyl-5-(3-(4-fluorobenzamido)-2-methylphenyl)-9H-carbazole-2-carboxamido)acetic acid (prepared as the TFA salt) | 538.9 $(M + H)^+$ |
| 25-4 | (2R)-1-(8-carbamoyl-5-(3-(4-fluorobenzamido)-2-methylphenyl)-9H-carbazole-2-carbonyl)pyrrolidine-2-carboxylic acid (prepared as the TFA salt) | 579.0 $(M + H)^+$ |
| 25-5 | (2S)-1-(8-carbamoyl-5-(3-(4-fluorobenzamido)-2-methylphenyl)-9H-carbazole-2-carbonyl)pyrrolidine-2-carboxylic acid (prepared as the TFA salt) | 578.9 $(M + H)^+$ |

Example 26-1

Preparation of 5-(2,6-difluorophenyl)-$N^2$-methoxy-$N^2$-methyl-2,3,4,9-tetrahydro-1H-carbazole-2,8-dicarboxamide

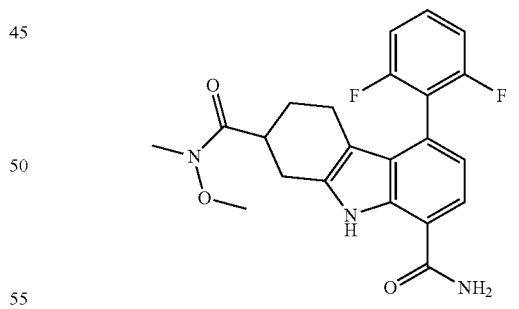

A solution of 8-carbamoyl-5-(2,6-difluorophenyl)-2,3,4,9-tetrahydro-1H-carbazole-2-carboxylic acid (Intermediate 23-3, 720 mg, 1.944 mmol) and TEA (1.084 mL, 7.78 mmol) in THF (5 mL) was treated with isobutyl chloroformate (266 mg, 1.944 mmol) at 0° C. After stirring for 10 min, a solution of N,O-dimethylhydroxylamine hydrochloric acid salt (190 mg, 1.944 mmol) in THF (2 mL) and water (0.5 mL) was added. The mixture was stirred for 30 min, then diluted with DCM, washed with NaHCO3 (aq) and water, and dried and concentrated. The residue was purified by column chromatography (eluting with EtOAc) to provide 5-(2,6-difluorophenyl)-$N^2$-methoxy-$N^2$-methyl-2,3,4,9-tetrahydro-1H-carbazole-2,8-dicarboxamide as a white solid (802 mg, 93%). $^1$H NMR (400 MHz, chloroform-d) δ 1.70-1.82 (m, 1 H) 1.90-1.99 (m, 1 H) 2.19-2.25 (m, 2 H) 2.32-2.42 (m, 1 H) 2.84-2.92 (m, 1 H) 3.05-3.19 (m, 1 H) 3.23 (s, 3 H) 3.70 (s, 3 H) 6.98-7.06 (m, 3 H) 7.35-7.42 (m, 2 H) 10.10 (s, 1 H). Mass spectrum m/z 414.2 (M+H)$^+$.

Example 27-1

Preparation of 2-acetyl-5-(2,6-difluorophenyl)-2,3,4,9-tetrahydro-1H-carbazole-8-carboxamide

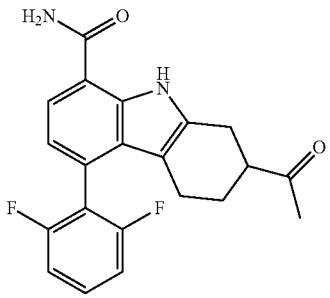 [SMILES: CC(=O)C1CCc2c([nH]c3c(C(N)=O)ccc(-c4c(F)cccc4F)c23)C1]

A solution of 5-(2,6-difluorophenyl)-N$^2$-methoxy-N$^2$-methyl-2,3,4,9-tetrahydro-1H-carbazole-2,8-dicarboxamide (Example 26-1, 719 mg, 1.739 mmol) in THF (1 mL) was treated with methylmagnesium bromide (3 M in diethyl ether, 2.90 mL, 8.70 mmol) at 0° C. After 20 min, additional methylmagnesium bromide (2.90 mL, 8.70 mmol) was added and stirring was continued for 30 min more. The mixture was treated with 1 M hydrochloric acid and extracted four times with DCM. The combined organic phases were washed with water, dried and concentrated. The residue was purified by column chromatography (eluting with hexane-EtOAc) and the resulting material was triturated with DCM to provide 2-acetyl-5-(2,6-difluorophenyl)-2,3,4,9-tetrahydro-1H-carbazole-8-carboxamide as an off-white solid (210 mg, 33%). $^1$H NMR (400 MHz, methanol-d$_4$) δ 7.59 (1 H, d, J=7.91 Hz), 7.39-7.49 (2 H, m), 7.01-7.09 (3 H, m), 6.90 (1 H, d, J=7.91 Hz), 2.86-2.97 (3 H, m), 2.24-2.33 (1 H, m), 2.22 (3 H, s), 2.01-2.18 (2 H, m), 1.54-1.66 (1 H, m). Mass spectrum m/z 369.1 (M+H)$^+$.

Examples 28-1 and 28-2

Preparation of two diastereomers of 5-(2,6-difluorophenyl)-2-(1-hydroxyethyl)-2,3,4,9-tetrahydro-1H-carbazole-8-carboxamide

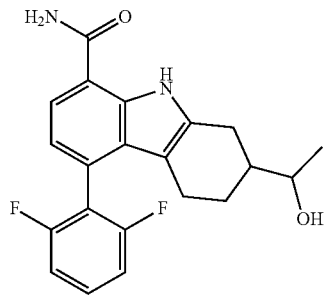 [SMILES: CC(O)C1CCc2c([nH]c3c(C(N)=O)ccc(-c4c(F)cccc4F)c23)C1]

A suspension of 2-acetyl-5-(2,6-difluorophenyl)-2,3,4,9-tetrahydro-1H-carbazole-8-carboxamide (Example 27-1, 30 mg, 0.081 mmol) and sodium borohydride (6.2 mg, 0.163 mmol) in methanol (1 mL) was stirred at rt for 1 h. The mixture was diluted with DCM, washed with NaHCO3 (aq) and water, and dried and concentrated. The residue was purified by preparative HPLC to provide two diastereomers of 5-(2,6-difluorophenyl)-2-(1-hydroxyethyl)-2,3,4,9-tetrahydro-1H-carbazole-8-carboxamide. Each one was partitioned between 1 M aqueous sodium hydroxide and DCM, followed by drying and concentration, to provide the separated racemic diastereomers of 5-(2,6-difluorophenyl)-2-(1-hydroxyethyl)-2,3,4,9-tetrahydro-1H-carbazole-8-carboxamide. The more polar diastereomer (Example 28-1) was a white solid (10 mg, 33%). $^1$H NMR (400 MHz, chloroform-d) δ 1.26 (d, J=6.59 Hz, 3 H) 1.30-1.43 (m, 1 H) 1.78-1.89 (m, 1 H) 1.97-2.05 (m, J=12.74 Hz, 1 H) 2.14-2.22 (m, 1 H) 2.24-2.35 (m, 1 H) 2.57 (dd, J=16.04, 10.77 Hz, 1 H) 2.81 (dd, J=16.48, 5.05 Hz, 1 H) 3.70-3.79 (m, 1 H) 6.96-7.04 (m, 3 H) 7.32-7.41 (m, 2 H) 10.05 (s, 1 H). Mass spectrum m/z 371.1 (M+H)$^+$. The less polar diastereomer (Example 28-2) was a white solid (8 mg, 27%). $^1$H NMR (400 MHz, chloroform-d) δ 1.26 (d, J=6.15 Hz, 3 H) 1.34-1.40 (m, 1 H) 1.42-1.53 (m, 1 H) 1.75-1.90 (m, 2 H) 2.24-2.35 (m, 1 H) 2.68 (dd, J=16.26, 10.11 Hz, 1 H) 2.94 (dd, J=16.26, 5.27 Hz, 1H) 3.80 (s, 1 H) 6.96-7.05 (m, 3 H) 7.34-7.40 (m, 2 H) 10.05 (s, 1 H). Mass spectrum m/z 371.1 (M+H)$^+$.

Example 29-1

Preparation of 2-(1-aminoethyl)-5-(2,6-difluorophenyl)-2,3,4,9-tetrahydro-1H-carbazole-8-carboxamide

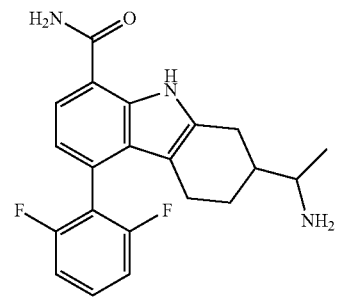 [SMILES: CC(N)C1CCc2c([nH]c3c(C(N)=O)ccc(-c4c(F)cccc4F)c23)C1]

A suspension of 2-acetyl-5-(2,6-difluorophenyl)-2,3,4,9-tetrahydro-1H-carbazole-8-carboxamide (Example 27-1, 30 mg, 0.081 mmol), ammonium acetate (25.1 mg, 0.326 mmol) and sodium triacetoxyborohydride (25.9 mg, 0.122 mmol) in DCM (1 mL) was heated at 50° C. for 1 h. The mixture was cooled, diluted with DCM, washed with NaHCO3 (aq) and water, and dried and concentrated. The residue was purified by preparative HPLC, and the appropriate effluent fractions were made basic with 1 M aqueous sodium hydroxide and extracted twice with DCM. The combined organic phases were washed with water, dried and concentrated to provide a mixture of diastereomers of 2-(1-aminoethyl)-5-(2,6-difluorophenyl)-2,3,4,9-tetrahydro-1H-carbazole-8-carboxamide as a white solid (20 mg, 67%). $^1$H NMR (400 MHz, methanol-d$_4$) δ 7.59 (1 H, d, J=7.47 Hz), 7.39-7.49 (1 H, m), 7.01-7.09 (2 H, m), 6.89 (1 H, d), 2.78-2.94 (2 H, m), 2.46-2.61 (1 H, m), 2.06-2.28 (2 H, m), 1.77-1.94 (1 H, m), 1.62-1.74 (1 H, m), 1.26-1.40 (1 H, m), 1.13 (3 H, d, J=6.59 Hz). Mass spectrum m/z 370.1 (M+H)$^+$.

The following compounds were also prepared using procedures demonstrated in Example 29-1, using the appropriate amine in place of ammonium acetate.

| Example | Compound name | Mass spectrum |
|---|---|---|
| 29-2 | 5-(2,6-difluorophenyl)-2-(1-(1-methylpiperidin-4-ylamino)ethyl)-2,3,4,9-tetrahydro-1H-carbazole-8-carboxamide (prepared as a mixture of diastereomers) | 467.2 (M + H)+ |
| 29-3 | 5-(2,6-difluorophenyl)-2-(1-morpholinoethyl)-2,3,4,9-tetrahydro-1H-carbazole-8-carboxamide (prepared as a mixture of diastereomers) | 440.2 (M + H)+ |

Example 30-1

Preparation of 4-(2-fluorophenyl)-7-(hydroxymethyl)-9H-carbazole-1-carboxamide

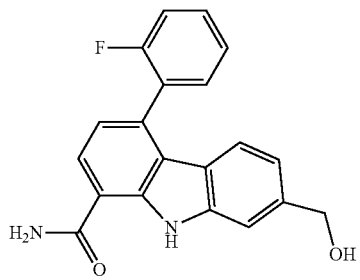 [SMILES: NC(=O)c1ccc(-c2ccccc2F)c2c1[nH]c1cc(CO)ccc12]

A solution of ethyl 8-carbamoyl-5-(2-fluorophenyl)-9H-carbazole-2-carboxylate (Example 3-12, 0.81 g, 2.152 mmol) in THF (26.9 mL) at 0° C. was treated with lithium aluminum hydride (1.0 M in THF, 3.01 mL, 3.01 mmol), and the mixture was stirred at rt for 5 h. Additional lithium aluminum hydride (1.3 mL, 1.3 mmol) was added and the mixture was stirred at rt overnight. The mixture was treated with methanol and TFA and diluted with EtOAc, washed with brine, dried and concentrated to provide impure 4-(2-fluorophenyl)-7-(hydroxymethyl)-9H-carbazole-1-carboxamide (0.78 g) contaminated with starting material. A small amount was purified by preparative HPLC to provide 4-(2-fluorophenyl)-7-(hydroxymethyl)-9H-carbazole-1-carboxamide, isolated as the TFA salt. $^1$H NMR (500 MHz, methanol-$d_4$) δ 7.82 (1 H, d, J=7.8 Hz), 7.51 (1 H, s), 7.44-7.50 (1 H, m), 7.42 (1 H, td, J=7.5, 1.9 Hz), 7.25-7.30 (1 H, m), 7.22 (1 H, t, J=9.2 Hz), 7.05 (1 H, d, J=8.3 Hz), 6.99 (1 H, d, J=7.8 Hz), 6.85 (1 H, dd, J=8.0, 1.4 Hz), 4.62 (2 H, s). Mass spectrum m/z 334.9 (M+H)+.

The following Examples/Intermediates were also prepared using procedures demonstrated in Example 30-1.

| Example/ Intermediates | Starting material | Compound name | Mass spectrum |
|---|---|---|---|
| 30-2 | Intermediate 48-1 | 4-bromo-7-(hydroxymethyl)-9H-carbazole-1-carboxamide | 319, 321 (M + H)+ |
| Intermediate 30-3(a) | Intermediate 47-1 | 5-bromo-2-(hydroxymethyl)-2,3,4,9-tetrahydro-1H-carbazole-8-carboxamide | 323, 325 (M + H)+ |

Example 31-1

Preparation of 2-(hydroxymethyl)-5-(2-methyl-3-(1-oxoisoindolin-2-yl)phenyl)-2,3,4,9-tetrahydro-1H-carbazole-8-carboxamide

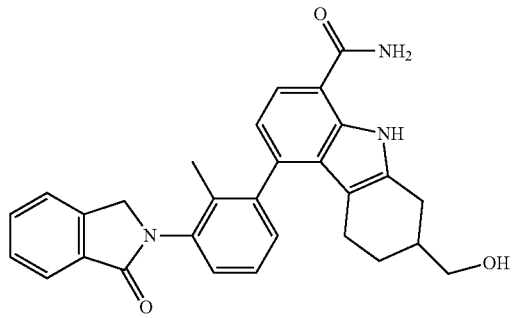 [SMILES: Cc1c(-c2ccc(C(N)=O)c3[nH]c4c(c23)CCC(CO)C4)cccc1N1Cc2ccccc2C1=O]

A mixture of 5-bromo-2-(hydroxymethyl)-2,3,4,9-tetrahydro-1H-carbazole-8-carboxamide (Intermediate 30-3 (a), 80 mg, 0.248 mmol), 2-(2-methyl-3-(4,4,5,5-tetramethyl-1,3,2-dioxaborolan-2-yl)phenyl)isoindolin-1-one (Intermediate 50-4, 130 mg, 0.371 mmol), 2 M aqueous tripotassium phosphate (0.371 mL, 0.743 mmol), and tetrakis(triphenylphosphine)palladium (14.30 mg, 0.012 mmol) in toluene (3 mL) and ethanol (1 mL) was sealed in a vial and heated at 100° C. for 6 hrs. The mixture was cooled and diluted with EtOAc, and the solution was washed with water, dried and concentrated. The residue was purified by column chromatography (eluting with a gradient from DCM to 96:3.6:0.4 DCM-methanol-28% aqueous ammonium hydroxide) to provide 2-(hydroxymethyl)-5-(2-methyl-3-(1-oxoisoindolin-2-yl)phenyl)-2,3,4,9-tetrahydro-1H-carbazole-8-carboxamide as a light yellow solid (68 mg, 53%). $^1$H NMR (400 MHz, chloroform-d) δ 7.79 (1 H, d, J=7.91 Hz), 7.46-7.53 (1 H, m), 7.38-7.44 (2 H, m), 7.30 (1 H, dd, J=7.91, 3.08 Hz), 7.14-7.26 (3 H, m), 6.77 (1 H, dd, J=7.69, 2.86 Hz), 4.59-4.74 (2 H, m), 3.39-3.54 (3 H, m), 2.72-2.80 (2 H, m), 2.30-2.44 (2 H, m), 1.80-2.10 (3 H, m), 1.75 (3 H, d, J=8.35 Hz). Mass spectrum m/z 466.1 (M+H)+.

Examples 31-2 and 31-3

Preparation of 5-(3-(5-tert-butyl-1,3-dioxoisoindolin-2-yl)-2-methylphenyl)-2-(hydroxymethyl)-2,3,4,9-tetrahydro-1H-carbazole-8-carboxamide and (5-(3-(5-tert-butyl-1,3-dioxoisoindolin-2-yl)-2-methylphenyl)-8-carbamoyl-2,3,4,9-tetrahydro-1H-carbazol-2-yl)mEtOAc

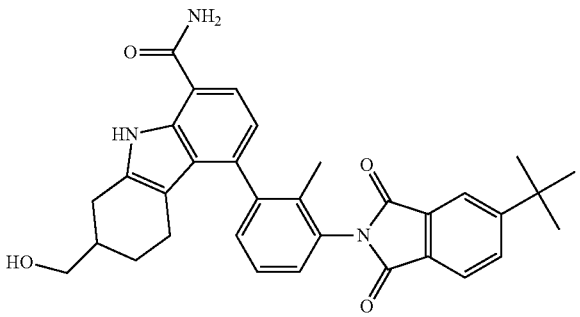

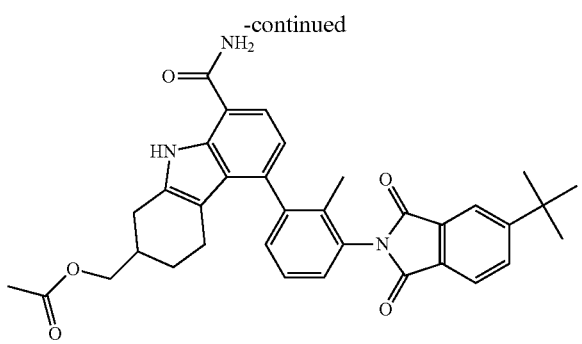

A mixture of 5-bromo-2-(hydroxymethyl)-2,3,4,9-tetrahydro-1H-carbazole-8-carboxamide (Intermediate 30-3 (a), 50 mg, 0.155 mmol), 5-tert-butyl-2-(2-methyl-3-(4,4,5,5-tetramethyl-1,3,2-dioxaborolan-2-yl)phenyl)isoindoline-1,3-dione (Intermediate 50-11, 97 mg, 0.232 mmol), 2 M aqueous tripotassium phosphate (0.232 mL, 0.464 mmol), and tetrakis(triphenylphosphine)palladium (8.9 mg, 7.7 μmol) in toluene (3 mL) and ethanol (1 mL) was heated at 100° C. in a sealed tube overnight. The mixture was cooled to rt, treated with 1 M hydrochloric acid, extracted with EtOAc, and the organic phase was dried and concentrated to provide 5-tert-butyl-2-(3-(8-carbamoyl-2-(hydroxymethyl)-2,3,4,9-tetrahydro-1H-carbazol-5-yl)-2-methylphenylcarbamoyl) benzoic acid (Mass spectrum m/z 554.4 (M+H)$^+$). Without purification, this material was dissolved in acetic acid (4 mL) and heated at 100° C. for 2 h, then was concentrated. The residue was purified by column chromatography (eluting with a gradient from DCM to 90:9:1 DCM-methanol-28% aqueous ammonium hydroxide), followed by purification by preparative HPLC. The appropriate effluent fractions were made basic with NaHCO3 (aq) and extracted with DCM, dried and concentrated to provide 5-(3-(5-tert-butyl-1,3-dioxoisoindolin-2-yl)-2-methylphenyl)-2-(hydroxymethyl)-2,3,4,9-tetrahydro-1H-carbazole-8-carboxamide (Example 31-2) as a light yellow solid (18 mg, 18%). $^1$H NMR (400 MHz, chloroform-d) δ 10.05 (1 H, s), 7.98-8.02 (1 H, m), 7.86-7.91 (1 H, m), 7.79-7.84 (1 H, m), 7.33-7.45 (4 H, m), 7.24-7.28 (2 H, m), 6.89-6.94 (1 H, m), 3.56-3.71 (2 H, m), 2.91 (1 H, dd, J=16.70, 4.83 Hz), 2.48-2.61 (1 H, m), 1.99-2.10 (2 H, m), 1.88-1.99 (2 H, m), 1.86 (3 H, s), 1.43-1.55 (2 H, m), 1.41 (9 H, s). Mass spectrum m/z 536.3 (M+H)$^+$. Also obtained was (5-(3-(5-tert-butyl-1,3-dioxoisoindolin-2-yl)-2-methylphenyl)-8-carbamoyl-2,3,4,9-tetrahydro-1H-carbazol-2-yl)mEtOAc (Example 31-3) as a light yellow solid (15 mg, 14%). $^1$H NMR (400 MHz, chloroform-d) δ 10.05 (1 H, s), 7.97-8.05 (1 H, m), 7.86-7.91 (1 H, m), 7.79-7.84 (1 H, m), 7.33-7.41 (3 H, m), 7.26-7.28 (1 H, m), 4.00-4.13 (2 H, m), 2.90 (2 H, td, J=10.88, 5.05 Hz), 2.46-2.71 (2 H, m), 2.12-2.34 (2 H, m), 2.08 (4 H, s), 1.87 (3 H, d, J=7.03 Hz), 1.45-1.54 (1 H, m), 1.41 (9 H, s). Mass spectrum m/z 578.3 (M+H)$^+$.

Example 31-4

Preparation of 4-(3-(4-fluorobenzamido)-2-methylphenyl)-7-(hydroxymethyl)-9H-carbazole-1-carboxamide

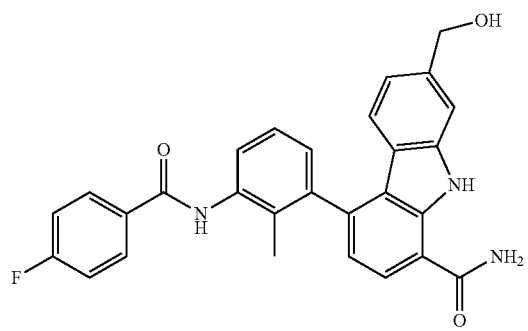 [SMILES: Cc1c(NC(=O)c2ccc(F)cc2)cccc1-c1ccc(C(N)=O)c2[nH]c3cc(CO)ccc3c12]

Using the procedure of Example 3-2,4-bromo-7-(hydroxymethyl)-9H-carbazole-1-carboxamide (Example 30-2, 800 mg, 2.51 mmol) and 4-fluoro-N-(2-methyl-3-(4,4,5,5-tetramethyl-1,3,2-dioxaborolan-2-yl)phenyl)benzamide (Intermediate 53-1, 979 mg, 2.76 mmol) were converted to 4-(3-(4-fluorobenzamido)-2-methylphenyl)-7-(hydroxymethyl)-9H-carbazole-1-carboxamide (550 mg, 47%). $^1$H NMR (400 MHz, DMSO-d$_6$) δ 11.50 (1 H, s), 10.15 (1 H, s), 8.21 (1 H, br. s.), 8.05-8.15 (2 H, m), 7.99 (1 H, d, J=7.9 Hz), 7.70 (1 H, s), 7.46-7.57 (2 H, m), 7.32-7.46 (3 H, m), 7.22 (1 H, dd, J=7.6, 1.0 Hz), 6.97 (1 H, d, J=7.7 Hz), 6.80-6.93 (2 H, m), 5.18 (1 H, t, J=5.7 Hz), 4.58 (2 H, d, J=5.5 Hz), 1.90 (3 H, s). Mass spectrum m/z 466.3 (M−H)$^-$.

The following compounds were also prepared using procedures demonstrated in Examples 31-1 through 31-4, from the starting materials indicated.

| Example | Starting materials | Compound name | Mass spectrum |
|---|---|---|---|
| 31-5 | Intermediate 30-3(a), Intermediate 50-15 | 5-(3-(5-tert-butyl-1-oxoisoindolin-2-yl)-2-methylphenyl)-2-(hydroxymethyl)-2,3,4,9-tetrahydro-1H-carbazole-8-carboxamide | 522.3 (M + H)$^+$ |
| 31-6 | Intermediate 30-3(a), Intermediate 50-14 | 5-(3-(6-tert-butyl-1-oxoisoindolin-2-yl)-2-methylphenyl)-2-(hydroxymethyl)-2,3,4,9-tetrahydro-1H-carbazole-8-carboxamide | 522.3 (M + H)$^+$ |
| 31-7 | Intermediate 30-3(a), Intermediate 50-19 | 5-(3-(5-fluoro-1-oxoisoindolin-2-yl)-2-methylphenyl)-2-(hydroxymethyl)-2,3,4,9-tetrahydro-1H-carbazole-8-carboxamide | 484.2 (M + H)$^+$ |
| 31-8 | Intermediate 30-3(a), Intermediate 50-18 | 2-(hydroxymethyl)-5-(2-methyl-3-(5-methyl-1-oxoisoindolin-2-yl)phenyl)-2,3,4,9-tetrahydro-1H-carbazole-8-carboxamide | 480.2 (M + H)$^+$ |
| 31-9 | Example 30-2, Intermediate 50-24 | 7-(hydroxymethyl)-4-(2-methyl-3-(4-oxoquinazolin-3(4H)-yl)phenyl)-9H-carbazole-1-carboxamide | 475.0 (M + H)$^+$ |

-continued

| Example | Starting materials | Compound name | Mass spectrum |
|---|---|---|---|
| 31-10 | Example 30-2, Intermediate 50-27 | 4-(3-(6-fluoro-4-oxoquinazolin-3(4H)-yl)-2-methylphenyl)-7-(hydroxymethyl)-9H-carbazole-1-carboxamide | 493.0 (M + H)⁺ |
| 31-11 | Example 30-2, Intermediate 50-8 | 7-(hydroxymethyl)-4-(2-methyl-3-(6-methyl-1-oxoisoindolin-2-yl)phenyl)-9H-carbazole-1-carboxamide | 458.0 (M + H − H₂O)⁺ |
| 31-12 | Example 30-2, Intermediate 50-5 | 4-(3-(6-fluoro-1-oxoisoindolin-2-yl)-2-methylphenyl)-7-(hydroxymethyl)-9H-carbazole-1-carboxamide | 462.1 (M + H − H₂O)⁺ |
| 31-13 | Example 30-2, Intermediate 50-38 | 7-(hydroxymethyl)-4-(2-methyl-3-(4-oxo-6-(trifluoromethoxy)quinazolin-3(4H)-yl)phenyl)-9H-carbazole-1-carboxamide | 541.0 (M + H − H₂O)⁺ |
| 31-14 | Example 30-2, Intermediate 50-48 | 4-(3-(8-fluoro-4-oxoquinazolin-3(4H)-yl)-2-methylphenyl)-7-(hydroxymethyl)-9H-carbazole-1-carboxamide | 475.1 (M + H − H₂O)⁺ |
| 31-15 | Example 30-2, Intermediate 50-54 | 7-(hydroxymethyl)-4-(2-methyl-3-(quinazolin-4-ylamino)phenyl)-9H-carbazole-1-carboxamide | 474.0 (M + H)⁺ |
| 31-16 | Example 30-2, Intermediate 50-55 | 4-(3-(5-fluoroquinazolin-4-ylamino)-2-methylphenyl)-7-(hydroxymethyl)-9H-carbazole-1-carboxamide | 492.1 (M + H)⁺ |
| 31-17 | Example 30-2, Intermediate 50-56 | 4-(3-(7-fluoroquinazolin-4-ylamino)-2-methylphenyl)-7-(hydroxymethyl)-9H-carbazole-1-carboxamide | 492.1 (M + H)⁺ |
| 31-18 | Example 30-2, Intermediate 50-57 | 4-(3-(8-fluoroquinazolin-4-ylamino)-2-methylphenyl)-7-(hydroxymethyl)-9H-carbazole-1-carboxamide | 492.1 (M + H)⁺ |

Example 32-1

Preparation of 4-(2-fluorophenyl)-7-(morpholinomethyl)-9H-carbazole-1-carboxamide

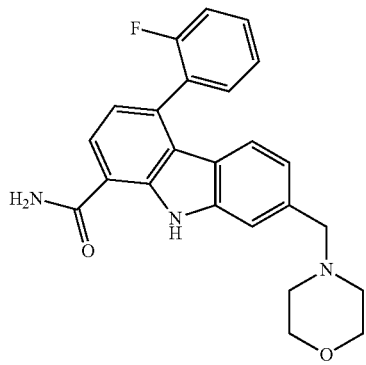 [SMILES: NC(=O)c1ccc(-c2ccccc2F)c2c1[nH]c1cc(CN3CCOCC3)ccc12]

A solution of 4-(2-fluorophenyl)-7-(hydroxymethyl)-9H-carbazole-1-carboxamide (Example 30-1, 223 mg, 0.667 mmol) and TEA (0.279 mL, 2.001 mmol) in THF (8 mL) was treated with methanesulfonyl chloride (0.104 mL, 1.334 mmol). The resulting suspension was stirred at rt for 15 min. The mixture was diluted with EtOAc, washed with water and brine, and dried and concentrated to provide crude (8-carbamoyl-5-(2-fluorophenyl)-9H-carbazol-2-yl)methyl methanesulfonate as a yellow glassy foam (300 mg, ca. 50% purity). A portion of this material (80 mg, 0.097 mmol) was dissolved in DMF (1 mL), treated with morpholine (84 mg, 0.970 mmol) and heated at 45° C. for 3 days. The mixture was purified by preparative HPLC to provide 4-(2-fluorophenyl)-7-(morpholinomethyl)-9H-carbazole-1-carboxamide (9.6 mg, 23%). ¹H NMR (400 MHz, methanol-d₄) δ 7.94 (1 H, d, J=7.8 Hz), 7.59 (1 H, s), 7.52-7.58 (1 H, m), 7.48-7.52 (1 H, m), 7.33-7.39 (1 H, m), 7.30 (1 H, t, J=9.0 Hz), 7.21 (1 H, d, J=8.3 Hz), 7.14 (1 H, d, J=7.8 Hz), 6.99 (1 H, dd, J=8.3, 1.5 Hz), 3.81 (2H, s), 3.71-3.77 (4 H, m), 2.66 (4 H, br. s.). Mass spectrum m/z 404.2 (M+H)⁺.

The following compounds were also prepared using procedures demonstrated in Example 32-1, using the appropriate amine in place of morpholine.

| Example | Compound name | Mass spectrum |
|---|---|---|
| 32-2 | 4-(2-fluorophenyl)-7-((4-methyl-piperazin-1-yl)methyl)-9H-carbazole-1-carboxamide | 417.2 (M + H)⁺ |
| 32-3 | 4-(2-fluorophenyl)-7-(piperidin-1-ylmethyl)-9H-carbazole-1-carboxamide (prepared as the TFA salt) | 402.2 (M + H)⁺ |

Example 33-1

Preparation of 7-(aminomethyl)-4-(2-methyl-3-(1-oxoisoindolin-2-yl)phenyl)-9H-carbazole-1-carboxamide

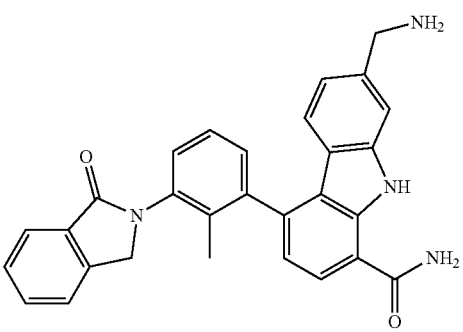 [SMILES: Cc1c(-c2ccc(C(N)=O)c3[nH]c4cc(CN)ccc4c23)cccc1N1Cc2ccccc2C1=O]

Step 1 A suspension of 4-bromo-7-(hydroxymethyl)-9H-carbazole-1-carboxamide (Example 30-2, 300 mg, 0.940 mmol) and TEA (0.262 mL, 1.880 mmol) in THF (9.4 mL) was treated dropwise with methanesulfonyl chloride (0.077 mL, 0.987 mmol) and the mixture was stirred at rt for 1 hr. It was treated with NaHCO3 (aq) and extracted with EtOAc. The organic phase was washed with brine, dried and concentrated to provide crude (5-bromo-8-carbamoyl-9H-carbazol-2-yl)methyl methanesulfonate as a light yellow solid (390 mg, 89%). This material was suspended in DMF (8.3 mL) and treated with sodium azide (271 mg, 4.17 mmol). After being stirred overnight at rt, the mixture was diluted with water and extracted with EtOAc. The organic phase was washed with brine, dried and concentrated to provide crude 7-(azidomethyl)-4-bromo-9H-carbazole-1-carboxamide as a light yellow solid (350 mg, 97%). $^1$H NMR (400 MHz, DMSO-$d_6$) δ 11.80 (1 H, s), 8.62 (1 H, d, J=8.4 Hz), 8.22 (1 H, br. s.), 7.88 (1 H, d, J=8.1 Hz), 7.83 (1 H, s), 7.58 (1 H, br. s.), 7.46 (1 H, d, J=8.4 Hz), 7.28 (1 H, dd, J=8.1, 1.5 Hz), 4.63 (2 H, s).

Step 2 A mixture of 7-(azidomethyl)-4-bromo-9H-carbazole-1-carboxamide (350 mg, 0.814 mmol), triphenylphosphine (427 mg, 1.627 mmol), and water (18 µL, 0.976 mmol) in THF (10 mL) was heated at 70° C. for 3.5 h. The mixture was cooled to rt and partitioned between EtOAc and 1 M hydrochloric acid. The pH of the aqueous phase was raised to 8-9 with sodium hydroxide pellets, and then was extracted with EtOAc. The organic phase was dried and concentrated to provide crude 7-(aminomethyl)-4-bromo-9H-carbazole-1-carboxamide as a yellow glassy foam (320 mg, 99%). $^1$H NMR (400 MHz, DMSO-$d_6$) δ 11.61 (1 H, br.), 8.47-8.55 (1 H, m), 8.19 (1 H, br. s.), 7.81-7.84 (1 H, m), 7.76 (1 H, s), 7.63-7.66 (1 H, m), 7.53-7.59 (2 H, m), 7.41 (1 H, d, J=8.1 Hz), 7.27 (1 H, dd, J=8.4, 1.3 Hz), 3.90 (2 H, s).

Step 3 Using the procedure of Example 3-2, crude 7-(aminomethyl)-4-bromo-9H-carbazole-1-carboxamide (320 mg, 0.805 mmol) and Intermediate 50-4 (309 mg, 0.885 mmol) were converted into crude 7-(aminomethyl)-4-(2-methyl-3-(1-oxoisoindolin-2-yl)phenyl)-9H-carbazole-1-carboxamide as a light yellow solid (ca. 50% pure, 570 mg, 77%). A small amount was purified by preparative HPLC to provide the TFA salt. $^1$H NMR (400 MHz, DMSO-$d_6$) δ 11.64 (1 H, s), 8.11 (3 H, br.), 7.98 (1 H, d, J=7.9 Hz), 7.68-7.74 (2 H, m), 7.62 (2 H, d, J=4.0 Hz), 7.57 (1 H, dd, J=7.9, 1.1 Hz), 7.51 (1 H, dd, J=7.8, 3.6 Hz), 7.44 (2 H, t, J=7.6 Hz), 7.27 (1 H, dd, J=7.6, 1.0 Hz), 6.96-7.08 (3 H, m), 4.78-5.00 (2 H, m), 4.06 (2 H, d, J=5.3 Hz), 1.76 (3 H, s). Mass spectrum m/z 483.2 (M+Na)$^+$.

Example 34-1

Preparation of 7-(acetamidomethyl)-4-(2-methyl-3-(1-oxoisoindolin-2-yl)phenyl)-9H-carbazole-1-carboxamide

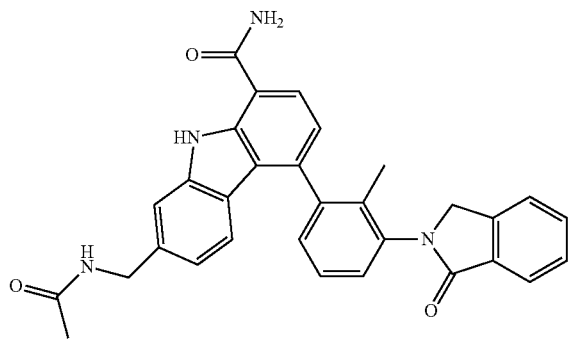 [SMILES: CC(=O)NCc1ccc2c(c1)[nH]c1c(C(N)=O)ccc(-c3cccc(N4Cc5ccccc5C4=O)c3C)c12]

A solution of crude 7-(aminomethyl)-4-(2-methyl-3-(1-oxoisoindolin-2-yl)phenyl)-9H-carbazole-1-carboxamide (Example 33-1, 60 mg, 0.065 mmol) and TEA (23 µL, 0.163 mmol) in THF (1.3 mL) was treated with acetic anhydride (7.4 µL, 0.078 mmol) and the mixture was stirred at rt overnight. The mixture was concentrated and the residue was purified by preparative HPLC. The appropriate effluent fractions were concentrated and the residue was partitioned between NaHCO3 (aq) and EtOAc. The organic phase was washed with brine, dried and concentrated to provide 7-(acetamidomethyl)-4-(2-methyl-3-(1-oxoisoindolin-2-yl)phenyl)-9H-carbazole-1-carboxamide as an off-white solid (12 mg, 36%). $^1$H NMR (400 MHz, DMSO-$d_6$) δ 11.51 (1 H, s), 8.29-8.45 (1 H, m), 8.18 (1 H, br. s.), 8.01 (1H, d, J=7.9 Hz), 7.81 (1 H, d, J=7.5 Hz), 7.69 (2 H, d, J=4.0 Hz), 7.60-7.65 (2 H, m), 7.57 (1 H, ddd, J=7.9, 4.2, 4.0 Hz), 7.50 (2 H, t, J=7.8 Hz), 7.34 (1 H, dd, J=7.7, 1.1 Hz), 6.94-7.06 (2 H, m), 6.87 (1 H, dd, J=8.3, 1.4 Hz), 4.90-5.04 (2 H, m), 4.35 (2H, t, J=5.2 Hz), 1.89 (3 H, s), 1.84 (3 H, s). Mass spectrum m/z 503.2 (M+H)$^+$.

Example 34-2

Preparation of 7-(2-hydroxyacetamido)methyl)-4-(2-methyl-3-(1-oxoisoindolin-2-yl)phenyl)-9H-carbazole-1-carboxamide

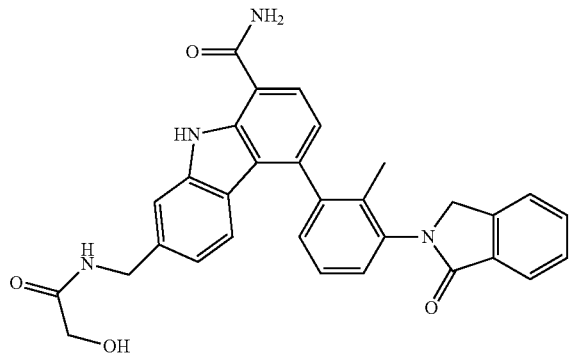 [SMILES: Cc1c(-c2ccc(C(N)=O)c3[nH]c4cc(CNC(=O)CO)ccc4c23)cccc1N1Cc2ccccc2C1=O]

A solution of crude 7-(aminomethyl)-4-(2-methyl-3-(1-oxoisoindolin-2-yl)phenyl)-9H-carbazole-1-carboxamide (Example 33-1, 25 mg, 0.054 mmol), glycolic acid (8.26 mg, 0.109 mmol), HOAT (13.30 mg, 0.098 mmol), and EDC (20.81 mg, 0.109 mmol) in acetonitrile-THF (2:1) (5 mL) was treated with DIEA (0.028 mL, 0.163 mmol) and stirred at rt overnight. The mixture was concentrated and purified by preparative HPLC. The appropriate effluent fractions were concentrated to afford an aqueous suspension, which was treated with NaHCO3 (aq). The precipitate was collected by filtration, washed with water and dried to provide 7-((2-hydroxyacetamido)methyl)-4-(2-methyl-3-(1-oxoisoindolin-2-yl)phenyl)-9H-carbazole-1-carboxamide (17 mg, 59%). $^1$H NMR (400 MHz, DMSO-$d_6$) δ 11.49 (1H, s), 8.22-8.28 (1 H, m), 8.17 (1 H, br. s.), 7.97-8.05 (1 H, m), 7.81 (1 H, d, J=7.5 Hz), 7.69 (2 H, d, J=3.7 Hz), 7.54-7.66 (3 H, m), 7.42-7.54 (2 H, m), 7.28-7.38 (1H, m), 7.03 (1 H, d, J=7.9 Hz), 6.94-7.00 (1 H, m), 6.86-6.94 (1 H, m), 5.45 (1 H, br.), 4.88-5.05 (2 H, m), 4.33-4.48 (2 H, m), 3.88 (2 H, s), 1.83 (3 H, s). Mass spectrum m/z 519.2 (M+H)$^+$.

The following compounds were also prepared using procedures demonstrated in Example 34-1, using appropriate acid anhydrides or acid chlorides.

| Example | Compound name | Mass spectrum |
|---|---|---|
| 34-3 | 4-(2-methyl-3-(1-oxoisoindolin-2-yl)phenyl)-7-(pivalamidomethyl)-9H-carbazole-1-carboxamide | 545.3 (M + H)⁺ |
| 34-4 | 7-(isobutyramidomethyl)-4-(2-methyl-3-(1-oxoisoindolin-2-yl)phenyl)-9H-carbazole-1-carboxamide | 531.3 (M + H)⁺ |

Example 35-1

Preparation of 7-((3-isopropylureido)methyl)-4-(2-methyl-3-(1-oxoisoindolin-2-yl)phenyl)-9H-carbazole-1-carboxamide

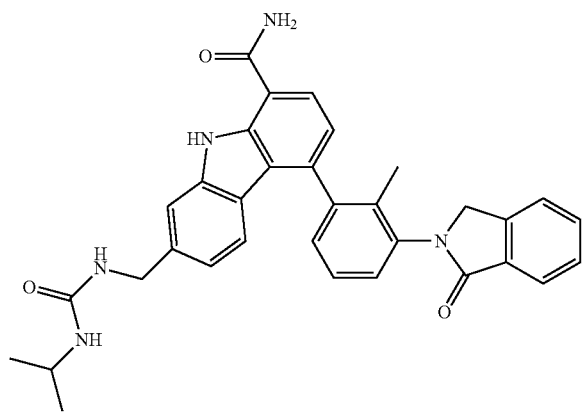 [SMILES: Cc1c(-c2ccc(C(N)=O)c3[nH]c4cc(CNC(=O)NC(C)C)ccc4c23)cccc1N1Cc2ccccc2C1=O]

A solution of 7-(aminomethyl)-4-(2-methyl-3-(1-oxoisoindolin-2-yl)phenyl)-9H-carbazole-1-carboxamide (Example 33-1, 30 mg, 0.065 mmol) and 2-isocyanatopropane (0.019 mL, 0.195 mmol) in THF (3 mL) was stirred at 40° C. overnight. The mixture was concentrated and purified by preparative HPLC. The appropriate effluent fractions were concentrated and partitioned between EtOAc and NaHCO3 (aq). The organic phase was dried and concentrated to provide 7-(3-isopropylureido)methyl)-4-(2-methyl-3-(1-oxoisoindolin-2-yl)phenyl)-9H-carbazole-1-carboxamide as a white solid (5.8 mg, 14%). $^1$H NMR (400 MHz, methanol-$d_4$) δ 7.84 (1 H, d, J=7.7 Hz), 7.77 (1 H, d, J=7.5 Hz), 7.53-7.63 (2 H, m), 7.38-7.51 (4 H, m), 7.30 (1 H, dd, J=7.2, 1.7 Hz), 6.93-6.99 (2 H, m), 6.85 (1 H, dd, J=8.3, 1.4 Hz), 4.79-4.91 (2 H, m), 4.33 (2 H, s), 3.69-3.78 (1 H, m), 1.79 (3 H, s), 1.03 (6 H, d, J=6.4 Hz). Mass spectrum m/z 546.3 (M+H)⁺.

Example 36-1

Preparation of 4-(2-methyl-3-(1-oxoisoindolin-2-yl)phenyl)-7-(methylsulfonamidomethyl)-9H-carbazole-1-carboxamide

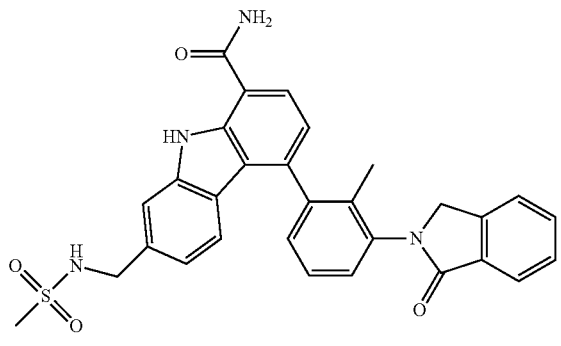 [SMILES: Cc1c(-c2ccc(C(N)=O)c3[nH]c4cc(CNS(C)(=O)=O)ccc4c23)cccc1N1Cc2ccccc2C1=O]

A solution of 7-(aminomethyl)-4-(2-methyl-3-(1-oxoisoindolin-2-yl)phenyl)-9H-carbazole-1-carboxamide (Example 33-1, 60 mg, 0.065 mmol) and TEA (23 μL, 0.163 mmol) in THF (1.3 mL) was treated with methanesulfonyl chloride (5.6 μL, 0.072 mmol) and the mixture was stirred at rt overnight. The mixture was concentrated and purified by preparative HPLC. The appropriate effluent fractions were concentrated and partitioned between EtOAc and NaHCO3 (aq). The organic phase was dried and concentrated, and the residue was purified further by column chromatography (eluting with a gradient from 40:60 hexane-EtOAc to EtOAc) to provide 4-(2-methyl-3-(1-oxoisoindolin-2-yl)phenyl)-7-(methylsulfonamidomethyl)-9H-carbazole-1-carboxamide as an off-white solid (7 mg, 18%). $^1$H NMR (400 MHz, DMSO-$d_6$) δ 11.57 (1 H, s), 8.19 (1 H, br. s.), 8.02 (1 H, d, J=7.7 Hz), 7.81 (1 H, d, J=7.7 Hz), 7.73 (1 H, s), 7.69 (2 H, d, J=3.7 Hz), 7.61-7.65 (1 H, m), 7.54-7.61 (2 H, m), 7.51 (2 H, t, J=7.7 Hz), 7.35 (1 H, dd, J=7.5, 1.1 Hz), 7.00-7.08 (2 H, m), 6.93-6.99 (1 H, m), 4.88-5.05 (2 H, m), 4.26 (2 H, d, J=5.9 Hz), 2.87 (3 H, s), 1.84 (3 H, s). Mass spectrum m/z 539.2 (M+H)⁺.

Example 37-1

Preparation of 4-(2-methyl-3-(1-oxoisoindolin-2-yl)phenyl)-7-((2-oxopyrrolidin-1-yl)methyl)-9H-carbazole-1-carboxamide

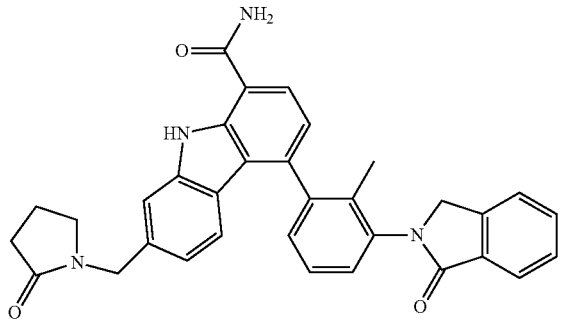 [SMILES: Cc1c(-c2ccc(C(N)=O)c3[nH]c4cc(CN5CCCC5=O)ccc4c23)cccc1N1Cc2ccccc2C1=O]

A solution of 7-(aminomethyl)-4-(2-methyl-3-(1-oxoisoindolin-2-yl)phenyl)-9H-carbazole-1-carboxamide (Example 33-1, 80 mg, 0.087 mmol) in THF (3 mL) was treated with DIEA (0.030 mL, 0.174 mmol) and a solution of 4-bromobutanoyl chloride (10 μL, 0.087 mmol) in DCM (1 mL) and the mixture was stirred at rt for 35 min. The reaction mixture was diluted with EtOAc, washed with NaHCO3 (aq) and brine, and dried and concentrated. The residue was dissolved in THF (6 mL) and treated with sodium hydride (60% oil dispersion, 24.32 mg, 0.608 mmol). The resulting mixture was stirred at 50° C. for 2 h, then was diluted with water and extracted with EtOAc. The organic phase was dried and concentrated, and the residue was purified by preparative HPLC to provide 4-(2-methyl-3-(1-oxoisoindolin-2-yl)phenyl)-7-((2-oxopyrrolidin-1-yl)methyl)-9H-carbazole-1-carboxamide as a white solid (2 mg, 3%). $^1$H NMR (400 MHz, DMSO-$d_6$) δ 11.44 (1 H, s), 8.11 (1 H, br. s.), 7.95 (1 H, d, J=7.9 Hz), 7.73 (1 H, d, J=7.5 Hz), 7.62 (2 H, d, J=3.7 Hz), 7.46-7.57 (3 H, m), 7.42 (2 H, t, J=7.7 Hz), 7.23-7.29 (1 H, m), 6.90-6.99 (2 H, m), 6.74 (1 H, dd, J=8.1, 1.5 Hz), 4.79-5.00 (2 H, m), 4.25-4.51 (2 H, m), 3.11-3.22 (2 H, m), 2.19-2.29 (2 H, m), 1.80-1.93 (2 H, m), 1.77 (3 H, s). Mass spectrum m/z 529.2 (M+H)$^+$.

Example 38-1

Preparation of 7-(acetamidomethyl)-4-(2-methyl-3-(6-methyl-1-oxoisoindolin-2-yl)phenyl)-9H-carbazole-1-carboxamide

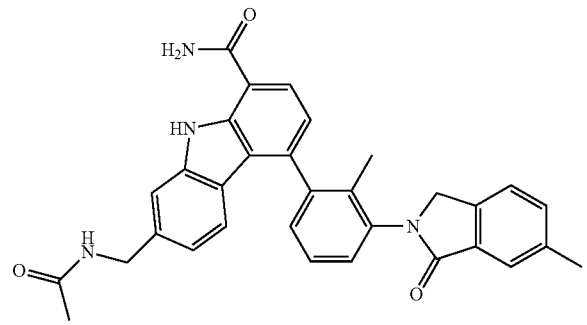 [SMILES: CC(=O)NCc1ccc2c(c1)[nH]c1c(C(N)=O)ccc(-c3cccc(N4Cc5ccc(C)cc5C4=O)c3C)c12]

Step 1 A suspension of 7-(aminomethyl)-4-bromo-9H-carbazole-1-carboxamide (prepared according to Step 2 of Example 33-1, 168 mg, 0.528 mmol) and TEA (0.184 mL, 1.320 mmol) in THF (18 mL) was treated with acetic anhydride (0.080 mL, 0.845 mmol). The mixture was stirred at rt for 2 h, then was partitioned between EtOAc and 1 M hydrochloric acid. The organic phase was washed with NaHCO3 (aq) and brine, dried and concentrated to provide 7-(acetamidomethyl)-4-bromo-9H-carbazole-1-carboxamide as an off-white solid. Mass spectrum m/z 359.9 (M+H)$^+$.

Step 2 Using the procedure of Example 3-2, 7-(acetamidomethyl)-4-bromo-9H-carbazole-1-carboxamide (25 mg, 0.069 mmol) and Intermediate 50-8 (30.3 mg, 0.083 mmol) were converted to 7-(acetamidomethyl)-4-(2-methyl-3-(6-methyl-1-oxoisoindolin-2-yl)phenyl)-9H-carbazole-1-carboxamide, obtained as a white solid (19 mg, 52%) $^1$H NMR (400 MHz, DMSO-$d_6$) δ 11.51 (1 H, s), 8.36 (1 H, t, J=5.8 Hz), 8.18 (1 H, br. s.), 8.01 (1 H, d, J=7.7 Hz), 7.54-7.66 (4 H, m), 7.49 (3H, t, J=7.6 Hz), 7.33 (1 H, dd, J=7.7, 1.1 Hz), 6.93-7.07 (2 H, m), 6.87 (1 H, dd, J=8.1, 1.3 Hz), 4.83-4.99 (2 H, m), 4.27-4.43 (2 H, m), 2.44 (3 H, s), 1.89 (3 H, s), 1.83 (3 H, s). Mass spectrum m/z 517.2 (M+H)$^+$.

The following compounds were also prepared using procedures demonstrated in Example 38-1 and similar procedures, using the starting material shown in place of Intermediate 50-8.

| Example | Starting material | Compound name | Mass spectrum |
|---|---|---|---|
| 38-2 | Intermediate 50-5 | 7-(acetamidomethyl)-4-(3-(6-fluoro-1-oxoisoindolin-2-yl)-2-methylphenyl)-9H-carbazole-1-carboxamide | 521.2 (M + H)$^+$ |
| 38-3 | Intermediate 50-27 | 7-(acetamidomethyl)-4-(3-(6-fluoro-4-oxoquinazolin-3(4H)-yl)-2-methylphenyl)-9H-carbazole-1-carboxamide | 534.1 (M + H)$^+$ |
| 38-4 | Intermediate 50-24 | 7-(acetamidomethyl)-4-(2-methyl-3-(4-oxoquinazolin-3(4H)-yl)phenyl)-9H-carbazole-1-carboxamide | 516.1 (M + H)$^+$ |
| 38-5 | Intermediate 50-48 | 7-(acetamidomethyl)-4-(3-(8-fluoro-4-oxoquinazolin-3(4H)-yl)-2-methylphenyl)-9H-carbazole-1-carboxamide | 534.1 (M + H)$^+$ |
| 38-6 | Intermediate 50-51 | 7-(acetamidomethyl)-4-(3-(8-methoxy-4-oxoquinazolin-3(4H)-yl)-2-methylphenyl)-9H-carbazole-1-carboxamide | 546.1 (M + H)$^+$ |

Example 39-1

Preparation of 4-(3-(4-fluorobenzamido)-2-methylphenyl)-7-(piperidin-1-ylmethyl)-9H-carbazole-1-carboxamide

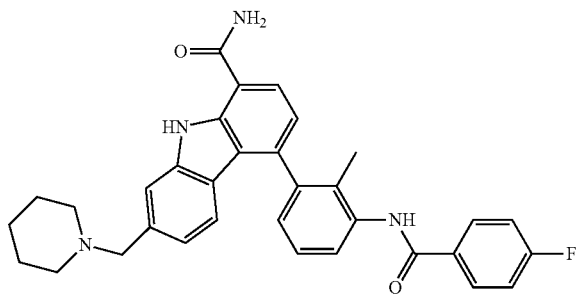 [SMILES: Cc1c(NC(=O)c2ccc(F)cc2)cccc1-c1ccc(C(N)=O)c2[nH]c3cc(CN4CCCCC4)ccc3c12]

Step 1 A solution of 4-(3-(4-fluorobenzamido)-2-methylphenyl)-7-(hydroxymethyl)-9H-carbazole-1-carboxamide (Example 31-4, 0.54 g, 1.155 mmol) in THF (38.5 mL) was treated with 1,1,1-tris(acetyloxy)-1,1-dihydro-1,2-benziodoxol-3-(1 H)-one (Dess-Martin periodinane, 0.784 g, 1.848 mmol) at rt and the mixture was stirred for 2 h. The mixture was partitioned between NaHCO3 (aq) and EtOAc. The organic phase was washed with brine, dried and concentrated. The residue was triturated with methanol and the solid was collected by filtration and dried to provide 4-(3-(4-fluorobenzamido)-2-methylphenyl)-7-formyl-9H-carbazole-1-carboxamide as an orange solid (458 mg, 85%). $^1$H NMR (400 MHz, DMSO-d$_6$) δ 11.98 (1 H, s), 10.16 (1 H, s), 10.03 (1 H, s), 8.23-8.32 (2 H, m), 8.05-8.14 (3 H, m), 7.60 (1 H, br. s.), 7.49-7.55 (1 H, m), 7.39-7.49 (2 H, m), 7.32-7.39 (2 H, m), 7.21-7.27 (1 H, m), 7.09 (2 H, t, J=8.1 Hz), 1.88 (3 H, s). Mass spectrum m/z 466.3 (M+H)$^+$.

Step 2 A suspension of 4-(3-(4-fluorobenzamido)-2-methylphenyl)-7-formyl-9H-carbazole-1-carboxamide (30 mg, 0.064 mmol) in THF (3 mL) was treated with piperidine (16.46 mg, 0.193 mmol) and sodium triacetoxyborohydride (34.1 mg, 0.161 mmol). The mixture was stirred at rt for 3.5 h, the was treated again with additional piperidine (16.5 mg, 0.193 mmol) and sodium triacetoxyborohydride (20 mg). After stirring overnight, the mixture was diluted with water and extracted with EtOAc. The organic phase was washed with brine, dried and concentrated. The residue was purified by preparative HPLC to provide 4-(3-(4-fluorobenzamido)-2-methylphenyl)-7-(piperidin-1-ylmethyl)-9H-carbazole-1-carboxamide (14 mg, 39%). $^1$H NMR (400 MHz, methanol-d$_4$) δ 8.06 (2 H, dd, J=8.7, 5.4 Hz), 7.98 (1 H, d, J=7.8 Hz), 7.63 (1 H, s), 7.52 (1 H, d, J=7.3 Hz), 7.44 (1 H, t, J=7.8 Hz), 7.18-7.31 (3 H, m), 7.07 (2 H, d, J=7.5 Hz), 6.96-7.02 (1 H, m), 3.96 (2 H, s), 2.72-2.88 (4 H, m), 1.99 (3 H, s), 1.63-1.75 (4 H, m), 1.48-1.60 (2 H, m). Mass spectrum m/z 535.2 (M+H)$^+$.

The following compounds were also prepared using procedures demonstrated in Example 39-1, using the appropriate amine in place of piperidine.

| Example | Compound name | Mass spectrum |
|---|---|---|
| 39-2 | 4-(3-(4-fluorobenzamido)-2-methylphenyl)-7-(morpholinomethyl)-9H-carbazole-1-carboxamide | 537.1 (M + H)$^+$ |
| 39-3 | 4-(3-(4-fluorobenzamido)-2-methylphenyl)-7-((4-methylpiperazin-1-yl)methyl)-9H-carbazole-1-carboxamide | 550.1 (M + H)$^+$ |
| 39-4 | 4-(3-(4-fluorobenzamido)-2-methylphenyl)-7-(pyrrolidin-1-ylmethyl)-9H-carbazole-1-carboxamide | 521.1 (M + H)$^+$ |
| 39-5 | 4-(3-(4-fluorobenzamido)-2-methylphenyl)-7-((2-hydroxyethylamino)methyl)-9H-carbazole-1-carboxamide | 511.0 (M + H)$^+$ |
| 39-6 | 4-(3-(4-fluorobenzamido)-2-methylphenyl)-7-((2-methoxyethylamino)methyl)-9H-carbazole-1-carboxamide | 525.1 (M + H)$^+$ |
| 39-7 | 4-(3-(4-fluorobenzamido)-2-methylphenyl)-7-(((RS)-3-hydroxypyrrolidin-1-yl)methyl)-9H-carbazole-1-carboxamide | 537.1 (M + H)$^+$ |
| 39-8 | 4-(3-(4-fluorobenzamido)-2-methylphenyl)-7-(((2-hydroxyethyl)(methyl)amino)methyl)-9H-carbazole-1-carboxamide | 524.9 (M + H)$^+$ |
| 39-9 | 4-(3-(4-fluorobenzamido)-2-methylphenyl)-7-(((RS)-2-(hydroxymethyl)morpholino)methyl)-9H-carbazole-1-carboxamide | 567.2 (M + H)$^+$ |
| 39-10 | 7-(cyclobutylamino)-4-(3-(4-fluorobenzamido)-2-methylphenyl)-9H-carbazole-1-carboxamide | 507.3 (M + H)$^+$ |
| 39-11 | 7-(cyclopentylamino)-4-(3-(4-fluorobenzamido)-2-methylphenyl)-9H-carbazole-1-carboxamide | 520.9 (M + H)$^+$ |
| 39-12 | 4-(3-(4-fluorobenzamido)-2-methylphenyl)-7-(neopentylamino)-9H-carbazole-1-carboxamide | 522.9 (M + H)$^+$ |
| 39-13 | 7-(cyclopropylmethylamino)-4-(3-(4-fluorobenzamido)-2-methylphenyl)-9H-carbazole-1-carboxamide | 506.8 (M + H)$^+$ |
| 39-14 | 4-(3-(4-fluorobenzamido)-2-methylphenyl)-7-(tetrahydro-2H-pyran-4-ylamino)-9H-carbazole-1-carboxamide | 536.8 (M + H)$^+$ |
| 39-15 | 4-(3-(4-fluorobenzamido)-2-methylphenyl)-7-((1-methyl-1H-imidazol-2-yl)methylamino)-9H-carbazole-1-carboxamide | 546.8 (M + H)$^+$ |
| 39-16 | 4-(3-(4-fluorobenzamido)-2-methylphenyl)-7-((1-methylpiperidin-4-yl)methylamino)-9H-carbazole-1-carboxamide (prepared as the TFA salt) | 563.9 (M + H)$^+$ |
| 39-17 | 7-(cyclopentylmethylamino)-4-(3-(4-fluorobenzamido)-2-methylphenyl)-9H-carbazole-1-carboxamide | 534.9 (M + H)$^+$ |
| 39-18 | 7-(cyclohexylamino)-4-(3-(4-fluorobenzamido)-2-methylphenyl)-9H-carbazole-1-carboxamide | 534.9 (M + H)$^+$ |

Example 40-1

Preparation of 4-(2-fluorophenyl)-7-hydroxy-9H-carbazole-1-carboxamide

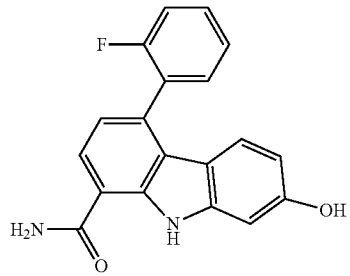 [SMILES: NC(=O)c1ccc(-c2ccccc2F)c2c1[nH]c1cc(O)ccc12]

Step 1 A solution of 4-(2-fluorophenyl)-7-(hydroxymethyl)-9H-carbazole-1-carboxamide (Example 30-1, 147 mg, 0.440 mmol) in DCM (3 mL), acetonitrile (5 mL) and THF (3 mL) was treated with 1,1,1-tris(acetyloxy)-1,1-dihydro-1,2-benziodoxol-3-(1 H)-one (Dess-Martin periodinane, 373 mg, 0.879 mmol). After 30 min at rt, the mixture was diluted with EtOAc (30 mL), washed twice with 1 M aqueous sodium sulfite and brine, dried and concentrated to give 4-(2-fluorophenyl)-7-formyl-9H-carbazole-1-carboxamide as a tan solid (ca. 80% purity, 163 mg, 87%), used without purification. Mass spectrum m/z 333.1 (M+H)$^+$.

Step 2 A solution of crude 4-(2-fluorophenyl)-7-formyl-9H-carbazole-1-carboxamide (25.2 mg, 0.076 mmol) in methanol (2 mL) at 0° C. was treated with 30% aqueous hydrogen peroxide (0.039 mL, 0.379 mmol) and sulfuric acid (0.020 mL, 0.379 mmol). After 1.5 h, additional hydrogen peroxide (0.100 mL) and sulfuric acid (0.050 mL) were added and the mixture was stirred at rt overnight. After 16 h, 1 M aqueous sodium hydroxide (2 mL) was added and the mixture was stirred for 1 h. The pH was adjusted to ca. 4 and the organic solvent was removed under vacuum. The aqueous residue was diluted with water and the precipitate was collected by filtration, washed with water and dried. The residue was purified by preparative HPLC to provide 4-(2-fluorophenyl)-7-hydroxy-9H-carbazole-1-carboxamide as tan solid after lypholization (5.1 mg, 21%). $^1$H NMR (400 MHz, methanol-d$_4$) δ 7.81 (1H, d, J=7.70 Hz), 7.45-7.64 (2 H, m), 7.21-7.42 (2 H, m), 7.03 (1 H, d, J=7.92 Hz), 6.90-6.99 (2 H, m), 6.45 (1 H, dd, J=8.58, 2.20 Hz). Mass spectrum m/z 321.0 (M+H)$^+$.

The following compound was also prepared using the procedures demonstrated in Example 40-1, substituting Example 31-11 in place of Example 30-1 as starting material:

| Example | Compound name | Mass spectrum |
|---|---|---|
| 40-2 | 7-hydroxy-4-(2-methyl-3-(6-methyl-1-oxoisoindolin-2-yl)phenyl)-9H-carbazole-1-carboxamide | 462.0 (M + H)$^+$ |

Example 41-1

Preparation of 7-hydroxy-4-(2-methyl-3-(1-oxoisoindolin-2-yl)phenyl)-9H-carbazole-1-carboxamide

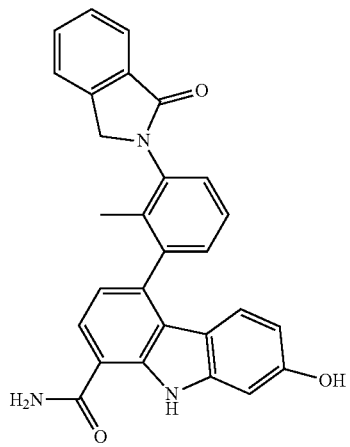 [SMILES: Cc1c(-c2ccc(C(N)=O)c3[nH]c4cc(O)ccc4c23)cccc1N1Cc2ccccc2C1=O]

Step 1 A partial solution of 4-bromo-7-(hydroxymethyl)-9H-carbazole-1-carboxamide (Example 30-2, 1.00 g, 3.13 mmol) in THF (75 mL) was stirred at rt and treated with 1,1,1-tris(acetyloxy)-1,1-dihydro-1,2-benziodoxol-3-(1 H)-one (Dess-Martin periodinane, 1.993 g, 4.70 mmol). After 45 min, the solution was diluted with EtOAc and washed with 5% aqueous sodium sulfite, NaHCO3 (aq), and brine, then was dried and concentrated. The residue was triturated with methanol, and the precipitate was collected by filtration, washed with methanol and dried to provide 4-bromo-7-formyl-9H-carbazole-1-carboxamide as a tan powder (ca. 85% purity, 948 mg, 81%) used without purification. $^1$H NMR (400 MHz, DMSO-d$_6$) δ 12.13 (1 H, s), 10.14 (1 H, s), 8.80 (1 H, d, J=8.1 Hz), 8.38 (1 H, d, J=0.9 Hz), 8.28 (1 H, br. s.), 7.97 (1 H, d, J=8.1 Hz), 7.83 (1 H, dd, J=8.3, 1.4 Hz), 7.64 (1 H, br. s.), 7.54 (1 H, d, J=8.1 Hz). Mass spectrum m/z 317, 319 (M+H)$^+$.

Step 2 Using the procedure of Example 3-2,4-bromo-7-formyl-9H-carbazole-1-carboxamide (75 mg, 0.236 mmol) and 2-(2-methyl-3-(4,4,5,5-tetramethyl-1,3,2-dioxaborolan-2-yl)phenyl)isoindolin-1-one (Intermediate 50-4, 83 mg, 0.236 mmol) were converted to 7-formyl-4-(2-methyl-3-(1-oxoisoindolin-2-yl)phenyl)-9H-carbazole-1-carboxamide as a gray-green powder (ca. 90% purity, 97 mg, 89%), used without further purification. Mass spectrum m/z 460.2 (M+H)$^+$.

Step 3 A suspension of 7-formyl-4-(2-methyl-3-(1-oxoisoindolin-2-yl)phenyl)-9H-carbazole-1-carboxamide (30 mg, 0.052 mmol) in methanol (1 mL) was treated with sulfuric acid (4.2 mL, 0.078 mmol) followed by 30% aqueous hydrogen peroxide (0.032 mL, 0.313 mmol), and stirred at rt for 23 h, The mixture was treated with 1 M aqueous sodium hydroxide (200 mL) and stirred for 1 h. The mixture was diluted with water and the precipitate was collected by filtration, washed with water and dried. The residue was purified by preparative HPLC to provide 7-hydroxy-4-(2-methyl-3-(1-oxoisoindolin-2-yl)phenyl)-9H-carbazole-1-carboxamide as a tan powder (3.6 mg, 15%). $^1$H NMR (400 MHz, methanol-d$_4$) δ 7.90 (1 H, d, J=7.5 Hz), 7.86 (1 H, d, J=7.9 Hz), 7.65-7.76 (2 H, m), 7.48-7.63 (3 H, m), 7.42 (1H, d, J=6.6 Hz), 7.03 (1 H, d, J=7.9 Hz), 6.98 (1 H, s), 6.92 (1 H, d, J=8.8 Hz), 6.54 (1H, d, J=9.0 Hz), 4.97 (2 H, s), 1.94 (3 H, s). Mass spectrum m/z 448.1 (M+H)+.

Example 42-1

Preparation of 8-carbamoyl-5-(2-fluorophenyl)-9H-carbazol-2-yl ethyl carbonate

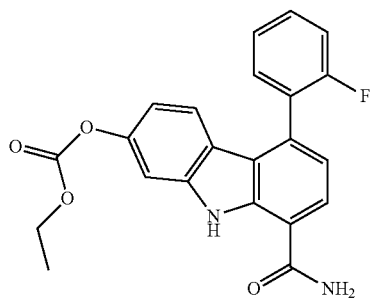 [SMILES: CCOC(=O)Oc1ccc2c(c1)[nH]c1c(C(N)=O)ccc(-c3ccccc3F)c12]

Ethyl chloroformate (8.19 mg, 0.075 mmol) was added to a solution of 4-(2-fluorophenyl)-7-hydroxy-9H-carbazole-1-carboxamide (Example 40-1, 18.6 mg, 0.058 mmol) in pyridine (1 mL). After 17 h, additional ethyl chloroformate (8.19 mg, 0.075 mmol) was added. After 5 h more, additional ethyl chloroformate (0.05 mL) was added. After 15 h more, the mixture was diluted with EtOAc (30 mL), washed with water (10 mL) and brine (5 mL), dried and concentrated. The residue was purified by preparative HPLC to provide 8-carbamoyl-5-(2-fluorophenyl)-9H-carbazol-2-yl ethyl carbonate as a white solid (7.0 mg, 28%). $^1$H NMR (400 MHz, chloroform-d) δ 10.44 (1 H, br. s.), 7.62 (1 H, dd, J=7.92, 1.98 Hz), 7.41-7.57 (2 H, m), 7.20-7.40 (4 H, m), 7.16 (1 H, dd, J=7.81, 1.65 Hz), 6.79-6.92 (1 H, m), 6.60 (2H, br. s.), 4.34 (2 H, q, J=7.26 Hz), 1.41 (3 H, t, J=7.15 Hz). Mass spectrum m/z 393.0 (M+H)+.

Example 43-1

Preparation of 8-carbamoyl-5-(2-fluorophenyl)-9H-carbazol-2-yl morpholine-4-carboxylate

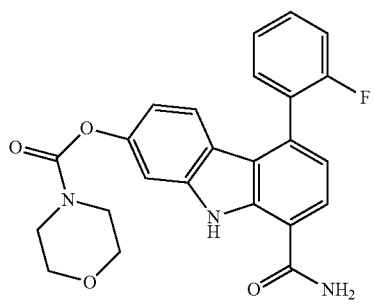 [SMILES: NC(=O)c1ccc(-c2ccccc2F)c2c1[nH]c1cc(OC(=O)N3CCOCC3)ccc12]

Morpholine-4-carbonyl chloride (11.29 mg, 0.075 mmol) was added to a solution of 4-(2-fluorophenyl)-7-hydroxy-9H-carbazole-1-carboxamide (Example 40-1, 18.6 mg, 0.058 mmol) in pyridine (1 mL). After 22 h at rt, additional morpholine-4-carbonyl chloride (11.29 mg, 0.075 mmol) was added. After 15 h, the mixture was diluted with EtOAc (30 mL), washed with water (10 mL) and brine (5 mL), and dried and concentrated. The residue was purified by preparative HPLC to provide 8-carbamoyl-5-(2-fluorophenyl)-9H-carbazol-2-yl morpholine-4-carboxylate as a white solid (7.9 mg, 27%). $^1$H NMR (400 MHz, chloroform-d) δ 9.94 (1 H, br. s.), 7.41-7.65 (3 H, m), 7.33 (2 H, t, J=8.14 Hz), 7.20 (1 H, d, J=8.58 Hz), 6.92-7.15 (4 H, m), 6.73 (1 H, dd, J=8.58, 1.98 Hz), 3.80 (4 H, t, J=4.62 Hz), 3.67-3.76 (2 H, m), 3.62 (2H, br. s.). Mass spectrum m/z 434.0 (M+H)+.

Example 44-1

Preparation of 4-(2-fluorophenyl)-7-methoxy-9H-carbazole-1-carboxamide

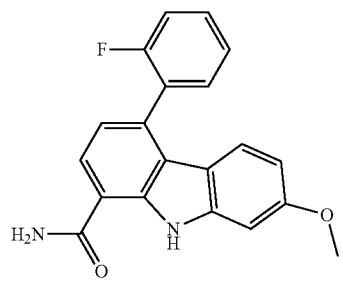 [SMILES: COc1ccc2c(c1)[nH]c1c(C(N)=O)ccc(-c3ccccc3F)c12]

Potassium carbonate (25.1 mg, 0.182 mmol) and iodomethane (4.9 mL, 0.079 mmol) were added to a solution of 4-(2-fluorophenyl)-7-hydroxy-9H-carbazole-1-carboxamide (Example 40-1, 19.4 mg, 0.061 mmol) in DMSO (1 mL) and the mixture was stirred at rt. After 17 h, the mixture was diluted with EtOAc (30 mL), washed with saturated aqueous ammonium chloride (5 mL), water (2×5 mL), and brine (5 mL), dried and concentrated. The residue was purified by preparative HPLC to provide 4-(2-fluorophenyl)-7-methoxy-9H-carbazole-1-carboxamide (1.9 mg, 9%). $^1$H NMR (400 MHz, chloroform-d) δ 10.39 (1 H, br. s.), 7.58 (1 H, d, J=7.70 Hz), 7.44-7.55 (2 H, m), 7.28-7.39 (2 H, m), 7.07-7.22 (2 H, m), 7.00 (1 H, d, J=2.20 Hz), 6.65 (1 H, dd, J=8.80, 2.42 Hz), 6.57 (2 H, br. s.), 3.88 (3 H, s). Mass spectrum m/z 335.0 (M+H)+.

Example 44-2

Preparation of 7-(2-methoxyethoxy)-4-(2-methyl-3-(6-methyl-1-oxoisoindolin-2-yl)phenyl)-9H-carbazole-1-carboxamide

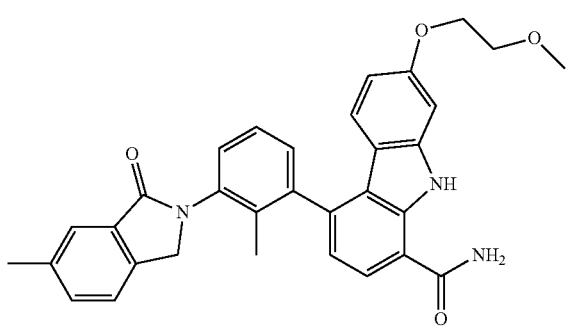

A mixture of 7-hydroxy-4-(2-methyl-3-(6-methyl-1-oxoisoindolin-2-yl)phenyl)-9H-carbazole-1-carboxamide (Example 40-2, 30 mg, 0.065 mmol) and potassium carbonate (18 mg, 0.130 mmol) in DMF (1.0 mL) was stirred at rt for 30 min, then was treated with 1-bromo-2-methoxyethane (14 mg, 0.098 mmol). The mixture was heated at 90° C. for 4 h, cooled to rt and concentrated under vacuum. The residue was purified by preparative HPLC to provide 7-(2-methoxyethoxy)-4-(2-methyl-3-(6-methyl-1-oxoisoindolin-2-yl)phenyl)-9H-carbazole-1-carboxamide as a white solid (12.5 mg, 35%). $^1$H NMR (400 MHz, DMSO-$d_6$) δ 11.39 (1 H, s), 8.17 (1 H, br. s.), 7.95 (1 H, d, J=7.9 Hz), 7.54-7.64 (3 H, m), 7.49 (3 H, t, J=8.0 Hz), 7.27-7.38 (2 H, m), 7.00 (1 H, d, J=7.9 Hz), 6.91 (1 H, d, J=8.8 Hz), 6.59 (1 H, dd, J=8.8, 2.4 Hz), 4.91 (2 H, d, J=3.3 Hz), 4.12 (2 H, dd, J=5.5, 3.1 Hz), 3.63-3.75 (2 H, m), 3.33 (3 H, s), 2.44 (3 H, s), 1.83 (3 H, s). Mass spectrum m/z 520.1 (M+H)$^+$.

Example 44-3

Preparation of 7-(2-hydroxyethoxy)-4-(2-methyl-3-(6-methyl-1-oxoisoindolin-2-yl)phenyl)-9H-carbazole-1-carboxamide

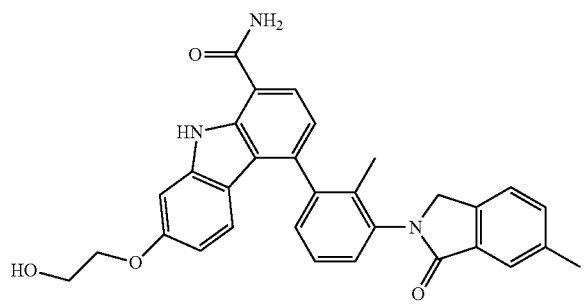 [SMILES: Cc1ccc2c(c1)C(=O)N(c1cccc(-c3ccc(C(N)=O)c4[nH]c5cc(OCCO)ccc5c34)c1C)C2]

A mixture of 7-hydroxy-4-(2-methyl-3-(6-methyl-1-oxoisoindolin-2-yl)phenyl)-9H-carbazole-1-carboxamide (Example 40-2, 30 mg, 0.065 mmol) and potassium carbonate (36 mg, 0.260 mmol) in DMF (1.0 mL) was stirred at rt for 30 min, then was treated with (2-bromoethoxy)(tert-butyl)dimethylsilane (62.2 mg, 0.260 mmol) and heated at 90° C. for 4 h. The mixture was filtered, the filtrate was treated with hydrogen chloride (4 M in dioxane, 1 mL) and the solution was stirred at rt overnight. The solution was concentrated under vacuum and the residue was purified by preparative HPLC to provide 7-(2-hydroxyethoxy)-4-(2-methyl-3-(6-methyl-1-oxoisoindolin-2-yl)phenyl)-9H-carbazole-1-carboxamide as an off-white solid (16.5 mg, 45%). $^1$H NMR (400 MHz, DMSO-$d_6$) δ 11.39 (1 H, s), 8.17 (1 H, br. s.), 7.94 (1H, d, J=7.9 Hz), 7.53-7.65 (3 H, m), 7.49 (3 H, t, J=7.8 Hz), 7.27-7.39 (2 H, m), 6.99 (1 H, d, J=7.7 Hz), 6.92 (1 H, d, J=8.8 Hz), 6.59 (1 H, dd, J=8.8, 2.4 Hz), 4.75-4.98 (3 H, m), 3.95-4.07 (2 H, m), 3.69-3.80 (2 H, m), 2.44 (3 H, s). Mass spectrum m/z 506.0 (M+H)$^+$.

Example 44-4

Preparation of racemic 7-((2,2-dimethyl-1,3-dioxolan-4-yl)methoxy)-4-(2-methyl-3-(6-methyl-1-oxoisoindolin-2-yl)phenyl)-9H-carbazole-1-carboxamide

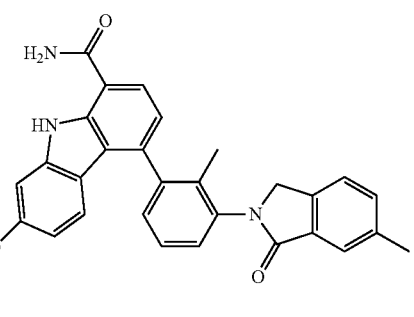

A mixture of 7-hydroxy-4-(2-methyl-3-(6-methyl-1-oxoisoindolin-2-yl)phenyl)-9H-carbazole-1-carboxamide (Example 40-2, 50 mg, 0.108 mmol) and potassium carbonate (30 mg, 0.217 mmol) in DMF (1.7 mL) was stirred at rt for 30 min, then was treated with racemic (4,4-dimethyl-1,3-dioxolan-2-yl)methyl 4-methylbenzenesulfonate (46.5 mg, 0.163 mmol). The resulting mixture was heated at 80° C. overnight. The mixture was cooled to rt, diluted with water and extracted with EtOAc. The organic phase was washed with brine, dried and concentrated. The residue was purified by column chromatography (eluting with a gradient from 50:50 to 80:20 EtOAc-hexane) to provide racemic 7-((2,2-dimethyl-1,3-dioxolan-4-yl)methoxy)-4-(2-methyl-3-(6-methyl-1-oxoisoindolin-2-yl)phenyl)-9H-carbazole-1-carboxamide as a light yellow solid (30 mg, 48%). Mass spectrum m/z 576.1 (M+H)$^+$.

Examples 44-5 and 44-6

Preparation of 7-(2-hydroxy-3-methoxypropoxy)-4-(2-methyl-3-(6-methyl-1-oxoisoindolin-2-yl)phenyl)-9H-carbazole-1-carboxamide and 7-(3-(dimethylamino)-2-hydroxypropoxy)-4-(2-methyl-3-(6-methyl-1-oxoisoindolin-2-yl)phenyl)-9H-carbazole-1-carboxamide

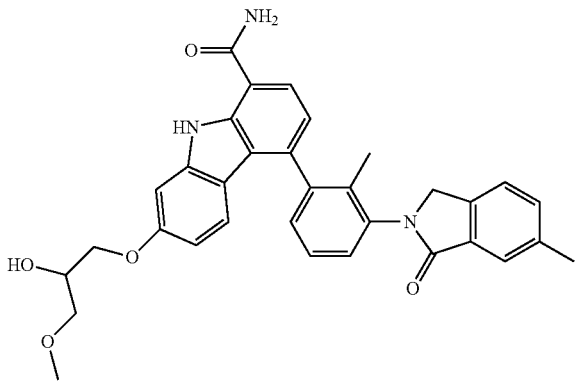

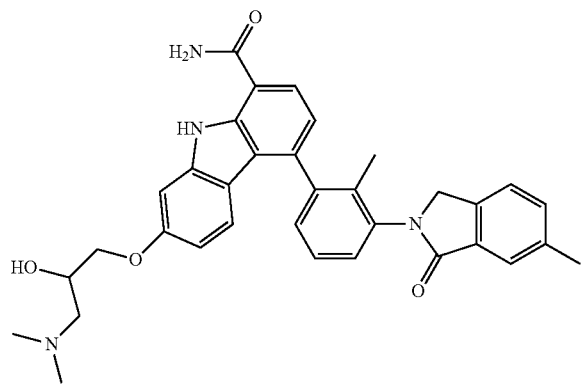

A mixture of 7-hydroxy-4-(2-methyl-3-(6-methyl-1-oxoisoindolin-2-yl)phenyl)-9H-carbazole-1-carboxamide (Example 40-2, 30 mg, 0.065 mmol) and potassium carbonate (36 mg, 0.260 mmol) in DMF (1.0 mL) was stirred at rt for 30 min, then was treated with 2-(bromomethyl)oxirane (27 mg, 0.195 mmol). The resulting mixture was heated at 90° C. for 3.5 h, cooled to rt and filtered. The filtrate was treated with methanol, stirred at rt for 2 h, then was then heated at 90° C. for 1 h. The mixture was concentrated under vacuum and purified by preparative HPLC to provide 7-(2-hydroxy-3-methoxypropoxy)-4-(2-methyl-3-(6-methyl-1-oxoisoindolin-2-yl)phenyl)-9H-carbazole-1-carboxamide (Example 44-5, 4.7 mg, 13%). $^1$H NMR (400 MHz, methanol-$d_4$) δ 7.83 (1 H, d, J=7.9 Hz), 7.72 (1 H, d, J=0.7 Hz), 7.46-7.52 (4 H, m), 7.38-7.45 (1 H, m), 7.04-7.12 (2 H, m), 6.99 (1 H, d, J=8.8 Hz), 6.70 (1 H, dd, J=8.7, 2.3 Hz), 4.86 (2 H, d, J=1.8 Hz), 4.03-4.22 (3 H, m), 3.53-3.65 (2H, m), 3.42 (3 H, s), 2.50 (3 H, s), 1.93 (3 H, s). Mass spectrum m/z 550.1 (M+H)$^+$. Also isolated was 7-(3-(dimethylamino)-2-hydroxypropoxy)-4-(2-methyl-3-(6-methyl-1-oxoisoindolin-2-yl)phenyl)-9H-carbazole-1-carboxamide (Example 44-6, 2.0 mg, 5%). Mass spectrum m/z 563.1 (M+H)$^+$.

The following compounds were also prepared using the procedures demonstrated in Example 44-2:

| Example | Compound name | Mass spectrum |
|---|---|---|
| 44-7 | 7-(2-fluoroethoxy)-4-(2-methyl-3-(6-methyl-1-oxoisoindolin-2-yl)phenyl)-9H-carbazole-1-carboxamide | 508.1 (M + H)$^+$ |
| 44-8 | 7-(2-hydroxypropoxy)-4-(2-methyl-3-(6-methyl-1-oxoisoindolin-2-yl)phenyl)-9H-carbazole-1-carboxamide | 520.1 (M + H)$^+$ |

Example 45-1

Preparation of (E)-7-((hydroxyimino)methyl)-4-(2-methyl-3-(6-methyl-1-oxoisoindolin-2-yl)phenyl)-9H-carbazole-1-carboxamide

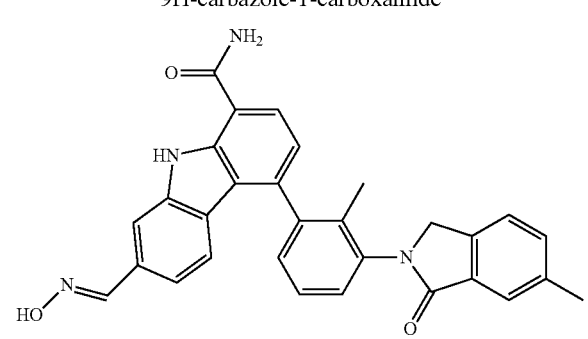

Step 1 A mixture of 4-bromo-7-formyl-9H-carbazole-1-carboxamide (prepared according to Step 1 of Example 41-1, 200 mg, 0.631 mmol) and hydroxylamine hydrochloric acid salt (65.7 mg, 0.946 mmol) in ethanol (3 mL) was treated with 2 M aqueous sodium carbonate (0.236 mL, 0.473 mmol) and heated at 80-90° C. After 17.5 h, the mixture was cooled to rt and partitioned between EtOAc and water. The organic phase was dried and concentrated, and the residue was triturated with methanol, and the precipitate was collected by filtration, rinsed with methanol and dried to provide (E)-4-bromo-7-((hydroxyimino)methyl)-9H-carbazole-1-carboxamide as a gray-tan solid (110 mg, 53%). $^1$H NMR (400 MHz, DMSO-$d_6$) δ 11.87 (1 H, s), 11.33 (1 H, s), 8.65 (1 H, d, J=8.4 Hz), 8.32 (1 H, s), 8.28 (1 H, br. s.), 8.09 (1 H, s), 7.92 (1 H, d, J=8.1 Hz), 7.64 (1 H, br. s.), 7.58 (1 H, d, J=8.6 Hz), 7.51 (1 H, d, J=8.1 Hz). Mass spectrum m/z 332, 334 (M+H)$^+$.

Step 2 Using the procedure of Example 3-2, (E)-4-bromo-7-((hydroxyimino)methyl)-9H-carbazole-1-carboxamide (82 mg, 0.247 mmol) and 6-methyl-2-(2-methyl-3-(4,4,5,5-tetramethyl-1,3,2-dioxaborolan-2-yl)phenyl)isoindolin-1-one (Intermediate 50-8, 90 mg, 0.247 mmol) were converted to (E)-7-((hydroxyimino)methyl)-4-(2-methyl-3-(6-methyl-1-oxoisoindolin-2-yl)phenyl)-9H-carbazole-1-carboxamide as a pale pink solid (52 mg, 40%). $^1$H NMR (400 MHz, methanol-$d_4$) δ 8.20 (1 H, s), 8.00 (1 H, d, J=7.7 Hz), 7.82 (1 H, s), 7.70 (1H, s), 7.49-7.59 (4 H, m), 7.43 (1 H, dd, J=6.7, 2.1 Hz), 7.31 (1 H, dd, J=8.3, 1.2 Hz), 7.11 (2 H, d, J=7.7 Hz), 4.92 (2 H, s), 2.50 (3 H, s), 1.92 (3 H, s). Mass spectrum m/z 489.3 (M+H)$^+$.

Example 46-1

Preparation of 5-(3-amino-2-methylphenyl)-2-((2-oxopyrrolidin-1-yl)methyl)-2,3,4,9-tetrahydro-1H-carbazole-8-carboxamide

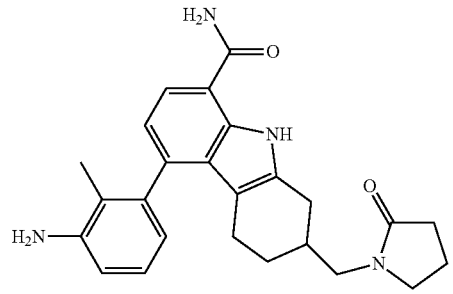 [SMILES: Cc1c(N)cccc1-c1ccc(C(N)=O)c2[nH]c3c(c12)CCC(CN1CCCC1=O)C3]

Step 1 A solution of 5-bromo-8-carbamoyl-2,3,4,9-tetrahydro-1H-carbazole-2-carboxylic acid (Intermediate 49-3, 2 g, 5.93 mmol) and TEA (2.067 mL, 14.83 mmol) in THF (20 mL) was treated with isobutyl chloroformate (0.810 g, 5.93 mmol) at 0° C. The mixture was stirred for 10 min, then was treated with a solution of N,O-dimethylhydroxylamine hydrochloric acid salt (0.579 g, 5.93 mmol) in THF (2 mL) and water (1 mL). The mixture was stirred at 0° C. for 1 h, then was diluted with DCM, washed with NaHCO3 (aq) and water, dried and concentrated. The residue was triturated with DCM to provide 5-bromo-$N^2$-methoxy-$N^2$-methyl-2,3,4,9-tetrahydro-1H-carbazole-2,8-dicarboxamide as a light yellow solid (1.73 g, 77%). Mass spectrum m/z 380, 382 (M+H)$^+$.

Step 2 A suspension of 5-bromo-$N^2$-methoxy-$N^2$-methyl-2,3,4,9-tetrahydro-1H-carbazole-2,8-dicarboxamide (1.73 g, 4.55 mmol) in THF (40 mL) was treated with lithium aluminum hydride (0.259 g, 6.82 mmol) portionwise over 30 min at 0° C. After 20 min, more lithium aluminum hydride (120 mg) was added portionwise, and the mixture was stirred at rt for 20 min. The reaction mixture was cooled to 0° C. and treated dropwise with 0.5 M hydrochloric acid, and the resulting mixture was extracted three times with DCM. The combined organic phases were washed with NaHCO3 (aq) and water, dried and concentrated to provide 5-bromo-2-formyl-2,3,4,9-tetrahydro-1H-carbazole-8-carboxamide as a yellow solid (1.31 g, 90%), used without further purification. Mass spectrum m/z 321, 323 (M+H)$^+$.

Step 3 A solution of crude 5-bromo-2-formyl-2,3,4,9-tetrahydro-1H-carbazole-8-carboxamide (1 g, 3.11 mmol) in DCM (20 mL) was treated with ammonium acetate (3.60 g, 46.7 mmol) and sodium triacetoxyborohydride (0.990 g, 4.67 mmol) at rt and stirred for 10 min. THF (2 mL) was added to try to dissolve the starting material, but no reaction was observed after 1 h. The mixture was concentrated and the residue was dissolved in DMSO (10 mL). Additional sodium triacetoxyborohydride (500 mg) was added and the mixture was stirred at rt overnight. The mixture was diluted with water and the precipitate was removed by filtration. The filtrate was treated with 1 M aqueous sodium hydroxide and extracted three times with EtOAc. The combined organic phases were washed with water, dried and concentrated to provide 2-(aminomethyl)-5-bromo-2,3,4,9-tetrahydro-1H-carbazole-8-carboxamide as a white solid (130 mg, 13%), used without further purification. Mass spectrum m/z 322, 324 (M+H)$^+$.

Step 4 A suspension of 2-(aminomethyl)-5-bromo-2,3,4,9-tetrahydro-1H-carbazole-8-carboxamide (130 mg, 0.403 mmol) and TEA (0.067 mL, 0.484 mmol) in THF (2 mL) was treated with 4-bromobutanoyl chloride (74.8 mg, 0.403 mmol). The mixture was stirred at rt for 20 min, diluted with DCM, washed with NaHCO3 (aq), dried and concentrated. The residue was purified by column chromatography (eluting with EtOAc) to provide 5-bromo-2-((4-bromobutanamido)methyl)-2,3,4,9-tetrahydro-1H-carbazole-8-carboxamide as a white solid (80 mg, 42%). Mass spectrum m/z 470, 472, 474 (M+H)$^+$.

Step 5 A solution of 5-bromo-2-(4-bromobutanamido)methyl)-2,3,4,9-tetrahydro-1H-carbazole-8-carboxamide (80 mg, 0.170 mmol) in DMF (1 mL) was treated with NaH (60% in mineral oil, pre-washed with hexane, 34 mg, 0.849 mmol). The mixture was stirred at rt for 30 min, the was diluted with water and extracted three times with DCM. The combined organic phases were dried and concentrated, and the residue was purified by column chromatography (eluting with 5% aqueous ammonium hydroxide-methanol-DCM) to provide 5-bromo-2-((2-oxopyrrolidin-1-yl)methyl)-2,3,4,9-tetrahydro-1H-carbazole-8-carboxamide as a light yellow solid, used without further purification (40 mg, 60%). Mass spectrum m/z 390, 392 (M+H)$^+$.

Step 6 Using the procedure of Example 3-2,5-bromo-2-((2-oxopyrrolidin-1-yl)methyl)-2,3,4,9-tetrahydro-1H-carbazole-8-carboxamide (40 mg, 0.102 mmol) and Intermediate 50-1 (22.5 mg, 0.102 mmol) were converted into 5-(3-amino-2-methylphenyl)-2-((2-oxopyrrolidin-1-yl)methyl)-2,3,4,9-tetrahydro-1H-carbazole-8-carboxamide as a white solid (2 mg, 5%). $^1$H NMR (400 MHz, methanol-d$_4$) δ 7.51-7.56 (1 H, m), 6.94-7.01 (1 H, m), 6.72-6.81 (2 H, m), 6.57 (1 H, t, J=6.59 Hz), 3.44-3.53 (2 H, m), 3.28-3.32 (7 H, m), 2.84 (1 H, dd, J=16.70, 4.83 Hz), 2.36-2.50 (3 H, m), 2.11-2.22 (1 H, m), 1.96-2.10 (4 H, m), 1.77-1.85 (3 H, m), 1.65 (1H, sxt), 1.20-1.37 (2 H, m). Mass spectrum m/z 417.3 (M+H)$^+$.

Example 47-1

Preparation of 5-(2-fluorophenyl)-2,3,4,9-tetrahydro-1H-carbazole-8-carboxamide

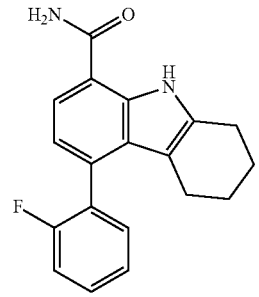 [SMILES: NC(=O)c1ccc(-c2ccccc2F)c2c3c([nH]c12)CCCC3]

Step 1 A mixture of methyl 2-amino-4-bromobenzoate (3.06 g, 13.3 mmol), 2-fluorophenylboronic acid (2.23 g, 16.0 mmol), tetrakis(triphenylphosphine)palladium (1.54 g, 1.33 mmol) and 1 M aqueous sodium carbonate (16.6 mL, 16.6 mmol) in 1,2-dimethoxyethane (66.5 mL) was stirred at 90° C. overnight. The mixture was cooled to rt, filtered through a pad of Celite and the solids were rinsed with EtOAc. The filtrate was washed with water and brine, dried and concentrated. The residue was purified by column chromatography (eluting with a gradient from hexane to 90:10 hexane-EtOAc) to provide methy 3-amino-2'-fluorobiphenyl-4-carboxylate (2.63 g, 81%) as a white solid. $^1$H NMR (400 MHz, chloroform-d) δ 7.90 (d, J=8.25 Hz, 1H), 7.38-7.46 (m, 1H), 7.27-7.35 (m, 1H), 7.08-7.22 (m, 2H), 6.85 (s, 1H), 6.82 (d, J=8.25 Hz, 1H), 5.83 (br s, 1H), 3.88 (s, 3H). Mass spectrum m/z 246.1 (M+H)$^+$.

Step 2 A solution of methyl 3-amino-2'-fluorobiphenyl-4-carboxylate (0.425 g, 1.73 mmol) in 1 M aqueous sodium hydroxide (6.9 mL, 6.9 mmol) and THF (3.5 mL) was heated at reflux overnight. The mixture was cooled to rt and concentrated almost to dryness. 6 M hydrochloric acid (0.1 mL) was added to the solution at 0° C. and the precipitate was collected by filtration, washed with water and dried to give 3-amino-2'-fluorobiphenyl-4-carboxylic acid (0.338 g, 84%) as a white solid. $^1$H NMR (400 MHz, DMSO-d$_6$) δ 7.87, d, 8.25, 1H), 7.50 (t, J=7.97, 1H), 7.47-7.55 (m, 1H), 7.25-7.36 (m, 2H), 6.92 (br s, 1H), 6.76 (s, 1H), 6.59 (d, J=7.70, 1H). Mass spectrum m/z 232.1 (M+H)$^+$.

Step 3 A solution of 3-amino-2'-fluorobiphenyl-4-carboxylic acid (0.104 g, 0.452 mmol) in concentrated hydrochloric acid (1.13 mL) at −10° C. was treated with a solution of sodium nitrite (0.037 g, 0.542 mmol) in water (1.13 mL). The mixture was maintained at ca. 0° C. for 30 min, then was treated with a cold solution of tin(II) chloride dihydrate (0.306 g, 1.355 mmol) in water (1.13 mL) while maintaining the temperature between 0-3° C. The mixture was stirred while warming to room temperature overnight. The precipitate was collected by filtration, washed with water and ether and dried to give 2'-fluoro-3-hydrazinylbiphenyl-4-carboxylic acid as the hydrochloric acid salt (0.068 g, 48%) as a white solid. $^1$H NMR (400 MHz, DMSO-$d_6$) δ 9.09 (br s, 1H), 7.91 (d, J=8.25 Hz, 1H), 7.58 (t, J=7.15 Hz, 1H), 7.38-7.49 (m, 1H), 7.19-7.33 (m, 3H), 7.12 (d, J=8.25 Hz, 1H). Mass spectrum m/z 247.1 (M+H)$^+$.

Step 4 A solution of 2'-fluoro-3-hydrazinylbiphenyl-4-carboxylic acid (0.306 g, 1.24 mmol) and cyclohexanone (0.183 g, 1.86 mmol) in acetic acid (6.2 mL) was heated at reflux under nitrogen for 2 h. The mixture was cooled to rt and concentrated. The residue was partitioned between EtOAc and 1 M hydrochloric acid. The organic layer was washed with brine, dried and concentrated. The residue was triturated with EtOAc and DCM to give 5-(2-fluorophenyl)-2,3,4,9-tetrahydro-1H-carbazole-8-carboxylic acid (0.132 g) as a white solid. The filtrate was purified by column chromatography (eluting with a gradient from hexane to 50:50 EtOAc-hexane) to give additional product (0.029 g, 41% total). $^1$H NMR (400 MHz, DMSO-$d_6$) δ 12.95 (br s, 1 H), 10.79 (s, 1 H), 7.68 (d, J=7.15, 1 H), 7.42-7.51 (m, 1 H), 7.24-7.34 (m, 3 H), 6.87 (d, J=7.15, 1 H), 2.67-2.82 (m, 2 H), 1.89-2.10 (m, 2 H), 1.65-1.81 (m, 2 H), 1.44-1.63 (m, 2 H). Mass spectrum m/z 310.1 (M+H)$^+$.

Step 5 A solution of 5-(2-fluorophenyl)-2,3,4,9-tetrahydro-1H-carbazole-8-carboxylic acid (0.097 g, 0.314 mmol), EDC (0.072 g, 0.376 mmol) and HOBT (0.058 g, 0.376 mmol) in THF (2.5 mL) and DCM (0.6 mL) was treated with 28% aqueous ammonium hydroxide (0.073 mL, 1.88 mmol). The mixture was stirred overnight. More EDC (0.072 g, 0.376 mmol), HOBT (0.058 g, 0.376 mmol) and 28% aqueous ammonium hydroxide (0.073 mL, 1.88 mmol) were added, and the mixture was heated at 50° C. in a sealed tube for 2 days. The mixture was cooled to rt, dissolved in EtOAc, washed with NaHCO3 (aq) and brine, dried and concentrated. The residue was purified by column chromatography (eluting with a gradient from DCM to 98:2 DCM-methanol) to give 5-(2-fluorophenyl)-2,3,4,9-tetrahydro-1H-carbazole-8-carboxamide (0.030 g, 30%) as an off-white solid. Mass spectrum m/z 309.0 (M+H)$^+$.

Example 47-2

Preparation of 5-(2-fluorophenyl)-3-phenoxy-2,3,4,9-tetrahydro-1H-carbazole-8-carboxamide

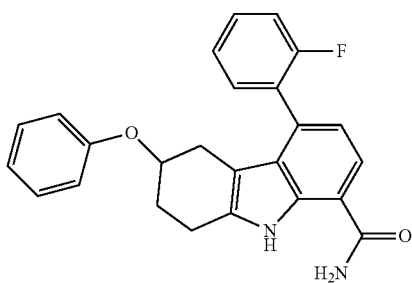 [SMILES: NC(=O)c1ccc(-c2ccccc2F)c2c3c([nH]c12)CCC(Oc1ccccc1)C3]

Step 1 A solution of 1,4-dioxaspiro[4.5]decan-8-ol (1.00 g, 6.32 mmol), phenol (0.714 g, 7.59 mmol) and triphenylphosphine (1.824 g, 6.95 mmol) in DCM (21.07 mL) was treated with diisopropyl azodicarboxylate (1.48 mL, 7.59 mmol) and the mixture was stirred at rt for 5 days. The mixture was concentrated and the residue was purified by column chromatography, eluting with a gradient from hexane to 80:20 hexane-EtOAc). The crude product was dissolved in EtOAc and the solution was washed twice with 1 M aqueous sodium hydroxide and brine, dried and concentrated to provide 8-phenoxy-1,4-dioxaspiro[4.5]decane as a colorless liquid (0.468 g, 32%). $^1$H NMR (500 MHz, chloroform-d) δ 7.16-7.24 (2 H, m), 6.81-6.89 (3 H, m), 4.30-4.38 (1 H, m), 3.85-3.93 (4 H, m), 1.80-1.90 (6 H, m), 1.50-1.59 (2 H, m).

Step 2 A solution of 8-phenoxy-1,4-dioxaspiro[4.5]decane (0.460 g, 1.963 mmol) in THF (5.0 mL) and 3 M hydrochloric acid (5 mL) was stirred at rt for 2 days. The mixture was extracted with EtOAc, and the organic phase was washed with brine, dried and concentrated to provide 4-phenoxycyclohexanone as a colorless oil (0.344 g, 92%). $^1$H NMR (500 MHz, chloroform-d) δ 7.22-7.27 (2 H, m), 6.87-6.94 (3 H, m), 4.62-4.66 (1 H, m), 2.59-2.68 (2 H, m), 2.19-2.30 (4 H, m), 1.96-2.04 (2 H, m). Mass spectrum m/z 191.1 (M+H)$^+$.

Step 3 Using the procedures of Example 47-1 Steps 4 and 5, 4-phenoxycyclohexanone was converted to 5-(2-fluorophenyl)-3-phenoxy-2,3,4,9-tetrahydro-1H-carbazole-8-carboxamide in 2.1% overall yield. $^1$H NMR (500 MHz, DMSO-$d_6$) δ 11.06 (1 H, s), 8.13 (1 H, br. s.), 7.71 (1 H, d, J=7.1 Hz), 7.26-7.53 (7H, m), 6.89-6.97 (4 H, m), 4.65-4.78 (1 H, m), 2.95 (2 H, t, J=6.3 Hz), 2.48 (1 H, dd, J=15.4, 3.8 Hz), 2.24-2.41 (1 H, m), 2.13 (1 H, br. s.), 1.91-2.04 (1 H, m). Mass spectrum m/z 401.2 (M+H)$^+$.

Intermediate 47-3(a)

Preparation of 5-(2-fluorophenyl)-3-(pyrimidin-5-yloxy)-2,3,4,9-tetrahydro-1H-carbazole-8-carboxamide

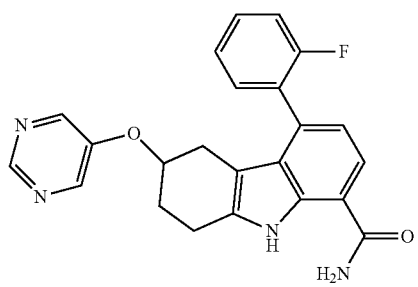 [SMILES: NC(=O)c1ccc(-c2ccccc2F)c2c3c([nH]c12)CCC(Oc1cncnc1)C3]

Step 1 Using the procedure of Example 47-1 Step 4, 2'-fluoro-3-hydrazinylbiphenyl-4-carboxylic acid (0.190 g, 0.770 mmol) and 4-hydroxycyclohexanone (0.132 g, 1.154 mmol) were converted into 5-(2-fluorophenyl)-3-hydroxy-2,3,4,9-tetrahydro-1H-carbazole-8-carboxylic acid as a light yellow solid (0.089 g, 36%). Mass spectrum m/z 326.1 (M+H)$^+$.

Step 2 A solution of 5-(2-fluorophenyl)-3-hydroxy-2,3,4,9-tetrahydro-1H-carbazole-8-carboxylic acid (0.069 g, 0.213 mmol) in DMF (1.07 mL) was treated with ammonium chloride (0.023 g, 0.427 mmol), HOAT (0.058 g, 0.427 mmol), EDC (0.082 g, 0.427 mmol) and DIEA (0.149 mL, 0.853 mmol) and stirred over a weekend. The mixture was diluted with DCM, washed with 5% hydrochloric acid, NaHCO3 (aq), brine and 10% aqueous lithium chloride, dried and concentrated to give 5-(2-fluorophenyl)-3-hydroxy-2,3,4,9-tetrahydro-1H-carbazole-8-carboxamide as a light yellow foam (0.045 g, 65%). Mass spectrum m/z 325.1 (M+H)$^+$.

Step 3 Using the procedure of Example 47-2 Step 1,5-(2-fluorophenyl)-3-hydroxy-2,3,4,9-tetrahydro-1H-carbazole-8-carboxamide (0.099 g, 0.306 mmol) and pyrimidin-5-ol (0.035 g, 0.368 mmol) were converted to 5-(2-fluorophenyl)-3-(pyrimidin-5-yloxy)-2,3,4,9-tetrahydro-1H-carbazole-8-carboxamide as a light yellow foam (0.054 g, 34%). Mass spectrum m/z 403.1 (M+H)$^+$.

Example 48-1

Preparation of 4-(2-fluorophenyl)-9H-carbazole-1-carboxamide

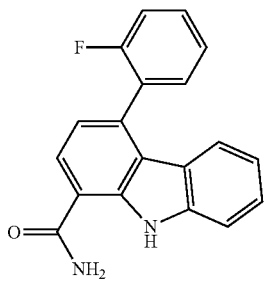 [SMILES: NC(=O)c1ccc(-c2ccccc2F)c2c1[nH]c1ccccc12]

A solution of 5-(2-fluorophenyl)-2,3,4,9-tetrahydro-1H-carbazole-8-carboxamide (Example 47-1, 0.024 g, 0.078 mmol) in toluene (0.39 mL) was treated with 2,3-dichloro-5,6-dicyano-1,4-benzoquinone (0.039 g, 0.171 mmol), and the mixture was heated to reflux. After 4 h, the mixture was cooled to rt. The solid was removed by filtration and rinsed with EtOAc. The filtrate was concentrated, diluted with methanol and subjected to preparative HPLC. The product-containing effluent was treated with NaHCO3 (aq) and concentrated. The residue was extracted three times with DCM, and the combined organic layers were dried and concentrated to give 4-(2-fluorophenyl)-9H-carbazole-1-carboxamide (0.0045 g, 19%) as a light tan solid. Mass spectrum m/z 305.0 (M+H)$^+$.

The following compounds were also prepared using procedures demonstrated in Example 48-1.

| Example | Starting material | Compound name | Mass spectrum |
|---|---|---|---|
| 48-2 | Example 47-2 | 4-(2-fluorophenyl)-6-phenoxy-9H-carbazole-1-carboxamide | 397.0 (M + H)$^+$ |
| 48-3 | Intermediate 47-3(a) | 4-(2-fluorophenyl)-6-(pyrimidin-5-yloxy)-9H-carbazole-1-carboxamide | 399.0 (M + H)$^+$ |
| 48-4 | Example 24-15 | 4-(2,6-difluorophenyl)-N$^7$-(tetrahydro-2H-pyran-4-yl)-9H-carbazole-1,7-dicarboxamide | 450.2 (M + H)$^+$ |

Example 49-1

Preparation of 7-(1-hydroxycyclopropyl)-4-(2-methyl-3-(1-oxoisoindolin-2-yl)phenyl)-9H-carbazole-1-carboxamide

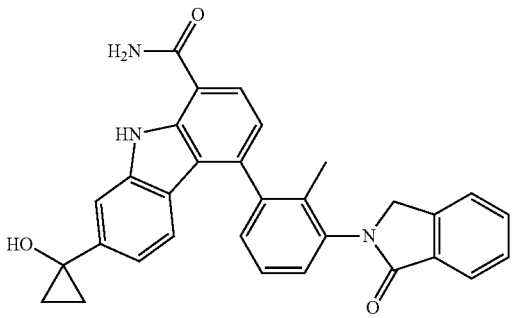 [SMILES: Cc1c(-c2ccc(C(N)=O)c3[nH]c4cc(C5(O)CC5)ccc4c23)cccc1N1Cc2ccccc2C1=O]

Step 1 A solution of ethyl 5-bromo-8-carbamoyl-9H-carbazole-2-carboxylate (Intermediate 48-1, 0.275 g, 0.761 mmol) was treated with titanium (IV) isopropoxide (0.31 mL, 1.07 mmol), followed by ethylmagnesium chloride (2 M in THF, 3.81 mL, 7.61 mmol). The mixture was stirred at rt for 1 h, then was cooled on ice and treated with water (10 mL). After 30 min, the solid was removed by filtration and rinsed with ether (150 mL). The organic layer was dried and concentrated to give 4-bromo-7-(1-hydroxycyclopropyl)-9H-carbazole-1-carboxamide as a yellow solid (0.220 g, 79%). $^1$H NMR (400 MHz, DMSO-d$_6$) δ 11.65 (1 H, s), 8.52 (1 H, d, J=8.4 Hz), 8.25 (1 H, br. s.), 7.84-7.89 (2 H, m), 7.61 (1 H, br. s.), 7.45 (1 H, d, J=8.1 Hz), 7.13 (1 H, dd, J=8.5, 1.7 Hz), 6.11 (1 H, s), 1.21-1.27 (2 H, m), 1.06-1.11 (2 H, m).

Step 2 A solution of 4-bromo-7-(1-hydroxycyclopropyl)-9H-carbazole-1-carboxamide (0.151 g, 0.436 mmol), tert-butylchlorodimethylsilane (0.079 g, 0.524 mmol) and imidazole (0.074 g, 1.091 mmol) in DMF (2.2 mL) was stirred at rt for 18 h. Additional tert-butylchlorodimethylsilane (0.079 g, 0.524 mmol) and imidazole (0.074 g, 1.091 mmol) were added and stirring was continued for 1 h. The mixture was diluted with EtOAc (75 mL) and washed seven times with brine. The organic layer was dried and concentrated and the residue was purified by column chromatography (eluting with a gradient from 90:10 to 50:50 hexane-EtOAc) to give 4-bromo-7-(1-(tert-butyldimethylsilyloxy)cyclopropyl)-9H-carbazole-1-carboxamide (0.144 g, 67%).

Step 3 Using the procedure of Example 31-1,4-bromo-7-(1-(tert-butyldimethylsilyloxy)cyclopropyl)-9H-carbazole-1-carboxamide (0.059 g, 0.129 mmol) and 2-(2-methyl-3-(4,4,5,5-tetramethyl-1,3,2-dioxaborolan-2-yl)phenyl)isoindolin-1-one (Intermediate 50-4, 0.054 g, 0.154 mmol) were converted to 7-(1-(tert-butyldimethylsilyloxy)cyclopropyl)-4-(2-methyl-3-(1-oxoisoindolin-2-yl)phenyl)-9H-carbazole-1-carboxamide (0.048 g, 60%).

Step 4 A solution of 7-(1-(tert-butyldimethylsilyloxy)cyclopropyl)-4-(2-methyl-3-(1-oxoisoindolin-2-yl)phenyl)-9H-carbazole-1-carboxamide (0.039 g, 0.065 mmol) in THF (0.66 mL) was treated with tetra-n-butylammonium fluoride (1 M in THF, 0.098 mL, 0.098 mmol). After 10 min, the mixture was combined with an identical reaction mixture done on 22% of the scale described, and the mixture was concentrated. The residue was purified by preparative HPLC. The appropriate effluent fractions were treated with NaHCO3 (aq) and partially concentrated. The aqueous residue was extracted three times with DCM and the combined organic phases were dried and concentrated to give 7-(1-hydroxycyclopropyl)-4-(2-methyl-3-(1-oxoisoindolin-2-yl)phenyl)-9H-carbazole-1-carboxamide as a white solid (23.3 mg, 60%). $^1$H NMR (500 MHz, DMSO-d$_6$) δ 11.42 (1 H, s), 8.18 (1 H, br. s.), 7.98 (1 H, d, J=7.7 Hz), 7.80 (1 H, d, J=7.7 Hz), 7.72 (1 H, s), 7.68 (2 H, d, J=3.8 Hz), 7.60 (1H, d, J=7.7 Hz), 7.56 (1 H, ddd, J=7.8, 4.1, 4.0 Hz), 7.49 (2 H, t, J=7.7 Hz), 7.33 (1H, d, J=7.1 Hz), 7.01 (1 H, d, J=7.7 Hz), 6.95 (1 H, d, J=8.2 Hz), 6.79 (1 H, d, J=8.2 Hz), 5.95 (1 H, s), 4.90-5.02 (2 H, m), 1.84 (3 H, s), 1.07-1.15 (2 H, m), 0.91-1.00 (2 H, m). Mass spectrum m/z 488.3 (M+H)$^+$.

Example 50-1

Preparation of benzyl 8-carbamoyl-5-(2-fluorophenyl)-9H-carbazol-2-ylcarbamate

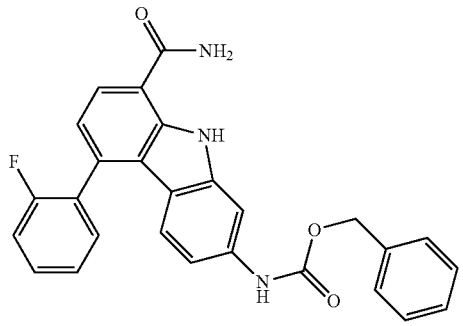 [SMILES: NC(=O)c1ccc(-c2ccccc2F)c2c1[nH]c1cc(NC(=O)OCc3ccccc3)ccc12]

A suspension of 8-carbamoyl-5-(2-fluorophenyl)-9H-carbazole-2-carboxylic acid (Example 23-2, 320 mg, 0.919 mmol) and 4 Å molecular sieves (60 mg) in 1,4-dioxane (15 mL) at 50° C. was treated with TEA (0.316 mL, 2.269 mmol) and diphenylphosphoryl azide (0.491 mL, 2.269 mmol). The mixture was stirred at 50° C. for 1.5 h, followed by addition of phenylmethanol (0.951 mL, 9.19 mmol). The mixture was then stirred at 80° C. for 18 h. The cooled mixture was partitioned between EtOAc and NaHCO3 (aq). The organic phase was washed with brine, dried and concentrated The residue was purified by column chromatography (eluting with 35:65 hexane-EtOAc). The residue after concentration was suspended in hexane and the precipitate was collected by filtration to provide benzyl 8-carbamoyl-5-(2-fluorophenyl)-9H-carbazol-2-ylcarbamate as an off-white solid (400 mg, 83%). $^1$H NMR (400 MHz, DMSO-d$_6$) δ 11.50 (s, 1 H) 9.83 (s, 1 H) 8.15 (br. s., 1 H) 8.00 (s, 1 H) 7.91 (d, J=7.69 Hz, 1 H) 7.45-7.64 (m, 3 H) 7.32-7.46 (m, 7 H) 7.03 (d, J=7.91 Hz, 1 H) 6.87-6.98 (m, 2 H) 5.15 (s, 2 H). Mass spectrum m/z 454.1 (M+H)$^+$.

The following Examples/Intermediates were also prepared using procedures demonstrated in Example 50-1.

| Example/Intermediate | Starting material | Compound name | Mass spectrum |
|---|---|---|---|
| Intermediate 50-2(a) | Intermediate 23-3 | benzyl 8-carbamoyl-5-(2,6-difluorophenyl)-2,3,4,9-tetrahydro-1H-carbazol-2-ylcarbamate | 476.1 (M + H)$^+$ |
| 50-3 | Intermediate 49-1 | benzyl 5-bromo-8-carbamoyl-9H-carbazol-2-ylcarbamate | 438, 440 (M + H)$^+$ |
| Intermediate 50-4(a) | Intermediate 49-3 | benzyl 5-bromo-8-carbamoyl-2,3,4,9-tetrahydro-1H-carbazol-2-ylcarbamate | 442, 444 (M + H)$^+$ |

Example 51-1

Preparation of benzyl 5-(3-amino-2-methylphenyl)-8-carbamoyl-2,3,4,9-tetrahydro-1H-carbazol-2-ylcarbamate

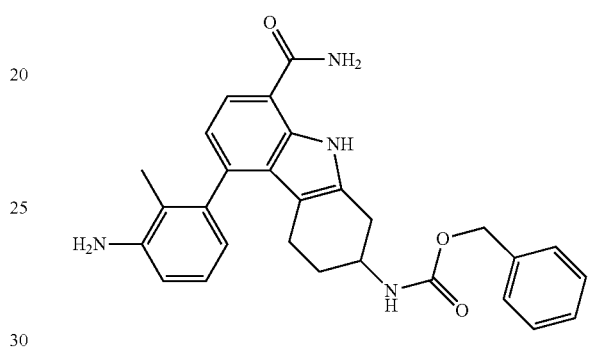

Using the procedure of Example 3-2, benzyl 5-bromo-8-carbamoyl-2,3,4,9-tetrahydro-1H-carbazol-2-ylcarbamate (Intermediate 50-4(a), 300 mg, 0.678 mmol) and 2-methyl-3-(4,4,5,5-tetramethyl-1,3,2-dioxaborolan-2-yl)aniline (Intermediate 50-1, 237 mg, 1.017 mmol) were converted into benzyl 5-(3-amino-2-methylphenyl)-8-carbamoyl-2,3,4,9-tetrahydro-1H-carbazol-2-ylcarbamate, TFA salt, isolated as a white solid after preparative HPLC purification (60 mg, 15%). $^1$H NMR (400 MHz, methanol-d$_4$) δ 7.63 (1 H, dd, J=7.7, 2.9 Hz), 7.18-7.46 (8 H, m), 6.82 (1H, dd, J=7.5, 2.8 Hz), 5.10 (2 H, s), 3.90 (1 H, br. s.), 3.14 (1 H, d, J=4.8 Hz), 2.72 (1H, br. s.), 1.77-2.19 (6 H, m), 1.51-1.68 (1 H, m). Mass spectrum m/z 469.3 (M+H)$^+$.

Example 51-2

Preparation of benzyl 5-(3-amino-2-methylphenyl)-8-carbamoyl-9H-carbazol-2-ylcarbamate

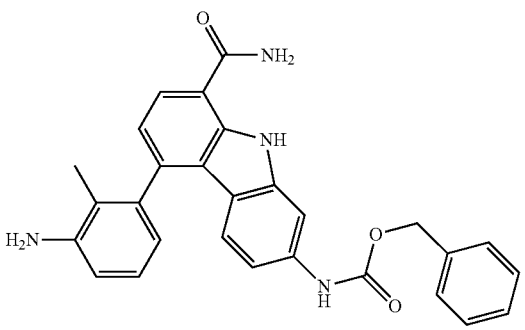 [SMILES: Cc1c(N)cccc1-c1ccc(C(N)=O)c2[nH]c3cc(NC(=O)OCc4ccccc4)ccc3c12]

Using the procedure of Example 3-2, benzyl 5-bromo-8-carbamoyl-9H-carbazol-2-ylcarbamatee (Example 50-3, Using the procedure of Example 3-2, benzyl 5-bromo-8-carbamoyl-9H-carbazol-2-ylcarbamatee (Example 50-3, 1.00 g, 2.28 mmol) and 2-methyl-3-(4,4,5,5-tetramethyl-1,3,2-dioxaborolan-2-yl)aniline (Intermediate 50-1, 638 mg, 2.74 mmol) were converted into benzyl 5-(3-amino-2-methylphenyl)-8-carbamoyl-9H-carbazol-2-ylcarbamate isolated as an off-white solid after trituration in methanol (ca. 80-85% purity, 860 mg, 65%). A portion was purified by preparative HPLC to provide the TFA salt. $^1$H NMR (400 MHz, DMSO-$d_6$) δ 11.45 (1 H, s), 9.81 (1 H, s), 8.13 (1 H, br. s.), 7.95 (1 H, s), 7.89 (1 H, d, J=7.5 Hz), 7.29-7.51 (6 H, m), 7.25 (1 H, d, J=7.9 Hz), 7.16 (1 H, d, J=7.5 Hz), 6.81-6.96 (3 H, m), 6.65 (1 H, d, J=8.8 Hz), 5.14 (2 H, s), 1.83 (3 H, s). Mass spectrum m/z 465.1 (M+H)$^+$.

Example 51-3

Preparation of benzyl 8-carbamoyl-5-(2-methyl-3-(1-oxoisoindolin-2-yl)phenyl)-9H-carbazol-2-ylcarbamate

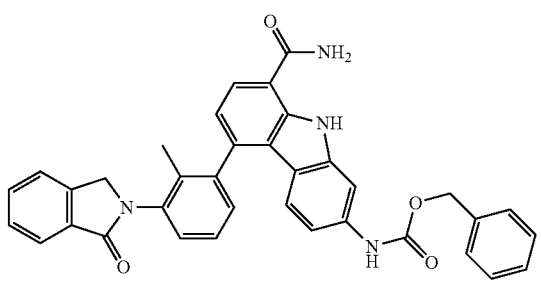 [SMILES: Cc1c(-c2ccc(C(N)=O)c3[nH]c4cc(NC(=O)OCc5ccccc5)ccc4c23)cccc1N1Cc2ccccc2C1=O]

Using the procedure of Example 31-1, benzyl 5-bromo-8-carbamoyl-9H-carbazol-2-ylcarbamate (Example 50-3, 400 mg, 0.913 mmol) and 2-(2-methyl-3-(4,4,5,5-tetramethyl-1,3,2-dioxaborolan-2-yl)phenyl)isoindolin-1-one (Intermediate 50-4, 414 mg, 1.19 mmol) were converted into benzyl 8-carbamoyl-5-(2-methyl-3-(1-oxoisoindolin-2-yl)phenyl)-9H-carbazol-2-ylcarbamate as a white solid (90% purity, 530 mg, 90%). $^1$H NMR (400 MHz, chloroform-d) δ 10.58 (1 H, s), 7.96 (1 H, d, J=7.91 Hz), 7.85 (1 H, br. s.), 7.61 (2 H, d, J=7.47 Hz), 7.54 (2 H, d, J=4.83 Hz), 7.33-7.45 (7 H, m), 7.06 (2 H, dd, J=12.52, 8.13 Hz), 6.93 (1 H, s), 6.84-6.88 (1 H, m), 5.22 (2 H, s), 4.82 (2 H, s), 1.94 (3 H, s). Mass spectrum m/z 581.3 (M+H)$^+$.

The following compound was also prepared using procedures demonstrated in Example 51-3, using Intermediate 50-15 in place of Intermediate 50-4.

| Example | Compound name | Mass spectrum |
|---|---|---|
| 51-4 | benzyl 5-(3-(5-tert-butyl-1-oxoisoindolin-2-yl)-2-methylphenyl)-8-carbamoyl-9H-carbazol-2-ylcarbamate | 637.2 (M + H)$^+$ |

Example 52-1

Preparation of benzyl 8-carbamoyl-5-(3-(5-fluoropicolinamido)-2-methylphenyl)-9H-carbazol-2-ylcarbamate

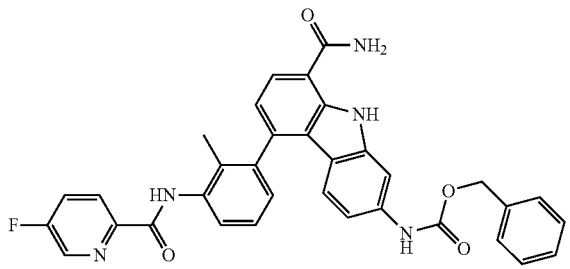 [SMILES: Cc1c(NC(=O)c2ccc(F)cn2)cccc1-c1ccc(C(N)=O)c2[nH]c3cc(NC(=O)OCc4ccccc4)ccc3c12]

A mixture of benzyl 5-(3-amino-2-methylphenyl)-8-carbamoyl-9H-carbazol-2-ylcarbamate (Example 51-2, 100 mg, 0.215 mmol), 5-fluoropicolinic acid (45.6 mg, 0.323 mmol), HOAT (44.0 mg, 0.323 mmol), and EDC (83 mg, 0.431 mmol) in DCM-THF (80:20, 12 mL) was treated with DIEA (0.150 mL, 0.861 mmol) and the solution was stirred at rt overnight. The mixture was concentrated and purified by preparative HPLC to provide benzyl 8-carbamoyl-5-(3-(5-fluoropicolinamido)-2-methylphenyl)-9H-carbazol-2-ylcarbamate as a white solid (47 mg, 36%). $^1$H NMR (400 MHz, DMSO-$d_6$) δ 11.48 (1 H, s), 10.41 (1 H, s), 9.83 (1 H, s), 8.74 (1 H, d, J=3.0 Hz), 8.27 (1 H, dd, J=8.8, 4.8 Hz), 8.09-8.21 (1 H, m), 7.96-8.03 (2 H, m), 7.94 (1 H, d, J=7.8 Hz), 7.85 (1 H, d, J=7.5 Hz), 7.29-7.51 (7 H, m), 7.15-7.21 (1 H, m), 6.91-6.98 (2 H, m), 6.79 (1 H, d, J=8.8 Hz), 5.16 (2 H, s), 1.96 (3 H, s). Mass spectrum m/z 588.1 (M+H)$^+$.

Example 52-2

Preparation of benzyl 8-carbamoyl-5-(2-methy-1-3-(picolinamido)phenyl)-2,3,4,9-tetrahydro-1H-carbazol-2-ylcarbamate

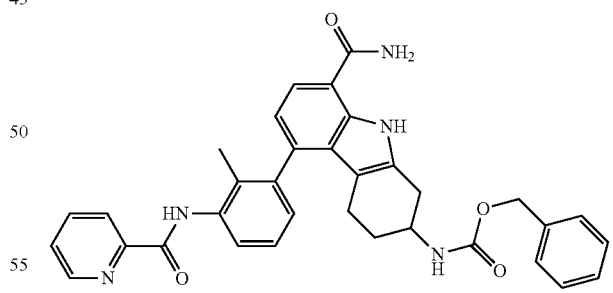

A solution of benzyl 5-(3-amino-2-methylphenyl)-8-carbamoyl-2,3,4,9-tetrahydro-1H-carbazol-2-ylcarbamate, TFA salt (Example 51-1, 55 mg, 0.094 mmol), TEA (0.066 mL, 0.472 mmol), and picolinoyl chloride hydrochloric acid salt (50.4 mg, 0.283 mmol) in DCM (8 mL) was stirred at rt overnight. The mixture was concentrated and purified by preparative HPLC to provide benzyl 8-carbamoyl-5-(2-methyl-3-(picolinamido)phenyl)-2,3,4,9-tetrahydro-1H-carbazol-2-ylcarbamate, isolated as the TFA salt, as a white solid (26 mg, 39%). $^1$H NMR (400 MHz, methanol-$d_4$) δ 8.59 (1 H, t, J=4.8 Hz), 8.14 (1 H, d, J=8.3 Hz), 7.89-7.99 (1 H, m), 7.85 (1 H, dd, J=9.9, 8.1 Hz), 7.50 (2 H, dd, J=7.7, 2.0 Hz), 7.11-7.32 (6 H, m), 7.01 (1 H, d, J=7.9 Hz), 6.74 (1 H, d, J=7.5 Hz), 4.96 (2 H, s), 3.68-3.87 (1 H, m), 2.96-3.10 (1 H, m), 2.49-2.66 (1 H, m), 1.82-2.11 (5 H, m), 1.73 (1 H, br. s.), 1.34-1.62 (1 H, m). Mass spectrum m/z 575.1 (M+H)+.

The following compounds were also prepared using procedures demonstrated in Examples 52-1 and 52-2, using the appropriate carboxylic acid or carboxylic acid chloride.

| Example/Intermediate | Compound name | Mass spectrum |
|---|---|---|
| 52-3 | benzyl 8-carbamoyl-5-(3-(4-fluorobenzamido)-2-methylphenyl)-9H-carbazol-2-ylcarbamate | 585.4 (M − H)− |
| 52-4 | benzyl 8-carbamoyl-5-(2-methyl-3-(picolinamido)phenyl)-9H-carbazol-2-ylcarbamate (prepared as the TFA salt) | 570.0 (M + H)+ |
| Intermediate 52-5 | benzyl 8-carbamoyl-5-(3-(4-fluorobenzamido)-2-methylphenyl)-2,3,4,9-tetrahydro-1H-carbazol-2-ylcarbamate | 591.3 (M + H)+ |
| Intermediate 52-6 | benzyl 8-carbamoyl-5-(2-imethyl-3-(1-methyl-1H-midazole-2-carboxamido)phenyl)-9H-carbazol-2-ylcarbamate | 573.4 (M + H)+ |

Example 53-1

Preparation of 5-(2,6-difluorophenyl)-2-ureido-2,3,4,9-tetrahydro-1H-carbazole-8-carboxamide

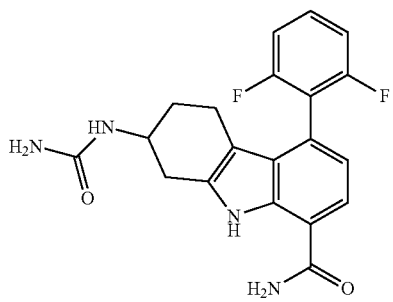 [SMILES: NC(=O)NC1CCc2c([nH]c3c(C(N)=O)ccc(-c4c(F)cccc4F)c23)C1]

A solution of 8-carbamoyl-5-(2,6-difluorophenyl)-2,3,4,9-tetrahydro-1H-carbazole-2-carboxylic acid (Intermediate 23-3, 30 mg, 0.081 mmol), diphenyl phosphorazidate (55.7 mg, 0.203 mmol) and TEA (0.028 mL, 0.203 mmol) in 1,4-dioxane (2 mL) was heated at 50° C. for 2 h. The mixture was cooled to rt and treated with 28% aqueous ammonium hydroxide (2 mL). After 20 min the mixture was diluted with DCM, washed with water, dried and concentrated, and the residue was purified by preparative HPLC. The appropriate effluent fractions were made basic with 1 M aqueous sodium hydroxide and extracted twice with DCM. The combined organic phases were washed with water, dried and concentrated to provide 5-(2,6-difluorophenyl)-2-ureido-2,3,4,9-tetrahydro-1H-carbazole-8-carboxamide as a white solid (9 mg, 28%). 1H NMR (400 MHz, methanol-d4) δ 1.60-1.72 (m, 1 H) 1.79-1.89 (m, 1 H) 2.13-2.32 (m, 2 H) 2.68 (dd, J=16.48, 7.25 Hz, 1 H) 3.13 (dd, J=16.70, 5.27 Hz, 1 H) 3.98-4.09 (m, J=6.15 Hz, 1 H) 4.58 (s, 1 H) 6.91 (d, J=7.91 Hz, 1 H) 7.05 (t, J=8.13 Hz, 2 H) 7.38-7.50 (m, 1 H) 7.60 (d, J=7.91 Hz, 1 H). Mass spectrum m/z 385.1 (M+H)+.

Example 54-1

Preparation of 7-amino-4-(2-fluorophenyl)-9H-carbazole-1-carboxamide

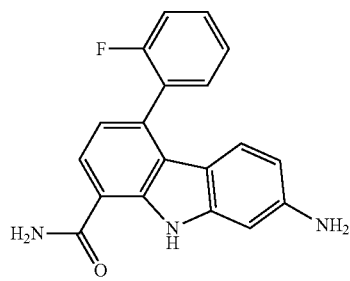 [SMILES: NC(=O)c1ccc(-c2ccccc2F)c2c1[nH]c1cc(N)ccc12]

A mixture of benzyl 8-carbamoyl-5-(2-fluorophenyl)-9H-carbazol-2-ylcarbamate (Example 50-1, 400 mg, 0.882 mmol), 10% palladium on charcoal (94 mg, 0.088 mmol) and ammonium formate (334 mg, 5.29 mmol) in methanol (20 mL) was heated at reflux for 1 h. The mixture was cooled to rt, diluted with methanol and filtered through a Celite pad. The filtrate was concentrated to give 7-amino-4-(2-fluorophenyl)-9H-carbazole-1-carboxamide in quantitative yield. 1H NMR (400 MHz, DMSO-d6) δ 11.07 (s, 1 H) 8.11 (br. s., 1 H) 7.78 (d, J=7.78 Hz, 1 H) 7.51 (d, J=2.01 Hz, 2 H) 7.35-7.47 (m, 3 H) 6.93 (d, J=7.78 Hz, 1 H) 6.79-6.84 (m, 1 H) 6.72 (d, J=8.03 Hz, 1 H) 6.24 (dd, J=8.41, 1.88 Hz, 1 H) 5.22 (s, 2 H). Mass spectrum m/z 320.1 (M+H)+.

Example 54-2

Preparation of 7-amino-4-bromo-9H-carbazole-1-carboxamide

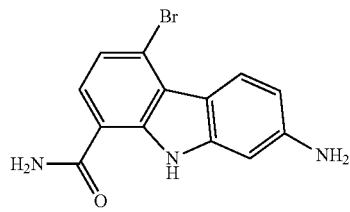 [SMILES: NC(=O)c1ccc(Br)c2c1[nH]c1cc(N)ccc12]

A suspension of benzyl 5-bromo-8-carbamoyl-9H-carbazol-2-ylcarbamate (Example 50-3, 2.18 g, 4.97 mmol) in hydrogen bromide (30-35% in acetic acid, 11.9 mL, 59.7 mmol) was stirred at rt for 30 min. The mixture was diluted with ether (100 mL) and the precipitate was collected by filtration, washed with ether and dried to provide 7-amino-4-bromo-9H-carbazole-1-carboxamide, hydrobromide salt, as a light yellow solid (2.20 g). 1H NMR (400 MHz, DMSO-d6) δ 12.02 (1 H, s), 8.69 (1 H, d, J=8.5 Hz), 8.28 (1 H, br. s.), 7.91 (1 H, d, J=8.0 Hz), 7.84 (1 H, d, J=1.8 Hz), 7.65 (1H, br. s.), 7.51 (1 H, d, J=8.3 Hz), 7.25 (1 H, dd, J=8.4, 1.9 Hz). Mass spectrum m/z 304, 306 (M+H)+. The salt was partitioned between EtOAc and NaHCO3 (aq). Residual solid was collected by filtration, washed with EtOAc and water and dried. The organic phase of the filtrate was separated, washed with brine, and dried and concentrated. The solid residue was combined with the filtered solid, dissolved in acetone, filtered to remove undissolved solid, and the filtrate was concentrated to provide 7-amino-4-bromo-9H-carbazole-1-carboxamide, hydrobromide salt, as a light yellow solid (1.62 g, 96%).

Examples 54-3 and 54-4

Preparation of 7-amino-4-(3-(5-tert-butyl-1-oxoisoindolin-2-yl)-2-methylphenyl)-9H-carbazole-1-carboxamide and 7-amino-6-bromo-4-(3-(5-tert-butyl-1-oxoisoindolin-2-yl)-2-methylphenyl)-9H-carbazole-1-carboxamide

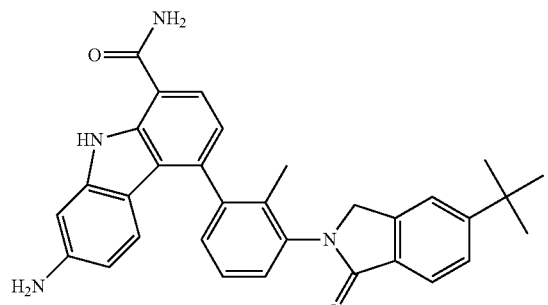

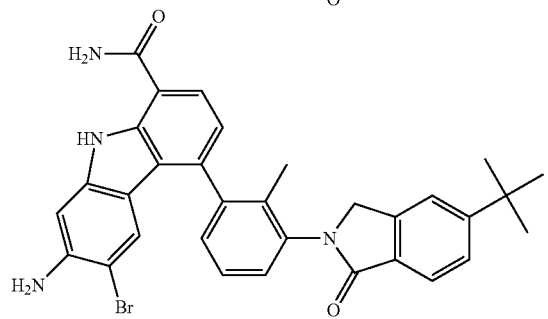

A solution of benzyl 5-(3-(5-tert-butyl-1-oxoisoindolin-2-yl)-2-methylphenyl)-8-carbamoyl-9H-carbazol-2-ylcarbamate (Example 51-4, 65 mg, 0.102 mmol) in hydrogen bromide (30-35% in acetic acid, 5 mL, 27.6 mmol) was stirred at rt for 1.5 h. The mixture was diluted with DCM and concentrated. The residue was dissolved in DCM containing a small amount of methanol and the solution was mixed with 1 M aqueous sodium hydroxide. The organic phase was separated, washed with water, dried and concentrated, and the residue was triturated with hexane. The residue was purified by column chromatography (eluting with a gradient from 97:2.7:0.3 to 90:9:1 DCM-methanol-28% aqueous ammonium hydroxide) to provide 7-amino-4-(3-(5-tert-butyl-1-oxoisoindolin-2-yl)-2-methylphenyl)-9H-carbazole-1-carboxamide as a white solid (Example 54-3, 45 mg, 88%) as a white solid. $^1$H NMR (400 MHz, chloroform-d) δ 10.32 (1 H, s), 7.89 (1 H, d, J=8.35 Hz), 7.57 (1 H, d, J=7.91 Hz), 7.49-7.55 (2 H, m), 7.35-7.47 (3 H, m), 7.04 (1 H, d, J=7.47 Hz), 6.93 (1 H, d, J=8.35 Hz), 6.74 (1 H, d, J=1.76 Hz), 6.46 (1 H, dd, J=8.57, 1.98 Hz), 4.79 (2 H, d, J=2.20 Hz), 3.84 (2 H, br. s.), 1.96 (3 H, s), 1.40 (9 H, s). Mass spectrum m/z 503.3 (M+H)$^+$. Also obtained was 7-amino-6-bromo-4-(3-(5-tert-butyl-1-oxoisoindolin-2-yl)-2-methylphenyl)-9H-carbazole-1-carboxamide as a white solid (Example 54-4, 5 mg, 8%). $^1$H NMR (400 MHz, chloroform-d) δ 10.34 (1 H, s), 7.89 (1 H, d, J=7.91 Hz), 7.53-7.59 (3 H, m), 7.44-7.48 (2 H, m), 7.35 (1 H, dd, J=5.71, 3.08 Hz), 7.05-7.08 (2 H, m), 6.84 (1 H, s), 4.83 (2 H, s), 4.22 (2 H, br. s.), 1.95 (3 H, s), 1.40 (9 H, s). Mass spectrum m/z 581, 583 (M+H)$^+$.

Example 54-5, 54-6 and 54-7

Preparation of 7-amino-4-(3-(4-fluorobenzamido)-2-methylphenyl)-9H-carbazole-1-carboxamide, 7-(benzylamino)-4-(3-(4-fluorobenzamido)-2-methylphenyl)-9H-carbazole-1-carboxamide and 7-(dibenzylamino)-4-(3-(4-fluorobenzamido)-2-methylphenyl)-9H-carbazole-1-carboxamide

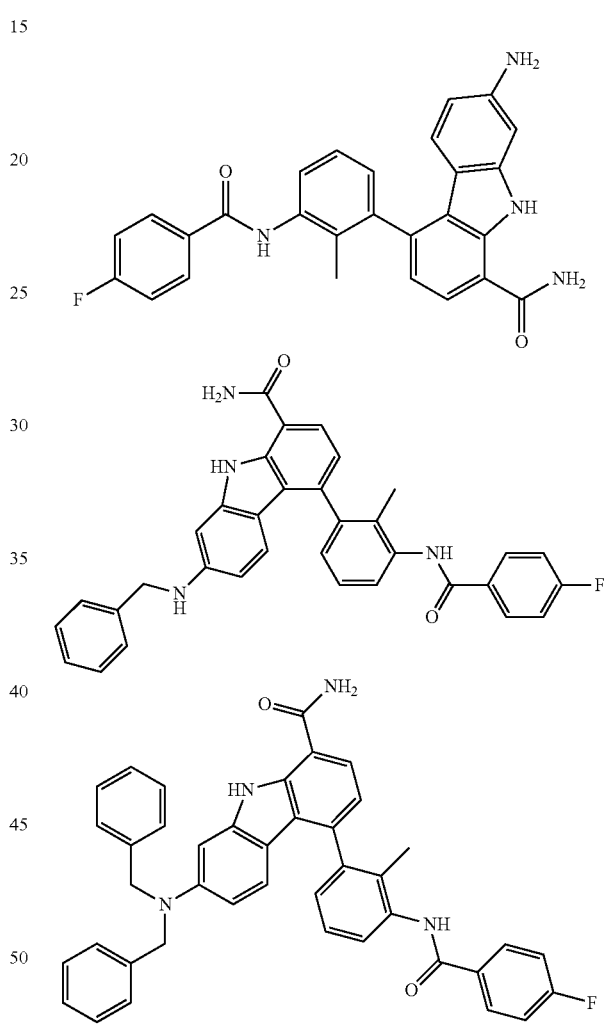

Using the procedure of Examples 54-3 and 54-4, benzyl 8-carbamoyl-5-(3-(4-fluorobenzamido)-2-methylphenyl)-9H-carbazol-2-ylcarbamate (Example 52-3, 720 mg, 1.227 mmol) was converted into 7-amino-4-(3-(4-fluorobenzamido)-2-methylphenyl)-9H-carbazole-1-carboxamide, purified by preparative HPLC and conversion to the free base (Example 54-5, 330 mg, 59%). $^1$H NMR (400 MHz, DMSO-d$_6$) δ 11.02 (1 H, s), 10.10 (1 H, s), 8.00-8.17 (3 H, m), 7.77 (1 H, d, J=7.9 Hz), 7.43-7.48 (1 H, m), 7.29-7.42 (4 H, m), 7.17 (1 H, d, J=6.6 Hz), 6.73-6.86 (2H, m), 6.60 (1 H, d, J=8.8 Hz), 6.21 (1 H, dd, J=8.6, 2.0 Hz), 5.17 (2 H, s), 1.90 (3 H, s). Mass spectrum m/z 453.0 (M+H)$^+$. Also obtained was 7-(benzylamino)-4-(3-(4-fluorobenzamido)-2-methylphenyl)-9H- carbazole-1-carboxamide (Example 54-6, 4.1 mg, 0.6%). $^1$H NMR (400 MHz, DMSO-d$_6$) δ 11.08 (1 H, br. s.), 10.09 (1 H, s), 8.02-8.12 (3 H, m), 7.79 (1 H, d, J=7.5 Hz), 7.43-7.48 (1 H, m), 7.25-7.41 (8 H, m), 7.18-7.24 (1 H, m), 7.16 (1 H, d, J=6.2 Hz), 6.84 (2 H, d, J=7.9 Hz), 6.61 (1 H, d, J=8.3 Hz), 6.28-6.36 (1 H, m), 4.29 (2 H, s), 1.89 (3 H, s). Mass spectrum m/z 543.0 (M+H)$^+$. Also obtained was 7-(dibenzylamino)-4-(3-(4-fluorobenzamido)-2-methylphenyl)-9H-carbazole-1-carboxamide (Example 54-7, 4.2 mg, 0.5%). $^1$H NMR (400 MHz, DMSO-d$_6$) δ 11.09 (1 H, s), 10.04 (1 H, s), 8.05 (3 H, dd, J=8.8, 5.3 Hz), 7.79 (1 H, d, J=7.9 Hz), 7.16-7.45 (15 H, m), 7.12 (1 H, d, J=6.2 Hz), 7.04 (1 H, d, J=2.2 Hz), 6.83 (1 H, d, J=7.5 Hz), 6.57 (1 H, d, J=8.8 Hz), 6.33 (1 H, dd, J=8.8, 2.2 Hz), 4.71 (4 H, s), 1.88 (3 H, s). Mass spectrum m/z 633.1 (M+H)$^+$.

The following compounds were also prepared using procedures demonstrated in Examples 54-1 through 54-7.

A mixture of 7-amino-4-(2-fluorophenyl)-9H-carbazole-1-carboxamide (Example 54-1, 30 mg, 0.094 mmol), 2-chloro-N-(2-chloroethyl)-N-methylethanamine hydrochloric acid salt (27.1 mg, 0.141 mmol) and sodium carbonate (49.8 mg, 0.470 mmol) in tert-butanol (2 mL) was heated at reflux overnight. The mixture was cooled to rt and concentrated. The residue was purified by preparative HPLC to provide 4-(2-fluorophenyl)-7-(4-methylpiperazin-1-yl)-9H-carbazole-1-carboxamide, TFA salt, as a light yellow solid (11 mg, 20%). $^1$H NMR (400 MHz, DMSO-d$_6$) δ 11.28 (s, 1 H) 8.13 (br. s., 1 H) 7.85 (d, J=7.91 Hz, 1 H) 7.41-7.59 (m, 3 H) 7.30-7.41 (m, 2 H) 7.25 (d, J=2.20 Hz, 1 H) 6.97 (d, J=7.91 Hz, 1 H) 6.89 (d, J=0.88 Hz, 1 H) 6.67 (d, J=2.20 Hz, 1 H) 3.70-3.82 (m, 2 H) 3.43-3.52 (m, 2 H) 3.08-3.19 (m, 2 H) 2.86-2.99 (m, 2 H) 2.80 (s, 3 H). Mass spectrum m/z 403.2 (M+H)$^+$.

| Example | Starting material | Compound name | Mass spectrum |
|---|---|---|---|
| 54-8 | Example 52-4 | 7-amino-4-(2-methyl-3-(picolinamido)phenyl)-9H-carbazole-1-carboxamide (prepared as the bis TFA salt) | 436.1 (M + H)$^+$ |
| 54-9 | Intermediate 52-5 | 2-amino-5-(3-(4-fluorobenzamido)-2-methylphenyl)-2,3,4,9-tetrahydro-1H-carbazole-8-carboxamide (prepared as the TFA salt) | 457.2 (M + H)$^+$ |
| 54-10 | Example 51-2 | 7-amino-4-(3-amino-2-methylphenyl)-9H-carbazole-1-carboxamide | 331.2 (M + H)$^+$ |
| 54-11 | Example 52-1 | 7-amino-4-(3-(5-fluoropicolinamido)-2-methylphenyl)-9H-carbazole-1-carboxamide | 450.0 (M + H)$^+$ |
| 54-12 | Example 52-1 | 7-(benzylamino)-4-(3-(5-fluoropicolinamido)-2-methylphenyl)-9H-carbazole-1-carboxamide | 544.0 (M + H)$^+$ |
| 54-13 | Example 52-2 | 2-amino-5-(2-methyl-3-(picolinamido)phenyl)-2,3,4,9-tetrahydro-1H-carbazole-8-carboxamide (prepared as the bis TFA salt) | 440.1 (M + H)$^+$ |
| 54-14 | Example 51-3 | 7-amino-4-(2-methyl-3-(1-oxoisoindolin-2-yl)phenyl)-9H-carbazole-1-carboxamide | 447.2 (M + H)$^+$ |
| 54-15 | Intermediate 52-6 | 7-amino-4-(2-methyl-3-(1-methyl-1H-imidazole-2-carboxamido)phenyl)-9H-carbazole-1-carboxamide | 439.2 (M + H)$^+$ |
| 54-16 | Intermediate 50-2(a) | 2-amino-5-(2,6-difluorophenyl)-2,3,4,9-tetrahydro-1H-carbazole-8-carboxamide | 342.1 (M + H)$^+$ |

Example 55-1

Preparation of 4-(2-fluorophenyl)-7-(4-methylpiperazin-1-yl)-9H-carbazole-1-carboxamide

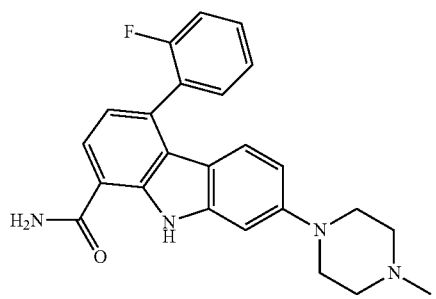 [SMILES: CN1CCN(c2ccc3c(c2)[nH]c2c(C(N)=O)ccc(-c4ccccc4F)c23)CC1]

The following Examples/Intermediates were also prepared using procedures demonstrated in Example 55-1, using (in the case of Example 55-2) 1-chloro-2-(2-chloroethoxy)ethane in place of 2-chloro-N-(2-chloroethyl)-N-methylethanamine hydrochloric acid salt.

| Example/ Intermediate | Starting material | Compound name | Mass spectrum |
|---|---|---|---|
| 55-2 | Example 54-1 | 4-(2-fluorophenyl)-7-morpholino-9H-carbazole-1-carboxamide, (prepared as the trifluroacetic acid salt) | 390.1 (M + H)$^+$ |
| Intermediate 55-3 | Example 54-2 | 4-bromo-7-(4-methylpiperazin-1-yl)-9H-carbazole-1-carboxamide | 387, 389 (M + H)$^+$ |

Example 56-1

Preparation of 442-fluorophenyl)-7-(1,1-dioxothiomorpholino)-9H-carbazole-1-carboxamide

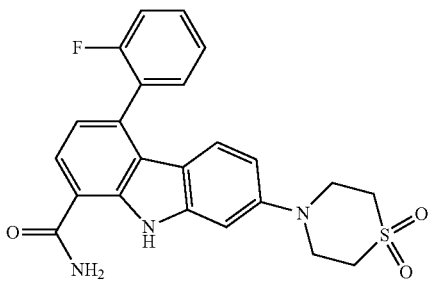 [SMILES: NC(=O)c1ccc(-c2ccccc2F)c2c1[nH]c1cc(N3CCS(=O)(=O)CC3)ccc12]

A suspension of 7-amino-4-(2-fluorophenyl)-9H-carbazole-1-carboxamide (Example 54-1, 36 mg, 0.113 mmol) in 2-propanol (1.0 mL) was treated with vinylsulfonylethene (20 μL, 0.199 mmol) at rt. The reaction mixture was heated at 100° C. for 26 h. The mixture was cooled to rt, concentrated and the residue was purified by preparative HPLC to provide 4-(2-fluorophenyl)-7-(1,1-dioxothiomorpholino)-9H-carbazole-1-carboxamide as a yellow solid (14 mg, 28%). $^1$H NMR (400 MHz, DMSO-$d_6$) δ 11.26 (1 H, s), 8.17 (1 H, br. s.), 7.90 (1 H, d, J=7.9 Hz), 7.47-7.62 (3H, m), 7.37-7.46 (2 H, m), 7.35 (1 H, d, J=1.8 Hz), 7.01 (1 H, d, J=7.9 Hz), 6.93 (1H, d, J=8.3 Hz), 6.74 (1 H, dd, J=9.0, 2.4 Hz), 3.77-3.81 (4 H, m), 3.08-3.19 (4 H, m). Mass spectrum m/z 438.1 (M+H)$^+$.

The following compound was also prepared using procedures demonstrated in Example 56-1, using Example 54-5 in place of Example 54-1 as the starting material.

| Example | Compound name | Mass spectrum |
|---------|---------------|---------------|
| 56-2 | 4-(3-(4-fluorobenzamido)-2-methylphenyl)-7-(1,1-dioxothiomorpholino)-9H-carbazole-1-carboxamide | 571.3 (M − H)$^-$ |

Example 57-1

Preparation of 7-acetamido-4-(2-fluorophenyl)-9H-carbazole-1-carboxamide

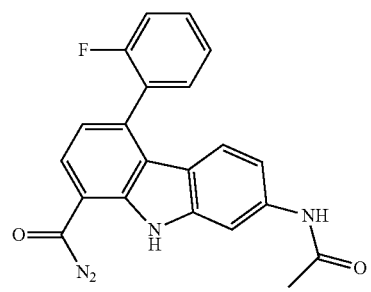

A solution of 7-amino-4-(2-fluorophenyl)-9H-carbazole-1-carboxamide (Example 54-1, 25 mg, 0.078 mmol) and TEA (0.022 mL, 0.157 mmol) in DCM-THF (2:1, 3 mL) was treated with acetyl chloride (6.7 μL, 0.094 mmol). The mixture was stirred at rt for 1 h, then was concentrated. The residue was purified by preparative HPLC to provide 7-acetamido-4-(2-fluorophenyl)-9H-carbazole-1-carboxamide, TFA salt, as a white solid (13 mg, 45%). $^1$H NMR (400 MHz, methanol-$d_4$) δ 7.95 (s, 1 H) 7.79 (d, J=7.91 Hz, 1 H) 7.36-7.53 (m, 2 H) 7.13-7.33 (m, 2 H) 6.98 (d, J=7.69 Hz, 2 H) 6.85 (d, J=10.33 Hz, 1 H) 2.05 (s, 3 H). Mass spectrum m/z 360.3 (M+H)$^+$.

Example 57-2

Preparation of 7-(2-(dimethylamino)acetamido)-4-(3-(4-fluorobenzamido)-2-methylphenyl)-9H-carbazole-1-carboxamide

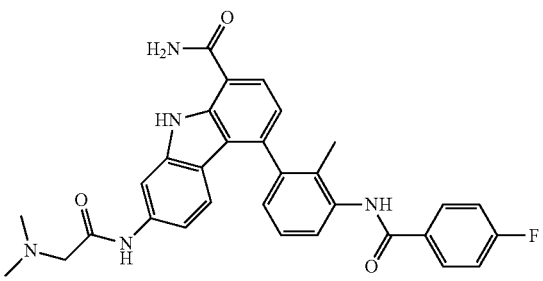 [SMILES: Cc1c(NC(=O)c2ccc(F)cc2)cccc1-c1ccc(C(N)=O)c2[nH]c3cc(NC(=O)CN(C)C)ccc3c12]

A solution of 7-amino-4-(3-(4-fluorobenzamido)-2-methylphenyl)-9H-carbazole-1-carboxamide (Example 54-5, 30 mg, 0.066 mmol), 2-(dimethylamino)acetic acid hydrochloric acid salt (13.9 mg, 0.099 mmol), HOAT (18.1 mg, 0.133 mmol), EDC (31.8 mg, 0.166 mmol), and TEA (0.037 mL, 0.265 mmol) in DCM-THF (2:1, 3 mL) was stirred at rt overnight. The mixture was concentrated and purified by preparative HPLC to provide 7-(2-(dimethylamino)acetamido)-4-(3-(4-fluorobenzamido)-2-methylphenyl)-9H-carbazole-1-carboxamide, TFA salt, as a white solid (22 mg, 50%). $^1$H NMR (500 MHz, methanol-$d_4$) δ 8.02 (1 H, d, J=1.1 Hz), 7.96 (2 H, dd, J=8.7, 5.4 Hz), 7.84 (1 H, d, J=7.8 Hz), 7.42 (1 H, d, J=7.2 Hz), 7.34 (1 H, t, J=7.6 Hz), 7.12-7.21 (3 H, m), 6.95 (1 H, d, J=7.8 Hz), 6.86-6.94 (2 H, m), 4.04 (2 H, s), 2.91 (s, 6 H), 1.90 (3 H, s). Mass spectrum m/z 538.1 (M+H)$^+$.

Example 57-3

Preparation of 7-((S)-2-aminopropanamido)-4-(3-(4-fluorobenzamido)-2-methylphenyl)-9H-carbazole-1-carboxamide

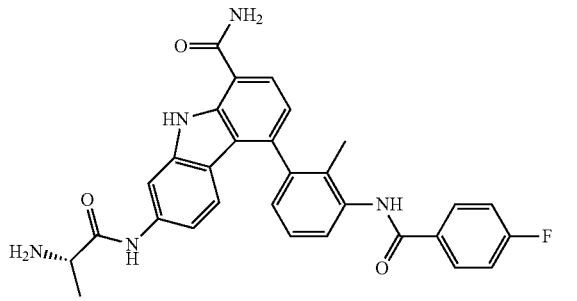 [SMILES: Cc1c(NC(=O)c2ccc(F)cc2)cccc1-c1ccc(C(N)=O)c2[nH]c3cc(NC(=O)[C@H](C)N)ccc3c12]

A solution of 7-amino-4-(3-(4-fluorobenzamido)-2-methylphenyl)-9H-carbazole-1-carboxamide (Example 54-5, 21.8 mg, 0.049 mmol), (S)-2-(tert-butoxycarbonylamino)propanoic acid (10.6 mg, 0.056 mmol), HOBT (8.6 mg, 0.056 mmol), EDC (10.8 mg, 0.056 mmol), and DIEA (0.043 mL, 0.250 mmol) in DMF (0.675 mL) was agitated at rt overnight. The mixture was concentrated and treated with TFA (0.5 mL) and DCM (0.5 mL). After 2 h, the solution was concentrated and the residue was purified by preparative HPLC to provide 7-((S)-2-aminopropanamido)-4-(3-(4-fluorobenzamido)-2-methylphenyl)-9H-carbazole-1-carboxamide, TFA salt (5.7 mg, 15%). Mass spectrum m/z 523.9 (M+H)$^+$.

The following Examples/Intermediates were also prepared using procedures demonstrated in Examples 57-1 through 57-3, using the appropriate acid or acid chloride.

| Example/Intermediate | Starting material | Compound name | Mass spectrum |
|---|---|---|---|
| 57-4 | Example 54-16 | 2-acetamido-5-(2,6-difluorophenyl)-2,3,4,9-tetrahydro-1H-carbazole-8-carboxamide | 384.2 (M + H)$^+$ |
| 57-5 | Example 54-5 | 7-acetamido-4-(3-(4-fluorobenzamido)-2-methylphenyl)-9H-carbazole-1-carboxamide | 495.2 (M + H)$^+$ |
| 57-6 | Example 54-5 | 4-(3-(4-fluorobenzamido)-2-methylphenyl)-7-(nicotinamido)-9H-carbazole-1-carboxamide (prepared as the TFA salt) | 558.1 (M + H)$^+$ |
| 57-7 | Example 54-5 | 4-(3-(4-fluorobenzamido)-2-methylphenyl)-7-(isonicotinamido)-9H-carbazole-1-carboxamide (prepared as the TFA salt) | 558.1 (M + H)$^+$ |
| 57-8 | Example 54-5 | 7-(3-(dimethylamino)propanamido)-4-(3-(4-fluorobenzamido)-2-methylphenyl)-9H-carbazole-1-carboxamide (prepared as the TFA salt) | 552.1 (M + H)$^+$ |
| 57-9 | Example 54-5 | 7-(cyclopropanecarboxamido)-4-(3-(4-fluorobenzamido)-2-methylphenyl)-9H-carbazole-1-carboxamide | 521.0 (M + H)$^+$ |
| 57-10 | Example 54-1 | 7-acrylamido-4-(2-fluorophenyl)-9H-carbazole-1-carboxamide | 374.0 (M + H)$^+$ |
| 57-11 | Example 54-5 | 4-(3-(4-fluorobenzamido)-2-methylphenyl)-7-(3-(4-hydroxyphenyl)propanamido)-9H-carbazole-1-carboxamide | 600.9 (M + H)$^+$ |
| 57-12 | Example 54-5 | 2-(8-carbamoyl-5-(3-(4-fluorobenzamido)-2-methylphenyl)-9H-carbazol-2-ylamino)-2-oxoEtOAc | 552.9 (M + H)$^+$ |
| 57-13 | Example 54-5 | 4-(3-(4-fluorobenzamido)-2-methylphenyl)-7-(2-(pyridin-4-yl)acetamido)-9H-carbazole-1-carboxamide (prepared as the TFA salt) | 571.9 (M + H)$^+$ |
| 57-14 | Example 54-5 | 4-(3-(4-fluorobenzamido)-2-methylphenyl)-7-(3-hydroxypropanamido)-9H-carbazole-1-carboxamide | 524.9 (M + H)$^+$ |
| 57-15 | Example 54-5 | 4-(3-(4-fluorobenzamido)-2-methylphenyl)-7-(2-(pyridin-3-yl)acetamido)-9H-carbazole-1-carboxamide (prepared as the TFA salt) | 571.9 (M + H)$^+$ |
| 57-16 | Example 54-5 | 4-(3-(4-fluorobenzamido)-2-methylphenyl)-7-(4-morpholinobutanamido)-9H-carbazole-1-carboxamide (prepared as the TFA salt) | 608.0 (M + H)$^+$ |
| 57-17 | Example 54-5 | 4-(3-(4-fluorobenzamido)-2-methylphenyl)-7-(1-methyl-1H-imidazole-2-carboxamido)-9H-carbazole-1-carboxamide (prepared as the TFA salt) | 560.9 (M + H)$^+$ |
| 57-18 | Example 54-5 | 4-(3-(4-fluorobenzamido)-2-methylphenyl)-7-(3-morpholinopropanamido)-9H-carbazole-1-carboxamide (prepared as the TFA salt) | 594.0 (M + H)$^+$ |
| 57-19 | Example 54-5 | 7-(4-chlorobenzamido)-4-(3-(4-fluorobenzamido)-2-methylphenyl)-9H-carbazole-1-carboxamide | 590.9 (M + H)$^+$ |

| Example/ Intermediate | Starting material | Compound name | Mass spectrum |
|---|---|---|---|
| 57-20 | Example 54-5 | 7-(4-cyanobenzamido)-4-(3-(4-fluorobenzamido)-2-methylphenyl)-9H-carbazole-1-carboxamide | 581.9 (M + H)+ |
| 57-21 | Example 54-5 | 7-(4-(dimethylamino)benzamido)-4-(3-(4-fluorobenzamido)-2-methylphenyl)-9H-carbazole-1-carboxamide | 599.9 (M + H)+ |
| 57-22 | Example 54-5 | 4-(3-(4-fluorobenzamido)-2-methylphenyl)-7-(4-methoxybenzamido)-9H-carbazole-1-carboxamide | 586.9 (M + H)+ |
| 57-23 | Example 54-5 | 4-(3-(4-fluorobenzamido)-2-methylphenyl)-7-isobutyramido-9H-carbazole-1-carboxamide | 522.9 (M + H)+ |
| 57-24 | Example 54-5 | 4-(3-(4-fluorobenzamido)-2-methylphenyl)-7-pivalamido-9H-carbazole-1-carboxamide | 537.0 (M + H)+ |
| 57-25 | Example 54-5 | 4-(3-(4-fluorobenzamido)-2-methylphenyl)-7-(2-phenylacetamido)-9H-carbazole-1-carboxamide | 570.9 (M + H)+ |
| 57-26 | Example 54-5 | N-(8-carbamoyl-5-(3-(4-fluorobenzamido)-2-methylphenyl)-9H-carbazol-2-yl)-1,2,3-thiadiazole-4-carboxamide | 564.8 (M + H)+ |
| 57-27 | Example 54-5 | 4-(3-(4-fluorobenzamido)-2-methylphenyl)-7-(2-hydroxy-2-phenylacetamido)-9H-carbazole-1-carboxamide | 586.9 (M + H)+ |
| 57-28 | Example 54-5 | 4-(3-(4-fluorobenzamido)-2-methylphenyl)-7-(pyrimidine-5-carboxamido)-9H-carbazole-1-carboxamide | 558.9 (M + H)+ |
| 57-29 | Example 54-5 | 7-(2-cyanoacetamido)-4-(3-(4-fluorobenzamido)-2-methylphenyl)-9H-carbazole-1-carboxamide | 519.9 (M + H)+ |
| 57-30 | Example 54-5 | 4-(3-(4-fluorobenzamido)-2-methylphenyl)-7-(3-methoxypropanamido)-9H-carbazole-1-carboxamide | 538.9 (M + H)+ |
| 57-31 | Example 54-5 | 7-(2-(1H-tetrazol-5-yl)acetamido)-4-(3-(4-fluorobenzamido)-2-methylphenyl)-9H-carbazole-1-carboxamide | 562.8 (M + H)+ |
| 57-32 | Example 54-5 | 4-(3-(4-fluorobenzamido)-2-methylphenyl)-7-(3-(2-oxopyrrolidin-1-yl)propanamido)-9H-carbazole-1-carboxamide | 591.9 (M + H)+ |
| 57-33 | Example 54-5 | 7-(3-(1H-imidazol-1-yl)propanamido)-4-(3-(4-fluorobenzamido)-2-methylphenyl)-9H-carbazole-1-carboxamide (prepared as the TFA salt) | 574.9 (M + H)+ |
| 57-34 | Example 54-5 | N-(8-carbamoyl-5-(3-(4-fluorobenzamido)-2-methylphenyl)-9H-carbazol-2-yl)morpholine-2-carboxamide (prepared as the TFA salt) | 565.9 (M + H)+ |
| 57-35 | Example 54-5 | 4-(3-(4-fluorobenzamido)-2-methylphenyl)-7-(piperidine-3-carboxamido)-9H-carbazole-1-carboxamide (prepared as the TFA salt) | 564.0 (M + H)+ |
| 57-36 | Example 54-5 | 4-(3-(4-fluorobenzamido)-2-methylphenyl)-7-((R)-piperidine-2-carboxamido)-9H-carbazole-1-carboxamide (prepared as the TFA salt) | 564.0 (M + H)+ |
| 57-37 | Example 54-5 | 7-(2-aminoacetamido)-4-(3-(4-fluorobenzamido)-2-methylphenyl)-9H-carbazole-1-carboxamide (prepared as the TFA salt) | 509.9 (M + H)+ |
| 57-38 | Example 54-5 | 7-(3-chlorobenzamido)-4-(3-(4-fluorobenzamido)-2-methylphenyl)-9H-carbazole-1-carboxamide | 590.8 (M + H)+ |
| 57-39 | Example 54-5 | 7-benzamido-4-(3-(4-fluorobenzamido)-2-methylphenyl)-9H-carbazole-1-carboxamide | 556.9 (M + H)+ |
| 57-40 | Example 54-5 | 7-(2-chlorobenzamido)-4-(3-(4-fluorobenzamido)-2-methylphenyl)-9H-carbazole-1-carboxamide | 590.8 (M + H)+ |
| 57-41 | Example 54-5 | 7-(4-acetamidobenzamido)-4-(3-(4-fluorobenzamido)-2-methylphenyl)-9H-carbazole-1-carboxamide | 613.9 (M + H)+ |
| 57-42 | Example 54-5 | 4-(3-(4-fluorobenzamido)-2-methylphenyl)-7-(3-methylbutanamido)-9H-carbazole-1-carboxamide | 536.9 (M + H)+ |
| 57-43 | Example 54-5 | 4-(3-(4-fluorobenzamido)-2-methylphenyl)-7-(pyrazine-2-carboxamido)-9H-carbazole-1-carboxamide | 558.9 (M + H)+ |

-continued

| Example/Intermediate | Starting material | Compound name | Mass spectrum |
|---|---|---|---|
| 57-44 | Example 54-5 | 4-(3-(4-fluorobenzamido)-2-methylphenyl)-7-(picolinamido)-9H-carbazole-1-carboxamide (prepared as the TFA salt) | 557.9 (M + H)+ |
| 57-45 | Example 54-5 | N-(8-carbamoyl-5-(3-(4-fluorobenzamido)-2-methylphenyl)-9H-carbazol-2-yl)thiazole-4-carboxamide | 563.8 (M + H)+ |
| 57-46 | Example 54-5 | 4-(3-(4-fluorobenzamido)-2-methylphenyl)-7-(2-(pyrazin-2-yl)acetamido)-9H-carbazole-1-carboxamide | 572.9 (M + H)+ |
| 57-47 | Example 54-5 | 4-(3-(4-fluorobenzamido)-2-methylphenyl)-7-(2-(pyridin-2-yl)acetamido)-9H-carbazole-1-carboxamide | 571.9 (M + H)+ |
| 57-48 | Example 54-14 | 7-isobutyramido-4-(2-methyl-3-(1-oxoisoindolin-2-yl)phenyl)-9H-carbazole-1-carboxamide | 517.3 (M + H)+ |
| 57-49 | Example 54-14 | 4-(2-methyl-3-(1-oxoisoindolin-2-yl)phenyl)-7-pivalamido-9H-carbazole-1-carboxamide | 531.3 (M + H)+ |
| 57-50 | Example 54-15 | 4-(2-methyl-3-(1-methyl-1H-imidazole-2-carboxamido)phenyl)-7-pivalamido-9H-carbazole-1-carboxamide (prepared as the TFA salt) | 523.4 (M + H)+ |
| Intermediate 57-51 | Example 54-2 | 4-bromo-7-pivalamido-9H-carbazole-1-carboxamide | 388, 390 (M + H)+ |
| Intermediate 57-52 | Example 54-2 | 4-bromo-7-(cyclopropanecarboxamido)-9H-carbazole-1-carboxamide | 372, 374 (M + H)+ |

Intermediate 58-1

Preparation of 4-bromo-7-(4-hydroxy-2,2-dimethylbutanamido)-9H-carbazole-1-carboxamide

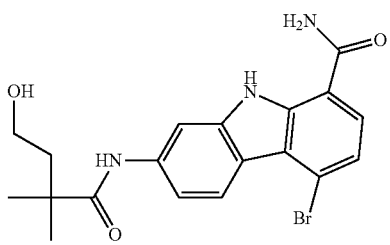 [SMILES: CC(C)(CCO)C(=O)Nc1ccc2c(c1)[nH]c1c(C(N)=O)ccc(Br)c12]

A mixture of 7-amino-4-bromo-9H-carbazole-1-carboxamide hydrobromide (Example 54-2, 500 mg, 1.299 mmol) and 3,3-dimethyldihydrofuran-2(3 H)-one (222 mg, 1.948 mmol) in THF (10 mL) was treated with trimethylaluminum (2 M in toluene, 562 mg, 7.79 mmol) dropwise at rt. The mixture was heated at 50° C. for 1.5 h, cooled to rt and treated with water. The mixture was filtered through Celite and the solids were washed thoroughly with DCM and methanol. The filtrate was washed with water, dried and concentrated, and the residue was purified by column chromatography (eluting with a gradient from DCM to 10% ammonia-methanol-DCM) to provide 4-bromo-7-(4-hydroxy-2,2-dimethylbutanamido)-9H-carbazole-1-carboxamide as a yellow solid (250 mg, 46%). Mass spectrum m/z 418, 420 (M+H)+.

Examples 59-1 and 59-2

Preparation of 4-(3-(4-fluorobenzamido)-2-methylphenyl)-7-(methylsulfonamido)-9H-carbazole-1-carboxamide and 4-(3-(4-fluorobenzamido)-2-methylphenyl)-7-(N-(methylsulfonyl)methylsulfonamido)-9H-carbazole-1-carboxamide

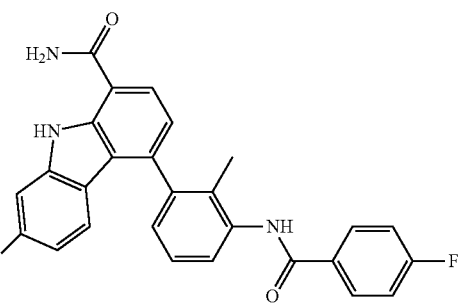

Example 60-1

Preparation of 7-(3-isopropylureido)-4-(2-methyl-3-(1-methyl-1H-imidazole-2-carboxamido)phenyl)-9H-carbazole-1-carboxamide

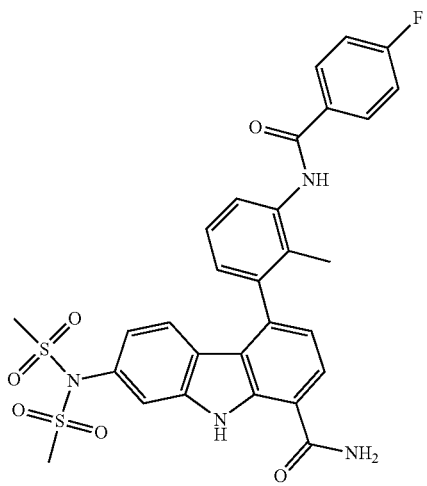

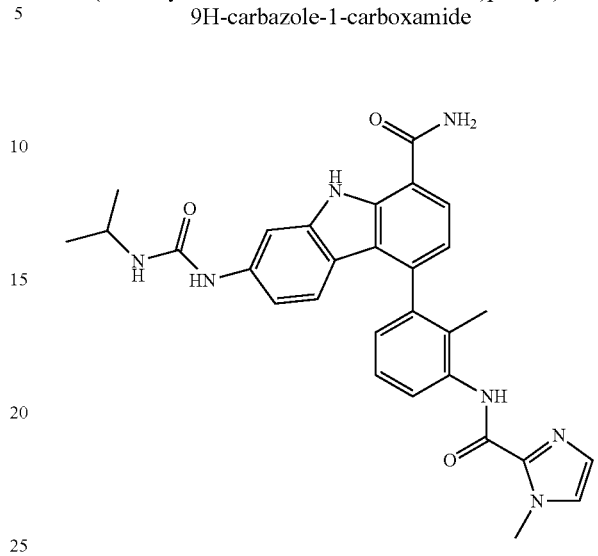

A solution of 7-amino-4-(3-(4-fluorobenzamido)-2-methylphenyl)-9H-carbazole-1-carboxamide (Example 54-5, 30 mg, 0.066 mmol) and TEA (0.018 mL, 0.133 mmol) in DCM-THF (2:1, 3 mL) was treated with methanesulfonyl chloride (10 μL, 0.133 mmol). The mixture was stirred at rt for 1.5 h, and was concentrated and purified by preparative HPLC to provide 4-(3-(4-fluorobenzamido)-2-methylphenyl)-7-(methylsulfonamido)-9H-carbazole-1-carboxamide as a white solid (Example 59-1, 3.5 mg, 9%). $^1$H NMR (500 MHz, methanol-$d_4$) δ 7.91-8.01 (2 H, m), 7.83 (1 H, d, J=7.8 Hz), 7.45 (1 H, d, J=1.7 Hz), 7.42 (1 H, d, J=7.8 Hz), 7.34 (1 H, t, J=7.8 Hz), 7.12-7.20 (3 H, m), 6.95 (1 H, d, J=7.8 Hz), 6.88 (1 H, d, J=8.6 Hz), 6.73 (1 H, dd, J=8.5, 2.1 Hz), 2.85 (3 H, s), 1.90 (3 H, s). Mass spectrum m/z 531.0 (M+H)$^+$. Also obtained was 4-(3-(4-fluorobenzamido)-2-methylphenyl)-7-(N-(methylsulfonyl)methylsulfonamido)-9H-carbazole-1-carboxamide as a white solid (Example 59-2, 14 mg, 28%). $^1$H NMR (400 MHz, DMSO-$d_6$) δ 11.67 (1 H, s), 10.08 (1 H, s), 8.21 (1 H, br. s.), 7.97-8.08 (3 H, m), 7.79 (1 H, d, J=1.8 Hz), 7.53 (1 H, br. s.), 7.48 (1 H, d, J=7.3 Hz), 7.26-7.39 (3 H, m), 7.15 (1 H, d, J=6.5 Hz), 6.93-7.03 (2 H, m), 6.86 (1 H, d, J=8.3 Hz), 3.46 (6 H, d, J=9.0 Hz), 1.86 (3 H, s). Mass spectrum m/z 607.2 (M−H)$^-$.

The following compound was also prepared using the procedure demonstrated in Examples 59-1 and 59-2, substituting Example 54-1 in place of Example 54-5 as starting material:

| Example | Compound name | Mass spectrum |
|---|---|---|
| 59-3 | 4-(2-fluorophenyl)-7-(methylsulfonamido)-9H-carbazole-1-carboxamide | 398.1 (M + H)$^+$ |

A solution of 7-amino-4-(2-methyl-3-(1-methyl-1H-imidazole-2-carboxamido)phenyl)-9H-carbazole-1-carboxamide (Example 54-15, 29 mg, 0.066 mmol) and 2-isocyanatopropane (0.019 mL, 0.198 mmol) in 1,2-dichloroethane (3 mL) was stirred at rt for 2.5 h, then at 50° C. for 2 h. Additional 2-isocyanatopropane was added and the mixture was stirred at 40° C. for 16 h. The mixture was concentrated and purified by HPLC. The appropriate effluent fractions were partially concentrated, treated with NaHCO3 (aq) and extracted with EtOAc. The organic phase was dried and concentrated to provide 7-(3-isopropylureido)-4-(2-methyl-3-(1-methyl-1H-imidazole-2-carboxamido)phenyl)-9H-carbazole-1-carboxamide as a pale pink solid (15 mg, 43%). $^1$H NMR (400 MHz, DMSO-$d_6$) δ 11.32 (1 H, s), 9.97 (1 H, s), 8.37 (1 H, s), 8.13 (1 H, br. s.), 7.88 (1 H, d, J=7.9 Hz), 7.81 (1 H, d, J=1.8 Hz), 7.76 (1 H, d, J=7.9 Hz), 7.40-7.48 (2 H, m), 7.38 (1 H, t, J=7.7 Hz), 7.13 (1 H, d, J=7.5 Hz), 7.06 (1 H, s), 6.82-6.92 (2 H, m), 6.73 (1 H, d, J=8.3 Hz), 5.98 (1 H, d, J=7.5 Hz), 4.01 (3 H, s), 3.68-3.81 (1 H, m), 1.89-1.95 (3 H, m), 1.07 (6 H, d). Mass spectrum m/z 524.3 (M+H)$^+$.

The following compounds were also prepared using the procedure demonstrated in Example 60-1, substituting Example 54-5 in place of Example 54-15 as starting material and using the appropriate isocyanate in place of 2-isocyanatopropane.

| Example | Compound name | Mass spectrum |
|---|---|---|
| 60-2 | 7-(3-(4-chlorophenyl)ureido)-4-(3-(4-fluorobenzamido)-2-methylphenyl)-9H-carbazole-1-carboxamide | 605.8 (M + H)$^+$ |
| 60-3 | 4-(3-(4-fluorobenzamido)-2-methylphenyl)-7-(3-phenylureido)-9H-carbazole-1-carboxamide | 571.9 (M + H)$^+$ |
| 60-4 | 7-(3-ethylureido)-4-(3-(4-fluorobenzamido)-2-methylphenyl)-9H-carbazole-1-carboxamide | 523.9 (M + H)$^+$ |
| 60-5 | 7-(3-tert-butylureido)-4-(3-(4-fluorobenzamido)-2-methylphenyl)-9H-carbazole-1-carboxamide | 551.9 (M + H)$^+$ |

-continued

| Example | Compound name | Mass spectrum |
|---|---|---|
| 60-6 | 4-(3-(4-fluorobenzamido)-2-methylphenyl)-7-(3-isopropylureido)-9H-carbazole-1-carboxamide | 537.9 (M + H)+ |

Example 61-1

Preparation of 4-(3-(4-fluorobenzamido)-2-methylphenyl)-7-(isopropylamino)-9H-carbazole-1-carboxamide

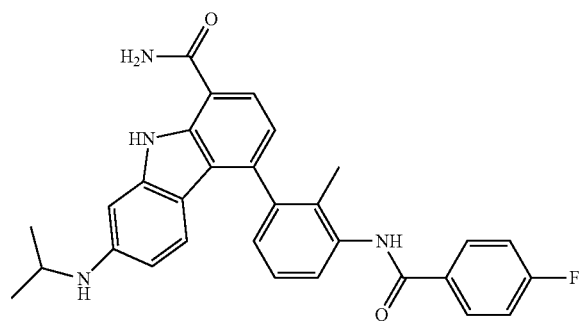 [SMILES: Cc1c(NC(=O)c2ccc(F)cc2)cccc1-c1ccc(C(N)=O)c2[nH]c3cc(NC(C)C)ccc3c12]

A suspension of 7-amino-4-(3-(4-fluorobenzamido)-2-methylphenyl)-9H-carbazole-1-carboxamide (Example 54-5, 1 g, 2.210 mmol), acetone (3.4 mL, 20 eq.), and acetic acid (0.443 mL, 7.74 mmol) in 1,2-dichloroethane (220 mL) was treated with sodium triacetoxyborohydride (1.639 g, 7.74 mmol) and stirred at 40° C. for 4 h. Additional sodium triacetoxyborohydride (520 mg, 1.1 eq) and acetic acid (0.19 mL, 1.5 eq) were added and the mixture was stirred overnight. The mixture was treated with NaHCO3 (aq) and the organic phase was separated, washed with brine, dried and concentrated. The residue was purified by preparative HPLC. The appropriate effluent fractions were made basic with NaHCO3 (aq) and extracted with EtOAc. The organic phase was washed with brine, dried and concentrated. The residue was triturated with methanol to provide 4-(3-(4-fluorobenzamido)-2-methylphenyl)-7-(isopropylamino)-9H-carbazole-1-carboxamide as an off-white solid (520 mg, 48%). $^1$H NMR (400 MHz, DMSO-$d_6$) δ 11.01 (1 H, s), 10.09 (1 H, s), 8.07 (3 H, dd, J=8.8, 5.3 Hz), 7.77 (1 H, d, J=7.9 Hz), 7.27-7.51 (5 H, m), 7.17 (1 H, d, J=6.2 Hz), 6.73-6.88 (2 H, m), 6.60 (1 H, d, J=8.3 Hz), 6.23 (1 H, dd, J=8.8, 2.2 Hz), 5.49 (1 H, d, J=7.9 Hz), 3.53 (1H, dd, J=13.8, 6.4 Hz), 1.90 (3 H, s), 1.04-1.21 (6 H, m). Mass spectrum m/z 495.1 (M+H)+.

The following Examples/Intermediates were also prepared using procedures demonstrated in Example 61-1, using the appropriate aldehyde or ketone in place of acetone.

| Example/ Intermediate | Starting material | Compound name | Mass spectrum |
|---|---|---|---|
| 61-2 | Example 54-5 | 4-(3-(4-fluorobenzamido)-2-methylphenyl)-7-(1-methylpiperidin-4-ylamino)-9H-carbazole-1-carboxamide | 550.1 (M + H)+ |
| 61-3 | Example 54-14 | 7-(isopropylamino)-4-(2-methyl-3-(1-oxoisoindolin-2-yl)phenyl)-9H-carbazole-1-carboxamide | 489.3 (M + H)+ |
| 61-4 | Example 54-15 | 7-(isopropylamino)-4-(2-methyl-3-(1-methyl-1H-imidazole-2-carboxamido)phenyl)-9H-carbazole-1-carboxamide | 481.2 (M + H)+ |
| 61-5 | Example 54-2 | 4-bromo-7-(isopropylamino)-9H-carbazole-1-carboxamide | 346, 348 (M + H)+ |
| Intermediate 61-6 | Example 54-2 | (S)-4-bromo-7-((2,2-dimethyl-1,3-dioxolan-4-ylmethyl)amino)-9H-carbazole-1-carboxamide | 418, 420 (M + H)+ |

Example 62-1

Preparation of 4-(2-methyl-3-(1-oxoisoindolin-2-yl)phenyl)-7-(2-oxopyrrolidin-1-yl)-9H-carbazole-1-carboxamide

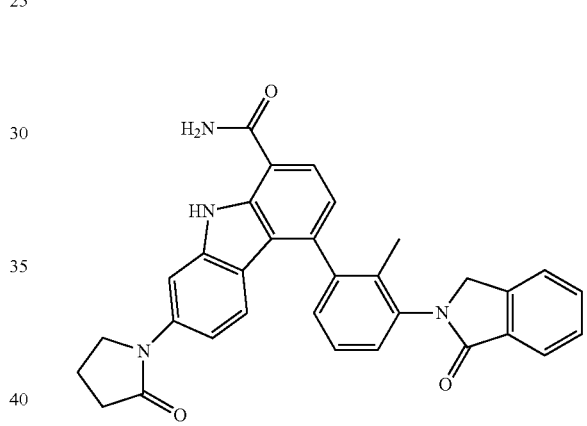

A solution of 7-amino-4-(2-methyl-3-(1-oxoisoindolin-2-yl)phenyl)-9H-carbazole-1-carboxamide (Example 54-14, 60 mg, 0.134 mmol) in THF (3 mL) was treated with TEA (0.019 mL, 0.134 mmol) and a solution of 4-bromobutanoyl chloride (24.92 mg, 0.134 mmol) in DCM (1 mL). The mixture was stirred at rt for 40 min, then was diluted with DCM, washed with water, dried and concentrated. The residue was dissolved in THF (5 mL) and added to a suspension of sodium hydride (60% oil dispersion, 40 mg, 1.000 mmol, pre-washed with hexane) in THF (5 mL). The mixture was stirred at rt overnight, then was heated at 65° C. for 30 min. The mixture was cooled to rt, poured into water and extracted with EtOAc. The organic phase was dried and concentrated, and the residue was purified by column chromatography (eluting with a gradient from 99:0.9:0.1 to 90:9:1 DCM-methanol-28% aqueous ammonium hydroxide) to provide 4-(2-methyl-3-(1-oxoisoindolin-2-yl)phenyl)-7-(2-oxopyrrolidin-1-yl)-9H-carbazole-1-carboxamide (50 mg, 66%) as a white solid. $^1$H NMR (400 MHz, chloroform-d) δ 10.67 (1 H, s), 7.96 (1 H, d, J=7.47 Hz), 7.91 (1 H, s), 7.74 (1 H, d, J=7.91 Hz), 7.62-7.67 (1 H, m), 7.52-7.58 (2 H, m), 7.45-7.48 (2 H, m), 7.38-7.42 (1 H, m), 7.22 (1 H, dd, J=8.79, 1.76 Hz), 7.11 (2 H, d, J=7.91 Hz), 4.86 (2 H, s), 3.90-4.02 (2 H, m), 2.66 (2 H, t, J=8.13 Hz), 2.16-2.25 (2 H, m), 1.94 (3 H, s). Mass spectrum m/z 515.3 (M+H)+.

The following compounds were also prepared using procedures demonstrated in Example 62-1.

| Example/ Intermediate | Starting material | Compound name | Mass spectrum |
|---|---|---|---|
| 62-2 | Example 54-5 | 4-(3-(4-fluorobenzamido)-2-methylphenyl)-7-(2-oxopyrrolidin-1-yl)-9H-carbazole-1-carboxamide | 521.1 (M + H)+ |
| 62-3 | Example 54-15 | 4-(2-methyl-3-(1-methyl-1H-imidazole-2-carboxamido)phenyl)-7-(2-oxopyrrolidin-1-yl)-9H-carbazole-1-carboxamide (prepared as the TFA salt) | 507.1 (M + H)+ |
| Intermediate 62-4 | Example 54-2 | 4-bromo-7-(2-oxopyrrolidin-1-yl)-9H-carbazole-1-carboxamide | 372, 374 (M + H)+ |

Intermediate 63-1

Preparation of 4-bromo-7-(3,3-dimethyl-2-oxopyrrolidin-1-yl)-9H-carbazole-1-carboxamide

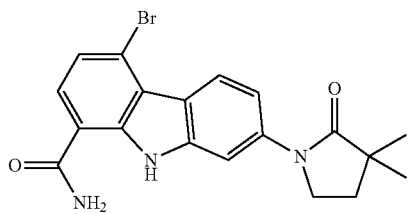 [SMILES: CC1(C)CCN(c2ccc3c(c2)[nH]c2c(C(N)=O)ccc(Br)c23)C1=O]

A solution of 4-bromo-7-(4-hydroxy-2,2-dimethylbutanamido)-9H-carbazole-1-carboxamide (Intermediate 58-1, 89 mg, 0.213 mmol), diethyl azodicarboxylate (0.051 mL, 0.319 mmol) and triphenylphosphine (84 mg, 0.319 mmol) in THF (1 mL) was stirred at rt for 1 h. More diethyl azodicarboxylate (0.051 mL, 0.319 mmol) and triphenylphosphine (84 mg, 0.319 mmol) were added, and these additions repeated again after 1 h more. The mixture was diluted with DCM, washed with NaHCO3 (aq) and water, and dried and concentrated. The residue was purified by column chromatography (eluting with a gradient from DCM to 90:9:1 DCM-methanol-28% aqueous ammonium hydroxide), then by preparative HPLC. The appropriate effluent fractions were made basic with 1 M aqueous sodium hydroxide and extracted twice with DCM. The combined organic phases were washed with water, dried and concentrated to provide 4-bromo-7-(3,3-dimethyl-2-oxopyrrolidin-1-yl)-9H-carbazole-1-carboxamide as a yellow solid (44 mg, 52%). $^1$H NMR (400 MHz, methanol-d$_4$) δ 8.66 (1 H, d, J=8.58 Hz), 7.94 (1 H, d, J=1.54 Hz), 7.73 (1 H, d, J=8.36 Hz), 7.55 (1 H, dd, J=8.80, 1.98 Hz), 7.39 (1 H, d, J=8.14 Hz), 3.97 (2 H, t, J=6.93 Hz), 2.11 (2 H, t, J=6.93 Hz), 1.28 (6 H, s). Mass spectrum m/z 400, 402 (M+H)+.

Intermediate 64-1

Preparation of 4-bromo-7-(2-oxooxazolidin-3-yl)-9H-carbazole-1-carboxamide

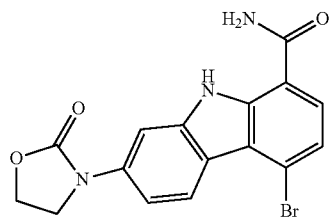 [SMILES: NC(=O)c1ccc(Br)c2c1[nH]c1cc(N3CCOC3=O)ccc12]

Using the procedure of Example 62-1, 7-amino-4-bromo-9H-carbazole-1-carboxamide (Example 54-2, 650 mg, 2.14 mmol) and 2-bromoethyl chloroformate (534 mg, 2.56 mmol) were converted to 4-bromo-7-(2-oxooxazolidin-3-yl)-9H-carbazole-1-carboxamide as a light yellow solid (688 mg, 71%). $^1$H NMR (400 MHz, DMSO-d$_6$) δ 11.72 (1 H, s), 8.55 (1 H, d, J=8.88 Hz), 8.20 (1 H, br. s.), 8.02 (1 H, d, J=2.22 Hz), 7.82 (1 H, d, J=8.32 Hz), 7.52-7.60 (2 H, m), 7.42 (1 H, d, J=8.05 Hz), 4.47-4.52 (2 H, m), 4.14-4.20 (2 H, m). Mass spectrum m/z 374, 376 (M+H)+.

Intermediate 65-1

Preparation of 4-bromo-7-(2-oxoimidazolidin-1-yl)-9H-carbazole-1-carboxamide

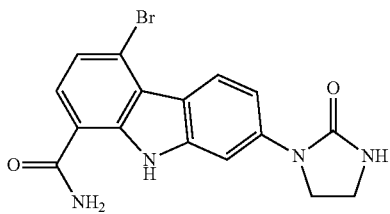 [SMILES: NC(=O)c1ccc(Br)c2c1[nH]c1cc(N3CCNC3=O)ccc12]

A solution of 7-amino-4-bromo-9H-carbazole-1-carboxamide hydrobromide (Example 54-2, 700 mg, 1.818 mmol) and DIEA (0.381 mL, 2.182 mmol) in DMF (5 mL) was treated with 1-chloro-2-isocyanatoethane (230 mg, 2.182 mmol). After 2 h, the mixture was treated with NaH (60% in mineral oil, 582 mg, 14.54 mmol). After 10 min, the mixture was diluted with water. The precipitate was collected by filtration, dried, triturated with methanol, collected again by filtration and dried to provide 4-bromo-7-(2-oxoimidazolidin-1-yl)-9H-carbazole-1-carboxamide as a light yellow solid (410 mg, 60%). $^1$H NMR (400 MHz, DMSO-d$_6$) δ 11.55 (1 H, s), 8.46 (1 H, d, J=8.80 Hz), 8.16 (1 H, br. s.), 7.92 (1 H, s), 7.77 (1 H, d, J=8.14 Hz), 7.63-7.68 (1 H, m), 7.52 (1 H, br. s.), 7.36-7.41 (1 H, m), 6.99 (1 H, s), 3.92-3.98 (2 H, m), 3.43-3.50 (2 H, m). Mass spectrum m/z 373, 375 (M+H)+.

Example 66-1

Preparation of 4-(3-(5-fluoro-1-oxoisoindolin-2-yl)-2-methylphenyl)-7-(2-oxopyrrolidin-1-yl)-9H-carbazole-1-carboxamide

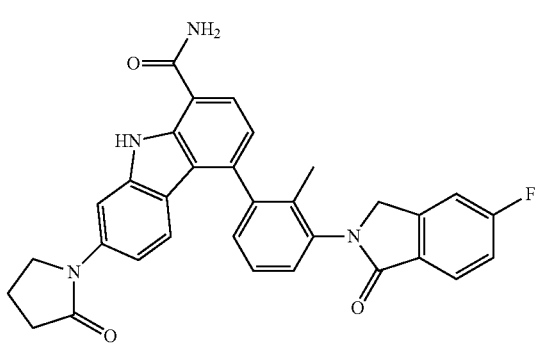 [SMILES: Cc1c(-c2ccc(C(N)=O)c3[nH]c4cc(N5CCCC5=O)ccc4c23)cccc1N1Cc2cc(F)ccc2C1=O]

Using the procedure of Example 31-1, 4-bromo-7-(2-oxopyrrolidin-1-yl)-9H-carbazole-1-carboxamide (Intermediate 62-4, 40 mg, 0.107 mmol) and 5-fluoro-2-(2-methyl-3-(4,4,5,5-tetramethyl-1,3,2-dioxaborolan-2-yl)phenyl)isoindolin-1-one (Intermediate 50-19, 51.3 mg, 0.140 mmol) were converted into 4-(3-(5-fluoro-1-oxoisoindolin-2-yl)-2-methylphenyl)-7-(2-oxopyrrolidin-1-yl)-9H-carbazole-1-carboxamide (30 mg, 52%). $^1$H NMR (400 MHz, methanol-$d_4$) δ 7.86-7.96 (3 H, m), 7.46-7.53 (2 H, m), 7.40-7.45 (1 H, m), 7.35 (1 H, dd, J=8.03, 2.01 Hz), 7.25-7.32 (1 H, m), 7.20 (1 H, dd, J=8.53, 2.01 Hz), 7.07-7.13 (2 H, m), 4.92 (2 H, s), 3.97-4.06 (2 H, m), 2.66 (2 H, t, J=8.03 Hz), 2.18-2.29 (2 H, m), 1.94 (3 H, s). Mass spectrum m/z 533.1 (M+H)$^+$.

Example 66-2

Preparation of 7-(isopropylamino)-4-(4-methyl-5-(5-methyl-1-oxoisoindolin-2-yl)pyridin-3-yl)-9H-carbazole-1-carboxamide

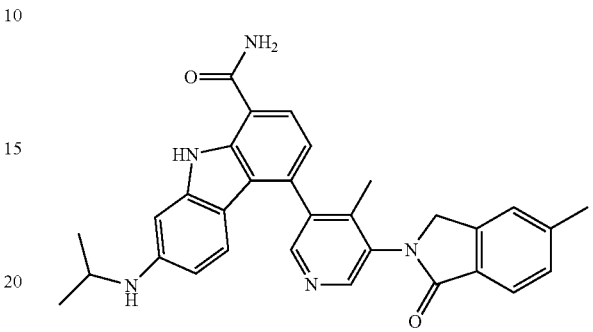

Using the procedure of Example 3-2, 4-bromo-7-(isopropylamino)-9H-carbazole-1-carboxamide (Example 61-5, 19.01 mg, 0.055 mmol) and 5-methyl-2-(4-methyl-5-(4,4,5,5-tetramethyl-1,3,2-dioxaborolan-2-yl)pyridin-3-yl)isoindolin-1-one (Intermediate 50-20, 20 mg, 0.055 mmol) were converted into 7-(isopropylamino)-4-(4-methyl-5-(5-methyl-1-oxoisoindolin-2-yl)pyridin-3-yl)-9H-carbazole-1-carboxamide (18 mg, 65%). $^1$H NMR (400 MHz, methanol-$d_4$) δ 8.65 (1 H, s), 8.46 (1H, s), 7.79 (1 H, d, J=7.92 Hz), 7.73 (1 H, d, J=7.70 Hz), 7.40 (1 H, s), 7.36 (1 H, d, J=7.70 Hz), 6.96 (1 H, d, J=7.92 Hz), 6.80 (1 H, d, J=8.58 Hz), 6.74 (1 H, d, J=1.98 Hz), 6.35-6.54 (1 H, m), 4.81-4.97 (2 H, m), 3.53-3.82 (1 H, m), 2.45 (3 H, s), 1.97 (3 H, s), 1.06-1.24 (6 H, m). Mass spectrum m/z 504.3 (M+H)$^+$.

The following compounds were prepared using the procedures demonstrated in Examples 66-1 and 66-2 and closely related procedures, and using the Examples and Intermediates shown as starting materials.

| Example | Starting materials | Compound name | Mass spectrum |
|---|---|---|---|
| 66-3 | Intermediate 55-3, Intermediate 50-1 | 4-(3-amino-2-methylphenyl)-7-(4-methylpiperazin-1-yl)-9H-carbazole-1-carboxamide (prepared as the TFA salt) | 414.2 (M + H)$^+$ |
| 66-4 | Example 61-5, Intermediate 50-1 | 4-(3-amino-2-methylphenyl)-7-(isopropylamino)-9H-carbazole-1-carboxamide | 373.3 (M + H)$^+$ |
| 66-5 | Intermediate 62-4, Intermediate 50-18 | 4-(2-methyl-3-(5-methyl-1-oxoisoindolin-2-yl)phenyl)-7-(2-oxopyrrolidin-1-yl)-9H-carbazole-1-carboxamide | 529.3 (M + H)$^+$ |
| 66-6 | Intermediate 62-4, Intermediate 51-2 | 4-(3-(5-chloro-1-oxoisoindolin-2-yl)-2-methylphenyl)-7-(2-oxopyrrolidin-1-yl)-9H-carbazole-1-carboxamide | 549.2 (M + H)$^+$ |
| 66-7 | Intermediate 62-4, Intermediate 50-1 | 4-(3-amino-2-methylphenyl)-7-(2-oxopyrrolidin-1-yl)-9H-carbazole-1-carboxamide | 399.1 (M + H)$^+$ |

-continued

| Example | Starting materials | Compound name | Mass spectrum |
|---|---|---|---|
| 66-8 | Intermediate 64-1, Intermediate 50-18 | 4-(2-methyl-3-(5-methyl-1-oxoisoindolin-2-yl)phenyl)-7-(2-oxooxazolidin-3-yl)-9H-carbazole-1-carboxamide | 531.3 (M + H)+ |
| 66-9 | Intermediate 64-1, Intermediate 51-2 | 4-(3-(5-chloro-1-oxoisoindolin-2-yl)-2-methylphenyl)-7-(2-oxooxazolidin-3-yl)-9H-carbazole-1-carboxamide | 551.2 (M + H)+ |
| 66-10 | Intermediate 64-1, Intermediate 50-4 | 4-(2-methyl-3-(1-oxoisoindolin-2-yl)phenyl)-7-(2-oxooxazolidin-3-yl)-9H-carbazole-1-carboxamide | 517.3 (M + H)+ |
| 66-11 | Intermediate 65-1, Intermediate 50-4 | 4-(2-methyl-3-(1-oxoisoindolin-2-yl)phenyl)-7-(2-oxoimidazolidin-1-yl)-9H-carbazole-1-carboxamide | 516.3 (M + H)+ |
| 66-12 | Intermediate 65-1, Intermediate 50-18 | 4-(2-methyl-3-(5-methyl-1-oxoisoindolin-2-yl)phenyl)-7-(2-oxoimidazolidin-1-yl)-9H-carbazole-1-carboxamide | 530.3 (M + H)+ |
| 66-13 | Intermediate 65-1, Intermediate 51-2 | 4-(3-(5-chloro-1-oxoisoindolin-2-yl)-2-methylphenyl)-7-(2-oxoimidazolidin-1-yl)-9H-carbazole-1-carboxamide | 550.3 (M + H)+ |
| 66-14 | Intermediate 65-1, Intermediate 50-19 | 4-(3-(5-fluoro-1-oxoisoindolin-2-yl)-2-methylphenyl)-7-(2-oxoimidazolidin-1-yl)-9H-carbazole-1-carboxamide | 534.3 (M + H)+ |
| 66-15 | Intermediate 61-6, Intermediate 50-4 | 7-(((S)-2,2-dimethyl-1,3-dioxolan-4-yl)methylamino)-4-(2-methyl-3-(1-oxoisoindolin-2-yl)phenyl)-9H-carbazole-1-carboxamide | 561.3 (M + H)+ |
| 66-16 | Intermediate 62-4, Intermediate 50-8 | 4-(2-methyl-3-(6-methyl-1-oxoisoindolin-2-yl)phenyl)-7-(2-oxopyrrolidin-1-yl)-9H-carbazole-1-carboxamide | 529.3 (M + H)+ |
| 66-17 | Intermediate 62-4, Intermediate 50-44 | 4-(3-(cyclopropanecarboxamido)-2-methylphenyl)-7-(2-oxopyrrolidin-1-yl)-9H-carbazole-1-carboxamide | 467.2 (M + H)+ |
| 66-18 | Intermediate 62-4, Intermediate 50-43 | 4-(2-methyl-3-(2-oxopiperidin-1-yl)phenyl)-7-(2-oxopyrrolidin-1-yl)-9H-carbazole-1-carboxamide | 481.3 (M + H)+ |
| 66-19 | Intermediate 62-4, Intermediate 50-29 | 4-(2-methyl-3-(1-oxoisoquinolin-2(1H)-yl)phenyl)-7-(2-oxopyrrolidin-1-yl)-9H-carbazole-1-carboxamide | 527.4 (M + H)+ |
| 66-20 | Intermediate 62-4, Intermediate 50-9 | 4-(3-(6-cyano-1-oxoisoindolin-2-yl)-2-methylphenyl)-7-(2-oxopyrrolidin-1-yl)-9H-carbazole-1-carboxamide | 540.4 (M + H)+ |
| 66-21 | Intermediate 64-1, Intermediate 50-44 | 4-(3-(cyclopropanecarboxamido)-2-methylphenyl)-7-(2-oxooxazolidin-3-yl)-9H-carbazole-1-carboxamide | 469.2 (M + H)+ |
| 66-22 | Intermediate 64-1, Intermediate 50-19 | 4-(3-(5-fluoro-1-oxoisoindolin-2-yl)-2-methylphenyl)-7-(2-oxooxazolidin-3-yl)-9H-carbazole-1-carboxamide | 535.1 (M + H)+ |
| 66-23 | Intermediate 64-1, Intermediate 50-29 | 4-(2-methyl-3-(1-oxoisoquinolin-2(1H)-yl)phenyl)-7-(2-oxooxazolidin-3-yl)-9H-carbazole-1-carboxamide | 529.3 (M + H)+ |
| 66-24 | Intermediate 65-1, Intermediate 50-29 | 4-(2-methyl-3-(1-oxoisoquinolin-2(1H)-yl)phenyl)-7-(2-oxoimidazolidin-1-yl)-9H-carbazole-1-carboxamide | 528.3 (M + H)+ |

-continued

| Example | Starting materials | Compound name | Mass spectrum |
|---|---|---|---|
| 66-25 | Intermediate 64-1, Intermediate 51-1 | 4-(3-(6-chloro-1-oxoisoindolin-2-yl)-2-methylphenyl)-7-(2-oxooxazolidin-3-yl)-9H-carbazole-1-carboxamide | 551.1 (M + H)$^+$ |
| 66-26 | Intermediate 64-1, Intermediate 50-8 | 4-(2-methyl-3-(6-methyl-1-oxoisoindolin-2-yl)phenyl)-7-(2-oxooxazolidin-3-yl)-9H-carbazole-1-carboxamide | 531.2 (M + H)$^+$ |
| 66-27 | Intermediate 65-1, Intermediate 50-8 | 4-(2-methyl-3-(6-methyl-1-oxoisoindolin-2-yl)phenyl)-7-(2-oxoimidazolidin-1-yl)-9H-carbazole-1-carboxamide | 530.1 (M + H)$^+$ |
| 66-28 | Intermediate 65-1, Intermediate 51-1 | 4-(3-(6-chloro-1-oxoisoindolin-2-yl)-2-methylphenyl)-7-(2-oxoimidazolidin-1-yl)-9H-carbazole-1-carboxamide | 550.1 (M + H)$^+$ |
| 66-29 | Intermediate 65-1, Intermediate 50-5 | 4-(3-(6-fluoro-1-oxoisoindolin-2-yl)-2-methylphenyl)-7-(2-oxoimidazolidin-1-yl)-9H-carbazole-1-carboxamide | 534.2 (M + H)$^+$ |
| 66-30 | Intermediate 57-51, Intermediate 50-8 | 4-(2-methyl-3-(6-methyl-1-oxoisoindolin-2-yl)phenyl)-7-pivalamido-9H-carbazole-1-carboxamide | 545.2 (M + H)$^+$ |
| 66-31 | Intermediate 57-51, Intermediate 50-5 | 4-(3-(6-fluoro-1-oxoisoindolin-2-yl)-2-methylphenyl)-7-pivalamido-9H-carbazole-1-carboxamide | 549.2 (M + H)$^+$ |
| 66-32 | Intermediate 57-51, Intermediate 50-18 | 4-(2-methyl-3-(5-methyl-1-oxoisoindolin-2-yl)phenyl)-7-pivalamido-9H-carbazole-1-carboxamide | 545.2 (M + H)$^+$ |
| 66-33 | Intermediate 57-51, Intermediate 51-2 | 4-(3-(5-chloro-1-oxoisoindolin-2-yl)-2-methylphenyl)-7-pivalamido-9H-carbazole-1-carboxamide | 565.2 (M + H)$^+$ |
| 66-34 | Intermediate 57-51, Intermediate 50-19 | 4-(3-(5-fluoro-1-oxoisoindolin-2-yl)-2-methylphenyl)-7-pivalamido-9H-carbazole-1-carboxamide | 549.3 (M + H)$^+$ |
| 66-35 | Intermediate 58-1, Intermediate 50-5 | 4-(3-(6-fluoro-1-oxoisoindolin-2-yl)-2-methylphenyl)-7-(4-hydroxy-2,2-dimethylbutanamido)-9H-carbazole-1-carboxamide | 579.4 (M + H)$^+$ |
| 66-36 | Intermediate 58-1, Intermediate 50-8 | 7-(4-hydroxy-2,2-dimethylbutanamido)-4-(2-methyl-3-(6-methyl-1-oxoisoindolin-2-yl)phenyl)-9H-carbazole-1-carboxamide | 575.2 (M + H)$^+$ |
| 66-37 | Intermediate 63-1, Intermediate 50-8 | 7-(3,3-dimethyl-2-oxopyrrolidin-1-yl)-4-(2-methyl-3-(6-methyl-1-oxoisoindolin-2-yl)phenyl)-9H-carbazole-1-carboxamide | 557.4 (M + H)$^+$ |
| 66-38 | Intermediate 63-1, Intermediate 50-5 | 7-(3,3-dimethyl-2-oxopyrrolidin-1-yl)-4-(3-(6-fluoro-1-oxoisoindolin-2-yl)-2-methylphenyl)-9H-carbazole-1-carboxamide | 561.4 (M + H)$^+$ |
| 66-39 | Intermediate 57-52, Intermediate 50-4 | 7-(cyclopropanecarboxamido)-4-(2-methyl-3-(1-oxoisoindolin-2-yl)phenyl)-9H-carbazole-1-carboxamide | 515.1 (M + H)$^+$ |
| 66-40 | Intermediate 64-1, Intermediate 50-20 | 4-(4-methyl-5-(5-methyl-1-oxoisoindolin-2-yl)pyridin-3-yl)-7-(2-oxooxazolidin-3-yl)-9H-carbazole-1-carboxamide | 532.2 (M + H)$^+$ |
| 66-41 | Intermediate 65-1, Intermediate 50-20 | 4-(4-methyl-5-(5-methyl-1-oxoisoindolin-2-yl)pyridin-3-yl)-7-(2-oxoimidazolidin-1-yl)-9H-carbazole-1-carboxamide | 531.3 (M + H)$^+$ |

Example 67-1

Preparation of 7-(2,3-dihydroxypropylamino)-4-(2-methyl-3-(1-oxoisoindolin-2-yl)phenyl)-9H-carbazole-1-carboxamide

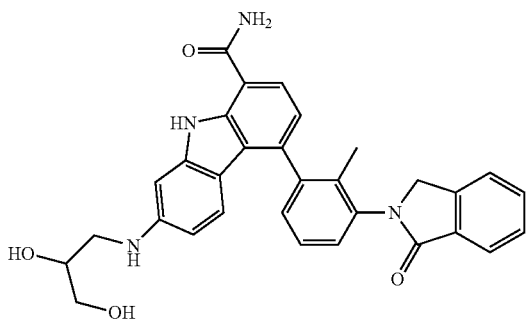 [SMILES: Cc1c(-c2ccc(C(N)=O)c3[nH]c4cc(NCC(O)CO)ccc4c23)cccc1N1Cc2ccccc2C1=O]

A solution of 74(S)-2,2-dimethyl-1,3-dioxolan-4-yl)methylamino)-4-(2-methyl-3-(1-oxoisoindolin-2-yl)phenyl)-9H-carbazole-1-carboxamide (Example 66-15, 50 mg, 0.089 mmol) in THF (1 mL) was treated with 2 M hydrochloric acid (4.46 mL, 8.92 mmol) and the mixture was stirred at rt for 1 h. The mixture was made basic with 1 M aqueous sodium hydroxide and extracted twice with DCM. The combined organic phases, along with some insoluble precipitate, were dried and concentrated. The residue was purified by column chromatography (eluting with a gradient from DCM to 90:9:1 DCM-methanol-28% aqueous ammonium hydroxide) to provide 7-(2,3-dihydroxypropylamino)-4-(2-methyl-3-(1-oxoisoindolin-2-yl)phenyl)-9H-carbazole-1-carboxamide as an orange solid (20 mg, 39%). $^1$H NMR (400 MHz, methanol-$d_4$) δ 7.90 (1 H, d, J=7.49 Hz), 7.79 (1 H, d, J=7.77 Hz), 7.67-7.74 (2 H, m), 7.58-7.62 (1 H, m), 7.49-7.55 (2 H, m), 7.42 (1 H, dd, J=6.94, 1.94 Hz), 6.99 (1H, d, J=7.77 Hz), 6.86 (1 H, d, J=8.32 Hz), 6.81 (1 H, d, J=1.94 Hz), 6.45 (1 H, dd, J=8.74, 1.80 Hz), 4.97 (2 H, s), 3.88-3.93 (1 H, m), 3.59-3.68 (2 H, m), 3.36-3.39 (1 H, m), 3.14-3.20 (1 H, m), 1.95 (3 H, s). Mass spectrum m/z 521.3 (M+H)$^+$.

Example 67-2

Preparation of racemic 7-(2,3-dihydroxypropoxy)-4-(2-methyl-3-(6-methyl-1-oxoisoindolin-2-yl)phenyl)-9H-carbazole-1-carboxamide

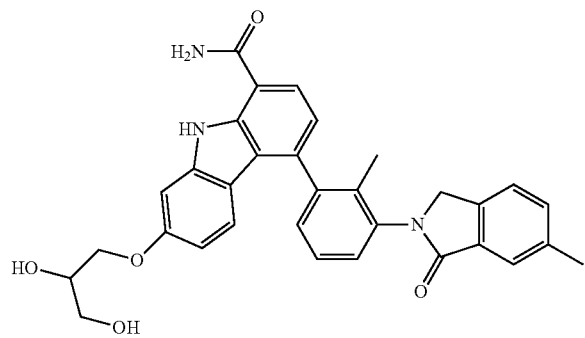 [SMILES: Cc1ccc2c(c1)C(=O)N(c1cccc(-c3ccc(C(N)=O)c4[nH]c5cc(OCC(O)CO)ccc5c34)c1C)C2]

A solution of racemic 7-((2,2-dimethyl-1,3-dioxolan-4-yl)methoxy)-4-(2-methyl-3-(6-methyl-1-oxoisoindolin-2-yl)phenyl)-9H-carbazole-1-carboxamide (Example 44-4, 30 mg, 0.052 mmol) in methanol-DMSO was treated with TFA (0.5 mL) and the solution was stirred overnight at rt. The mixture was concentrated and purified by preparative HPLC to provide 7-(2,3-dihydroxypropoxy)-4-(2-methyl-3-(6-methyl-1-oxoisoindolin-2-yl)phenyl)-9H-carbazole-1-carboxamide as a white solid (9.4 mg, 32%). $^1$H NMR (400 MHz, DMSO-$d_6$) δ 11.39 (1 H, s), 8.16 (1 H, br. s.), 7.94 (1 H, d, J=7.7 Hz), 7.54-7.65 (3 H, m), 7.49 (3 H, t, J=7.9 Hz), 7.25-7.38 (2 H, m), 6.99 (1 H, d, J=7.7 Hz), 6.92 (1 H, d, J=8.8 Hz), 6.60 (1 H, d, J=1.3 Hz), 4.82-5.01 (3 H, m), 4.60-4.71 (1 H, m), 3.96-4.08 (1 H, m), 3.76-3.96 (2 H, m), 3.48 (2H, t, J=5.6 Hz), 2.44 (3 H, s), 1.77-1.88 (3 H, m). Mass spectrum m/z 536.1 (M+H)$^+$.

Example 68-1

Preparation of 4-bromo-7-((RS)-1,2-dihydroxyethyl)-9H-carbazole-1-carboxamide

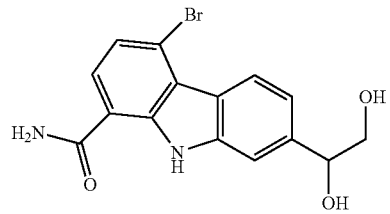 [SMILES: NC(=O)c1ccc(Br)c2c1[nH]c1cc(C(O)CO)ccc12]

Step 1 A solution of potassium tert-butoxide (3.40 g, 30.3 mmol) in THF (249 mL) at 0° C. was treated with methyltriphenylphosphonium bromide (8.79 g, 24.60 mmol), forming a bright yellow suspension. After 1 h, 4-bromo-7-formyl-9H-carbazole-1-carboxamide (prepared according to the procedure of Step 1 of Example 41-1, 4 g, 9.46 mmol) was added, and the resulting suspension was warmed to rt and stirred for 3 h. Water was added and the mixture was extracted with EtOAc. The organic phase was washed with brine, dried and concentrated. The residue was purified by column chromatography (eluting with a gradient from 70:30 hexane-EtOAc to EtOAc). The crude material was suspended in methanol, and the precipitate was collected by filtration and dried. The filtrate was concentrated to provide additional solid which was collected by filtration, dried and combined with the first crop to provide 4-bromo-7-vinyl-9H-carbazole-1-carboxamide as a light brown solid (1.66 g, ca. 90% purity, 50%). $^1$H NMR (400 MHz, DMSO-$d_6$) δ 11.68 (1 H, s), 8.52 (1 H, d, J=8.3 Hz), 8.06-8.29 (1 H, m), 7.79-7.88 (2 H, m), 7.58 (1 H, br. s.), 7.35-7.45 (2 H, m), 6.78-6.98 (1 H, m), 5.88 (1 H, d, J=17.6 Hz), 5.32 (1 H, d). Mass spectrum m/z 344, 346 (M+H)$^+$.

Step 2 A solution of 4-bromo-7-vinyl-9H-carbazole-1-carboxamide (1.66 g, 4.74 mmol) and 4-methylmopholine N-oxide (0.833 g, 7.11 mmol) in acetone (172 mL) and water (17.2 mL) was treated with osmium tetroxide, 2.5 wt % in tert-butanol (0.238 mL, 0.019 mmol). The mixture was stirred at rt overnight, then was treated with additional 4-methylmorpholine N-oxide (0.8 eq., 0.42 g) and osmium tetroxide solution (0.004 eq., 0.2 mL). The mixture was stirred over a weekend, then was treated with sodium sulfite (2.99 g, 23.70 mmol) and stirred for 30 min. The mixture was filtered through a pad of Celite, and the solids were washed with acetone and THF. The filtrates were concentrated and purified by column chromatography (eluting with a gradient from 70:30 EtOAc-hexane to EtOAc, followed by 95:5 EtOAc-methanol) to afford 4-bromo-7-((RS)-1,2-dihydroxyethyl)-9H-carbazole-1-carboxamide as an off-white solid (1.47 g, 86%). $^1$H NMR (400 MHz, DMSO-$d_6$) δ 11.45 (1 H, s), 8.33 (1 H, d, J=8.1 Hz), 8.00 (1 H, br. s.), 7.58-7.68 (2 H, m), 7.35 (1H, br. s.), 7.22 (1 H, d, J=8.1 Hz), 7.07 (1 H, d, J=8.4 Hz), 5.14 (1 H, d, J=4.0 Hz), 4.41-4.62 (2 H, m), 3.32 (2 H, t, J=5.7 Hz). Mass spectrum m/z 331, 333 (M+H—$H_2O$)$^+$.

Intermediates 69-1 and 69-2

Preparation of Purified Enantiomers of 4-bromo-7-(1,2-dihydroxyethyl)-9H-carbazole-1-carboxamide 4-Bromo-7-((RS)-1,2-dihydroxyethyl)-9H-carbazole-1-carboxamide (Example 68-1, 453 mg) was subjected to chiral supercritical fluid chromatography (WhelkO-1(R,R) 25×3 cm, 5 mM column at 35° C., eluting with 75:25 carbon dioxide-methanol at 180 mL/min) to provide a faster-eluting enantiomer (Intermediate 69-1, 181 mg) and a slower-eluting enantiomer (Intermediate 69-2). Enantiomeric purities were determined to be >99.5% by analytical chiral chromatography. The absolute configurations were not determined.

Example 70-1

Preparation of 7-((R,S)-1,2-dihydroxyethyl)-4-(2-methyl-3-(5-methyl-1-oxoisoindolin-2-yl)phenyl)-9H-carbazole-1-carboxamide

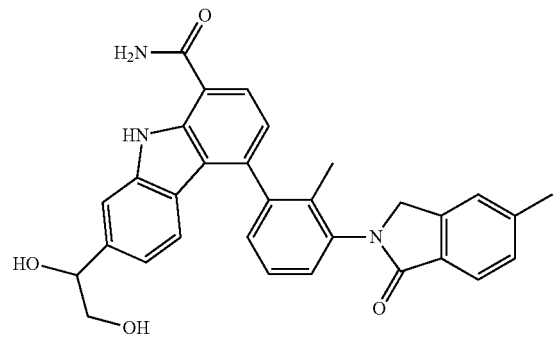 [SMILES: Cc1ccc2c(c1)CN(c1cccc(-c3ccc(C(N)=O)c4[nH]c5cc(C(O)CO)ccc5c34)c1C)C2=O]

Using the procedure of Example 3-2, 4-bromo-7-(1,2-dihydroxyethyl)-9H-carbazole-1-carboxamide (Example 68-1, 40 mg, 0.115 mmol) and 5-methyl-2-(2-methyl-3-(4,4,5,5-tetramethyl-1,3,2-dioxaborolan-2-yl)phenyl)isoindolin-1-one (Intermediate 50-18, 41.6 mg, 0.115 mmol) were converted into 7-((RS)-1,2-dihydroxyethyl)-4-(2-methyl-3-(5-methyl-1-oxoisoindolin-2-yl)phenyl)-9H-carbazole-1-carboxamide as a white solid (30 mg, 49%). $^1$H NMR (400 MHz, methanol-$d_4$) δ 7.96 (1 H, d, J=7.70 Hz), 7.76 (1 H, d, J=7.70 Hz), 7.66 (1 H, d, J=4.18 Hz), 7.47-7.57 (3 H, m), 7.38-7.44 (2 H, m), 7.02-7.12 (3 H, m), 4.81-4.85 (1 H, m), 3.68-3.72 (2 H, m), 2.52 (3 H, s), 1.91 (3 H, s). Mass spectrum m/z 488.3 (M+H)$^+$.

The following compounds were prepared using the procedures demonstrated in Example 70-1 and closely related procedures, using the Intermediates shown in place of Intermediate 50-18.

| Example | Starting materials | Compound name | Mass spectrum |
|---|---|---|---|
| 70-2 | Intermediate 53-1 | 7-((RS)-1,2-dihydroxyethyl)-4-(3-(4-fluorobenzamido)-2-methylphenyl)-9H-carbazole-1-carboxamide | 520.3 (M + Na)$^+$ |
| 70-3 | Intermediate 50-4 | 7-((RS)-1,2-dihydroxyethyl)-4-(2-methyl-3-(1-oxoisoindolin-2-yl)phenyl)-9H-carbazole-1-carboxamide | 515.4 (M + Na)$^+$ |
| 70-4 | Intermediate 50-1 | 4-(3-amino-2-methylphenyl)-7-((RS)-1,2-dihydroxyethyl)-9H-carbazole-1-carboxamide | 376.3 (M + H)$^+$ |
| 70-5 | Intermediate 50-8 | 7-((RS)-1,2-dihydroxyethyl)-4-(2-methyl-3-(6-methyl-1-oxoisoindolin-2-yl)phenyl)-9H-carbazole-1-carboxamide | 529.2 (M + Na)$^+$ |
| 70-6 | Intermediate 50-5 | 7-((RS)-1,2-dihydroxyethyl)-4-(3-(6-fluoro-1-oxoisoindolin-2-yl)-2-methylphenyl)-9H-carbazole-1-carboxamide | 533.2 (M + Na)$^+$ |
| 70-7 | Intermediate 50-19 | 7-((RS)-1,2-dihydroxyethyl)-4-(3-(5-fluoro-1-oxoisoindolin-2-yl)-2-methylphenyl)-9H-carbazole-1-carboxamide | 492.3 (M + H − $H_2O$)$^+$ |
| 70-8 | Intermediate 50-20 | 7-((RS)-1,2-dihydroxyethyl)-4-(4-methyl-5-(5-methyl-1-oxoisoindolin-2-yl)pyridin-3-yl)-9H-carbazole-1-carboxamide (prepared as the TFA salt) | 507.2 (M + H)$^+$ |
| 70-9 | Intermediate 50-5 | 7-(1,2-dihydroxyethyl)-4-(3-(6-fluoro-1-oxoisoindolin-2-yl)-2-methylphenyl)-9H-carbazole-1-carboxamide[a] | 532.2 (M + Na)$^+$ |

-continued

| Example | Starting materials | Compound name | Mass spectrum |
|---|---|---|---|
| 70-10 | Intermediate 50-5 | 7-(1,2-dihydroxyethyl)-4-(3-(6-fluoro-1-oxoisoindolin-2-yl)-2-methylphenyl)-9H-carbazole-1-carboxamide[b] | 532.2 (M + Na)+ |
| 70-11 | Intermediate 50-8 | 7-(1,2-dihydroxyethyl)-4-(2-methyl-3-(6-methyl-1-oxoisoindolin-2-yl)phenyl)-9H-carbazole-1-carboxamide[a] | 529.2 (M + Na)+ |
| 70-12 | Intermediate 50-8 | 7-(1,2-dihydroxyethyl)-4-(2-methyl-3-(6-methyl-1-oxoisoindolin-2-yl)phenyl)-9H-carbazole-1-carboxamide[b] | 529.2 (M + Na)+ |
| 70-13 | Intermediate 50-27 | 7-(1,2-dihydroxyethyl)-4-(3-(6-fluoro-4-oxoquinazolin-3(4H)-yl)-2-methylphenyl)-9H-carbazole-1-carboxamide | 523.3 (M + H)+ |
| 70-14 | Intermediate 50-26 | 4-(3-(6-chloro-4-oxoquinazolin-3(4H)-yl)-2-methylphenyl)-7-(1,2-dihydroxyethyl)-9H-carbazole-1-carboxamide | 539.0 (M + H)+ |
| 70-15 | Intermediate 50-13 | 7-(1,2-dihydroxyethyl)-4-(2-methyl-3-(1-oxo-4,5,6,7-tetrahydro-1H-isoindol-2(3H)-yl)phenyl)-9H-carbazole-1-carboxamide | 478.1 (M + H − $H_2O$)+ |
| 70-16 | Intermediate 50-6 | 7-(1,2-dihydroxyethyl)-4-(3-(5-methoxy-1-oxoisoindolin-2-yl)-2-methylphenyl)-9H-carbazole-1-carboxamide | 504.1 (M + H − $H_2O$)+ |
| 70-17 | Intermediate 50-54 | 7-(1,2-dihydroxyethyl)-4-(2-methyl-3-(quinazolin-4-ylamino)phenyl)-9H-carbazole-1-carboxamide | 504.1 (M + H)+ |

[a]Prepared from Intermediate 69-1
[b]Prepared from Intermediate 69-2

Intermediate 71-1

Preparation of 4-bromo-7-(2,2-dimethyl-1,3-dioxolan-4-yl)-9H-carbazole-1-carboxamide

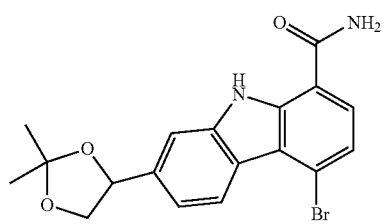 [SMILES: CC1(C)OCC(c2ccc3c(c2)[nH]c2c(C(N)=O)ccc(Br)c23)O1]

A mixture of 4-bromo-7-(1,2-dihydroxyethyl)-9H-carbazole-1-carboxamide (Example 68-1, 50 mg, 0.143 mmol) and p-toluenesulfonic acid monohydrate (8.2 mg, 0.043 mmol) in 2,2-dimethoxypropane (1.76 mL, 14.32 mmol) was stirred at rt. DMF (0.5 mL) was added and the mixture was stirred overnight. The mixture was diluted with EtOAc and washed with NaHCO3 (aq) and brine, then dried and concentrated. The residue was purified by column chromatography (eluting with a gradient from 75:25 to 50:50 hexane-EtOAc) to provide 4-bromo-7-(2,2-dimethyl-1,3-dioxolan-4-yl)-9H-carbazole-1-carboxamide as a light yellow solid (40 mg, 75% purity, 54%). Mass spectrum m/z 389, 391 (M+H)+.

Example 72-1

Preparation of 7-(2,2-dimethyl-1,3-dioxolan-4-yl)-4-(2-methyl-3-(6-methyl-1-oxoisoindolin-2-yl)phenyl)-9H-carbazole-1-carboxamide

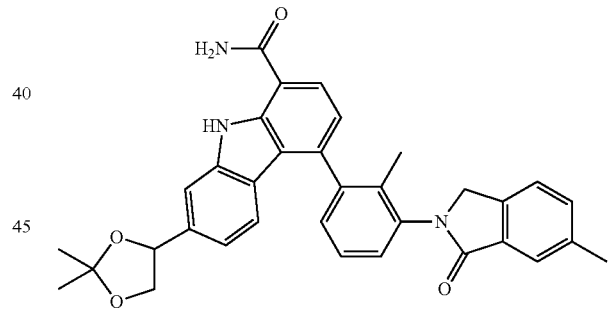

Using the procedure of Example 3-2, 4-bromo-7-(2,2-dimethyl-1,3-dioxolan-4-yl)-9H-carbazole-1-carboxamide (Intermediate 71-1, 40 mg, 0.077 mmol) and 6-methyl-2-(2-methyl-3-(4,4,5,5-tetramethyl-1,3,2-dioxaborolan-2-yl)phenyl)isoindolin-1-one (Intermediate 50-8, 30.8 mg, 0.085 mmol) were converted into 7-(2,2-dimethyl-1,3-dioxolan-4-yl)-4-(2-methyl-3-(6-methyl-1-oxoisoindolin-2-yl)phenyl)-9H-carbazole-1-carboxamide as a white solid (23 mg, 88% purity, 43%). $^1$H NMR (400 MHz, DMSO-$d_6$) δ 11.60 (1 H, s), 8.21 (1 H, br. s.), 8.03 (1 H, d, J=7.7 Hz), 7.81 (1 H, s), 7.55-7.64 (3 H, m), 7.44-7.55 (3 H, m), 7.34 (1 H, dd, J=7.5, 1.1 Hz), 6.98-7.07 (2 H, m), 6.87-6.98 (1 H, m), 5.11-5.20 (1 H, m), 4.83-4.99 (2 H, m), 4.32 (1 H, ddd, J=8.0, 6.3, 1.5 Hz), 3.56-3.67 (1 H, m), 2.44 (3 H, s), 1.83 (3 H, d, J=2.9 Hz), 1.51 (3 H, d, J=3.7 Hz), 1.43 (3 H, s). Mass spectrum m/z 568.2 (M+Na)+.

Example 73-1

Preparation of 5-bromo-2-(2-hydroxypropan-2-yl)-2,3,4,9-tetrahydro-1H-carbazole-8-carboxamide

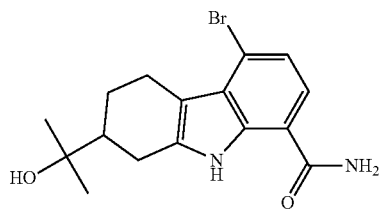 [SMILES: CC(C)(O)C1CCc2c([nH]c3c(C(N)=O)ccc(Br)c23)C1]

A solution of ethyl 5-bromo-8-carbamoyl-2,3,4,9-tetrahydro-1H-carbazole-2-carboxylate (Intermediate 46-1, 2 g, 5.48 mmol) in THF (100 mL) cooled in an ice bath was treated with methyllithium (1.6 M in diethyl ether, 17.11 mL, 27.4 mmol). After 1 h, the mixture was treated slowly with a mixture of 1 M hydrochloric acid (20 mL) and ice (20 g). The organic layer was separated, and the aqueous layer was extracted twice with DCM. The combined organic phases were washed with water and brine, dried and concentrated. The residue was triturated with DCM to provide 5-bromo-2-(2-hydroxypropan-2-yl)-2,3,4,9-tetrahydro-1H-carbazole-8-carboxamide as a light yellow solid (1.72 g, 89%). $^1$H NMR (400 MHz, methanol-$d_4$) δ 7.38 (1 H, d, J=8.14 Hz), 7.16 (1 H, d, J=8.14 Hz), 3.37-3.45 (1 H, m), 2.90-2.97 (1 H, m), 2.79-2.89 (1 H, m), 2.54-2.64 (1 H, m), 2.20-2.28 (1 H, m), 1.80-1.90 (1 H, m, J=11.94, 11.94, 4.95, 2.20 Hz), 1.41-1.53 (1 H, m, J=12.43, 12.43, 12.32, 5.28 Hz), 1.30 (6 H, s). Mass spectrum m/z 351, 353 (M+H)$^+$.

The following Intermediate was also prepared using the procedure demonstrated in Example 73-1, substituting Intermediate 48-1 in place of Intermediate 46-1 as starting material.

| Intermediate | Compound name | Mass spectrum |
|---|---|---|
| 73-2 | 4-bromo-7-(2-hydroxypropan-2-yl)-9H-carbazole-1-carboxamide | 329, 331 (M + H − H$_2$0)$^+$ |

Intermediate 74-1

Preparation of 4-bromo-7-isopropyl-9H-carbazole-1-carboxamide

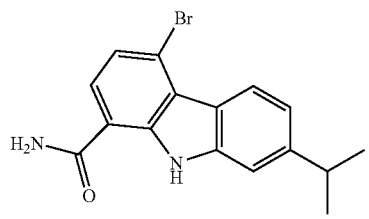 [SMILES: CC(C)c1ccc2c(c1)[nH]c1c(C(N)=O)ccc(Br)c12]

A suspension of 4-bromo-7-(2-hydroxypropan-2-yl)-9H-carbazole-1-carboxamide (Intermediate 73-2, 300 mg, 0.864 mmol) in DCM (2 mL) was treated with triethylsilane (1.380 mL, 8.64 mmol) and then slowly with TFA (0.666 mL, 8.64 mmol) and the mixture was stirred at rt for 40 min. The resulting suspension was diluted with DCM and the resulting solution was washed with NaHCO3 (aq). The organic phase was washed with water and brine, and dried and concentrated to give 4-bromo-7-isopropyl-9H-carbazole-1-carboxamide as a white solid (280 mg, 98%). $^1$H NMR (400 MHz, chloroform-d) δ 10.50 (1 H, br. s.), 8.63 (1 H, d, J=8.1 Hz), 7.32-7.40 (3 H, m), 7.22 (1 H, dd, J=8.4, 1.3 Hz), 5.97 (2 H, br. s.), 3.02-3.18 (1 H, m), 1.35 (6 H, d, J=6.8 Hz). Mass spectrum m/z 331, 333 (M+H)$^+$.

Intermediate 75-1

Preparation of 4-bromo-7-(2-methoxypropan-2-yl)-9H-carbazole-1-carboxamide

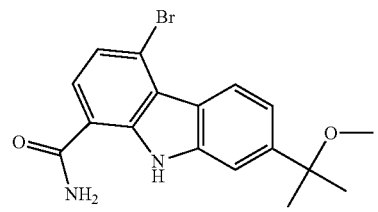 [SMILES: COC(C)(C)c1ccc2c(c1)[nH]c1c(C(N)=O)ccc(Br)c12]

A solution of 4-bromo-7-(2-hydroxypropan-2-yl)-9H-carbazole-1-carboxamide (Intermediate 73-2, 120 mg, 0.346 mmol) and TFA (0.013 mL, 0.173 mmol) in methanol (2 mL) was stirred at rt over a weekend. The mixture was diluted with DCM, washed with 1 M aqueous sodium hydroxide and water, dried and concentrated. The residue was combined with that from another reaction done with 20 mg of Intermediate 73-2, and purified by column chromatography (eluting with hexane-EtOAc) to provide 4-bromo-7-(2-methoxypropan-2-yl)-9H-carbazole-1-carboxamide as a white solid (112 mg, 77%). $^1$H NMR (400 MHz, chloroform-d) δ 10.53 (1 H, br. s.), 8.68 (1 H, d, J=8.36 Hz), 7.59 (1 H, d, J=1.10 Hz), 7.36-7.44 (3H, m), 3.13 (3 H, s), 1.64 (6 H, s). Mass spectrum m/z 361, 363 (M+H)$^+$.

Intermediate 75-2

Preparation of 4-bromo-7-(2-(2-hydroxyethoxy)propan-2-yl)-9H-carbazole-1-carboxamide

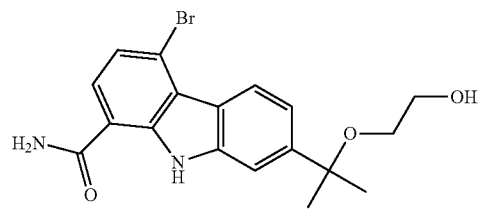 [SMILES: CC(C)(OCCO)c1ccc2c(c1)[nH]c1c(C(N)=O)ccc(Br)c12]

A mixture of 4-bromo-7-(2-hydroxypropan-2-yl)-9H-carbazole-1-carboxamide (Intermediate 73-2, 300 mg, 0.864 mmol), p-toluenesulfonic acid monohydrate (8.2 mg, 0.043 mmol) and ethylene glycol (1.45 mL) was stirred at rt overnight. The resulting suspension was treated with NaHCO3 (aq) and diluted with water. The precipitate was collected by filtration, washed with water and dried to provide 4-bromo-7-(2-(2-hydroxyethoxy)propan-2-yl)-9H-carbazole-1-carboxamide as a white solid (324 mg, 96%). $^1$H NMR (400 MHz, methanol-$d_4$) δ 8.65 (1 H, d, J=8.58 Hz), 7.77 (1 H, d, J=1.10 Hz), 7.75 (1 H, d, J=8.14 Hz), 7.44 (1 H, dd, J=8.36, 1.54 Hz), 7.40 (1 H, d), 3.69 (2 H, t, J=5.17 Hz), 3.32-3.34 (2 H, m), 1.68 (6 H, s). Mass spectrum m/z 413, 415 (M+Na)$^+$.

The following compound was also prepared using the procedures demonstrated in Intermediates 75-1 and 75-2, using Example 70-11 in place of Intermediate 46-1 as starting material.

| Example | Compound name | Mass spectrum |
|---|---|---|
| 75-3 | (RS)-7-(2-hydroxy-1-methoxyethyl)-4-(2-methyl-3-(6-methyl-1-oxoisoindolin-2-yl)phenyl)-9H-carbazole-1-carboxamide | 543.1 (M + Na)$^+$ |

Example 76-1

Preparation of 5-(3-(5-tert-butyl-1-oxoisoindolin-2-yl)-2-methylphenyl)-2-(2-hydroxypropan-2-yl)-2,3,4,9-tetrahydro-1H-carbazole-8-carboxamide

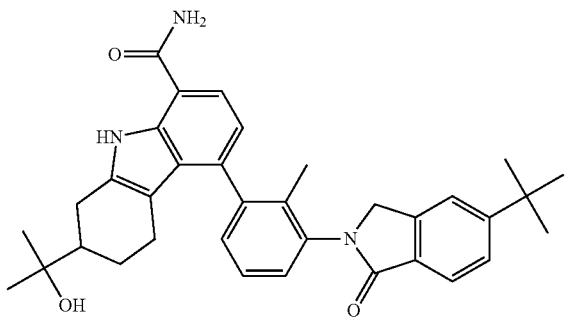 [SMILES: Cc1c(-c2ccc(C(N)=O)c3[nH]c4c(c23)CCC(C(C)(C)O)C4)cccc1N1Cc2cc(C(C)(C)C)ccc2C1=O]

Using the procedure of Example 31-1,5-bromo-2-(2-hydroxypropan-2-yl)-2,3,4,9-tetrahydro-1H-carbazole-8-carboxamide (Example 73-1, 30 mg, 0.085 mmol) and 5-tert-butyl-2-(2-methyl-3-(4,4,5,5-tetramethyl-1,3,2-dioxaborolan-2-yl)phenyl)isoindolin-1-one (Intermediate 50-15, 51.9 mg, 0.128 mmol) were converted into 5-(3-(5-tert-butyl-1-oxoisoindolin-2-yl)-2-methylphenyl)-2-(2-hydroxypropan-2-yl)-2,3,4,9-tetrahydro-1H-carbazole-8-carboxamide (25 mg, 51%). $^1$H NMR (400 MHz, chloroform-d) δ 10.05 (1 H, s), 7.88 (1 H, dd, J=8.35, 2.20 Hz), 7.53-7.59 (2 H, m), 7.36 (1 H, dd, J=7.47, 3.95 Hz), 7.28-7.33 (2 H, m), 7.26-7.28 (1 H, m), 6.90 (1 H, t, J=7.91 Hz), 4.69-4.83 (2 H, m), 2.90 (1 H, dd, J=16.04, 5.05 Hz), 2.54-2.67 (1 H, m), 1.96-2.23 (3 H, m), 1.93 (3 H, d, J=17.14 Hz), 1.74-1.89 (1 H, m), 1.58-1.68 (1 H, m), 1.39 (9 H, s), 1.31-1.37 (1 H, m), 1.23-1.26 (6 H, m). Mass spectrum m/z 550.3 (M+H)$^+$.

Example 76-2

Preparation of 7-(2-hydroxypropan-2-yl)-4-(2-methyl-3-(8-oxoimidazo[1,2-a]pyrazin-7(8 H)-yl)phenyl)-9H-carbazole-1-carboxamide

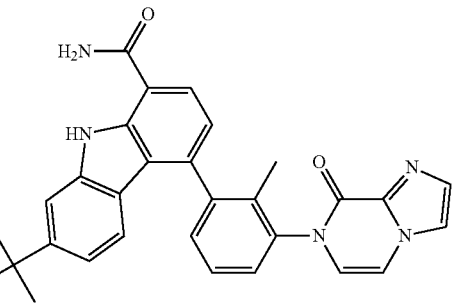

Using the procedure of Example 3-2,4-bromo-7-(2-hydroxypropan-2-yl)-9H-carbazole-1-carboxamide (Intermediate 73-2, 30 mg, 0.086 mmol) and 7-(2-methyl-3-(4,4,5,5-tetramethyl-1,3,2-dioxaborolan-2-yl)phenyl)imidazo[1,2-a]pyrazin-8(7 H)-one (Intermediate 50-30, 48.6 mg, 0.104 mmol) were converted into 7-(2-hydroxypropan-2-yl)-4-(2-methyl-3-(8-oxoimidazo[1,2-a]pyrazin-7(8 H)-yl)phenyl)-9H-carbazole-1-carboxamide (4.3 mg, 8.5%). $^1$H NMR (400 MHz, DMSO-$d_6$) δ 11.20 (1 H, d, J=8.6 Hz), 7.94 (1 H, br. s.), 7.77 (1 H, dd, J=9.7, 7.9 Hz), 7.66-7.70 (1 H, m), 7.61-7.66 (1 H, m), 7.49 (1 H, dd, J=14.2, 5.8 Hz), 7.28-7.36 (3 H, m), 7.15-7.29 (2 H, m), 6.93-7.00 (1 H, m), 6.85-6.90 (1 H, m), 6.79 (1 H, dd, J=15.4, 7.7 Hz), 6.57 (1 H, d, J=8.4 Hz), 4.76 (1 H, d, J=12.5 Hz), 1.52-1.60 (3 H, m), 1.21-1.30 (6 H, m). Mass spectrum m/z 514.2 (M+Na)$^+$.

The following compounds were prepared using the procedures demonstrated in Examples 76-1 and 76-2 and closely related procedures, and using the Examples and Intermediates shown as starting materials.

| Example | Starting materials | Compound name | Mass spectrum |
|---|---|---|---|
| 76-3 | Example 73-1, Intermediate 50-14 | 5-(3-(6-tert-butyl-1-oxoisoindolin-2-yl)-2-methylphenyl)-2-(2-hydroxypropan-2-yl)-2,3,4,9-tetrahydro-1H-carbazole-8-carboxamide | 550.3 (M + H)$^+$ |
| 76-4 | Example 73-1, Intermediate 50-5 | 5-(3-(6-fluoro-1-oxoisoindolin-2-yl)-2-methylphenyl)-2-(2-hydroxypropan-2-yl)-2,3,4,9-tetrahydro-1H-carbazole-8-carboxamide | 512.4 (M + H)$^+$ |
| 76-5 | Example 73-1, Intermediate 50-8 | 2-(2-hydroxypropan-2-yl)-5-(2-methyl-3-(6-methyl-1-oxoisoindolin-2-yl)phenyl)-2,3,4,9-tetrahydro-1H-carbazole-8-carboxamide | 508.4 (M + H)$^+$ |

-continued

| Example | Starting materials | Compound name | Mass spectrum |
|---|---|---|---|
| 76-6 | Example 73-1, Intermediate 50-49 | 2-(2-hydroxypropan-2-yl)-5-(2-methyl-3-(3-oxo-1H-pyrrolo[3,4-c]pyridin-2(3H)-yl)phenyl)-2,3,4,9-tetrahydro-1H-carbazole-8-carboxamide | 495.4 (M + H)+ |
| 76-7 | Example 73-1, Intermediate 50-50 | (Z)-5-(3-(furo[3,4-c]pyridin-3(1H)-ylideneamino)-2-methylphenyl)-2-(2-hydroxypropan-2-yl)-2,3,4,9-tetrahydro-1H-carbazole-8-carboxamide | 495.4 (M + H)+ |
| 76-8 | Intermediate 74-1, Intermediate 50-49 | 7-isopropyl-4-(2-methyl-3-(3-oxo-1H-pyrrolo[3,4-c]pyridin-2(3H)-yl)phenyl)-9H-carbazole-1-carboxamide | 475.4 (M + H)+ |
| 76-9 | Intermediate 74-1, Intermediate 50-50 | (Z)-4-(3-(furo[3,4-c]pyridin-3(1H)-ylideneamino)-2-methylphenyl)-7-isopropyl-9H-carbazole-1-carboxamide | 475.4 (M + H)+ |
| 76-10 | Example 73-1, Intermediate 50-23 | 2-(2-hydroxypropan-2-yl)-5-(2-methyl-3-(2-methyl-4-oxoquinazolin-3(4H)-yl)phenyl)-2,3,4,9-tetrahydro-1H-carbazole-8-carboxamide | 421.4 (M + H)+ |
| 76-11 | Intermediate 73-2, Intermediate 50-19 | 4-(3-(5-fluoro-1-oxoisoindolin-2-yl)-2-methylphenyl)-7-(2-hydroxypropan-2-yl)-9H-carbazole-1-carboxamide | 490.3 (M + H − H$_2$O)+ |
| 76-12 | Intermediate 73-2, Intermediate 50-4 | 7-(2-hydroxypropan-2-yl)-4-(2-methyl-3-(1-oxoisoindolin-2-yl)phenyl)-9H-carbazole-1-carboxamide | 472.3 (M + H − H$_2$O)+ |
| 76-13 | Intermediate 73-2, Intermediate 51-2 | 4-(3-(5-chloro-1-oxoisoindolin-2-yl)-2-methylphenyl)-7-(2-hydroxypropan-2-yl)-9H-carbazole-1-carboxamide | 506.2 (M + H − H$_2$O)+ |
| 76-14 | Intermediate 73-2, Intermediate 50-8 | 7-(2-hydroxypropan-2-yl)-4-(2-methyl-3-(6-methyl-1-oxoisoindolin-2-yl)phenyl)-9H-carbazole-1-carboxamide | 486.3 (M + H − H$_2$O)+ |
| 76-15 | Intermediate 73-2, Intermediate 50-5 | 4-(3-(6-fluoro-1-oxoisoindolin-2-yl)-2-methylphenyl)-7-(2-hydroxypropan-2-yl)-9H-carbazole-1-carboxamide | 530.4 (M + Na)+ |
| 76-16 | Intermediate 73-2, Intermediate 50-18 | 7-(2-hydroxypropan-2-yl)-4-(2-methyl-3-(5-methyl-1-oxoisoindolin-2-yl)phenyl)-9H-carbazole-1-carboxamide | 486.3 (M + H − H$_2$O)+ |
| 76-17 | Intermediate 73-2, Intermediate 50-29 | 7-(2-hydroxypropan-2-yl)-4-(2-methyl-3-(1-oxoisoquinolin-2(1H)-yl)phenyl)-9H-carbazole-1-carboxamide | 502.4 (M + H)+ |
| 76-18 | Intermediate 73-2, Intermediate 50-49 | 7-(2-hydroxypropan-2-yl)-4-(2-methyl-3-(3-oxo-1H-pyrrolo[3,4-c]pyridin-2(3H)-yl)phenyl)-9H-carbazole-1-carboxamide | 491.4 (M + H)+ |
| 76-19 | Intermediate 73-2, Intermediate 50-50 | (Z)-4-(3-(furo[3,4-c]pyridin-3(1H)-ylideneamino)-2-methylphenyl)-7-(2-hydroxypropan-2-yl)-9H-carbazole-1-carboxamide | 491.4 (M + H)+ |
| 76-20 | Intermediate 73-2, Intermediate 50-7 | 7-(2-hydroxypropan-2-yl)-4-(2-methyl-3-(1-oxo-6-(trifluoromethyl)isoindolin-2-yl)phenyl)-9H-carbazole-1-carboxamide | 540.1 (M + H − H$_2$O)+ |
| 76-21 | Intermediate 75-1, Intermediate 50-7 | 7-(2-methoxypropan-2-yl)-4-(2-methyl-3-(1-oxo-6-(trifluoromethyl)isoindolin-2-yl)phenyl)-9H-carbazole-1-carboxamide | 594.2 (M + Na)+ |
| 76-22 | Intermediate 73-2, Intermediate 50-23 | 7-(2-hydroxypropan-2-yl)-4-(2-methyl-3-(2-methyl-4-oxoquinazolin-3(4H)-yl)phenyl)-9H-carbazole-1-carboxamide | 517.4 (M + H)+ |
| 76-23 | Intermediate 73-2, Intermediate 50-17 | 4-(3-(4-fluoro-1-oxoisoindolin-2-yl)-2-methylphenyl)-7-(2-hydroxypropan-2-yl)-9H-carbazole-1-carboxamide | 490.3 (M + H − H$_2$O)+ |
| 76-24 | Intermediate 73-2, Intermediate 50-16 | 4-(3-(7-fluoro-1-oxoisoindolin-2-yl)-2-methylphenyl)-7-(2-hydroxypropan-2-yl)-9H-carbazole-1-carboxamide | 490.4 (M + H − H$_2$O)+ |

-continued

| Example | Starting materials | Compound name | Mass spectrum |
|---|---|---|---|
| 76-25 | Intermediate 73-2, Intermediate 50-24 | 7-(2-hydroxypropan-2-yl)-4-(2-methyl-3-(4-oxoquinazolin-3(4H)-yl)phenyl)-9H-carbazole-1-carboxamide | 503.4 (M + H)+ |
| 76-26 | Intermediate 73-2, Intermediate 50-25 | 4-(3-(5-fluoro-4-oxoquinazolin-3(4H)-yl)-2-methylphenyl)-7-(2-hydroxypropan-2-yl)-9H-carbazole-1-carboxamide | 521.3 (M + H)+ |
| 76-27 | Intermediate 73-2, Intermediate 50-26 | 4-(3-(6-chloro-4-oxoquinazolin-3(4H)-yl)-2-methylphenyl)-7-(2-hydroxypropan-2-yl)-9H-carbazole-1-carboxamide | 537.4 (M + H)+ |
| 76-28 | Intermediate 73-2, Intermediate 50-28 | 7-(2-hydroxypropan-2-yl)-4-(2-methyl-3-(6-methyl-4-oxoquinazolin-3(4H)-yl)phenyl)-9H-carbazole-1-carboxamide | 517.4 (M + H)+ |
| 76-29 | Intermediate 74-1, Intermediate 50-16 | 4-(3-(7-fluoro-1-oxoisoindolin-2-yl)-2-methylphenyl)-7-isopropyl-9H-carbazole-1-carboxamide | 492.4 (M + H)+ |
| 76-30 | Intermediate 74-1, Intermediate 50-5 | 4-(3-(6-fluoro-1-oxoisoindolin-2-yl)-2-methylphenyl)-7-isopropyl-9H-carbazole-1-carboxamide | 492.4 (M + H)+ |
| 76-31 | Intermediate 74-1, Intermediate 50-7 | 7-isopropyl-4-(2-methyl-3-(1-oxo-6-(trifluoromethyl)isoindolin-2-yl)phenyl)-9H-carbazole-1-carboxamide | 542.4 (M + H)+ |
| 76-32 | Intermediate 73-2, Intermediate 50-6 | 7-(2-hydroxypropan-2-yl)-4-(3-(5-methoxy-1-oxoisoindolin-2-yl)-2-methylphenyl)-9H-carbazole-1-carboxamide | 502.1 (M + H − H2O)+ |
| 76-33 | Intermediate 73-2, Intermediate 50-27 | 4-(3-(6-fluoro-4-oxoquinazolin-3(4H)-yl)-2-methylphenyl)-7-(2-hydroxypropan-2-yl)-9H-carbazole-1-carboxamide | 521.4 (M + H)+ |
| 76-34 | Intermediate 74-1, Intermediate 50-27 | 4-(3-(6-fluoro-4-oxoquinazolin-3(4H)-yl)-2-methylphenyl)-7-isopropyl-9H-carbazole-1-carboxamide | 505.4 (M + H)+ |
| 76-35 | Example 73-1, Intermediate 50-27 | 5-(3-(6-fluoro-4-oxoquinazolin-3(4H)-yl)-2-methylphenyl)-2-(2-hydroxypropan-2-yl)-2,3,4,9-tetrahydro-1H-carbazole-8-carboxamide | 525.4 (M + H)+ |
| 76-36 | Intermediate 73-2, Intermediate 50-1 | 4-(3-amino-2-methylphenyl)-7-(2-hydroxypropan-2-yl)-9H-carbazole-1-carboxamide | 374.1 (M + H)+ |
| 76-37 | Intermediate 75-1, Intermediate 50-1 | 4-(3-amino-2-methylphenyl)-7-(2-methoxypropan-2-yl)-9H-carbazole-1-carboxamide | 356.1 (M + H − CH3OH)+ |
| 76-38 | Intermediate 73-2, Intermediate 50-12 | 7-(2-hydroxypropan-2-yl)-4-(2-methyl-3-(1-oxo-1H-isoindol-2(3H,3aH,4H,5H,6H,7H,7aH)-yl)phenyl)-9H-carbazole-1-carboxamide | 478.1 (M + H − H2O)+ |
| 76-39 | Intermediate 73-2, Intermediate 50-13 | 7-(2-hydroxypropan-2-yl)-4-(2-methyl-3-(1-oxo-4,5,6,7-tetrahydro-1H-isoindol-2(3H)-yl)phenyl)-9H-carbazole-1-carboxamide | 476.2 (M + H − H2O)+ |
| 76-40 | Example 73-1, Intermediate 50-24 | 2-(2-hydroxypropan-2-yl)-5-(2-methyl-3-(4-oxoquinazolin-3(4H)-yl)phenyl)-2,3,4,9-tetrahydro-1H-carbazole-8-carboxamide | 507.4 (M + H)+ |
| 76-41 | Example 73-1, Intermediate 50-25 | 5-(3-(5-fluoro-4-oxoquinazolin-3(4H)-yl)-2-methylphenyl)-2-(2-hydroxypropan-2-yl)-2,3,4,9-tetrahydro-1H-carbazole-8-carboxamide | 525.4 (M + H)+ |
| 76-42 | Example 73-1, Intermediate 50-26 | 5-(3-(6-chloro-4-oxoquinazolin-3(4H)-yl)-2-methylphenyl)-2-(2-hydroxypropan-2-yl)-2,3,4,9-tetrahydro-1H-carbazole-8-carboxamide | 541.4 (M + H)+ |
| 76-43 | Example 73-1, Intermediate 50-28 | 2-(2-hydroxypropan-2-yl)-5-(2-methyl-3-(6-methyl-4-oxoquinazolin-3(4H)-yl)phenyl)-2,3,4,9-tetrahydro-1H-carbazole-8-carboxamide | 521.4 (M + H)+ |

| Example | Starting materials | Compound name | Mass spectrum |
|---|---|---|---|
| 76-44 | Example 73-1, Intermediate 50-7 | 2-(2-hydroxypropan-2-yl)-5-(2-methyl-3-(1-oxo-6-(trifluoromethyl)isoindolin-2-yl)phenyl)-2,3,4,9-tetrahydro-1H-carbazole-8-carboxamide | 562.4 (M + H)+ |
| 76-45 | Example 73-1, Intermediate 50-12 | 2-(2-hydroxypropan-2-yl)-5-(2-methyl-3-(1-oxo-1H-isoindol-2(3H,3aH,4H,5H,6H,7H,7aH)-yl)phenyl)-2,3,4,9-tetrahydro-1H-carbazole-8-carboxamide | 500.2 (M + H)+ |
| 76-46 | Example 73-1, Intermediate 50-13 | 2-(2-hydroxypropan-2-yl)-5-(2-methyl-3-(1-oxo-4,5,6,7-tetrahydro-1H-isoindol-2(3H)-yl)phenyl)-2,3,4,9-tetrahydro-1H-carbazole-8-carboxamide | 498.2 (M + H)+ |
| 76-47 | Example 73-1, Intermediate 50-1 | 5-(3-amino-2-methylphenyl)-2-(2-hydroxypropan-2-yl)-2,3,4,9-tetrahydro-1H-carbazole-8-carboxamide | 378.2 (M + H)+ |
| 76-48 | Intermediate 75-2, Intermediate 50-7 | 7-(2-(2-hydroxyethoxy)propan-2-yl)-4-(2-methyl-3-(1-oxo-6-(trifluoromethyl)isoindolin-2-yl)phenyl)-9H-carbazole-1-carboxamide | 624.2 (M + Na)+ |
| 76-49 | Intermediate 75-2, Intermediate 50-50 | (Z)-4-(3-(furo[3,4-c]pyridin-3(1H)-ylideneamino)-2-methylphenyl)-7-(2-(2-hydroxyethoxy)propan-2-yl)-9H-carbazole-1-carboxamide | 535.2 (M + H)+ |
| 76-50 | Intermediate 75-1, Intermediate 50-49 | 7-(2-methoxypropan-2-yl)-4-(2-methyl-3-(3-oxo-1H-pyrrolo[3,4-c]pyridin-2(3H)-yl)phenyl)-9H-carbazole-1-carboxamide | 473.1 (M + H − CH$_3$OH)+ |
| 76-51 | Intermediate 73-2, Intermediate 50-48 | 4-(3-(8-fluoro-4-oxoquinazolin-3(4H)-yl)-2-methylphenyl)-7-(2-hydroxypropan-2-yl)-9H-carbazole-1-carboxamide | 521.3 (M + H)+ |
| 76-52 | Intermediate 75-2, Intermediate 50-24 | 7-(2-(2-hydroxyethoxy)propan-2-yl)-4-(2-methyl-3-(4-oxoquinazolin-3(4H)-yl)phenyl)-9H-carbazole-1-carboxamide | 569.1 (M + Na)+ |
| 76-53 | Intermediate 75-1, Intermediate 50-27 | 4-(3-(6-fluoro-4-oxoquinazolin-3(4H)-yl)-2-methylphenyl)-7-(2-methoxypropan-2-yl)-9H-carbazole-1-carboxamide | 557.1 (M + Na)+ |
| 76-54 | Intermediate 75-2, Intermediate 50-27 | 4-(3-(6-fluoro-4-oxoquinazolin-3(4H)-yl)-2-methylphenyl)-7-(2-(2-hydroxyethoxy)propan-2-yl)-9H-carbazole-1-carboxamide | 587.1 (M + Na)+ |
| 76-55 | Intermediate 75-1, Intermediate 50-24 | 7-(2-methoxypropan-2-yl)-4-(2-methyl-3-(4-oxoquinazolin-3(4H)-yl)phenyl)-9H-carbazole-1-carboxamide | 517.1 (M + H)+ |
| 76-56 | Intermediate 75-1, Intermediate 50-5 | 4-(3-(6-fluoro-1-oxoisoindolin-2-yl)-2-methylphenyl)-7-(2-methoxypropan-2-yl)-9H-carbazole-1-carboxamide | 490.0 (M + H − CH$_3$OH)+ |
| 76-57 | Intermediate 73-2, Intermediate 50-51 | 7-(2-hydroxypropan-2-yl)-4-(3-(8-methoxy-4-oxoquinazolin-3(4H)-yl)-2-methylphenyl)-9H-carbazole-1-carboxamide | 533.2 (M + H)+ |
| 76-58 | Intermediate 73-2, Intermediate 50-52 | 7-(2-hydroxypropan-2-yl)-4-(3-(5-methoxy-4-oxoquinazolin-3(4H)-yl)-2-methylphenyl)-9H-carbazole-1-carboxamide | 533.2 (M + H)+ |
| 76-59 | Intermediate 73-2, Intermediate 50-53 | 7-(2-hydroxypropan-2-yl)-4-(3-(7-methoxy-4-oxoquinazolin-3(4H)-yl)-2-methylphenyl)-9H-carbazole-1-carboxamide | 533.2 (M + H)+ |
| 76-60 | Example 73-1, Intermediate 50-38 | 7-(2-hydroxypropan-2-yl)-4-(2-methyl-3-(4-oxo-6-(trifluoromethoxy)quinazolin-3(4H)-yl)phenyl)-9H-carbazole-1-carboxamide | 587.1 (M + H)+ |
| 76-61 | Intermediate 73-2, Intermediate 50-43 | 7-(2-hydroxypropan-2-yl)-4-(2-methyl-3-(2-oxopiperidin-1-yl)phenyl)-9H-carbazole-1-carboxamide | 456.2 (M + H)+ |
| 76-62 | Intermediate 73-2, Intermediate 50-9 | 4-(3-(6-cyano-1-oxoisoindolin-2-yl)-2-methylphenyl)-7-(2-hydroxypropan-2-yl)-9H-carbazole-1-carboxamide | 497.1 (M + H − H$_2$O)+ |

| Example | Starting materials | Compound name | Mass spectrum |
|---|---|---|---|
| 76-63 | Example 73-1, Intermediate 50-48 | 5-(3-(8-fluoro-4-oxoquinazolin-3(4H)-yl)-2-methylphenyl)-2-(2-hydroxypropan-2-yl)-2,3,4,9-tetrahydro-1H-carbazole-8-carboxamide | 525.2 (M + H)+ |
| 76-64 | Example 73-1, Intermediate 50-51 | 2-(2-hydroxypropan-2-yl)-5-(3-(8-methoxy-4-oxoquinazolin-3(4H)-yl)-2-methylphenyl)-2,3,4,9-tetrahydro-1H-carbazole-8-carboxamide | 537.2 (M + H)+ |
| 76-65 | Intermediate 73-2, Intermediate 50-58 | 7-(2-hydroxypropan-2-yl)-4-(2-methyl-3-(8-methyl-4-oxoquinazolin-3(4H)-yl)phenyl)-9H-carbazole-1-carboxamide | 517.2 (M + H)+ |
| 76-66 | Intermediate 73-2, Intermediate 50-59 | 7-(2-hydroxypropan-2-yl)-4-(3-(6-methoxy-4-oxoquinazolin-3(4H)-yl)-2-methylphenyl)-9H-carbazole-1-carboxamide | 533.2 (M + H)+ |
| 76-67 | Intermediate 73-2, Intermediate 50-60 | 4-(3-(7-fluoro-4-oxoquinazolin-3(4H)-yl)-2-methylphenyl)-7-(2-hydroxypropan-2-yl)-9H-carbazole-1-carboxamide | 521.1 (M + H)+ |

Example 76-15

1H NMR (400 MHz, CHLOROFORM-d) δ ppm 10.60 (1 H, s), 7.70 (1 H, d, J=1.10 Hz), 7.63-7.68 (2 H, m), 7.52 (1 H, dd, J=8.36, 4.40 Hz), 7.44-7.48 (2 H, m), 7.31-7.41 (2 H, m), 7.21 (1 H, dd, J=8.36, 1.76 Hz), 7.06-7.11 (2 H, m), 4.82 (2H, s), 2.01 (1 H, s), 1.97 (3 H, s), 1.66 (6 H, s).

Example 76-25

1H NMR (400 MHz, CHLOROFORM-d) δ ppm 10.57 (1 H, d, J=15.19 Hz), 8.38-8.43 (1 H, m), 8.15 (1 H, d, J=6.60 Hz), 7.78-7.84 (2 H, m), 7.68-7.72 (1 H, m), 7.66 (1 H, dd, J=7.92, 2.20 Hz), 7.42-7.60 (4 H, m), 7.27 (1 H, d), 7.12-7.16 (1 H, m), 6.90-7.08 (1 H, m), 1.91 (3 H, d, J=11.88 Hz), 1.63-1.67 (6 H, m).

Example 76-32

1H NMR (400 MHz, CHLOROFORM-d) δ ppm 10.56 (1 H, s), 7.86 (1 H, d, J=8.36 Hz), 7.67 (1 H, d, J=1.32 Hz), 7.64 (1 H, d, J=7.92 Hz), 7.41-7.44 (2 H, m), 7.32-7.37 (1 H, m), 7.19 (1 H, dd, J=8.36, 1.54 Hz), 7.00-7.10 (4 H, m), 4.77 (2H, s), 3.90 (3 H, s), 1.95 (3 H, s), 1.63 (6 H, s)

Example 76-51

1H NMR (400 MHz, CHLOROFORM-d) δ ppm 10.59 (1 H, d), 8.18 (2 H, d, J=7.26 Hz), 7.71 (1 H, dd, J=10.01, 0.99 Hz), 7.65 (1 H, t, J=7.70 Hz), 7.41-7.59 (5 H, m), 7.20-7.29 (1 H, m), 7.07 (1 H, dd, J=17.83, 7.70 Hz), 6.87-7.15 (1 H, m), 2.00 (1 H, d, J=14.97 Hz), 1.89 (3 H, d, J=12.54 Hz), 1.64 (6 H, s).

Example 77-1

Preparation of 4-(3-(5-fluoropicolinamido)-2-methylphenyl)-7-(4-methylpiperazin-1-yl)-9H-carbazole-1-carboxamide

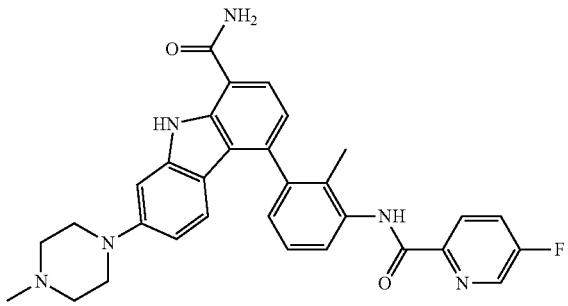 [SMILES: Cc1c(NC(=O)c2ccc(F)cn2)cccc1-c1ccc(C(N)=O)c2[nH]c3cc(N4CCN(C)CC4)ccc3c12]

A mixture of 4-(3-amino-2-methylphenyl)-7-(4-methylpiperazin-1-yl)-9H-carbazole-1-carboxamide, TFA salt (Example 66-3, 40 mg, 0.076 mmol), 5-fluoropicolinic acid (16.1 mg, 0.114 mmol), HOAT (15.5 mg, 0.114 mmol), and EDC (29.1 mg, 0.152 mmol) in acetonitrile (4 mL) was treated with DIEA (0.265 mL, 1.516 mmol). The resulting solution was stirred at rt for 4 h, then was concentrated and purified by preparative HPLC to provide 4-(3-(5-fluoropicolinamido)-2-methylphenyl)-7-(4-methylpiperazin-1-yl)-9H-carbazole-1-carboxamide, TFA salt, as a light brown solid (20 mg, 37%). 1H NMR (400 MHz, methanol-d4) δ 8.47 (1 H, d, J=2.8 Hz), 8.21 (1 H, dd, J=8.8, 4.5 Hz), 7.85-7.91 (1 H, m), 7.78 (1 H, d, J=7.8 Hz), 7.72 (1 H, td, J=8.6, 2.9 Hz), 7.33 (1 H, t, J=7.8 Hz), 7.09-7.16 (1 H, m), 7.07 (1 H, d, J=2.0 Hz), 6.91 (1 H, d, J=7.8 Hz), 6.81 (1 H, d, J=8.5 Hz), 6.59 (1 H, dd, J=8.8, 2.0 Hz), 3.71-3.84 (2 H, m), 3.44-3.55 (2 H, m), 3.10-3.19 (2 H, m), 2.91-3.04 (2H, m), 2.87 (3 H, s), 1.93 (3 H, s). Mass spectrum m/z 537.1 (M+H)+.

Example 77-2

Preparation of N-(3-(1-carbamoyl-7-(4-methylpiperazin-1-yl)-9H-carbazol-4-yl)-2-methylphenyl)thiazole-2-carboxamide

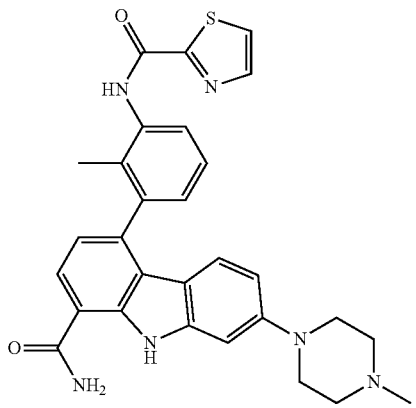 [SMILES: Cc1c(NC(=O)c2nccs2)cccc1-c1ccc(C(N)=O)c2[nH]c3cc(N4CCN(C)CC4)ccc3c12]

A solution of 4-(3-amino-2-methylphenyl)-7-(4-methylpiperazin-1-yl)-9H-carbazole-1-carboxamide, TFA salt (Example 66-3, 30 mg, 0.047 mmol) and TEA (0.026 mL, 0.187 mmol) in DCM-THF (2:1, 3 mL) was treated with thiazole-2-carbonyl chloride, hydrochloric acid salt (8.3 mg, 0.056 mmol) and stirred at rt for 1.5 h. The mixture was concentrated and purified by preparative HPLC to provide N-(3-(1-carbamoyl-7-(4-methylpiperazin-1-yl)-9H-carbazol-4-yl)-2-methylphenyl)thiazole-2-carboxamide, TFA salt, as a white solid (19 mg, 56%). $^1$H NMR (500 MHz, DMSO-$d_6$) δ 11.24 (1 H, s), 10.38 (1 H, s), 8.09-8.14 (1 H, m), 8.07 (1 H, d, J=3.1 Hz), 8.04 (1 H, d, J=3.1 Hz), 7.86 (1 H, d, J=8.0 Hz), 7.57 (1 H, d, J=7.5 Hz), 7.41 (1H, br. s.), 7.34 (1 H, t, J=7.8 Hz), 7.23 (1 H, d, J=1.9 Hz), 7.13 (1 H, d, J=6.7 Hz), 6.87 (1 H, d, J=7.8 Hz), 6.75 (1 H, d, J=8.9 Hz), 6.63 (1 H, dd, J=8.9, 2.2 Hz), 3.69-3.79 (2 H, m), 3.43-3.50 (2 H, m), 3.06-3.18 (2 H, m), 2.87-2.97 (2 H, m), 2.79 (3H, br. s.), 1.87 (3 H, s). Mass spectrum m/z 525.1 (M+H)$^+$.

The following compound was also prepared using the procedure demonstrated in Example 77-1:

| Example | Compound name | Mass spectrum |
|---|---|---|
| 77-3 | N-(3-(1-carbamoyl-7-(4-methylpiperazin-1-yl)-9H-carbazol-4-yl)-2-methylphenyl)-5-methylthiazole-2-carboxamide (prepared as the TFA salt) | 539.1 (M + H)$^+$ |

Example 78-1

Preparation of 7-(1,2-dihydroxyethyl)-4-(3-(5-fluoropicolinamido)-2-methylphenyl)-9H-carbazole-1-carboxamide

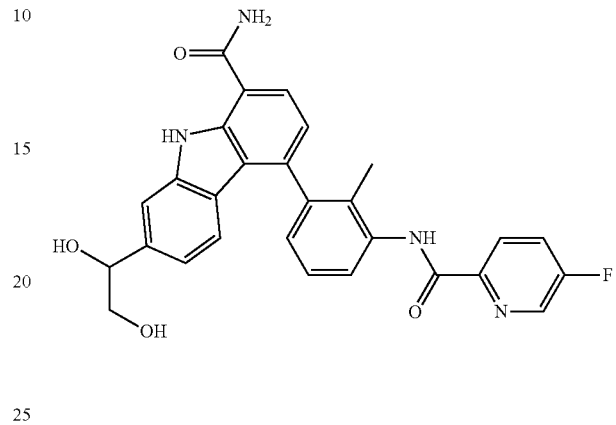

A solution of 4-(3-amino-2-methylphenyl)-7-(1,2-dihydroxyethyl)-9H-carbazole-1-carboxamide (Example 70-4, 28 mg, 0.075 mmol), 5-fluoropicolinic acid (15.8 mg, 0.112 mmol), HOAT (18.3 mg, 0.134 mmol), and EDC (28.6 mg, 0.149 mmol) in acetonitrile-THF (2:1, 3 mL) was treated with DIEA (0.039 mL, 0.224 mmol) and stirred at rt overnight. The mixture was concentrated and purified by preparative HPLC. The residue from concentration of the appropriate effluent fractions was partitioned between NaHCO3 (aq) and EtOAc, and the organic phase was washed with brine, dried and concentrated to provide 7-(1,2-dihydroxyethyl)-4-(3-(5-fluoropicolinamido)-2-methylphenyl)-9H-carbazole-1-carboxamide as an off-white solid (20 mg, 53%). $^1$H NMR (400 MHz, DMSO-$d_6$) δ 11.47 (1H, s), 10.38 (1H, s), 8.74 (1H, d, J=2.6 Hz), 8.28 (1H, dd, J=8.8, 4.8 Hz), 8.10-8.23 (1H, m), 7.95-8.04 (2H, m), 7.87-7.93 (1H, m), 7.72 (1H, s), 7.46-7.52 (1H, m), 7.43 (1H, t, J=7.6 Hz), 7.18 (1H, d, J=6.6 Hz), 6.97 (1H, d, J=7.7 Hz), 6.82-6.92 (2H, m), 5.22 (1H, t, J=3.5 Hz), 4.66-4.72 (1H, m), 4.56-4.64 (1H, m), 3.44 (2H, t, J=6.1 Hz), 1.97 (3H, s). Mass spectrum m/z 521.3 (M+Na)$^+$.

The following compound was also prepared using the procedure demonstrated in Example 78-1.

| Example | Compound name | Mass spectrum |
|---|---|---|
| 78-2 | 7-(1,2-dihydroxyethyl)-4-(2-methyl-3-(1-methyl-1H-imidazole-2-carboxamido)phenyl)-9H-carbazole-1-carboxamide | 484.4 (M + H)$^+$ |

Example 79-1

Preparation of 4-(2-methyl-3-(6-methylquinazolin-4-ylamino)phenyl)-7-(2-oxopyrrolidin-1-yl)-9H-carbazole-1-carboxamide

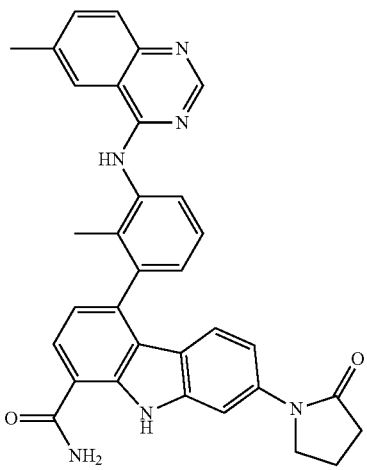 [SMILES: Cc1ccc2ncnc(Nc3cccc(-c4ccc(C(N)=O)c5[nH]c6cc(N7CCCC7=O)ccc6c45)c3C)c2c1]

A suspension of 4-chloro-6-methylquinazoline (prepared by the procedure used in Steps 1 and 2 of the preparation of Intermediate 32-1, 16.81 mg, 0.094 mmol) and 4-(3-amino-2-methylphenyl)-7-(2-oxopyrrolidin-1-yl)-9H-carbazole-1-carboxamide (Intermediate 65-1, 25 mg, 0.063 mmol) in isopropanol (0.75 mL) was treated with hydrogen chloride (4 M in 1,4-dioxane) (0.019 mL, 0.075 mmol) and heated by microwave irradiation in a sealed tube at 140° C. for 45 min. The mixture was concentrated and the residue was purified by preparative HPLC. The residue from concentration of the appropriate effluent fractions was partitioned between NaHCO3 (aq) and EtOAc, and the aqueous phase was extracted twice more with EtOAc. The combined organic phases were dried and concentrated to provide 4-(2-methyl-3-(6-methylquinazolin-4-ylamino)phenyl)-7-(2-oxopyrrolidin-1-yl)-9H-carbazole-1-carboxamide as a tan solid (7.4 mg, 20%). $^1$H NMR (400 MHz, methanol-$d_4$) δ 8.43 (1H, s), 8.22 (1H, s), 7.97 (1H, d, J=7.7 Hz), 7.84 (1H, d, J=1.3 Hz), 7.67-7.77 (2H, m), 7.46-7.58 (2H, m), 7.36 (1H, dd, J=7.3, 1.5 Hz), 7.21-7.30 (2H, m), 7.13 (1H, d, J=7.9 Hz), 3.98-4.07 (2H, m), 2.65 (2H, t, J=8.1 Hz), 2.60 (3H, s), 2.18-2.28 (2H, m), 1.96 (3H, s). Mass spectrum m/z 541.5 (M+H)$^+$.

The following compounds were also prepared using the procedure demonstrated in Example 79-1, using the appropriate chloroquinazoline in place of 4-chloro-6-methylquinazoline.

| Example | Compound name | Mass spectrum |
| --- | --- | --- |
| 79-2 | 4-(2-methyl-3-(7-methylquinazolin-4-ylamino)phenyl)-7-(2-oxopyrrolidin-1-yl)-9H-carbazole-1-carboxamide | 541.5 (M + H)$^+$ |
| 79-3 | 4-(3-(6-fluoroquinazolin-4-ylamino)-2-methylphenyl)-7-(2-oxopyrrolidin-1-yl)-9H-carbazole-1-carboxamide | 545.4 (M + H)$^+$ |
| 79-4 | 4-(3-(7-fluoroquinazolin-4-ylamino)-2-methylphenyl)-7-(2-oxopyrrolidin-1-yl)-9H-carbazole-1-carboxamide | 545.4 (M + H)$^+$ |

Example 80-1

Preparation of 7-(isopropylamino)-4-(2-methyl-3-(8-oxoimidazo[1,2-a]pyrazin-7(8H)-yl)phenyl)-9H-carbazole-1-carboxamide

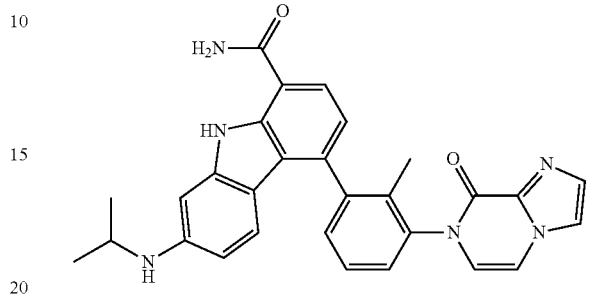

Step 1 A solution of tris(dibenzylideneacetone)dipalladium (33 mg, 0.036 mmol) and tricyclohexylphosphine (0.182 mL, 0.173 mmol) in 1,4-dioxane (9 mL), purged with nitrogen, was combined with 4-bromo-7-(isopropylamino)-9H-carbazole-1-carboxamide (Example 61-5, 250 mg, 0.722 mmol), 4,4,4',4',5,5,5',5'-octamethyl-2,2'-bi(1,3,2-dioxaborolane) (202 mg, 0.794 mmol) and potassium acetate (142 mg, 1.444 mmol). The mixture was heated with stirring in a sealed tube at 90° C. for 5.5 h. The mixture was cooled to rt and partitioned between water and EtOAc. The aqueous phase was extracted twice with EtOAc, and the combined organic phases were dried and concentrated. The residue was subjected to column chromatography (eluting with a gradient from 60:40 to 20:80 hexane-EtOAc) to provide 7-(isopropylamino)-4-(4,4,5,5-tetramethyl-1,3,2-dioxaborolan-2-yl)-9H-carbazole-1-carboxamide as an impure yellow solid (ca. 35% purity, 170 mg, 21%), used without further purification. Mass spectrum m/z 394.2 (M+H)$^+$.

Step 2 A suspension of impure 7-(isopropylamino)-4-(4,4,5,5-tetramethyl-1,3,2-dioxaborolan-2-yl)-9H-carbazole-1-carboxamide (60 mg, 0.053 mmol), 7-(3-bromo-2-methylphenyl)imidazo[1,2-a]pyrazin-8(7H)-one TFA salt (Intermediate 11-1, 22.3 mg, 0.053 mmol), tetrakis(triphenylphosphine)palladium (3.1 mg, 0.003 mmol) and 2 M aqueous sodium carbonate (0.080 mL, 0.160 mmol) in toluene-ethanol (4:1, 1.3 mL) was heated under nitrogen at 90° C. overnight. The mixture was concentrated and the residue was purified by preparative HPLC. The appropriate effluent fractions were concentrated and the residue was partitioned between NaHCO3 (aq) and EtOAc. The organic phase was dried and concentrated to provide 7-(isopropylamino)-4-(2-methyl-3-(8-oxoimidazo[1,2-a]pyrazin-7(8H)-yl)phenyl)-9H-carbazole-1-carboxamide as a light yellow solid. $^1$H NMR (400 MHz, DMSO-$d_6$) δ 10.83-10.99 (1H, m), 8.01 (1H, br. s.), 7.83 (1H, dd, J=4.5, 1.0 Hz), 7.68-7.77 (1H, m), 7.59-7.67 (1H, m), 7.38-7.50 (3H, m), 7.24-7.38 (2H, m), 7.08 (1H, dd, J=8.4, 5.9 Hz), 6.76-6.87 (1.55H, m), 6.73 (1H, dd, J=7.4, 1.9 Hz), 6.48 (0.45; H, d, J=8.8 Hz), 6.13-6.29 (1H, m), 5.44 (1H, t, J=8.3 Hz), 3.40-3.55 (1H, m), 1.70 (3H, d, J=11.4 Hz), 1.09 (6H, td, J=5.8, 3.4 Hz). Mass spectrum m/z 491.3 (M+H)$^+$.

The following compound was also prepared using procedures demonstrated in Example 80-1, using Intermediate 29-1 in place of Intermediate 11-1.

| Example | Compound name | Mass spectrum |
|---|---|---|
| 80-2 | 7-(isopropylamino)-4-(2-methyl-3-(2-methyl-8-oxoimidazo[1,2-a]pyrazin-7(8H)-yl)phenyl)-9H-carbazole-1-carboxamide | 505.2 (M + H)+ |

Example 81-1

Preparation of 4-(3-(8-fluoroquinazolin-4-ylamino)-2-methylphenyl)-7-(2-hydroxypropan-2-yl)-9H-carbazole-1-carboxamide

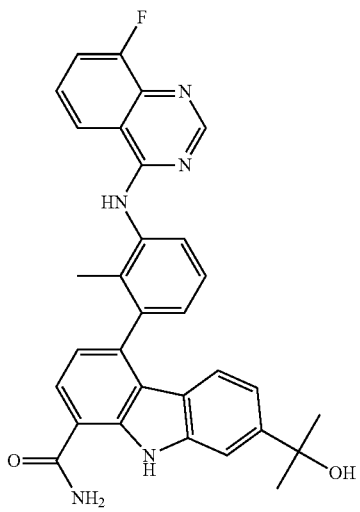 [SMILES: Cc1c(Nc2ncnc3c(F)cccc23)cccc1-c1ccc(C(N)=O)c2[nH]c3cc(C(C)(C)O)ccc3c12]

Step 1 A solution of tris(dibenzylideneacetone)dipalladium (274 mg, 0.30 mmol) and tricyclohexylphosphine (1.51 mL, 1.438 mmol) in 1,4-dioxane (75 mL), purged with nitrogen, was combined with 4-bromo-7-(2-hydroxypropan-2-yl)-9H-carbazole-1-carboxamide (Example 73-1, 2.08 g, 5.99 mmol), 4,4,4',4',5,5,5',5'-octamethyl-2,2'-bi(1,3,2-dioxaborolane) (1.826 g, 7.19 mmol) and potassium acetate (1.176 g, 11.98 mmol). The mixture was heated with stirring in a sealed tube at 90° C. for 5 h. The mixture was cooled to rt, filtered through Celite and the solids were washed with EtOAc. The filtrate was concentrated and the residue was subjected to column chromatography (eluting with a gradient from 60:40 hexane-EtOAc to EtOAc) to provide 7-(2-hydroxypropan-2-yl)-4-(4,4,5,5-tetramethyl-1,3,2-dioxaborolan-2-yl)-9H-carbazole-1-carboxamide as an impure yellow solid (2.03 g, 72%), used without further purification. Mass spectrum m/z 377.2 (M+H—$H_2O$)+.

Step 2 A mixture of 7-(2-hydroxypropan-2-yl)-4-(4,4,5,5-tetramethyl-1,3,2-dioxaborolan-2-yl)-9H-carbazole-1-carboxamide (ca. 60% purity, 35 mg, 0.053 mmol), N-(3-bromo-2-methylphenyl)-8-fluoroquinazolin-4-amine (Intermediate 32-7, 17.69 mg, 0.053 mmol), and 2 M aqueous sodium carbonate (0.067 mL, 0.133 mmol) in toluene (0.8 mL) and ethanol (0.200 mL) was purged with argon, treated with tetrakis(triphenylphosphine)palladium (3.1 mg, 0.003 mmol) and heated at 90° C. in a sealed tube for 16.5 h. The mixture was cooled to rt and concentrated. The residue was purified by preparative HPLC and the appropriate effluent fractions were treated with NaHCO3 (aq) and partially concentrated at rt. The resulting aqueous suspension was filtered and the precipitate was washed with water and dried to provide 4-(3-(8-fluoroquinazolin-4-ylamino)-2-methylphenyl)-7-(2-hydroxypropan-2-yl)-9H-carbazole-1-carboxamide as a white solid (18.0 mg, 61%). $^1$H NMR (400 MHz, DMSO-$d_6$) δ 11.41 (1H, s), 10.08 (1H, s), 8.56 (1H, s), 8.35 (1H, d, J=8.4 Hz), 8.16 (1H, br. s.), 7.99 (1H, d, J=7.9 Hz), 7.87 (1H, s), 7.70 (1H, dd, J=10.2, 8.3 Hz), 7.60 (1H, td, J=8.1, 5.2 Hz), 7.42-7.54 (3H, m), 7.28 (1H, dd, J=7.3, 1.3 Hz), 7.11 (2H, s), 7.01 (1H, d, J=7.7 Hz), 5.00 (1H, s), 1.85 (3H, s), 1.49 (6H, s). Mass spectrum m/z 520.1 (M+H)+.

The following compounds were prepared using the procedures demonstrated in Example 81-1 and closely related procedures, and using the Intermediates shown in place of Intermediate 32-7.

| Example/ Intermediate | Starting materials | Compound name | Mass spectrum |
|---|---|---|---|
| 81-2 | Intermediate 29-2 | 7-(2-hydroxypropan-2-yl)-4-(2-methyl-3-(2-methyl-8-oxoimidazo[1,2-a]pyrazin-7(8H)-yl)phenyl)-9H-carbazole-1-carboxamide | 506.3 (M + H)+ |
| 81-3 | Intermediate 29-1 | 7-(2-hydroxypropan-2-yl)-4-(2-methyl-3-(3-methyl-8-oxoimidazo[1,2-a]pyrazin-7(8H)-yl)phenyl)-9H-carbazole-1-carboxamide | 506.3 (M + H)+ |
| 81-4 | Intermediate 31-1 | 4-(3-((1H-indazol-1-yl)methyl)-2-methylphenyl)-7-(2-hydroxypropan-2-yl)-9H-carbazole-1-carboxamide | 489.3 (M + H)+ |
| 81-5 | Intermediate 31-2 | 4-(3-((2H-indazol-2-yl)methyl)-2-methylphenyl)-7-(2-hydroxypropan-2-yl)-9H-carbazole-1-carboxamide | 489.3 (M + H)+ |
| 81-6 | Intermediate 31-3 | 4-(3-((1H-benzo[d]imidazol-1-yl)methyl)-2-methylphenyl)-7-(2-hydroxypropan-2-yl)-9H-carbazole-1-carboxamide | 489.3 (M + H)+ |
| 81-7 | Intermediate 30-1 | 7-(2-hydroxypropan-2-yl)-4-(2-methyl-3-(2-oxo-3-m-tolylimidazolidin-1-yl)phenyl)-9H-carbazole-1-carboxamide | 555.3 (M + Na)+ |
| 81-8 | Intermediate 32-2 | 7-(2-hydroxypropan-2-yl)-4-(2-methyl-3-(6-methylquinazolin-4-ylamino)phenyl)-9H-carbazole-1-carboxamide | 516.4 (M + H)+ |
| 81-9 | Intermediate 32-5 | 7-(2-hydroxypropan-2-yl)-4-(2-methyl-3-(7-methylquinazolin-4-ylamino)phenyl)-9H-carbazole-1-carboxamide | 516.5 (M + H)+ |

-continued

| Example/ Intermediate | Starting materials | Compound name | Mass spectrum |
|---|---|---|---|
| 81-10 | Intermediate 32-4 | 4-(3-(6-fluoroquinazolin-4-ylamino)-2-methylphenyl)-7-(2-hydroxypropan-2-yl)-9H-carbazole-1-carboxamide | 520.4 (M + H)$^+$ |
| 81-11 | Intermediate 32-3 | 4-(3-(7-fluoroquinazolin-4-ylamino)-2-methylphenyl)-7-(2-hydroxypropan-2-yl)-9H-carbazole-1-carboxamide | 520.4 (M + H)$^+$ |
| 81-12 | Intermediate 32-8 | 7-(2-hydroxypropan-2-yl)-4-(3-(6-methoxyquinazolin-4-ylamino)-2-methylphenyl)-9H-carbazole-1-carboxamide | 532.1 (M + H)$^+$ |
| 81-13 | Intermediate 32-1 | 7-(2-hydroxypropan-2-yl)-4-(3-(7-methoxyquinazolin-4-ylamino)-2-methylphenyl)-9H-carbazole-1-carboxamide | 532.1 (M + H)$^+$ |
| 81-14 | Intermediate 32-6 | 4-(3-(5-fluoroquinazolin-4-ylamino)-2-methylphenyl)-7-(2-hydroxypropan-2-yl)-9H-carbazole-1-carboxamide | 520.1 (M + H)$^+$ |
| 81-15 | Intermediate 41-2 | 7-(2-hydroxypropan-2-yl)-4-(3-(6-methoxy-1-oxo-3,4-dihydroisoquinolin-2(1H)-yl)-2-methylphenyl)-9H-carbazole-1-carboxamide | 535.2 (M + H)$^+$ |
| 81-16 | Intermediate 41-4 | 7-(2-hydroxypropan-2-yl)-4-(2-methyl-3-(1-oxo-1,2,3,4-tetrahydroisoquinolin-5-yloxy)phenyl)-9H-carbazole-1-carboxamide | 502.1 (M + H − H$_2$O)$^+$ |
| 81-17 | Intermediate 41-3 | 4-(3-(5-hydroxy-1-oxo-3,4-dihydroisoquinolin-2(1H)-yl)-2-methylphenyl)-7-(2-hydroxypropan-2-yl)-9H-carbazole-1-carboxamide | 542.1 (M + Na)$^+$ |
| 81-18 | Intermediate 41-5 | 4-(3-(7-chloro-1-oxo-3,4-dihydroisoquinolin-2(1H)-yl)-2-methylphenyl)-7-(2-hydroxypropan-2-yl)-9H-carbazole-1-carboxamide | 538.2 (M + H)$^+$ |
| 81-19 | Intermediate 41-1 | 7-(2-hydroxypropan-2-yl)-4-(2-methyl-3-(1-oxo-3,4-dihydroisoquinolin-2(1H)-yl)phenyl)-9H-carbazole-1-carboxamide | 504.1 (M + H)$^+$ |
| 81-20 | Intermediate 41-6 | 4-(3-(6-fluoro-1-oxo-3,4-dihydroisoquinolin-2(1H)-yl)-2-methylphenyl)-7-(2-hydroxypropan-2-yl)-9H-carbazole-1-carboxamide | 522.1 (M + H)$^+$ |
| 81-21 | Intermediate 41-7 | 4-(3-(3,4-dimethyl-2-oxo-2,5-dihydro-1H-pyrrol-1-yl)-2-methylphenyl)-7-(2-hydroxypropan-2-yl)-9H-carbazole-1-carboxamide | 490.1 (M + Na)$^+$ |
| 81-22 | Intermediate 41-8 | 7-(2-hydroxypropan-2-yl)-4-(2-methyl-3-(3-methyl-2-oxopyridin-1(2H)-yl)phenyl)-9H-carbazole-1-carboxamide | 466.1 (M + H)$^+$ |
| 81-23 | Intermediate 41-9 | 4-(3-(4,4-dimethyl-2-oxopyrrolidin-1-yl)-2-methylphenyl)-7-(2-hydroxypropan-2-yl)-9H-carbazole-1-carboxamide | 452.1 (M + H − H$_2$O)$^+$ |
| 81-24 | Intermediate 42-1 | 7-(2-hydroxypropan-2-yl)-4-(3-(isobenzofuran-1(3H)-ylidenemethyl)-2-methylphenyl)-9H-carbazole-1-carboxamide | 471.0 (M + H − H$_2$O)$^+$ |
| Intermediate 81-25 | 2,6-dibromo-toluene | 4-(3-bromo-2-methylphenyl)-7-(2-hydroxypropan-2-yl)-9H-carbazole-1-carboxamide | 419, 421 (M + H)$^+$ |
| 81-26 | Intermediate 32-9 | 7-(2-hydroxypropan-2-yl)-4-(2-methyl-3-(quinazolin-4-ylamino)phenyl)-9H-carbazole-1-carboxamide | 502.2 (M + H)$^+$ |
| Intermediate 81-27 | Intermediate 41-10 | 1-(3-(1-carbamoyl-7-(2-hydroxypropan-2-yl)-9H-carbazol-4-yl)-2-methylphenyl)-5-oxopyrrolidine-3-carboxylic acid | 468.3 (M + H − H$_2$O)$^+$ |
| 81-28 | Intermediate 30-3 | 7-(2-hydroxypropan-2-yl)-4-(2-methyl-3-(2-oxo-3-phenylimidazolidin-1-yl)phenyl)-9H-carbazole-1-carboxamide | 542.1 (M + Na)$^+$ |
| 81-29 | Intermediate 30-4 | 4-(3-(3-tert-butyl-2-oxoimidazolidin-1-yl)-2-methylphenyl)-7-(2-hydroxypropan-2-yl)-9H-carbazole-1-carboxamide | 521.1 (M + Na)$^+$ |
| 81-30 | Intermediate 45-1 | 4-(3-(4-carbamoyl-2-oxopyrrolidin-1-yl)-2-methylphenyl)-7-(2-hydroxypropan-2-yl)-9H-carbazole-1-carboxamide | 507.0 (M + Na)$^+$ |
| 81-31 | Intermediate 22-1 | 7-(2-hydroxypropan-2-yl)-4-(2-methyl-3-((2-oxoindolin-3-ylidene)methyl)phenyl)-9H-carbazole-1-carboxamide | 484.1 (M + H − H$_2$O)$^+$ |
| 81-32 | Intermediate 55-1 | 4-(3-(5-hydroxy-1-oxoisoindolin-2-yl)-2-methylphenyl)-7-(2-hydroxypropan-2-yl)-9H-carbazole-1-carboxamide | 528.0 (M + Na)$^+$ |

| Example/ Intermediate | Starting materials | Compound name | Mass spectrum |
|---|---|---|---|
| 81-33 | Intermediate 1-3 | 7-(2-hydroxypropan-2-yl)-4-(3-(6-methoxy-1-oxoisoindolin-2-yl)-2-methylphenyl)-9H-carbazole-1-carboxamide | 502.0 (M + H − H$_2$O)$^+$ |
| 81-34 | Intermediate 30-2 | 4-(3-(3-benzyl-2-oxoimidazolidin-1-yl)-2-methylphenyl)-7-(2-hydroxypropan-2-yl)-9H-carbazole-1-carboxamide | 555.2 (M + Na)$^+$ |
| 81-35 | Intermediate 56-1 | 7-(2-hydroxypropan-2-yl)-4-(2-methyl-3-(2-oxo-4-phenyl-2,3-dihydro-1H-imidazol-1-yl)phenyl)-9H-carbazole-1-carboxamide | 539.1 (M + Na)$^+$ |
| 81-36 | Intermediate 57-1 | benzyl 1-(3-(1-carbamoyl-7-(2-hydroxypropan-2-yl)-9H-carbazol-4-yl)-2-methylphenyl)-2-oxopyrrolidin-3-ylcarbamate | 573.2 (M + H − H$_2$O)$^+$ |

Example 81-15

1H NMR (400 MHz, CHLOROFORM-d) δ ppm 8.09-8.15 (1H, m), 7.61-7.68 (2H, m), 7.38-7.42 (2H, m), 7.22-7.33 (3H, m), 7.09-7.15 (1H, m), 6.86-6.93 (1H, m), 6.74 (1H, t), 4.03-4.09 (1H, m), 3.87 (3H, d, J=2.42 Hz), 3.76-3.85 (1H, m), 3.18-3.30 (1H, m), 3.09 (1H, ddd, J=16.29, 5.39, 5.17 Hz), 1.97-2.02 (3H, m), 1.61-1.66 (6H, m).

Example 82-1

Preparation of 7-(2-hydroxypropan-2-yl)-4-(3-(4-methoxy-2-oxo-2,5-dihydro-1H-pyrrol-1-yl)-2-methylphenyl)-9H-carbazole-1-carboxamide

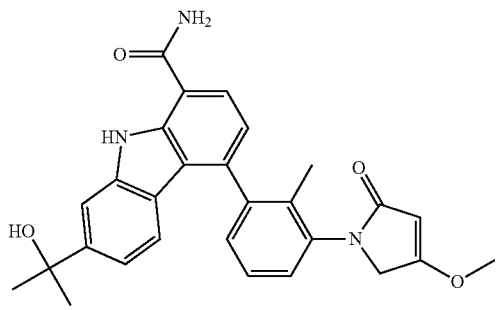 [SMILES: COC1=CC(=O)N(c2cccc(-c3ccc(C(N)=O)c4[nH]c5cc(C(C)(C)O)ccc5c34)c2C)C1]

A mixture of 4-(3-bromo-2-methylphenyl)-7-(2-hydroxypropan-2-yl)-9H-carbazole-1-carboxamide (Intermediate 81-25, 70 mg, 0.160 mmol), 4-methoxy-1H-pyrrol-2(5H)-one (362 mg, 3.20 mmol), cesium carbonate (78 mg, 0.24 mmol), tris(dibenzylideneacetone)dipalladium (14.7 mg, 0.016 mmol) and 4,5-bis(diphenylphosphino)-9,9-dimethylxanthene (xantphos, 27.8 mg, 0.048 mmol) in 1,4-dioxane (2 mL) was purged with nitrogen and heated via microwave irradiation in a sealed tube at 100° C. for 1 h. The mixture was diluted with DCM, washed with NaHCO3 (aq), dried and concentrated. The residue was purified by preparative HPLC, and the appropriate effluent fractions were treated with NaHCO3 (aq) and extracted with DCM. The combined organic phases were washed with water, dried and concentrated to provide as a white solid (20 mg, 27%). $^1$H NMR (400 MHz, methanol-d$_4$) δ 7.91 (1H, d, J=7.70 Hz), 7.73 (1H, d, J=0.88 Hz), 7.39-7.46 (2H, m), 7.31-7.34 (1H, m), 7.09 (1H, dd, J=8.47, 1.65 Hz), 7.01 (1H, d, J=7.70 Hz), 6.98 (1H, d, J=8.36 Hz), 5.29 (1H, s), 4.37-4.49 (2H, m), 3.91 (3H, s), 1.90 (3H, s), 1.58 (3H, s), 1.57 (3H, s). Mass spectrum m/z 492.0 (M+Na)$^+$.

Examples 83-1 and 83-2

Preparation of (RS)-2-(8-carbamoyl-5-(2-methyl-3-(6-methyl-1-oxoisoindolin-2-yl)phenyl)-9H-carbazol-2-yl)-2-hydroxyethyl butyrate and (RS)-1-(8-carbamoyl-5-(2-methyl-3-(6-methyl-1-oxoisoindolin-2-yl)phenyl)-9H-carbazol-2-yl)ethane-1,2-diyl dibutyrate

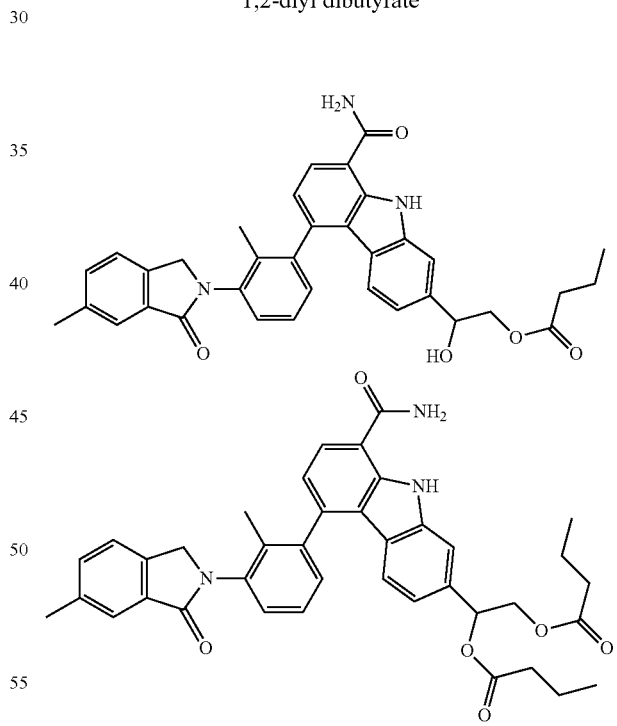

A solution of 7-(1,2-dihydroxyethyl)-4-(2-methyl-3-(6-methyl-1-oxoisoindolin-2-yl)phenyl)-9H-carbazole-1-carboxamide (Example 70-11, 30 mg, 0.059 mmol), butyric anhydride (29 μL, 0.178 mmol), and pyridine (48 μL, 0.593 mmol) in THF-DCM (1:1, 2.4 mL) was stirred at rt overnight. Additional butyric anhydride (0.03 mL, 3 eq.) was added and the mixture was again stirred at rt overnight. The mixture was concentrated and purified by preparative HPLC. The appropriate effluent fractions were partially concentrated and the resulting aqueous suspension was treated with NaHCO3 (aq). The precipitate was collected by filtration, washed with water and dried to provide (RS)-2-(8-carbamoyl-5-(2-methyl-3-(6-methyl-1-oxoisoindolin-2-yl)phenyl)-9H-carbazol-2-yl)-2-hydroxyethyl butyrate as a white solid (Example 83-1, 10.5 mg, 28%). ¹H NMR (400 MHz, DMSO-d₆) δ 11.53 (1H, s), 8.19 (1H, br. s.), 8.02 (1H, d, J=7.9 Hz), 7.76 (1H, d, J=10.1 Hz), 7.54-7.64 (3H, m), 7.50 (3H, t, J=7.0 Hz), 7.34 (1H, dd, J=7.7, 1.1 Hz), 6.93-7.06 (3H, m), 5.60 (1H, dd, J=8.9, 4.3 Hz), 4.89-4.94 (2H, m), 4.82-4.89 (1H, m), 4.05-4.13 (2H, m), 2.44 (3H, s), 2.27 (2H, td, J=7.3, 1.1 Hz), 1.83 (3H, s), 1.51 (2H, qd, J=7.3, 1.8 Hz), 0.83 (3H, td, J=7.4, 2.2 Hz). Mass spectrum m/z 599.2 (M+Na)⁺. Also isolated was (RS)-1-(8-carbamoyl-5-(2-methyl-3-(6-methyl-1-oxoisoindolin-2-yl)phenyl)-9H-carbazol-2-yl)ethane-1,2-diyl dibutyrate as a white solid (Example 83-2, 16 mg, 41%). ¹H NMR (400 MHz, methanol-d₄) δ 7.87 (1H, d, J=7.7 Hz), 7.57 (2H, d, J=10.1 Hz), 7.34-7.48 (4H, m), 7.30 (1H, dd, J=6.9, 1.9 Hz), 6.89-7.06 (3H, m), 5.95-6.11 (1H, m), 4.80 (2H, s), 4.21-4.36 (2H, m), 2.38 (3H, s), 2.24-2.33 (2H, m), 2.19 (2H, td, J=7.3, 1.1 Hz), 1.80 (3H, s), 1.44-1.63 (4H, m), 0.76-0.90 (6H, m). Mass spectrum m/z 668.3 (M+Na)⁺.

Example 83-3 and 83-4

Preparation of 1-(8-carbamoyl-5-(2-methyl-3-(6-methyl-1-oxoisoindolin-2-yl)phenyl)-9H-carbazol-2-yl)ethane-1,2-diylbis(2-aminopropanoate) and 2-(8-carbamoyl-5-(2-methyl-3-(6-methyl-1-oxoisoindolin-2-yl)phenyl)-9H-carbazol-2-yl)-2-hydroxyethyl 2-aminopropanoate A solution of 7-(1,2-dihydroxyethyl)-4-(2-methyl-3-(6-methyl-1-oxoisoindolin-2-yl)phenyl)-9H-carbazole-1-carboxamide (Example 70-11, 30 mg, 0.059 mmol), 2-(tert-butoxycarbonylamino)propanoic acid (11.8 mg, 0.062 mmol), EDC (34.1 mg, 0.178 mmol), and DMAP (2.2 mg, 0.018 mmol) in DMF (2.4 mL) was stirred at rt overnight. Additional 2-(tert-butoxycarbonylamino)propanoic acid (16 mg) and EDC (17 mg, 1.5 eq.) were added and the mixture was again stirred at rt overnight. TFA (0.3 mL) was added and the mixture was stirred at rt for 1 h, then at 60° C. for 2 h, then at rt overnight. The reaction mixture was concentrated and purified by preparative HPLC. The appropriate effluent fractions were concentrated, treated with hydrogen chloride (4 M in 1,4-dioxane) and water, and the mixture was lyophilized to provide 1-(8-carbamoyl-5-(2-methyl-3-(6-methyl-1-oxoisoindolin-2-yl)phenyl)-9H-carbazol-2-yl)ethane-1,2-diyl-bis(2-aminopropanoate), hydrochloric acid salt, as a white solid (17 mg, 37%). ¹H NMR (400 MHz, DMSO-d₆) δ 11.44-11.63 (1H, m), 8.43 (6H, br. s.), 8.17 (1H, br. s.), 7.93-8.06 (1H, m), 7.69-7.85 (1H, m), 7.34-7.62 (6H, m), 7.16-7.29 (1H, m), 6.86-7.09 (3H, m), 5.98-6.17 (1H, m), 4.72-4.96 (2H, m), 4.31-4.65 (2H, m), 3.96-4.25 (2H, m), 2.38 (3H, s), 1.76 (3H, s), 1.43 (3H, dd, J=7.0, 3.7 Hz), 1.24-1.38 (3H, m). Mass spectrum m/z 648.2 (M+H)⁺. Also isolated was 2-(8-carbamoyl-5-(2-methyl-3-(6-methyl-1-oxoisoindolin-2-yl)phenyl)-9H-carbazol-2-yl)-2-hydroxyethyl 2-aminopropanoate, TFA salt, as a white solid (4 mg, 9%). ¹H NMR (400 MHz, methanol-d₄) δ 7.85-7.91 (1H, m), 7.53-7.60 (2H, m), 7.38-7.48 (4H, m), 7.26-7.33 (1H, m), 7.02-7.09 (1H, m), 6.94-7.02 (2H, m), 5.90-5.97 (0.3H, m), 4.99 (0.7H, dd, J=7.3, 3.7 Hz), 4.78-4.84 (2H, m), 3.72-4.42 (3H, m), 2.38 (3H, s), 1.75-1.82 (3H, m), 1.34-1.57 (3H, m). Mass spectrum m/z 577.2 (M+H)⁺.

The following compounds were also prepared using procedures demonstrated in Examples 83-1 through 83-4, using the appropriate acid or acid anhydride.

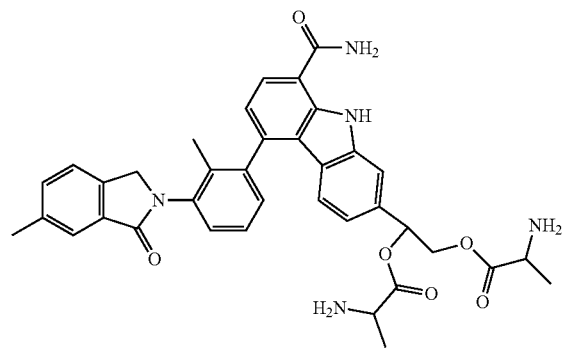

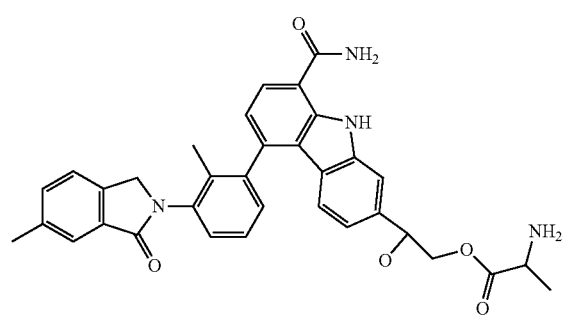

| Example | Compound name | Mass spectrum |
|---|---|---|
| 83-5 | 1-(8-carbamoyl-5-(2-methyl-3-(6-methyl-1-oxoisoindolin-2-yl)phenyl)-9H-carbazol-2-yl)ethane-1,2-diyl diacetate | 612.2 (M + Na)⁺ |
| 83-6 | 1-(8-carbamoyl-5-(2-methyl-3-(6-methyl-1-oxoisoindolin-2-yl)phenyl)-9H-carbazol-2-yl)ethane-1,2-diyl bis(2-amino-3-methylbutanoate) (prepared as the hydrochloric acid salt) | 704.2 (M + H)⁺ |
| 83-7 | 2-(8-carbamoyl-5-(2-methyl-3-(6-methyl-1-oxoisoindolin-2-yl)phenyl)-9H-carbazol-2-yl)-2-hydroxyethyl 2-amino-3-methylbutanoate (prepared as the TFA salt) | 605.1 (M + H)⁺ |

Intermediate 84-1

Preparation of 4-(2-fluoro-3-hydroxyphenyl)-7-(4-methylpiperazine-1-carbonyl)-9H-carbazole-1-carboxamide

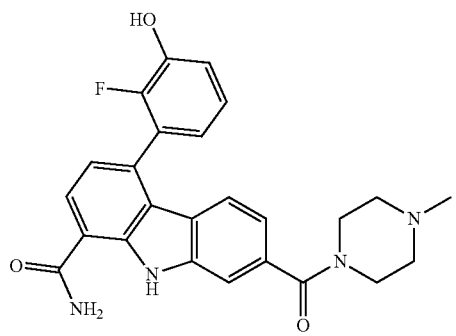 [SMILES: CN1CCN(C(=O)c2ccc3c(c2)[nH]c2c(C(N)=O)ccc(-c4cccc(O)c4F)c23)CC1]

A solution of 4-(2-fluoro-3-methoxyphenyl)-7-(4-methylpiperazine-1-carbonyl)-9H-carbazole-1-carboxamide (Example 3-137, 3.6 g, 7.82 mmol) in DCM (42 mL) was stirred at 0° C. and treated with boron tribromide (1 M in DCM, 94 mL, 94 mmol) and the mixture was stirred at rt overnight. The mixture was cooled again to 0° C. and treated slowly with methanol. The mixture was concentrated and purified by column chromatography on neutral alumina (eluting with 90:10 EtOAc-methanol) to provide 4-(2-fluoro-3-hydroxyphenyl)-7-(4-methylpiperazine-1-carbonyl)-9H-carbazole-1-carboxamide as a light colored solid (2.0 g, 57%). $^1$H NMR (400 MHz, DMSO-$d_6$) δ 11.75 (s, 1H), 10.08 (s, 1H), 8.25 (br. s., 1H), 8.05 (d, J=7.6 Hz, 1H), 7.81 (s, 1H), 7.59 (br. s., 1H), 7.17 (m, 3H), 7.11 (d, J=7.6 Hz, 1H), 6.99 (dd, J=8.0, 1.2 Hz, 1H), 6.91 (t, J=7.2 Hz, 1H), 3.51 (br. s., 2H), 3.34 (m, 5H), 2.34 (br. s., 4H). Mass spectrum m/z 447.0 (M+H)$^+$.

Example 85-1

Preparation of 4-(3-(2-(dimethylamino)ethoxy)-2-fluorophenyl)-7-(4-methylpiperazine-1-carbonyl)-9H-carbazole-1-carboxamide

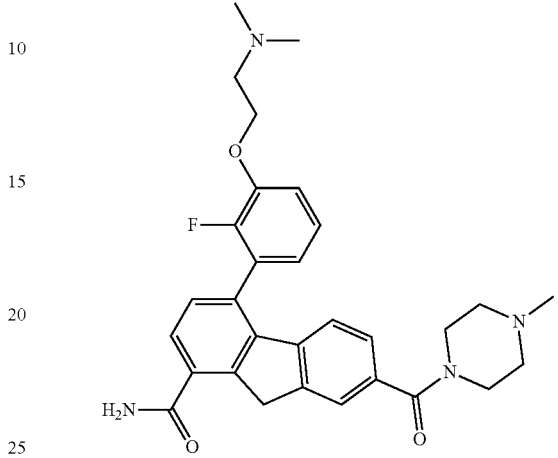

A mixture of 4-(2-fluoro-3-hydroxyphenyl)-7-(4-methylpiperazine-1-carbonyl)-9H-carbazole-1-carboxamide (Intermediate 84-1, 20 mg, 0.045 mmol) and polymer-supported triphenylphosphine (2.63 mmol/g, 0.358 mmol) in 1,4-dioxane was treated at 0° C. with a solution of diethyl azodicarboxylate (19.5 mg, 0.157 mmol) in THF (0.5 mL), followed after 5 min by a solution of 2-(dimethylamino)ethanol (10 mg, 0.112 mmol) in THF (0.5 mL). The mixture was heated in a sealed tube by microwave irradiation at 90-100° C. for 30 min. The resulting mixture was filtered, the solids were washed with methanol, and the filtrates were concentrated and purified by preparative HPLC to provide 4-(3-(2-(dimethylamino)ethoxy)-2-fluorophenyl)-7-(4-methylpiperazine-1-carbonyl)-9H-carbazole-1-carboxamide. Mass spectrum m/z 518.2 (M+H)$^+$.

The following compounds were also prepared using procedures demonstrated in Example 85-1, using the appropriate alcohol in place of 2-(dimethylamino)ethanol.

| Example | Compound name | Mass spectrum |
| --- | --- | --- |
| 85-2 | 4-(2-fluoro-3-phenethoxyphenyl)-7-(4-methylpiperazine-1-carbonyl)-9H-carbazole-1-carboxamide | 551.2 (M + H)$^+$ |
| 85-3 | 4-(2-fluoro-3-(isopentyloxy)phenyl)-7-(4-methylpiperazine-1-carbonyl)-9H-carbazole-1-carboxamide | 517.2 (M + H)$^+$ |
| 85-4 | 4-(2-fluoro-3-propoxyphenyl)-7-(4-methylpiperazine-1-carbonyl)-9H-carbazole-1-carboxamide | 489.2 (M + H)$^+$ |
| 85-5 | 4-(2-fluoro-3-(3-phenylpropoxy)phenyl)-7-(4-methylpiperazine-1-carbonyl)-9H-carbazole-1-carboxamide | 565.2 (M + H)$^+$ |
| 85-6 | 4-(2-fluoro-3-(4-phenylbutoxy)phenyl)-7-(4-methylpiperazine-1-carbonyl)-9H-carbazole-1-carboxamide | 579.2 (M + H)$^+$ |
| 85-7 | 4-(2-fluoro-3-(2-(1-methylpyrrolidin-2-yl)ethoxy)phenyl)-7-(4-methylpiperazine-1-carbonyl)-9H-carbazole-1-carboxamide | 558.2 (M + H)$^+$ |
| 85-8 | 4-(3-ethoxy-2-fluorophenyl)-7-(4-methylpiperazine-1-carbonyl)-9H-carbazole-1-carboxamide | 475.2 (M + H)$^+$ |
| 85-9 | 4-(3-(benzyloxy)-2-fluorophenyl)-7-(4-methylpiperazine-1-carbonyl)-9H-carbazole-1-carboxamide | 537.2 (M + H)$^+$ |

-continued

| Example | Compound name | Mass spectrum |
|---|---|---|
| 85-10 | 4-(2-fluoro-3-(4-methoxybenzyloxy)phenyl)-7-(4-methylpiperazine-1-carbonyl)-9H-carbazole-1-carboxamide | 567.2 (M + H)+ |
| 85-11 | 4-(2-fluoro-3-isobutoxyphenyl)-7-(4-methylpiperazine-1-carbonyl)-9H-carbazole-1-carboxamide | 503.2 (M + H)+ |
| 85-12 | 4-(2-fluoro-3-(1-methylpiperidin-4-yloxy)phenyl)-7-(4-methylpiperazine-1-carbonyl)-9H-carbazole-1-carboxamide | 544.2 (M + H)+ |
| 85-13 | 4-(2-fluoro-3-(2-(piperidin-1-yl)ethoxy)phenyl)-7-(4-methylpiperazine-1-carbonyl)-9H-carbazole-1-carboxamide | 558.2 (M + H)+ |
| 85-14 | 4-(2-fluoro-3-isopropoxyphenyl)-7-(4-methylpiperazine-1-carbonyl)-9H-carbazole-1-carboxamide | 489.2 (M + H)+ |
| 85-15 | 4-(3-(2-(1H-imidazol-1-yl)ethoxy)-2-fluorophenyl)-7-(4-methylpiperazine-1-carbonyl)-9H-carbazole-1-carboxamide | 541.2 (M + H)+ |
| 85-16 | 4-(2-fluoro-3-(pyrazin-2-ylmethoxy)phenyl)-7-(4-methylpiperazine-1-carbonyl)-9H-carbazole-1-carboxamide | 539.2 (M + H)+ |
| 85-17 | 4-(2-fluoro-3-(thiazol-2-ylmethoxy)phenyl)-7-(4-methylpiperazine-1-carbonyl)-9H-carbazole-1-carboxamide | 544.2 (M + H)+ |

Example 86-1

Preparation of 4-(3-(6-fluoro-1-oxoisoindolin-2-yl)-2-methylphenyl)-7-(methylsulfonamidomethyl)-9H-carbazole-1-carboxamide

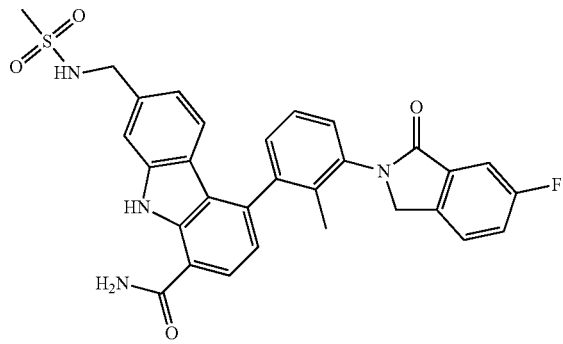 [SMILES: Cc1c(-c2ccc(C(N)=O)c3[nH]c4cc(CNS(C)(=O)=O)ccc4c23)cccc1N1Cc2ccc(F)cc2C1=O]

A suspension of 7-(aminomethyl)-4-bromo-9H-carbazole-1-carboxamide (Step 2 of Example 33-1, 100 mg, 0.314 mmol) and TEA (0.110 mL, 0.786 mmol) in DMF-THF-DCM (25:25:50, 6 mL) was treated dropwise with methanesulfonyl chloride (37 µL, 0.471 mmol) and the resulting mixture was stirred at rt for 3 h. The mixture was partitioned between NaHCO3 (aq) and EtOAc, and the organic phase was washed with brine, dried and concentrated to provide crude 4-bromo-7-(methylsulfonamidomethyl)-9H-carbazole-1-carboxamide as a yellow solid (130 mg, 88%). Without purification, using the procedure of Example 3-2, this material (25 mg, 0.063 mmol) and 6-fluoro-2-(2-methyl-3-(4,4,5,5-tetramethyl-1,3,2-dioxaborolan-2-yl)phenyl)isoindolin-1-one (Intermediate 50-5, 27.8 mg, 0.076 mmol) were converted into 4-(3-(6-fluoro-1-oxoisoindolin-2-yl)-2-methylphenyl)-7-(methylsulfonamidomethyl)-9H-carbazole-1-carboxamide (22 mg, 58%). $^1$H NMR (400 MHz, DMSO-$d_6$) δ 11.58 (1H, s), 8.20 (1H, br. s.), 8.03 (1H, d, J=7.9 Hz), 7.70-7.78 (2H, m), 7.45-7.67 (6H, m), 7.36 (1H, dd, J=7.7, 1.1 Hz), 7.00-7.07 (2H, m), 6.93-7.00 (1H, m), 4.86-5.04 (2H, m), 4.26 (2H, d, J=6.2 Hz), 2.87 (3H, s), 1.84 (3H, s). Mass spectrum m/z 557.1 (M+H)+.

The following compounds were also prepared using the procedures demonstrated in Example 86-1 and closely related procedures, and using the Intermediates shown in place of Intermediate 50-5.

| Example | Starting materials | Compound name | Mass spectrum |
|---|---|---|---|
| 86-2 | Intermediate 50-8 | 4-(2-methyl-3-(6-methyl-1-oxoisoindolin-2-yl)phenyl)-7-(methylsulfonamidomethyl)-9H-carbazole-1-carboxamide | 553.1 (M + H)+ |
| 86-3 | Intermediate 50-51 | 4-(3-(8-methoxy-4-oxoquinazolin-3(4H)-yl)-2-methylphenyl)-7-(methylsulfonamidomethyl)-9H-carbazole-1-carboxamide | 582.1 (M + H)+ |
| 86-4 | Intermediate 50-48 | 4-(3-(8-fluoro-4-oxoquinazolin-3(4H)-yl)-2-methylphenyl)-7-(methylsulfonamidomethyl)-9H-carbazole-1-carboxamide | 570.0 (M + H)+ |

Example 87-1

Preparation of 4-(3-(4-(dimethylcarbamoyl)-2-oxopyrrolidin-1-yl)-2-methylphenyl)-7-(2-hydroxypropan-2-yl)-9H-carbazole-1-carboxamide

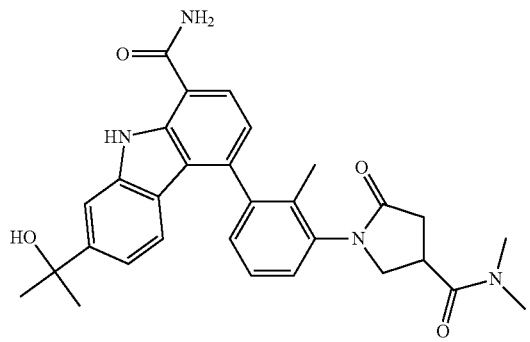 [SMILES: Cc1c(-c2ccc(C(N)=O)c3[nH]c4cc(C(C)(C)O)ccc4c23)cccc1N1CC(C(=O)N(C)C)CC1=O]

A solution of 1-(3-(1-carbamoyl-7-(2-hydroxypropan-2-yl)-9H-carbazol-4-yl)-2-methylphenyl)-5-oxopyrrolidine-3- carboxylic acid (Intermediate 81-27, 49 mg, 0.101 mmol), dimethylamine (2 M in THF, 0.252 mL, 0.505 mmol), EDC (38.7 mg, 0.202 mmol) and HOBT (30.9 mg, 0.202 mmol) in THF (2 mL) was stirred at rt overnight. Additional dimethylamine (2 M in THF, 0.252 mL, 0.505 mmol), EDC (38.7 mg, 0.202 mmol) and HOBT (30.9 mg, 0.202 mmol) were added along with DMF (0.5 mL) and the mixture was again stirred overnight. The mixture was diluted with DCM, washed with NaHCO3 (aq), dried and concentrated. The residue was purified by preparative HPLC, and the appropriate effluent fractions were made basic with 1 M aqueous sodium hydroxide and extracted twice with DCM. The organic phase was washed with water, dried and concentrated. The residue was purified by column chromatography (eluting with DCM-methanol-ammonia) to provide 4-(3-4-(dimethylcarbamoyl)-2-oxopyrrolidin-1-yl)-2-methylphenyl)-7-(2-hydroxypropan-2-yl)-9H-carbazole-1-carboxamide as a white solid (8 mg, 15%). $^1$H NMR (400 MHz, methanol-$d_4$) δ 7.91 (1H, d, J=7.7 Hz), 7.73 (1H, d, J=1.1 Hz), 7.40-7.49 (2H, m), 7.33 (1H, dd, J=6.5, 2.3 Hz), 7.07 (1H, ddd, J=8.5, 1.4, 1.3 Hz), 7.01 (1H, d, J=7.9 Hz), 6.94 (1H, br. s.), 3.84-4.13 (3H, m), 3.13 (3H, 2 s), 2.97 (3H, 2 s), 2.85-2.94 (1H, m), 2.74-2.83 (1H, m), 1.93 (3H, s), 1.57 (6H, 2 s). Mass spectrum m/z 495.1 (M+H—$H_2O$)$^+$.

Example 88-1

Preparation of 4-(3-(3,4-dimethyl-2-oxopyrrolidin-1-yl)-2-methylphenyl)-7-(2-hydroxypropan-2-yl)-9H-carbazole-1-carboxamide

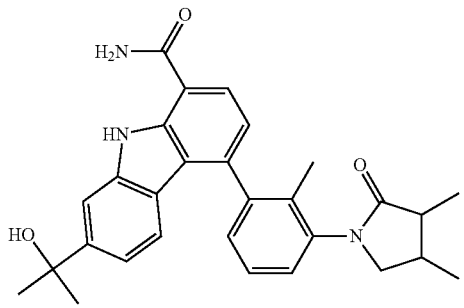 [SMILES: Cc1c(-c2ccc(C(N)=O)c3[nH]c4cc(C(C)(C)O)ccc4c23)cccc1N1CC(C)C(C)C1=O]

A mixture of 4-(3-(3,4-dimethyl-2-oxo-2,5-dihydro-1H-pyrrol-1-yl)-2-methylphenyl)-7-(2-hydroxypropan-2-yl)-9H-carbazole-1-carboxamide (Example 81-21, 20 mg, 0.043 mmol) and ammonium formate (27.0 mg, 0.428 mmol) in methanol (5 mL) was treated with 10% palladium on charcoal (20 mg, 0.019 mmol). The mixture was stirred under nitrogen at rt for 2 h. Additional ammonium formate (27.0 mg, 0.428 mmol) was added and the mixture was stirred at rt overnight. More ammonium formate (57 mg) and 10% palladium on charcoal (40 mg) were added, and after 6 h more additional ammonium formate (57 mg) was added. The mixture was again stirred overnight, then was diluted with DCM and filtered through Celite. The filtrate was washed with water, dried and concentrated. The residue was purified by preparative HPLC and the appropriate effluent fractions were made basic with 1 M aqueous sodium hydroxide and extracted twice with DCM. The combined organic phases were washed with water, dried and concentrated to provide 4-(3-(3,4-dimethyl-2-oxopyrrolidin-1-yl)-2-methylphenyl)-7-(2-hydroxypropan-2-yl)-9H-carbazole-1-carboxamide as a white solid (11 mg, 55%), which was a mixture of diastereomers. Mass spectrum m/z 452.1 (M+H—$H_2O$)$^+$.

Example 89-1

Preparation of 4-(3-(6-fluoro-4-oxoquinazolin-3 (4H)-yl)-2-methylphenyl)-7-(methylsulfonylmethyl)-9H-carbazole-1-carboxamide

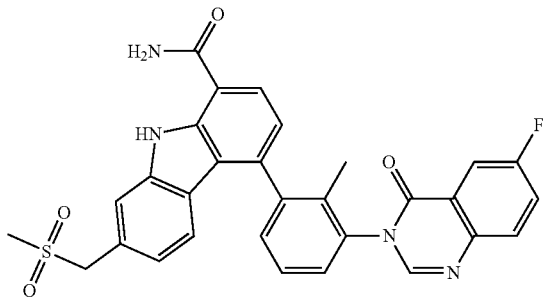 [SMILES: Cc1c(-c2ccc(C(N)=O)c3[nH]c4cc(CS(C)(=O)=O)ccc4c23)cccc1-n1cnc2ccc(F)cc2c1=O]

Step 1 A mixture of 4-bromo-7-(hydroxymethyl)-9H-carbazole-1-carboxamide (Example 30-2, 403 mg, 1.263 mmol), N-chlorosuccinimide (219 mg, 1.642 mmol) and triphenylphosphine (431 mg, 1.642 mmol) in DCM (50 mL) was heated at reflux for 1 h. The mixture was cooled to rt, washed with brine, and the aqueous layer was extracted with DCM. The aqueous layer was filtered and the collected precipitate was washed with water. The organic layers and the collected precipitate were combined and the mixture was concentrated under vacuum. The residue was dissolved in THF (20 mL) and DMSO (5 mL) and the solution was treated with sodium thiomethoxide (115 mg, 1.642 mmol). The mixture was stirred at rt for 30 min, diluted with EtOAc, washed twice with water, and the aqueous phase was extracted with EtOAc. The combined organic phases were dried and concentrated. The residue was purified by column chromatography (eluting with EtOAc-hexane) to provide 4-bromo-7-(methylthiomethyl)-9H-carbazole-1-carboxamide as a white solid (168 mg, 38%) used without further purification. $^1$H NMR (400 MHz, chloroform-d) δ 8.67 (1H, d, J=8.1 Hz), 7.46-7.52 (2H, m), 7.36-7.41 (1H, m), 7.26-7.29 (1H, m), 3.87 (2H, s), 2.03 (3H, s). Mass spectrum m/z 349, 351 (M+H)$^+$.

Step 2 A suspension of 4-bromo-7-(methylthiomethyl)-9H-carbazole-1-carboxamide (168 mg, 0.481 mmol) in DCM (10 mL) and THF (2 mL) was treated with 3-chloroperoxybenzoic acid (166 mg, 0.962 mmol) and the mixture was stirred at rt for 30 min. The mixture was treated with NaHCO3 (aq) and the organic phase was separated. The insoluble solid in the aqueous phase was collected by filtration and washed with water. The organic phase and the precipitate were combined and the mixture was concentrated. The residue was triturated with methanol to provide 4-bromo-7-(methylsulfonylmethyl)-9H-carbazole-1-carboxamide as a white solid (180 mg, 98%), used without further purification. $^1$H NMR (400 MHz, methanol-$d_4$) δ xx. Mass spectrum m/z 403, 405 (M+H)$^+$.

Step 3 Following the procedure of Example 31-1 but using THF as the solvent instead of toluene-ethanol, 4-bromo-7-(methylsulfonylmethyl)-9H-carbazole-1-carboxamide (50 mg, 0.131 mmol) and 6-fluoro-3-(2-methyl-3-(4,4,5,5-tetramethyl-1,3,2-dioxaborolan-2-yl)phenyl)quinazolin-4 (3H)-one (Intermediate 50-27, 50 mg, 0.131 mmol) were converted to 4-(3-(6-fluoro-4-oxoquinazolin-3(4H)-yl)-2-methylphenyl)-7-(methylsulfonylmethyl)-9H-carbazole-1-carboxamide as a white solid (16 mg, 22%). $^1$H NMR (400

MHz, methanol-$d_4$) δ 8.20-8.28 (1H, m), 7.95-8.02 (2H, m), 7.82-7.89 (1H, m), 7.66-7.71 (1H, m), 7.56-7.66 (2H, m), 7.47-7.56 (1H, m), 6.97-7.33 (3H, m), 4.46-4.52 (2H, m), 2.84 (3H, s), 1.90 (3H, s). Mass spectrum m/z 555.0 (M+H)$^+$.

The following compounds were also prepared using the procedures demonstrated in Example 89-1 and closely related procedures, using the Intermediates shown in place of Intermediate 50-27.

| Example | Starting materials | Compound name | Mass spectrum |
|---------|--------------------|--------------|---------------|
| 89-2 | Intermediate 50-5 | 4-(3-(6-fluoro-1-oxoisoindolin-2-yl)-2-methylphenyl)-7-(methylsulfonylmethyl)-9H-carbazole-1-carboxamide | 542.1 (M + H)$^+$ |
| 89-3 | Intermediate 50-6 | 4-(3-(5-methoxy-1-oxoisoindolin-2-yl)-2-methylphenyl)-7-(methylsulfonylmethyl)-9H-carbazole-1-carboxamide | 554.1 (M + H)$^+$ |

What is claimed is:

1. A method of treating a disease, comprising administering to a patient in need of such treatment a therapeutically-effective amount of a compound according to formula (I) or a salt thereof, wherein the disease is systemic lupus erythematosus (SLE), rheumatoid arthritis, multiple sclerosis (MS), inflammatory bowel disease, B-cell lymphoma, B-cell leukemia, or transplant rejection; wherein said compound according to formula (I) is:

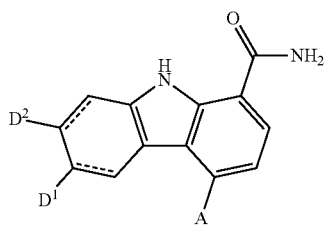

(I)

wherein
the dashed lines are either single or double bonds;
A is halo, $C_{3-10}$ carbocycle substituted with 0-3 B, $C_{6-10}$ mono- or bicyclic aryl substituted with 0-3 B, a 5-14 membered heterocyclyl containing 1-4 heteroatoms selected from N, O, and S, substituted with 0-3 B, or a 5-10 membered heteroaryl containing 1-4 heteroatoms selected from N, O, and S, substituted with 0-3 B;
B is $R^1$, halogen, cyano, nitro, —O—$R^1$, —C(=O)—$R^1$, —C(=O)O—$R^1$, —C(=O)N$R^{11}$—$R^1$, —S(=O)$_2$—$R^1$, —N$R^{11}$C(=O)—$R^1$, —N$R^{11}$C(=O)N$R^{11}$—$R^1$, —N$R^{11}$C(=O)O—$R^1$, —N(C(=O)O—$R^1$)$_2$, —N$R^{11}$S(=O)$_2$—$R^1$, —N(S(=O)$_2$—$R^1$)$_2$, or —N$R^{11}$—$R^1$;
$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;
$R^{1a}$ is hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 R$^a$, $C_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

one of D$^1$ and D$^2$ is D and the other is H or halo;
D is —R$^2$, halogen, —(C(R$^{11}$)$_2$)$_r$—R$^2$, —O—R$^2$, —C(=O)—R$^2$, —C(=O)O—R$^2$, —C(=O)NR$^{11}$—R$^2$, —S(=O)$_2$—R$^2$, —S(=O)—R$^2$, —NR$^{11}$C(=O)—R$^2$, —NR$^{11}$C(=O)NR$^{11}$—R$^2$, —NR$^{11}$C(=O)O—R$^2$, —NR$^{11}$S(=O)$_2$—R$^2$, —NR$^{11}$—R$^2$, —C(=O)NR$^{11}$—O—R$^2$, —OC(=O)O—R$^2$, —O$^1$C(=O)—R$^2$, or CH=N—OH;
with the proviso that A is not halo when D is —C(=O) O—R$^2$,
$R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, or a 5-10 membered heteroaryl containing 1-4 heteroatoms selected from N, O, and S, substituted with 0-3 $R^{2a}$;
$R^{2a}$ is hydrogen, =O, F, Cl, Br, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$,—(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$,$C_{1-6}$ alkyl substituted with 0-2 R$^a$, $C_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-2 R$^a$;
$R^{11}$ is independently hydrogen, $C_{1-4}$ alkyl substituted with 0-1 R$^f$, CH$_2$-phenyl, or —(CH$_2$)$_r$-5-7 membered heterocycle comprising carbon atoms and 1-4 heteroatoms selected from N, O, and S(O)$_p$;
alternatively, $R^{11}$ and along with another $R^{11}$, $R^1$, or $R^2$ on the same nitrogen atom may join to form an azetidinyl, pyrrolidinyl, piperidinyl, morpholinyl, or 4—(C$_{1-6}$ alkyl)piperazinyl;
$R^a$ is hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$ R$^c$, $C_{1-6}$ alkyl substituted with 0-1 R$^f$, $C_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$; alternatively two R$^a$ on adjacent or the same carbon atom form a cyclic acetal of the formula —O—(CH$_2$)$_n$—O— or —O—CF$_2$—O—, wherein n is selected from 1 or 2;
$R^b$ is hydrogen, $C_{1-6}$ alkyl substituted with 0-2 R$^d$, $C_{1-6}$ haloalkyl, $C_{3-6}$ cycloalkyl substituted with 0-2 R$^d$, or —(CH$_2$)$_r$-phenyl substituted with 0-2 R$^d$;
$R^c$ is $C_{1-6}$ alkyl substituted with 0-1 R$^f$, $C_{3-6}$ cycloalkyl, or —(CH$_2$)$_r$-phenyl substituted with 0-1 R$^f$;
$R^d$ is hydrogen, F, Cl, Br, OCF$_3$, CF$_3$, CN, NO$_2$, —OR$^e$, —(CH$_2$)$_r$C(O)R$^e$, —NR$^e$R$^e$, —NR$^e$C(O)OR$^e$, $C_{1-6}$ alkyl, or —(CH$_2$)$_r$-phenyl;
$R^e$ is hydrogen, $C_{1-6}$ alkyl, $C_{3-6}$ cycloalkyl, or —(CH$_2$)$_r$-phenyl;

$R^f$ is hydrogen, halo, $NH_2$, OH, or $OCH_3$;

r is 0, 1, 2, 3, or 4; and p is 0, 1, or 2;

wherein the method of treating a disease does not include prevention.

2. The method of treating a disease according to claim 1, wherein:

A is halo, $C_{3-10}$ cycloalkyl substituted with 0-3 B, $C_{6-10}$ mono- or bicyclic aryl substituted with 0-3 B, a 5-10 membered heterocyclyl containing 1-4 heteroatoms selected from N, O, and S, substituted with 0-3 B, or a 5-10 membered heteroaryl containing 1-4 heteroatoms selected from N, O, and S, substituted with 0-3 B;

B is $R^1$, halogen, cyano, nitro, —O—$R^1$, —C(=O)—$R^1$, —C(=O)O—$R^1$, —C(=O)$NR^{11}$—$R^1$, —S(=O)$_2$—$R^1$, —$NR^{11}$C(=O)—$R^1$, —$NR^{11}$C(=O)$NR^{11}$—$R^1$, —$NR^{11}$C(=O)O—$R^1$, —$NR^{11}$S(=O)$_2$—$R^1$, —N(S(=O)$_2$—$R^1$)$_2$, or —$NR^{11}$—$R^1$;

$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, $CF_3$, $CHF_2$, CN, $NO_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 R$^a$, $C_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

one of $D^1$ and $D^2$ is D and the other is H;

D is —$R^2$, halogen, —(C($R^{11}$)$_2$)$_r$—$R^2$, —(O)—$R^2$, —C(=O)—$R^2$, —C(=O)O—$R^2$, —C(=O)$NR^{11}$—$R^2$, —S(=O)$_2$—$R^2$, —$NR^{11}$C(=O)—$R^2$, —$NR^{11}$C(=O)$NR^{11}$—$R^2$, —$NR^{11}$C(=O)O—$R^2$, $NR^{11}$S(=O)$_2$—$R^2$, or —$NR^{11}$—$R^2$;

$R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, or a 5-10 membered heteroaryl containing 1-4 heteroatoms selected from N, O, and S, substituted with 0-3 $R^{2a}$;

$R^{2a}$ is hydrogen, =O, F, Cl, Br, $OCF_3$, CN, $NO_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 R$^a$, $C_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$, substituted with 0-1 R$^a$; $R^{11}$ is independently hydrogen or $C_{1-4}$ alkyl; alternatively, $R^{11}$ and along with another $R^{11}$, $R^1$, or $R^2$ on the same nitrogen atom may join to form an azetidinyl, pyrrolidinyl, piperidinyl, morpholinyl, or 4-($C_{1-6}$ alkyl)piperazinyl; $R^a$ is hydrogen, F, Cl, Br, $OCF_3$, $CF_3$, $CHF_2$, CN, $NO_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl, $C_{1-6}$ haloalkyl, —(CH$_2$)$_r$-3-14 membered carbocylce, or —(CH$_2$)$_r$-5-7 membered heterocycle comprising carbon atoms and 1-4 heteroatoms selected from N, O, and S(O)$_p$, alternatively two $R^a$ on adjacent or the same carbon atom form a cyclic acetal of the formula —O—(CH$_2$)$_n$—O— or —O—CF$_2$—O—, wherein n is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or —(CH$_2$)$_r$-phenyl substituted with 0-2 $R^d$;

$R^c$ is $C_{1-6}$ alkyl, $C_{3-6}$ cycloalkyl, or —(CH$_2$)$_r$-phenyl;

$R^d$ is hydrogen, F, Cl, Br, $OCF_3$, $CF_3$, CN, $NO_2$, —OR$^e$, —(CH$_2$)$_r$C(O)R$^b$, —NR$^e$R$^e$, —NR$^e$C(O)OR$^c$, $C_{1-6}$ alkyl, or —(CH$_2$)$_r$-phenyl;

$R^e$ is hydrogen, $C_{1-6}$ alkyl, $C_{3-6}$ cycloalkyl, or —(CH$_2$)$_r$-phenyl;

r is 0, 1, 2, 3, or 4; and p is 0, 1, or 2.

3. The method of treating a disease according to claim 1, wherein said compound according to formula (I) or a salt thereof is:

D is a —$R^2$, —(CH$_2$)$_r$—$R^2$, —O—$R^2$, —C(=O)—$R^2$, —C(=O)O—$R^2$, —C(=O)$NR^{11}$—$R^2$, —S(=O)$_2$—$R^2$, —S(=O)—$R^2$, —$NR^{11}$C(=O)—$R^2$, —$NR^{11}$C(=O)$NR^{11}$—$R^2$, —$NR^{11}$C(=O)O—$R^2$, —$NR^{11}$S(=O)$_2$—$R^2$, or —$NR^{11}$—$R^2$;

$R^2$ is hydrogen, $C_{1-6}$ alkyl substituted with 0-3 $R^{2a}$, $C_{2-6}$ alkenyl substituted with 0-3 $R^{2a}$, $C_{3-10}$ cycloalkyl substituted with 0-3 $R^{2a}$, —$C_{6-10}$ aryl substituted with 0-3 $R^{2a}$, a 5-10 membered heterocyclyl containing 1-4 heteroatoms selected from N, O, and S, substituted with 0-3 $R^{2a}$, or a 5-10 membered heteroaryl containing 1-4 heteroatoms selected from N, O, and S, substituted with 0-3 $R^{2a}$;

$R^{2a}$ is hydrogen, =O, F, Cl, Br, $OCF_3$, $CF_3$, $CHF_2$, CN, $NO_2$, OR$^b$, SR$^b$, —C(O)R$^b$, —C(O)OR$^b$, —OC(O)R$^b$, —NR$^{11}$R$^{11}$, —C(O)NR$^{11}$R$^{11}$, —NR$^b$C(O)R$^c$, —NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 R$^a$, —(CH$_2$)$_r$-3-14 membered carbocycle substituted with 0-1 R$^a$, wherein the carbocycle is cyclopropyl, cyclobutyl, cyclopentyl or cyclohexyl; or —(CH$_2$)$_r$-5-7 membered heterocycle comprising carbon atoms and 1-4 heteroatoms selected from N, O, and S(O)$_p$ substituted with 0-2 R$^a$; and r is 0, 1, or 2.

4. The method of treating a disease according to claim 1, wherein said compound according to formula (I) or a salt thereof is:

A is halo, $C_{3-10}$ carbocycle substituted with 0-3 B $C_{6-10}$ mono- or bicyclic aryl substituted with 0-3 -B, a 5-14 membered heterocyclyl containing 1-4 heteroatoms selected from N, O, and S, substituted with 0-3 B, or a 5-10 membered heteroaryl containing 1-4 heteroatoms selected from N, O, and S, substituted with 0-3 B;

B is $R^1$, halogen, cyano, nitro, —O—$R^1$, —C(=O)—$R^1$, —C(=O)O—$R^1$, —C(=O)$NR^{11}$—$R^1$, —S(=O)$_2$—$R^1$, —$NR^{11}$C(=O)—$R^1$, —$NR^{11}$C(=O)$NR^{11}$—$R^1$, —$NR^{11}$S(=O)$_2$—$R^1$, —N(S(=O)$_2$—$R^1$)$_2$, or —$NR^{11}$—$R^1$; and $R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$.

5. The method of treating a disease according to claim 1, wherein said compound according to formula (I) or a salt thereof is:

$R^2$ is hydrogen, $C_{1-6}$ alkyl substituted with 0-3 $R^{2a}$, ethenyl, $C_{3-10}$ cycloalkyl substituted with 0-3 $R^{2a}$, $C_{6-10}$ aryl substituted with 0-3 $R^{2a}$, or a 5-10 membered heterocyclyl containing 1-4 heteroatoms selected from N, O, and S, substituted with 0-3 $R^{2a}$, wherein the heterocyclyl is pyrrolidinyl, piperidinyl, morpholinyl, piperazinyl, tetrahydropyranyl, oxazolidinyl (oxazolidin-one), imidazolidinyl (imidazolidin-one), dioxalanyl, or

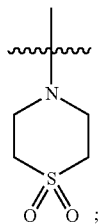

or a 5-10 membered heteroaryl containing 1-4 heteroatoms selected from N, O, and S, substituted with 0-3 $R^{2a}$, wherein the heteroaryl is pyrimidinyl, imidazolyl, pyrazinyl, thiadiazolyl, pyridinyl, quinolinyl, isoquinolinyl, or thiazolyl.

6. The method of treating a disease according to claim 1, wherein said compound according to formula (I) or a salt thereof is:

A is $C_6$ carbocycle substituted with 0-3 B, $C_{6-10}$ mono- or bicyclic aryl substituted with 0-3 -B, a 5-14 membered heterocyclyl containing 1-4 heteroatoms selected from N, O, and S, substituted with 0-3 -B, wherein the heterocyclyl is chromanyl, 3,4-dihydro-2H-benzo[e][1,3] oxazin-2-one, pyrrolidinyl, piperidinyl, morpholinyl or piperazinyl; or a 5-10 membered heteroaryl containing 1-4 heteroatoms selected from N, O, and S, substituted with 0-3 -B, wherein the heteroaryl is pyridinyl, quinolinyl, isoquinolinyl, indolyl, indazolyl, benzimidazolyl, furanyl, benzofuranyl, dibenzofuranyl, imidazolyl, pyrazolyl, or thiazolyl;

$R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is 4,5,6,7-tetrahydrobenzo[d]thiazolyl, isoindolinyl, imidazo[1,2-a]pyrazin-8(7H)-one, 1H-pyrrolo[3,4-c]pyridin-3(2H)-one, 1,3-dihydrofuro [3,4-c]pyridine, phthalazine, isoquinolin-1(2H)-one, isoindolinyl, isoindoline-1,3-dione, quinazolin-4(3H)-one,

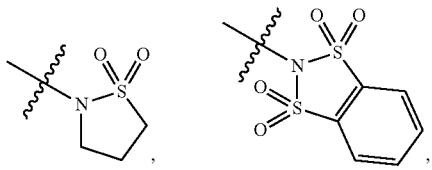

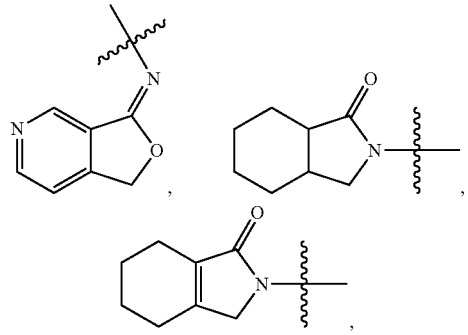

pyrrolidinyl, piperidinyl, morpholinyl or piperazinyl; or a 5-10 membered heteroaryl containing 1-4 heteroatoms selected from N, O, and S, substituted with 0-3 $R^{1a}$ wherein the heteroaryl is indazolyl, imidazolyl, pyrimidinyl, benzimidazolyl, benzothiazolyl, quinolinyl, quinazolinyl, quinazolin-4(3H)-one pyridinyl, or thiazolyl.

7. The method of treating a disease according to claim 1, wherein said compound according to formula (I) or a salt thereof is a compound of formula (Ia) or (Ib):

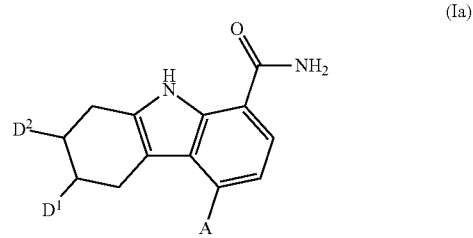

(Ia)

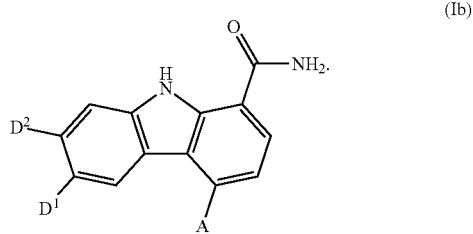

(Ib)

8. The method of treating a disease according to claim 1, wherein said compound according to formula (I) or a salt thereof is:

$R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-1 $R^f$, $C_{1-6}$ haloalkyl, —$(CH_2)_r$-3-6 membered carbocycle, or —$(CH_2)_r$-5-7 membered heterocycle comprising carbon atoms and 1-4 heteroatoms selected from N, O, and $S(O)_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or —($CH_2$)$_r$-phenyl substituted with 0-2 $R^d$;

$R^c$ is $C_{1-6}$ alkyl substituted with 0-1 $R^f$, $C_{3-6}$ cycloalkyl, or —($CH_2$)$_r$-phenyl substituted with 0-1 $R^f$;

$R^d$ is hydrogen, F, Cl, Br, $OCF_3$, $CF_3$, CN, $NO_2$, —$OR^e$, —C(O)$R^e$, —$NR^eR^e$, —$NR^eC(O)OR^c$, $C_{1-6}$ alkyl, or —($CH_2$)$_r$-phenyl;

$R^e$ is hydrogen, $C_{1-6}$ alkyl, $C_{3-6}$ cycloalkyl, or —($CH_2$)$_r$-phenyl;

$R^f$ is hydrogen, halo, or $NH_2$; and r is 0 or 1.

9. The method of treating a disease according to claim 1, wherein said compound according to formula (I) or a salt thereof is:

$R^a$ is hydrogen, F, Cl, Br, $OCF_3$, $CF_3$, $CHF_2$, CN, $NO_2$, —$OR^b$, —$SR^b$, —C(O)$R^b$, —C(O)$OR^b$, —OC(O)$R^b$, —$NR^{11}R^{11}$, —C(O)$NR^{11}R^{11}$, —$NR^bC(O)R^c$, —$NR^bC(O)OR^c$, —$NR^bC(O)NR^{11}R^{11}$, —S(O)$_p$$NR^{11}R^{11}$, —$NR^bS(O)_pR^c$, —S(O)$R^c$, —S(O)$_2R^c$, $C_{1-6}$ alkyl, $C_{1-6}$ haloalkyl, —($CH_2$)$_r$-3-6 membered carbocycle phenyl, or —($CH_2$)$_r$-5-7 membered heterocycle comprising carbon atoms and 1-4 heteroatoms selected from N, O, and S(O)$_p$, wherein the heterocycle is thiazolyl, pyridinyl, piperidinyl, morpholinyl, piperazinyl, pyrrolidinyl, pyrrolidin-one, $R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or —($CH_2$)$_r$-phenyl substituted with 0-2 $R^d$;

$R^c$ is $C_{1-6}$ alkyl, $C_{3-6}$ cycloalkyl, or —($CH_2$)$_r$-phenyl;

$R^d$ is hydrogen, F, Cl, Br, $OCF_3$, $CF_3$, CN, $NO_2$, —$OR^e$, —C(O)$R^e$, —$NR^eR^e$, —$NR^eC(O)OR^c$, $C_{1-6}$ alkyl, or —($CH_2$)$_r$-phenyl; and $R^e$ is hydrogen, $C_{1-6}$ alkyl, $C_{3-6}$ cycloalkyl, or —($CH_2$)$_r$-phenyl.

10. The method of treating a disease according to claim 1, wherein said compound according to formula (I) or a salt thereof is a compound of formula (Ia) or (Ib):

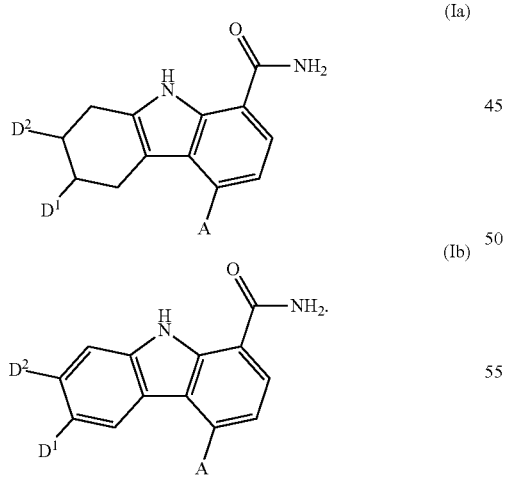

(Ia)

(Ib)

A is $C_{3-10}$ carbocycle substituted with 0-3 B, wherein the carbocycle is cyclohexyl or cyclohexenyl, $C_{6-10}$ mono- or bicyclic aryl substituted with 0-3 B, wherein the aryl group is phenyl or naphthyl; a 5-10 membered heterocyclyl containing 1-4 heteroatoms selected from N, O, and S, substituted with 0-3 B, wherein the heterocyclyl group is chromanyl, 3,4-dihydro-2H-benzo[e][1,3]oxazin-2-one, pyrrolidinyl or piperidinyl; or a 5-10 membered heteroaryl containing 1-4 heteroatoms selected from N, O, and S, substituted with 0-3 -B, wherein the heteroaryl group is pyridinyl, quinolinyl, isoquinolinyl, indolyl, indazolyl, benzimidazolyl, furanyl, benzofuranyl, dibenzofuranyl, imidazolyl, pyrazolyl or thiazolyl;

B is $R^1$, halogen, —C(═O)O—$R^1$, —S(═O)$_2$—$R^1$, —$NR^{11}C(═O)$—$R^1$, —$NR^{11}C(═O)NR^{11}$—$R^1$, —$NR^{11}S(═O)_2$—$R^1$, N(S(═O)$_2$—$R^1$)$_2$, or —$NR^{11}$—$R^1$;

$R^1$ is hydrogen, trifluoromethyl, $C_{1-4}$ alkyl substituted with 0-1 $R^{1a}$, phenyl substituted with 0-3 $R^{1a}$, or a 5-10 membered heteroaryl containing 1-4 heteroatoms selected from N, O, and S, substituted with 0-3 $R^{1a}$, wherein the heteroaryl is pyridyl or thiazolyl;

one of $D^1$ and $D^2$ is D and the other is hydrogen;

D is $R^2$, —C(═O)—$R^2$, —$OR^2$, —C(═O)$NR^{11}R^2$, $NR^{11}C(═O)R^2$, —$NR^{11}C(═O)NR^{11}$—$R^2$, —$NR^{11}S(═O)_2$—$R^2$, or —$NR^{11}$—$R^2$;

$R^2$ is hydrogen, $C_{2-6}$ alkyl substituted with 0-3 $R^{2a}$, or a 5-10 membered heterocyclyl containing 1-4 heteroatoms selected from N, O, and S, substituted with 0-3 $R^{2a}$ where the heterocyclyl is tetrazolyl, pyrrolidinyl, piperidinyl, piperazinyl or morpholinyl; and $R^{2a}$ is $C_{1-4}$ alkyl, wherein the alkyl is methyl, ethyl, propyl, i-propyl, butyl, and t-butyl, substituted with 0-1 $R^a$.

11. The method of treating a disease according to claim 1, wherein said compound according to formula (I) or a salt thereof is a compound of formula (Ic):

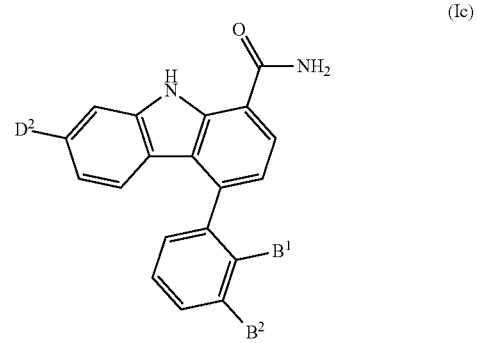

(Ic)

or a salt thereof, wherein $B^1$ is methyl or fluorine;

$B^2$ is $R^{1b}$, —$NR^{11}C(═O)$—$R^{1c}$, —$NR^{11}C(═O)NR^{11}$—$R^{1d}$, or —$NR^{11}$—$R^{1e}$;

$R^{1b}$ is

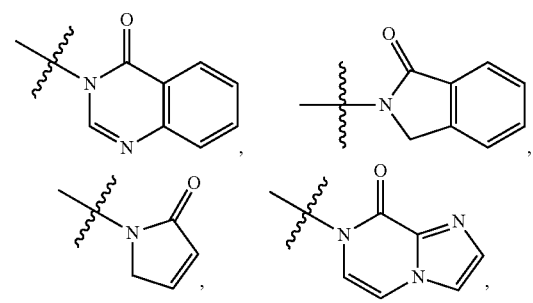

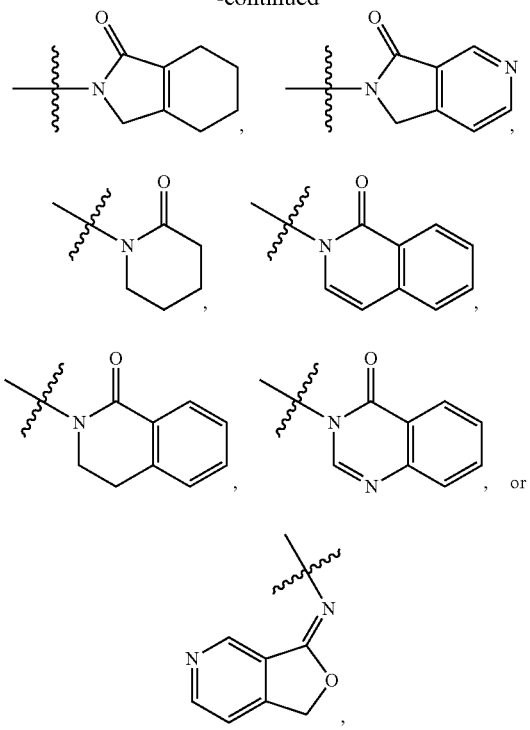

any of which are substituted with 0-3 $R^{1a}$;

$R^{1c}$ is $C_{1-6}$ alkyl, phenyl substituted with 0-2 $R^a$, cyclopropyl, $CH_2$-tetrazolyl, or pyridyl, thiazolyl, imidazolyl, benzimidazolyl, or pyrimidinyl, any of which are substituted with 0-2 $R^a$;

$R^{1d}$ is thiazolyl substituted with 0-1 $R^{1a}$;

$R^{1e}$ is quinazolinyl substituted with 0-1 $R^{1a}$;

$R^{1a}$ is selected from hydrogen, halo, CN, methyl, ethyl, $CF_3$, OH, O-methyl, $CO_2CH_3$, $N(CH_3)_2$, $NC(O)CH_3$, $D^2$ is $-R^2$, $-(C(R^{11})_2)_r-R^2$, $-OR^2$, $-C(=O)-R^2$, $-C(=O)NR^{11}-R^2$, $-NR^{11}C(=O)-R^2$, $-NR^{11}C(=O)NR^{11}-R^2$, $-NR^{11}-R^2$, or $-OC(=O)-R^2$;

provided that $D^2$ is not hydrogen;

$R^2$ is hydrogen, $C_{1-6}$ alkyl substituted with 0-3 $R^{2a}$, $C_{3-10}$ cyclopropyl substituted with 0-3 $R^{2a}$, or a 5-10 membered heterocyclyl containing 1-4 heteroatoms selected from N, O, and S, substituted with 0-3 $R^{2a}$, wherein the heterocyclyl is selected from piperazinyl, pyrrolidinyl, tetrahydrofuranyl, morpholinyl, dioxolanyl, piperidinyl, oxazolidinyl (oxazolidin-one), imidazolidinyl (imidazolidin-one), or a 5-10 membered heteroaryl containing 1-4 heteroatoms selected from N, O, and S, substituted with 0-3 $R^{2a}$, wherein the heteroaryl is selected from pyridinyl, imidazolyl, pyrazinyl, pyrimidinyl, tetrazolyl, thiadiazolyl;

$R^{2a}$ is hydrogen, $-(CH_2)_rOR^b$, $-(CH_2)_rOC(O)R^b$, $-(CH_2)_rNR^{11}R^{11}$, $-NR^bC(O)NR^{11}R^{11}$, $-NR^bS(O)_pR^c$, $C_{1-6}$ alkyl substituted with 0-2 $R^a$, or $-(CH_2)_r$-5-7 membered heterocycle comprising carbon atoms and 1-4 heteroatoms selected from N, O, and $S(O)_p$ substituted with 0-2 $R^a$, wherein the heterocycle is selected from pyridinyl, pyrrolidinyl, pyrrolidinonyl, morpholinyl, imidazolyl, piperidinyl;

$R^{11}$ is hydrogen or $C_{1-4}$ alkyl substituted with 0-1 $R^f$;

$R^a$ is hydrogen, $-OR^b$, $-NR^{11}R^{11}$, or $-(CH_2)_r$-5-7 membered heterocycle comprising carbon atoms and 1-4 heteroatoms selected from N, O, and $S(O)_p$, wherein the heterocycle is imidazolyl or morpholinyl;

$R^b$ is hydrogen or $C_{1-6}$ alkyl substituted with 0-2 $R^d$;

$R^c$ is $C_{1-6}$ alkyl;

$R^d$ is hydrogen, $-OR^e$, or $-NR^eR^e$;

$R^e$ is hydrogen or $C_{1-6}$ alkyl; and $R^f$ is hydrogen, $NH_2$, OH, or $OCH_3$.

12. The method of treating a disease according to claim 11, wherein the disease is systemic lupus erythematosus (SLE).

13. The method of treating a disease according to claim 1, wherein the disease is rheumatoid arthritis.

14. The method of treating a disease according to claim 1, wherein the disease is multiple sclerosis (MS).

15. The method of treating a disease according to claim 11, wherein the disease is inflammatory bowel disease.

16. The method of treating a disease according to claim 11, wherein the disease is B-cell lymphoma.

17. The method of treating a disease according to claim 11, wherein the disease is B-cell leukemia.

18. The method of treating a disease according to claim 11, wherein the disease is transplant rejection.

19. The method of treating a disease according to claim 11, wherein the disease is rheumatoid arthritis.

20. The method of treating a disease according to claim 11, wherein the disease is multiple sclerosis (MS).

* * * * *

UNITED STATES PATENT AND TRADEMARK OFFICE
CERTIFICATE OF CORRECTION

PATENT NO. : 8,362,065 B2
APPLICATION NO. : 13/292153
DATED : January 29, 2013
INVENTOR(S) : Qingjie Liu et al.

It is certified that error appears in the above-identified patent and that said Letters Patent is hereby corrected as shown below:

Title Page 2
Col. 2, line 18, under Foreign Patent Documents, delete "WO 20081057254" and insert -- WO 2008/057254 --, therefor.

In the Claims:

Claim 1, col. 265, line 56, delete "$R^{1'}$" and insert -- $R^1$ --, therefor;

Claim 2, col. 268, line 5, delete "carbocylce," and insert -- carbocycle, --, therefor; and Claim 11, col. 273, lines 15-20, after " " delete " 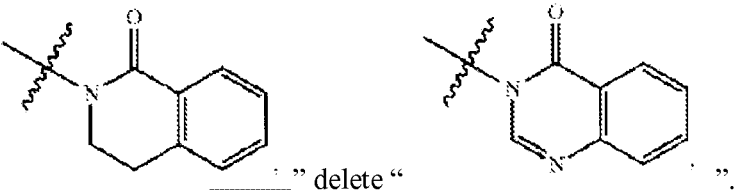 ".

Signed and Sealed this
Twenty-seventh Day of August, 2013

Teresa Stanek Rea
*Acting Director of the United States Patent and Trademark Office*